(12) United States Patent
Grandea, III et al.

(10) Patent No.: US 8,974,788 B2
(45) Date of Patent: *Mar. 10, 2015

(54) COMPOSITIONS AND METHODS FOR THE THERAPY AND DIAGNOSIS OF INFLUENZA

(75) Inventors: Andres G. Grandea, III, Shoreline, WA (US); Gordon King, Shoreline, WA (US); Thomas C. Cox, Redmond, WA (US); Ole Olsen, Everett, WA (US); Jennifer Mitcham, Redmond, WA (US); Matthew Moyle, Redmond, WA (US); Phil Hammond, Seattle, WA (US)

(73) Assignee: Theraclone Sciences, Inc., Seattle, WA (US)

( * ) Notice: Subject to any disclaimer, the term of this patent is extended or adjusted under 35 U.S.C. 154(b) by 622 days.

This patent is subject to a terminal disclaimer.

(21) Appl. No.: 12/855,553

(22) Filed: Aug. 12, 2010

(65) Prior Publication Data

US 2011/0070235 A1    Mar. 24, 2011

Related U.S. Application Data

(60) Provisional application No. 61/234,154, filed on Aug. 14, 2009.

(51) Int. Cl.
*A61K 39/42* (2006.01)
*A61P 31/16* (2006.01)
*C12Q 1/70* (2006.01)
*G01N 33/569* (2006.01)
*C07K 16/10* (2006.01)
*A61K 39/00* (2006.01)

(52) U.S. Cl.
CPC ...... *G01N 33/56983* (2013.01); *C07K 16/1018* (2013.01); *A61K 2039/505* (2013.01); *C07K 2317/21* (2013.01); *C07K 2317/34* (2013.01); *C07K 2317/515* (2013.01); *C07K 2317/92* (2013.01); *G01N 2333/11* (2013.01)
USPC .................. 424/139.1; 424/141.1; 424/142.1; 424/159.1

(58) Field of Classification Search
CPC .......... A61K 39/42; A61P 31/16; C12Q 1/70
See application file for complete search history.

(56) References Cited

U.S. PATENT DOCUMENTS

| 8,080,244 B2 * | 12/2011 | Bradbury .................... 424/130.1 |
| 8,192,927 B2 * | 6/2012 | Van Den Brink et al. ........ 435/5 |
| 8,329,188 B2 * | 12/2012 | Moyle et al. ................ 424/186.1 |
| 2012/0064085 A1 * | 3/2012 | Bradbury .................... 424/147.1 |

FOREIGN PATENT DOCUMENTS

| WO | WO-2008028946 A2 | 3/2008 |
| WO | WO-2008036675 A2 | 3/2008 |
| WO | WO-2009064805 A1 | 5/2009 |

OTHER PUBLICATIONS

Straight et al. "Antibody Contributes to Heterosubtypic Protection Against Influenza A-Induced Tachypnea in Cotton Rats." *Virol. J.* 5(Mar. 2008):44.
Wu et al. "Heterosubtypic Protection Conferred by Combined Vaccination with M2e Peptide and Split Influenza Vaccine." *Vaccine.* 27.43(Dec. 2008):6095-6101.
Kitikoon et al. "The Antibody Responses to Swine Influenza Virus (SIV) Recombinant Matrix 1 (rM1), Matrix 2 (M2), and Hemagglutinin (HA) Proteins." *Vet. Microbiol.* 126.1-3(Jul. 2007): 51-62.
Heinen et al. "Vaccination of Pigs with a DNA Construct Expressing an Influenza Virus M2-Nucleoprotein Fusion Protein Exacerbates Disease after Challenge with Influenza A Virus." *J. Gen. Virol.* 83.Part 8(Aug. 2002):1851-1859.
Crisci et al. "Chimeric Calicivirus-Like Particles Elicit Protective Anti-Viral Cytotoxic Responses Without Adjuvant." *Virol.* 387.2(2009):303-312.
Grgacic et al. "Virus-Like Particles: Passport to Immune Recognition." *Methods.* 40.1(2006):60-65.
Jennings et al. "The Coming of Age of Virus-Like Particle Vaccines." *Biol. Chem.* 389.5(2008):521-536.

\* cited by examiner

*Primary Examiner* — Agnieszka Boesen
(74) *Attorney, Agent, or Firm* — Cooley LLP; Ivor R. Elrifi

(57) ABSTRACT

The present invention provides compositions, vaccines, and methods for diagnosing, treating, and preventing influenza infection using a combination of antibodies raised against the influenza hemagglutinin and the matrix 2 ectodomain polypeptides.

14 Claims, 37 Drawing Sheets

FIG. 3A

FULL-LENGTH M2 VARIANT BINDING
AMINO ACID SEQUENCES OF EXTRACELLULAR DOMAINS OF M2 VARIANTS.

| SEQ ID: No: | | | | | | | | | 10 | | | | | | | 20 | | | | | |
|---|---|---|---|---|---|---|---|---|---|---|---|---|---|---|---|---|---|---|---|---|---|
| 1 A.Brevig.Mission.1.1918.H1N1 | M | S | L | L | T | E | V | E | T | P | T | R | N | E | W | G | C | R | C | N | D | S | S | D |
| 2 A.Fort Monmouth.1.1947.H1N1 | M | S | L | L | T | E | V | E | T | P | T | K | N | E | W | E | C | R | C | N | D | S | S | D |
| 3 A.Singapore.02.2005.H3N2 | M | S | L | L | T | E | V | E | T | P | I | R | N | E | W | E | C | R | C | N | D | S | S | D |
| 679 A.Wisconsin.10.98.H1N1 | M | S | L | L | T | E | V | E | T | P | I | K | N | G | W | E | C | K | C | N | D | S | S | D |
| 5 A.Wisconsin.301.1976.H1N1 | M | S | L | L | T | E | V | E | T | P | I | R | S | E | W | G | C | R | C | N | D | S | S | D |
| 6 A.Panama.1.66.H2N2 | M | S | F | L | P | E | V | E | T | P | I | R | N | E | W | G | C | R | C | N | D | S | S | D |
| 7 A.New York.321.1999.H3N2 | M | S | L | L | T | E | V | E | T | P | I | R | N | E | W | G | C | R | C | N | D | S | S | N |
| 8 A.Caracas.1.71.H3N2 | M | S | L | L | T | E | V | E | T | P | I | R | K | E | W | G | C | R | C | N | D | S | S | D |
| 9 A.Taiwan.3.71.H3N2 | M | S | F | L | T | E | V | E | T | P | I | R | N | E | W | G | C | R | C | N | D | S | S | D |
| 10 A.Wuhan.359.95.H3N2 | M | S | L | P | T | E | V | E | T | P | I | R | S | E | W | G | C | R | C | N | D | S | S | D |
| 11 A.Hong Kong.1144.99.H3N2 | M | S | L | L | P | E | V | E | T | P | I | R | N | E | W | G | C | R | C | N | D | S | S | D |
| 12 A.Hong Kong.1180.99.H3N2 | M | S | L | L | P | E | V | E | T | P | I | R | N | G | W | G | C | R | C | N | D | S | S | D |
| 13 A.Hong Kong.1774.99.H3N2 | M | S | L | L | T | E | V | E | T | P | T | R | N | G | W | E | C | R | C | S | G | S | S | D |
| 14 A.New York.217.02 H1N2 | M | S | L | L | T | E | V | E | T | P | I | R | N | E | W | E | Y | R | C | N | D | S | S | D |
| 15 A.New York.300.2003.H1N2 | M | S | L | L | T | E | V | E | T | P | I | R | N | E | W | E | Y | R | C | S | D | S | S | D |
| 16 A.swine.Spain.54008.2004.H3N2 | M | S | L | L | T | E | V | E | T | P | T | R | N | G | W | E | C | R | Y | S | D | S | S | D |
| 17 A.Guangzhou.333.99.H9N2 | M | S | F | L | T | E | V | E | T | L | T | R | N | G | W | E | C | R | C | S | D | S | S | D |
| 18 A.Hong Kong.1073.99.H9N2 | M | S | L | L | T | E | V | E | T | L | T | R | N | G | W | E | C | K | C | R | D | S | S | D |
| 19 A.Hong Kong.1.68.H3N2 | M | S | L | L | T | E | V | E | T | P | I | R | N | E | W | G | C | R | C | N | D | S | S | D |
| 20 A.swine.Hong Kong.126.1982.H3N2 | M | S | L | L | T | E | V | E | T | P | I | R | S | E | W | G | C | R | C | N | D | S | G | D |
| 21 A.New York.703.1995.H3N2 | M | S | L | L | T | E | V | E | T | P | I | R | N | E | W | E | C | R | C | N | G | S | S | D |
| 22 A.swine.Quebec.192.81 H1N1 | M | S | L | P | T | E | V | E | T | P | I | R | N | E | W | G | C | R | C | N | D | S | S | D |
| 23 A.Puerto Rico.8.34.H1N1 | M | S | L | L | T | E | V | E | T | P | I | R | N | E | W | E | C | R | C | N | G | S | S | D |
| 24 A.Hong Kong.485.97.H5N1 | M | S | L | L | T | E | V | D | T | L | T | R | N | G | W | G | C | R | C | S | D | S | S | D |
| 25 A.Hong Kong.542.97.H5N1 | M | S | L | L | T | E | V | E | T | L | T | K | N | G | W | G | C | R | C | S | D | S | S | D |
| 26 A.silky chicken.Shantou.1826.2004.H | M | S | L | L | T | E | V | E | T | P | T | R | N | G | W | E | C | K | C | S | D | S | S | D |
| 27 A.chicken.Taiwan.0305.04.H6N1 | M | S | L | L | T | E | V | E | T | H | T | R | N | G | W | E | C | K | C | S | D | S | S | D |
| 28 A.Quail.Arkansas.16309-7.94.H7N3 | M | S | L | L | T | E | V | K | T | P | T | R | N | G | W | E | C | K | C | S | D | S | S | D |
| 29 A.Hong Kong.486.97.H5N1 | M | S | L | L | T | E | V | E | T | L | T | R | N | G | W | G | C | R | C | S | D | S | S | D |
| 30 A.Chicken.Pennsylvania.13552-1.98 | M | S | L | L | T | E | V | E | T | P | T | R | D | G | W | E | C | K | C | S | D | S | S | D |
| 31 A.chicken.Heilongjiang.48.01.H9N2 | M | S | L | L | T | E | V | E | T | P | T | R | N | G | W | G | C | R | C | N | D | S | S | D |
| 32 A.swine.Korea.S5.2005.H1N2 | M | S | L | L | T | E | V | E | T | P | T | R | N | G | W | E | C | K | C | N | D | S | S | D |
| 33 A.Hong Kong.1073.99.H9N2 | M | S | L | L | T | E | V | E | T | L | T | R | N | G | W | E | C | K | C | S | D | S | S | D |
| 34 A.Wisconsin.3523.88.H1N1 | M | S | L | L | T | E | V | E | T | P | I | R | N | E | W | G | C | K | C | N | D | S | S | D |
| 35 A.X-31 Vaccine strain H3N2 | M | S | F | L | T | E | V | E | T | P | I | R | N | E | W | G | C | R | C | N | G | S | S | D |
| 36 A.Chicken.Rostock.8.1934.H7N1 | M | S | L | L | T | E | V | E | T | P | T | R | N | G | W | E | C | R | C | N | D | S | S | D |
| 37 A.environment.New York.16326-1.2 | M | S | L | L | T | E | V | E | T | P | I | R | K | G | W | E | C | N | C | S | D | S | S | D |
| 38 A.Indonesia.560H.2006.H5N1 | M | S | L | L | T | E | V | E | T | P | T | R | N | E | W | E | C | R | C | S | D | S | S | D |
| 39 A.Chicken.Hong Kong.SF1.03.H9N2 | M | S | L | L | T | G | V | E | T | H | T | R | N | G | W | G | C | K | C | S | D | S | S | D |
| 40 A.chicken.Hong Kong.YU427.03.H9N | M | S | L | L | P | E | V | E | T | H | T | R | N | G | W | G | C | R | C | S | D | S | S | D |

EXTRACELLULAR SEQUENCE OF D20 IS IDENTICAL
TO #19, HK483 TO #29, AND VN1203 TO #38.

CROSS REACTIVITY BINDING OF ANTI-M2 ANTIBODIES TO VARIANT M2 PEPTIDES

| seqNo | Name | Size | Description | ELISA (OD 450) | | | |
|---|---|---|---|---|---|---|---|
| | | | | 14C2 | 8i10 | 23K12 | 2N9 |
| 680 | M2 | 23 aa | SLLTEVETPIRNEWGCRCNDSSD | + | - | - | - |
| 681 | M2SG | 23 aa | SLLTEVETPIRSEWGCRCNDSGD | + | - | - | - |
| 682 | M2EG | 23 aa | SLLTEVETPIRNEWECRCNGSSD | + | - | - | - |
| 683 | M2P | 23 aa | SLPTEVETPIRNEWGCRCNDSSD | + | - | - | - |
| 684 | M2G | 23 aa | SLLTEVETPIRNEWGCRCNGSSD | + | - | - | - |
| 685 | M2DLTGS | 23 aa | SLLTEVDTLTRNGWGCRCSDSSD | - | - | + | - |
| 686 | M2KNS | 23 aa | SLLTEVETPIRKEWGCNCSDSSD | + | - | - | - |
| 687 | M2LGS | 23 aa | SLLTEVETLIRNGWGCRCSDSSD | - | - | - | - |
| 688 | M2LTKGS | 23 aa | SLLTEVETLTKNGWGCRCSDSSD | - | - | - | - |
| 689 | M2SY | 23 aa | SLLTEVETPIRSEWGCRYNDSSD | + | - | - | - |
| 690 | M2TGEKS | 23 aa | SLLTEVETPTRNGWECKCSDSSD | + | - | - | - |
| 691 | M2HTGEKS | 23 aa | SLLTEVETHTRNGWECKCSDSSD | - | - | - | - |
| 692 | M2KTGEKS | 23 aa | SLLTEVKTPTRNGWECKCSDSSD | - | - | - | - |
| 693 | M2LTGS | 23 aa | SLLTEVETLTRNGWGCRCSDSSD | - | - | + | - |
| 694 | M2TDGEKS | 23 aa | SLLTEVETPTRDGWECKCSDSSD | + | - | - | - |
| 695 | M2TGS | 23 aa | SLLTEVETPTRNGWGCRCSDSSD | + | - | W | - |
| 696 | M2TGEK | 23 aa | SLLTEVETPTRNGWECKCNDSSD | + | - | - | - |
| 697 | M2LTGEKS | 23 aa | SLLTEVETLTRNGWECKCSDSSD | - | - | W | - |
| 698 | M2K | 23 aa | SLLTEVETPIRNEWGCKCNDSSD | + | W | + | - |
| 699 | M2FG | 23 aa | SFLTEVETPIRNEWGCRCNGSSD | + | W | - | - |
| 700 | M2TGE | 23 aa | SLLTEVETPTRNGWECRCNDSSD | + | - | - | - |
| 701 | M2KGENS | 23 aa | SLLTEVETPIRKGWECNCSDSSD | + | - | - | - |
| 702 | M2TES | 23 aa | SLLTEVETPTRNEWECRCSDSSD | + | - | - | - |
| 703 | M2GHTGKS | 23 aa | SLLTGVETHTRNGWGCKCSDSSD | - | - | - | - |
| 704 | M2PHTGS | 23 aa | SLLPEVETHTRNGWGCRCSDSSD | - | - | - | - |

PERCENTAGE COMPARED RELATIVE TO BINDING TO WILD-TYPE PEPTIDE (Seq 1)   NOTE: mAbs WERE TESTED AT 5 μg/mL

>25 %   -   NO BINDING
25 - 40 %   W   WEAK BINDING
> 40 %   +   POSITIVE BINDING

FIG. 6A

BINDING ACTIVITY OF M2 ANTIBODIES TO TRUNCATED M2 PEPTIDES

| seqNo | Name | Size | Description | 14C2 | 8i10 | 23K12 | 2N9 |
|---|---|---|---|---|---|---|---|
| 680 | M2 | 23 aa | SLLTEVETPIRNEWGCRCNDSSD | 3.85 | 0.11 | 0.22 | 0.06 |
| 705 | M16 | 16 aa | LLTEVETPIRNEWGCR | 3.94 | 0.09 | 0.21 | 0.09 |
| 706 | M15 | 15 aa | LTEVETPIRNEWGCR | 3.95 | 0.09 | 0.21 | 0.09 |
| 707 | M12 | 12 aa | VETPIRNEWGCR | 0.15 | 0.09 | 0.20 | 0.09 |
| 708 | CM17 | 17 aa | ETPIRNEWGCRCNDSSD | 0.19 | 0.11 | 0.34 | 0.11 |
| 709 | CM16 | 16 aa | TPIRNEWGCRCNDSSD | 0.23 | 0.13 | 0.35 | 0.12 |
| 710 | CM15 | 15 aa | PIRNEWGCRCNDSSD | 0.19 | 0.12 | 0.34 | 0.11 |
| 711 | CM14 | 14 aa | IRNEWGCRCNDSSD | 0.23 | 0.14 | 0.36 | 0.13 |
| 712 | CM13 | 13 aa | RNEWGCRCNDSSD | 0.22 | 0.14 | 0.34 | 0.13 |
| 713 | CM12 | 12 aa | NEWGCRCNDSSD | 0.27 | 0.14 | 0.39 | 0.14 |
| 714 | NM17 | 17 aa | SLLTEVETPIRNEWGCR | 3.99 | 0.26 | 0.58 | 0.10 |
| 715 | NM16 | 16 aa | SLLTEVETPIRNEWGC | 3.90 | 0.29 | 0.62 | 0.09 |
| 716 | NM15 | 15 aa | SLLTEVETPIRNEWG | 3.97 | 0.12 | 0.30 | 0.11 |
| 717 | NM14 | 14 aa | SLLTEVETPIRNEW | 3.97 | 0.11 | 0.24 | 0.09 |
| 718 | NM13 | 13 aa | SLLTEVETPIRNE | 0.18 | 0.11 | 0.25 | 0.10 |
| 719 | NM12 | 12 aa | SLLTEVETPIRN | 0.20 | 0.10 | 0.24 | 0.09 |
| 720 | NM11 | 11 aa | SLLTEVETPIR | 0.21 | 0.13 | 0.30 | 0.12 |
| 721 | NM10 | 10 aa | SLLTEVETPI | 0.17 | 0.10 | 0.24 | 0.10 |
| 722 | NM8 | 8 aa | SLLTEVET | 0.15 | 0.10 | 0.20 | 0.09 |
| 723 | NM7 | 7 aa | SLLTEVE | 0.14 | 0.10 | 0.20 | 0.08 |
| 724 | NM9 | 9 aa | SLLTEVETP | 0.21 | 0.12 | 0.30 | 0.19 |
| 19 | M2e | 24 aa | MSLLTEVETPIRNEWGCRCNDSSD | 3.98 | 0.13 | 0.43 | 0.10 |
| CMV | HVIR1 | | | 0.16 | 0.11 | 0.21 | 3.99 |

NOTE: mAbs WERE TESTED AT 5 μg/mL

FIG. 12A
Heavy Chain

GROUP A

| | FR1 | CDR1 | | | FR2 | | | CDR2 | | FR3 |
|---|---|---|---|---|---|---|---|---|---|---|
| Germline VH 4-59*01 | QVQLQESGPGLVKPSETLSLTCTVS | GGSISS--YY | WSW | IRQPPGKGLEWIG | Y | F | IYYSGST | NYNP |
| TCN-032 | | S | | | | | | G | N | K |
| 43J7 | LL D A | T | | | R | D | F | F | NG | K |
| 53P10 | LL D A | T | D | | R | D | F | F | NG | K |
| 44I10 | L D A | T | D | | R | D | F | F | NG | K |
| 55J6 | | A | D | | | | F | F | NR | K T |
| 52C13 | | A | D | | | | F | | NR | K T |
| 39P23 | R S | N | SF | G | E | | | | N | K |
| 36G5 | | | DF | | | | | V | NR | K S |
| 48P18 | | A | H | | | | H | V | N | Y |
| 59J21 | RV R | | N | | | | H | | DY R | F |
| 20I23 | V K | D | S | I | | | | L | | K Y S |

GROUP C

| | FR1 | CDR1 | | FR2 | | | CDR2 | FR3 |
|---|---|---|---|---|---|---|---|---|
| Germline VH 4-31*03 | QVQLQESGPGLVKPSQTLSLTCTVS | GGSISSGGVV | WSW | IRQHPGKGLEWIG | V | IVVSGST | VVNP |
| 62B11 | A E | D T A | T | R | | F | N | |
| 41G23 | Q | PV G | S | N | Q | V F | MFH P | R |

GROUP B

| | FR1 | CDR1 | | FR2 | | | CDR2 | FR3 |
|---|---|---|---|---|---|---|---|---|
| Germline VH 3-66*01 | EVQLVESGGGLVQPGGSLRLSCAAS | GFTVSS--NY | MSW | VRQAPGKGLEMVSV | | IYSGGST | YYAD |
| TCN-031 | | | | N | | F | ETR | |
| 44H4 | T | LS | T | N | | F | ETR | |
| 45O19 | T | LS | T | N | | F | ETR | |
| 60D19 | DM P | S | IN | | D | | ADR | S |

FIG. 12A (continued)

Heavy Chain

| Group | Antibody | FR3 | CDR3 | FR4 | Gamma joining segment |
|---|---|---|---|---|---|
| GROUP A | Germline VH 4-59*01 | SLKSRVTISVDTSKNQFSLKLSSVTAADTAVYYC | AR | WGQGTLVTVSS | |
| | TCN-032 | Q S V TM | -ASCSGGYCILLDY | | HJ4*02 |
| | 43J7 | A L K T ES | HDVKFSGSYYVAS | R | HJ4*02 |
| | 53P10 | A L K T G | HDAKFSGSYYVAS | R | HJ4*02 |
| | 44I10 | A L K T G | HDAKFSGSYYVAS | R | HJ4*02 |
| | 55J6 | L AE R R G | HVGGH--TYGIDV | | HJ4*02 |
| | 52C13 | L AE R R | HVGGH--TYGIDV | | HJ4*02 |
| | 39P23 | R S LYM R | -HDDASHGYS IS- | H | HJ4*01 |
| | 36G5 | A M NM | K-NGRSSTSWGIDV | K | HJ6*04 |
| | 48P18 | L A L R T S | PLGSR-YYYGMDV | T | HJ6*02 |
| | 59J21 | Q P A L R T S | PLGIL-HYYAMDL | T | HJ6*02 |
| | 20I23 | T L L F | F | TGSESTTGYGMDV | T | HJ6*02 |

GROUP C

| | | FR3 | | CDR3 | FR4 | |
|---|---|---|---|---|---|---|
| | Germline VH 4-31*03 | SLKSRVTISVDTSKNQFSLKLSSVTAADTAVYYC | AR | | | |
| | 62B11 | L | | AASTSVLGYGMDV | T | IG HJ6*02 (a) |
| | 41G23 | T I LV | F | -VGQMDKYYAMDV | T | IG HJ6*02 |

GROUP B

| | | FR3 | | CDR3 | FR4 | |
|---|---|---|---|---|---|---|
| | Germline VH 3-66*01 | SVKGRFTIISRDNSKNTLYLQMNSLRAFDTAVYYC | AR | | | |
| | TCN-031 | SF VF | | CLSRM-RGYGLDV | T | IG HJ3*01 |
| | 44H4 | V H N | V | -VQRL--SYGMDV | T | IG HJ6*02 |
| | 45O19 | V H N | | -VQRL--SYGMDV | T | IG HJ6*02 |
| | 60D19 | V SHD V | | -VQKS--SYGMDV | T | IG HJ6*02 |

FIG. 12B
Kappa Chain

FIG. 12B (continued)

| Germline Vkappa 1-39*01 | F S G S G S G T D F T L T I S S L Q P E D F A T Y Y C | Q Q S Y S T P | F G G G T R V E I K | Kappa joining segment |
|---|---|---|---|---|
| TCN-032 | | P · L T | | KJ4*01 |
| 43J7 | A | N · = | Q K L | KJ2*01 or KJ2*02 or KJ2*03 or KJ2*04 |
| 53P10 | A S | N · = | Q K L | KJ2*01 or KJ2*02 or KJ2*03 or KJ2*04 |
| 44I10 | R | N · = | Q K L | KJ2*01 or KJ2*02 or KJ2*03 or KJ2*04 |
| 55J6 | | N · = | P L | KJ5*01 |
| 52C13 | A G | N · = | Q L | KJ5*01 |
| 39P23 | A | F N · = | Q L | KJ1*01 |
| 36G5 | | P A · | Q K DM | KJ3*01 |
| 48P18 | D S | V A · | P K V | KJ4*01 |
| 59J21 | T N I T | V = = | K | KJ4*01 |
| 20I23 | | P A · | L | KJ5*01 |
| 62B11 | G | | Q L | KJ5*01 |
| 41G23 | A | T M = · | Q L | KJ5*01 |
| 23K12 | A S V | T = = · | Q K L | KJ2*01 or KJ*02 |
| 44H4 | A S | T = = · | Q L | KJ5*01 |
| 45O19 | T E | T F = = | Q L | KJ5*01 |
| 60D19 | | T F = = · | Q K L | KJ2*01 or KJ2*02 or KJ2*03 or KJ2*04 (a) |

US 8,974,788 B2

COMPOSITIONS AND METHODS FOR THE THERAPY AND DIAGNOSIS OF INFLUENZA

RELATED APPLICATIONS

This application claims the benefit of provisional application U.S. Ser. No. 61/234,154, filed Aug. 14, 2009, the contents of which are herein incorporated by reference in their entirety.

INCORPORATION OF SEQUENCE LISTING

The contents of the text file named "37418-512001USSeqList.txt," which was created on Sep. 24, 2010 and is 567 KB in size, are hereby incorporated by reference in their entirety.

FIELD OF THE INVENTION

The present invention relates generally to prevention, diagnosis, therapy and monitoring of influenza infection. The invention is more specifically related to compositions containing a combination of human antibodies raised against either the influenza hemagglutinin or matrix 2 protein. Such compositions are useful in pharmaceutical compositions for the prevention and treatment of influenza, and for the diagnosis and monitoring of influenza infection.

BACKGROUND OF THE INVENTION

Influenza virus infects 5-20% of the population and results in 30,000-50,000 deaths each year in the U.S. Disease caused by influenza A viral infections is typified by its cyclical nature. Antigenic drift and shift allow for different A strains to emerge every year. Added to that, the threat of highly pathogenic strains entering into the general population has stressed the need for novel therapies for flu infections. The predominant fraction of neutralizing antibodies is directed to the polymorphic regions of the hemagglutinin and neuraminidase proteins. Another recent focus has been on the relatively invariant matrix 2 (M2) protein. Potentially, a neutralizing MAb to M2 would be an adequate therapy for all influenza A strains.

The M2 protein is found in a homotetramer that forms an ion channel and is thought to aid in the uncoating of the virus upon entering the cell. After infection, M2 can be found in abundance at the cell surface. It is subsequently incorporated into the virion coat, where it only comprises about 2% of total coat protein. The M2 extracellular domain (M2e) is short, with the aminoterminal 2-24 amino acids displayed outside of the cell. Anti-M2 MAbs to date have been directed towards this linear sequence. Thus, they may not exhibit desired binding properties to cellularly expressed M2, including conformational determinants on native M2.

SUMMARY OF THE INVENTION

The invention provides diagnostic, prophylactic, and therapeutic compositions including a human antibody raised against the Influenza hemagglutinin protein and a human monoclonal antibody raised against the Influenza M2 protein. Moreover, the invention provides diagnostic, prophylactic, and therapeutic compositions including a human antibody raised against an epitope of the Influenza hemagglutinin protein and a human monoclonal antibody raised against an epitope of the Influenza M2 protein. Furthermore, these compositions are pharmaceutical compositions that include a pharmaceutical carrier. These compositions address a long-felt need in the art for pharmaceutical compositions that both strongly neutralizes Influenza virus infection and recognizes constant regions within proteins common to all Influenza strains.

Specifically, the invention provides a composition including: (a) a human antibody that specifically binds to an epitope of the hemagglutinin (HA) glycoprotein of an influenza virus; and (b) a human monoclonal antibody that specifically binds to an epitope in the extracellular domain of the matrix 2 ectodomain (M2e) polypeptide of an influenza virus. In certain embodiments of this composition, the human monoclonal antibody that specifically binds an epitope of the M2e polypeptide is TCN-032 (8110), 21B15, TCN-031 (23K12), 3241_G23, 3244_I10, 3243_J07, 3259_J21, 3245_O19, 3244_H04, 3136_G05, 3252_C13, 3255_J06, 3420_I23, 3139_P23, 3248_P18, 3253_P10, 3260_D19, 3362_B11, or 3242_P05. Moreover, the human antibody that specifically binds an epitope of the HA glycoprotein is optionally SC06-141, SC06-255, SC06-257, SC06-260, SC06-261, SC06-262, SC06-268, SC06-272, SC06-296, SC06-301, SC06-307, SC06-310, SC06-314, SC06-323, SC06-325, SC06-327, SC06-328, SC06-329, SC06-331, SC06-332, SC06-334, SC06-336, SC06-339, SC06-342, SC06-343, SC06-344, CR6141, CR6255, CR6257, CR6260, CR6261, CR6262, CR6268, CR6272, CR6296, CR6301, CR6307, CR6310, CR6314, CR6323, CR6325, CR6327, CR6328, CR6329, CR6331, CR6332, CR6334, CR6336, CR6339, CR6342, CR6343, or CR6344.

The epitope of the HA glycoprotein is optionally GVT-NKVNSIIDK (SEQ ID NO: 198), GVTNKVNSIINK (SEQ ID NO: 283), GVTNKENSIIDK (SEQ ID NO: 202), GVT-NKVNRIIDK (SEQ ID NO: 201), GITNKVNSVIEK (SEQ ID NO: 281), GITNKENSVIEK (SEQ ID NO: 257), GIT-NKVNSIIDK (SEQ ID NO: 225), and KITSKVNNIVDK (SEQ ID NO: 216). The influenza hemaglutinin (HA) glycoprotein includes an HA1 and HA2 subunit. Exemplary epitopes of the HA glycoprotein include the HA1 subunit, HA2 subunit, or both the HA1 and HA2 subunits. Alternatively, or in addition, the epitope of the M2e polypeptide is a discontinuous epitope. For example, the epitope of the M2e polypeptide includes the amino acid at positions 2, 5, and 6 of MSLLTEVETPTRNEWGCRCNDSSD (SEQ ID NO: 1).

The invention further provides a composition including: (a) an isolated human anti-HA antibody, or an antigen-binding fragment thereof, including a heavy chain variable region (VH) domain and a light chain variable (VL) domain, wherein the VH domain and the VL domain each contain three complementarity determining regions 1 to 3 (CDR1-3), and wherein each CDR includes the following amino acid sequences: VH CDR1: SEQ ID NOs: 566, 571, 586, 597, 603, 609, 615, 627, 633, 637, 643, 649, 658, 664, 670, 303, 251, 242, or 222; VH CDR2: SEQ ID NOs: 567, 572, 587, 592, 598, 604, 610, 616, 628, 634, 638, 644, 650, 655, 659, 665, 671, 306, 249, 307, or 221; VH CDR3: SEQ ID NOs: 568, 573, 588, 593, 599, 605, 611, 617, 629, 635, 639, 645, 651, 656, 660, 666, 672, 298, 246, 290, or 220; VL CDR1: SEQ ID NOs: 569, 574, 577, 580, 583, 589, 594, 600, 606, 612, 618, 621, 624, 630, 640, 646, 652, 661, 667, 285, 289, 245, 224, or 219; VL CDR2: SEQ ID NOs: 570, 575, 578, 581, 584, 590, 595, 601, 607, 613, 619, 622, 625, 631, 641, 647, 653, 662, 668, 305, 248, 299, 223, or 231; VL CDR3: SEQ ID NOs: 200, 576, 579, 582, 585, 591, 596, 602, 608, 614, 620, 623, 626, 632, 636, 642, 648, 654, 657, 663, 669, 308, 247, 250, 227, or 280; and (b) an isolated anti-matrix 2 ectodomain (M2e) antibody, or antigen-binding fragment thereof, including a heavy chain variable (VH) domain and a light chain variable (VL) domain, wherein the VH domain and the VL domain each contain three complementarity determining regions 1 to 3 (CDR1-3), and wherein each CDR includes the following amino acid sequences: VH CDR1: SEQ ID NOs: 72, 103, 179, 187, 203, 211, 228, 252, 260, 268, 284, 293, or 301; VH CDR2: SEQ ID NOs: 74, 105, 180, 188, 204, 212, 229, 237, 253, 261, 269, 285, or 294; VH CDR3 SEQ ID NOs: 76, 107, 181, 189, 197, 205, 213, 230, 238, 254, 262, 270, 286, or 295; VL CDR1: SEQ ID NOs: 59, 92, 184, 192, 208, 192, 223, 241, 265, or 273; VL CDR2: SEQ ID NOs: 61, 94, 185, 193, 209, 217, 226, 234, 258, 274, or 282; and VL CDR3: SEQ ID NOs: 63, 96, 186, 194, 210, 218, 243, 259, 267, 275, 291, or 300.

Alternatively, or in addition, the invention provides a composition including: (a) an isolated human anti-HA antibody, or an antigen-binding fragment thereof, including a heavy chain variable region (VH) domain and a light chain variable (VL) domain, wherein the VH domain and the VL domain each contain three complementarity determining regions 1 to 3 (CDR1-3), and wherein each CDR includes the following amino acid sequences: VH CDR1: SEQ ID NOs: 566, 571, 586, 597, 603, 609, 615, 627, 633, 637, 643, 649, 658, 664, 670, 303, 251, 242, or 222; VH CDR2: SEQ ID NOs: 567, 572, 587, 592, 598, 604, 610, 616, 628, 634, 638, 644, 650, 655, 659, 665, 671, 306, 249, 307, or 221; VH CDR3: SEQ ID NOs: 568, 573, 588, 593, 599, 605, 611, 617, 629, 635, 639, 645, 651, 656, 660, 666, 672, 298, 246, 290, or 220; VL CDR1: SEQ ID NOs: 569, 574, 577, 580, 583, 589, 594, 600, 606, 612, 618, 621, 624, 630, 640, 646, 652, 661, 667, 285, 289, 245, 224, or 219; VL CDR2: SEQ ID NOs: 570, 575, 578, 581, 584, 590, 595, 601, 607, 613, 619, 622, 625, 631, 641, 647, 653, 662, 668, 305, 248, 299, 223, or 231; VL CDR3: SEQ ID NOs: 200, 576, 579, 582, 585, 591, 596, 602, 608, 614, 620, 623, 626, 632, 636, 642, 648, 654, 657, 663, 669, 308, 247, 250, 227, or 280; and (b) an isolated anti-matrix 2 ectodomain (M2e) antibody, or antigen-binding fragment thereof, including a heavy chain variable (VH) domain and a light chain variable (VL) domain, wherein the VH domain and the VL domain each contain three complementarity determining regions 1 to 3 (CDR1-3), and wherein each CDR includes the following amino acid sequences: VH CDR1: SEQ ID NOs: 109, 112, 182, 190, 206, 214, 239, 255, 263, 271, 287, 296, or 304; VH CDR2: SEQ ID NOs: 110, 113, 183, 191, 207, 215, 232, 240, 256, 264, 272, 288, or 297; VH CDR3 SEQ ID NOs: 76, 107, 181, 189, 197, 205, 213, 230, 238, 254, 262, 270, 286, or 295; VL CDR1: SEQ ID NOs: 59, 92, 184, 192, 208, 192, 223, 241, 265, or 273; VL CDR2: SEQ ID NOs: 61, 94, 185, 193, 209, 217, 226, 234, 258, 274, or 282; and VL CDR3: SEQ ID NOs: 63, 96, 186, 194, 210, 218, 243, 259, 267, 275, 291, or 300.

The invention provides a composition including: (a) an isolated human anti-HA antibody, or an antigen-binding fragment thereof, including a heavy chain variable region (VH) domain, wherein the VH domain includes the following amino acid sequences: SEQ ID NOs 309, 313, 317, 321, 325, 329, 333, 337, 341, 345, 349, 353, 357, 361, 365, 369, 373, 377, 381, 385, 389, 393, 397, 401, 405, 409, 199, 417, 423, 429, 435, 441, 447, 453, 459, 465, 471, 477, 483, 489, 495, 501, 507, 513, 519, 525, 531, 537, 543, 550, 556, or 562, and a light chain variable (VL) domain, wherein the VL domain includes the following amino acid sequences: SEQ ID NOs 310, 314, 318, 322, 326, 330, 334, 338, 342, 346, 350, 354, 358, 362, 366, 370, 374, 378, 382, 386, 390, 394, 398, 402, 406, 410, 414, 420, 426, 432, 438, 444, 450, 456, 462, 468, 474, 480, 486, 492, 498, 504, 510, 516, 522, 528, 534, 540, 547, 553, 559, or 565; and (b) an isolated anti-matrix 2 ectodomain (M2e) antibody, or antigen-binding fragment thereof, including a heavy chain variable (VH) domain, wherein the VH domain includes the following amino acid sequences: SEQ ID NOs 44, 277, 276, 50, 236, 235, 116, 120, 124, 128, 132, 136, 140, 144, 148, 152, 156, 160, 164, 168, 172, or 176, and a light chain variable (VL) domain, wherein the VL domain includes the following amino acid sequences: SEQ ID NOs 46, 52, 118, 122, 126, 130, 134, 138, 142, 146, 150, 154, 158, 162, 166, 170, 175, or 178.

Furthermore, the invention provides a multivalent vaccine composition including any of the compositions described herein containing an isolated human anti-HA antibody, or an antigen-binding fragment thereof and an isolated anti-matrix 2 ectodomain (M2e) antibody, or antigen-binding fragment thereof. Alternatively, the multivalent vaccine includes antibodies that bind to the epitopes to which the antibodies of the invention bind. Exemplary antibodies of the invention include, but are not limited to, TCN-032 (8I10), 21B15, TCN-031 (23K12), 3241_G23, 3244_I10, 3243_J07, 3259_J21, 3245_O19, 3244_H04, 3136_G05, 3252_C13, 3255_J06, 3420_I23, 3139_P23, 3248_P18, 3253_P10, 3260_D19, 3362_B11, 3242_P05, SC06-141, SC06-255, SC06-257, SC06-260, SC06-261, SC06-262, SC06-268, SC06-272, SC06-296, SC06-301, SC06-307, SC06-310, SC06-314, SC06-323, SC06-325, SC06-327, SC06-328, SC06-329, SC06-331, SC06-032, SC06-334, SC06-336, SC06-339, SC06-342, SC06-343, SC06-344, CR6141, CR6255, CR6257, CR6260, CR6261, CR6262, CR6268, CR6272, CR6296, CR6301, CR6307, CR6310, CR6314, CR6323, CR6325, CR6327, CR6328, CR6329, CR6331, CR6332, CR6334, CR6336, CR6339, CR6342, CR6343, and CR6344. For examply, the multivalent vaccine may include one or more of the following epitopes: GVTNKVNSIIDK (SEQ ID NO: 198), GVTNKVNSIINK (SEQ ID NO: 283), GVTNKENSIIDK (SEQ ID NO: 202), GVTNKVNRIIDK (SEQ ID NO: 201), GITNKVNSVIEK (SEQ ID NO: 281), GITNKENSVIEK (SEQ ID NO: 257), GITNKVNSIIDK (SEQ ID NO: 225), KITSKVNNIVDK (SEQ ID NO: 216), MSLLTEVETPTRNEWGCRCNDSSD (SEQ ID NO: 1), and MSLLTEVETPTRNEWGCRCNDSSD (SEQ ID NO: 1) provided in its native conformation.

The multivalent vaccine also includes a composition including: (a) a human antibody that specifically binds to an epitope of the hemagglutinin (HA) glycoprotein of an influenza virus; and (b) a human monoclonal antibody that specifically binds to an epitope in the extracellular domain of the matrix 2 ectodomain (M2e) polypeptide of an influenza virus.

The invention provides a pharmaceutical composition including any one of the compositions described herein. Moreover, the pharmaceutical composition includes a pharmaceutical carrier.

The invention provides a method for stimulating an immune response in a subject, including administering to the subject the pharmaceutical composition described herein. The pharmaceutical composition may administered prior to or after exposure of the subject to an Influenza virus.

The invention also provides a method for the treatment of an influenza virus infection in a subject in need thereof, including administering to the subject the pharmaceutical composition described herein. The subjection may have been exposed to an influenza virus. Alternatively, or in addition, the subject has not been diagnosed with an influenza infection. The pharmaceutical composition may administered prior to or after exposure of the subject to an Influenza virus. Preferably, the pharmaceutical composition is administered at a dose sufficient to promote viral clearance or eliminate influenza infected cells.

The invention further provides a method for the prevention of an influenza virus infection in a subject in need thereof, including administering to the subject a vaccine composition described herein, prior to exposure of the subject to an influenza virus. In certain embodiments of this method, the subject is at risk of contracting an influenza infection. The pharmaceutical composition may administered prior to or after exposure of the subject to an Influenza virus. Preferably, the pharmaceutical composition is administered at a dose sufficient to promote viral clearance or eliminate influenza infected cells.

The treatment and prevention methods provided by the invention further include administering an anti-viral drug, a viral entry inhibitor or a viral attachment inhibitor. Exemplary anti-viral drugs include, but are not limited to, a neuraminidase inhibitor, a HA inhibitor, a sialic acid inhibitor, or an M2 ion channel inhibitor. In certain aspects of these methods, the M2 ion channel inhibitor is amantadine or rimantadine. In other aspects of these methods, the neuraminidase inhibitor is zanamivir or oseltamivir phosphate. The antiviral drug may administered prior to or after exposure of the subject to an Influenza virus.

The treatment and prevention methods provided by the invention further include administering a second anti-Influenza A antibody. The second antibody is optionally an antibody described herein. The second antibody may administered prior to or after exposure of the subject to an Influenza virus.

The invention provides a method for determining the presence of an Influenza virus infection in a subject, including the steps of (a) contacting a biological sample obtained from the subject with any one of the antibodies or pharmaceutical compositions described herein; (b) detecting an amount of the antibody that binds to the biological sample; and (c) comparing the amount of antibody that binds to the biological sample to a control value, and therefrom determining the presence of the Influenza virus in the subject. Optionally, the control value is determined by contacting a control sample obtained from the subject with any one of the antibodies or pharmaceutical compositions described herein and detecting an amount of the antibody that binds to the control sample.

The invention also provides a diagnostic kit including any one of the antibodies, compositions, or pharmaceutical compositions described herein.

The invention further provides a prophylactic kit including a vaccine composition described herein. Preferably, the vaccine is a multivalent vaccine. The term "multivalent vaccine" describes a single vaccine that elicits an immune response either to more than one infectious agent, e.g. the influenza HA glycoprotein and the influenza M2e polypeptide, or to several different epitopes of a molecule, e.g. HA epitopes shown in SEQ ID NOs 198, 283, 202, 201, 281, 257, 225, and 216. Alternatively, or in addition, the term multivalent vaccine is meant to describe the administration of a combination of human antibodies raised against more than one infectious agent, e.g. the influenza HA glycoprotein and the influenza M2e polypeptide.

Other features and advantages of the invention will be apparent from and are encompassed by the following detailed description and claims.

BRIEF DESCRIPTION OF THE DRAWINGS

FIG. 6A is a chart showing cross reactivity binding of anti-M2 antibodies to variant M2 peptides. (SEQ ID NOS 680-704, respectively, in order of appearance), FIG. 6B is a chart showing binding activity of M2 antibodies to truncated M2 peptides. (SEQ ID NOS 680, 705-724 & 19, respectively, in order of appearance)

FIGS. 12A-B are amino acid sequences of the variable regions of anti-M2e mAbs. Framework regions 1-4 (FR 1-4) and complementarity determining regions 1-3 (CDR 1-3) for VH and Vk are shown. FR, CDR, and gene names are defined using the nomenclature in the IMGT database (IMGT®, the International ImMunoGeneTics Information System® http://www.imgt.org). Grey boxes denote identity with the germline sequence which is shown in light blue boxes, hyphens denote gaps, and white boxes are amino acid replacement mutations from the germline.

DETAILED DESCRIPTION

Figure 1:
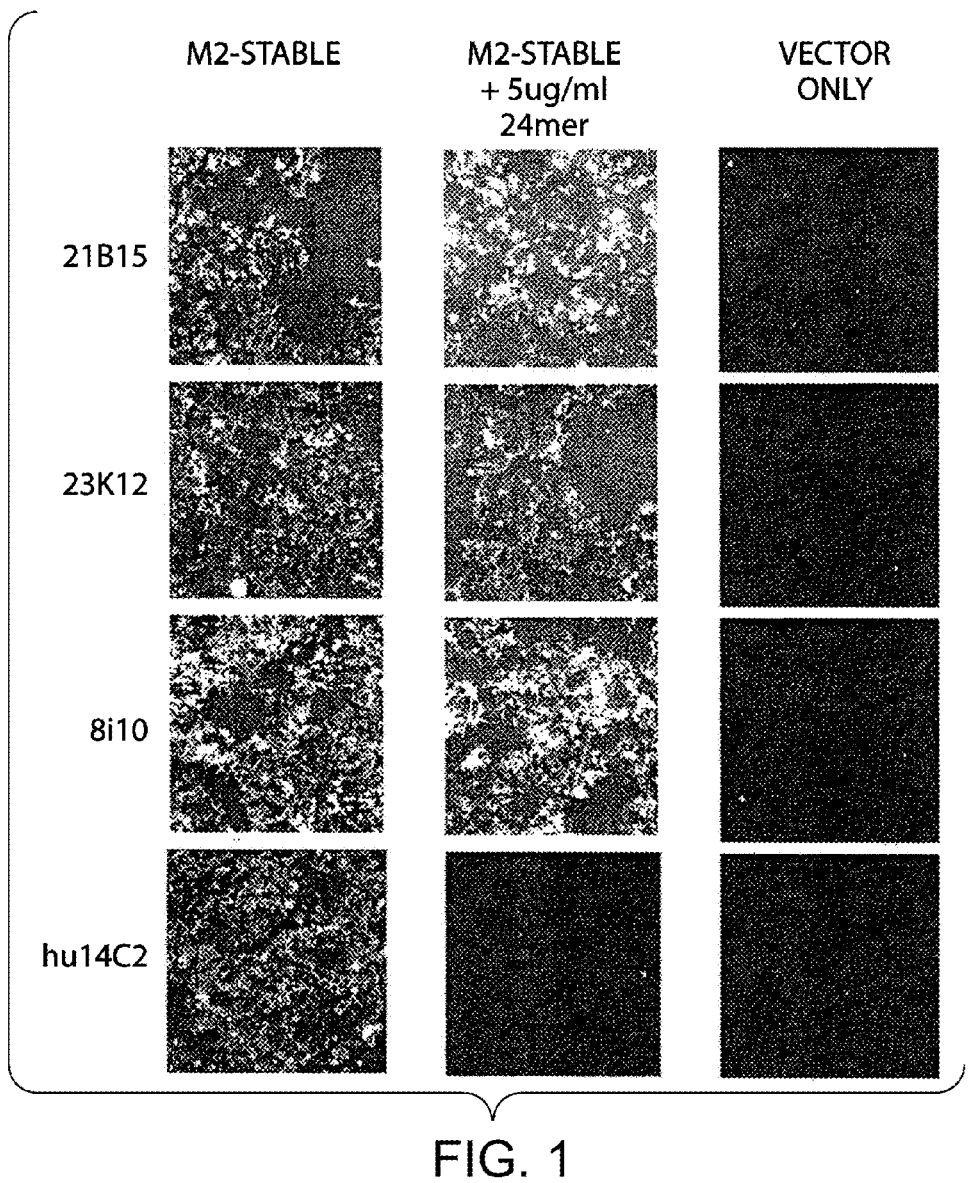
FIG. 1 shows the binding of three antibodies of the present invention and control hu14C2 antibody to 293-HEK cells transfected with an M2 expression construct or control vector, in the presence or absence of free M2 peptide.

Influenza viruses consist of three types, A, B and C. Influenza A viruses infect a wide variety of birds and mammals, including humans, horses, marine mammals, pigs, ferrets, and chickens. In animals most influenza A viruses cause mild localized infections of the respiratory and intestinal tract. However, highly pathogenic influenza A strains such as H5N1 exist that cause systemic infections in poultry in which mortality may reach 100%. Animals infected with influenza A often act as a reservoir for the influenza viruses and certain subtypes have been shown to cross the species barrier to humans.

Influenza A viruses can be classified into subtypes based on allelic variations in antigenic regions of two genes that encode surface glycoproteins, namely, hemagglutinin (HA) and neuraminidase (NA) which are required for viral attachment and cellular release. Other major viral proteins include the nucleoprotein, the nucleocapsid structural protein, membrane proteins (M1 and M2), polymerases (PA, PB and PB2) and non-structural proteins (NS1 and NS2). Currently, sixteen subtypes of HA (H1-H16) and nine NA (N1-N9) antigenic variants are known in influenza A virus. Previously, only three subtypes have been known to circulate in humans (H1N1, H1N2, and H3N2).

However, in recent years, the pathogenic H5N1 subtype of avian influenza A has been reported to cross the species barrier and infect humans as documented in Hong Kong in 1997 and 2003, leading to the death of several patients. In humans, the avian influenza virus infects cells of the respiratory tract as well as the intestinal tract, liver, spleen, kidneys and other organs. Symptoms of avian influenza infection include fever, respiratory difficulties including shortness of breath and cough, lymphopenia; diarrhea and difficulties regulating blood sugar levels. In contrast to seasonal influenza, the group most at risk is healthy adults, which make up the bulk of the population. Due to the high pathogenicity of certain avian influenza A subtypes, particularly H5N1, and their demonstrated ability to cross over to infect humans, there is a significant economic and public health risk associated with these viral strains, including a real epidemic and pandemic threat. The scale of the threat is illustrated by the 1918 influenza pandemic which killed over 50 million people.

Currently, no effective vaccines for H5N1 infection are available, so passive immunotherapy with immunoglobulins may be an alternative strategy. Use of passive immunization during the 1918 pandemic reportedly halved the death rate. In view of their therapeutic benefit in humans, there is thus a need for antibodies, preferably human antibodies, capable of neutralizing influenza infection, including H5N1.

The invention provides compositions including human antibodies raised against two influenza proteins, hemagglutinin (HA) and matrix 2 ectodomain (M2e), and shows that these compositions can be used in medicine, in particular for diagnosis, prevention and treatment of influenza infections, including H5N1.

HuM2e Antibodies

The present invention provides fully human monoclonal antibodies specifically directed against M2e. Optionally, the antibody is isolated form a B-cell from a human donor. Exemplary monoclonal antibodies include TCN-032 (8I10), 21B15, TCN-031 (23K12), 3241_G23, 3244_I10, 3243_J07, 3259_J21, 3245_O19, 3244_H04, 3136_G05, 3252_C13, 3255_J06, 3420_I23, 3139_P23, 3248_P18, 3253_P10, 3260_D19, 3362_B11, and 3242_P05.described herein. Alternatively, the monoclonal antibody is an antibody that binds to the same epitope as TCN-032 (8I10), 21B15, TCN-031 (23K12), 3241_G23, 3244_I10, 3243_J07, 3259_J21, 3245_O19, 3244_H04, 3136_G05, 3252_C13, 3255_J06, 3420_I23, 3139_P23, 3248_P18, 3253_P10, 3260_D19, 3362_B11, and 3242_P05. The antibodies respectively referred to herein are huM2e antibodies. The huM2e antibody has one or more of the following characteristics: a) binds to an epitope in the extracellular domain of the matrix 2 ectodomain (M2e) polypeptide of an influenza virus; b) binds to influenza A infected cells; or c) binds to influenza A virus.

The epitope that huM2e antibody binds to is a non-linear epitope of a M2 polypeptide. Preferably, the epitope includes the amino terminal region of the M2e polypeptide. More preferably the epitope wholly or partially includes the amino acid sequence SLLTEV (SEQ ID NO: 42). Most preferably, the epitope includes the amino acid at position 2, 5 and 6 of the M2e polypeptide when numbered in accordance with SEQ ID NO: 1. The amino acid at position 2 is a serine; at position 5 is a threonine; and at position 6 is a glutamic acid.

A huM2e antibody contains a heavy chain variable having the amino acid sequence of SEQ ID NOs: 44, 277, 276, 50, 236, 235, 116, 120, 124, 128, 132, 136, 140, 144, 148, 152, 156, 160, 164, 168, 172, or 176 and a light chain variable having the amino acid sequence of SEQ ID NOs: 46, 52, 118, 122, 126, 130, 134, 138, 142, 146, 150, 154, 158, 162, 166, 170, 174, or 178. Preferably, the three heavy chain CDRs include an amino acid sequence at least 90%, 92%, 95%, 97% 98%, 99% or more identical to the amino acid sequence of SEQ ID NOs: 72, 74, 76, 103, 105, 107, 179, 180, 181, 187, 188, 189, 197, 203, 204, 205, 21, 212, 213, 228, 229, 230, 237, 238, 252, 253, 254, 260, 261, 262, 268, 269, 270, 284, 285, 286, 293, 294, 295, and 301 (as determined by the Kabat method) or SEQ ID NOs: 109, 110, 76, 112, 113, 107, 182, 183, 181, 190, 191, 189, 197, 206, 207, 205, 214, 215, 213, 232, 230, 239, 240, 238, 255, 256, 254, 263, 264, 262, 271, 272, 270, 287, 288, 286, 296, 297, 295, and 304 (as determined by the Chothia method) and a light chain with three CDRs that include an amino acid sequence at least 90%, 92%, 95%, 97% 98%, 99% or more identical to the amino acid sequence of SEQ ID NOs: 59, 60, 61, 92, 94, 96, 184, 185, 186, 192, 193, 194, 208, 209, 210, 217, 218, 226, 223, 234, 241, 243, 258, 259, 265, 267, 273, 274, 275, 282, 291, and 300 (as determined by the Kabat method) or SEQ ID NOs: 59, 60, 61, 92, 94, 96, 184, 185, 186, 192, 193, 194, 208, 209, 210, 217, 218, 226, 223, 234, 241, 243, 258, 259, 265, 267, 273, 274, 275, 282, 291, and 300 (as determined by the Chothia method). The antibody binds M2e.

The heavy chain of a M2e antibody is derived from a germ line V (variable) gene such as, for example, the IgHV4 or the IgHV3 germline gene.

The M2e antibodies of the invention include a variable heavy chain ($V_H$) region encoded by a human IgHV4 or the IgHV3 germline gene sequence. A IgHV4 germline gene sequence are shown, e.g., in Accession numbers L10088, M29812, M95114, X56360 and M95117. IgHV3 germline gene sequence are shown, e.g., in Accession numbers X92218, X70208, Z27504, M99679 and AB019437. The M2e antibodies of the invention include a $V_H$ region that is encoded by a nucleic acid sequence that is at least 80% homologous to the IgHV4 or the IgHV3 germline gene sequence. Preferably, the nucleic acid sequence is at least 90%, 95%, 96%, 97% homologous to the IgHV4 or the IgHV3 germline gene sequence, and more preferably, at least 98%, 99% homologous to the IgHV4 or the IgHV3 germline gene sequence. The $V_H$ region of the M2e antibody is at least 80% homologous to the amino acid sequence of the $V_H$ region encoded by the IgHV4 or the IgHV3 $V_H$ germline gene sequence. Preferably, the amino acid sequence of $V_H$ region of the M2e antibody is at least 90%, 95%, 96%, 97% homologous to the amino acid sequence encoded by the IgHV4 or the IgHV3 germline gene sequence, and more preferably, at least 98%, 99% homologous to the sequence encoded by the IgHV4 or the IgHV3 germline gene sequence.

The M2e antibodies of the invention also include a variable light chain ($V_L$) region encoded by a human IgKV1 germline gene sequence. A human IgKV1 $V_L$ germline gene sequence is shown, e.g., Accession numbers X59315, X59312, X59318, J00248, and Y14865. Alternatively, the M2e antibodies include a $V_L$ region that is encoded by a nucleic acid sequence that is at least 80% homologous to the IgKV1 germline gene sequence. Preferably, the nucleic acid sequence is at least 90%, 95%, 96%, 97% homologous to the IgKV1 germline gene sequence, and more preferably, at least 98%, 99% homologous to the IgKV1 germline gene sequence. The $V_L$ region of the M2e antibody is at least 80% homologous to the amino acid sequence of the $V_L$ region encoded the IgKV1 germline gene sequence. Preferably, the amino acid sequence of $V_L$ region of the M2e antibody is at least 90%, 95%, 96%, 97% homologous to the amino acid sequence encoded by the IgKV1 germline gene sequence, and more preferably, at least 98%, 99% homologous to the sequence encoded by e the IgKV1 germline gene sequence.

In another aspect the invention provides a composition including an huM2e antibody according to the invention. In various aspects the composition further includes an anti-viral drug, a viral entry inhibitor or a viral attachment inhibitor.

The anti-viral drug is for example a neuraminidase inhibitor, a HA inhibitor, a sialic acid inhibitor or an M2 ion channel inhibitor. The M2 ion channel inhibitor is for example amantadine or rimantadine. The neuraminidase inhibitor for example zanamivir, or oseltamivir phosphate. In a further aspect the composition further includes a second anti-influenza A antibody.

In a further aspect the huM2e antibodies according to the invention are operably-linked to a therapeutic agent or a detectable label.

Additionally, the invention provides methods for stimulating an immune response, treating, preventing or alleviating a symptom of an influenza viral infection by administering an huM2e antibody to a subject Optionally, the subject is further administered with a second agent such as, but not limited to, an influenza virus antibody, an anti-viral drug such as a neuraminidase inhibitor, a HA inhibitor, a sialic acid inhibitor or an M2 ion channel inhibitor, a viral entry inhibitor or a viral attachment inhibitor. The M2 ion channel inhibitor is, for example, amantadine or rimantadine. The neuraminidase inhibitor is, for example, zanamivir or oseltamivir phosphate. The subject is suffering from or is predisposed to developing an influenza virus infection, such as, for example, an autoimmune disease or an inflammatory disorder.

In another aspect, the invention provides methods of administering the huM2e antibody of the invention to a subject prior to, and/or after exposure to an influenza virus. For example, the huM2e antibody of the invention is used to treat or prevent rejection influenza infection. The huM2e antibody is administered at a dose sufficient to promote viral clearance or eliminate influenza A infected cells.

Also included in the invention is a method for determining the presence of an influenza virus infection in a patient, by contacting a biological sample obtained from the patient with a humM2e antibody; detecting an amount of the antibody that binds to the biological sample; and comparing the amount of antibody that binds to the biological sample to a control value.

The invention further provides a diagnostic kit comprising a huM2e antibody.

Other features and advantages of the invention will be apparent from and are encompassed by the following detailed description and claims.

The present invention provides fully human monoclonal antibodies specific against the extracellular domain of the matrix 2 (M2) polypeptide. The antibodies are respectively referred to herein as huM2e antibodies.

M2 is a 96 amino acid transmembrane protein present as a homotetramer on the surface of influenza virus and virally infected cells. M2 contains a 23 amino acid ectodomain (M2e) that is highly conserved across influenza A strains. Few amino acid changes have occurred since the 1918 pandemic strain thus M2e is an attractive target for influenza therapies. In prior studies, monoclonal antibodies specific to the M2 ectodomain (M2e) were derived upon immunizations with a peptide corresponding to the linear sequence of M2e. In contrast, the present invention provides a novel process whereby full-length M2 is expressed in cell lines, which allows for the identification of human antibodies that bound this cell-expressed M2e. The huM2e antibodies have been shown to bind conformational determinants on the M2-transfected cells, as well as native M2, either on influenza infected cells, or on the virus itself. The huM2e antibodies did not bind the linear M2e peptide, but they do bind several natural M2 variants, also expressed upon cDNA transfection into cell lines. Thus, this invention has allowed for the identification and production of human monoclonal antibodies that exhibit novel specificity for a very broad range of influenza A virus strains. These antibodies may be used diagnostically to identify influenza A infection and therapeutically to treat influenza A infection.

The huM2e antibodies of the invention have one or more of the following characteristics: the huM2e antibody binds a) to an epitope in the extracellular domain of the matrix 2 (M2) polypeptide of an influenza virus; b) binds to influenza A infected cells; and/or c) binds to influenza A virus (i.e., virons). The huM2e antibodies of the invention eliminate influenza infected cells through immune effector mechanisms, such as ADCC, and promote direct viral clearance by binding to influenza virons. The huM2e antibodies of the invention bind to the amino-terminal region of the M2e polypeptide. Preferably, the huM2e antibodies of the invention bind to the amino-terminal region of the M2e polypeptide wherein the N-terminal methionine residue is absent. Exemplary M2e sequences include those sequences listed on Table 1 below

TABLE 1

| Type | Name | Subtype | M2E Sequence | SEQ ID NO |
|---|---|---|---|---|
| A | BREVIG MISSION.1.1918 | H1N1 | MSLLTEVETPTRNEWGCRCNDSSD | SEQ ID NO: 1 |
| A | FORT MONMOUTH.1.1947 | H1N1 | MSLLTEVETPTKNEWECRCNDSSD | SEQ ID NO: 2 |
| A | .SINGAPORE.02.2005 | H3N2 | MSLLTEVETPIRNEWECRCNDSSD | SEQ ID NO: 3 |
| A | WISCONSIN.10.98 | H1N1 | MSLLTEVETPIRNGWECKCNDSSD | SEQ ID NO: 4 |
| A | WISCONSIN.301.1976 | H1N1 | MSLLTEVETPIRSEWGCRCNDSSD | SEQ ID NO: 5 |
| A | PANAMA.1.66 | H2N2 | MSFLPEVETPIRNEWGCRCNDSSD | SEQ ID NO: 6 |
| A | NEW YORK.321.1999 | H3N2 | MSLLTEVETPIRNEWGCRCNDSSN | SEQ ID NO: 7 |
| A | CARACAS.1.71 | H3N2 | MSLLTEVETPIRKEWGCRCNDSSD | SEQ ID NO: 8 |
| A | TAIWAN.3.71 | H3N2 | MSFLTEVETPIRNEWGCRCNDSSD | SEQ ID NO: 9 |
| A | WUHAN.359.95 | H3N2 | MSLPTEVETPIRSEWGCRCNDSSD | SEQ ID NO: 10 |
| A | HONG KONG.1144.99 | H3N2 | MSLLPEVETPIRNEWGCRCNDSSD | SEQ ID NO: 11 |
| A | HONG KONG.1180.99 | H3N2 | MSLLPEVETPIRNGWGCRCNDSSD | SEQ ID NO: 12 |

TABLE 1-continued

| Type | Name | Subtype | M2E Sequence | SEQ ID NO |
|---|---|---|---|---|
| A | HONG KONG.1774.99 | H3N2 | MSLLTEVETPTRNGWECRCSGSSD | SEQ ID NO: 13 |
| A | NEW YORK.217.02 | H1N2 | MSLLTEVETPIRNEWEYRCNDSSD | SEQ ID NO: 14 |
| A | NEW YORK.300.2003 | H1N2 | MSLLTEVETPIRNEWEYRCSDSSD | SEQ ID NO: 15 |
| A | SWINE.SPAIN.54008.2004 | H3N2 | MSLLTEVETPTRNGWECRYSDSSD | SEQ ID NO: 16 |
| A | GUANGZHOU.333.99 | H9N2 | MSFLTEVETLTRNGWECRCSDSSD | SEQ ID NO: 17 |
| A | HONG KONG.1073.99 | H9N2 | MSLLTEVETLTRNGWECKCRDSSD | SEQ ID NO: 18 |
| A | HONG KONG.1.68 | H3N2 | MSLLTEVETPIRNEWGCRCNDSSD | SEQ ID NO: 19 |
| A | SWINE.HONG KONG.126.1982 | H3N2 | MSLLTEVETPIRSEWGCRCNDSGD | SEQ ID NO: 20 |
| A | NEW YORK.703.1995 | H3N2 | MSLLTEVETPIRNEWECRCNGSSD | SEQ ID NO: 21 |
| A | SWINE.QUEBEC.192.81 | H1N1 | MSLPTEVETPIRNEWGCRCNDSSD | SEQ ID NO: 22 |
| A | PUERTO RICO.8.34 | H1N1 | MSLLTEVETPIRNEWGCRCNGSSD | SEQ ID NO: 23 |
| A | HONG KONG.485.97 | H5N1 | MSLLTEVDTLTRNGWGCRCSDSSD | SEQ ID NO: 24 |
| A | HONG KONG.542.97 | H5N1 | MSLLTEVETLTKNGWGCRCSDSSD | SEQ ID NO: 25 |
| A | SILKY CHICKEN.SHANTOU.1826.2004 | H9N2 | MSLLTEVETPTRNGWECKCSDSSD | SEQ ID NO: 26 |
| A | CHICKEN.TAIWAN.0305.04 | H6N1 | MSLLTEVETHTRNGWECKCSDSSD | SEQ ID NO: 27 |
| A | QUAIL.ARKANSAS.16309-7.94 | H7N3NSA | MSLLTEVKTPTRNGWECKCSDSSD | SEQ ID NO: 28 |
| A | HONG KONG.486.97 | H5N1 | MSLLTEVETLTRNGWGCRCSDSSD | SEQ ID NO: 29 |
| A | CHICKEN.PENNSYLVANIA.13552-1.98 | H7N2NSB | MSLLTEVETPTRDGWECKCSDSSD | SEQ ID NO: 30 |
| A | CHICKEN.HEILONGJIANG.48.01 | H9N2 | MSLLTEVETPTRNGWGCRCSDSSD | SEQ ID NO: 31 |
| A | SWINE.KOREA.S5.2005 | H1N2 | MSLLTEVETPTRNGWECKCNDSSD | SEQ ID NO: 32 |
| A | HONG KONG.1073.99 | H9N2 | MSLLTEVETLTRNGWECKCSDSSD | SEQ ID NO: 33 |
| A | WISCONSIN.3523.88 | H1N1 | MSLLTEVETPIRNEWGCKCNDSSD | SEQ ID NO: 34 |
| A | X-31 VACCINE STRAIN | H3N2 | MSFLTEVETPIRNEWGCRCNGSSD | SEQ ID NO: 35 |
| A | CHICKEN.ROSTOCK.8.1934 | H7N1 | MSLLTEVETPTRNGWECRCNDSSD | SEQ ID NO: 36 |
| A | ENVIRONMENT.NEW YORK.16326-1.2005 | H7N2 | MSLLTEVETPIRKGWECNCSDSSD | SEQ ID NO: 37 |
| A | INDONESIA.560H.2006 | H5N1 | MSLLTEVETPTRNEWECRCSDSSD | SEQ ID NO: 38 |
| A | CHICKEN.HONG KONG.SF1.03 | H9N2 | MSLLTGVETHTRNGWGCKCSDSSD | SEQ ID NO: 39 |
| A | CHICKEN.HONGKONG.YU427.03 | H9N2 | MSLLPEVETHTRNGWGCRCSDSSD | SEQ ID NO: 40 |

In one embodiment, the huM2e antibodies of the invention bind to a M2e that wholly or partially includes the amino acid residues from position 2 to position 7 of M2e when numbered in accordance with SEQ ID NO: 1. For example, the huM2e antibodies of the invention bind wholly or partially to the amino acid sequence SLLTEVET (SEQ ID NO: 41) Most preferably, the huM2e antibodies of the invention bind wholly or partially to the amino acid sequence SLLTEV (SEQ ID NO: 42) Preferably, the huM2e antibodies of the invention bind to non-linear epitope of the M2e protein. For example, the huM2e antibodies bind to an epitope comprising position 2, 5, and 6 of the M2e polypeptide when numbered in accordance to SEQ ID NO: 1 where the amino acid at a) position 2 is a serine; b) position 5 is a threonine; and c) position 6 is a glutamic acid. Exemplary huM2e monoclonal antibodies that bind to this epitope are the TCN-032 (8I10), 21B15, TCN-031 (23K12), 3241_G23, 3244_I10, 3243_J07, 3259_I21, 3245_O19, 3244_H04, 3136_G05, 3252_C13, 3255_J06, 3420_I23, 3139_P23, 3248_P18, 3253_P10, 3260_D19, 3362_B11, and 3242_P05 antibodies described herein.

The TCN-032 (8I10) antibody includes a heavy chain variable region (SEQ ID NO: 44) encoded by the nucleic acid sequence shown below in SEQ ID NO: 43, a short heavy chain variable region (SEQ ID NO: 277) encoded by the nucleic acid sequence shown below in SEQ ID NO: 278, a long heavy chain variable region (SEQ ID NO: 276) encoded by the nucleic acid sequence shown below in SEQ ID NO: 196, and a light chain variable region (SEQ ID NO: 46) encoded by the nucleic acid sequence shown in SEQ ID NO: 45.

The amino acids encompassing the CDRs as defined by Chothia, C. et al. (1989, Nature, 342: 877-883) are underlined and those defined by Kabat E. A. et al. (1991, Sequences of Proteins of Immunological Interest, 5th edit., NIH Publication no. 91-3242 U.S. Department of Heath and Human Services.) are highlighted in bold in the sequences below.

The heavy chain CDRs of the TCN-032 (8I10) antibody have the following sequences per Kabat definition: NYYWS (SEQ ID NO: 72), FIYYGGNTKYNPSLKS (SEQ ID NO: 74) and ASCSGGYCILD (SEQ ID NO: 76). The light chain CDRs of the TCN-032 (8I10) antibody have the following sequences per Kabat definition: RASQNIYKYLN (SEQ ID NO: 59), AA SGLQS (SEQ ID NO: 61) and QQSYSPPLT (SEQ ID NO: 63).

The heavy chain CDRs of the TCN-032 (8I10) antibody have the following sequences per Chothia definition: GSSISN (SEQ ID NO: 109), FIYYGGNTK (SEQ ID NO: 110) and ASCSGGYCILD (SEQ ID NO: 76). The light chain CDRs of the TCN-032 (8I10) antibody have the following sequences per *Chothia* definition: RASQNIYKYLN (SEQ ID NO: 59), AASGLQS (SEQ ID NO: 61) and QQSYSPPLT (SEQ ID NO: 63).

```
TCN-032 (8I10) VH nucleotide sequence:
                            (SEQ ID NO: 43)
CAGGTGCAATTGCAGGAGTCGGGCCCAGGACTGGTGAAGCCTTCGGAG
ACCCTGTCCCTCACCTGCACTGTCTCTGGTTCGTCCATCAGTAATTAC
TACTGGAGCTGGATCCGGCAGTCCCCAGGGAAGGGACTGGAGTGGATT
GGGTTTATCTATTACGGTGGAAACACCAAGTACAATCCCTCCCTCAAG
AGCCGCGTCACCATATCACAAGACACTTCCAAGAGTCAGGTCTCCCTG
ACGATGAGCTCTGTGACCGCTGCGGAATCGGCCGTCTATTTCTGTGCG
AGAGCGTCTTGTAGTGGTGGTTACTGTATCCTTGACTACTGGGGCCAG
GGAACCCTGGTCACCGTCTCG TCN-032 (8I10) VH amino acid sequence:
                            (SEQ ID NO: 44)
Kabat Bold, Chothia underlined
Q V Q L Q E S G P G L V K P S E T L S L T
C T V S G S S I S N Y Y W S W I R Q S P G
K G L E W I G F I Y Y G G N T K Y N P S L
K S R V T I S Q D T S K S Q V S L T M S S
V T A A E S A V Y F C A R A S C S G G Y C
I L D Y W G Q G T L V T V S TCN-032 (8I10) VH short nucleotide sequence:
                            (SEQ ID NO: 278)
CAGGTGCAATTGCAGGAGTCGGGCCCAGGACTGGTGAAGCCTTCGGAG
ACCCTGTCCCTCACCTGCACTGTCTCTGGTTCGTCCATCAGTAATTAC
TACTGGAGCTGGATCCGGCAGTCCCCAGGGAAGGGACTGGAGTGGATT
GGGTTTATCTATTACGGTGGAAACACCAAGTACAATCCCTCCCTCAAG
AGCCGCGTCACCATATCACAAGACACTTCCAAGAGTCAGGTCTCCCTG
ACGATGAGCTCTGTGACCGCTGCGGAATCGGCCGTCTATTTCTGTGCG
AGAGCGTCTTGTAGTGGTGGTTACTGTATCCTTGACTACTGGGGCCAG
GGAACCCTGGTCACCGT TCN-032 (8I10) VH short amino acid sequence:
                            (SEQ ID NO: 277)
Kabat Bold, Chothia underlined
Q V Q L Q E S G P G L V K P S E T L S L T
C T V S G S S I S N Y Y W S W I R Q S P G
K G L E W I G F I Y Y G G N T K Y N P S L
K S R V T I S Q D T S K S Q V S L T M S S
V T A A E S A V Y F C A R A S C S G G Y C
I L D Y W G Q G T L V T TCN-032 (8I10) VH long nucleotide sequence:
                            (SEQ ID NO: 196)
CAGGTGCAATTGCAGGAGTCGGGCCCAGGACTGGTGAAGCCTTCGGAG
ACCCTGTCCCTCACCTGCACTGTCTCTGGTTCGTCCATCAGTAATTAC
TACTGGAGCTGGATCCGGCAGTCCCCAGGGAAGGGACTGGAGTGGATT
GGGTTTATCTATTACGGTGGAAACACCAAGTACAATCCCTCCCTCAAG
AGCCGCGTCACCATATCACAAGACACTTCCAAGAGTCAGGTCTCCCTG
ACGATGAGCTCTGTGACCGCTGCGGAATCGGCCGTCTATTTCTGTGCG
AGAGCGTCTTGTAGTGGTGGTTACTGTATCCTTGACTACTGGGGCCAG
GGAACCCTGGTCACCGTCTCGAGC TCN-032 (8I10) VH long amino acid sequence:
                            (SEQ ID NO: 276)
Kabat Bold, Chothia underlined
Q V Q L Q E S G P G L V K P S E T L S L T
C T V S G S S I S N Y Y W S W I R Q S P G
K G L E W I G F I Y Y G G N T K Y N P S L
K S R V T I S Q D T S K S Q V S L T M S S
V T A A E S A V Y F C A R A S C S G G Y C
I L D Y W G Q G T L V T V S S TCN-032 (8I10) VL nucleotide sequence:
                            (SEQ ID NO: 45)
GACATCCAGATGACCCAGTCTCCATCCTCCCTGTCTGCATCTGTAGGA
GACAGAGTCACCATCACTTGCCGGGCGAGTCAGAACATTTACAAGTAT
TTAAATTGGTATCAGCAGAGACCAGGGAAAGCCCCTAAGGGCCTGATC
TCTGCTGCATCCGGGTTGCAAAGTGGGGTCCCATCAAGGTTCAGTGGC
AGTGGATCTGGGACAGATTTCACTCTCACCATCACCAGTCTGCAACCT
GAAGATTTTGCAACTTACTACTGTCAACAGAGTTACAGTCCCCCTCTC
ACTTTCGGCGGAGGGACCAGGGTGGAGATCAAAC TCN-032 (8I10) VL amino acid sequence:
                            (SEQ ID NO: 46)
Kabat Bold, Chothia underlined
D I Q M T Q S P S S L S A S V G D R V T I
T C R A S Q N I Y K Y L N W Y Q Q R P G K
A P K G L I S A A S G L Q S G V P S R F S
G S G S G T F T T L T I T S L Q P E D F A
T Y Y C Q Q S Y S P P L T F G G G T R V E
I K
```

The 21B15 antibody includes a heavy chain variable region (SEQ ID NO: 44) encoded by the nucleic acid sequence shown below in SEQ ID NO: 47, a short heavy chain variable region (SEQ ID NO: 277) encoded by the nucleic acid sequence shown below in SEQ ID NO: 278, a long heavy chain variable region (SEQ ID NO: 276) encoded by the nucleic acid sequence shown below in SEQ ID NO: 196, and a light chain variable region (SEQ ID NO: 46) encoded by the nucleic acid sequence shown in SEQ ID NO: 48.

The amino acids encompassing the CDRs as defined by Chothia et al. 1989, are underlined and those defined by Kabat et al., 1991 are highlighted in bold in the sequences below.

The heavy chain CDRs of the 21B15 antibody have the following sequences per Kabat definition: NYYWS (SEQ ID NO: 72), FIYYGGNTKYNPSLKS (SEQ ID NO: 74) and ASCSGGYCILD (SEQ ID NO: 76). The light chain CDRs of the 21B15 antibody have the following sequences per Kabat definition: RASQNIYKYLN (SEQ ID NO: 59), AASGLQS (SEQ ID NO: 61) and QQSYSPPLT (SEQ ID NO: 63).

The heavy chain CDRs of the 21B15 antibody have the following sequences per Chothia definition: GSSISN (SEQ ID NO: 109), FIYYGGNTK (SEQ ID NO: 110) and ASC-SGGYCILD (SEQ ID NO: 76). The light chain CDRs of the 21B15 antibody have the following sequences per Chothia definition: RASQNIYKYLN (SEQ ID NO: 59), AASGLQS (SEQ ID NO: 61) and QQSYSPPLT (SEQ ID NO: 63).

21B15 VH nucleotide sequence:
(SEQ ID NO: 47)
CAGGTGCAATTGCAGGAGTCGGGCCCAGGACTGGTGAAGCCTTCGGAG
ACCCTGTCCCTCACCTGCACTGTCTCTGGTTCGTCCATCAGTAATTAC
TACTGGAGCTGGATCCGGCAGTCCCCAGGGAAGGGACTGGAGTGGATT
GGGTTTATCTATTACGGTGGAAACACCAAGTACAATCCCTCCCTCAAG
AGCCGCGTCACCATATCACAAGACACTTCCAAGAGTCAGGTCTCCCTG
ACGATGAGCTCTGTGACCGCTGCGGAATCGGCCGTCTATTTCTGTGCG
AGAGCGTCTTGTAGTGGTGGTTACTGTATCCTTGACTACTGGGGCCAG
GGAACCCTGGTCACCGTCTCG 21B15 VH amino acid sequence:
(SEQ ID NO: 44)
Kabat Bold, Chothia underlined
Q V Q L Q E S G P G L V K P S E T L S L T
C T V S <u>G S S I S N Y Y W S</u> W I R Q S P G
K G L W I G G <u>F I Y Y G G N T K Y N P S L</u>
K S R V T I S Q D T S K S Q V S L T M S S
V T A A E S A V Y F C A R <u>**A S C S G G Y C
I L D**</u> Y W G Q G T L V T V S 21B15 VH short nucleotide sequence:
(SEQ ID NO: 278)
CAGGTGCAATTGCAGGAGTCGGGCCCAGGACTGGTGAAGCCTTCGGAG
ACCCTGTCCCTCACCTGCACTGTCTCTGGTTCGTCCATCAGTAATTAC
TACTGGAGCTGGATCCGGCAGTCCCCAGGGAAGGGACTGGAGTGGATT
GGGTTTATCTATTACGGTGGAAACACCAAGTACAATCCCTCCCTCAAG
AGCCGCGTCACCATATCACAAGACACTTCCAAGAGTCAGGTCTCCCTG
ACGATGAGCTCTGTGACCGCTGCGGAATCGGCCGTCTATTTCTGTGCG
AGAGCGTCTTGTAGTGGTGGTTACTGTATCCTTGACTACTGGGGCCAG
GGAACCCTGGTCACCGT 21B15 VH short amino acid sequence:
(SEQ ID NO: 277)
Kabat Bold, Chothia underlined
Q V Q L Q E S G P G L V K P S E T L S L T
C T V S <u>G S S I S N Y Y W S</u> W I R Q S P G
K G L E W I G <u>F I Y Y G G N T K Y N P S L</u>
K S R V T I S Q D T S K S Q V S L T M S S
V T A A E S A V Y F C A R <u>**A S C S G G Y C
I L D**</u> Y W G Q G T L V T 21B15 VH long nucleotide sequence:
(SEQ ID NO: 196)
CAGGTGCAATTGCAGGAGTCGGGCCCAGGACTGGTGAAGCCTTCGGAG
ACCCTGTCCCTCACCTGCACTGTCTCTGGTTCGTCCATCAGTAATTAC
TACTGGAGCTGGATCCGGCAGTCCCCAGGGAAGGGACTGGAGTGGATT
GGGTTTATCTATTACGGTGGAAACACCAAGTACAATCCCTCCCTCAAG
AGCCGCGTCACCATATCACAAGACACTTCCAAGAGTCAGGTCTCCCTG
ACGATGAGCTCTGTGACCGCTGCGGAATCGGCCGTCTATTTCTGTGCG
AGAGCGTCTTGTAGTGGTGGTTACTGTATCCTTGACTACTGGGGCCAG
GGAACCCTGGTCACCGTCTCGAGC 21B15 VH long amino acid sequence:
(SEQ ID NO: 276)
Kabat Bold, Chothia underlined
Q V Q L Q E S G P G L V K P S E T L S L T
C T V S <u>G S S I S N Y Y W S</u> W I R Q S P G
K G L E W I G <u>F I Y Y G G N T K Y N P S L</u>
K S R V T I S Q D T S K S Q V S L T M S S
V T A A E S A V Y F C A R <u>**A S C S G G Y C
I L D**</u> Y W G Q G T L V T V S S 21B15 VL nucleotide sequence:
(SEQ ID NO: 48)
GACATCCAGGTGACCCAGTCTCCATCCTCCCTGTCTGCATCTGTAGGA
GACAGAGTCACCATCACTTGCCGCGCGAGTCAGAACATTTACAAGTAT
TTAAATTGGTATCAGCAGAGACAGGGAAAGCCCCTAAGGGCCTGATC
TCTGCTGCATCCGGGTTGCAAAGTGGGGTCCCATCAAGGTTCAGTGGC
AGTGGATCTGGGACAGATTTCACTCTCACCATCACCAGTCTGCAACCT
GAAGATTTTGCAACTTACTACTGTCAACAGAGTTACAGTCCCCCTCTC
ACTTTCGGCGGAGGGACCAGGGTGGATATCAAAC 21B15 VL amino acid sequence:
(SEQ ID NO: 292)
Kabat Bold, Chothia underlined
D I Q V T Q S P S S L S A S V G D R V T I -continued
T C <u>R A S Q N I Y K Y L N</u> W Y Q Q R P G K
A P K G L I S <u>A A S G L Q S</u> G V P S R F S
G S G S G T D F T L T I T S L Q P E D F A
T Y Y C <u>Q Q S Y S P P L T</u> F G G G T R V D
I K The TCN-031 (23K12) antibody includes a heavy chain variable region (SEQ ID NO: 50) encoded by the nucleic acid sequence shown below in SEQ ID NO: 49, a short heavy chain variable region (SEQ ID NO: 236) encoded by the nucleic acid sequence shown below in SEQ ID NO: 244, a long heavy chain variable region (SEQ ID NO: 195) encoded by the nucleic acid sequence shown below in SEQ ID NO: 235, and a light chain variable region (SEQ ID NO: 52) encoded by the nucleic acid sequence shown in SEQ ID NO: 51.

The amino acids encompassing the CDRs as defined by Chothia et al., 1989 are underlined and those defined by Kabat et al., 1991 are highlighted in bold in the sequences below.

The heavy chain CDRs of the TCN-031 (23K12) antibody have the following sequences per Kabat definition: SNYMS (SEQ ID NO: 103), VIYSGGSTYYADSVK (SEQ ID NO: 105) and CLSRMRGYGLDV (SEQ ID NO: 107). The light chain CDRs of the TCN-031 (23K12) antibody have the following sequences per Kabat definition: RTSQSISSYLN (SEQ ID NO: 92), AASSLQSGVPSRF (SEQ ID NO: 94) and QQSYSMPA (SEQ ID NO: 96).

The heavy chain CDRs of the TCN-031 (23K12) antibody have the following sequences per Chothia definition: GFTVSSN (SEQ ID NO: 112), VIYSGGSTY (SEQ ID NO: 113) and CLSRMRGYGLDV (SEQ ID NO: 107). The light chain CDRs of the TCN-031 (23K12) antibody have the following sequences per Chothia definition: RTSQSISSYLN (SEQ ID NO: 92), AASSLQSGVPSRF (SEQ ID NO: 94) and QQSYSMPA (SEQ ID NO: 96).

TCN-031 (23K12) VH nucleotide sequence:
(SEQ ID NO: 49)
GAGGTGCAGCTGGTGGAGTCTGGGGGAGGCTTGGTCCAGCCTGGGGGG
TCCCTGAGAATCTCCTGTGCAGCCTCTGGATTCACCGTCAGTAGCAAC
TACATGAGTTGGGTCCGCCAGGCTCCAGGGAAGGGGCTGGAGTGGGTC
TCAGTTATTTATAGTGGTGGTAGCACATACTACGCAGACTCCGTGAAG
GGCAGATTCTCCTTCTCCAGAGACAACTCCAAGAACACAGTGTTTCTT
CAAATGAACAGCCTGAGAGCCGAGGACACGGCTGTGTATTACTGTGCG
AGATGTCTGAGCAGGATGCGGGGTTACGGTTTAGACGTCTGGGGCCAA
GGGACCACGGTCACCGTCTCG TCN-031 (23K12) VH amino acid sequence:
(SEQ ID NO: 50)
Kabat Bold, Chothia underlined
E V Q L V E S G G G L V Q P G G S L R I S
C A A S <u>G F T V S S N Y M S</u> W V R Q A P G
K G L E W V S <u>V I Y S G G S T Y Y A D S V</u>
K G R F S F S R D N S K N T V F L Q M N S
L R A E D T A V Y Y C A R <u>**C L S R M R G Y
G L D V**</u> W G Q G T T V T V S TCN-031 (23K12) VH short nucleotide sequence:
(SEQ ID NO: 244)
GAGGTGCAGCTGGTGGAGTCTGGGGGAGGCTTGGTCCAGCCTGGGGGG
TCCCTGAGAATCTCCTGTGCAGCCTCTGGATTCACCGTCAGTAGCAAC
TACATGAGTTGGGTCCGCCAGGCTCCAGGGAAGGGGCTGGAGTGGGTC
TCAGTTATTTATAGTGGTGGTAGCACATACTACGCAGACTCCGTGAAG
GGCAGATTCTCCTTCTCCAGAGACAACTCCAAGAACACAGTGTTTCTT
CAAATGAACAGCCTGAGAGCCGAGGACACGGCTGTGTATTACTGTGCG
AGATGTCTGAGCAGGATGCGGGGTTACGGTTTAGACGTCTGGGGCCAA
GGGACCACGGTCACCGT TCN-031 (23K12) VH short amino acid sequence:
(SEQ ID NO: 236)
Kabat Bold, Chothia underlined
E V Q L V E S G G G L V Q P G G S L R I S
C A A S <u>G F T V S S N Y M S</u> W V R Q A P G

```
                                              -continued
K G L E W V S V I Y S G G S T Y Y A D S V
K G R F S F S R D N S K N T V F L Q M N S
L R A E D T A V Y Y C A R C L S R M R G Y
G L D V W G Q G T T V T V S TCN-031 (23K12) VH long nucleotide sequence:
                                            (SEQ ID NO: 195)
GAGGTGCAGCTGGTGGAGTCTGGGGGAGGCTTGGTCCAGCCTGGGGGG
TCCCTGAGAATCTCCTGTGCAGCCTCTGGATTCACCGTCAGTAGCAAC
TACATGAGTTGGGTCCGCCAGGCTCCAGGGAAGGGGCTGGAGTGGGTC
TCAGTTATTTATAGTGGTGGTAGCACATACTACGCAGACTCCGTGAAG
GGCAGATTCTCCTTCTCCAGAGACAACTCCAAGAACACAGTGTTTCTT
CAAATGAACAGCCTGAGAGCCGAGGACACGGCTGTGTATTACTGTGCG
AGATGTCTGAGCAGGATGCGGGGTTACGGTTTAGACGTCTGGGGCCAA
GGGACCACGGTCACCGTCTCGAGC TCN-031 (23K12) VH long amino acid sequence:
                                            (SEQ ID NO: 235)
Kabat Bold, Chothia underlined
E V Q L V E S G G G L V Q P G G S L R I S
C A A S G F T V S S N Y M S W V R Q A P G
K G L E W V S V I Y S G G S T Y Y A D S V
K G R F S F S R D N S K N T V F L Q M N S
L R A E D T A V Y Y C A R C L S R M R G Y
G L D V W G Q G T T V T V S S TCN-031 (23K12) VL nucleotide sequence:
                                            (SEQ ID NO: 51)
GACATCCAGATGACCCAGTCTCCATCCTCCCTGTCTGCATCTGTAGGA
GACAGAGTCACCATCACTTGCCGGACAAGTCAGAGCATTAGCAGCTAT
TTAAATTGGTATCAGCAGAAACCAGGGAAAGCCCCTAAACTCCTGATC
TATGCTGCATCCAGTTTGCAAAGTGGGGTCCCATCAAGGTTCAGTGGC
AGTGGATCTGGGACAGATTTCACTCTCACCATCAGCGGTCTGCAACCT
GAAGATTTTGCAACCTACTACTGTCAACAGAGTTACAGTATGCCTGCC
TTTGGCCAGGGGACCAAGCTGGAGATCAAA TCN-031 (23K12) VL amino acid sequence:
                                            (SEQ ID NO: 52)
Kabat Bold, Chothia underlined
D I Q M T Q S P S S L S A S V G D R V T I
T C R T S Q S I S S Y L N W Y Q Q K P G K
A P K L L I Y A A S S L Q S G V P S R F S
G S G S G T D F T L T I S G L Q P E D F A
T Y Y C Q Q S Y S M P A F G Q G T K L E I
K
```

The 3241_G23 antibody (also referred to herein as G23) includes a heavy chain variable region (SEQ ID NO: 116) encoded by the nucleic acid sequence shown below in SEQ ID NO: 115, and a light chain variable region (SEQ ID NO: 118) encoded by the nucleic acid sequence shown in SEQ ID NO: 117.

The amino acids encompassing the CDRs as defined by Chothia et al., 1989 are underlined and those defined by Kabat et al., 1991 are highlighted in bold in the sequences below.

The heavy chain CDRs of the G23 antibody have the following sequences per Kabat definition: GGGYSWN (SEQ ID NO: 179), FMFHSGSPRYNPTLKS (SEQ ID NO 180) and VGQMDKYYAMDV (SEQ ID NO: 181). The light chain CDRs of the G23 antibody have the following sequences per Kabat definition: RASQSIGAYVN (SEQ ID NO: 184), GASNLQS (SEQ ID NO: 185) and QQTYSTPIT (SEQ ID NO: 186).

The heavy chain CDRs of the G23 antibody have the following sequences per Chothia definition: GGPVSGGG (SEQ ID NO: 182), FMFHSGSPR (SEQ ID NO: 183) and VGQMDKYYAMDV (SEQ ID NO: 181). The light chain CDRs of the G23 antibody have the following sequences per Chothia definition: RASQSIGAYVN (SEQ ID NO: 184), GASNLQS (SEQ ID NO: 185) and QQTYSTPIT (SEQ ID NO: 186).

```
3241_G23 VH nucleotide sequence
                                            (SEQ ID NO: 115)
CAGGTGCAGCTGCAGCAGTCGGGCCCAGGACTGGTGAAGCCTTCACAGAC
CCTGTCCCTCACTTGCACTGTCTCTGGTGGCCCCGTCAGCGGTGGTGGTT
ACTCCTGGAACTGGATCCGCCAACGCCCAGGACAGGGCCTGGAGTGGGTT
GGGTTCATGTTTCACAGTGGGAGTCCCCGCTACAATCCGACCCTCAAGAG
TCGAATTACCATCTCAGTCGACACGTCTAAGAACCTGGTCTCCCTGAAGC
TGAGCTCTGTGACGGCCGCGGACACGGCCGTGTATTTTTGTGCGCGAGTG
GGGCAGATGGACAAGTACTATGCCATGGACGTCTGGGGCCAAGGGACCAC
GGTCACCGTCTCGAGC 3241_G23 VH amino acid sequence
                                            (SEQ ID NO: 116)
Kabat Bold, Chothia underlined
QVQLQQSGPGLVKPSQTLSLTCTVSGGPVSGGGYSWNWIRQRPGQGLEWV
GFMFHSGSPRYNPTLKSRITISVDTSKNLVSLKLSSVTAADTAVYFCARV
GQMDKYYAMDVWGQGTTVTVSS 3241_G23 VL nucleotide sequence
                                            (SEQ ID NO: 117)
GACATCCAGATGACCCAGTCTCCATCCTCCCTGTCTTCCTCTGTCGGAGA
CAGAGTCACCATCACTTGCCGGGCAAGTCAGAGCATTGGCGCCTATGTAA
ATTGGTATCAACAGAAAGCAGGGAAAGCCCCCCAGGTCCTGATCTTTGGT
GCTTCCAATTTACAAAGCGGGGTCCCATCAAGGTTCAGTGGCAGTGGATC
TGGGACAGATTTCACTCTCACCATCAGCAGTCTGCAACCTGAAGACTTTG
CAACTTACTTCTGTCAACAGACTTACAGTACCCCGATCACCTTCGGCCAA
GGGACACGACTGGAGATTAAACG 3241_G23 VL amino acid sequence
                                            (SEQ ID NO: 118)
Kabat Bold, Chothia underlined
DIQMTQSPSSLSSSVGDRVTITCRASQSIGAYVNWYQQKAGKAPQVLIFG
ASNLQSGVPSRFSGSGSGTDFTLTISSLQPEDFATYFCQQTYSTPITFGQ
GTRLEIK
```

The 3244_I10 antibody (also referred to herein as I10) includes a heavy chain variable region (SEQ ID NO: 120) encoded by the nucleic acid sequence shown below in SEQ ID NO: 119, and a light chain variable region (SEQ ID NO: 122) encoded by the nucleic acid sequence shown in SEQ ID NO: 121.

The amino acids encompassing the CDRs as defined by Chothia et al., 1989 are underlined and those defined by Kabat et al., 1991 are highlighted in bold in the sequences below.

The heavy chain CDRs of the I10 antibody have the following sequences per Kabat definition: SDYWS (SEQ ID NO: 187), FFYNGGSTKYNPSLKS (SEQ ID NO: 188) and HDAKFSGSYYVAS (SEQ ID NO: 189). The light chain CDRs of the I10 antibody have the following sequences per Kabat definition: RASQSISTYLN (SEQ ID NO: 192), GATNLQS (SEQ ID NO: 193) and QQSYNTPLI (SEQ ID NO: 194).

The heavy chain CDRs of the I10 antibody have the following sequences per Chothia definition: GGSITS (SEQ ID NO: 190), FFYNGGSTK (SEQ ID NO: 191) and HDAKFSGSYYVAS (SEQ ID NO: 189).

```
3244_I10 VH nucleotide sequence
                                            (SEQ ID NO: 119)
CAGGTCCAGCTGCAGGAGTCGGGCCCAGGACTGCTGAAGCCTTCGGACAC
CCTGGCCCTCACTTGCACTGTCTCTGGTGGCTCCATCACCAGTGACTACT
GGAGCTGGATCCGGCAACCCCCAGGGAGGGGACTGGACTGGATCGGATTC
TTCTATAACGGCGGAAGCACCAAGTACAATCCCTCCCTCAAGAGTCGAGT
CACCATTTCAGCGGACACGTCCAAGAACCAGTTGTCCCTGAAATTGACCT
CTGTGACCGCCGCAGACACGGGCGTGTATTATTGTGCGAGACATGATGCC
AAATTTAGTGGGAGCTACTACGTTGCCTCCTGGGGCCAGGGAACCCGAGT
CACCGTCTCGAGC 3244_I10 VH amino acid sequence
                                            (SEQ ID NO: 120)
QVQLQESGPGLLKPSDTLALTCTVSGGSITSDYWSWIRQPPGRGLDWIGF
FYNGGSTKYNPSLKSRVTISADTSKNQLSLKLTSVTAADTGVYYCARHDA
KFSGSYYVASWGQGTRVTVSS
```

3244_I10 VL nucleotide sequence
(SEQ ID NO: 121)
```
GACATCCAGATGACCCAGTCTCCATCCTCCCTGTCTGCATCTGTAGGAGA
CAGAGTCACCATCTCTTGCCGGGCAAGTCAGAGCATTAGCACCTATTTAA
ATTGGTATCAGCAGCAACCTGGGAAAGCCCCTAAGGTCCTCATTTTTGGT
GCAACCAACTTGCAAAGTGGGGTCCCATCTCGCTTCAGTGGCAGTGGATC
TGGGACAGATTTCACTCTCACCATCAGCAGTCTGCAACCTGAAGATTTTG
CAACTTACTACTGTCAACAGAGTTACAATACCCCCTCATTTTTGGCCAG
GGGACCAAGCTGGAGATCAAACG
```

3244_I10 VL amino acid sequence
(SEQ ID NO: 122)
DIQMTQSPSSLSASVGDRVTISCRASQSISTYLNWYQQQPGKAPKVLIF<u>G</u>
<u>ATNLQS</u>GVPSRFSGSGSGTDFTLTISSLQPEDFATYYCQQSYNTPLIFGQ
GTKLEIK The 3243_J07 antibody (also referred to herein as J07) includes a heavy chain variable region (SEQ ID NO: 124) encoded by the nucleic acid sequence shown below in SEQ ID NO: 123, and a light chain variable region (SEQ ID NO: 126) encoded by the nucleic acid sequence shown in SEQ ID NO: 125.

The amino acids encompassing the CDRs as defined by Chothia et al., 1989 are underlined and those defined by Kabat et al., 1991 are highlighted in bold in the sequences below.

The heavy chain CDRs of the J07 antibody have the following sequences per Kabat definition: SDYWS (SEQ ID NO: 187), FFYNGGSTKYNPSLKS (SEQ ID NO: 188) and HDVKFSGSYYVAS (SEQ ID NO: 197). The light chain CDRs of the J07 antibody have the following sequences per Kabat definition: RASQSISTYLN (SEQ ID NO: 192), GATNLQS (SEQ ID NO: 193) and QQSYNTPLI (SEQ ID NO: 194).

The heavy chain CDRs of the J07 antibody have the following sequences per Chothia definition: GGSITS (SEQ ID NO: 190), FFYNGGSTK (SEQ ID NO: 191) and HDVKFSGSYYVAS (SEQ ID NO: 197). The light chain CDRs of the J07 antibody have the following sequences per Chothia definition: RASQSISTYLN (SEQ ID NO: 192), GATNLQS (SEQ ID NO: 193) and QQSYNTPLI (SEQ ID NO: 194).

3243_J07 VH nucleotide sequence
(SEQ ID NO: 123)
```
CAGGTCCAGCTGCAGGAGTCGGGCCCAGGACTGCTGAAGCCTTCGGACAC
CCTGGCCCTCACTTGCACTGTCTCTGGTGGCTCCATCACCAGTGACTACT
GGAGCTGGATCCGGCAACCCCCAGGGAGGGGACTGGACTGGATCGGATTC
TTCTATAACGGCGGGAGCACCAAGTACAATCCTCCCTCAAGAGTCGAGT
CACCATATCAGCGGACACGTCCAAGAACCAGTTGTCCCTGAAATTGACCT
CTGTGACCGCCGCAGACACGGGCGTGTATTATTGTGCGAGACATGATGTC
AAATTTAGTGGGAGCTACTACGTTGCCTCCTGGGGCCAGGGAACCCGAGT
CACCGTCTCGAGC
```

3243_J07 VH amino acid sequence
(SEQ ID NO: 124)
QVQLQESGPGLLKPSDTLALTCTVS<u>GGSITSDYWS</u>WIRQPPGRGLDWIG<u>F</u>
<u>FYNGGSTKYNPSLKS</u>RVTISADTSKNQLSLKLTSVTAADTGVYYCAR<u>HDV</u>
<u>KFSGSYYVAS</u>WGQGTRVTVSS

3243_J07 VL nucleotide sequence
(SEQ ID NO: 125)
```
GACATCCAGATGACCCAGTCTCCATCCTCCCTGTCTGCATCTGTAGGAGA
CAGAGTCACCATCTCTTGCCGGGCAAGTCAGAGCATTAGCACCTATTTAA
ATTGGTATCAGCAGCAACCTGGGAAAGCCCCTAAGGTCCTGATCTCTGGT
GCAACCAACTTGCAAAGTGGGGTCCCATCTCGCTTCAGTGGCAGTGGATC
TGGGACAGATTTCACTCTCACCATCAGCAGTCTGCAACCTGAAGATTTTG
CAACTTACTACTGTCAACAGAGTTACAATACCCCCTCATTTTTGGCCAG
GGGACCAAGCTGGAGATCAAACG
```

3243_J07 VL amino acid sequence
(SEQ ID NO: 126)
DIQMTQSPSSLSASVGDRVTISCRASQSISTYLNWYQQQPGKAPKVLIS<u>G</u>
<u>ATNLQS</u>GVPSRFSGSGSGTDFTLTISSLQPEDFATYYCQQSYNTPLIFGQ
GTKLEIK The 3259_J21 antibody (also referred to herein as J21) includes a heavy chain variable region (SEQ ID NO: 128) encoded by the nucleic acid sequence shown below in SEQ ID NO: 127, and a light chain variable region (SEQ ID NO: 130) encoded by the nucleic acid sequence shown in SEQ ID NO: 129.

The amino acids encompassing the CDRs as defined by Chothia et al., 1989 are underlined and those defined by Kabat et al., 1991 are highlighted in bold in the sequences below.

The heavy chain CDRs of the J21 antibody have the following sequences per Kabat definition: SYNWI (SEQ ID NO: 203), HIYDYGRTFYNSSLQS (SEQ ID NO: 204) and PLGILHYYAMDL (SEQ ID NO: 205). The light chain CDRs of the J21 antibody have the following sequences per Kabat definition: RASQSIDKFLN (SEQ ID NO: 208), GASNLHS (SEQ ID NO: 209) and QQSFSVPA (SEQ ID NO: 210).

The heavy chain CDRs of the J21 antibody have the following sequences per Chothia definition: GGSISS (SEQ ID NO: 206), HIYDYGRTF (SEQ ID NO: 207) and PLGILHYYAMDL (SEQ ID NO: 205). The light chain CDRs of the J21 antibody have the following sequences per Chothia definition: RASQSIDKFLN (SEQ ID NO: 208), GASNLHS (SEQ ID NO: 209) and QQSFSVPA (SEQ ID NO: 210).

3259_J21 VH nucleotide sequence
(SEQ ID NO: 127)
```
CAGGTGCAGCTGCAGGAGTCGGGCCCACGAGTGGTGAGGCCTTCGGAGAC
CCTGTCCCTCACCTGCACTGTCTCGGGGGGCTCCATCAGTTCTTACAACT
GGATTTGGATCCGGCAGCCCCCTGGGAAGGGACTGGAGTGGATTGGGCAC
ATATATGACTATGGGAGGACCTTCTACAACTCCTCCCTCCAGAGTCGACC
TACCATATCTGTAGACGCGTCCAAGAATCAGCTCTCCCTGCGATTGACCT
CTGTGACCGCCTCAGACACGGCCGTCTATTACTGTGCGAGACCTCTCGGT
ATACTCCACTACTACGCGATGGACCTCTGGGGCCAAGGGACCACGGTCAC
CGTCTCGAGC
```

3259_J21 VH amino acid sequence
(SEQ ID NO: 128)
QVQLQESGPRVVRPSETLSLTCTVS<u>GGSISSYNWI</u>WIRQPPGKGLEWIG<u>H</u>
<u>IYDYGRTFYNSSLQS</u>RPTISVDASKNQLSLRLTSVTASDTAVYYCAR<u>PLG</u>
<u>ILHYYAMDL</u>WGQGTTVTVSS

3259_J21 VL nucleotide sequence
(SEQ ID NO: 129)
```
GACATCCAGATGACCCAGTCTCCATTATCCGTGTCTGTATCTGTCGGGGA
CAGGGTCACCATCGCTTGCCGGGCAAGTCAGAGTATTGACAAGTTTTTAA
ATTGGTATCAGCAGAAACCAGGGAAAGCCCCTAAACTCCTGATCTATGGT
GCCTCCAATTTGCACAGTGGGGCCCCATCAAGGTTCAGTGCCAGTGGGTC
TGGGACAGACTTCACTCTAACAATCACCAATATACAGACTGAAGATTTCG
CAACTTACCTCTGTCAACAGAGTTTCAGTGTCCCCGCTTTCGGCGGAGGG
ACCAAGGTTGAGATCAAACG
```

3259_J21 VL amino acid sequence
(SEQ ID NO: 130)
DIQMTQSPLSVSVSVGDRVTIACRASQSIDKFLNWYQQKPGKAPKLLIY<u>G</u>
<u>ASNLHS</u>GAPSRFSASGSGTDFTLTITNIQTEDFATYLCQQSFSVPAFGGG
TKVEIK The 3245_O19 antibody (also referred to herein as O19) includes a heavy chain variable region (SEQ ID NO: 132) encoded by the nucleic acid sequence shown below in SEQ ID NO: 131, and a light chain variable region (SEQ ID NO: 134) encoded by the nucleic acid sequence shown in SEQ ID NO: 133.

The amino acids encompassing the CDRs as defined by Chothia et al., 1989 are underlined and those defined by Kabat et al., 1991 are highlighted in bold in the sequences below.

The heavy chain CDRs of the O19 antibody have the following sequences per Kabat definition: STYMN (SEQ ID NO: 211), VFYSETRTYYADSVKG (SEQ ID NO: 212) and VQRLSYGMDV (SEQ ID NO: 213). The light chain CDRs of the O19 antibody have the following sequences per Kabat definition: RASQSISTYLN (SEQ ID NO: 192), GASTLQS (SEQ ID NO: 217) and QQTYSIPL (SEQ ID NO: 218).

The heavy chain CDRs of the O19 antibody have the following sequences per Chothia definition: GLSVSS (SEQ ID NO: 214), VFYSETRTY (SEQ ID NO: 215) and VQRLSYGMDV (SEQ ID NO: 213). The light chain CDRs of the O19 antibody have the following sequences per Chothia definition: RASQSISTYLN (SEQ ID NO: 192), GASTLQS (SEQ ID NO: 217) and QQTYSIPL (SEQ ID NO: 218).

3245_O19 VH nucleotide sequence
(SEQ ID NO: 131)
GAGGTGCAACTGGTGGAGTCTGGAGGGGGCTTGGTCCAGCCTGGGGGGTC
CCTGAGACTCTCCTGTACGGCCTCTGGGTTAAGTGTCAGTTCCACCTACA
TGAACTGGGTCCGCCAGGCTCCAGGGAAGGGGCTGGAATGGGTCTCAGTT
TTTTATAGTGAGACCAGGACGTACTACGCAGACTCCGTGAAGGGCCGATT
CACCGTCTCCAGACACAATTCCAACAACACGCTCTATCTTCAGATGAACA
GCCTGAGAGTTGAAGACACGGCCGTGTATTATTGTGCGAGAGTCCAGAGA
TTGTCGTACGGTATGGACGTCTGGGGCCAAGGGACCACGGTCACCGTCTC
GAGC 3245_O19 VH amino acid sequence
(SEQ ID NO: 132)
EVQLVESGGGLVQPGGSLRLSCTAS<u>GLSV</u>SSTYMNWVRQAPGKGLEWVS<u>V
FYSETRTY</u>YADSVKGRFTVSRHNSNNTLYLQMNSLRVEDTAVYYCARVQR
LSYGMDVWGQGTTVTVSS 3245_O19 VL nucleotide sequence
(SEQ ID NO: 133)
GACATCCAGATGACCCAGTCTCCATCCTCCCTGTCTGCATCTGTTGGAGA
CAGAGTCACCATCACTTGCCGGGCAAGTCAGAGCATTAGCACCTATTTAA
ATTGGTATCAGAAGAGACCAGGGAAAGCCCCTAAACTCCTGGTCTATGGT
GCATCCACTTTGCAGAGTGGGGTCCCATCAAGGTTCAGTGGCAGTGGATC
TGGGACAGATTTCACTCTCACCATCGCCAGTCTGCAACCTGAAGATTCTG
CAACTTACTACTGTCAACAGACTTACAGTATCCCCCTCTTCGGCCAGGGG
ACACGGCTGGAGATTAAACG 3245_O19 VL amino acid sequence
(SEQ ID NO: 134)
DIQMTQSPSSLSASVGDRVTITCRASQSISTYLNWYQKRPGKAPKLLVYG
ASTLQSGVPSRFSGSGSGTDFTLTIASLQPEDSATYYCQQTYSIPLFGQG
TRLEIK The 3244_H04 antibody (also referred to herein as H04) includes a heavy chain variable region (SEQ ID NO: 136) encoded by the nucleic acid sequence shown below in SEQ ID NO: 135, and a light chain variable region (SEQ ID NO: 138) encoded by the nucleic acid sequence shown in SEQ ID NO: 137.

The amino acids encompassing the CDRs as defined by Chothia et al., 1989 are underlined and those defined by Kabat et al., 1991 are highlighted in bold in the sequences below.

The heavy chain CDRs of the H04 antibody have the following sequences per Kabat definition: STYMN (SEQ ID NO: 211), VFYSETRTYYADSVKG (SEQ ID NO: 212) and VQRLSYGMDV (SEQ ID NO: 213). The light chain CDRs of the H04 antibody have the following sequences per Kabat definition: RASQSISTYLN (SEQ ID NO: 192), GASSLQS (SEQ ID NO: 226) and QQTYSIPL (SEQ ID NO: 218).

The heavy chain CDRs of the H04 antibody have the following sequences per Chothia definition: GLSVSS (SEQ ID NO: 214), VFYSETRTY (SEQ ID NO: 215) and VQRLSYGMDV (SEQ ID NO: 213). The light chain CDRs of the H04 antibody have the following sequences per Chothia definition: RASQSISTYLN (SEQ ID NO: 192), GASSLQS (SEQ ID NO: 226) and QQTYSIPL (SEQ ID NO: 218).

3244_H04 VH nucleotide sequence
(SEQ ID NO: 135)
GAGGTGCAGCTGGTGGAATCTGGAGGGGGCTTGGTCCAGCCTGGGGGGTC
CCTGAGACTCTCCTGTACAGCCTCTGGGTTAAGCGTCAGTTCCACCTACA
TGAACTGGGTCCGCCAGGCTCCAGGGAAGGGGCTGGAATGGGTCTCAGTT
TTTTATAGTGAAACCAGGACGTATTACGCAGACTCCGTGAAGGGCCGATT
CACCGTCTCCAGACACAATTCCAACAACACGCTGTATCTTCAAATGAACA
GCCTGAGAGCTGAAGACACGGCCGTGTATTATTGTGCGAGAGTCCAGAGA
CTGTCATACGGTATGGACGTCTGGGGCCAAGGGACCACGGTCACCGTCTC
GAGC 3244_H04 VH amino acid sequence
(SEQ ID NO: 136)
EVQLVESGGGLVQPGGSLRLSCTAS<u>GLSV</u>SSTYMNWVRQAPGKGLEWVS<u>V
FYSETRTY</u>YADSVKGRFTVSRHNSNNTLYLQMNSLRAEDTAVYYCARVQR
LSYGMDVWGQGTTVTVSS 3244_H04 VL nucleotide sequence
(SEQ ID NO: 137)
GACATCCAGATGACCCAGTCTCCATCGTCCCTGTCTGCATCTGTAGGAGA
CAGAGTCACCATCACTTGCCGGGCAAGTCAGAGCATTAGCACCTATTTAA
ATTGGTATCAGAAGAGACCAGGGAAAGCCCCTAAACTCCTGGTCTATGGT
GCATCCAGTTTGCAGAGTGGGGTCCCATCAAGGTTCAGTGGCAGTGGATC
TGGGACAGATTTCACTCTCACCATCGCCAGTCTGCAACCTGAAGATTCTG
CAGTTTATTACTGTCAACAGACTTACAGTATCCCCCTCTTCGGCCAGGGG
ACACGACTGGAGATTAAACG 3244_H04 VL amino acid sequence
(SEQ ID NO: 138)
DIQMTQSPSSLSASVGDRVTITCRASQSISTYLNWYQKRPGKAPKLLVYG
ASSLQSGVPSRFSGSGSGTDFTLTIASLQPEDSAVYYCQQTYSIPLFGQG
TRLEIK The 3136_O05 antibody (also referred to herein as G05) includes a heavy chain variable region (SEQ ID NO: 140) encoded by the nucleic acid sequence shown below in SEQ ID NO: 139, and a light chain variable region (SEQ ID NO: 142) encoded by the nucleic acid sequence shown in SEQ ID NO: 141.

The amino acids encompassing the CDRs as defined by Chothia et al., 1989 are underlined and those defined by Kabat et al., 1991 are highlighted in bold in the sequences below.

The heavy chain CDRs of the G05 antibody have the following sequences per Kabat definition: SDFWS (SEQ ID NO: 228), YVYNRGSTKYSPSLKS (SEQ ID NO: 229) and NGRSSTSWGIDV (SEQ ID NO: 230). The light chain CDRs of the 3136_G05 antibody have the following sequences per Kabat definition: RASQSISTYLH (SEQ ID NO: 233), AASSLQS (SEQ ID NO: 234) and QQSYSPPLT (SEQ ID NO: 63).

The heavy chain CDRs of the 3136_G05 antibody have the following sequences per Chothia definition: GGSISS (SEQ ID NO: 206), YVYNRGSTK (SEQ ID NO: 232) and NGRSSTSWGIDV (SEQ ID NO: 230). The light chain CDRs of the 3136_G05 antibody have the following sequences per Chothia definition: RASQSISTYLH (SEQ ID NO: 233), AASSLQS (SEQ ID NO: 234) and QQSYSPPLT (SEQ ID NO: 63).

3136_G05 VH nucleotide sequence
(SEQ ID NO: 139)
CAGGTGCAGCTGCAGGAGTCGGGCCCAGGACTGGTGAAGCCCTCGGAGAC
CCTGTCCCTCACCTGCAGTGTCTCTGGTGGCTCCATTAGTAGTGATTTCT
GGAGTTGGATCCGACAGCCCCCAGGGAAGGGACTGGAGTGGATTGGGTAT
GTCTATAACAGAGGGAGCACTAAGTACAGTCCCTCCCTCAAGAGTCGAGT
CACCATATCAGCAGACATGTCCAAGAACCAGTTTTCCCTGAATATGAGTT
CTGTGACCGCTGCGGACACGGCCGTGTATTACTGTGCGAAAAATGGTCGA
AGTAGCACCAGTTGGGGCATCGACGTCTGGGGCAAAGGGACCACGGTCAC
CGTCTCGAGC 3136_G05 VH amino acid sequence
(SEQ ID NO: 140)
QVQLQESGPGLVKPSETLSLTCSVS<u>GGSISS</u>SDFWSWIRQPPGKGLEWIG<u>Y
VYNRGSTK</u>YSPSLKSRVTISADMSKNQFSLNMSSVTAADTAVYYCAKNGR
SSTSWGIDVWGKGTTVTVSS 3136_G05 VL nucleotide sequence
(SEQ ID NO: 141)
GACATCCAGATGACCCAGTCTCCATCCTCCCTGTCTGCATCTGTGGGAGA
CAGACTCACCATCACTTGCCGGGCAAGTCAGAGCATTAGCACTATTTAC
ATTGGTATCAGCAGAAACCAGGGAAAGCCCCTAAACTCCTGATCTATGCT
GCATCCAGTTTGCAAAGTGGGGTCCCATCAAGGTTCAGTGGCAGTAGATC
AGGAACAGATTTCACTCTCACCATCAGCAGTCTGCAACCTGATGACTTTG
CAACTTACTACTGTCAACAGAGTTACAGTCCCCCCCTCACTTTCGGCCCT
GGGACCAAAGTGGATATGAAACG 3136_G05 VL amino acid sequence
(SEQ ID NO: 142)
DIQMTQSPSSLSASVGDRLTITCRASQSISTYLHWYQQKPGKAPKLLIYA
ASSLQSGVPSRFSGSRSGTDFTLTISSLQPDDFATYYCQQSYSPPLTFGP
GTKVDMK The 3252_C13 antibody (also referred to herein as C13) includes a heavy chain variable region (SEQ ID NO: 144) encoded by the nucleic acid sequence shown below in SEQ ID NO: 143, and a light chain variable region (SEQ ID NO: 146) encoded by the nucleic acid sequence shown in SEQ ID NO: 145.

The amino acids encompassing the CDRs as defined by Chothia et al., 1989 are underlined and those defined by Kabat et al., 1991 are highlighted in bold in the sequences below.

The heavy chain CDRs of the C13 antibody have the following sequences per Kabat definition: SDYWS (SEQ ID NO: 187), YIYNRGSTKYTPSLKS (SEQ ID NO: 237) and HVGGHTYGIDY (SEQ ID NO: 238). The light chain CDRs of the C13 antibody have the following sequences per Kabat definition: RASQSISNYLN (SEQ ID NO: 241), AASSLQS (SEQ ID NO: 234) and QQSYNTPIT (SEQ ID NO: 243).

The heavy chain CDRs of the C13 antibody have the following sequences per Chothia definition: GASISS (SEQ ID NO: 239), YIYNRGSTK (SEQ ID NO: 240) and HVGGHTYGIDY (SEQ ID NO: 238). The light chain CDRs of the C13 antibody have the following sequences per Chothia definition: RASQSISNYLN (SEQ ID NO: 241), AASSLQS (SEQ ID NO: 234) and QQSYNTPIT (SEQ ID NO: 243).

3252_C13 VH nucleotide sequence
(SEQ ID NO: 143)
CAGGTGCAGCTGCAGGAGTCGGGCCCAGGACTGGTGAAGCCTTCGGAGAC
CCTGTCCCTCACCTGCACTGTCTCTGGTGCCTCCATCAGTAGTGACTACT
GGAGCTGGATCCGGCTGCCCCCAGGGAAGGGACTGGAGTGGATTGGGTAT
ATCTATAATAGAGGGAGTACCAAGTACACCCCCTCCCTGAAGAGTCGAGT
CACCATATCACTAGACACGGCCGAGAACCAGTTCTCCCTGAGGCTGAGGT
CGGTGACCGCCGCAGACACGGCCATCTATTACTGTGCGAGACATGTAGGT
GGCCACACCTATGGAATTGATTACTGGGGCCAGGGAACCCTGGTCACCGT
CTCGAGC 3252_C13 VH amino acid sequence
(SEQ ID NO: 144)
QVQLQESGPGLVKPSETLSLTCTVSGASISSDYWSWIRLPPGKGLEWIGY
IYNRGSTKYTPSLKSRVTISLDTAENQFSLRLRSVTAADTAIYYCARHVG
GHTYGIDYWGQGTLVTVSS 3252_C13 VL nucleotide sequence
(SEQ ID NO: 145)
GACATCCAGATGACCCAGTCTCCATCGTCCCTGTCTGCCTCTGTAGGAGA
CAGAGTCACCATCACTTGCCGGGCAAGTCAGAGCATTAGCAACTATTTAA
ATTGGTATCAACACAAACCTGGGGAAGCCCCCAAGCTCCTGAACTATGCT
GCGTCCAGTTTGCAAAGTGGGGTCCCATCAAGGTTCAGTGCCAGTGGATC
TGGGACAGATTTCACTCTCACCATCAGCAGTCTTCAACCTGAAGATTTTG
CCACTTACTACTGTCAACAGAGTTACAATACTCCGATCACCTTCGGCCAA
GGGACACGACTGGAAATTAAACG 3252_C13 VL amino acid sequence
(SEQ ID NO: 146)
DIQMTQSPSSLSASVGDRVTITCRASQSISNYLNWYQHKPGEAPKLLNYA
ASSLQSGVPSRFSASGSGTDFTLTISSLQPEDFATYYCQQSYNTPITFGQ
GTRLEIK The 3259_J06 antibody (also referred to herein as J06) includes a heavy chain variable region (SEQ ID NO: 148) encoded by the nucleic acid sequence shown below in SEQ ID NO: 147, and a light chain variable region (SEQ ID NO: 150) encoded by the nucleic acid sequence shown in SEQ ID NO: 149.

The amino acids encompassing the CDRs as defined by Chothia et al., 1989 are underlined and those defined by Kabat et al., 1991 are highlighted in bold in the sequences below.

The heavy chain CDRs of the J06 antibody have the following sequences per Kabat definition: SDYWS (SEQ ID NO: 187), YIYNRGSTKYTPSLKS (SEQ ID NO: 237) and HVGGHTYGIDY (SEQ ID NO: 238). The light chain CDRs of the J06 antibody have the following sequences per Kabat definition: RASQSISNYLN (SEQ ID NO: 241), AASSLQS (SEQ ID NO: 234) and QQSYNTPIT (SEQ ID NO: 243).

The heavy chain CDRs of the J06 antibody have the following sequences per Chothia definition: GASISS (SEQ ID NO: 239), YIYNRGSTK (SEQ ID NO: 240) and HVGGHTYGIDY (SEQ ID NO: 238). The light chain CDRs of the J06 antibody have the following sequences per Chothia definition: RASQSISNYLN (SEQ ID NO: 241), AASSLQS (SEQ ID NO: 234) and QQSYNTPIT (SEQ ID NO: 243).

3255_J06 VH nucleotide sequence
(SEQ ID NO: 147)
CAGGTGCAGCTGCAGGAGTCGGGCCCAGGACTGGTGAAGCCTTCGGAGAC
CCTGTCCCTCACCTGCACTGTCTCTGGTGCCTCCATCAGTAGTGACTACT
GGAGCTGGATCCGGCTGCCCCCAGGGAAGGGACTGGAGTGGATTGGGTAT
ATCTATAATAGAGGGAGTACCAAGTACACCCCCTCCCTGAAGAGTCGAGT
CACCATATCACTAGACACGGCCGAGAACCAGTTCTCCCTGAGGCTGAGGT
CGGTGACCGCCGCAGACACGGCCGTCTATTACTGTGCGAGACATGTGGGT
GGCCACACCTATGGAATTGATTACTGGGGCCAGGGAACCCTGGTCACCGT
CTCGAGC 3255_J06 VH amino acid sequence
(SEQ ID NO: 148)
QVQLQESGPGLVKPSETLSLTCTVSGASISSDYWSWIRLPPGKGLEWIGY
IYNRGSTKYTPSLKSRVTISLDTAENQFSLRLRSVTAADTAVYYCARHVG
GHTYGIDYWGQGTLVTVSS 3255_J06 VL nucleotide sequence
(SEQ ID NO: 149)
GACATCCAGATGACCCAGTCTCCATCGTCCCTGTCTGCCTCTGTAGGAGA
CAGAGTCACCATCACTTGCCGGGCAAGTCAGAGCATTAGCAACTATTTAA
ATTGGTATCAACACAAACCTGGGGAAGCCCCCAAGCTCCTGAACTATGCT
GCGTCCAGTTTGCAAAGTGGGGTCCCATCAAGGTTCAGTGCCAGTGGATC
TGGGACAGATTTCACTCTCAGCATCAGCGGTCTTCAACCTGAAGATTTTG
CCACTTACTACTGTCAACAGAGCTACAATACTCCGATCACCTTCGGCCCA
GGGACACGACTGGAAATTAAACG 3255_J06 VL amino acid sequence
(SEQ ID NO: 150)
DIQMTQSPSSLSASVGDRVTITCRASQSISNYLNWYQHKPGEAPKLLNYA
ASSLQSGVPSRFSASGSGTDFTLSISGLQPEDFATYYCQQSYNTPITFGP
GTRLEIK The 3410_I23 antibody (also referred to herein as I23) includes a heavy chain variable region (SEQ ID NO: 152) encoded by the nucleic acid sequence shown below in SEQ ID NO: 151, and a light chain variable region (SEQ ID NO: 154) encoded by the nucleic acid sequence shown in SEQ ID NO: 153.

The amino acids encompassing the CDRs as defined by Chothia et al., 1989 are underlined and those defined by Kabat et al., 1991 are highlighted in bold in the sequences below.

The heavy chain CDRs of the 3410_I23 antibody have the following sequences per Kabat definition: SYSWS (SEQ ID NO: 252), YLYYSGSTKYNPSLKS (SEQ ID NO: 253) and TGSESTTGYGMDV (SEQ ID NO: 254). The light chain CDRs of the 3410_I23 antibody have the following sequences per Kabat definition: RASQSISTYLN (SEQ ID NO: 192), AASSLHS (SEQ ID NO: 258) and QQSYSPPIT (SEQ ID NO: 259).

The heavy chain CDRs of the 3410_I23 antibody have the following sequences per Chothia definition: GDSISS (SEQ ID NO: 255), YLYYSGSTK (SEQ ID NO: 256) and TGSESTTGYGMDV (SEQ ID NO: 254). The light chain CDRs of the 3410_I23 antibody have the following sequences per Chothia definition: RASQSISTYLN (SEQ ID NO: 192), AASSLHS (SEQ ID NO: 258) and QQSYSPPIT (SEQ ID NO: 259).

3420_I23 VH nucleotide sequence
(SEQ ID NO: 151)
CAGGTGCAGCTGCAGGAGTCGGGCCCAGGACTGGTGAAGCCTTCGGAGAC
CCTGTCCGTCACCTGCAAAGTCTCTGGTGACTCCATCAGTAGTTATTCCT
GGAGCTGGATCCGGCAGCCCCCAGGGAAGGGACTGGAGTGGGTTGGCTAT
TTGTATTATAGTGGGAGCACCAAGTACAACCCCTCCCTCAAGAGTCGAAC
CACCATATCAGTAGACACGTCCACGAACCAGTTGTCCCTGAAGTTGAGTT
TTGTGACCGCCGCGGACACGGCCGTGTATTTCTGTGCGAGAACCGGCTCG
GAATCTACTACCGGCTACGGTATGGACGTCTGGGGCCAAGGGACCACGGT
CACCGTCTCGAGC 3420_I23 VH amino acid sequence
(SEQ ID NO: 152)
QVQLQESGPGLVKPSETLSVTCKVSGDSISSYSWSWIRQPPGKGLEWVGY
LYYSGSTKYNPSLKSRTTISVDTSTNQLSLKLSFVTAADTAVYFCARTGS
ESTTGYGMDVWGQGTTVTSS 3420_I23 VL nucleotide sequence
(SEQ ID NO: 153)
GACATCCAGATGACCCAGTCTCCATCCTCCCTGTCTGCATCTGTAGGAGA
CAGAGTCACCATCACTTGCCGGGCAAGTCAGAGCATTAGCACCTATTTAA
ATTGGTATCAGCAGAAACCAGGGAAAGCCCCTAAGCTCCTGATCTATGCT
GCATCCAGTTTGCACAGTGGGGTCCCATCAAGGTTCAGTGGCAGTGGATC
TGGGACAGATTTCGCTCTCACCATCAGCAGTCTGCAACCTGAAGATTTTG
CAACTTACTACTGTCAACAGAGTTACAGTCCCCCGATCACCTTCGGCCAA
GGGACACGACTGGAGATTAAACG 3420_I23 VL amino acid sequence
(SEQ ID NO: 154)
DIQMTQSPSSLSASVGDRVTITCRASQSISTYLNWYQQKPGKAPKLLIYA
ASSLHSGVPSRFSGSGSGTDFALTISSLQPEDFATYYCQQSYSPPITFGQ
GTRLEIK The 3139_P23 antibody (also referred to herein as P23) includes a heavy chain variable region (SEQ ID NO: 156) encoded by the nucleic acid sequence shown below in SEQ ID NO: 155, and a light chain variable region (SEQ ID NO:158) encoded by the nucleic acid sequence shown in SEQ ID NO:157.

The amino acids encompassing the CDRs as defined by Chothia et al., 1989 are underlined and those defined by Kabat et al., 1991 are highlighted in bold in the sequences below.

The heavy chain CDRs of the P23 antibody have the following sequences per Kabat definition: NSFWG (SEQ ID NO: 260), YVYNSGNTKYNPSLKS (SEQ ID NO: 261) and HDDASHGYSIS (SEQ ID NO: 262). The light chain CDRs of the 3139_P23 antibody have the following sequences per Kabat definition: RASQTISTYLN (SEQ ID NO: 265), AASGLQS (SEQ ID NO: 61) and QQSYNTPLT (SEQ ID NO: 267).

The heavy chain CDRs of the 3139_P23 antibody have the following sequences per Chothia definition: GGSISN (SEQ ID NO: 263), YVYNSGNTK (SEQ ID NO: 264) and HDDASHGYSIS (SEQ ID NO: 262). The light chain CDRs of the 3139_P23 antibody have the following sequences per Chothia definition: RASQTISTYLN (SEQ ID NO: 265), AASGLQS (SEQ ID NO: 61) and QQSYNTPLT (SEQ ID NO: 267).

3139_P23 VH nucleotide sequence
(SEQ ID NO: 155)
CAGGTGCAGCTGCAGGAGTCGGGCCCAAGACTGGTGAAGCCTTCGGAGAG
CCTGTCCCTCACCTGCACTGTCTCTGGTGGCTCCATTAGTAATTCCTTCT
GGGGCTGGATCCGGCAGCCCCCAGGGGAGGGACTGGAGTGGATTGGTTAT
GTCTATAACAGTGGCAACACCAAGTACAATCCCTCCCTCAAGAGTCGAGT
CACCATTTCGCGCGACACGTCCAAGAGTCAACTCTACATGAAGCTGAGGT
CTGTGACCGCCGCTGACACGGCCGTGTACTACTGTGCGAGGCATGACGAC
GCAAGTCATGGCTACAGCATCTCCTGGGGCCACGGAACCCTGGTCACCGT
CTCGAGC 3139_P23 VH amino acid sequence
(SEQ ID NO: 156)
QVQLQESGPRLVKPSESLSLTCTVSGGSISNSFWGWIRQPPGEGLEWIGY
VYNSGNTKYNPSLKSRVTISRDTSKSQLYMKLRSVTAADTAVYYCARHDD
ASHGYSISWGHGTLVTVSS 3139_P23 VL nucleotide sequence
(SEQ ID NO: 157)
GACATCCAGATGACCCAGTCTCCATCCTCCCTGTCTGCATCTGTAGGGGA
CAGAGTCACCATCACTTGCCGGGCAAGTCAGACCATTAGTACTTATTTAA
ATTGGTATCAACAGAAATCAGGGAAAGCCCCTAAGCTCCTGATCTATGCT
GCATCCGGTTTGCAAAGTGGAGTCCCATCAAGGTTCAGTGGCAGTGGATC
TGGGACAGATTTCACTCTCACCATCAGCAGTCTTCAACCTGAAGATTTTG
CAACTTACTTCTGTCAACAGAGTTACAATACTCCCCTGACGTTCGGCCAA
GGGACCAAGGTGGAAATCAAA 3139_P23 VL amino acid sequence
(SEQ ID NO: 158)
DIQMTQSPSSLSASVGDRVTITCRASQTISTYLNWYQQKSGKAPKLLIYA
ASGLQSGVPSRFSGSGSGTDFTLTISSLQPEDFATYFCQQSYNTPLTFGQ
GTKVEIK The 3248_P18 antibody (also referred to herein as P18) includes a heavy chain variable region (SEQ ID NO: 160) encoded by the nucleic acid sequence shown below in SEQ ID NO: 159, and a light chain variable region (SEQ ID NO: 162) encoded by the nucleic acid sequence shown in SEQ ID NO: 161.

The amino acids encompassing the CDRs as defined by Chothia et al., 1989 are underlined and those defined by Kabat et al., 1991 are highlighted in bold in the sequences below.

The heavy chain CDRs of the 3248_P18 antibody have the following sequences per Kabat definition: AYHWS (SEQ ID NO: 268), HIFDSGSTYYNPSLKS (SEQ ID NO: 269) and PLGSRYYYGMDV (SEQ ID NO: 270). The light chain CDRs of the 3248_P18 antibody have the following sequences per Kabat definition: RASQSISRYLN (SEQ ID NO: 273), GASTLQN (SEQ ID NO: 274) and QQSYSVPA (SEQ ID NO: 275).

The heavy chain CDRs of the 3248_P18 antibody have the following sequences per Chothia definition: GGSISA (SEQ ID NO: 271), HIFDSGSTY (SEQ ID NO: 272) and PLGSRYYYGMDV (SEQ ID NO: 270). The light chain CDRs of the 3248_P18 antibody have the following sequence's per Chothia definition: RASQSISRYLN (SEQ ID NO: 273), GASTLQN (SEQ ID NO: 274) and QQSYSVPA (SEQ ID NO: 275).

3248_P18 VH nucleotide sequence
(SEQ ID NO: 159)
CAGGTGCAACTGCAGGAGTCGGGCCCAGGACTGGTGAAGCCTTCGGAGAC
CCTGTCCCTCACCTGCACTGTCTCGGGTGGCTCCATCAGTGCTTACCACT
GGAGCTGGATCCGCCAGCCCCCAGGGAAGGGACTGGAGTGGATTGGACAC
ATCTTTGACAGTGGGAGCACTTACTACAACCCCTCCCTTAAGAGTCGAGT
CACCATATCACTAGACGCGTCCAAGAACCAGCTCTCCCTGAGATTGACCT
CTGTGACCGCCTCAGACACGGCCATATATTACTGTGCGAGACCTCTCGGG
AGTCGGTACTATTACGGAATGGACGTCTGGGGCCAAGGGACCACGGTCAC
CGTCTCGAGC 3248_P18 VH amino acid sequence
(SEQ ID NO: 160)
QVQLQESGPGLVKPSETLSLTCTVSGGSISAYHWSWIRQPPGKGLEWIGH -continued

IFDSGSTYYNPSLKSRVTISLDASKNQLSLRLTSVTASDTAIYYCAR**PLG
SRYYYGMDV**WGQGTTVTVSS

3248_P18 VL nucleotide sequence
(SEQ ID NO: 161)
GACATCCAGATGACCCAGTCTCCGTCCTCCCTGTCTGCATCTGTCGGAGA
CAGAGTCACCATCACTTGCCGGGCAAGTCAGAGTATTAGCAGGTATTTAA
ATTGGTATCAGCAGAAACCAGGGAAAGCCCCTAAGCTCCTGATCTATGGT
GCCTCCACTTTGCAAATGGGGCCCCATCAAGGTTCAGCGGCAGTGGATC
TGGGACAGATTTCACTCTCACCATCAGCAGTCTACAACCTGAAGATTCCG
CAACTTACCTCTGTCAACAGATTACAGTGTCCCTGCTTTCGGCGGAGGA
ACCAAGGTGGAGGTCAAA 3248_P18 VL amino acid sequence
(SEQ ID NO: 162)
DIQMTQSPSSLSASVGDRVTITCRASQSISRYLNWYQQKPGKAPKLLIY**G
ASTLQNGAPSRFSGSGSGTDFTLTISSLQPEDSATYLCQQSYSVPA**FGGG
TKVEVK The 3253_P10 antibody (also referred to herein as P10) includes a heavy chain variable region (SEQ ID NO: 164) encoded by the nucleic acid sequence shown below in SEQ ID NO: 163, and a light chain variable region (SEQ ID NO: 166) encoded by the nucleic acid sequence shown in SEQ ID NO: 165.

The amino acids encompassing the CDRs as defined by Chothia et al., 1989 are underlined and those defined by Kabat et al., 1991 are highlighted in bold in the sequences below.

The heavy chain CDRs of the 3253_P10 antibody have the following sequences per Kabat definition: SDYWS (SEQ ID NO: 187), FFYNGGSTKYNPSLKS (SEQ ID NO: 188) and HDAKFSGSYYVAS (SEQ ID NO: 189). The light chain CDRs of the 3253_P10 antibody have the following sequences per Kabat definition: RASQSISTYLN (SEQ ID NO: 192), GATDLQS (SEQ ID NO: 282) and QQSYNTPLI (SEQ ID NO: 194).

The heavy chain CDRs of the 3253_P10 antibody have the following sequences per Chothia definition: GGSITS (SEQ ID NO: 190), FFYNGGSTK (SEQ ID NO: 191) and HDAKFSGSYYVAS (SEQ ID NO: 189). The light chain CDRs of the 3253_P10 antibody have the following sequences per Chothia definition: RASQSISTYLN (SEQ ID NO: 192), GATDLQS (SEQ ID NO: 282) and QQSYNTPLI (SEQ ID NO: 194).

3253_P10 VH nucleotide sequence
(SEQ ID NO: 163)
CAGGTCCAGCTGCAGGAGTCGGGCCCAGGACTGCTGAAGCCTTCGGACAC
CCTGGCCCTCACTTGCACTGTCTCTGGTGGCTCCATCACCAGTGACTACT
GGAGCTGGATCCGGCAACCCCCAGGGAGGGGACTGGACTGGATCGGATTC
TTCTATAACGGCGGAGCACCAAGTACAATCCCTCCCTCAAGAGTCGAGT
CACCATATCAGCGGACACGTCCAAGAACCAGTTGTCCCTGAAATTGACCT
CTGTGACCGCCGCAGACACGGGCGTGTATTATTGTGCGAGACATGATGCC
AAATTTAGTGGGAGCTACTACGTTGCCTCCTGGGGCCAGGGAACCCGAGT
CACCGTCTCGAGC 3253_P10 VH amino acid sequence
(SEQ ID NO: 164)
QVQLQESGPGLLKPSDTLALTCTVSGGSITSDYWSWIRQPPGRGLDWIG**F
FYNGGSTKYNPSLKSRVTISADTSKNQLSLKLTSVTAADTGVYYCARHDA
KFSGSYYVAS**WGQGTRVTVSS 3253_P10 VL nucleotide sequence
(SEQ ID NO: 165)
GACATCCAGATGACCCAGTCTCCCTCCTCCCTGTCTGCATCTGTAGGAGA
CAGAGTCACCATCTCTTGCCGGGCAAGTCAGAGCATTAGCACCTATTTAA
ATTGGTATCAGCAGCAACCTGGGAAAGCCCCTAAGGTCCTGATCTCTGGT
GCAACCGACTTGCAAAGTGGGGTCCCATCTCGCTTCAGTGGCAGTGGATC
TGGGACAGATTTCACTCTCACCATCAGCAGTCTGCAACCTGAAGATTTTG
CAACTTACTACTGTCAACAGAGTTACAATACCCCCCTCATTTTTGGCCAG
GGGACCAAGCTGGAGATCAAA 3253_P10 VL amino acid sequence
(SEQ ID NO: 166)
DIQMTQSPSSLSASVGDRVTISCRASQSISTYLNWYQQQPGKAPKVLIS**G
ATDLQSGVPSRFSGSGSGTDFTLTISSLQPEDFATYYCQQSYNTPLI**FGQ
GTKLEIK The 3260_D19 antibody (also referred to herein as D19) includes a heavy chain variable region (SEQ ID NO: 168) encoded by the nucleic acid sequence shown below in SEQ ID NO: 167, and a light chain variable region (SEQ ID NO: 170) encoded by the nucleic acid sequence shown in SEQ ID NO: 169.

The amino acids encompassing the CDRs as defined by Chothia et al., 1989 are underlined and those defined by Kabat et al., 1991 are highlighted in bold in the sequences below.

The heavy chain CDRs of the 3260_D19 antibody have the following sequences per Kabat definition: DNYIN (SEQ ID NO: 284), VFYSADRTSYADSVKG (SEQ ID NO: 285) and VQKSYYGMDV (SEQ ID NO: 286). The light chain CDRs of the 3260_D19 antibody have the following sequences per Kabat definition: RASQSISRYLN (SEQ ID NO: 273), GAS-SLQS (SEQ ID NO: 226) and QQTFSIPL (SEQ ID NO: 291).

The heavy chain CDRs of the 3260_D19 antibody have the following sequences per Chothia definition: GFSVSD (SEQ ID NO: 287), VFYSADRTS (SEQ ID NO: 288) and VQKSYYGMDV (SEQ ID NO: 286). The light chain CDRs of the 3260_D19 antibody have the following sequences per Chothia definition: RASQSISRYLN (SEQ ID NO: 273), GASSLQS (SEQ ID NO: 226) and QQTFSIPL (SEQ ID NO: 291).

3260_D19 VH nucleotide sequence
(SEQ ID NO: 167)
GACATGCAGCTGGTGGAGTCTGGAGGAGGCTTGGTCCCGCCGGGGGGGTC
CCTGAGACTCTCCTGCGCAGCCTCTGGGTTTTCCGTCAGTGACAACTACA
TAAACTGGGTCCGCCAGGCTCCAGGGAAGGGGCTGGACTGGGTCTCAGTC
TTTTATAGTGCTGATAGAACATCCTACGCAGACTCCGTGAAGGGCCGATT
CACCGTCTCCAGCCACGATTCCAAGAACACAGTGTACCTTCAAATGAACA
GTCTGAGAGCTGAGGACACGGCCGTTTATTACTGTGCGAGAGTTCAGAAG
TCCTATTACGGTATGGACGTCTGGGGCCAAGGGACCACGGTCACCGTCTC
GAGC 3260_D19 VH amino acid sequence
(SEQ ID NO: 168)
DMQLVESGGGLVPPGGSLRLSCAASGFSVSDDNYINWVRQAPGKGLDWVS**V
FYSADRTSYADSVKGRFTVSSHDSKNTVYLQMNSLRAEDTAVYYCARVQK
SYYGMDV**WGQGTTVTVSS 3260_D19 VL nucleotide sequence
(SEQ ID NO: 169)
GGCATCCAGATGACCCAGTCTCCATCCTCCCTGTCTGCATCTGTAGGAGA
CAGAGTCACCATCACTTGCCGGGCAAGTCAGAGCATTAGCAGATATTTAA
ATTGGTATCTGCAGAAACCAGGGAAAGCCCCTAAGCTCCTGATCTCTGGT
GCATCCAGTTTGCAAAGTGGGGTCCCATCAAGGTTCAGTGGCACTGGGTC
TGGGACAGAATTCACTCTCACCATCAGCAGTTTGCAACCTGAAGATTTTG
CAACTTACTACTGTCAACAGACTTTCAGTATCCCTCTTTTTGGCCAGGGG
ACCAAGGTGGAGATCAAA 3260_D19 VL amino acid sequence
(SEQ ID NO: 170)
GIQMTQSPSSLSASVGDRVTITCRASQSISRYLNWYLQKPGKAPKLLIS**G
ASSLQSGVPSRFSGTGSGTEFTLTISSLQPEDFATYYCQQTFSEPL**FGQG
TKVEIK The 3362_B11 antibody (also referred to herein as B11) includes a heavy chain variable region (SEQ ID NO: 172) encoded by the nucleic acid sequence shown below in SEQ ID NO: 171, and a light chain variable region (SEQ ID NO: 174) encoded by the nucleic acid sequence shown in SEQ ID NO: 173.

The amino acids encompassing the CDRs as defined by Chothia et al., 1989 are underlined and those defined by Kabat et al., 1991 are highlighted in bold in the sequences below.

The heavy chain CDRs of the B11 antibody have the following sequences per Kabat definition: SGAYYWT (SEQ ID NO: 293), YIYYSGNTYYNPSLKS (SEQ ID NO: 294) and AASTSVLGYGMDV (SEQ ID NO: 295). The light chain CDRs of the B11 antibody have the following sequences per Kabat definition: RASQSISRYLN (SEQ ID NO: 273), AASSLQS (SEQ ID NO: 234) and QQSYSTPLT (SEQ ID NO: 300).

The heavy chain CDRs of the B11 antibody have the following sequences per Chothia definition: GDSITSGA (SEQ ID NO: 296), YIYYSGNTY (SEQ ID NO: 297) and AASTS-VLGYGMDV (SEQ ID NO: 295). The light chain CDRs of the B11 antibody have the following sequences per Chothia definition: RASQSISRYLN (SEQ ID NO: 273), AASSLQS (SEQ ID NO: 234) and QQSYSTPLT (SEQ ID NO: 300).

3362_B11 VH nucleotide sequence
(SEQ ID NO: 171)
CAGGTGCAGCTGCAGGCGTCGGGCCCAGGACTGGTGAAGCCTTCAGAGAC
CCTGTCCCTCACCTGCACTGTCTCTGGTGACTCCATCACCAGTGGTGCTT
ACTACTGGACCTGGATCCGCCAGCACCCAGGGAAGGGCCTGGAGTGGATT
GGGTACATCTATTACAGTGGGAACACCTACTACAACCCGTCCCTCAAGAG
TCGAGTTACCATATCACTAGACACGTCTAAGAACCAGTTCTCCCTGAAGG
TGAACTCTGTGACTGCCGCGGACACGGCCGTATATTACTGTGCGCGAGCT
GCTTCGACTTCAGTGCTAGGATACGGTATGGACGTCTGGGGCCAAGGGAC
CACGGTCACCGTCTCGAGC 3362_B11 VH amino acid sequence
(SEQ ID NO: 172)
QVQLQASGPGLVKPSETLSLTCTVSGDSITSGAYYWTWIRQHPGKGLEWI
GYIYYSGNTYYNPSLKSRVTISLDTSKNQFSLKVNSVTAADTAVYYCARA
ASTSVLGYGMDVWGQGTTVTSS 3362_B11 VL nucleotide sequence
(SEQ ID NO: 173)
GACATCCAGATGACCCAGTCTCCATCCTCCCTGTCTGCATCTGTAGGAGA
CAGAGTCACCATCACTTGCCGGGCAAGTCAGAGCATTAGCAGATATTTAA
ATTGGTATCAGCAGGAACCAGGGAAGGCCCCTAAGCTCCTGGTCTATGCT
GCATCCAGTTTGCAAAGTGGGGTCCCATCAAGGTTCAGTGGCAGTGGATC
TGGGACAGATTTCACTCTCACCATAAGCAGTCTTCAACCTGAAGATTTTG
CAACTTACTACTGTCAACAGAGTTATAGTACCCCCCTCACCTTCGGCCAA
GGGACACGACTGGAGATTAAA 3362_B11 VH amino acid sequence
(SEQ ID NO: 174)
DIQMTQSPSSLSASVGDRVTITCRASQSISRYLNWYQQEPGKAPKLLVYA
ASSLQSGVPSRFSGSGSGTDFTLTISSLQPEDFATYYCQQSYSTPLTFGQ
GTRLEIK The 3242_P05 antibody (also referred to herein as P05) includes a heavy chain variable region (SEQ ID NO: 176) encoded by the nucleic acid sequence shown below in SEQ ID NO: 175, and a light chain variable region (SEQ ID NO: 178) encoded by the nucleic acid sequence shown in SEQ ID NO: 177.

The amino acids encompassing the CDRs as defined by Chothia et al., 1989 are underlined and those defined by Kabat et al., 1991 are highlighted in bold in the sequences below.

The heavy chain CDRs of the 3242_P05 antibody have the following sequences per Kabat definition: VSDNYIN (SEQ ID NO: 301), VFYSADRTSYADSVKG (SEQ ID NO: 285) and VQKSYYGMDV (SEQ ID NO: 286). The light chain CDRs of the 3242_P05 antibody have the following sequences per Kabat definition: RASQSISRYLN (SEQ ID NO: 273), GASSLQS (SEQ ID NO: 226) and QQTFSIPL (SEQ ID NO: 291).

The heavy chain CDRs of the 3242_P05 antibody have the following sequences per Chothia definition: SGFSV (SEQ ID NO: 304), VFYSADRTS (SEQ ID NO: 288) and VQKSYYGMDV (SEQ ID NO: 286). The light chain CDRs of the 3242_P05 antibody have the following sequences per Chothia definition: The light chain CDRs of the 3242_P05 antibody have the following sequences per Kabat definition: RASQSISRYLN (SEQ ID NO: 273), GASSLQS (SEQ ID NO: 226) and QQTFSIPL (SEQ ID NO: 291).

3242_P05 VH nucleotide sequence
(SEQ ID NO: 175)
GACATGCAGCTGGTGGAGTCTGGAGGAGGCTTGGTCCCGCCGGGGGGGTC
CCTGAGACTCTCCTGCGCAGCCTCTGGGTTTTCCGTCAGTGACAACTACA
TAAACTGGGTCCGCCAGGCTCCAGGGAAGGGGCTGGACTGGGTCTCAGTC
TTTTATAGTGCTGATAGAACATCCTACGCAGACTCCGTGAAGGGCCGATT
CACCGTCTCCAGCCACGATTCCAAGAACACAGTGTACCTTCAAATGAACA
GTCTGAGAGCTGAGGACACGGCCGTTTATTACTGTGCGAGAGTTCAGAAG
TCCTATTACGGTATGGACGTCTGGGGCCAAGGGACCACGGTCACCGTCTC
GAGC 3242_P05 VH amino acid sequence
(SEQ ID NO: 176)
DMQLVESGGGLVPPGGSLRLSCAASGFSVSDNYINWVRQAPGKGLDWVSV
FYSADRTSYADSVKGRFTVSSHDSKNTVYLQMNSLRAEDTAVYYCARVQK
SYYGMDVWGQGTTVTSS 3242_P05 VL nucleotide sequence
(SEQ ID NO: 177)
GGCATCCAGATGACCCAGTCTCCATCCTCCCTGTCTGCATCTGTAGGAGA
CAGAGTCACCATCACTTGCCGGGCAAGTCAGAGCATTAGCAGATATTTAA
ATTGGTATCTGCAGAAACCAGGGAAAGCCCCTAAGCTCCTGATCTCTGGT
GCATCCAGTTTGCAAAGTGGGGTCCCATCAAGGTTCAGTGGCACTGGGTC
TGGGACAGAATTCACTCTCACCATCAGCAGTTTGCAACCTGAAGATTTTG
CAACTTACTACTGTCAACAGACTTTCAGTATCCCTCTTTTTGGCCAGGGG
ACCAAGGTGGAGATCAAA 3242_P05 VL amino acid sequence
(SEQ ID NO: 178)
GIQMTQSPSSLSASVGDRVTITCRASQSISRYLNWYLQKPGKAPKLLISG
ASSLQSGVPSRFSGTGSGTEFTLTISSLQPEDFATYYCQQTFSIPLFGQG
TKVEIK HuM2e antibodies of the invention also include antibodies that include a heavy chain variable amino acid sequence that is at least 90%, 92%, 95%, 97% 98%, 99% or more identical the amino acid sequence of SEQ ID NO: 44, 277, 276, 50, 236, 235, 116, 120, 124, 128, 132, 136, 140, 144, 148, 152, 156, 160, 164, 168, 172, or 176. and/or a light chain variable amino acid that is at least 90%, 92%, 95%, 97% 98%, 99% or more identical the amino acid sequence of SEQ ID NO: 46, 52, 118, 122, 126, 130, 134, 138, 142, 146, 150, 154, 158, 162, 166, 170, 174, 178.

Alternatively, the monoclonal antibody is an antibody that binds to the same epitope as TCN-032 (8I10), 21B15, TCN-031 (23K12), 3241_G23, 3244_I10, 3243_J07, 3259_J21, 3245_O19, 3244_J104, 3136_G05, 3252_C13, 3255_J06, 3420_I23, 3139_P23, 3248_P18, 3253_P10, 3260_D19, 3362_B11, or 3242_P05.

The heavy chain of a M2e antibody is derived from a germ line V (variable) gene such as, for example, the IgHV4 or the IgHV3 germline gene.

The M2e antibodies of the invention include a variable heavy chain ($V_H$) region encoded by a human IgHV4 or the IgHV3 germline gene sequence. An IgHV4 germline gene sequence is shown, e.g., in Accession numbers L10088, M29812, M95114, X56360 and M95117. An IgHV3 germline gene sequence is shown, e.g., in Accession numbers X92218, X70208, Z27504, M99679 and AB019437. The M2e antibodies of the invention include a $V_H$ region that is encoded by a nucleic acid sequence that is at least 80% homologous to the IgHV4 or the IgHV3 germline gene sequence. Preferably, the nucleic acid sequence is at least 90%, 95%, 96%, 97% homologous to the IgHV4 or the IgHV3 germline gene sequence, and more preferably, at least 98%, 99% homologous to the IgHV4 or the IgHV3 germline gene sequence. The $V_H$ region of the M2e antibody is at least 80% homologous to the amino acid sequence of the $V_H$ region encoded by the IgHV4 or the IgHV3 $V_H$ germline gene sequence. Preferably, the amino acid sequence of $V_H$ region of the M2e antibody is at least 90%, 95%, 96%, 97% homologous to the amino acid sequence encoded by the IgHV4 or the IgHV3 germline gene sequence, and more preferably, at least 98%, 99% homologous to the sequence encoded by the IgHV4 or the IgHV3 germline gene sequence.

The M2e antibodies of the invention also include a variable light chain ($V_L$) region encoded by a human IgKV1 germline gene sequence. A human IgKV1 $V_L$ germline gene sequence is shown, e.g., Accession numbers X59315, X59312, X59318, J00248, and Y14865. Alternatively, the M2e antibodies include a $V_L$ region that is encoded by a nucleic acid sequence that is at least 80% homologous to the IgKV1 germline gene sequence. Preferably, the nucleic acid sequence is at least 90%, 95%, 96%, 97% homologous to the IgKV1 germline gene sequence, and more preferably, at least 98%, 99% homologous to the IgKV1 germline gene sequence. The $V_L$ region of the M2e antibody is at least 80% homologous to the amino acid sequence of the $V_L$ region encoded the IgKV1 germline gene sequence. Preferably, the amino acid sequence of $V_L$ region of the M2e antibody is at least 90%, 95%, 96%, 97% homologous to the amino acid sequence encoded by the IgKV1 germline gene sequence, and more preferably, at least 98%, 99% homologous to the sequence encoded by e the IgKV1 germline gene sequence.

HA Antibodies

The HA antibodies of the invention may also be capable of specifically binding to one or more fragments of influenza virus H5N1, such as the surface glycoproteins, hemagglutinin (HA) and neuraminidase (NA), which are required for viral attachment and cellular release, or membrane proteins (M1 and M2). In a specific embodiment, the HA antibodies of the invention are capable of specifically binding to the HA molecule of H5N1 strains. They may be capable of specifically binding to the HA1 and/or HA2 subunit of the HA molecule. They may be capable of specifically binding to linear or structural and/or conformational epitopes on the HA1 and/or HA2 subunit of the HA molecule. The HA molecule may be purified from viruses or recombinantly produced and optionally isolated before use. Alternatively, HA may be expressed on the surface of cells.

For diagnostic purposes, the HA antibodies may also be capable of specifically binding to proteins not present on the surface of H5N1 including the nucleoprotein, the nucleocapsid structural protein, polymerases (PA, PB and PB2), and non-structural proteins (NS1 and NS2). The nucleotide and/or amino acid sequence of proteins of various H5N1 strains can be found in the GenBank-database, NCBI Influenza Virus Sequence Database, Influenza Sequence Database (ISD), EMBL-database and/or other databases. It is well within the reach of the skilled person to find such sequences in the respective databases. In another embodiment the HA antibodies of the invention are capable of specifically binding to a fragment of the above-mentioned proteins and/or polypeptides, wherein the fragment at least includes an antigenic determinant recognized by the HA antibodies of the invention. An "antigenic determinant" as used herein is a moiety that is capable of binding to an HA antibody of the invention with sufficiently high affinity to form a detectable antigen-antibody complex. As used herein, the terms "antigenic determinant" and "epitope" are equivalents. The HA antibodies of the invention may or may not be capable of specifically binding to the extracellular part of HA (also called herein soluble HA (sHA)).

The HA antibodies of the invention can be intact immunoglobulin molecules such as polyclonal or monoclonal antibodies or the HA antibodies can be antigen-binding fragments including, but not limited to, Fab, F(ab'), F(ab')2, Fv, dAb, Fd, complementarity determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to influenza virus H5N1 strains or a fragment thereof. In a preferred embodiment the HA antibodies are human monoclonal antibodies.

HA antibodies can be used in non-isolated or isolated form. Furthermore, the HA antibodies can be used alone or in a mixture including at least one HA antibody (or variant or fragment thereof). Thus, HA antibodies can be used in combination, e.g., as a pharmaceutical composition comprising two or more antibodies of the invention, variants or fragments thereof. For example, antibodies having different, but complementary activities can be combined in a single therapy to achieve a desired prophylactic, therapeutic or diagnostic effect, but alternatively, antibodies having identical activities can also be combined in a single therapy to achieve a desired prophylactic, therapeutic or diagnostic effect. Optionally, the mixture further includes at least one other therapeutic agent. Preferably, the therapeutic agent such as, e.g., M2 inhibitors (e.g., amantadine, rimantadine) and/or neuraminidase inhibitors (e.g., zanamivir, oseltamivir) is useful in the prophylaxis and/or treatment of an influenza virus H5N1 infection.

Typically, HA antibodies can bind to their binding partners, i.e. influenza virus H5N1 or fragments thereof, with an affinity constant (Kd-value) that is lower than $0.2 \times 10^{-4}$ M, $1.0 \times 10^{-5}$ M, $1.0 \times 10^{-6}$ M, $1.0 \times 10^{-7}$ M, preferably lower than $1.0 \times 10^{-8}$ M, more preferably lower than $1.0 \times 10^{-9}$ M, more preferably lower than $1.0 \times 10^{-10}$ M, even more preferably lower than $1.0 \times 10^{-11}$ M, and in particular lower than $1.0 \times 10^{-12}$ M. The affinity constants can vary for antibody isotypes. For example, affinity binding for an IgM isotype refers to a binding affinity of at least about $1.0 \times 10^{-7}$ M. Affinity constants can for instance be measured using surface plasmon resonance, for example using the BIACORE system (Pharmacia Biosensor AB, Uppsala, Sweden).

HA antibodies may bind to influenza virus H5N1 or a fragment thereof in soluble form such as for instance in a sample or in suspension or may bind to influenza virus H5N1 or a fragment thereof bound or attached to a carrier or substrate, e.g., microtiter plates, membranes and beads, etc. Carriers or substrates may be made of glass, plastic (e.g., polystyrene), polysaccharides, nylon, nitrocellulose, or Teflon, etc. The surface of such supports may be solid or porous and of any convenient shape. Furthermore, the HA antibodies may bind to influenza virus H5N1 in purified/isolated or non purified/non-isolated form.

HA antibodies exhibit neutralizing activity. Neutralizing activity can for instance be measured as described in International Patent Application PCT/EP2007/059356 (Publication No. WO 2008/028946, the contents of which are incorporated herein in their entirety). Alternative assays measuring neutralizing activity are described in for instance WHO Manual on Animal Influenza Diagnosis and Surveillance, Geneva: World Health Organization, 2005, version 2002.5.

The invention relates to an isolated human HA antibody that recognizes and binds to an epitope in the HA2 subunit of the influenza haemagglutinin protein (HA), characterized in that said HA antibody has neutralizing activity against an influenza virus, for instance, including HA of the H5 subtype. Examples of influenza strains that contain such a HA of the H5 subtype and that are important strains in view of pandemic threats are H5N1, H5N2, H5N8, and H5N9. Particularly preferred are HA antibodies that at least neutralize the H5N1 influenza strain. Preferably, HA antibodies do not depend on an epitope in the HA1 subunit of the HA protein for binding to said HA protein.

DEFINITIONS

The term "human HA antibody" describes an intact immunoglobulin including monoclonal antibodies, such as chimeric, humanized or human monoclonal antibodies, or to an antigen-binding and/or variable domain comprising fragment of an immunoglobulin that competes with the intact immunoglobulin for specific binding to the binding partner of the immunoglobulin, e.g. H5N1. Regardless of structure, the antigen binding fragment binds with the same antigen that is recognized by the intact immunoglobulin. An antigen-binding fragment can comprise a peptide or polypeptide comprising an amino acid sequence of at least 2, 5, 10, 15, 20, 25, 30, 35, 40, 50, 60, 70, 80, 90, 100, 125, 150, 175, 200, or 250 contiguous amino acid residues of the amino acid sequence of the HA antibody.

The term "HA antibody", includes all immunoglobulin classes and subclasses known in the art. Depending on the amino acid sequence of the constant domain of their heavy chains, HA antibodies can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

Antigen-binding fragments include, inter alia, Fab, F(ab'), F(ab')2, Fv, dAb, Fd, complementarity determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in Antibodies: A Laboratory Manual, Edited by: E. Harlow and D, Lane (1988), Cold Spring Harbor Laboratory, Cold Spring Harbor, N.Y., which is incorporated herein by reference. An HA antibody or antigen-binding fragment thereof may have one or more binding sites. If there is more than one binding site, the binding sites may be identical to one another or they may be different.

With respect to HA antibodies, the term "complementarity determining regions" (CDR) as used herein means sequences within the variable regions of HA antibodies, such as immunoglobulins, that usually contribute to a large extent to the antigen binding site which is complementary in shape and charge distribution to the epitope recognized on the antigen. The CDR regions of HA antibodies can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes of HA antibodies may also consist of posttranslational modifications of proteins.

The term "functional variant", as used herein, refers to an HA antibody that includes a nucleotide and/or amino acid sequence that is altered by one or more nucleotides and/or amino acids compared to the nucleotide and/or amino acid sequences of the parental HA antibody and that is still capable of competing for binding to the binding partner, e.g. H5N1, with the parental HA antibody. In other words, the modifications in the amino acid and/or nucleotide sequence of the parental HA antibody do not significantly affect or alter the binding characteristics of the HA antibody encoded by the nucleotide sequence or containing the amino acid sequence, i.e. the antibody is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may include natural as well as non-natural nucleotides and amino acids.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), non-polar side chains (e.g., glycine, alanine, valine, leucine, isoleucine, proline, phenylalanine, methionine), beta-branched side chains (e.g., threonine, valine, isoleucine) and aromatic side chains (e.g., tyrosine, phenylalanine, tryptophan). It will be clear to the skilled artisan that other classifications of amino acid residue families than the one used above can also be employed. Furthermore, a HA antibody functional variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any suitable method known in the art.

The term "human", when applied to HA antibodies, refers to molecules that are either directly derived from a human or based upon a human sequence. When an HA antibody is derived from or based on a human sequence and subsequently modified, it is still to be considered human as used throughout the specification. In other words, the term human, when applied to HA antibodies is intended to include antibodies having variable and constant regions derived from human germline immunoglobulin sequences or based on variable or constant regions occurring in a human or human lymphocyte and modified in some form. Thus, the human HA antibodies may include amino acid residues not encoded by human germline immunoglobulin sequences, contain substitutions and/or deletions (e.g., mutations introduced by for instance random or site-specific mutagenesis in vitro or by somatic mutation in vivo). "Based on" as used herein refers to the situation that a nucleic acid sequence may be exactly copied from a template, or with minor mutations, such as by error-prone PCR methods, or synthetically made matching the template exactly or with minor modifications. Semi-synthetic molecules based on human sequences are also considered to be human as used herein.

Single Chain HA Antibodies

The heavy chain of an HA antibody is derived from a germ line V (variable) gene such as, for example, the VH1 or VH3 germline gene (see, Tomlinson I M, Williams S C, Ignatovitch O, Corbett S J, Winter G. V-BASE Sequence Directory. Cambridge, United Kingdom: MRC Centre for Protein Engineering (1997)). The HA antibodies of the invention include a $V_H$ region that is encoded by a nucleic acid sequence that is at least 80% homologous to the VH1 or VH3 germline gene sequence. Preferably, the nucleic acid sequence is at least 90%, 95%, 96%, 97% homologous to the VH1 or VH3 germline gene sequence, and more preferably, at least 98%, 99% homologous to the VH1 or VH3 germline gene sequence. The $V_H$ region of the HA antibody is at least 80% homologous to the amino acid sequence of the $V_H$ region encoded by the VH1 or VH3 $V_H$ germline gene sequence. Preferably, the amino acid sequence of $V_H$ region of the HA antibody is at least 90%, 95%, 96%, 97% homologous to the amino acid sequence encoded by the VH1 or VH3 germline gene sequence, and more preferably, at least 98%, 99% homologous to the sequence encoded by the VH1 or VH3 germline gene sequence.

In certain aspects of the invention the VH1 germline gene is VH1 (1-2), VH1 (1-18), VH1 (3-23), or VH1 (1-69). In other aspects of the invention the VH3 germline gene is VH3 (3-21)

The HA antibodies of the invention also include a variable light chain ($V_L$) region encoded by a human germline gene sequence selected from the group consisting of VKI, VKII, VKIII, VKIV, VL1, VL2, and VL3 (see, Tomlinson I M, Williams S C, Ignatovitch O, Corbett S J, Winter G. V-BASE Sequence Directory. Cambridge, United Kingdom: MRC Centre for Protein Engineering (1997)). Alternatively, the HA antibodies include a $V_L$ region that is encoded by a nucleic acid sequence that is at least 80% homologous to the germline gene sequence of VKI, VKII, VKIII, VKIV, VL1, VL2, or VL3. Preferably, the nucleic acid sequence is at least 90%, 95%, 96%, 97% homologous to the germline gene sequence of VKI, VKII, VKIII, VKIV, VL1, VL2, or VL3, and more preferably, at least 98%, 99% homologous to the germline gene sequence of VKI, VKII, VKIII, VKIV, VL1, VL2, or VL3. The $V_L$ region of the HA antibody is at least 80% homologous to the amino acid sequence of the $V_L$ region encoded the germline gene sequence of VKI, VKII, VKIII, VKIV, VL1, VL2, or VL3. Preferably, the amino acid sequence of $V_L$ region of the HA antibody is at least 90%, 95%, 96%, 97% homologous to the amino acid sequence encoded by the germline gene sequence of VKI, VKII, VKIII, VKIV, VL1, VL2, or VL3, and more preferably, at least 98%, 99% homologous to the sequence encoded by the germline gene sequence of VKI, VKII, VKIII, VKIV, VL1, VL2, or VL3.

In certain aspects of the invention the VKI germline gene is VKI (A20), the VKII germline gene is VKII (A3), the VKIII germline gene is VKIII (A27), and the VKIV germline gene is VKIV (B3). In other aspects of the invention, the VL1 germline gene is VL1 (V1-13), VL1 (V1-16), VL1 (V1-17), or VL1 (V1-19). Alternatively, the VL2 germline gene is VL2 (V1-3) or VL2 (V1-4). Furthermore, the VL3 germline gene is VL3 (V2-14).

Specific combinations of a VH- and HL-locus are provided for each HA antibody described below.

The CDR regions of the HA antibodies of the invention were determined according to Kabat et al. (1991) as described in Sequences of Proteins of Immunological Interest. In certain embodiments of the invention, HA antibodies contain two, three, four, five or all six CDR regions as disclosed herein. Preferably, HA antibodies contain at least two of the CDRs disclosed herein.

The SC06-141 HA-specific single-chain Fv antibody includes a heavy chain variable region (SEQ ID NO: 309) and a light chain variable region (SEQ ID NO: 310) encoded by the nucleic acid sequence shown in SEQ ID NO: 311 and the amino acid sequence shown in SEQ ID NO: 312. The VH-locus is VH1 (1-18) and the VL locus is HKIV (B3).

The amino acids encompassing the CDRs are highlighted in bold in the sequences below. The heavy chain CDRs of the SC06-141 antibody have the following CDR sequences: GYYVY (HCDR1, SEQ ID NO: 566), WISAYNGNTNYAQKFQG (HCDR2, SEQ ID NO: 567) and SRSLDV (HCDR3, SEQ ID NO: 568). The light chain CDRs of the SC06-141 antibody have the following CDR sequences: KSSQSVLYSSNNKNYLA (LCDR1, SEQ ID NO: 569), WASTRES (LCDR2, SEQ ID NO: 570) and QQYYSTPLT (LCDR3, SEQ ID NO: 200).

```
SC06-141 nucleotide sequence
                                                              (SEQ ID NO: 311)
         gaggtccagc tggtgcagtc tggggctgag gtgaagaagc ctggggcctc agtgaaggtc    60
         tcctgcaagg cttctgggta caccttcacc ggctactatg tgtactgggt gcgacaggcc   120
         cctggacaag ggcttgagtg gatgggatgg atcagcgctt acaatggtaa cacaaactat   180
         gcacagaagt tccagggcag agtcacgatt accgcggaca atccacgag cacagcctac    240
         atggagctga gcagcctgag atctgaagac acggctgtgt attactgtgc gagaagtaga   300
         tccctggacg tctggggcca agggaccacg gtcaccgtct cgagcggtac gggcggttca   360
         ggcggaaccg gcagcggcac tggcgggtcg acggatgttg tgatgactca gtctccagac   420
         tccctggctg tgtctctggg cgagagggcc accatcaact gcaagtccag ccagagtgtt   480
         ttatacagct ccaacaataa gaactactta gcttggtacc agcagaaacc aggacagcct   540
         cctaagctgc tcatttactg ggcatctacc cgggaatccg gggtccctga ccgattcagt   600
         ggcagcgggt ctgggacaga tttcactctc accatcagca gcctgcaggc tgaagatgtg   660
         gcagtttatt actgtcagca atattatagt actcctctca ctttcggcgg agggaccaaa   720
         gtggatatca aacgt                                                     735

SC06-141 amino acid sequence
                                                              (SEQ ID NO: 312)
EVQLVQSGAEVKKPGASVKVSCKASGYTFTGYYVYWVRQAPGQGLEWMGWISAYNGNT
NYAQKFQGRVTITADKSTSTAYMELSSLRSEDTAVYYCARSRSLDVWGQGTTVTVSSGTG
GSGGTGSGTGGSTDVVMTQSPDSLAVSLGERATINCKSSQSVLYSSNNKNYLAWYQQKPG
QPPKLLIYWASTRESGVPDRFSGSGSGTDFTLTISSLQAEDVAVYYCQQYYSTPLTFGGGTK
VDIKR SC06-141 VH amino acid sequence
                                                              (SEQ ID NO: 309)
EVQLVQSGAEVKKPGASVKVSCKASGYTFTGYYVYWVRQAPGQGLEWMG**WISAYNGN
TNYAQKFQGRVTITADKSTSTAYMELSSLRSEDTAVYYCARSRSLDV**WGQGTTVTVSS
```

```
SC06-141 VL amino acid sequence
                                                           (SEQ ID NO: 310)
DVVMTQSPDSLAVSLGERATINCKSSQSVLYSSNNKNYLAWYQQKPGQPPKLLIYWAST
RESGVPDRFSGSGSGTDFTLTISSLQAEDVAVYYCQQYYSTPLTFGGGTKVDIKR
```

The SC06-255 HA-specific single-chain Fv antibody includes a heavy chain variable region (SEQ ID NO: 313) and a light chain variable region (SEQ ID NO: 314) encoded by the nucleic acid sequence shown in SEQ ID NO: 315 and the amino acid sequence shown in SEQ ID NO: 316. The VH-locus is VH1 (1-69) and the VL locus is VL1 (V1-16).

The amino acids encompassing the CDRs are highlighted in bold in the sequences below. The heavy chain CDRs of the SC06-255 antibody have the following CDR sequences: SYAIS (HCDR1, SEQ ID NO: 571), GIIPIFGTTKYAPKFQG (HCDR2, SEQ ID NO: 572) and HMGYQVRETMDV (HCDR3, SEQ ID NO: 573). The light chain CDRs of the SC06-255 antibody have the following CDR sequences: SGSTFNIGSNAVD (LCDR1, SEQ ID NO: 574), SNNQRPS (LCDR2, SEQ ID NO: 575) and AAWDDILNVPV (LCDR3, SEQ ID NO: 576).

```
SC06-255 nucleotide sequence
                                                           (SEQ ID NO: 315)
gaggtgcagc tggtggagtc tgggggctgag gtgaagaagc ctgggtcctc ggtgaaagtc    60
tcttgcaagg cttctggagg cccttccgc agctatgcta tcagctgggt gcgacaggcc   120
cctggacaag ggcctgagtg gatgggaggg atcatcccta tttttggtac aacaaaatac   180
gcaccgaagt tccagggcag agtcacgatt accgcggacg atttcgcggg cacagtttac   240
atggagctga gcagcctgcg atctgaggac acggccatgt actactgtgc gaaacatatg   300
gggtaccagg tgcgcgaaac tatggacgtc tggggccaaag ggaccacggt caccgtctcg   360
agcggtacgg gcggttcagg cggaaccggc agcggcactg gcgggtcgac gtcctatgtg   420
ctgactcagc caccctcagc gtctgggacc cccgggcaga gggtcaccat ctcttgttct   480
ggaagcacgt tcaacatcgg aagtaatgct gtagactggt accggcagct cccaggaacg   540
gcccccaaac tcctcatcta tagtaatgct cagcggccct cagggggtccc tgaccgattc   600
tctggctcca ggtctggcac ctcagcctcc ctggccatca gtgggctcca gtctgaggat   660
gaggctgatt attactgtgc agcatgggat gacatcctga atgttccggt attcggcgga   720
gggaccaagc tgaccgtcct aggt                                          744

SC06-255 amino acid sequence
                                                           (SEQ ID NO: 316)
EVQLVESGAEVKKPGSSVKVSCKASGGPFRSYAISWVRQAPGQGPEWMGGIIPIFGTTKYA
PKFQGRVTITADDFAGTVYMELSSLRSEDTAMYYCAKHMGYQVRETMDVWGKGITVTV
SSGTGGSGGTGSGTGGSTSYVLTQPPSASGTPGQRVTISCSGSTFNIGSNAVDWYRQLPGTA
PKLLIYSNNQRPSGVPDRFSGSRSGTSASLAISGLQSEDEADYYCAAWDDILNVPVFGGGT
KLTVLG SC06-255 VH amino acid sequence
                                                           (SEQ ID NO: 313)
EVQLVESGAEVKKPGSSVKVSCKASGGPFRSYAISWVRQAPGQGPEWMGGIIPIFGTTKY
APKFQGRVTITADDFAGTVYMELSSLRSEDTAMYYCAKHMGYQVRETMDVWGKG
TTVTVSS SC06-255 VL amino acid sequence
                                                           (SEQ ID NO: 314)
SYVLTQPPSASGTPGQRVTISCSGSTFNIGSNAVDWYRQLPGTAPKLLIYSNNQRPSGVPD
RFSGSRSGTSASLAISGLQSEDEADYYCAAWDDILNVPVFGGGTKLTVLG
```

The SC06-257 HA-specific single-chain Fv antibody includes a heavy chain variable region (SEQ ID NO: 317) and a light chain variable region (SEQ ID NO: 318) encoded by the nucleic acid sequence shown in SEQ ID NO: 319 and the amino acid sequence shown in SEQ ID NO: 320. The VH-locus is VH1 (1-69) and the VL locus is VL2 (V1-4).

The amino acids encompassing the CDRs are highlighted in bold in the sequences below. The heavy chain CDRs of the SC06-257 antibody have the following CDR sequences: SYAIS (HCDR1, SEQ ID NO: 571), GIIPIFGTTKYAPKFQG (HCDR2, SEQ ID NO: 572) and HMGYQVRETMDV (HCDR3, SEQ ID NO: 573). The light chain CDRs of the SC06-257 antibody have the following CDR sequences: TGTSSDVGGYNYVS (LCDR1, SEQ ID NO: 577), EVSNRPS (LCDR2, SEQ ID NO: 578) and SSYTSSSTY (LCDR3, SEQ ID NO: 579).

```
SC06-257 nucleotide sequence
                                                           (SEQ ID NO: 319)
caggtccagc tggtgcagtc tgggggctgag gtgaagaagc ctgggtcctc ggtgaaagtc    60
tcttgcaagg cttctggagg cccttccgc agctatgcta tcagctgggt gcgacaggcc   120
cctggacaag ggcctgagtg gatgggaggg atcatcccta tttttggtac aacaaaatac   180
```

```
                                              -continued
gcaccgaagt tccagggcag agtcacgatt accgcggacg atttcgcggg cacagtttac      240
atggagctga gcagcctgcg atctgaggac acggccatgt actactgtgc gaaacatatg      300
gggtaccagg tgcgcgaaac tatggacgtc tggggcaaag gaccacggt caccgtctcg       360
agcggtacgg gcggttcagg cggaaccggc agcggcactg gcgggtcgac gcagtctgcc      420
ctgactcagc ctgccgccgt gtctgggtct cctggacagt cgatcaccat ctcctgcact      480
ggaaccagca gtgacgttgg tggttataac tatgtctcct ggtaccaaca gcacccaggc      540
aaagccccca aactcatgat ttatgaggtc agtaatcggc cctcagggt ttctaatcgc       600
ttctctggct ccaagtctgg caacacgcc tccctgacca tctctgggct ccaggctgag      660
gacgaggctg attattactg cagctcatat acaagcagca gcacttatgt cttcggaact      720
gggaccaagg tcaccgtcct aggt                                              744

SC06-257 amino acid sequence
                                                    (SEQ ID NO: 320)
QVQLVQSGAEVKKPGSSVKVSCKASGGPFRSYAISWVRQAPGQGPEWMGGIIPIFGTTKY
APKFQGRVTITADDFAGTVYMELSSLRSEDTAMYYCAKHMGYQVRETMDVWGKGTTVT
VSSGTGGSGGTGSGTGGSTQSALTQPAAVSGSPGQSITISCTGTSSDVGGYNYVSWYQQHP
GKAPKLMIYEVSNRPSGVSNRFSGSKSGNTASLTISGLQAEDEADYYCSSYTSSSTYVFGTG
TKVTVLG SC06-257 VH amino acid sequence
                                                    (SEQ ID NO: 317)
QVQLVQSGAEVKKPGSSVKVSCKASGGPFRSYAISWVRQAPGQGPEWMGGIIPIFGTTKY
APKFQGRVTITADDFAGTVYMELSSLRSEDTAMYYCAKHMGYQVRETMDVWGKGTTV
TVSS SC06-257 VL amino acid sequence
                                                    (SEQ ID NO: 318)
QSALTQPAAVSGSPGQSITISCTGTSSDVGGYNYVSWYQQHPGKAPKLMIYEVSNRPSGV
SNRFSGSKSGNTASLTISGLQAEDEADYYCSSYTSSSTYVFGTGTKVTVLG
```

The SC06-260 HA-specific single-chain Fv antibody includes a heavy chain variable region (SEQ ID NO: 321) and a light chain variable region (SEQ ID NO: 322) encoded by the nucleic acid sequence shown in SEQ ID NO: 323 and the amino acid sequence shown in SEQ ID NO: 324. The VH-locus is VH1 (1-69) and the VL locus is VL1 (V1-17).

```
SC06-260 nucleotide sequence
                                                    (SEQ ID NO: 323)
            gaggtgcagc tggtggagtc tggggctgag gtgaagaagc ctgggtcctc ggtgaaagtc      60
            tcttgcaagg cttctggagg cccttccgc agctatgcta tcagctgggt gcgacaggcc      120
            cctggacaag ggcctgagtg gatgggaggg atcatcccta ttttggtac aacaaaatac       180
            gcaccgaagt tccagggcag agtcacgatt accgcggacg atttcgcggg cacagtttac      240
            atggagctga gcagcctgcg atctgaggac acggccatgt actactgtgc gaaacatatg      300
            gggtaccagg tgcgcgaaac tatggacgtc tggggcaaag gaccacggt caccgtctcg       360
            agcggtacgg gcggttcagg cggaaccggc agcggcactg gcgggtcgac gtcctatgtg      420
            ctgactcagc caccctcagt ctctgggacc gggtcaccat ctcttgctct                 480
            ggaagccgct ccaacgtcgg agataattct gtatattggt atcaacacgt cccagaaatg      540
            gcccccaaac tcctcgtcta taagaatact caacggccct caggagtccc tgcccggttt      600
            tccggctcca agtctggcac ttcagcctcc ctggccatca ttggcctcca gtccggcgat      660
            gaggctgatt attattgtgt ggcatgggat gacagcgtag atggctatgt cttcggatct      720
            gggaccaagg tcaccgtcct aggt                                              744

SC06-260 amino acid sequence
                                                    (SEQ ID NO: 324)
EVQLVESGAEVKKPGSSVKVSCKASGGPFRSYAISWVRQAPGQGPEWMGGIIPIFGTTKYA
PKFQGRVTITADDFAGTVYMELSSLRSEDTAMYYCAKHMGYQVRETMDVWGKGTTVTV
SSGTGGSGGTGSGTGGSTSYVLTQPPSVSGTPGQRVTISCSGSRSNVGDNSVYWYQHVPE
MAPKLLVYKNTQRPSGVPARFSGSKSGTSASLAIIGLQSGDEADYYCVAWDDSVDGYVFG
SGTKVTVLG SC06-260 VH amino acid sequence
                                                    (SEQ ID NO: 321)
EVQLVESGAEVKKPGSSVKVSCKASGGPFRSYAISWVRQAPGQGPEWMGGIIPIFGTTKY
APKFQGRVTITADDFAGTVYMELSSLRSEDTAMYYCAKHMGYQVRETMDVWGKGTTV
TVSS SC06-260 VL amino acid sequence
                                                    (SEQ ID NO: 322)
SYVLTQPPSVSGTPGQRVTISCSGSRSNVGDNSVYWYQHVPEMAPKLLVYKNTQRPSGVP
ARFSGSKSGTSASLAIIGLQSGDEADYYCVAWDDSVDGYVFGSGTKVTVLG
```

The amino acids encompassing the CDRs are highlighted in bold in the sequences below. The heavy chain CDRs of the SC06-260 antibody have the following CDR sequences: SYAIS (HCDR1, SEQ ID NO: 571), GIIPIFGTTKYAPK- FQG (HCDR2, SEQ ID NO: 572) and HMGYQVRETMDV (HCDR3, SEQ ID NO: 573). The light chain CDRs of the SC06-260 antibody have the following CDR sequences: SGSRSNVGDNSVY (LCDR1, SEQ ID NO: 580), KNTQRPS (LCDR2, SEQ ID NO: 581) and VAWDDS-VDGYV (LCDR3, SEQ ID NO: 582).

The SC06-261 HA-specific single-chain Fv antibody includes a heavy chain variable region (SEQ ID NO: 325) and a light chain variable region (SEQ ID NO: 326) encoded by the nucleic acid sequence shown in SEQ ID NO: 327 and the amino acid sequence shown in SEQ ID NO: 328. The VH-locus is VH1 (1-69) and the VL locus is VL1 (V1-19).

The amino acids encompassing the CDRs are highlighted in bold in the sequences below. The heavy chain CDRs of the SC06-261 antibody have the following CDR sequences: SYAIS (HCDR1, SEQ ID NO: 571), GIIPIFGTTKYAPK-FQG (HCDR2, SEQ ID NO: 572) and HMGYQVRETMDV (HCDR3, SEQ ID NO: 573). The light chain CDRs of the SC06-261 antibody have the following CDR sequences: SGSSSNIGNDYVS (LCDR1, SEQ ID NO: 583), DNN-KRPS (LCDR2, SEQ ID NO: 584) and ATWDRRPTAYVV (LCDR3, SEQ ID NO: 585).

```
SC06-261 nucleotide sequence
                                                          (SEQ ID NO: 327)
gaggtgcagc tggtggagtc tggggctgag gtgaagaagc ctgggtcctc ggtgaaagtc     60
tcttgcaagg cttctggagg ccccttccgc agctatgcta tcagctgggt gcgacaggcc    120
cctggacaag ggcctgagtg gatgggaggg atcatcccta tttttggtac aacaaaatac    180
gcaccgaagt tccagggcag agtcacgatt accgcggacg atttcgcggg cacagtttac    240
atggagctga gcagcctgcg atctgaggac acggccatgt actactgtgc gaaacatatg    300
gggtaccagg tgcgcgaaac tatggacgtc tggggcaaag ggaccacggt caccgtctcg    360
agcggtacgg gcggttcagg cggaaccggc agcggcactg gcggtcgac gcagtcgtg      420
ttgacgcagc cgccctcagt gtctgcggcc ccaggacaga aggtcaccat ctcctgctct    480
ggaagcagct ccaacattgg gaatgattat gtatcctggt accagcagct cccaggaaca    540
gccccaaac  tcctcattta tgacaataat aagcgaccct cagggattcc tgaccgattc    600
tctggctcca agtctggcac gtcagccacc ctgggcatca ccggactcca gactggggac    660
gaggccaact attactgcgc aacatgggat cgccgcccga ctgcttatgt tgtcttcggc    720
ggagggacca agctgaccgt cctaggt                                        747

SC06-261 amino acid sequence
                                                          (SEQ ID NO: 328)
EVQLVESGAEVKKPGSSVKVSCKASGGPPFRSYAISWVRQAPGQGPEWMGGIIPIFGTTKYA
PKFQGRVTITADDFAGTVYMELSSLRSEDTAMYYCAKHMGYQVRETMDVWGKGTTVTV
SSGTGGSGGTGSGTGGSTQSVLTQPPSVSAAPGQKVTISCSGSSSNIGNDYVSWYQQLPGT
APKLLIYDNNKRPSGIPDRFSGSKSGTSATLGITGLQTGDEANYYCATWDRRPTAYVVFGG
GTKLTVLG SC06-261 VH amino acid sequence
                                                          (SEQ ID NO: 325)
EVQLVESGAEVKKPGSSVKVSCKASGGPPFRSYAISWVRQAPGQGPEWMG**GIIPIFGTTKY
APKFQGRVTITADDFAGTVYMELSSLRSEDTAMYYCAKHMGYQVRETMDV**WGKGTTV
TVSS SC06-261 VL amino acid sequence
                                                          (SEQ ID NO: 326)
SVLTQPPSVSAAPGQKVTISCSGSSSNIGNDYVSWYQQLPGTAPKLLIYDNNKRPSGIPDRF
SGSKSGTSATLGITGLQTGDEANYYCATWDRRPTAYVVFGGGTKLTVLG
```

The SC06-262 HA-specific single-chain Fv antibody includes a heavy chain variable region (SEQ ID NO: 329) and a light chain variable region (SEQ ID NO: 330) encoded by the nucleic acid sequence shown in SEQ ID NO: 331 and the amino acid sequence shown in SEQ ID NO: 332. The VH-locus is VH1 (1-69) and the VL locus is VKI (A20).

The amino acids encompassing the CDRs are highlighted in bold in the sequences below. The heavy chain CDRs of the SC06-262 antibody have the following CDR sequences: GSAIS (HCDR1, SEQ ID NO: 586), GISPLFGTTNYAQK-FQG (HCDR2, SEQ ID NO: 587) and GPKYYSEYMDV (HCDR3, SEQ ID NO: 588). The light chain CDRs of the SC06-262 antibody have the following CDR sequences: RASQGISSYLA (LCDR1, SEQ ID NO: 589), DASTLRS (LCDR2, SEQ ID NO: 590) and QRYNSAPPI (LCDR3, SEQ ID NO: 591).

```
SC06-262 nucleotide sequence
                                                          (SEQ ID NO: 331)
caggtacagc tgcagcagtc aggggctgag gtgaagaagc ctgggtcctc ggtgaaggtc     60
tcctgcaagg tttccggagt cattttcagc ggcagtgcga tcagctgggt gcgacaggcc    120
cctggacaag gccttgagtg gatgggaggg atcagccctc tctttggcac aacaaattac    180
gcacaaaagt tccagggcag agtcacgatt accgcggacc aatccacgaa cacaacctac    240
atggaggtga acagcctgag atatgaggac acggccgtgt atttctgtgc gcgaggtcca    300
aaatattaca gtgagtacat ggacgtctgg ggcaaaggga ccacggtcac cgtctcgagc    360
ggtacgggcg gttcaggcgg aaccggcagc ggcactggcg ggtcgacgga catccagatg    420
acccagtctc catcctccct gtctgcatct gtaggagaca gagtcaccat cacttgccgg    480
gcgagtcagg gcattagcag ttatttagcc tggtatcagc agaagccagg gaaagttcct    540
acactcctga tctatgatgc atccactttg cgatcagggg tcccatctcg cttcagtggc    600
agtggatctg cgacagattt cactctcacc atcagcagcc tgcagcctga agatgttgca    660
acttattact gtcaaaggta taacagtgcc cccccgatca ccttcggcca agggacacga    720
ctggagatta aacgt                                                    735

SC06-262 amino acid sequence
                                                          (SEQ ID NO: 332)
QVQLQQSGAEVKKPGSSVKVSCKVSGVIFSGSAISWVRQAPGQGLEWMGGISPLFGTTNY
AQKFQGRVTITADQSTNTTYMEVNSLRYEDTAVYFCARGPKYYSEYMDVWGKGTTVTVS
SGTGGSGGTGSGTGGSTDIQMTQSPSSLSASVGDRVTITCRASQGISSYLAWYQQKPGKVP
TLLIYDASTLRSGVPSRFSGSGSATDFTLTISSLQPEDVATYYCQRYNSAPPITFGQGTRLEIK
R
```

```
SC06-262 VH amino acid sequence
                                                           (SEQ ID NO: 329)
QVQLQQSGAEVKKPGSSVKVSCKVSGVIFSGSAISWVRQAPGQGLEWMGGISPLFGTTN
YAQKFQGRVTITADQSTNTTYMEVNSLRYEDTAVYFCARGPKYYSEYMDVWGKGTTVT
VSS SC06-262 VL amino acid sequence
                                                           (SEQ ID NO: 330)
DIQMTQSPSSLSASVGDRVTITCRASQGISSYLAWYQQKPGKVPTLLIYDASTLRSGVPSRF
SGSGSATDFTLTISSLQPEDVATYYCQRYNSAPPITFGQGTRLEIKR
```

The SC06-268 HA-specific single-chain Fv antibody includes a heavy chain variable region (SEQ ID NO: 333) and a light chain variable region (SEQ ID NO: 334) encoded by the nucleic acid sequence shown in SEQ ID NO: 335 and the amino acid sequence shown in SEQ ID NO: 336. The VH-locus is VH1 (1-69) and the VL locus is VL3 (V2-14).

The amino acids encompassing the CDRs are highlighted in bold in the sequences below. The heavy chain CDRs of the SC06-268 antibody have the following CDR sequences: SYAIS (HCDR1, SEQ ID NO: 571), GIMGMFGTT-NYAQKFQG (HCDR2, SEQ ID NO: 592) and SSGYYPEY-FQD (HCDR3, SEQ ID NO: 593). The light chain CDRs of the SC06-268 antibody have the following CDR sequences: SGHKLGDKYVS (LCDR1, SEQ ID NO: 594), QDNRRPS (LCDR2, SEQ ID NO: 595) and QAWDSSTA (LCDR3, SEQ ID NO: 596).

The SC06-272 HA-specific single-chain Fv antibody includes a heavy chain variable region (SEQ ID NO: 337) and a light chain variable region (SEQ ID NO: 338) encoded by the nucleic acid sequence shown in SEQ ID NO: 339 and the amino acid sequence shown in SEQ ID NO: 340. The VH-locus is VH1 (1-69) and the VL locus is VL2 (V1-3).

The amino acids encompassing the CDRs are highlighted in bold in the sequences below. The heavy chain CDRs of the SC06-272 antibody have the following CDR sequences: SYAIT (HCDR1, SEQ ID NO: 597), GIIGMFGSTNYAQN-FQG (HCDR2, SEQ ID NO: 598) and STGYYPAYLHH (HCDR3, SEQ ID NO: 599). The light chain CDRs of the SC06-272 antibody have the following CDR sequences: TGTSSDVGGYNYVS (LCDR1, SEQ ID NO: 577). DVSKRPS (LCDR2, SEQ ID NO: 601) and SSYTSSSTHV (LCDR3, SEQ ID NO: 602).

SC06-268 nucleotide sequence (SEQ ID NO: 335)

```
caggtccagc tggtacagtc tggggctgag gtgaagaagc ctgggtcctc ggtgaaggtc    60
tcctgcaagg cttctggagg caccttcagt agttatgcta tcagctgggt gcgacaggcc   120
cctggacaag ggcttgagtg gatgggagga atcatgggta tgtttggcac aactaactac   180
gcacagaagt tccagggcag agtcacgatt accgcggacg aattcacgag cgcagcctac   240
atggagctga ggagcctgag atctgaggac acggccgtct actactgtgc gaggtctagt   300
ggttattacc ccgaatactt ccaggactgg ggccagggca ccctggtcac cgtctcgagc   360
ggtacgggcg gttcaggcgg aaccggcagc ggcactggcg ggtcgacgca gtctgtgctg   420
actcagccac cctcagagtc cgtgtcccca ggacagacag ccagcgtcac ctgctctgga   480
cataaattgg gggataaata tgtttcgtgg tatcagcaga agccaggcca gtcccctgta   540
ttactcatct atcaagataa caggcggccc tcagggatcc ctgagcgatt cataggctcc   600
aactctggga acacagccac tctgaccatc agcgggaccc aggctctgga tgaggctgac   660
tattactgtc aggcgtggga cagcagcact gcggttttcg gcggagggac caagctgacc   720
gtcctaggt                                                            729
```

SC06-268 amino acid sequence (SEQ ID NO: 336)

QVQLVQSGAEVKKPGSSVKVSCKASGGTFSSYAISWVRQAPGQGLEWMGGIMGMFGTTN
YAQKFQGRVTITADEFTSAAYMELRSLRSEDTAVYYCARSSGYYPEYFQDWGQGTLVTVS
SGTGGSGGTGSGTGGSTQSVLTQPPSESVSPGQTASVTCSGHKLGDKYVSWYQQKPGQSP
VLLIYQDNRRPSGIPERFIGSNSGNTATLTISGTQALDEADYYCQAWDSSTAVFGGGTKLTV
LG

SC06-268 VH amino acid sequence (SEQ ID NO: 333)

QVQLVQSGAEVKKPGSSVKVSCKASGGIFSSYAISWVRQAPGQGLEWMGGIMGMFGTT
NYAQKFQGRVTITADEFTSAAYMELRSLRSEDTAVYYCARSSGYYPEYFQDWGQGTLVT
VSS

SC06-268 VL amino acid sequence (SEQ ID NO: 334)

QSVLTQPPSESVSPGQTASVTCSGHKLGDKYVSWYQQKPGQSPVLLIYQDNRRPSGIPERF
IGSNSGNTATLTISGTQALDEADYYCQAWDSSTAVFGGGTKLTVLG

```
SC06-272 nucleotide sequence
                                                                 (SEQ ID NO: 339)
cagatgcagc tggtgcagtc tggggctgag gtgaagaagc ctgggtcctc ggtgaaggtc    60
tcctgcaagg cttctggagg caccttctcc agttatgcta tcacctgggt gcgacaggcc   120
cctggacaag ggcttgagtg gatgggaggg atcatcggta tgtttggttc aacaaactac   180
gcacagaact tccagggcag agtcacgatt accgcggacg aatccacgag cacagcctac   240
atggagctga gcagcctcag atctgaggac acggccgtgt attactgtgc gagaagtact   300
ggttattacc ctgcatacct ccaccactgg ggccagggca ccctggtcac cgtctcgagc   360
ggtacgggcg gttcaggcgg aaccggcagc ggcactggcg gtcgacgca gtctgccctg   420
actcagcctc gctcagtgtc cgggtctcct ggacagtcag tcaccatctc ctgcactgga   480
accagcagtg atgttggtgg ttataactat gtctcctggt accaacagca cccaggcaaa   540
gcccccaaac tcatgattta tgatgtcagt aagcggccct caggggtccc tgatcgcttc   600
tctggctcca agtctggcaa cacggcctcc ctgaccatct ctgggctcca ggctgaggat   660
gaggctgatt attactgcag ctcatataca agcagcagca ctcatgtctt cggaactggg   720
accaaggtca ccgtcctagg t                                             741

SC06-272 amino acid sequence
                                                                 (SEQ ID NO: 340)
QMQLVQSGAEVKKPGSSVKVSCKASGGTFSSYAITWVRQAPGQGLEWMGGIIGMFGSTY
AQNFQGRVTITADESTSTAYMELSSLRSEDTAVYYCARSTGYYPAYLHHWGQGTLVTVS
SGTGGSGGTGSGTGGSTQSALTQPRSVSGSPGQSVTISCTGTSSDVGGYNYVSWYQQHPG
KAPKLMIYDVSKRPSGVPDRFSGSKSGNTASLTISGLQAEDEADYYCSSYTSSSTHVFGTG
TKVTVLG SC06-272 VH amino acid sequence
                                                                 (SEQ ID NO: 337)
QMQLVQSGAEVKKPGSSVKVSCKASGGTFSSYAITWVRQAPGQGLEWMGGIIGMFGST
NYAQNFQGRVTITADESTSTAYMELSSLRSEDTAVYYCARSTGYYPAYLHHWGQGTLVT
VSS SC06-272 VL amino acid sequence
                                                                 (SEQ ID NO: 338)
QSALTQPRSVSGSPGQSVTISCTGTSSDVGGYNYVSWYQQHPGKAPKLMIYDVSKRPSGV
PDRFSGSKSGNTASLTISGLQAEDEADYYCSSYTSSSTHVFGTGTKVTVLG
```

The SC06-296 HA-specific single-chain Fv antibody includes a heavy chain variable region (SEQ ID NO: 341) and a light chain variable region (SEQ ID NO: 342) encoded by the nucleic acid sequence shown in SEQ ID NO: 343 and the amino acid sequence shown in SEQ ID NO: 344. The VH-locus is VH1 (1-2) and the VL locus is VKIII (A27).

The amino acids encompassing the CDRs are highlighted in bold in the sequences below. The heavy chain CDRs of the SC06-296 antibody have the following CDR sequences: SYYMH (HCDR1, SEQ ID NO: 603), WINPNSGGT-NYAQKFQG (HCDR2, SEQ ID NO: 604) and EGKWG-PQAAFDI (HCDR3, SEQ ID NO: 605). The light chain CDRs of the SC06-296 antibody have the following CDR sequences: RASQSVSSSYLA (LCDR1, SEQ ID NO: 646). DASSRAT (LCDR2, SEQ ID NO: 607) and QQYGSSLW (LCDR3, SEQ ID NO: 608).

```
SC06-296 nucleotide sequence
                                                                 (SEQ ID NO: 343)
         gaggtgcagc tggtggagac cggggctgag gtgaagaagc ctggggcctc agtgaaggtt    60
         tcctgcaagg catctggata caccttcacc agctactata tgcactgggt gcgacaggcc   120
         cctggacaag ggcttgagtg gatgggatgg atcaacccta acagtggtgg cacaaactat   180
         gcacagaagt tccagggcag ggtcaccatg accagggaca cgtccatcag cacagcctac   240
         atggagctga gcaggctgag atctgacgac acggccgtgt attactgtgc gagagaggg   300
         aaatggggac tcaagcggc ttttgatatc tggggccaag ggacaatggt caccgtctcg   360
         agcggtacgg gcggttcagg cggaaccggc agcggcactg gcgggtcgac ggaaattgtg   420
         atgacgcagt ctccaggcac cctgtctttg tctccagggg aaagagccac cctctcctgc   480
         agggccagtc agagtgttag cagcagctac ttagcctggt accagcagaa acctggccag   540
         gctcccaggc tcctcatcta tgatgcatcc agcagggcca ctgacatccc agacaggttc   600
         agtggcagtg ggtctgggac agacttcact ctcaccatca gcagactgga gcctgaagat   660
         tttgcagtgt attactgtca gcagtatggt agctcacttt ggacgttcgg ccaagggacc   720
         aaggtggaga tcaaacgt                                                  738

SC06-296 amino acid sequence
                                                                 (SEQ ID NO: 344)
         EVQLVETGAEVKKPGASVKVSCKASGYTFTSYYMHWVRQAPGQGLEWMGWINPNSGGT
         NYAQKFQGRVTMTRDTSISTAYMELSRLRSDDTAVYYCAREGKWGPQAAFDIWGQGTM
         VTVSSGTGGSGGTGSGTGGSTEIVMTQSPGTLSLSPGERATLSCRASQSVSSSYLAWYQQK
         PGQAPRLLIYDASSRATDIPDRFSGSGSGTDFTLTISRLEPEDFAVYYCQQYGSSLWTFGQG
         TKVEIKR SC06-296 VH amino acid sequence
                                                                 (SEQ ID NO: 341)
         EVQLVETGAEVKKPGASVKVSCKASGYTFTSYYMHWVRQAPGQGLEWMGWINPNSGG
         TNYAQKFQGRVTMTRDTSISTAYMELSRLRSDDTAVYYCAREGKWGPQAAFDIWGQGT
         MVTVSS
```

SC06-296 VL amino acid sequence
(SEQ ID NO: 342)
EIVMTQSPGTLSLSPGERATLSCRASQSVSSSYLAWYQQKPGQAPRLLIYDASSRATDIPDR
FSGSGSGTDFTLTISRLEPEDFAVYYCQQYGSSLWTFGQGTKVEIKR The SC06-301 HA-specific single-chain Fv antibody includes a heavy chain variable region (SEQ ID NO: 345) and a light chain variable region (SEQ ID NO: 346) encoded by the nucleic acid sequence shown in SEQ ID NO: 347 and the amino acid sequence shown in SEQ ID NO: 348. The VH-locus is VH1 (3-23) and the VL locus is VKII (A3).

The amino acids encompassing the CDRs are highlighted in bold in the sequences below. The heavy chain CDRs of the SC06-301 antibody have the following CDR sequences: IYAMS (HCDR1, SEQ ID NO: 609), AISSSGDSTYYADSVKG (HCDR2, SEQ ID NO: 610) and AYGYTFDP (HCDR3, SEQ ID NO: 611). The light chain CDRs of the SC06-301 antibody have the following CDR sequences: RSSQSLLHSNGYNYLD (LCDR1, SEQ ID NO: 612), LGSNRAS (LCDR2, SEQ ID NO: 613) and MQALQTPL (LCDR3, SEQ ID NO: 614).

```
SC06-301 nucleotide sequence
                                                  (SEQ ID NO: 347)
gaggtgcagc tggtagagtc tggggaggc ttggtacagc ctgggggtc cctgagactc       60
tcctgtgcag cctctggatt cacctttagc atctatgcca tgagctgggt ccgccaggca    120
ccagggaagg ggctggagtg ggtctcagct attagtagta gtggtgatag cacatactac    180
gcagactccg tgaagggccg gttcaccatc tccagagaca acgccaggaa cacgctgtat    290
ctgcaaatga acagtctgag agccgaggac acggctgtgt attactgtgc gagagcgtat    300
ggctacacgt tcgacccctg gggccaggga accctggtca ccgtctcgag cggtacgggc    360
ggttcaggcg gaaccggcag cggcactggc gggtcgacgg aaattgtgct gactcagtct    420
ccactctccc tgcccgtcac cctggagag ccggcctcca tctcctgcag gtctagtcag     480
agcctcctgc atagtaatgg atacaactat ttggattggt acctgcagaa gccagggcag    590
tctccacagc tcctgatcta tttgggttct aatcgggcct ccggggtccc tgacaggttc    600
agtggcagtg gatcaggcac agattttaca ctgaaaatca gcagagtgga ggctgaggat    660
gttggggttt attactgcat gcaagctcta caaactcccc tcactttcgg cggagggacc    720
aaggtggaga tcaaacgt                                                  738

SC06-301 amino acid sequence
                                                  (SEQ ID NO: 348)
EVQLVESGGGLVQPGGSLRLSCAASGFTFSIYAMSWVRQAPGKGLEWVSAISSSGDSTYY
ADSVKGRFTISRDNARNTLYLQMNSLRAEDTAVYYCARAYGYTFDPWGQGTLVTVSSGT
GGSGGTGSGTGGSTEIVLTQSPLSLPVTPGEPASISCRSSQSLLHSNGYNYLDWYLQKPGQS
PQLLIYLGSNRASGVPDRFSGSGSGTDFTLKISRVEAEDVGVYYCMQALQTPLTFGGGTKV
EIKR SC06-301 VH amino acid sequence
                                                  (SEQ ID NO: 345)
EVQLVESGGGLVQPGGSLRLSCAASGFTFSIYAMSWVRQAPGKGLEWVSAISSSGDSTYY
ADSVKGRFTISRDNARNTLYLQMNSLRAEDTAVYYCARAYGYTFDPWGQGTLVTVSS SC06-301 VL amino acid sequence
                                                  (SEQ ID NO: 346)
EIVLTQSPLSLPVTPGEPASISCRSSQSLLHSNGYNYLDWYLQKPGQSPQLLIYLGSNRASG
VPDRFSGSGSGTDFTLKISRVEAEDVGVYYCMQALQTPLTFGGGTKVEIKR
```

The SC06-307 HA-specific single-chain Fv antibody includes a heavy chain variable region (SEQ ID NO: 349) and a light chain variable region (SEQ ID NO: 350) encoded by the nucleic acid sequence shown in SEQ ID NO: 351 and the amino acid sequence shown in SEQ ID NO: 352. The VH-locus is VH3 (3-21) and the VL locus is VKIII (A27).

The amino acids encompassing the CDRs are highlighted in bold in the sequences below. The heavy chain CDRs of the SC06-307 antibody have the following CDR sequences: SYSMN (HCDR1, SEQ ID NO: 615), SISSSSSYIYYVDSVKG (HCDR2, SEQ ID NO: 616) and GGGSYGAYEGFDY (HCDR3, SEQ ID NO: 617). The light chain CDRs of the SC06-307 antibody have the following CDR sequences: RASQRVSSYLA (LCDR1, SEQ ID NO: 618), GASTRAA (LCDR2, SEQ ID NO: 619) and QQYGRTPLT (LCDR3, SEQ ID NO: 620).

```
SC06-307 nucleotide sequence
                                                  (SEQ ID NO: 351)
caggtccagc tggtgcagtc tggggaggc ctggtcaagc ctgggggtc cctgagactc        60
tcctgtgcag cctctggatt caccttcagt agctatagca tgaactgggt ccgccaggct    120
ccagggaagg ggctggagtg ggtctcatcc attagtagta gtagtagtta catatactac    180
```

```
                                -continued
gtagactcag tgaagggccg attcaccatc tccagagaca acgccaagaa ctcactgtat    240
ctgcaaatga acagcctgag agccgaggac acggctgtgt attactgtgc gagaggtggt    300
gggagctacg gggcctacga aggctttgac tactggggcc agggcaccct ggtcaccgtc    360
tcgagcggta cgggcggttc aggcggaacc ggcagcggca ctggcgggtc gacggaaatt    420
gtgctgactc agtctccagg caccctgtct ttgtctccag gggaaagagc caccctctcc    480
tgcagggcca gtcagcgtgt tagcagctac ttagcctggt accaacagaa acctggccag    540
gctcccaggc tcctcatcta tggtgcatcc accagggccg ctggcatccc agacaggttc    600
agtggcagtg ggtctgggac agacttcact ctcaccatca gcagactgga gcctgaagat    660
tctgcagtgt attactgtca gcagtatggt aggacaccgc tcactttcgg cggagggacc    720
aaggtggaga tcaaacgt                                                  738

SC06-307 amino acid sequence
                                                           (SEQ ID NO: 352)
QVQLVQSGGGLVKPGGSLRLSCAASGFTFSSYSMNWVRQAPGKGLEWVSSISSSSSYIYYV
DSVKGRFTISRDNAKNSLYLQMNSLRAEDTAVYYCARGGGSYGAYEGFDYWGQGTLVTV
SSGTGGSGGTGSGTGGSTEIVLTQSPGTLSLSPGERATLSCRASQRVSSYLAWYQQKPGQA
PRLLIYGASTRAAGIPDRFSGSGSGTDFTLTISRLEPEDSAVYYCQQYGRTPLTFGGGTKVEI
KR SC06-307 VH amino acid sequence
                                                           (SEQ ID NO: 349)
QVQLVQSGGGLVKPGGSLRLSCAASGFTFSSYSMNWVRQAPGKGLEWVS**SISSSSSYIYY
VDSVKGRFTISRDNAKNSLYLQMNSLRAEDTAVYYCARGGGSYGAYEGFDY**WGQGTLV
TVSS SC06-307 VL amino acid sequence
                                                           (SEQ ID NO: 350)
EIVLTQSPGTLSLSPGERATLSCRASQRVSSYLAWYQQKPGQAPRLLIYGASTRAAGIPDR
FSGSGSGTDFTLTISRLEPEDSAVYYCQQYGRTPLTFGGGTKVEIKR
```

The SC06-310 HA-specific single-chain Fv antibody includes a heavy chain variable region (SEQ ID NO: 353) and a light chain variable region (SEQ ID NO: 354) encoded by the nucleic acid sequence shown in SEQ ID NO: 355 and the amino acid sequence shown in SEQ ID NO: 356. The VH-locus is VH1 (1-69) and the VL locus is VL3 (V2-14).

FQG (HCDR2, SEQ ID NO: 572) and HMGYQVRETMDV (HCDR3, SEQ ID NO: 573). The light chain CDRs of the SC06-310 antibody have the following CDR sequences: GGNNIGSKSVH (LCDR1, SEQ ID NO: 621), DDSDRPS (LCDR2, SEQ ID NO: 622) and QVWDSSSDHAV (LCDR3, SEQ ID NO: 623).

```
SC06-310 nucleotide sequence
                                                           (SEQ ID NO: 355)
                 gaggtgcagc tggtggagtc tggggctgag gtgaagaagc ctggggcctc ggtgaaagtc    60
                 tcttgcaagg cttctggagg cccttccgc agctatgcta tcagctgggt gcgacaggcc    120
                 cctggacaag ggcctgagtg gatgggaggg atcatcccta tttttggtac aacaaaatac    180
                 gcaccgaagt tccagggcag agtcacgatt accgcggacg atttcgcggg cacagtttac    240
                 atggagctga gcagcctgcg atctgaggac acggccatgt actactgtgc gaaacatatg    300
                 gggtaccagg tgcgcgaaac tatggacgtc tggggcaaag ggaccacggt caccgtctcg    360
                 agcggtacgg gcggttcagg cggaaccggc agcggcactg gcgggtcgac gtcctatgtg    420
                 ctgactcagc cacctgtcgg gtcagtggcc ccaggacaga cggccaggat tacctgtggg    480
                 ggaaacaaca ttggaagtaa aagtgtgcac tggtaccagc agaagccagg ccaggcccct    540
                 gtgctggtcg tctatgatga tagcgaccgg ccctcaggga tccctgagcg attctctggc    600
                 tccaactctg gaacacggc accctgacc atcagcaggg tcgaagccgg ggatgaggcc    660
                 gactattact gtcaggtgtg ggatagtagt agtgatcatg ctgtgttcgg aggaggcacc    720
                 cagctgaccg tcctcggt                                                  738

SC06-310 amino acid sequence
                                                           (SEQ ID NO: 356)
EVQLVESGAEVKKPGSSVKVSCKASGGPFRSYAISWVRQAPGQGPEWMGGIIPIFGTTKYA
PKFQGRVTITADDFAGTVYMELSSLRSEDTAMYYCAKHMGYQVRETMDVWGKGTTVTV
SSGTGGSGGTGSGTGGSTSYVLTQPPSVSVAPGQTARITCGGNNIGSKSVHWYQQKPGQAP
VLVVYDDSDRPSGIPERFSGSNSGNTATLTISRVEAGDEADYYCQVWDSSSDHAVFGGGT
QLTVLG SC06-310 VH amino acid sequence
                                                           (SEQ ID NO: 353)
EVQLVESGAEVKKPGSSVKVSCKASGGPFRSYAISWVRQAPGQGPEWMG**GIIPIFGTTKY
APKFQGRVTITADDFAGTVYMELSSLRSEDTAMYYCAKHMGYQVRETMDV**WGKGTTV
TVSS SC06-310 VL amino acid sequence
                                                           (SEQ ID NO: 354)
SYVLTQPPSVSVAPGQTARITCGGNNIGSKSVHWYQQKPGQAPVLVVYDDSDRPSGIPER
FSGSNSGNTATLTISRVEAGDEADYYCQVWDSSSDHAVFGGGTQLTVLG
```

The amino acids encompassing the CDRs are highlighted in bold in the sequences below. The heavy chain CDRs of the SC06-310 antibody have the following CDR sequences: SYAIS (HCDR1, SEQ ID NO: 571), GIIPIFGTTKYAPK- The SC06-314 HA-specific single-chain Fv antibody includes a heavy chain variable region (SEQ ID NO: 357) and a light chain variable region (SEQ ID NO: 358) encoded by the nucleic acid sequence shown in SEQ ID NO: 359 and the amino acid sequence shown in SEQ ID NO: 360. The VH-locus is VH1 (1-69) and the VL locus is VL1 (V1-17).

The amino acids encompassing the CDRs are highlighted in bold in the sequences below. The heavy chain CDRs of the SC06-314 antibody have the following CDR sequences: SYAIS (HCDR1, SEQ ID NO: 571), GIIPIFGTTKYAPK-FQG (HCDR2, SEQ ID NO: 572) and HMGYQVRETMDV (HCDR3, SEQ ID NO: 573). The light chain CDRs of the SC06-314 antibody have the following CDR sequences: SGSSSNIGSNYVY (LCDR1, SEQ ID NO: 624), RDGQRPS (LCDR2, SEQ ID NO: 625) and ATWDDNLS-GPV (LCDR3, SEQ ID NO: 626).

the nucleic acid sequence shown in SEQ ID NO: 363 and the amino acid sequence shown in SEQ ID NO: 364. The VH-locus is VH1 (1-69) and the VL locus is VKIII (A27).

The amino acids encompassing the CDRs are highlighted in bold in the sequences below. The heavy chain CDRs of the SC06-323 antibody have the following CDR sequences: SYGIS (HCDR1, SEQ ID NO: 627), DIIGMFGSTNYAQN-FQG (HCDR2, SEQ ID NO: 628) and SSGYYPAYLPH (HCDR3, SEQ ID NO: 629). The light chain CDRs of the SC06-323 antibody have the following CDR sequences:

```
SC06-314 nucleotide sequence
                                                     (SEQ ID NO: 359)
gaggtgcagc tggtggagtc tggggctgag gtgaagaagc ctgggtcctc ggtgaaagtc    60
tcttgcaagg cttctggagg cccttccgc agctatgcta tcagctgggt gcgacaggcc   120
cctggacaag ggcctgagtg gatgggaggg atcatcccta ttttgggtac aacaaaatac   180
gcaccgaagt tccagggcag agtcacgatt accgcggacg atttcgcggg cacagtttac   240
atggagctga gcagcctgcg atctgaggac acggccatgt actactgtgc gaaacatatg   300
gggtaccagg tgcgcgaaac tatggacgtc tggggcaaag ggaccacggt caccgtctcg   360
agcggtacgg gcggttcagg cggaaccggc agcggcactg gcgggtcgac gtcctatgtg   420
ctgactcagc caccctcagc gtctgggacc cccgggcaga gggtcaccat ctcttgttct   480
ggaagcagct ccaacatcgg aagtaattat gtatactggt accagcagct cccaggcacg   540
gccccaaac tcctcatcta tagggatggt cagcggccct caggggtccc tgaccgattc   600
tctggctcca agtctggcac ctcagcctcc ctggccatca gtggactccg gtccgatgat   660
gaggctgatt attactgtgc aacatgggat gacaacctga gtggtccagt attcggcgga   720
gggaccaagc tgaccgtcct aggt                                          744

SC06-314 amino acid sequence
                                                     (SEQ ID NO: 360)
EVQLVESGAEVKKPGSSVKVSCKASGGPFRSYAISWVRQAPGQGPEWMGGIIPIFGTTKYA
PKFQGRVTITADDFAGTVYMELSSLRSEDTAMYYCAKHMGYQVRETMDVWGKGTTVTV
SSGTGGSGGTGSGTGGSTSYVLTQPPSASGTPGQRVTISCSGSSSNIGSNYVYWYQQLPGTA
PKLLIYRDGQRPSGVPDRFSGSKSGTSASLAISGLRSDDEADYYCATWDDNLSGPVFGGGT
KLTVLG SC06-314 VH amino acid sequence
                                                     (SEQ ID NO: 357)
EVQLVESGAEVKKPGSSVKVSCKASGGPFRSYAISWVRQAPGQGPEWMGGIIPIFGTTKY
APKFQGRVTITADDFAGTVYMELSSLRSEDTAMYYCAKHMGYQVRETMDVWGKGTTV
TVSS SC06-314 VL amino acid sequence
                                                     (SEQ ID NO: 358)
SYVLTQPPSASGTPGQRVTISCSGSSSNIGSNYVYWYQQLPGTAPKLLIYRDGQRPSGVPD
RFSGSKSGTSASLAISGLRSDDEADYYCATWDDNLSGPVFGGGTKLTVLG
```

The SC06-323 HA-specific single-chain Fv antibody includes a heavy chain variable region (SEQ ID NO: 361) and a light chain variable region (SEQ ID NO: 362) encoded by RASQSVSSSYLA (LCDR1, SEQ ID NO: 646). GASSRAT (LCDR2, SEQ ID NO: 631) and QQYGSSPRT (LCDR3, SEQ ID NO: 632).

```
SC06-323 nucleotide sequence
                                                     (SEQ ID NO: 363)
gaggtgcagc tggtggagtc tggggctgag gtgaagaagc cagggtcctc ggtgaaggtc    60
tcctgtaagg cctctggagg caccttctcc agctatggta tcagctgggt gcgacaggcc   120
cctggacaag ggcttgagtg gatgggagac atcatcggta tgtttggttc aacaaactac   180
gcacagaact tccagggcag actcacgatt accgcggacg aatccacgag cacagcctac   240
atggagctga gcagcctgag atctgaggac acggccgtgt attactgtgc gagaagtagt   300
ggttattacc ctgcatacct ccccactggg gccagggca ccttggtcac cgtctcgagc   360
ggtacgggcg gttcaggcgg aaccggcagc ggcactggcg ggtcgacgga aattgtgttg   420
acccagtctc caggcaccct gtctttgtct ccaggggaaa gagccaccct ctcctgcagg   480
gccagtcaga gtgttagcag cagctactta gcctggtacc agcagaaacc tggccaggct   540
cccaggctcc tcatctatgg tgcatccagc agggccactg gcatcccaga caggttcagt   600
ggcagtgggt ctgggacaga cttcactctc accatcagca gactggagcc tgaagatttt   660
gcagtgtatt actgtcagca gtatggtagc tcacccagaa ctttcggcgg agggaccaag   720
gtggagatca aacgt                                                    735

SC06-323 amino acid sequence
                                                     (SEQ ID NO: 364)
EVQLVESGAEVKKPGSSVKVSCKASGGTFSSYGISWVRQAPGQGLEWMGDIIGMFGSTNY
AQNFQGRLTITADESTSTAYMELSSLRSEDTAVYYCARSSGYYPAYLPHWGQGTLVTVSS
GTGGSGGTGSGTGGSTEIVLTQSPGTLSLSPGERATLSCRASQSVSSSYLAWYQQKPGQAP
RLLIYGASSRATGIPDRFSGSGSGTDFTLTISRLEPEDFAVYYCQQYGSSPRTFGGGTKVEIK
R
```

```
SC06-323 VH amino acid sequence
                                                           (SEQ ID NO: 361)
EVQLVESGAEVKKPGSSVKVSCKASGGTFSSYGISWVRQAPGQGLEWMGDIIGMFGSTNY
AQNFQGRLTITADESTSTAYMELSSLRSEDTAVYYCARSSGYYPAYLPHWGQGTLVTVSS SC06-323 VL amino acid sequence
                                                           (SEQ ID NO: 362)
EIVLTQSPGTLSLSPGERATLSCRASQSVSSSYLAWYQQKPGQAPRLLIYGASSRATGIPDRF
SGSGSGTDFTLTISRLEPEDFAVYYCQQYGSSPRTFGGGTKVEIKR
```

The SC06-325 HA-specific single-chain Fv antibody includes a heavy chain variable region (SEQ ID NO: 365) and a light chain variable region (SEQ ID NO: 366) encoded by the nucleic acid sequence shown in SEQ ID NO: 367 and the amino acid sequence shown in SEQ ID NO: 368. The VH-locus is VH1 (1-69) and the VL locus is VL2 (V1-4).

The amino acids encompassing the CDRs are highlighted in bold in the sequences below. The heavy chain CDRs of the SC06-325 antibody have the following CDR sequences: FYSMS (HCDR1, SEQ ID NO: 633), GIIPMFGTTNYAQK-FQG (HCDR2, SEQ ID NO: 634) and GDKGIYYYYMDV (HCDR3, SEQ ID NO: 635). The light chain CDRs of the SC06-325 antibody have the following CDR sequences: TGTSSDVGGYNYVS (LCDR1, SEQ ID NO: 577), EVSN-RPS (LCDR2, SEQ ID NO: 578) and SSYTSSSTLV (LCDR3, SEQ ID NO: 636).

The SC06-327 HA-specific single-chain Fv antibody includes a heavy chain variable region (SEQ ID NO: 369) and a light chain variable region (SEQ ID NO: 370) encoded by the nucleic acid sequence shown in SEQ ID NO: 371 and the amino acid sequence shown in SEQ ID NO: 372. The VH-locus is VH1 (1-69) and the VL locus is VL3 (V2-14).

The amino acids encompassing the CDRs are highlighted in bold in the sequences below. The heavy chain CDRs of the SC06-327 antibody have the following CDR sequences: THAIS (SEQ ID NO: 637), GIIAIFGTANYAQKFQG (SEQ ID NO: 638) and GSGYHISTPFDN (SEQ ID NO: 639). The light chain CDRS of the SC06-327 antibody have the following CDR sequences: GGNNIGSKGVH (SEQ ID NO: 640), DDSDRPS (SEQ ID NO: 622) and QVWDSSSDHVV (SEQ ID NO: 642).

```
SC06-325 nucleotide sequence
                                                           (SEQ ID NO: 367)
gaggtgcagc tggtggagtc tggggctgag gtgaagaagc cggggtcctc ggtgaaggtc    60
tcctgcaagg cttctggagg caccttcagc ttctattcta tgagctgggt gcgacaggcc   120
cctggacaag gacttgagtg gatgggaggg atcatcccta tgtttggtac aacaaactac   180
gcacagaagt tccagggcag agtcacgatt accgcggtcg aatccacgag cacagcctac   240
atggaggtga gcagcctgag atctgaggac acggccgttt attactgtgc gagaggtgat   300
aagggtatct actactacta catggacgtc tggggcaaag ggaccacggt caccgtctcg   360
agcggtacgg gcggttcagg cggaaccggc agcggcactg gcgggtcgac gcagtctgcc   420
ctgactcagc ctgcctccgt gtctgggtct cctggacagt cgatcaccat ctcctgcact   480
ggaaccagca gtgacgttgg tggttataac tatgtctcct ggtaccaaca gcacccaggc   540
aaagccccca aactcatgat ttatgaggtc agtaatcggc cctcagggt  ttctaatcgc   600
ttctctggct ccaagtctgg caacacggcc tccctgacca tctctgggct ccaggctgag   660
gacgaggctg attattactg cagctcatat acaagcagca gcactcttgt cttcggaact   720
gggaccaagg tcaccgtcct aggt                                          744

SC06-325 amino acid sequence
                                                           (SEQ ID NO: 368)
EVQLVESGAEVKKPGSSVKVSCKASGGTFSFYSMSWVRQAPGQGLEWMGGIIPMFGTTN
YAQKFQGRVTITAVESTSTAYMEVSSLRSEDTAVYYCARGDKGIYYYMDVWGKGTTVT
VSSGTGGSGGTGSGTGGSTQSALTQPASVSGSPGQSITISCTGTSSDVGGYNYVSWYQQHP
GKAPKLMIYEVSNRPSGVSNRFSGSKSGNTASLTISGLQAEDEADYYCSSYTSSSTLVFGTG
TKVTVLG SC06-325 VH amino acid sequence
                                                           (SEQ ID NO: 365)
EVQLVESGAEVKKPGSSVKVSCKASGGTFSFYSMSWVRQAPGQGLEWMG**GIIPMFGTTN
YAQKFQGRVTITAVESTSTAYMEVSSLRSEDTAVYYCARGDKGIVYYYMDV**WGKGTTV
TVSS SC06-325 VL amino acid sequence
                                                           (SEQ ID NO: 366)
QSALTQPASVSGSPGQSITISCTGTSSDVGGYNYVSWYQQHPGKAPKLMIYEVSNRPSGVS
NRFSGSKSGNTASLTISGLQAEDEADYYCSSYTSSSTLVFGTGTKVTVLG
```

SC06-327 nucleotide sequence (SEQ ID NO: 371)

```
gaggtgcagc tggtggagac cggggctgag gtgaagaagc ctgggtcctc ggtgaaggtc   60
tcctgcaagg cctctggagg caccttcagg acccatgcta tcagttgggt gcgacaggcc  120
cctggacaag ggcttgagtg gatgggaggg atcatcgcta tcttcggaac agcaaactac  180
gcacagaagt tccagggcag aatcacgatt accgcggacg aatccacgag tacagcctac  240
atggagctga gcagcctgag atctgaggac acggccgtgt atttctgtgc gagaggcagt  300
ggttatcata tatcgacacc ctttgacaac tggggccagg gaaccctggt caccgtctcg  360
agcggtacgg gcggttcagg cggaaccggc agcggcactg gcgggtcgac gtcctatgtg  420
ctgactcagc caccctcggt gtcagtggcc ccaggacaga cggccaggat tacctgtggg  480
ggaaacaaca ttggaagtaa aggtgtgcac tggtaccagc agaagcctgg ccaggcccct  540
gtgctggtcg tctatgatga tagcgaccgg ccctcaggga tccctgagcg attctctggc  600
tccaactctg gaacacggc caccctgacc atcagcaggg tcgaagccgg ggatgaggcc  660
gactattact gtcaggtgtg ggatagtagt agtgatcatg tggtattcgg cggagggacc  720
aagctgaccg tcctaggt                                                 738
```

SC06-327 amino acid sequence (SEQ ID NO: 372)

EVQLVETGAEVKKPGSSVKVSCKASGGTFRTHAISWVRQAPGQGLEWMGGIIAIFGTANY
AQKFQGRITITADESTSTAYMELSSLRSEDTAVYFCARGSGYHISTPFDNWGQGTLVTVSSG
TGGSGGTGSGTGGSTSYVLTQPPSVSVAPGQTARITCGGNNIGSKGVHWYQQKPGQAPVL
VVYDDSDRPSGIPERFSGSNSGNTATLTISRVEAGDEADYYCQVWDSSSDHVVFGGGTKLT
VLG

SC06-327 VH amino acid sequence (SEQ ID NO: 369)

EVQLVETGAEVKKPGSSVKVSCKASGGTFRTHAISWVRQAPGQGLEWMGG**IIAIFGTAN
YAQKFQGRITITADESTSTAYMELSSLRSEDTAVYFCARGSGYHISTPFDN**WGQGTLVTV
SS

SC06-327 VL amino acid sequence (SEQ ID NO: 370)

SYVLTQPPSVSVAPGQTARITCGGNNIGSKGVHWYQQKPGQAPVLVVYDDSDRPSGIPER
FSGSNSGNTATLTISRVEAGDEADYYCQVWDSSSDHVVFGGGTKLTVLG

The SC06-328 HA-specific single-chain Fv antibody includes a heavy chain variable region (SEQ ID NO: 373) and a light chain variable region (SEQ ID NO: 374) encoded by the nucleic acid sequence shown in SEQ ID NO: 375 and the amino acid sequence shown in SEQ ID NO: 376. The VH-locus is VH1 (1-69) and the VL locus is VKIII (A27).

The amino acids encompassing the CDRs are highlighted in bold in the sequences below. The heavy chain CDRs of the SC06-328 antibody have the following CDR sequences: GYAIS (HCDR1, SEQ ID NO: 643), GIIPIFGTTNYAQKFQG (HCDR2, SEQ ID NO: 644) and VKDGYCTLTSCPVGWYFDL (HCDR3, SEQ ID NO: 645). The light chain CDRs of the SC06-328 antibody have the following CDR sequences: RASQSVSSSYLA (LCDR1, SEQ ID NO: 646), GASSRAT (LCDR2, SEQ ID NO: 631). and QQYGSSLT (LCDR3, SEQ ID NO: 648).

SC06-328 nucleotide sequence (SEQ ID NO: 375)

```
gaggtgcagc tggtggagtc tggggctgag gtgaagaagc ctgggtcctc ggtgaaggtc   60
tcctgcaagg cttctggaca catcttcagc ggctatgcaa tcagttgggt gcgacaggcc  120
cctggacaag ggcttgagtg gatgggaggg atcatcccta tctttggtac aacaaactac  180
gcacagaagt tccagggcag agtcacgatt accgcggacc aatccacgag cacagcctac  240
atggacctga gcaacttgag atctgaggac acggccgtct attactgtgc gagagtaaaa  300
gatggatatt gtactcttac cagctgccct gtcggctggt acttcgatct ctggggccgt  360
ggcaccctgg tcactgtctc gagcggtacg ggcggttcag gcggaaccgg cagcggcact  420
ggcgggtcga cggaaattgt gatgacgcag tctccaggca ccctgtcttt gtctccaggg  480
gaaagagcca ccctctcgtg cagggccagt cagagtgtta gcagcagcta cttagcctgg  540
taccagcaga aacctggcca ggctccccga ctcctcatct ttggtgcctc cagcagggcc  600
actggcatcc cagacaggtt cagtggcagt gggtctggga cagacttcac tctcaccatc  660
agcagactgg agcctgaaga ttttgcagtg tattactgtc agcagtatgg tagctcactc  720
actttcggcg gagggaccaa gctggagatc aaacgt                             756
```

SC06-328 amino acid sequence (SEQ ID NO: 376)

EVALVESGAEVKKPGSSVKVSCKASGHIFSGYAISWVRQAPGQGLEWMGGIIPIFGTTNYA
QKFQGRVTITADQSTSTAYMDLSNLRSEDTAVYYCARVKDGYCTLTSCPVGWYFDLWGR
GTLVTVSSGTGGSGGTGSGTGGSTEIVMTQSPGTLSLSPGERATLSCRASQSVSSSYLA
WYQQKPGQAPRLLIFGASSRATGIPDRFSGSGSGTDFTLTISRLEPEDFAVYYCQQY
GSSLTFGGGTKLEIKR

SC06-328 VH amino acid sequence (SEQ ID NO: 373)

EVALVESGAEVKKPGSSVKVSCKASGHIFSGYAISWVRQAPGQGLEWMGG**IIPIFGTTNY
AQKFQGRVTITADQSTSTAYMDLSNLRSEDTAVYYCARVKDGYCTLTSCPVGWYFDL**W
GRGTLVTVSS

SC06-328 VL amino acid sequence (SEQ ID NO: 374)

EIVMTQSPGTLSLSPGERATLSCRASQSVSSSYLAWYQQKPGQAPRLLIFGASSRA
TGIPDRFSGSGSGTDFTLTISRLEPEDFAVYYCQQYGSSLTFGGGTKLEIKR

The SC06-329 HA-specific single-chain Fv antibody includes a heavy chain variable region (SEQ ID NO: 377) and a light chain variable region (SEQ ID NO: 378) encoded by the nucleic acid sequence shown in SEQ ID NO: 379 and the amino acid sequence shown in SEQ ID NO: 380. The VH-locus is VH1 (1-69) and the VL locus is VKIII (A27).

The amino acids encompassing the CDRs are highlighted in bold in the sequences below. The heavy chain CDRs of the SC06-329 antibody have the following CDR sequences: SNSIS (HCDR1, SEQ ID NO: 649), GIFALFGTTDYAQK-FQG (HCDR2, SEQ ID NO: 650) and GSGYTTRNYFDY (HCDR3, SEQ ID NO: 651). The light chain CDRs of the SC06-329 antibody have the following CDR sequences: RASQSVSSNYLG (LCDR1, SEQ ID NO: 652), GASSRAS (LCDR2, SEQ ID NO: 653) and QQYGSSPLT (LCDR3, SEQ ID NO: 654).

The SC06-331 HA-specific single-chain Fv antibody includes a heavy chain variable region (SEQ ID NO: 381) and a light chain variable region (SEQ ID NO: 382) encoded by the nucleic acid sequence shown in SEQ ID NO: 383 and the amino acid sequence shown in SEQ ID NO: 384. The VH-locus is VH1 (1-69) and the VL locus is VL3 (V2-14).

The amino acids encompassing the CDRs are highlighted in bold in the sequences below. The heavy chain CDRs of the SC06-331antibody have the following CDR sequences: SYAIS (HCDR1, SEQ ID NO: 571), GIIGMFGTANYAQK-FQG (HCDR2, SEQ ID NO: 655) and GNYYYESSLDY (HCDR3, SEQ ID NO: 656). The light chain CDRs of the SC06-331 antibody have the following CDR sequences: GGNNIGSKSVH (LCDR1, SEQ ID NO: 621), DDSDRPS (LCDR2, SEQ ID NO: 622) and QVWDSSSDH (LCDR3, SEQ ID NO: 657).

SC06-329 nucleotide sequence (SEQ ID NO: 379)

```
gaggtccagc tggtacagtc tggggctgag gttaagaagc ctgggtcctc ggtgaaggtc      60
tcctgcaagg cttctggagg catcttcaga agcaattcta tcagttgggt gcgacaggcc     120
cctgggcaag gcttgagtg gatgggaggg atcttcgctc ttttcggaac aacagactac      180
gcgcagaagt tccagggcag agtcacgatt accgcggacg aatcttcgac acagtctac     240
ctggagctga gtagcctgac atctgaggac acggccgttt attactgtgc gagaggcagt    300
ggctacacca cacgcaacta ctttgactac tggggccagg gcaccctggt caccgtctcg    360
agcggtacgg gcggttcagg cggaaccggc agcggcactg gcgggtcgac ggaaattgtg    420
ctgactcagt ctccaggcac cctgtctttg tctccagggg aaagagccac actcctgc      480
agggccagtc agagtgttag cagcaactac ttaggctggt accagcagaa acctggccag    540
gctcccaggc tcctgatcta tggtgcatcc agcagggcca gtggcatccc agacaggttc    600
agtggcggtg ggtctgggac agacttcact ctcaccatca gcagactgga gcctgaagat    660
tttgcagtgt attactgtca gcagtatggt agctcacccc tcactttcgg cggagggacc    720
aaggtggaga tcaaacgt                                                   738
```

SC06-329 amino acid sequence (SEQ ID NO: 380)

EVQLVQSGAEVKKPGSSVKVSCKASGGIFRSNSISWVRQAPGQGLEWMGGIFALFGTTDY
AQKFQGRVTITADESSTTVYLELSSLTSEDTAVYYCARGSGYTTRNYFDYWGQGTLVTVS
SGTGGSGGTGSGTGGSTEIVLTQSPGTLSLSPGERATLSCRASQSVSSNYLGWTQQKPGQA
PRLLIYGASSRASGIPDRFSGGGSGTDFTLTISRLEPEDFAVYYCQQYGSSPLTFGGGTKVEI
KR

SC06-329 VH amino acid sequence (SEQ ID NO: 377)

EVQLVQSGAEVKKPGSSVKVSCKASGGIFRSNSISWVRQAPGQGLEWMGGIFALFGTTD
YAQKFQGRVTITADESSTTVYLELSSLTSEDTAVYYCARGSGYTTRNYFDYWGQGTLVT
VSS

SC06-329 VL amino acid sequence (SEQ ID NO: 378)

EIVLTQSPGTLSLSPGERATLSCRASQSVSSNYLGWTQQKPGQAPRLLIYGASSRASGIPDR
FSGGGSGTDFTLTISRLEPEDFAVYYCQQYGSSPLTFGGGTKVEIKR

SC06-331 nucleotide sequence (SEQ ID NO: 383)

```
gaggtgcagc tggtggagtc tggggctgag gtgaagaagc ctgggtcctc ggtgaaggtc   60
tcctgcaagg cttctggagg caccttcagc agctatgcta tcagctgggt gcgacaggcc  120
cctggacaag ggcttgagtg gatggggagg atcatcggta tgttcggtac agcaaactac  180
gcacagaagt tccagggcag agtcacgatt accgcggacg aatttacgag cacagcctac  240
atggagctga gcagcctgag atctgaggac acggccgtgt attactgtgc gagaggaaat  300
tattactatg agagtagtct cgactactgg ggccagggaa ccctggtcac cgtctcgagc  360
ggtacgggcg gttcaggcgg aaccggcagc ggcactggcg gtcgacgca gtctgtcgtg  420
acgcagccgc cctcggtgtc agtggcccca ggacagacga ccaggattac ctgtggggga  480
aacaacattg aagtaaaaag tgtgcactgg taccagcaga agccaggcca ggcccctgtg  540
ctggtcgtct atgatgatag cgaccggccc tcagggatcc ctgagcgatt ctctggctcc  600
aactctggga acacggccac cctgaccatc agcagggtcg aagccgggga tgaggccgac  660
tattactgtc aggtgtggga tagtagtagt gatcattatg tcttcggaac tgggaccaag  720
gtcaccgtcc taggt                                                   735
```

SC06-331 amino acid sequence (SEQ ID NO: 384)

EVQLVESGAEVKKPGSSVKVSCKASGGTFSSYAISWVRQAPGQGLEWMGGIIGMFGTANY
AQKFQGRVTITADEFTSTAYMELSSLRSEDTAVYYCARGNYYYESSLDYWGQGTLVTVSS
GTGGSGGTGSGTGGSTQSVVTQPPSVSVAPGQTARITCGGNNIGSKSVHWYQQKPGQAPV
LVVYDDSDRPSGIPERFSGSNSGNTATLTISRVEAGDEADYYCQVWDSSSDHYVFGTGTKV
TVLG

SC06-331 VH amino acid sequence (SEQ ID NO: 381)

EVQLVESGAEVKKPGSSVKVSCKASGGTFSSSYAISWVRQAPGQGLEWMG**GIIGMFGTAN
YAQKFQGRVTITADEFTSTAYMELSSLRSEDTAVYYCARGNYYYESSLDY**WGQGTLVTV
SS

SC06-331 VL amino acid sequence (SEQ ID NO: 382)

QSVVTQPPSVSVAPGQTARITCGGNNIGSKSVHWYQQKPGQAPVLVVYDDSDRPSGIPER
FSGSNSGNTATLTISRVEAGDEADYYCQVWDSSSDHYVFGTGTKVTVLG

The SC06-332 HA-specific single-chain Fv antibody includes a heavy chain variable region (SEQ ID NO: 385) and a light chain variable region (SEQ ID NO: 386) encoded by the nucleic acid sequence shown in SEQ ID NO: 387 and the amino acid sequence-shown in SEQ ID NO: 388. The VH-locus is VH1 (1-69) and the VL locus is VKI (A20).

The amino acids encompassing the CDRs are highlighted in bold in the sequences below. The heavy chain CDRs of the SC06-332 antibody have the following CDR sequences: NFAIN (HCDR1, SEQ ID NO: 658), GIIAVFGTTKYAHK-FQG (HCDR2, SEQ ID NO: 659) and GPHYYSSYMDV (HCDR3, SEQ ID NO: 660). The light chain CDRs of the SC06-332 antibody have the following CDR sequences: RASQGISTYLA (LCDR1, SEQ ID NO: 661), AASTLQS (LCDR2, SEQ ID NO: 662) and QKYNSAPS (LCDR3, SEQ ID NO: 663).

SC06-332 nucleotide sequence (SEQ ID NO: 387)

```
caggtgcagc tggtgcagtc tggggctgag gtgaagaagc ctgggtcctc ggtaaaggtc   60
tcctgcaagg cttctggagg ccccttccgc aattttgcta tcaactgggt gcgacaggcc  120
cctggacaag ggcttgagtg gatgggaggg atcatcgctg tctttgggac gacaaagtac  180
gcacataagt tccagggcag agtcaccatc accgcggacg actccacaaa tacagcttac  240
atggagctgg gcagcctgaa atctgaggac acggccgtgt attactgtgc gagaggtccc  300
cactactact cctcctacat ggacgtctgg ggcgaaggga ccacggtcac cgtctcgagc  360
ggtacgggcg gttcaggcgg aaccggcagc ggcactggcg gtcgacgga catccagttg  420
acccagtctc catcctccct gtctgcatct gtaggagaca gagtcaccat cacttgccgg  480
gcgagtcagg gcattagcac ttatttagcc tggtatcagc agaaacccgg gaaagttcct  540
aaactcctga tctatgctgc atccactttg caatcagggg tcccatctcg gttcagtggc  600
agtggatctg ggacagattt cactctcacc atcagcagcc tgcagcctga agatgttgca  660
acttattact gtcaaaagta taacagtgcc ccttctttcg gccctgggac caaagtggat  720
atcaaacgt                                                          729
```

SC06-332 amino acid sequence (SEQ ID NO: 388)

QVQLVQSGAEVKKPGSSVKVSCKASGGPFRNFAINWVRQAPGQGLEWMGGIIAVFGTTK
YAHKFQGRVTITADDSTNTAYMELGSLKSEDTAVYYCARGPHYYSSYMDVWGEGTTVTV
SSGTGGDGGTGSGTGGSTDIQLTQSPSSLSASVGDRVTITCRASQGISTYLAWYQQKPGKV
PKLLIYAASTLQSGVPSRFSGSGSGTDFTLTISSLQPEDVATYYCQKYNSAPSFGPGTKVDIK
R

SC06-332 VH amino acid sequence (SEQ ID NO: 385)

QVQLVQSGAEVKKPGSSVKVSCKASGGPFRNFAINWVRQAPGQGLEWMG**GIIAVFGTTK
YAHKFQGRVTITADDSTNTAYMELGSLKSEDTAVYYCARGPHYYSSYMDV**WGEGTTVT
VSS

-continued

SC06-332 VL amino acid sequence
(SEQ ID NO: 386)
DIQLTQSPSSLSASVGDRVTITCRASQGISTYLAWYQQKPGKVPKLLIYAASTLQSGVPSRF
SGSGSGTDFTLTISSLQPEDVATYYCQKYNSAPSFGPGTKVDIKR The SC06-334 HA-specific single-chain Fv antibody includes a heavy chain variable region (SEQ ID NO: 389) and a light chain variable region (SEQ ID NO: 390) encoded by the nucleic acid sequence shown in SEQ ID NO: 391 and the amino acid sequence shown in SEQ ID NO: 392. The VH-locus is VH1 (1-69) and the VL locus is VL3 (V2-14).

The amino acids encompassing the CDRs are highlighted in bold in the sequences below. The heavy chain CDRs of the SC06-334 antibody have the following CDR sequences: SNAVS (HCDR1, SEQ ID NO: 664), GILGVFGSPSYAQK-FQG (HCDR2, SEQ ID NO: 665) and GPTYYYSYMDV (HCDR3, SEQ ID NO: 666). The light chain CDRs of the SC06-334 antibody have the following CDR sequences: GGNNIGRNSVH (LCDR1, SEQ ID NO: 667), DDSDRPS (LCDR2, SEQ ID NO: 622). and QVWHSSSDHYV (LCDR3, SEQ ID NO: 669).

The SC06-336 HA-specific single-chain Fv antibody includes a heavy chain variable region (SEQ ID NO: 393) and a light chain variable region (SEQ ID NO: 394) encoded by the nucleic acid sequence shown in SEQ ID NO: 395 and the amino acid sequence shown in SEQ ID NO: 396. The VH-locus is VH1 (1-69) and the VL locus is VKIII (A27).

The amino acids encompassing the CDRs are highlighted in bold in the sequences below. The heavy chain CDRs of the SC06-336 antibody have the following CDR sequences: SYAIS (HCDR1, SEQ ID NO: 670), GIFGMFGTANYAQK-FQG (HCDR2, SEQ ID NO: 671) and SSGYYPQYFQD (HCDR3, SEQ ID NO: 672). The light chain CDRs of the SC06-336 antibody have the following CDR sequences: RASQSVSSSYLA (LCDRI, SEQ ID NO: 646), GASSRAT (LCDR2, SEQ ID NO: 631). and QQYGSSSLT (LCDR3, SEQ ID NO: 308).

```
SC06-334 nucleotide sequence
                                                    (SEQ ID NO: 391)
gaggtgcagc tggtggagac tggggctgag gtgaagaagc ctgggtcctc ggtgaaggtc    60
ccctgcaaat cttctggaag ccccttcagg agtaatgctg tcagctgggt gcgacaggcc   120
cccggacaag gcttgagtg gtgggagga atcctcggtg tctttggttc accaagctac    180
gcacagaagt tccagggcag agtcacgatt accgcggacg aatccaccaa cacagtccac   240
atggagctga gaggtttgag atctgaggac acgccgtgt attattgtgc gagaggtcct    300
acctactact actcctacat ggacgtctgg ggcaaaggga ccacggtcac cgtctcgagc   360
ggtacgggcg gttcaggcgg aaccggcagc ggcactggcg gtcgacgtc ctatgtgctg    420
actcagccac cctcggagtc agtggcccca ggacagacgg ccaggattac ctgtggggga   480
aataacattg gaagaaatag tgtgcactgg tatcagcaga agccaggcca ggcccctgtg   540
ctggtcgtgt atgatgatag cgaccggccc tcagggatcc ctgagcgatt ttctggctcc   600
aagtctggga cacgccac cctgattatc agcagggtcg aagtcgggga tgaggccgac    660
tactactgtc aggtgtggca tagtagtagt gatcattatg tcttcggaac tgggaccaag   720
gtcaccgtcc taggt                                                    735
```

SC06-334 amino acid sequence
(SEQ ID NO: 392)
EVALVETGAEVKKPGSSVKVPCKSSGSPFRSNAVSWVRQAPGQGLEWVGGILGVFGSPSY
AQKFQGRVTITADESTNTVHMELRGLRSEDTAVYYCARGPTYYYSYMDVWGKGTTVTVS
SGTGGSGGTGSGTGGSTSYVLTQPPSESVAPGQTARITCGGNNIGRNSVHWYQQKPGQAP
VLVVYDDSDRPSGIPERFSGSKSGNTATLIISRVEVGDEADYYCQVWHSSSDHYVFGTGTK
VTVLG SC06-334 VH amino acid sequence
(SEQ ID NO: 389)
EVALVETGAEVKKPGSSVKVPCKSSGSPFRSNAVSWVRQAPGQGLEWVG**GILGVFGSPS
YAQKFQGRVTITADESTNTVHMELRGLRSEDTAVYYCARGPTYYYSYMDV**WGKGTTVT
VSS SC06-334 VL amino acid sequence
(SEQ ID NO: 390)
SYVLTQPPSESVAPGQTARITCGGNNIGRNSVHWYQQKPGQAPVLVVYDDSDRPSGIPER
FSGSKSGNTATLIISRVEVGDEADYYCQVWHSSSDHYVFGTGTKVTVLG SC06-336 nucleotide sequence (SEQ ID NO: 395)

```
cagatgcagc tggtacaatc tggagctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaggg atcttcggta tgtttgggac agcaaactac   180
gcgcagaagt tccagggcag agtcacgatt accgcggacg aattcacgag cgcggcctac   240
atggagctga gcagcctggg atctgaggac acggccatgt attactgtgc gaggtctagt   300
ggttattacc cccaatactt ccaggactgg ggccagggca ccctggtcac cgtctcgagc   360
ggtacgggcg gttcaggcgg aaccggcagc ggcactggcg gtcgacgga aattgtgatg    420
acacagtctc caggcaccct gtctttgtct ccagggcaaa gagccaccct ctcctgcagg   480
gccagtcaga gtgttagcag cagctactta gcctggtacc agcagaaacc tggccaggct   540
cccagactcc tcatgtatgg tgcatccagc agggccactg gcatcccaga caggttcagt   600
ggcagtgggt ctgggacaga cttcactctc accatcagca gactggagcc tgaagatttt   660
gcagtgtatt actgtcagca gtatggtagc tcatcgctca ctttcggcgg agggaccaag   720
ctggagatca aacgt                                                    735
```

SC06-336 amino acid sequence (SEQ ID NO: 396)

QMQLVQSGAEVKKPGSSVKVSCKASGGTFSSYAISWVRQAPGQGLEWMGGIFGMFGTAN
YAQKFQGRVTITADEFTSAAYMELSSLGSEDTAMYYCARSSGYYPQYFQDWGQGTLVTV
SSGTGGSGGTGSGTGGSTEIVMTQSPGTLSLSPGQRATLSCRASQSVSSSYLAWYQQKPGQ
APRLLMYGASSRATGIPDRFSGSGSGTDFTLTISRLEPEDFAVYYCQQYGSSSLTFGGGTKL
EIKR

SC06-336 VH amino acid sequence (SEQ ID NO: 393)

QMQLVQSGAEVKKPGSSVKVSCKASGGTFSSYAISWVRQAPGQGLEWMG**GIFGMFGTA
NYAQKFQGRVTITADEFTSAAYMELSSLGSEDTAMYYCARSSGYYPQYFQD**WGQGTLV
TVSS

SC06-336 VL amino acid sequence (SEQ ID NO: 394)

EIVMTQSPGTLSLSPGQRATLSCRASQSVSSSYLAWYQQKPGQAPRLLMYGASSRATGIPD
RFSGSGSGTDFTLTISRLEPEDFAVYYCQQYGSSSLTFGGGTKLEIKR

The SC06-339 HA-specific single-chain Fv antibody includes a heavy chain variable region (SEQ ID NO: 397) and a light chain variable region (SEQ ID NO: 398) encoded by the nucleic acid sequence shown in SEQ ID NO: 399 and the amino acid sequence shown in SEQ ID NO: 400. The VH-locus is VH1 (1-69) and the VL locus is VL3 (V2-14).

The amino acids encompassing the CDRs are highlighted in bold in the sequences below. The heavy chain CDRs of the SC06-339 antibody have the following CDR sequences: SYAIS (HCDR1, SEQ ID NO: 303), GIIAIFHTPKYAQK-FQG (HCDR2, SEQ ID NO: 306) and GSTYDFSSGLDY (HCDR3, SEQ ID NO: 725). The light chain CDRs of the SC06-339 antibody have the following CDR sequences: GGNNIGSKSVH (LCDR1, SEQ ID NO: 621), DDSDRPS (LCDR2, SEQ ID NO: 622) and QVWDSSSDHVV (LCDR3, SEQ ID NO: 642).

SC06-339 nucleotide sequence (SEQ ID NO: 399)

```
gaggtgcagc tggtggagtc cggggctgag gtgaagaagc ctgggtcctc ggtgaaggtc    60
tcctgcaagg cttctggagg catcttcaac agttatgcta tcagctgggt gcgacaggcc   120
cctggacaag ggcttgagtg gatgggaggc atcatcgcta tctttcatac accaaagtac   180
gcacagaagt tccagggcag agtcacgatt accgcggacg aatccacgaa cacagcctac   240
atggaactga agcctgaaa atctgaggac acggccctgt attactgtgc gagagggtcc   300
acttacgatt tttcgagtgg ccttgactac tggggccagg gaacccctggt caccgtctcg   360
agcggtacgg gcggttcagg cggaaccggc agcggcactg gcgggtcgac gcaggcaggg   420
ctgactcagc caccctcggt gtcagtggcc ccaggacaga cggccaggat tacctgtggg   480
ggaaacaaca ttggaagtaa aagtgtgcac tggtaccagc agaagccagg ccaggcccct   540
gtcctagtcg tctatgatga tagcgaccgg ccctcaggga tccctgagcg attctctggc   600
tccaactctg gaaacacggc caccctgacc atcagcaggg tcgaagccgg ggatgaggcc   660
gactattact gtcaggtgtg ggatagtagt agtgatcatg tggtattcgg cggagggacc   720
aagctgaccg tcctaggt                                                 738
```

SC06-339 amino acid sequence (SEQ ID NO: 400)

EVQLVESGAEVKKPGSSVKVSCKASGGIFNSYAISWVRQAPGQGLEWMGGIIAIFHTPKYA
QKFQGRVTITADESTNTAYMELRSLKSEDTALYYCARGSTYDFSSGLDYWGQGTLVTVSS
GTGGSGGTGSGTGGSTQAGLTQPPSVSVAPGQTARITCGGNNIGSKSVHWYQQKPGQAPV
LVVYDDSDRPSGIPERFSGSNSGNTATLTISRVEAGDEADYYCQVWDSSSDHVVFGGGTKL
TVLG

SC06-339 VH amino acid sequence (SEQ ID NO: 397)

EVQLVESGAEVKKPGSSVKVSCKASGGIFNSYAISWVRQAPGQGLEWMG**GIIAIFHTPKY
AQKFQGRVTITADESTNTAYMELRSLKSEDTALYYCARGSTYDFSSGLDY**WGQGTLVTV
SS

SC06-339 VL amino acid sequence (SEQ ID NO: 398)

QAGLTQPPSVSVAPGQTARITCGGNNIGSKSVHWYQQKPGQAPVLVVYDDSDRPSGIPER
FSGSNSGNTATLTISRVEAGDEADYYCQVWDSSSDHVVFGGGTKLTVLG

The SC06-342 HA-specific single-chain Fv antibody includes a heavy chain variable region (SEQ ID NO: 401) and a light chain variable region (SEQ ID NO: 402) encoded by the nucleic acid sequence shown in SEQ ID NO: 403 and the amino acid sequence shown in SEQ ID NO: 404. The VH-locus is VH1 (1-69) and the VL locus is VKIV (B3).

The amino acids encompassing the CDRs are highlighted in bold in the sequences below. The heavy chain CDRs of the SC06-342 antibody have the following CDR sequences: SYAIS (HCDR1, SEQ ID NO: 251), GVIPIFRTANYAQNFQG (HCDR2, SEQ ID NO: 249) and LNYHDSGTYYNAPRGWFDP (HCDR3, SEQ ID NO: 246). The light chain CDRs of the SC06-342 antibody have the following CDR sequences: KSSQSILNSSNNKNYLA (LCDR1, SEQ ID NO: 245), WASTRES (LCDR2, SEQ ID NO: 570) and QQYYSSPPT (LCDR3, SEQ ID NO: 250).

The SC06-343 HA-specific single-chain Fv antibody includes a heavy chain variable region (SEQ ID NO: 405) and a light chain variable region (SEQ ID NO: 406) encoded by the nucleic acid sequence shown in SEQ ID NO: 407 and the amino acid sequence shown in SEQ ID NO: 408. The VH-locus is VH1 (1-69) and the VL locus is VL3 (V2-14).

The amino acids encompassing the CDRs are highlighted in bold in the sequences below. The heavy chain CDRs of the SC06-343 antibody have the following CDR sequences: YYAMS (HCDR1, SEQ ID NO: 242), GISPMFGTTTYAQKFQG (HCDR2, SEQ ID NO: 307) and SSNYYDSVYDY (HCDR3, SEQ ID NO: 290). The light chain CDRs of the SC06-343 antibody have the following CDR sequences: GGHNIGSNSVH (LCDR1, SEQ ID NO: 224), DNSDRPS (LCDR2, SEQ ID NO: 223) and QVWGSSSDH (LCDR3, SEQ ID NO: 227).

```
SC06-342 nucleotide sequence
                                                   (SEQ ID NO: 403)
caggtccagc tggtgcagtc tggggctgag gtgaagaagc ctgggtcctc ggtgaaggtc    60
tcctgcaagg cttctggagg cttcttcagc agctatgcta tcagctgggt gcgccaggcc   120
cctggacaag gacttgagtg gatgggggg  gtcatcccta tctttcgtac agcaaactac   180
gcacagaact tccagggcag agtcaccatt accgcggacg aattcacatc gtatatggag   240
ctgagcagcc tgagatctga cgacacggcc gtgtattact gtgcgaggtt gaattaccat   300
gattcgggga cttattataa cgcccccgg  ggctggttcg accctgggg  ccagggaacc   360
ctggtcaccg tctcgagcgg tacgggcggt tcaggcggaa ccggcagcgg cactggcggg   420
tcgacggaca tccagatgac ccagtctcca gactccctgg ctgtgtctct gggcgagaag   480
gccaccatca actgcaagtc cagccagagt attttaaaca gctccaacaa taagaactac   540
ttagcttggt accagcagaa accaggacag cctcctaagc tgctcattta ctgggcatct   600
acccgggaat ccggggtccc tgaccgattc agtggcagcg gtctgggac  agatttcact   660
ctcaccatca gcagcctgca ggctgaagat gtggcagttt attactgtca gcaatattat   720
agtagtccgc cgacgttcgg ccaagggacc aaggtggaaa tcaaacgt              768

SC06-342 amino acid sequence
                                                   (SEQ ID NO: 404)
QVQLVQSGAEVKKPGSSVKVSCKASGGFFSSYAISWVRQAPGQGLEWMGGVIPIFRTANY
AQNFQGRVTITADEFTSYMELSSLRSDDTAVYYCARLNYHDSGTYYNAPRGWFDPWGQG
TLVTVSSGTGGSGGTGSGTGGSTDIQMTQSPDSLAVSLGEKATINCKSSQSILNSSNNKNYL
AWYQQKPGQPPKLLIYWASTRESGVPDRFSGSGSGTDFTLTISSLQAEDVAVYYCQQYYSS
PPTFGQGTKVEIKR SC06-342 VH amino acid sequence
                                                   (SEQ ID NO: 401)
QVQLVQSGAEVKKPGSSVKVSCKASGGFFSSYAISWVRQAPGQGLEWMG**GVIPIFRTAN
YAQNFQGRVTITADEFTSYMELSSLRSDDTAVYYCARLNYHDSGTYYNAPRGWFDP**WG
QGTLVTVSS SC06-342 VL amino acid sequence
                                                   (SEQ ID NO: 402)
DIQMTQSPDSLAVSLGEKATINCKSSQSILNSSNNKNYLAWYQQKPGQPPKLLIY**WASTR
ESGVPDRFSGSGSGTDFTLTISSLQAEDVAVYYCQQYYSSPPT**FGQGTKVEIKR
```

SC06-343 nucleotide sequence (SEQ ID NO: 407)

```
caggtccagc tggtgcagtc tggagctgag gtgaagaagc ctgggtcctc ggtgaaggtc   60
tcctgcaagg cttctggagt caccttcagt tactatgcta tgagctgggt gcgacaggcc  120
cctggacaag ggcttgagtg gatgggagga atcagccctc tgtttgggac aacaacctac  180
gcacagaagt tccagggcag agtcacgatt actgcggacg actccacgag tacagcctac  240
atggaggtga ggagcctgag atctgaggac acggccgtgt attactgtgc gagatcttcg  300
aattactatg atagtgtata tgactactgg ggccagggaa ccctggtcac cgtctcgagc  360
ggtacgggcg gttcaggcgg aaccggcagc ggcactggcg ggtcgacgca gtctgtcgtg  420
acgcagccgc cctcggagtc agtggcccca ggacagacag ccaggattac ctgtggggga  480
cataacattg gaagtaatag tgtgcactgg taccagcaga agccaggcca ggcccctgtg  540
ctggtcgtgt atgataatag cgaccggccc tcagggatcc ctgagcgatt ctctggctcc  600
aactctggga acacgccac cctgaccatc agcagggtcg aagccgggga tgaggccgac  660
tattactgtc aggtgtgggg tagtagtagt gaccattatg tcttcggaac tgggaccaag  720
gtcaccgtcc taggt                                                  735
```

SC06-343 amino acid sequence (SEQ ID NO: 408)

QVQLVQSGAEVKKPGSSVKVSCKASGVTFSYYAMSWVRQAPGQGLEWMGGISPMFGTTT
YAQKFQGRVTITADDSTSTAYMEVRSLRSEDTAVYYCARSSNYYDSVYDYWGQGTLVTV
SSGTGGSGGTGSGTGGSTQSVVTQPPSESVAPGQTARITCGGHNIGSNSVHWYQQKPGQAP
VLVVYDNSDRPSGIPERFSGSNSGNTATLTISRVEAGDEADYYCQVWGSSSDHYVFGTGTK
VTVLG

SC06-343 VH amino acid sequence (SEQ ID NO: 405)

QVQLVQSGAEVKKPGSSVKVSCKASGVTFSYYAMSWVRQAPGQGLEWMG**GISPMFGTT
TYAQKFQGRVTITADDSTSTAYMEVRSLRSEDTAVYYCARSSNYYDSVYDY**WGQGTLVT
VSS

SC06-343 VL amino acid sequence (SEQ ID NO: 406)

QSVVTQPPSESVAPGQTARITCGGHNIGSNSVHWYQQKPGQAPVLVVYDNSDRPSGIPER
FSGSNSGNTATLTISRVEAGDEADYYCQVWGSSSDHYVFGTGTKVTVLG

The SC06-344 HA-specific single-chain Fv antibody includes a heavy chain variable region (SEQ ID NO: 409) and a light chain variable region (SEQ ID NO: 410) encoded by the nucleic acid sequence shown in SEQ ID NO: 411 and the amino acid sequence shown in SEQ ID NO: 412. The VH-locus is VH1 (1-69) and the VL locus is VL1 (V1-13).

The amino acids encompassing the CDRs are highlighted in bold in the sequences below. The heavy chain CDRs of the SC06-344 antibody have the following CDR sequences: NYAMS (HCDR1, SEQ ID NO: 222), GIIAIFGTPKYAQK-FQG (HCDR2, SEQ ID NO: 221) and IPHYNFGSGSYFDY (HCDR3, SEQ ID NO: 220). The light chain CDRs of the SC06-344 antibody have the following CDR sequences: TGSSSNIGAGYDVH (LCDR1, SEQ ID NO: 219), GNSN-RPS (LCDR2, SEQ ID NO: 231) and GTWDSSLSAYV (LCDR3, SEQ ID NO: 280).

SC06-344 nucleotide sequence (SEQ ID NO: 411)

```
caggtgcagc tggtgcagtc tggggctgag gtgaagaagc ctgggtcctc ggtgagagtc   60
tcctgcaagg cttctggaag catcttcaga aactatgcta tgagctgggt gcgacaggcc  120
cctggacaag ggcttgagtg gatgggaggg atcatcgcta tttttgggac accaaagtac  180
gcacagaagt tccagggcag agtcacgatt accgcggacg aatcgacgag cactgtctac  240
atgaactga gcggactgag atctgaggac acggccatgt attactgtgc gaggattccc  300
cactataatt ttggttcggg gagttatttc gactactggg gccagggaac cctggtcacc  360
gtctcgagcg gtacgggcgg ttcaggcgga accggcagcg gcactggcgg gtcgacgact  420
gtgttgacac agccgccctc agtgtctggg gccccaggagc agagggtcac catctcctgc  480
actgggagca gctccaacat cggggcaggt tatgatgtac actggtacca gcagcttcca  540
ggaacagccc ccaaactcct catctatggt aacagcaatc ggccctcagg ggtccctgac  600
cgattctctg gctccaagtc tggcacgtca gccaccctgg gcatcaccgg actccagact  660
ggggacgagg ccgattatta ctgcgaaaca tgggatagca gcctgagtgc ttatgtcttc  720
ggaactggga ccaaggtcac cgtcctaggt                                  750
```

SC06-344 amino acid sequence (SEQ ID NO: 412)

QVQLVQSGAEVKKPGSSVRVSCKASGSIFRNYAMSWVRQAPGQGLEWMGGIIAIFGTPKY
AQKFQGRVTITADESTSTVYMELSGLRSEDTAMYYCARIPHYNFGSGSYFDYWGQGTLVT
VSSGTGGSGGTGSGTGGSTTVLTQPPSVSGAPGQRVTISCTGSSSNIGAGYDVHWYQQLPG
TAPKLLIYGNSNRPSGVPDRFSGSKSGTSATLGITGLQTGDEADYYCGTWDSSLSAYVFGT
GTKVTVLG

SC06-344 VH amino acid sequence (SEQ ID NO: 409)

QVQLVQSGAEVKKPGSSVRVSCKASGSIFRNYAMSWVRQAPGQGLEWMG**GIIAIFGTPK
YAQKFQGRVTITADESTSTVYMELSGLRSEDTAMYYCARIPHYNFGSGSYFDY**WGQGTL
VTVSS

-continued

SC06-344 VL amino acid sequence
(SEQ ID NO: 410)
TVLTQPPSVSGAPGQRVTISCTGSSSNIGAGYDVHWYQQLPGTAPKLLIYGNSNRPSGVPD
RFSGSKSGTSATLGITGLQTGDEADYYCGTWDSSLSAYVFGTGTKVTVLG IgG HA Antibodies The CR6141 HA-specific IgG antibody includes a heavy chain variable region (SEQ ID NO: 199) encoded by the heavy chain nucleotide sequence shown in SEQ ID NO: 279 and the heavy chain amino acid sequence shown in SEQ ID NO: 413. The CR6141 HA-specific IgG antibody also includes a light chain variable region (SEQ ID NO: 414) encoded by the light chain nucleotide sequence shown in SEQ ID NO: 415 and the light chain amino acid sequence shown in SEQ ID NO: 416.

```
CR6141 Heavy Chain nucleotide sequence
                                                     (SEQ ID NO: 279)
gaggtccagc tggtgcagtc tggggctgag gtgaagaagc ctggggcctc agtgaaggtc     60
tcctgcaagg cttctgggta caccttcacc ggctactatg tgtactgggt gcgacaggcc    120
cctggacaag gcttgagtg gatgggatgg atcagcgctt acaatggtaa cacaaactat    180
gcacagaagt tccagggcag agtcacgatt accgcggaca atccacgag cacagcctac    240
atggagctga gcagcctgag atctgaagac acggctgtgt attactgtgc gagaagtaga    300
tccctggacg tctgggggcca agggaccacg gtcaccgtct cgagtgctag caccaaggggc   360
cccagcgtgt tccccctggc ccccagcagc aagagcacca gcggcggcac agccgccctg    420
ggctgcctgg tgaaggacta cttccccgaa cccgtgaccg tgagctggaa cagcggcgcc    480
ttgaccagcg gcgtgcacac cttccccgcc gtgctgcaga gcagcggcct gtacagcctg    540
agcagcgtgg tgaccgtgcc cagcagcagc ctgggcaccc agacctacat ctgcaacgtg    600
aaccacaagc ccagcaacac caaggtggac aaacgcgtgg agcccaagag ctgcgacaag    660
acccacacct gccccccctg ccctgccccc gagctgctgg gcggaccctc cgtgttcctg    720
ttcccccca agcccaagga cacctcatg atcagccga ccccgaggt gacctgcgtg    780
gtggtggacg tgagccacga ggaccccgag gtgaagttca actggtacgt ggacggcgtg    840
gaggtgcaca cgccaagac caagccccgg gaggagcagt acaacagcac ctaccgggtg    900
gtgagcgtgc tcaccgtgct gcaccaggac tggctgaacg gcaaggagta caagtgcaag    960
gtgagcaaca aggccctgcc tgcccccatc gagaagacca tcagcaaggc caagggccag   1020
cccggagc ccaggtgta caccctgccc cccagccga aggagatgac caagaaccag   1080
gtgtccctca cctgtctggt gaagggcttc taccccagcg acatcgccgt gggagtggggag  1140
agcaacggcc agcccgagaa caactacaag accacccccc ctgtgctgga cagcgacggc   1200
agcttcttcc tgtacagcaa gctcaccgtg gacaagagcc ggtggcagca gggcaacgtg   1260
ttcagctgca gcgtgatgca cgaggccctg cacaaccact acacccagaa gagcctgagc   1320
ctgagccccg gcaag                                                   1335

CR6141 Heavy Chain amino acid sequence
                                                     (SEQ ID NO: 413)
EVQLVQSGAEVKKPGASVKVSCKASGYTFTGYYVYWVRQAPGQGLEWMGWISAYNGNT
NYAQKFQGRVTITADKSTSTAYMELSSLRSEDTAVYYCARSRSLDVWGQGTTVTVSSAST
KGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNV
FSCSVMHEALHNHYTQKSLSLSPGK CR6141 VH amino acid sequence
                                                     (SEQ ID NO: 199)
EVQLVQSGAEVKKPGASVKVSCKASGYTFTGYYVYWVRQAPGQGLEWMGWISAYNGNT
NYAQKFQGRVTITADKSTSTAYMELSSLRSEDTAVYYCARSRSLDVWGQGTTVTVSS CR6141 Light Chain nucleotide sequence
                                                     (SEQ ID NO: 415)
gatgttgtga tgactcagtc tccagactcc ctggctgtgt ctctgggcga gagggccacc     60
atcaactgca agtccagcca gagtgtttta tacagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
cctctcactt tcggcggagg gaccaaagtg gatatcaaac gtgcggccgc acccagcgtg    360
ttcatcttcc ccccctccga cgagcagctg aagagcggca ccgccagcgt ggtgtgcctg    420
ctgaacaact ctctacccccg ggaggccaag gtgcagtgga aggtggacaa cgccctgcag   480
agcggcaaca gccaggagag cgtgaccgag caggacagca aggactccac ctacagcctg    540
agcagcaccc tcaccctgag caaggccgac tacgagaagc acaaggtgta cgcctgcgag    600
gtgacccacc agggcctgag cagccccgtg accaagagct caaccgggg cgagtgt       657

CR6141 Light Chain amino acid sequence
                                                     (SEQ ID NO: 416)
DVVMTQSPDSLAVSLGERATINCKSSQSVLYSSNNKNYLAWYQQKPGQPPKLLIYWASTR
ESGVPDRFSGSGSGTDFTLTISSLQAEDVAVYYCQQYYSTPLTFGGGTKVDIKRAAAPSVFI
FPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC
```

CR6141 VL amino acid sequence
(SEQ ID NO: 414)

DVVMTQSPDSLAVSLGERATINCKSSQSVLYSSNNKNYLAWYQQKPGQPPKLLIYWASTR
ESGVPDRFSGSGSGTDFTLTISSLQAEDVAVYYCQQYYSTPLTFGGGTKVDIKR

The CR6255 HA-specific IgG antibody includes a heavy chain variable region (SEQ ID NO: 417) encoded by the heavy chain nucleotide sequence shown in SEQ ID NO: 418 and the heavy chain amino acid sequence shown in SEQ ID NO: 419. The CR6255 HA-specific IgG antibody also includes a light chain variable region (SEQ ID NO: 420) encoded by the light chain nucleotide sequence shown in SEQ ID NO: 421 and the light chain amino acid sequence shown in SEQ ID NO: 422.

CR6255 Heavy Chain nucleotide sequence
(SEQ ID NO: 418)

```
gaggtgcagc tggtggagtc tggggctgag gtgaagaagc ctgggtcctc ggtgaaagtc    60
tcttgcaagg cttctggagg ccccttccgc agctatgcta tcagctgggt gcgacaggcc   120
cctggacaag ggcctgagtg gatgggaggg atcatcccta tttttggtac aacaaaatac   180
gcaccgaagt tccagggcag agtcacgatt accgcggacg atttcgcggg cacagtttac   240
atggagctga gcagcctgcg atctgaggac acggccatgt actactgtgc gaaacatatg   300
gggtaccagg tgcgcgaaac tatggacgtc tggggcaaag ggaccacggt caccgtctcg   360
agtgctagca ccaagggccc cagcgtgttc cccctggcgc cctgctccaa gagcaccagc   420
ggcggcacag ccgccctggg ctgcctggtg aaggactact cccccgagcc cgtgaccgtg   480
agctggaaca gcggcgcctt gaccagcggc gtgcacacct tcccggccgt gctgcagagc   540
agcggcctgt acagcctgag cagcgtggtg accgtgccca gcagcagcct gggcacccag   600
acctacatct gcaacgtgaa ccacaagccc agcaacacca aggtggacaa acgcgtggag   660
cccaagagct gcgacaagac ccacacctgc cccccctgcc ctgccccga gctgctgggc   720
ggaccctccg tgttcctgtt cccccccaag cccaaggaca ccctcatgat cagccggacc   780
cccgaggtga cctgcgtggt ggtggacgtg agccacgagg accccgaggt gaagttcaac   840
tggtacgtgg acggcgtgga ggtgcacaac gccaagacaa agccccggga ggagcagtac   900
aacagcacct accgggtggt gagcgtgctc accgtgctgc accaggactg gctgaacggc   960
aaggagtaca gtgcaaggt gagcaacaag gccctgcctg cccccatcga agaccatc    1020
agcaaggcca agggccagcc ccgggagccc caggtgtaca ccctgccccc cagccgggag  1080
gagatgacca agaaccaggt gtccctcacc tgtctggtga agggcttcta ccccagcgac  1140
atcgccgtgg agtgggagag caacggccag cccgagaaca actacaagac caccccccct  1200
gtgctggaca gcgacggcag cttcttcctg tacagcaagc tcaccgtgga caagagccgg  1260
tggcagcagg gcaacgtgtt cagctgcagc gtgatgcacg aggccctgca caaccactac  1320
acccagaaga gcctgagcct gagccccggc aag                               1353
```

CR6255 Heavy Chain amino acid sequence
(SEQ ID NO: 419)

EVQLVESGAEVKKPGSSVKVSCKASGGPFRSYAISWVRQAPGQGPEWMGGIIIPIFGTTKYA
PKFQGRVTITADDFAGTVYMELSSLRSEDTAMYYCAKHMGYQVRETMDVWGKGTTVTV
SSASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHTCPPCTAPELLG
GPSVFLFPPKPKDTLMISRTPEVTCVVVDVSHEDPEVKFNWYVDGVEVHNAKTKPREEQY
NSTYRVVSVLTVLHQDWLNGKEYKCKVSKNALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK

CR6255 VH amino acid sequence
(SEQ ID NO: 417)

EVQLVESGAEVKKPGSSVKVSCKASGGPFRSYAISWVRQAPGQGPEWMGGIIPIFGTTKY
APKFQGRVTITADDFAGTVYMELSSLRSEDTAMYYCAKHMGYQVRETMDVWGKGTTVT
VSS

CR6255 Light Chain nucleotide sequence
(SEQ ID NO: 421)

```
tcctatgtgc tgactcagcc accctcagcg tctgggaccc ccgggcagag ggtcaccatc    60
tcttgttctg gaagcacgtt caacatcgga gtaatgctta tagactggta ccggcagctc   120
ccaggaacgg ccccccaaact cctcatctat agtaataatc agcggccctc aggggtccct   180
gaccgattct ctggctccag gtctggcacc tcagcctccc tggccatcag tgggctccag   240
tctgaggatg aggctgatta ttactgtgca gcatgggatg acatcctgaa tgttccggta   300
ttcggcggag ggaccaagct gaccgtccta ggtgcggccg caggccagcc caaggccgct   360
cccagcgtga ccctgttccc cccctcctcc gaggagctgc aggccaacaa ggccaccctg   420
gtgtgcctca tcagcgactt ctaccctggc gccgtgaccg tggcctggaa ggccgacagc   480
agccccgtga aggccggcgt ggagaccacc accccagca agcagagcaa caacaagtac   540
gccgccagca gctacctgag cctcaccccc gagcagtgga gagccaccg agctacagc    600
tgccaggtga cccacgaggg cagcaccgtg gagaagaccg tggcccccac cgagtgcagc   660
```

CR6255 Light Chain amino acid sequence
(SEQ ID NO: 422)

SYVLTQPPSASGTPGQRVTISCSGSTFNIGSNAVDWYRQLPGTAPKLLIYSNNQRPSGVPDR
FSGSRSGTSASLAISGLQSEDEADYYCAAWDDILNVPVFGGGTKLTVLGAAAGQPKAAPS

-continued

VTLFPPSSEELQANKATLVCLISDFYPGAVTVAWKADSSPVKAGVETTTPSKQSNNKYAAS
SYLSLTPEQWKSHRSYSCQVTHEGSTVEKTVAPTECS

CR6255 VL amino acid sequence
(SEQ ID NO: 420)
SYVLTQPPSASGTPGQRVTISCSGSTFNIGSNAVDWYRQLPGTAPKLLIYSNNQRPSGVPDR
FSGSRSGTSASLAISGLQSEDEADYYCAAWDDILNVPVFGGGTKLTVLG The CR6257 HA-specific IgG antibody includes a heavy chain variable region (SEQ ID NO: 423) encoded by the heavy chain nucleotide sequence shown in SEQ ID NO: 424 and the heavy chain amino acid sequence shown in SEQ ID NO: 425. The CR6257 HA-specific IgG antibody also includes a light chain variable region (SEQ ID NO: 426) encoded by the light chain nucleotide sequence shown in SEQ ID NO: 427 and the light chain amino acid sequence shown in SEQ ID NO: 428.

```
CR6257 Heavy Chain nucleotide sequnece
                                                   (SEQ ID NO: 424)
caggtccagc tggtgcagtc tggggctgag gtgaagaagc ctgggtcctc ggtgaaagtc    60
tcttgcaagg cttctggagg cccttccgc agctatgcta tcagctgggt gcgacaggcc   120
cctggacaaa ggcctgagtg gatgggaggg atcatcccta tttttggtac aacaaaatac   180
gcaccgaagt tccagggcag agtcacgatt accgcggacg atttcgcggg cacagtttac   240
atggagctga gcagcctgcg atctgaggac acggccatgt actactgtgc gaaacatatg   300
gggtaccagg tgcgcgaaac tatggacgtc tggggcaaag gaccacggt caccgtctcg   360
agtgctagca ccaagggccc cagcgtgttc cccctgcccc ccagcagcaa gagcaccagc   420
ggcggcacag ccgccctggg ctgcctggtg aaggactact ccccgagcc cgtgaccgtg   480
agctggaaca gcggcgcctt gaccagcggc gtgcacacct tccccgccgt gctgcagagc   540
agcggcctgt acagcctgag cagcgtggtg accgtgccca gcagcagcct gggcacccag   600
acctacatct gcaacgtgaa ccacaagccc agcaacacca aggtggacaa acgcgtggag   660
cccaaggctgcgacaagac ccacacctgc ccccctgcc ctgccccga gctgctgggc   720
ggaccctccg tgttcctgtt ccccccaag cccaaggaca ccctcatgat cagccggacc   780
cccgaggtga cctgcgtggt ggtggacgtg agccacgagg accccgaggt gaagttcaac   840
tggtacgtgg acggcgtgga ggtgcacaac gccaagacca gccccggga ggagcagtac   900
aacagcacct accgggtggt gagcgtgctc accgtgctgc accaggactg gctgaacggc   960
aaggagtaca agtgcaaggt gagcaacaag gccctgcctg ccccatcga gaagaccatc  1020
agcaaggcca agggccagcc ccgggagccc caggtgtaca ccctgccccc cagccgggag  1080
gagatgacca gaaccaggt gtccctcacc tgtctggtga aggcttcta ccccagcgac  1140
atcgccgtgg agtgggagag caacggccag cccgagaaca actacaagac cacccccct  1200
gtgctggaca gcgacggcag cttcttcctg tacagcaagc tcaccgtgga caagagccgg  1260
tggcagcagg gcaacgtgtt cagctgcagc gtgatgcacg aggccctgca caaccactac  1320
acccagaaga gcctgagcct gagccccggc aag                               1353

CR6257 Heavy Chain amino acid sequence
                                                   (SEQ ID NO: 425)
QVQLVQSGAEVKKPGSSVKVSCKASGGPFRSYAISWVRQAPGQGPEWMGGIIPIFGTTKY
APKFQGRVTITADDFAGTVYMELSSLRSEDTAMYYCAKHMGYQVRETMDVWGKGTTVT
VSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDLNGKEYKCKVSNKALPAPIEKTISKAKGQPREPQVYTLPPSRE
EMTKNQVSLTCLVKGFYPSIDIAVEWESNGQPENNYKTTPPVLDSDGSFFLYSKLTVDKSR
WQQGNVFSCSVMHEALHNHYTQKSLSLSPGK CR6257 VH amino acid sequence
                                                   (SEQ ID NO: 423)
QVQLVQSGAEVKKPGSSVKVSCKASGGPFRSYAISWVRQAPGQGPEWMGGIIPIFGTTKY
APKFQGRVTITADDFAGTVYMELSSLRSEDTAMYYCAKHMGYQVRETMDVWGKGTTVT
VSS CR6257 Light Chain nucleotide sequence
                                                   (SEQ ID NO: 427)
cagtctgccc tgactcagcc tgccgccgtg tctgggtctc ctggacagtc gatcaccatc    60
tcctgcactg gaaccagcag tgacgttggt ggttataact atgtctcctg gtaccaacag   120
cacccaggca aagcccccaa actcatgatt tatgaggtca gtaatcggcc ctcaggggtt   180
tctaatcgct tctctggctc caagtctggc aacacggcct ccctgaccat ctctgggctc   240
caggctgagg acgaggctga ttattactgc agctcatata caagcagcag cacttatgtc   300
ttcggaactg ggaccaaggt caccgtccta ggtgcggccg caggccagcc caaggccgct   360
cccagcgtga ccctgttccc cccctcctcc gaggagctgc aggccaacaa ggccacccct   420
gtgtgcctca tcagcgactt ctaccctggc gccgtgaccg tggcctggaa ggccgacagc   480
agccccgtga aggccggcgt ggagaccacc accccagca gcagagcaa caacaagtac   540
gccgccagca gctacctgag cctcaccccc gagcagtgga agagcaccg agctacagc   600
tgccaggtga cccacgaggg cagcaccgtg gagaagaccg tggcccccac cgagtgcagc   660
```

-continued

CR6257 Light Chain amino acid sequence
(SEQ ID NO: 428)
QSALTQPAAVSGSPGQSITISCTGISSDVGGYNYVSWYQQHPGKAPKLMIYEVSNRPSGVS
NRFSGSKSGNTASLTISGLQAEDEADYYCSSYTSSSTYVFGTGTKVTVLGAAAGQPKAAPS
VTLFPPSSEELQANKATLVCLISDFYPGAVTVAWKADSSPVKAGVETTTPSKQSNNKYAAS
SYLSLTPEQWKSHRSYS CQVTHEGSTVEKTVAPTECS CR6257 VL amino acid sequence
(SEQ ID NO: 426)
QSALTQPAAVSGSPGQSITISCTGTSSDVGGYNYVSWYQQHPGKAPKLMIYEVSNRPSGVS
NRFSGSKSGNTASLTISGLQAEDEADYYCSSYTSSSTYVFGTGTKVTVLG The CR6260 HA-specific IgG antibody includes a heavy chain variable region (SEQ ID NO: 429) encoded by the heavy chain nucleotide sequence shown in SEQ ID NO: 430 and the heavy chain amino acid sequence shown in SEQ ID NO: 431. The CR6260 HA-specific IgG antibody also includes a light chain variable region (SEQ ID NO: 432) encoded by the light chain nucleotide sequence shown in SEQ ID NO: 433 and the light chain amino acid sequence shown in SEQ ID NO: 434.

```
CR6260 Heavy Chain nucleotide sequence
                                                   (SEQ ID NO: 430)
gaggtgcagc tggtggagtc tggggctgag gtgaagaagc ctgggtcctc ggtgaaagtc   60
tcttgcaagg cttctggagg ccccttccgc agctatgcta tcagctgggt gcgacaggcc  120
cctgacaag ggcctgagtg gatgggaggg atcatcccta tttttggtac aacaaaatac  180
gcaccgaagt tccagggcag agtcacgatt accgcggacg atttcgcggg cacagtttac  240
atggagctga gcagcctgcg atctgaggac acggccatgt actactgtgc gaaacatatg  300
gggtaccagg tgcgcgaaac tatggacgtc tggggcaaag ggaccacggt caccgtctcg  360
agtgctagca ccaagggccc cagcgtgttc ccctggccc ccagcagcaa gagcaccagc  420
ggcggcacag ccgccctggg ctgcctggtg aaggactact cccccgagcc cgtgaccgtg  480
agctggaaca gcggcgcctt gaccagcggc gtgcacaccc tcccccgcgt gctgcagacc  540
agcggcctgt acagcctgag cagcgtggtg accgtgccca gcagcagcct gggcacccag  600
acctacatct gcaacgtgaa ccacaagccc agcaacacca aggtggacaa acgcgtggag  660
cccaagagct gcgacaagac ccacacctgc cccccctgcc ctgccccga gctgctgggc  720
ggacccteg tgttcctgtt cccccccaag ccaaggaca ccctcatgat cagccggacc  780
cccgaggtga cctgcgtggt ggtggacgtg agccacgagg accccgaggt gaagttcaac  840
tggtacgtgg acggcgtgga ggtgcacaac gccaagacca gccccgggga ggagcagtac  900
aacagcacct accgggtggt gagcgtgctc accgtgctgc accaggactg gctgaacggc  960
aaggagtaca agtgcaaggt gagcaacaag gccctgccct cccccatcga gaagaccatc 1020
agcaaggcca agggccagcc ccgggagccc caggtgtaca ccctgccccc cagccgggag 1080
gagatgacca gaaccaggt gtccctcacc tgtctggtga agggcttcta ccccagcgac 1140
atcgccgtgg agtgggagag caacggccag cccgagaaca actacaagac cacccccct 1200
gtgctggaca gcgacggcag cttcttcctg tacagcaagc tcaccgtgga caagagccgg 1260
tggcagcagg gcaacgtgtt cagctgcagc gtgatgcacg aggccctgca caaccactac 1320
acccagaaga gcctgagcct gagccccggc aag                              1353

CR6260 Heavy Chain amino acid sequence
                                                   (SEQ ID NO: 431)
EVQLVESGAEVKKPGSSVKVSCKASGGPFRSYAISWVRQAPGQGPEWMGGIIPIFGTTKYA
PKFQGRVTITADDFAGTVYMELSSLRSEDTAMYYCAKHMGYQVRETMDVWGKGTTVTV
SSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK CR6260 VH amino acid sequence
                                                   (SEQ ID NO: 429)
EVQLVESGAEVKKPGSSVKVSCKASGGPFRSYAISWVRQAPGQGPEWMGGIIPIFGTTKYA
PKFQGRVTITADDFAGTVYMELSSLRSEDTAMYYCAKHMGYQVRETMDVWGKGTTVTV
SS CR6260 Light Chain nucleotide sequence
                                                   (SEQ ID NO: 433)
tcctatgtgc tgactcagcc accctcagtc tctgggaccc ccgggcagag ggtcaccatc   60
tcttgctctg gaagccgctc caacgtcgga gataattctg tatattggta tcaacacgtc  120
ccagaaatgg cccccaaact cctcgtctat aagaatactc aacggcctc aggagtccct  180
gcccggtttt ccggctccaa gtctggcact tcagcctccc tggccatcat tggcctccag  240
tccggcgatg aggctgatta ttattgtgtg gcatggagat acagcgtaga tggctatgtc  300
ttcggatctg gaccaaggt caccgtccta ggtgcggccg caggccagcc caaggccgct  360
cccagcgtga ccctgttccc ccctcctcc gaggagctgc aggccaacaa ggccaccctg  420
gtgtgcctca tcagcgactt ctaccctggc gccgtgaccg tggcctggaa ggccgacagc  480
agccccgtga aggccggcgt ggagaccacc acccccagca gcagagcaa caacaagtac  540
```

-continued

```
gccgccagca gctacctgag cctcaccccc gagcagtgga agagccaccg gagctacagc 600
tgccaggtga cccacgaggg cagcaccgtg gagaagaccg tggcccccac cgagtgcagc 660
```

CR6260 Light Chain amino acid sequence
(SEQ ID NO: 434)
SYVLTQPPSVSGTPGQRVTISCSGSRSNVGDNSVYWYQHVPEMAPKLLVYKNTQRPSGVP
ARFSGSKSGTSASLAIIGLQSGDEADYYCVAWDDSVDGYVFGSGTKVTVLGAAAGQPKAA
PSVTLFPPSSEELQANKATLVCLISDFYPGAVTVAWKADSSPVKAGVETTTPSKQSNNKY
AASSYLSLTPEQWKSHRSYSCQVTHEGSTVEKTVAPTECS CR6260 VL amino acid sequence
(SEQ ID NO: 432)
SYVLTQPPSVSGTPGQRVTISCSGSRSNVGDNSVYWYQHVPEMAPKLLVYKNTQRPSGVP
ARFSGSKSGTSASLAIIGLQSGDEADYYCVAWDDSVDGYVFGSGTKVTVLG The CR6261 HA-specific IgG antibody includes a heavy chain variable region (SEQ ID NO: 435) encoded by the heavy chain nucleotide sequence shown in SEQ ID NO: 436 and the heavy chain amino acid sequence shown in SEQ ID NO: 437. The CR6261 HA-specific IgG antibody also includes a light chain variable region (SEQ ID NO: 438) encoded by the light chain nucleotide sequence shown in SEQ ID NO: 439 and the light chain amino acid sequence shown in SEQ ID NO: 440.

```
CR6261 Heavy Chain nucleotide sequence
                                                    (SEQ ID NO: 436)
gaggtgcagc tggtggagtc tgggctgag gtgaagaagc ctgggtcctc ggtgaaagtc   60
tcttgcaagg cttctggagg cccttccgc agctatgcta tcagctgggt gcgacaggcc  120
cctggacaag ggcctgagtg gatgggaggg atcatcccta tttttggtac aacaaaatac  180
gcaccgaagt tccagggcag agtcacgatt accgcggacg atttcgcggg cacagtttac  240
atggagctga gcagcctgcg atctgaggac acggccatgt actactgtgc gaaacatatg  300
gggtaccagg tgcgcgaaac tatggacgtc tggggcaaag ggaccacggt caccgtctcg  360
agtgctagca ccaagggccc catcgtgttc cccctgccca gcagcaag gagcaccagc  420
ggcggcacag ccgccctggg ctgcctggtg aaggactact ccccgagcc cgtgaccgtg  480
agctggaaca gcggcgcctt gaccagcggc gtgcacacct tcccgccgt gctgcagagc  540
agcggcctgt acagcctgag cagcgtggtg accgtgccca gcagcagcct gggcacccag  600
acctacatct gcaacgtgaa ccacaagccc agcaacacca aggtggacaa acgcgtggag  660
cccaagagct gcgacaagac ccacacctgc ccccccgc ctgccccga gctgctgggc  720
ggaccctccg tgttcctgtt cccccccaag cccaaggaca ccctcatgat cagccggacc  780
cccgaggtga cctgcgtggt ggtggacgtg agccacgagg accccgaggt gaagttcaac  840
tggtacgtgg acggcgtgga ggtgcacaac gccaagacca agccccggga ggagcagtac  900
aacagcacct accgggtggt gagcgtgctc accgtgctgc accaggactg gctgaacggc  960
aaggagtaca agtgcaaggt gagcaacaag gccctgcctg cccccatcga aagaccatc 1020
agcaaggcca agggccagcc ccgggagccc caggtgtaca cctgccccc cagccgggag 1080
gagatgacca agaaccaggt gtccctcacc tgtctgggtga agggcttcta ccccagcgac 1140
atcgccgtgg agtgggagag caacggccag cccgagaaca actacaagac cacccccct 1200
gtgctggaca gcgacggcag cttcttcctg tacagcaagc tcaccgtgga caagagccgg 1260
tggcagcagg gcaacgtgtt cagctgcagc gtgatgcacg aggccctgca caaccactac 1320
acccagaaga gcctgagcct gagccccggc aag                              1353
```

CR6261 Heavy Chain amino acid sequence
(SEQ ID NO: 437)
EVQLVESGAEVKKPGSSVKVSCKASGGPFRSYAISWVRQAPGQGPEWMGGIIPIFGTTKYA
PKFQGRVTITADDFAGTVYMELSSLRSEDTAMYYCAKHMGYQVRETMDVWGKGTTVTV
SSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK CR6261 VH amino acid sequence
(SEQ ID NO: 435)
EVQLVESGAEVKKPGSSVKVSCKASGGPFRSYAISWVRQAPGQGPEWMGGIIPIFGTTKYA
PKFQGRVTITADDFAGTVYMELSSLRSEDTAMYYCAKHMGYQVRETMDVWGKGTTVTV
SS

```
CR6261 Light Chain nucleotide sequence
                                                    (SEQ ID NO: 439)
cagtctgtgt tgacgcagcc gccctcagtg tctgcggccc caggacagaa ggtcaccatc   60
tcctgctctg gaagcagctc caacattggg aatgattatg tatcctggta ccagcagctc  120
ccaggaacag cccccaaact cctcatttat gacaataata agcgaccctc agggattcct  180
gaccgattct ctggctccaa gtctggcacg tcagccaccc tgggcatcac cggactccag  240
actggggacg aggccaacta ttactgcgca acatgggatc gccgcccgac tgcttatgtt  300
gtcttcggcg gagggaccaa gctgaccgtc ctaggtgcgg ccgcaggcca gcccaaggcc  360
gctcccagcg tgaccctgtt cccccccctcc tccgaggagc tgcaggccaa caaggccacc  420
```

-continued
```
ctggtgtgcc tcatcagcga cttctaccct ggcgccgtga ccgtggcctg gaaggccgac  480
agcagcccg  tgaaggccgg cgtggagacc accacccca  gcaagcagag caacaacaag  540
tacgccgcca gcagctacct gagcctcacc cccgagcagt ggaagagcca ccggagctac  600
agctgccagg tgacccacga gggcagcacc gtggagaaga ccgtggcccc caccgagtgc  660
```

CR6261 Light Chain amino acid sequence
(SEQ ID NO: 440)
```
QSVLTQPPSVSAAPGQKVTISCSGSSSNIGNDYVSWYQQLPGTAPKLLIYDNNKRPSGIPDR
FSGSKSGTSATLGITGLQTGDEANYYCATWDRRPTAYVVFGGGTKLTVLGAAAGQPKAAP
SVTLFPPSSEELQANKATLVCLISDFYPGAVTVAWKADSSPVKAGVETTTPSKQSNNKYAA
SSYLSLTPEQWKSHRSYSCQVTHEGSTVEKTVAPTECS
```

CR6261 VL amino acid sequence
(SEQ ID NO: 438)
```
QSVLTQPPSVSAAPGQKVTISCSGSSSNIGNDYYSWYQQLPGTAPKLLIYDNNKRPSGIPDR
FSGSKSGTSATLGITGLQTGDEANYYCATWDRRPTAYVVFGGGTKLTVLG
```

The CR6262 HA-specific IgG antibody includes a heavy chain variable region (SEQ ID NO: 441) encoded by the heavy chain nucleotide sequence shown in SEQ ID NO: 442 and the heavy chain amino acid sequence shown in SEQ ID NO: 443. The CR6262 HA-specific IgG antibody also includes a light chain variable region (SEQ ID NO: 444) encoded by the light chain nucleotide sequence shown in SEQ ID NO: 445 and the light chain amino acid sequence shown in SEQ ID NO: 446.

CR6262 Heavy Chain nucleotide sequence
(SEQ ID NO: 442)
```
caggtacagc tgcagcagtc aggggctgag gtgaagaagc ctgggtcctc ggtgaaggtc   60
tcctgcaagg tttccggagt cattttcagc ggcagtgcga tcagctgggt gcgacaggcc  120
cctggacaag gccttgagtg gatgggaggg atcagccctc tctttggcac aacaaattac  180
gcacaaaagt tccagggcag agtcacgatt accgcggacc aatccacgaa cacaacctac  240
atggaggtga acagcctgag atatgaggac acggccgtgt atttctgtgc gcgaggtcca  300
aaatattaca gtgagtacat ggacgtctgg ggcaaaggga ccacggtcac cgtctctcagt  360
gctagcacca agggcccag  cgtgttcccc ctggccccca gcagcaagag caccagcggc  420
ggcacagcct cctgggctg  cctggtgaag gactacttcc ccgagcccgt gaccgtgagc  480
tggaacagcg gcgccttgac cagcggcgtg cacaccttcc ccgccgtgct gcagagcagc  540
ggcctgtaca gcctgagcag cgtggtgacc gtgcccagca gcagcctggg cacccagacc  600
tacatctgca acgtgaacca caagcccagc aacaccaagg tggacaaacg cgtggagccc  660
aagagctgcg acaagaccca cacctgcccc cctgccctg  ccccgagct  gctgggcgga  720
ccctccgtgt tcctgttccc ccccaagccc aaggacaccc tcatgatcag ccggacccc   780
gaggtgacct gcgtggtggt ggacgtgagc cacgaggacc ccgaggtgaa gttcaactgg  840
tacgtggacg gcgtggaggt gcacaacgcc aagaccaagc ccgggagga  gcagtacaac  900
agcacctacc gggtggtgag cgtgctcacc gtgctgcacc aggactggct gaacggcaag  960
gagtacaagt gcaaggtgag caacaaggcc ctgcctgccc ccatcgagaa gaccatcagc 1020
aaggccaagg gccagccccg ggagccccag cgtgtacaccc tgcccccag  ccggagga  1080
atgaccaaga accaggtgtc cctcacctgt ctggtgaagg gcttctaccc cagcgacatc 1140
gccgtggagt gggagagcaa cggccagccc gagaacaact acaagaccac ccccctgtg  1200
ctggacagcg acggcagctt cttcctgtac agcaagctca ccgtgacaa  gagccggtgg 1260
cagcagggca acgtgttcag ctgcagcgtg atgcacgagg ccctgcacaa ccactacacc 1320
cagaagagcc tgagcctgag ccccggcaag                                  1350
```

CR6262 Heavy Chain amino acid sequence
(SEQ ID NO: 443)
```
QVQLQQSGAEVKKPGSSVKVSCKVSGVIFSGSAISWVRQAPGQGLEWMGGISPLFGTTNY
AQKFQGRVTITADQSTNTTYMEVNSLRYEDTAVYFCARGPKYYSEYMDVWGKGTTVTVS
SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK
```

CR6262 VH amino acid sequence
(SEQ ID NO: 441)
```
QVQLQQSGAEVKKPGSSVKVSCKVSGVIFSGSAISWVRQAPGQGLEWMGGISPLFGTTNY
AQKFQGRVTITADQSTNTTYMEVNSLRYEDTAVYFCARGPKYYSEYMDVWGKGTTVTVS
S
```

CR6262 Light Chain nucleotide sequence
(SEQ ID NO: 445)
```
gacatccaga tgacccagtc tccatcctcc ctgtctgcat ctgtaggaga cagagtcacc   60
atcacttgcc gggcgagtca gggcattagc agttatttag cctggtatca gcagaagcca  120
gggaaagttc ctacactcct gatctatgat gcatccactt tgcgatcagg ggtcccatct  180
cgcttcagtg gcagtggatc tgcgacagat ttcactctca ccatcagcag cctgcagcct  240
gaagatgttg caacttatta ctgtcaaagg tataacagtg ccccccgat  caccttcggc  300
```

-continued
```
caagggacac gactggagat taaacgtgcg gccgcaccca gcgtgttcat cttcccccc  360
tccgacgagc agctgaagag cggcaccgcc agcgtggtgt gcctgctgaa caacttctac  420
ccccgggagg ccaaggtgca gtggaaggtg gacaacgccc tgcagagcgg caacagccag  480
gagagcgtga ccgagcagga cagcaaggac tccacctaca gcctgagcag cacccttacc  540
ctgagcaagg ccgactacga gaagcacaag gtgtacgcct gcgaggtgac ccaccagggc  600
ctgagcagcc ccgtgaccaa gagcttcaac cggggcgagt gt                    642

CR6262 Light Chain amino acid sequence
                                                      (SEQ ID NO: 446)
DIQMTQSPSSLSASVGDRVTITCRASQGISSYLAWYQQKPGKVPTLLIYDASTLRSGVPSRF
SGSGSATDFTLTISSLQPEDVATYYCQRYNSAPPITFGQGTRLEIKRAAAPSVFIFPPSDEQLK
SGTASVVCLLNNFYPREAKVQWKVDNALQSGNSQESVTEQDSKDSTYSLSSTLTLSKADY
EKHKVYACEVTHQGLSSPVTKSFNRGEC CR6262 VL amino acid sequence
                                                      (SEQ ID NO: 444)
DIQMTQSPSSLSASVGDRVTITCRASQGISSYLAWYQQKPGKVPTLLIYDASTLRSGVPSRF
SGSGSATDFTLTISSLQPEDVATYYCQRYNSAPPITFGQGTRLEIKR
```

The CR6268 HA-specific IgG antibody includes a heavy chain variable region (SEQ ID NO: 447) encoded by the heavy chain nucleotide sequence shown in SEQ ID NO: 448 and the heavy chain amino acid sequence shown in SEQ ID NO: 449. The CR6268 HA-specific IgG antibody also includes a light chain variable region (SEQ ID NO: 450) encoded by the light chain nucleotide sequence shown in SEQ ID NO: 451 and the light chain amino acid sequence shown in SEQ ID NO: 452.

```
CR6268 Heavy Chain nucleotide sequence
                                                      (SEQ ID NO: 448)
caggtccagc tggtacagtc tggggctgag gtgaagaagc ctgggtcctc ggtgaaggtc   60
tcctgcaagg cttctggagg caccttcagt agttatgcta tcagctgggt gcgacaggcc  120
cctggacaag ggcttgagtg gatgggagga atcatgggta tgtttggcac aactaactac  180
gcacagaagt tccagggcag agtcacgatt accgcggacg aattcacgag cgcagcctac  240
atggagctga ggagcctgag atctgaggac acggccgtct actactgtgc gaggtctagt  300
ggttattacc ccgaatactt ccaggactgg ggccagggca ccctggtcac cgtctcgagt  360
gctagcacca agggcccag cgtgttcccc ctggcccca gcagcaagag caccagcggc  420
ggcacagccg ccctgggctg cctggtgaag gactacttcc ccgagccgt gaccgtgagc  480
tggaacagcg gcgccttgac cagcggcgtg cacaccttcc ccgccgtgct gcagagcagc  540
ggcctgtaca gcctgagcag cgtggtgacc gtgcccagca gcagcctggg cacccagacc  600
tacatctgca acgtgaacca caagcccagc aacaccaagg tggacaaacg cgtggagccc  660
aagagctgcg acaagaccca cacctgcccc cctgccctg ccccgagct gctgggcgga  720
ccctccgtgt tcctgttccc ccccaagccc aaggacaccc tcatgatcag ccggaccccc  780
gaggtgacct gcgtggtggt ggacgtgagc cacgaggacc ccgaggtgaa gttcaactgg  840
tacgtggacg gcgtggaggt gcacaacgcc aagaccaagc cccgggagga gcagtacaac  900
agcacctacc gggtggtgag cgtgctcacc gtgctgcacc aggactggct gaacggcaag  960
gagtacaagt gcaaggtgag caacaaggcc ctgcctgccc ccatcgagaa gaccatcagc 1020
aaggccaagg gccagccccg ggagcccag gtgtacaccc tgcccccag ccgggaggag 1080
atgaccaaga accaggtgtc cctcacctgt ctggtgaagg gcttctaccc cagcgacatc 1140
gccgtggagt gggagagcaa cggccagccc gagaacaact acaagaccac cccccctgtg 1200
ctggacagcg acggcagctt cttcctgtac agcaagctca ccgtggacaa gagccggtgg 1260
cagcagggca acgtgttcag ctgcagcgtg atgcacgagg ccctgcacaa ccactacacc 1320
cagaagagcc tgagcctgag ccccggcaag                                 1350

CR6268 Heavy Chain amino acid sequence
                                                      (SEQ ID NO: 449)
QVQLVQSGAEVKKPGSSVKVSCKASGGTFSSYAISWVRQAPGQGLEWMGGIMGMFGTTN
YAQKFQGRVTITADEFTSAAYMELRSLRSEDTAVYYCARSSGYYPEYFQDWGQGTLVTVS
SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK CR6268 VH amino acid sequence
                                                      (SEQ ID NO: 447)
QVQLVQSGAEVKKPGSSVKVSCKASGGTFSSYAISWVRQAPGQGLEWMGGIMGMFGTTN
YAQKFQGRVTITADEFTSAAYMELRSLRSEDTAVYYCARSSGYYPEYFQDWGQGTLVTVS
S CR6268 Light Chain nucleotide sequence
                                                      (SEQ ID NO: 451)
cagtctgtgc tgactcagcc accctcagag tccgtgtccc caggacagac agccagcgtc   60
acctgctctg gacataaatt gggggataaa tatgtttcgt ggtatcagca gaagccaggc  120
cagtcccctg tattactcat ctatcaagat aacaggcggc cctcagggat ccctgagcga  180
```

-continued
```
ttcataggct ccaactctgg gaacacagcc actctgacca tcagcgggac ccaggctctg 240
gatgaggctg actattactg tcaggcgtgg gacagcagca ctgcggtttt cggcggaggg 300
accaagctga ccgtcctagg tgcggccgca ggccagccca aggccgctcc cagcgtgacc 360
ctgttccccc cctcctccga ggagctgcag gccaacaagg ccaccctggt gtgcctcatc 420
agcgacttct accctggcgc cgtgaccgtg gcctggaagg ccgacagcag cccgtgaag 480
gccggcgtgg agaccaccac ccccagcaag cagagcaaca acaagtacgc cgccagcagc 540
tacctgagcc tcaccccga gcagtggaag agccaccgga gctacagctg ccaggtgacc 600
cacgagggca gcaccgtgga gaagaccgtg gcccccaccg agtgcagc         648
```

CR6268 Light Chain amino acid sequence
(SEQ ID NO: 452)
QSVLTQPPSESVSPGQTASVTCSGHKLGDKYVSWYQQKPGQSPVLLIYQDNRRPSGIPERFI
GSNSGNTATLTISGTQALDEADYYCQAWDSSTAVFGGGTKLTVLGAAAGQPKAAPSVTLF
PPSSEELQANKATLVCLISDFYPGAVTVAWKADSSPVKAGVETTTPSKQSNNKYAASSYLS
LTPEQWKSHRSYSCQVTHEGSTVEKTVAPTECS CR6268 VL amino acid sequence
(SEQ ID NO: 450)
QSVLTQPPSESVSPGQTASVTCSGHKLGDKYVSWYQQKPGQSPVLLIYQDNRRPSGIPERFI
GSNSGNTATLTISGTQALDEADYYCQAWDSSTAVFGGGTKLTVLG The CR6272 HA-specific IgG antibody includes a heavy chain variable region (SEQ ID NO: 453) encoded by the heavy chain nucleotide sequence shown in SEQ ID NO: 454 and the heavy chain amino acid sequence shown in SEQ ID NO: 455. The CR6272 HA-specific IgG antibody also includes a light chain variable region (SEQ ID NO: 456) encoded by the light chain nucleotide sequence shown in SEQ ID NO: 457 and the light chain amino acid sequence shown in SEQ ID NO: 458.

CR6272 Heavy Chain nucleotide sequence
(SEQ ID NO: 454)
```
cagatgcagc tggtgcagtc tggggctgag gtgaagaagc ctgggtcctc ggtgaaggtc   60
tcctgcaagg cttctggagg caccttctcc agttatgcta tcacctgggt gcgacaggcc  120
cctgacaag ggcttgagtg gatgggaggg atcatcggta tgtttggttc aacaaactac  180
gcacagaact tccagggcag agtcacgatt accgcggacg aatccacgag cacagcctac  240
atggagctga gcagcctcag atctgaggac acggccgtgt attactgtgc gagaagtact  300
ggttattacc ctgcatacct ccaccactgg ggccagggca ccctggtcac cgtctcgagt  360
gctagcacca agggcccag cgtgttcccc ctggccccca gcagcaagag caccagcggc  420
ggcacagcgg ccctgggctg cctggtgaag gactacttcc ccgagcccgt gaccgtgagc  480
tggaacagcg gcgccttgac cagcggcgtg cacaccttcc ccgccgtgct gcagagcagc  540
ggcctgtaca gcctgagcag cgtggtgacc gtgcccagca gcagcctggg cacccagacc  600
tacatctgca acgtgaacca caagcccagc aacaccaagg tggacaaacg cgtgagccc  660
aagagctgcg acaagaccca cacctgcccc cctgccctg ccccgagct gctgggcgga  720
ccctccgtgt tcctgttccc ccccaagccc aaggacaccc tcatgatcag ccggacccc  780
gaggtgacct gcgtggtggt ggacgtgagc cacgaggacc ccgaggtgaa gttcaactgg  840
tacgtggacg gcgtggaggt gcacaacgcc aagaccaagc ccgggagga gcagtacaac  900
agcacctacc gggtggtgag cgtgctcacc gtgctgcacc aggactggct gaacggcaag  960
gagtacaagt gcaaggtgag caacaaggcc ctgcctgccc ccatcgagaa gaccatcagc 1020
aaggccaagg gccagccccg ggagcccag gtgtacaccc tgcccccag ccggagggag 1080
atgaccaaga accaggtgtc cctcacctgt ctggtgaagg gcttctaccc cagcgacatc 1140
gccgtggagt gggagagcaa cggccagccc gagaacaact acaagaccac ccccctgtg 1200
ctggacagcg acggcagctt cttcctgtac agcaagctca ccgtggacaa gagccggtgg 1260
cagcagggca acgtgttcag ctgcagcgtg atgcacgagg ccctgcacaa ccactacacc 1320
cagaagagcc tgagcctgag ccccggcaag                                 1350
```

CR6272 Heavy Chain amino acid sequence
(SEQ ID NO: 455)
QMQLVQSGAEVKKPGSSVKVSCKASGGTFSSYAITWVRQAPGQGLEWMGGIIGMFGSTN
YAQNFQGRVTITADESTSTAYMELSSLRSEDTAVYYCARSTGYPAYLHHWGQGTLVTVS
SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK CR6272 VH amino acid sequence
(SEQ ID NO: 453)
QMQLVQSGAEVKKPGSSVKVSCKASGGTFSSYAITWVRQAPGQGLEWMGGIIGMFGSTN
YAQNFQGRVTITADESTSTAYMELSSLRSEDTAVYYCARSTGYPAYLHHWGQGTLVTVS
S CR6272 Light Chain nucleotide sequence
(SEQ ID NO: 457)
```
cagtctgccc tgactcagcc tcgctcagtg tccgggtctc ctggacagtc agtcaccatc   60
```

-continued

```
tcctgcactg gaaccagcag tgatgttggt ggttataact atgtctcctg gtaccaacag  120
cacccaggca aagcccccaa actcatgatt tatgatgtca gtaagcggcc ctcaggggtc  180
cctgatcgct tctctggctc caagtctggc aacacggcct ccctgaccat ctctgggctc  240
caggctgagg atgaggctga ttattactgc agctcatata caagcagcag cactcatgtc  300
ttcggaactg ggaccaaggt caccgtccta ggtgcggccg caggccagcc caaggccgct  360
cccagcgtga ccctgttccc ccctcctcc gaggagctgc aggccaacaa ggccaccctg  420
gtgtgcctca tcagcgactt ctaccctggc gccgtgaccg tggcctggaa ggccgacagc  480
agccccgtga aggccggcgt ggagaccacc accccagca agcagagcaa caacaagtac  540
gccgccagca gctacctgag cctcacccc gagcagtgga gagccaccg gagctacagc  600
tgccaggtga cccacgaggg cagcaccgtg gagaagaccg tggcccccac cgagtgcagc  660
```

CR6272 Light Chain amino acid sequence
(SEQ ID NO: 458)
QSALTQPRSVSGSPGQSVTISCTGTSSDVGGYNYVSWYQQHPGKAPKLMIYDVSKRPSGVP
DRFSGSKSGNTASLTISGLQAEDEADYYCSSYTSSSTHVFGTGTKVTVLGAAAGQPKAAPS
VTLFPPSSEELQANKATLVCLISDFYPGAVTVAWKADSSPVKAGVETTTPSKQSNNKYAAS
SYLSLTPEQWKSHRSYSCQVTHEGSTVEKTVAPTECS CR6272 VL amino acid sequence
(SEQ ID NO: 456)
GSALTQPRSVSGSPGQSVTISCTGTSSDVGGYNYVSWYQQHPGKAPKLMIYDVSKRPSGVP
DRFSGSKSGNTASLTISGLQAEDEADYYCSSYTSSSTHVFGTGTKVTVLG The CR696 HA-specific IgG antibody includes a heavy chain variable region (SEQ ID NO: 459) encoded by the heavy chain nucleotide sequence shown in SEQ ID NO: 460 and the heavy chain amino acid sequence shown in SEQ ID NO: 461. The CR6296 HA-specific IgG antibody also includes a light chain variable region (SEQ ID NO: 462) encoded by the light chain nucleotide sequence shown in SEQ ID NO: 463 and the light chain amino acid sequence shown in SEQ ID NO: 464.

```
CR6296 Heavy Chain nucletide sequence
                                                (SEQ ID NO: 460)
gaggtgcagc tggtggagac cggggctgag gtgaagaagc ctggggcctc agtgaaggtt   60
tcctgcaagg catctggata caccttcacc agctactata tgcactgggt gcgacaggcc  120
cctggacaag ggcttgagtg gatgggatgg atcaacccta cagtggtgg cacaaactat  180
gcacagaagt tcagggcag ggtcaccatg accaggaca cgtccatcag cacagcctac  240
atggagctga gcaggctgag atctgacgac acggccgtgt attactgtgc gagagaggg  300
aaatggggac ctcaagcggc ttttgatatc tggggccaag ggacaatggt caccgtctcg  360
agtgctagca ccaagggccc cagcgtgttc cccctggccc cagcagcaa gagcaccagc  420
ggcggcacag ccgcccgggg ctgcctggtg aaggactact cccccgagcc cgtgaccgtg  480
agctggaaca gcggcgcctt gaccagcggc gtgcacacct ccccgccgt gctgcagagc  540
agcggcctgt acagcctgag cagcgtggtg accgtgccca gcagcagcct gggcacccag  600
acctacatct gcaacgtgaa ccacaagccc agcaacacca aggtggacaa gcgcgtggag  660
cccaagagct gcgacaagac ccacacctgc cccccctgcc ctgcccccga gctgctgggc  720
ggaccctcg tgttcctgtt ccccccaag cccaaggaca ccctcatgat cagccggacc  780
cccgaggtga cctgcgtggt ggtggacgtg agccacgagg accccgaggt gaagttcaac  840
tggtacgtgg acggcgtgga ggtgcacaac gccaagacca gccccggga ggagcagtac  900
aacagcaccct accgggtggt gagcgtgctc accgtgctgc accaggactg gctgaacggc  960
aaggagtaca agtgcaaggt gagcaacaag gccctgcctg cccccatcga aagaccatc  1020
agcaaggcca agggccagcc ccgggagccc caggtgtaca cctgcccccc cagccgggag 1080
gagatgacca gaaccaggt gtccctcacc tgtctgtga agggcttcta cccagcgac   1140
atcgccgtgg agtgggagag caacggccag cccgagaaca actacaagac caccccct   1200
gtgctggaca gcgacggcag cttcttcctg tacagcaagc tcaccgtgga caagagccgg 1260
tggcagcagg gcaagctgtt cagctgcagc gtgatgcacg aggccctgca caaccactac 1320
acccagaaga gcctgagcct gagccccggc aag                              1353
```

CR6296 Heavy Chain amino acid sequence
(SEQ ID NO: 461)
EVQLVETGAEVKKPGASVKVSCKASGYTFTSYYMHWVRQAPGQGLEWMGWINPNSGGT
NYAQKFQGRVTMTRDTSISTAYMELSRLRSDDTAVYCAREGKWGPQAAFDIWGQGTM
VTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPAPELL
GGPSVFLFPPKPKDTLMISRTPEVTCVVVDVSHEDPEVKFNWYDGVEVHNAKTKPREEQ
YNSTYRVVSVLTVHQDWLNGKEYKCKVSNKALPAPIEKTISKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK CR6296 VH amino acid sequence
(SEQ ID NO: 459)
EVQLVETGAEVKKPGASVKVSCKASGYTFTSYYMHWVRQAPGQGLEWMGWINPNSGGT
NYAQKFQGRVTMTRDTSISTAYMELSRLRSDDTAVYYCAREGKWGPQAAFDIWGQGTM
VTVSS -continued CR6296 Light Chain nucleotide sequence (SEQ ID NO: 463)

```
gaaattgtga tgacgcagtc tccaggcacc ctgtctttgt ctccagggga aagagccacc   60
ctctcctgca gggccagtca gagtgttagc agcagctact tagcctggta ccagcagaaa  120
cctggccagg ctcccaggct cctcatctat gatgcatcca gcagggccac tgacatccca  180
gacaggttca gtggcagtgg gtctgggaca gacttcactc tcaccatcag cagactggag  240
cctgaagatt ttgcagtgta ttactgtcag cagtatggta gctcactttg gacgttcggc  300
caagggacca aggtggagat caaacgtgcg gccgcaccca gcgtgttcat cttcccccca  360
tccgacgagc agctgaagag cggcaccgcc agcgtggtgt gcctgctgaa caacttctac  420
ccccgggagg ccaaggtgca gtggaaggtg gacaacgccc tgcagagcgg caacagccag  480
gagagcgtga ccgagcagga cagcaaggac tccacctaca gcctgagcag cacccttacc  540
ctgagcaagg ccgactacga aagcacaag gtgtacgcct gcgaggtgac ccaccagggc  600
ctgagcagcc ccgtgaccaa gagcttcaac cggggcgagt gt                     642
```

CR6296 Light Chain amino acid sequence (SEQ ID NO: 464)

EIVMTQSPGTLSLSPGERATLSCRASQSVSSSYLAWYQQKPGQAPRLLIYDASSRATDIPDR
FSGSGSGTDFTLTISRLEPEDFAVYYCQQYGSSLWTFGQGTKVEIKRAAAPSVFIFPPSDEQL
KSGTASVVCLLNNFYPREAKVQWKVDNALQSGNSQESVTEQDSKDSTYSLSSTLTLSKAD
YEKHKVYACEVTHQGLSSPVTKSFNRGEC

CR6296 VL amino acid sequence (SEQ ID NO: 462)

EIVMTQSPGTLSLSPGERATLSCRASQSVSSSYLAWYQQKPGQAPRLLIYDASSRATDIPDR
FSGSGSGTDFTLTISRLEPEDFAVYYCQQYGSSLWTFGQGTKVEIKR

The CR6301 HA-specific IgG antibody includes a heavy chain variable region (SEQ ID NO: 465) encoded by the heavy chain nucleotide sequence shown in SEQ ID NO: 466 and the heavy chain amino acid sequence shown in SEQ ID NO: 467. The CR6301 HA-specific IgG antibody also includes a light chain variable region (SEQ ID NO: 468) encoded by the light chain nucleotide sequence shown in SEQ ID NO: 469 and the light chain amino acid sequence shown in SEQ ID NO: 470.

CR6301 Heavy Chain nucleotide sequence (SEQ ID NO: 466)

```
gaggtgcagc tggtagagtc tgggggaggc ttggtacagc ctgggggtc cctgagactc    60
tcctgtgcag cctctggatt cacctttagc atctatgcca tgagctgggt ccgccaggca  120
ccagggaagg ggctggagtg ggtctcagct attagtagta gtggtgatag cacatactac  180
gcagactccg tgaagggccg gttcaccatc tccagagaca acgccaggaa cacgctgtat  240
ctgcaaatga acagtctgag agccgaggac acggctgtgt attactgtgc gagagcgtat  300
ggctacacgt tcgaccctg ggggcaggga accctggtca ccgtctccag tgctagcacc  360
aagggcccca gcgtgttccc cctggccccc agcagcaaga gcaccagcgg cggcacagcc  420
gccctgggct gcctggtgaa ggactacttc cccgagcccg tgaccgtgag ctggaacagc  480
ggcgccttga ccagcggcgt gcacaccttc ccggccgtgc tgcagagcag cggcctgtac  540
agcctgagca gcgtggtgac cgtgcccagc agcagcctgg gcacccagac ctacatctgc  600
aacgtgaacc acaagcccag caacaccaag gtggacaaac gcgtggagcc caagagctgc  660
gacaagaccc acacctgccc cccctgccct gcccccgagc tgctgggcgg accctccgtg  720
ttcctgttcc cccccaagcc caaggacacc ctcatgatca gccggacccc cgaggtgacc  780
tgcgtggtgg tggacgtgag ccacgaggac cccgaggtga agttcaactg gtacgtggac  840
ggcgtggagg tgcacaacgc caagaccaag cccggaggg agcagtacaa cagcacctac  900
cgggtggtga gcgtgctcac cgtgctgcac caggactggc tgaacggcaa ggagtacaag  960
tgcaaggtga gcaacaaggc cctgcctgcc cccatcgaga agaccatcag caaggccaag 1020
ggccagcccc gggagcccca ggtgtacacc ctgcccccca gccgggagga gatgaccaag 1080
aaccaggtgt ccctcacctg tctggtgaag ggcttctacc ccagcgacat cgccgtggag 1140
tgggagagca acggccagcc cgagaacaac tacaagacca ccccccctgt gctggacagc 1200
gacggcagct tcttcctgta cagcaagctc accgtggaca agagccggtg gcagcagggc 1260
aacgtgttca gctgcagcgt gatgcacgag gccctgcaca accactacac ccagaagagc 1320
ctgagcctga gccccggcaa g                                           1341
```

CR6301 Heavy Chain amino acid sequence (SEQ ID NO: 467)

EVQLVESGGGLVQPGGSLRLSCAASGFTFSIYAMSWVRQAPGKGLEWVSAISSSGDSTYY
ADSVKGRFTISRDNARNTLYLQMNSLRAEDTAVYYCARAYGYTFDPWGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNV
FSCSVMHEALHNHYTQKSLSLSPGK

CR6301 VH amino acid sequence
(SEQ ID NO: 465)

EVQLVESGGGLVQPGGSLRLSCAASGFTFSIYAMSWVRQAPGKGLEWVSAISSSGDSTYY
ADSVKGRFTISRDNARNTLYLQMNSLRAEDTAVYYCARAYGYTFDPWGQGTLVTVSS

CR6301 Light Chain nucleotide sequence
(SEQ ID NO: 469)

```
gaaattgtgc tgactcagtc tccactctcc ctgcccgtca ccctggaga gccggcctcc   60
atctcctgca ggtctagtca gagcctcctg catagtaatg gatacaacta tttggattgg  120
tacctgcaga agccagggca gtctccacag ctcctgatct atttgggttc taatcgggcc  180
tccggggtcc ctgacaggtt cagtggcagt ggatcaggca cagattttac actgaaaatc  240
agcagagtgg aggctgagga tgttggggtt tattactgca tgcaagctct acaaactccc  300
ctcactttcg gcggagggac caaggtggag atcaaacgtg cggccgcacc cagcgtgttc  360
atcttcccc cctccgacga gcagctgaag agcggcaccg ccagcgtggt gtgcctgctg  420
aacaacttct accccggga ggccaaggtg cagtggaagg tggacaacgc cctgcagagc  480
ggcaacagcc aggagagcgt gaccgagcag gacagcaagg actccaccta cagcctgagc  540
agcaccctca ccctgagcaa ggccgactac gagaagcaca aggtgtacgc ctgcgaggtg  600
acccaccagg gcctgagcag ccccgtgacc aagagcttca ccggggcga gtgt          654
```

CR6301 Light Chain amino acid sequence
(SEQ ID NO: 470)

EIVLTQSPLSLQVTPGEPASISCRSSQSLLHSNGYNYLDWYLQKPGQSPQLLIYLGSNRASGV
PDRFSGSGSGTDFTLKISRVEAEDVGVYYCMQALQTPLTFGGGTKVEIKRAAAPSVFIFPPS
DEQLKSGTASVVCLLNNFYPREAKVQWKVDNALQSGNSQESVTEQDSKDSTYSLSSTLTL
SKADYEKHKVYACEVTHQGLSSPVTKSFNRGEC

CR6301 VL amino acid sequence
(SEQ ID NO: 468)

EIVLTQSPLSLPVTPGEPASISCRSSQSLLHSNGYNYLDWYLQKPGQSPQLLIYLGSNRASGV
PDRFSGSGSGTDFTLKISRVEAEDVGVYYCMQALQTPLTFGGGTKVEIKR

The CR6307 HA-specific IgG antibody includes a heavy chain variable region (SEQ ID NO: 471) encoded by the heavy chain nucleotide sequence shown in SEQ ID NO: 472 and the heavy chain amino acid sequence shown in SEQ ID NO: 473. The CR6307 HA-specific IgG antibody also includes a light chain variable region (SEQ ID NO: 474) encoded by the light chain nucleotide sequence shown in SEQ ID NO: 475 and the light chain amino acid sequence shown in SEQ ID NO: 476.

CR6307 Heavy Chain nucleotide sequence
(SEQ ID NO: 472)

```
caggtccagc tggtgcagtc tgggggaggc ctggtcaagc ctggggggtc cctgagactc   60
tcctgtgcag cctctggatt caccttcagt agctatagca tgaactgggt ccgccaggct  120
ccagggaagg ggctggagtg ggtctcatcc attagtagta gtagtagtta catatactac  180
gtagactcag tgaagggccg attcaccatc tccagagaca acgccaagaa ctcactgtat  240
ctgcaaatga acagcctgag agccgaggac acggctgtgt attactgtgc gagaggtggt  300
gggagctacg gggcctacga aggctttgac tactggggcc agggcaccct ggtcaccgtc  360
tcgagtgcta gcaccaaggg cccagcgtg ttccccctgg ccccagcag caagagcacc  420
agcggcggca cagccgccct gggctgcctg gtgaaggact acttcccga gcccgtgacc  480
gtgagctgga acagcggcgc cttgaccagc ggcgtgcaca ccttcccgc cgtgctgcag  540
agcagcggcc tgtacagcct gagcagcgtg gtgaccgtgc ccagcagcag cctgggcacc  600
cagacctaca tctgcaacgt gaaccacaag cccagcaaca ccaaggtgga caagcgcgtg  660
gagcccaaga gctgcgacaa gacccacacc tgcccccct gccctgcccc cgagctgctg  720
ggcggacct ccgtgttcct gttcccccc aagcccaagg acaccctcat gatcagccgg  780
accccgagg tgacctgcgt ggtggtggac gtgagccacg aggacccga ggtgaagttc  840
aactggtacg tggacggcgt ggaggtgcac aacgccaaga ccaagcccg ggaggagcag  900
tacaacagca cctaccgggt ggtgagcgtg ctcaccgtgc tgcaccagga ctggctgaac  960
ggcaaggagt acaagtgcaa ggtgagcaac aaggccctgc ctgcccccat cgagaagacc 1020
atcagcaagg ccaaggcca gccccgggag cccaggtgt acaccctgcc cccagccgg 1080
gaggagatga ccaagaacca ggtgtccctc acctgtctgg tgaagggctt ctacccagc 1140
gacatcgccg tggagtggga gagcaacggc cagcccgaga caactacaa gaccacccc 1200
cctgtgctgg acagcgacgg cagcttcttc ctgtacagca agctcaccgt ggacaagagc 1260
cggtggcagc agggcaacgt gttcagctgc agcgtgatgc acgaggccct gcacaaccac 1320
tacacccaga agagcctgag cctgagcccc ggcaag                            1356
```

CR6307 Heavy Chain amino acid sequence
(SEQ ID NO: 473)

QVQLVQSGGGLVKPGGSLRLSCAASGFTFSSYSMNWVRQAPGKGLEWVSSISSSSSYIYYV
DSVKGRFTISRDNAKNSLYLQMNSLRAEDTAVYYCARGGGSYGAYEGFDYWGQGTLVTV
SSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST

```
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK

CR6307 VH amino acid sequence
                                                      (SEQ ID NO: 471)
QVQLVQSGGGLVKPGGSLRLSCAASGFTFSSYSMNWVRQAPGKGLEWVSSISSSSSYIYYV
DSVKGRFTISRDNAKNSLYLQMNSLRAEDTAVYYCARGGGSYGAYEGFDYWGQGTLVTV
SS CR6307 Light Chain nucleotide sequence
                                                      (SEQ ID NO: 475)
gaaattgtgc tgactcagtc tccaggcacc ctgtctttgt ctccagggga aagagccacc  60
ctctcctgca gggccagtca gcgtgttagc agctacttag cctggtacca acagaaacct 120
ggccaggctc ccaggctcct catctatggt gcatccacca gggccgctgg catcccagac 180
aggttcagtg gcagtgggtc tgggacagac ttcactctca ccatcagcag actgagcct 240
gaagattctg cagtgtatta ctgtcagcag tatggtagga caccgctcac tttcggcgga 300
gggaccaagg tggagatcaa acgtgcggcc gcacccagcg tgttcatctt cccccctcc 360
gacgagcagc tgaagagcgg caccgccagc gtggtgtgcc tgctgaacaa cttctacccc 420
cgggaggcca aggtgcagtg gaaggtggac aacgccctgc agagcggcaa cagccaggag 480
agcgtgaccg agcaggacag caaggactcc acctacagcc tgagcagcac cctcaccctg 540
agcaaggccg actacgagaa gcacaaggtg tacgcctgcg aggtgaccca ccagggcctg 600
agcagccccg tgaccaagag cttcaaccgg ggcgagtgt                        639

CR6307 Light Chain amino acid sequence
                                                      (SEQ ID NO: 476)
EIVLTQSPGTLSLSPGERATLSCRASQRVSSYLAWYQQKPGQAPRLLIYGASTRAAGIPDRF
SGSGSGTDFTLTISRLEPEDSAVYYCQQYGRTPLTFGGGTKVEIKRAAAPSVFIFPPSDEQLK
SGTASVVCLLNNFYPREAKVQWKVDNALQSGNSQESVTEQDSKDSTYSLSSTLTLSKADY
EKHKVYACEVTHQGLSSPVTKSFNRGEC CR6307 VL amino acid sequence
                                                      (SEQ ID NO: 474)
EIVLYQSPGTLSLSPGERATLSCRASQRVSSYLAWYQQKPGQAPRLLIYGASTRAAGIPDRF
SGSGSGTDFTLTISRLEPEDSAVYYCQQYGRTPLTFGGGTKVEIKR
```

The CR6310 HA-specific IgG antibody includes a heavy chain variable region (SEQ ID NO: 477) encoded by the heavy chain nucleotide sequence shown in SEQ ID NO: 478 and the heavy chain amino acid sequence shown in SEQ ID NO: 479. The CR6310 HA-specific IgG antibody also includes a light chain variable region (SEQ ID NO: 480) encoded by the light chain nucleotide sequence shown in SEQ ID NO: 481 and the light chain amino acid sequence shown in SEQ ID NO: 482.

```
CR6310 Heavy Chain nucleotide sequence
                                                      (SEQ ID NO: 478)
gaggtgcagc tggtggagtc tggggctgag gtgaagaagc ctgggtcctc ggtgaaagtc   60
tcttgcaagg cttctggagg cccttccgc agctatgcta tcagctgggt gcgacaggcc  120
cctggacaag ggcctgagtg gatgggaggg atcatcccta tttttggtac aacaaaatac 180
gcaccgaagt tccagggcag agtcacgatt accgcggacg atttcgcggg cacagtttac 240
atggagctga gcagcctgcg atctgaggac acggccatgt actactgtgc gaaacatatg 300
gggtaccagg tgcgcgaaac tatggacgtc tggggcaaag ggaccacggt caccgtctcg 360
agtgctagca ccaagggccc cagcgtgttc cccctggcc ccagcagcaa gagcaccagc  420
ggcggcacag ccgccctggg ctgcctggtg aaggactact tccccgagcc cgtgaccgtg 480
agctggaaca gcggcgcctt gaccagcggc gtgcacacct tccccgccgt gctgcagagc 540
agcggcctgt acagcctgag cagcgtggtg accgtgccca gcagcagcct gggcacccag 600
acctacatct gcaacgtgaa ccacaagccc agcaacacca agtgcgacaa acgcgtggag 660
cccaagagct cgacaagac ccacacctgc cccccgcc ctgccccga gctgctgggc    720
ggaccctccg tgttcctgtt ccccccaag cccaaggaca ccctcatgat cagccggacc  780
cccgaggtga cctgcgtggt ggtggacgtg agccacgagg accccgaggt gaagttcaac 840
tggtacgtgg acggcgtgga ggtgcacaac gccaagacca agccccggga ggagcagtac 900
aacagcacct accgggtggt gagcgtgctc accgtgctgc accaggactg gctgaacggc 960
aaggagtaca agtgcaaggt gagcaacaag gccctgcctg cccccatcga gaagaccatc 1020
agcaaggcca agggccagcc ccgggagccc caggtgtaca cctgccccc cagccgggag 1080
gagatgacca agaaccaggt gtccctcacc tgtctggtga agggcttcta ccccagcgac 1140
atcgccgtgg agtgggagag caacggccag cccgagaaca actacaagac cacccccct  1200
gtgctggaca gcgacggcag cttcttcctg tacagcaagc tcaccgtgga caagagccgg 1260
tggcagcagg gcaacgtgtt cagctgcagc gtgatgcacg aggccctgca caaccactac 1320
acccagaaga gcctgagcct gacccccggc aag                             1353

CR6310 Heavy Chain amino acid sequence
                                                      (SEQ ID NO: 479)
EVQLVESGAEVKKPGSSVKVSCKASGGPFRSYAISWVRQAPGQGPEWMGGIIPIFGTTKYA
PKFQGRVTITADDFAGTVYMELSSLRSEDTAMYYCAKHMGYQVRETMDVWGKGTTVTV
SSASTKGPSVFPLAPSSKSTSGGTAALGCLVKDYFPEPVTVSWNSGALTSGVHTFPAVLQSS
```

-continued

```
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK

CR6310 VH amino acis sequence
                                                       (SEQ ID NO: 477)
EVQLVESGAEVKKPGSSVKVSCKASGGPFRSYAISWVRQAPGQGPEWMGGIIPIFGTTKYA
PKFQGRVTITADDFAGTVYMELSSLRSEDTAMYYCAKHMGYQVRETMDVWGKGTTVTV
SS CR6310 Light Chain nucleotide sequence
                                                       (SEQ ID NO: 481)
tcctatgtgc tgactcagcc accctcggtg tcagtggccc caggacagac ggccaggatt  60
acctgtgggg gaaacaacat tggaagtaaa agtgtgcact ggtaccagca gaagccaggc 120
caggcccctg tgctggtcgt ctatgatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcatgc tgtgttcgga 300
ggaggcaccc agctgaccgt cctcggtgcg gccgcaggcc agcccaaggc cgctcccagc 360
gtgaccctgt tccccccctc ctccgaggag ctgcaggcca acaaggccac cctggtgtgc 420
ctcatcagcg acttctaccc tggcgccgtg accgtgcct ggaaggccga cagcagcccc 480
gtgaaggccg gcgtggagac caccaccccc agcaaggcag caacaacaa gtacgccgcc 540
agcagctacc tgagcctcac ccccgagcag tggaagagcc accggagcta cagctgccag 600
gtgacccacg agggcagcac cgtggagaag accgtggccc ccaccgagtg cagc      654

CR6310 Light Chain amino acid sequence
                                                       (SEQ ID NO: 482)
SYVLIQPPSVSVAPGQTARITCGGNNIGSKSVHWYQQKPGQAPVLVVYDDSDRPSGIPERF
SGSNSGNTATLTISRVEAGDEADYYCQVWDSSSDHAVFGGGTQLTVLGAAAGQPKAAPS
VTLFPPSSEELQANKATLVCLISDFYPGAVTVAWKADSSPVKAGVETTTPSKQSNNKYAAS
SYLSLTPEQWKSHRSYSCQVTHEGSTVEKTVAPTECS CR6310 VL amino acid sequence
                                                       (SEQ ID NO: 480)
SYVLTQPPSVSVAPGQTARITCGGNNIGSKSVHWYQQKPGQAPVLVVYDDSDRPSGIPERF
SGSNSGNTATLTISRVEAGDEADYYCQVWDSSSDHAVFGGGTQLTVLG
```

The CR6314 HA-specific IgG antibody includes a heavy chain variable region (SEQ ID NO: 483) encoded by the heavy chain nucleotide sequence shown in SEQ ID NO: 484 and the heavy chain amino acid sequence shown in SEQ ID NO: 485. The CR6314 HA-specific IgG antibody also includes a light chain variable region (SEQ ID NO: 486) encoded by the light chain nucleotide sequence shown in SEQ ID NO: 487 and the light chain amino acid sequence shown in SEQ ID NO: 488.

```
CR6314 Heavy Chain nucleotide sequence
                                                       (SEQ ID NO: 484)
gaggtgcagc tggtggagtc tggggctgag gtgaagaagc ctgggtcctc ggtgaaagtc  60
tcttgcaagg cttctggagg cccttccgc agctatgcta tcagctgggt gcgacaggcc 120
cctggacaag gccctgagtg gatgggaggg atcatcccta tttttggtac aacaaaatac 180
gcaccgaagt tccagggcag agtcacgatt accgcggacg atttcgcggg cacagtttac 240
atggagctga gcagcctgcg atctgaggac acggccatgt actactgtgc gaaacatatg 300
gggtaccagg tgcgcgaaac tatggacgtc tggggcaaag ggaccacggt caccgtctcg 360
agtgctagca ccaagggccc cagcgtgttc ccctggccc ccagcagcaa gagcaccagc 420
ggcggcacag ccgccctggg ctgcctggtg aaggactact ccccgagcc cgtgaccgtg 480
agctggaaca gcggcgcctt gaccagcggc gtgcacacct tcccggccgt gctgcagagc 540
agcggcctgt acagcctgag cagcgtggtg accgtgccca gcagcagcct gggcacccag 600
acctacatct gcaacgtgaa ccacaagccc agcaacacca aggtggacaa gcgcgtggag 660
cccaagagct gcgacaagac ccacacctgc cccccctgcc ctgcccccga gctgctgggc 720
ggaccctccg tgttcctgtt ccccccaag ccaaggaca ccctcatgat cagccggacc 780
cccgaggtga cctgcgtggt ggtggacgtg agccacgagg accccgaggt gaagttcaac 840
tggtacgtgg acggcgtgga ggtgcacaac gccaagacca gccccggga ggagcagtac 900
aacagcacct accgggtggt gagcgtgctc accgtgctgc accaggactg gctgaacggc 960
aaggagtaca agtgcaaggt gagcaacaag gccctgccc ccatcgaa gaagaccatc 1020
agcaaggcca agggccagcc ccgggagccc caggtgtaca ccctgccccc cagccggag 1080
gagatgacca gaaccaggt gtccctcacc tgtctggtga agggcttcta ccccagcgac 1140
atcgccgtgg agtgggagag caacggccag cccgagaaca actacaagac cacccccct 1200
gtgctggaca gcgacggcag cttcttcctg tacagcaagc tcaccgtgga caagagccgg 1260
tggcagcagg gcaacgtgtt cagctgcagc gtgatgcacg aggccctgca caaccactac 1320
acccagaaga gcctgagcct gagccccggc aag                              1353

CR6314 Heavy Chain amino acid sequence
                                                       (SEQ ID NO: 485)
EVQLVESGAEVKKPGSSVKVSCKASGGPFRSYAISWVRQAPGQGPEWMGGIIPIFGTTKYA
```

-continued
```
PKFQGRVTITADDFAGTVYMELSSLRSEDTAMYYCAKHMGYQVRETMDVWGKGTTVTV
SSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK CR6314 VH amino acid sequence
                                                    (SEQ ID NO: 483)
EVQLVESGAEVKKPGSSVKVSCKASGGPFRSYAISWVRQAPGQGPEWMGGIIPIFGTTKYA
PKFQGRVTITADDFAGTVYMELSSLRSEDTAMYYCAKHMGYQVRETMDVWGKGTTVTV
SS CR6314 Light Chain nucleotide sequence
                                                    (SEQ ID NO: 487)
tcctatgtgc tgactcagcc accctcagcg tctgggaccc ccgggcagag ggtcaccatc  60
tcttgttctg gaagcagctc caacatcgga agtaattatg tatactggta ccagcagctc 120
ccaggcacgg ccccccaaact cctcatctat agggatggtc agcggccctc aggggtccct 180
gaccgattct ctggctccaa gtctggcacc tcagcctccc tggccatcag tggactccgg 240
tccgatgatg aggctgatta ttactgtgca acatgggatg acaacctgag tggtccagta 300
ttcggcggag ggaccaagct gaccgtccta ggtgcggccg caggccagcc caggccgct 360
cccagcgtga ccctgttccc ccctcctcc gaggagctgc aggccaacaa ggccaccctg 420
gtgtgcctca tcagcgactt ctaccctggc gccgtgaccg tggcctggaa ggccgacagc 480
agccccgtga aggccggcgt ggagaccacc accccagca agcagagcaa caacaagtac 540
gccgccagca gctacctgag cctcacccc gagcagtgga gagcaccg gagctacagc 600
tgccaggtga cccacgaggg cagcaccgtg gagaagaccg tggcccccac cgagtgcagc 660

CR6314 Light Chain amino acid sequence
                                                    (SEQ ID NO: 488)
SYVLTQPPSASGTPGQRVTISCSGSSSNIGSNYVYWYQQLPGTAPKLLIYRDGQRPSGVPDR
FSGSKSGTSASLAISGLRSDDEADYYCATWDDNLSGPVFGGGTKLTVLGAAAQPKAAPSV
TLFPPSSEELQANKATLVCLISDFYPGAVTVAWKADSSPVKAGVETTTPSKQSNNKYAASS
YLSLTPGQWKSHRSYSCQVTHEGSTVEKTVAPTECSG CR6314 VL amino acid sequence
                                                    (SEQ ID NO: 486)
SYVLTQPPSASGTPGQRVTISCSGSSSNIGSNYVYWYQQLPGTAPKLLIYRDGQRPSGVPDR
FSGSKSGTSASLAISGLRSDDEADYYCATWDDNLSGPVFGGGTKLTVLG
```

The CR6323 HA-specific IgG antibody includes a heavy chain variable region (SEQ ID NO: 489) encoded by the heavy chain nucleotide sequence shown in SEQ ID NO: 490 and the heavy chain amino acid sequence shown in SEQ ID NO: 491. The CR6323 HA-specific IgG antibody also includes a light chain variable region (SEQ ID NO: 492) encoded by the light chain nucleotide sequence shown in SEQ ID NO: 493 and the light chain amino acid sequence shown in SEQ ID NO: 494.

```
CR6323 Heavy Chain nucleotide sequence
                                                    (SEQ ID NO: 490)
gaggtgcagc tggtggagtc tggggctgag gtgaagaagc cagggtcctc ggtgaaggtc   60
tcctgtaagg cctctggagg caccttctcc agctatggta tcagctgggt gcgacaggcc  120
cctggacaag ggcttgagtg gatgggagac atcatcggta tgtttggttc aacaaactac  180
gcacagaact tccagggcag aactcacgat accgcgagct aatccacgag cacagcctac  240
atggagctga gcagcctgag atctgaggac acggccgtgt attactgtgc gagaagtagt  300
ggttattacc ctgcatacct ccccactgg ggccagggca ccttggtcac cgtctcgagt  360
gctagcacca agggccccag cgtgttcccc ctggcccca gcagcaagag caccagcggc  420
ggcacagccg ccctgggctg cctggtgaag gactacttcc ccgagcccgt gaccgtgagc  480
tggaacagcg gcgccttgac cagcggcgtg cacaccttcc ccgccgtgct gcagagcagc  540
ggcctgtaca gcctgagcag cgtggtgacc gtgcccagca gcagcctggg cacccagacc  600
tacatctgca acgtgaacca caagcccagc aacaccaagg tggacaaacg cgtggagccc  660
aagagctgcg acaagaccca cacctgcccc cctgccctg ccccgagct gctgggcgga  720
ccctccgtgt tcctgttccc cccaagccc aaggacaccc tcatgatcag ccggacccc  780
gaggtgacct gcgtggtggt ggacgtgagc cacgaggacc ccgaggtgaa gttcaactgg  840
tacgtggacg gcgtggaggt gcacaacgcc aagaccaagc ccgggagga gcagtacaac  900
agcacctacc gggtggtgag cgtgctcacc gtgctgcacc aggactggct gaacggcaag  960
gagtacaagt gcaaggtgag caacaaggcc ctgcctgccc catcgagaa gaccatcagc 1020
aaggccaagg ccagccccg ggagcccag gtgtacaccc tgcccccag ccgggaggag 1080
atgaccaaga accaggtgtc cctcacctgt ctggtgaagg gcttctaccc cagcgacatc 1140
gccgtggagt gggagagcaa cggccagccc gagaacaact acaagaccac cccccctgtg 1200
ctggacagcg acggcagctt cttcctgtac agcaagctca ccgtggacaa gagccggtgg 1260
cagcagggca acgtgttcag ctgcagcgtg atgcacgagg ccctgcacaa ccactacacc 1320
cagaagagcc tgagcctgag ccccggcaag                                  1350
```

CR6323 Heavy Chain amino acid sequence
(SEQ ID NO: 491)
EVQLVESGAEVKKPGSSVKVSCKASGGTFSSYGISWVRQAPGQGLEWMGDIIGMFGSTNY
AQNFQGRLTITADESTSTAYMELSSLRSEDTAVYYCARSSGYYPAYLPHWGQGTLVTVSS
AASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK CR6323 VH amino acid sequence
(SEQ ID NO: 489)
EVQLVESGAEVKKPGSSVKVSCKASGGTFSSYGISWVRQAPGQGLEWMGDIIGMFGSTNY
AQNFQGRLTITADESTSTAYMELSSLRSEDTAVYYCARSSGYYPAYLPHWGQGTLVTVSS CR6323 Light Chain nucleotide sequence
(SEQ ID NO: 493)
```
gaaattgtgt tgacccagtc tccaggcacc ctgtctttgt ctccagggga aagagccacc  60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcacccag aactttcggc 300
ggagggacca aggtggagat caaacgtgcg ccgcaccca gcgtgttcat cttccccccc 360
tccgacgagc agctgaagag cggcaccgcc agcgtggtgt gcctgctgaa caacttctac 420
ccccggagag ccaaggtgca gtggaaggtg gacaacgccc tgcagagcgg caacagccag 480
gagagcgtga ccgagcagga cagcaaggac tccacctaca gcctgagcag caccctcacc 540
ctgagcaagg ccgactacga gaagcacaag gtgtacgcct gcgaggtgac ccaccagggc 600
ctgagcagcc ccgtgaccaa gagcttcaac cggggcgagt gt                    642
```

CR6323 Light Chain amino acid sequence
(SEQ ID NO: 494)
EIVLTQSPGTLSLSPGERATLSCRASQSVSSSYLAWYQQKPGQAPRLLIYGASSRATGIPDRF
SGSGSGTDFTLTISRLEPEDFAVYYCQQYGSSPRTFGGGTKVEIKRAAAPSVFIFPPSDEQLK
SGTASVVCLLNNFYPREAKVQWKVDNALQSGNSQESVTEQDSKDSTYSLSSTLTLSKADY
EKHKVYACEVTHQGLSSPVTKSFNRGEC CR6323 VL amino acid sequence
(SEQ ID NO: 492)
EIVLTQSPGTLSLSPGERATLSCRASQSVSSSYLAWYQQKPGQAPRLLIYGASSRATGIPDRF
SGSGSGTDFTLTISRLEPEDFAVYYCQQYGSSPRTFGGGTKVEIKR The CR6325 HA-specific IgG antibody includes a heavy chain variable region (SEQ ID NO: 495) encoded by the heavy chain nucleotide sequence shown in SEQ ID NO: 496 and the heavy chain amino acid sequence shown in SEQ ID NO: 497. The CR6325 HA-specific IgG antibody also includes a light chain variable region (SEQ ID NO: 498) encoded by the light chain nucleotide sequence shown in SEQ ID NO: 499 and the light chain amino acid sequence shown in SEQ ID NO: 500.

CR6325 Heavy Chain nucleotide sequence
(SEQ ID NO: 496)
```
gaggtgcagc tggtggagtc tggggctgag gtgaagaagc cggggtcctc ggtgaaggtc   60
tcctgcaagg cttctggagg caccttcagc ttctattcta tgagctgggt gcgacaggcc  120
cctggacaag gacttgagtg gatgggaggg atcatcccta tgtttggtac aacaaactac  180
gcacagaagt tccagggcag agtcacgatt accgcggtcg aatccacgag cacagcctac  240
atggaggtga gcagcctgag atctgaggac acggccgttt attactgtgc gagaggtgat  300
aagggtatct actactacta catgtgacgtc tgggggcaag ggaccacggt caccgtctcg  360
agtgctagca ccaagggccc cagcgtgttc cccctggccc ccagcagcaa gagcaccagc  420
ggcggcacag ccgccctggg ctgcctggtg aaggactact ccccgagcc cgtgaccgtg  480
agctggaaca gcggcgcctt gaccagcggc gtgcacacct tccctccgt gctgcagagc  540
agcggcctgt acagcctgag cagcgtggtg accgtgccca gcagcagcct gggcacccag  600
acctacatct gcaacgtgaa ccacaagccc agcaacacca aggtggacaa gcgcgtggag  660
cccaagagct gcgacaagac ccacacctgc ccccctgcc ctgcccccga gctgctgggc  720
ggacctccg tgttcctgtt ccccccaag cccaaggaca ccctcatgat cagccggacc  780
cccgaggtga cctgcgtggt ggtggacgtg agccacgagg accccgaggt gaagttcaac  840
tggtacgtgg acggcgtgga ggtgcacaac gccaagacca gccccggga ggagcagtac  900
aacagcacct accgggtggt gagcgtgctc accgtgctgc accaggactg gctgaacggc  960
aaggagtaca agtgcaaggt gagcaacaag gccctgcctg ccccatcga aagaccatc  1020
agcaaggcca agggccagcc ccgggagccc caggtgtaca cctgccccc cagccggag  1080
gagatgacca agaaccaggt gtccctcacc tgtctggtga agggcttcta ccccagcgac  1140
atcgccgtgg agtgggagag caacggccag cccgagaaca actacaagac cacccccct  1200
```

-continued

```
gtgctggaca gcgacggcag cttcttcctg tacagcaagc tcaccgtgga caagagccgg 1260
tggcagcagg gcaacgtgtt cagctgcagc gtgatgcacg aggccctgca caaccactac 1320
acccagaaga gcctgagcct gagccccggc aag                              1353
```

CR6325 Heavy Chain amino acid sequence
(SEQ ID NO: 497)
EVQLVESGAEVKKPGSSVKVSCKASGGTFSFYSMSWVRQAPGQGLEWMGGIIPMFGTTN
YAQKFQGRVTITAVESTSTAYMEVSSLRSEDTAVYYCARGDKGIYYYYMDVWGKGTTVT
VSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQ
QGNVFSCSVMHEALHNHYTQKSLSLSPGK CR6325 VH amino acid sequence
(SEQ ID NO: 495)
EVQLVESGAEVKKPGSSVKVSCKASGGTFSFYSMSWVRQAPGQGLEWMGGIIPMFGTTN
YAQKFQGRVTITAVESTSTAYMEVSSLRSEDTAVYYCARGDKGIYYYYMDVWGKGTTVT
VSS CR6325 Light Chain nucleotide sequence
(SEQ ID NO: 499)
```
cagtctgccc tgactcagcc tgcctccgtg tctgggtctc ctggacagtc gatcaccatc  60
tcctgcactg gaaccagcag tgacgttggt ggttataact atgtctcctg gtaccaacag 120
cacccaggca aagcccccaa actcatgatt tatgaggtca gtaatcggcc ctcagggggtt 180
tctaatcgct tctctggctc caagtctggc aacacggcct ccctgaccat tctctgggctc 240
caggctgagg acgaggctga ttattactgc agctcatata aagcagcag cactcttgtc 300
ttcggaactg ggaccaaggt caccgtccta ggtgcgccg caggccagcc caaggccgct 360
cccagcgtga cctgttccc ccctcctcc gaggagctgc aggccaacaa ggccacctg 420
gtgtgcctca tcagcgactt ctaccctggc gccgtgaccg tggcctggaa ggccgacagc 480
agcccgtga aggccggcgt ggagaccacc accccagca agcagaagcaa caacaagtac 540
gccgccagca gctacctgag cctcaccccc gagcagtgga gagccaccg gagctacagc 600
tgccaggtga cccacgaggg cagcaccgtg gagaagaccg tggcccccac cgagtgcagc 660
```

CR6325 Light Chain amino acid sequence
(SEQ ID NO: 500)
QSALTQPASVSGSPGQSITISCTGTSSDVGGYNYVSWYQQHPGKAPKLMIYEVSNRPSGVS
NRFSGSKSGNTASLTISGLQAEDEADYYCSSYTSSSTLVFGTGTKVTVLGAAAGQPKAAPS
VTLFPPSSEELQANKATLVCLISDFYPGAVTVAWKADSSPVKAGVETTTPSKQSNNKYAAS
SYLSLTPEQWKSHRSYSCQVTHEGSTVEKTVAPTECS CR6325 VL amino acid sequence
(SEQ ID NO: 498)
QSALTQPASVSGSPGQSITISCTGTSSDVGGYNYVSWYQQHPGKAPKLMIYEVSNRPSGVS
NRFSGSKSGNTASLTISGLQAEDEADYYCSSYTSSSTLVFGTGTKVTVLG The CR6327 HA-specific IgG antibody includes a heavy chain variable region (SEQ ID NO: 501) encoded by the heavy chain nucleotide sequence shown in SEQ ID NO: 502 and the heavy chain amino acid sequence shown in SEQ ID NO: 503. The CR6327 HA-specific IgG antibody also includes a light chain variable region (SEQ ID NO: 504) encoded by the light chain nucleotide sequence shown in SEQ ID NO: 505 and the light chain amino acid sequence shown in SEQ ID NO: 506.

CR6327 Heavy Chain nucleotide sequence
(SEQ ID NO: 502)
```
gaggtgcagc tggtggagac cggggctgag gtgaagaagc ctgggtcctc ggtgaaggtc   60
tcctgcaagg cctctggagg caccttcagg acccatgcta tcagttgggt gcgacaggcc  120
cctgacaag ggcttgagtg gatgggaggg atcatcgcta tcttcggaac agcaaactac  180
gcacagaagt tccagggcag aatcacgatt accgcgacg aatccacgag tacagcctac  240
atggagctga gcagcctgag atctgaggac acggccgtgt atttctgtgc gagaggcagt  300
ggttatcata tatcgacacc ctttgacaac tggggccagg gaaccctggt caccgtctcg  360
agtgctagca ccaagggccc cagcgtgttc cccctggccc ccagcagcaa gagcaccagc  420
ggcggcacag ccgcctgggg ctgcctggtg aaggactact tccccgagcc cgtgaccgtg  480
agctggaaca gcggcgcctt gaccagcggc gtgcacacct tccccgccgt gctgcagagc  540
agcggcctgt acagcctgag cagcgtggtg accgtgccca gcagcagcct gggcacccag  600
acctacatct gcaacgtgaa ccacaagccc agcaacacca aggtggacaa gcgcgtggag  660
cccaagagct gcgacaagac ccacacctgc cccccctgcc ctgcccccga gctgctgggc  720
ggaccctccg tgttcctgtt cccccccaag ccaaggaca cttcatgat cagccgggacc  780
cccgaggtga cctgcgtggt ggtggacgtg agccacgagg accccgaggt gaagttcaac  840
tggtacgtgg acggcgtgga ggtgcacaac gccaagacca gcccgggga ggagcagtac  900
aacagcacct accgggtggt gagcgtgctc accgtgctgc accaggactg gctgaacggc  960
aaggagtaca agtgcaaggt gagcaacaag gccctgcctg cccccatcga gaagaccatc 1020
agcaaggcca agggccagcc ccgggagccc caggtgtaca ccctgccccc cagccgggag 1080
```

-continued

```
gagatgacca agaaccaggt gtccctcacc tgtctggtga agggcttcta ccccagcgac    1140
atcgccgtgg agtgggagag caacggccag cccgagaaca actacaagac cacccccct     1200
gtgctggaca gcgacggcag cttcttcctg tacagcaagc tcaccgtgga caagagccgg    1260
tggcagcagg gcaacgtgtt cagctgcagc gtgatgcacg aggccctgca caaccactac    1320
acccagaaga gcctgagcct gagccccggc aag                                 1353
```

CR6327 Heavy Chain amino acid sequence (SEQ ID NO: 503)

```
EVQLVETGAEVKKPGSSVKVSCKASGGTFRTHAISWVRQAPGQGLEWMGGIIAIFGTANY
AQKFQGRITITADESTSTAYMELSSLRSEDTAVYFCARGSGYHISTPFDNWGQGTLVTVSSA
STKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK
```

CR6327 VH amino acid sequence (SEQ ID NO: 501)

```
EVQLVETGAEVKKPGSSVKVSCKASGGTFRTHAISWVRQAPGQGLEWMGGIIAIFGTANY
AQKFOGRITITADESTSTAYMELSSLRSEDTAVYFCARGSGYHISTPFDNWGQGTLVTVSS
```

CR6327 Light Chain nucleotide sequence (SEQ ID NO: 505)

```
tcctatgtgc tgactcagcc accctcggtg tcagtggccc caggacagac ggccaggatt     60
acctgtgggg gaaacaacat tggaagtaaa ggtgtgcact ggtaccagca gaagcctggc    120
caggccctg tgctggtcgt ctatgatgat agcgaccggc cctcagggat ccctgagcga     180
ttctctggct ccaactctgg gaacacggcc accctgacca tcagcagggt cgaagcgggg    240
gatgaggccg actattactg tcaggtgtgg atagtagta gtgatcatgt ggtattcggc     300
ggagggacca agctgaccgt cctaggtgcg gccgcaggcc agcccaaggc cgctcccagc    360
gtgaccctgt tccccccctc ctccgaggag ctgcaggcca caaggccac cctggtgtgc    420
ctcatcagcg acttctaccc tggcgccgtg accgtggcct ggaaggccga cagcagcccc    480
gtgaaggccg gcgtggagac caccccccc agcaagcaga gcaacaacaa gtacgccgcc    540
agcagctacc tgagcctcac ccccgagcag tggaagagcc accggagcta cagctgccag    600
gtgacccacg agggcagcac cgtggagaag accgtggccc ccaccgagtg cagc          654
```

CR6327 Light Chain amino acid sequence (SEQ ID NO: 506)

```
SYVLTQPPSVSVAPGQTARITCGGNNIGSKGVHWYQQKPGQAPVLVVYDDSDRPSGIPERF
SGSNSGNTATLTISRVEAGDEADYYCQVWDSSSDHVVFGGGTKLTVLGAAAGQPKAAPS
VTLFPPSSEELQANKATLVCLISDFYPGAVTVAWKADSSPVKAGVETTTPSKQSNNKYAAS
SYLSLTPEQWKSHRSYSCQVTHEGSTVEKTVAPTECS
```

CR6327 VL amino acid sequence (SEQ ID NO: 504)

```
SYVLTQPPSVSVAPGQTARITCGGNNIGSKGVHWYQQKPGQAPVLVVYDDSDRPSGIPERF
SGSNSGNTATLTISRVEAGDEADYYCQVWDSSSDHVVFGGGTKLTVLG
```

The CR6328 HA-specific IgG antibody includes a heavy chain variable region (SEQ ID NO: 507) encoded by the heavy chain nucleotide sequence shown in SEQ ID NO: 508 and the heavy chain amino acid sequence shown in SEQ ID NO: 509. The CR6328 HA-specific IgG antibody also includes a light chain variable region (SEQ ID NO: 510) encoded by the light chain nucleotide sequence shown in SEQ ID NO: 511 and the light chain amino acid sequence shown in SEQ ID NO: 512.

CR6328 Heavy Chain nucleotide sequence (SEQ ID NO: 508)

```
gaggtgcagc tggtggagtc tggggctgag gtgaagaagc ctgggtcctc ggtgaaggtc      60
tcctgcaagg cttctggaca catcttcagc ggctatgcaa tcagttgggt gcgacaggcc     120
cctggacaag ggcttgagtg gatgggaggg atcatcccta tctttggtac aacaaactac    180
gcacagaagt tccagggcag agtcacgatt accgcggacc aatccacgag cacagcctac    240
atggacctga gcaacttgag atctgaggac acggccgtct attactgtgc gagagtgaaa    300
gatggatatt gtactcttac cagctgccct gtcggctggt acttcgatct ctggggccgt    360
ggcaccctgg tcactgtctc gagtgctagc accaaggcc cgagcgtgtt ccccctggcc    420
cccagcagca gagcaccag cggcggcaca gccgccctgg gctgcctggt gaaggactac    480
ttccccgagc ccgtgaccgt gagctggaac agcggcgcct tgaccagcgg cgtgcacacc    540
ttccccgccg tgctgcagag cagcggcctg tacagcctga gcagcgtggt gaccgtgccc    600
agcagcagcc tgggcaccca gacctacatc tgcaacgtga accacaagcc cagcaacacc    660
aaggtggaca agcgcgtgga gcccaagagc tgcgacaaga ctcacacctg ccccccctgc    720
cctgcccccg agctgctggg cggaccctcc gtgttcctgt tccccccaa gcccaaggac    780
accctcatga tcagcggac cccgaggtg acctgcgtgg tggtggacgt gagccacgag    840
gaccccgagg tgaagttcaa ctggtacgtg gacggcgtgg aggtgcacaa cgccaagacc    900
aagccccggg aggagcagta caacagcacc taccgggtgg tgagcgtgct caccgtgctg    960
caccaggact ggctgaacgg caaggagtac aagtgcaagg tgagcaacaa ggcccctgcc    1020
```

```
                                     -continued
gcccccatcg agaagaccat cagcaaggcc aagggccagc cccgggagcc ccaggtgtac      1080
accctgcccc ccagccggga ggagatgacc aagaaccagg tgtccccac ctgtctggtg       1140
aagggcttct accccagcga catcgccgtg gagtgggaga gcaacggcca gcccgagaac     1200
aactacaaga ccaccccccc tgtgctggac agcgacggca gcttcttcct gtacagcaag     1260
ctcaccgtgg acaagagccg gtggcagcag ggcaacgtgt tcagctgcag cgtgatgcac     1320
gaggccctgc acaaccacta cacccagaag agcctgagcc tgagcccgg caag            1374

CR6328 Heavy Chain amino acid sequence
                                                           (SEQ ID NO: 509)
EVQLVESGAEVKKPGSSVKVSCKASGHIFSGYAISWVRQAPGQGLEWMGGIIPIFGTTNYA
QKFQGRVTITADQSTSTAYMDLSNLRSEDTAVYYCARVKDGYCTLTSCPVGWYFDLWGR
GTLVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKRVEPKSCDKTHTCPPCPAP
ELLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK CR6328 VH amino acid sequence
                                                           (SEQ ID NO: 507)
EVQLVESGAEVKKPGSSVKVSCKASGHIFSGYAISWVRQAPGQGLEWMGGIIPIFGTTNYA
QKFQGRVTITADQSTSTAYMDLSNLRSEDTAVYYCARVKDGYCTLTSCPVGWYFDLWGR
GTLVTVSS CR6328 Light Chain nucleotide sequence
                                                           (SEQ ID NO: 511)
gaaattgtga tgacgcagtc tccaggcacc ctgtctttgt ctccagggga aagagccacc       60
ctctcgtgca gggccagtca gagtgttagc agcagctact tagcctggta ccagcagaaa      120
cctggccagg ctcccaggct cctcatcttt ggtgcctcca gcagggccac tggcatccca      180
gacaggttca gtggcagtgg gtctgggaca gacttcactc tcaccatcag cagactggag      240
cctgaagatt ttgcagtgta ttactgtcag cagtatggta gctcactcac tttcggcgga     300
gggaccaagc tggagatcaa acgtgcggc gcacccagcg tgttctactt cccccctcc       360
gacgagcagc tgaagagcgg caccgccagc gtggtgtgcc tgctgaacaa cttctacccc    420
cgggaggcca aggtgcagtg gaaggtggac aacgccctgc agagcggcaa cagccaggag    480
agcgtgaccg agcaggacag caaggactcc acctacagcc tgagcagcac cctcaccctg     540
agcaaggccg actacgagaa gcacaaggtg tacgcctgcg aggtgaccca ccagggcctg    600
agcagccccg tgaccaagag cttcaaccgg ggcgagtgt                            639

CR6328 Light Chain amino acid sequence
                                                           (SEQ ID NO: 512)
EIVMTQSPGTLSLSPGERATLSCRASQSVSSSYLAWYQQKPGQAPRLLIFGASSRATGIPDR
FSGSGSGTDFTLTISRLEPEDFAVYYCQQYGSSLTFGGGTKLEIKRAAAPSVFIFPPSDEQLK
SGTASVVCLLNNFYPREAKVQWKVDNALQSGNSQESVTEQDSKDSTYSLSSTLTLSKADY
EKHKVYACEVTHQGLSSPVTKSFNRGEC CR6328 VL amino acid sequence
                                                           (SEQ ID NO: 510)
EIVMTQSPGTLSLSPGERATLSCRASQSVSSSYLAWYQQKPGQAPRLLIFGASSRATGIPDR
FSGSGSGTDFTLTISRLEPEDFAVYYCQQYGSSLTFGGGTKLEIKR
```

The CR6329 HA-specific IgG antibody includes a heavy chain variable region (SEQ ID NO: 513) encoded by the heavy chain nucleotide sequence shown in SEQ ID NO: 514 and the heavy chain amino acid sequence shown in SEQ ID NO: 515. The CR6329 HA-specific IgG antibody also includes a light chain variable region (SEQ ID NO: 516) encoded by the light chain nucleotide sequence shown in SEQ ID NO: 517 and the light chain amino acid sequence shown in SEQ ID NO: 518.

```
CR6329 Heavy Chain nucleotide sequence
                                                           (SEQ ID NO: 514)
gaggtccagc tggtacagtc tggggctgag gttaagaagc ctgggtcctc ggtgaaggtc       60
tcctgcaagg cttctggagg catcttcaga agcaattcta tcagttgggt gcgacaggcc      120
cctgggcaag ggcttgagtg gatgggaggg atcttcgctc ttttcggaac aacagactac      180
gcgcagaagt tccagggcag agtcacgatt accgcggacg aatcttcgac cacagtctac      240
ctggactga gtagcctgac atctgaggac acggccgttt attactgtgc gagaggcagt      300
ggctacacca cacgcaacta ctttgactac tggggccagg gcaccctggt caccgtctcg    360
agtgctagca ccaagggccc cagcgtgttc ccctggccc ccagcagcaa gagcaccagc     420
ggcggcacag ccgccctggg ctgcctggtg aaggactact ccccgagcc cgtgaccgtg    480
agctggaaca gcggcgcctt gaccagcggc gtgcacacct ccccgccgt gctgcagagc    540
agcggcctgt acagcctgag cagcgtggtg accgtgccca gcagcagcct gggcacccag   600
acctacatct gcaacgtgaa ccacaagccc agcaacacca aggtggacaa acgcggtggag  660
cccaagagct gcgacaagac ccacacctgc ccccctgcc ctgccccga gctgctgggc     720
ggaccctccg tgttcctgtt cccccccaag cccaaggaca ccctcatgat cagccggacc    780
cccgaggtga cctgcgtggt ggtggacgtg agccacgagg accccgaggt gaagttcaac    840
tggtacgtgg acggcgtgga ggtgcacaac gccaagacca gcccgggag ggagcagtac    900
```

```
aacagcacct accgggtggt gagcgtgctc accgtgctgc accaggactg gctgaacggc      960
aaggagtaca agtgcaaggt gagcaacaag gccctgcctg cccccatcga agaccatc       1020
agcaaggcca agggccagcc ccgggagccc caggtgtaca ccctgccccc cagccgggag     1080
gagatgacca gaaccaggt gtccctcacc tgtctggtga agggcttcta ccccagcgac      1140
atcgccgtgg agtgggagag caacggccag cccgagaaca actacaagac cacccccct     1200
gtgctggaca gcgacggcag cttcttcctg tacagcaagc tcaccgtgga caagagccgg    1260
tggcagcagg gcaacgtgtt cagctgcagc gtgatgcacg aggccctgca caaccactac   1320
acccagaaga gcctgagcct gagccccggc aag                                1353

CR6329 Heavy Chain amino acid sequence
                                                          (SEQ ID NO: 515)
EVQLVQSGAEVKKPGSSVKVSCKASGGIFRSNSISWVRQAPGQGLEWMGGIFALFGTTDY
AQKFQGRVTITADESSTTVYLELSSLTSEDTAVYYCARGSGYTTRNYFDYWGQGTLVTVS
SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK CR6329 VH amino acid sequence
                                                          (SEQ ID NO: 513)
EVQLVQSGAEVKKPGSSVKVSCKASGGIFRSNSISWVRQAPGQGLEWMGGIFALFGTTDY
AQKFQGRVTITADESSTTVYLELSSLTSEDTAVYYCARGSGYTTRNYFDYWGQGTLVTVS
S CR6329 Light Chain nucleotide sequence
                                                          (SEQ ID NO: 517)
gaaattgtgc tgactcagtc tccaggcacc ctgtctttgt ctccagggga aagagccaca     60
ctctcctgca gggccagtca gagtgttagc agcaactact taggctggta ccagcagaaa   120
cctggccagg ctcccaggct cctgatctat ggtgcatcca gcagggccag tggcatccca   180
gacaggttca gtggcggtgg gtctgggaca gacttcactc tcaccatcag cagactggag   240
cctgaagatt ttgcagtgta ttactgtcag cagtatggta gctcacccct cactttcggc   300
ggagggacca aggtggagat caaacgtgcg ccgcaggcc agcccaaggc cgctcccagc    360
gtgaccctgt tccccccctc ctccgaggag ctgcaggcca acaaggccac cctggtgtgc   420
ctcatcagcg acttctaccc tggcgccgtg accgtggcct ggaaggccga cagcagcccc   480
gtgaaggccg gcgtggagac caccaccccc agcaagcaga gcaacaacaa gtacgccgcc   540
agcagctacc tgagcctcac ccccgagcag tggaagagcc accggagcta cagctgccag   600
gtgacccacg agggcagcac cgtggagaag accgtggccc ccaccgagtg cagc          654

CR6329 Light Chain amino acid sequence
                                                          (SEQ ID NO: 518)
EIVLTQSPGTLSLSPGERATLSCRASQSVSSNYLGWYQQKPGQAPRLLIYGASSRASGIPDR
FSGGGSGTDFTLTISRLEPEDFAVYYCQQYGSSPLTFGGGTKVEIKRAAAGQPKAAPSVTLF
PPSSEELQANKATLVCLISDFYPGAVTVAWKADSSPVKAGVETTTPSKQSNNKYAASSYLS
LTPEQWKSHRSYSCQVTHEGSTVEKTVAPTECS CR6329 VL amino acid sequence
                                                          (SEQ ID NO: 516)
EIVLTQSPGTLSLSPGERATLSCRASQSVSSNYLGWYQQKPGQAPRLLIYGASSRASGIPDR
FSGGGSGTDFTLTISRLEPEDFAVYYCQQYGSSPLTFGGGTKVEIKR
```

The CR6331 HA-specific IgG antibody includes a heavy chain variable region (SEQ ID NO: 519) encoded by the heavy chain nucleotide sequence shown in SEQ ID NO: 520 and the heavy chain amino acid sequence shown in SEQ ID NO: 521. The CR6331 HA-specific IgG antibody also includes a light chain variable region (SEQ ID NO: 522) encoded by the light chain nucleotide sequence shown in SEQ ID NO: 523 and the light chain amino acid sequence shown in SEQ ID NO: 524.

```
CR6331 Heavy Chain nucleotide sequence
                                                          (SEQ ID NO: 520)
gaggtgcagc tggtggagtc tggggctgag gtgaagaagc ctgggtcctc ggtgaaggtc      60
tcctgcaagg cttctggagg caccttcagc agctatgcta tcagctgggt gcgacaggcc    120
cctggacaag ggcttgagtg gatgggaggg atcatcggta tgttcggtac agcaaactac    180
gcacagaagt tccagggcag agtcacgatt accgcggacg aatttacgag cacagcctac    240
atggagctga gcagcctgag atctgaggac acggccgtgt attactgtgc gagaggaaat    300
tattactatg agagtagtct cgactactgg ggccagggaa ccctggtcac cgtctcgagt    360
gctagcacca agggcccag cgtgttccc ctggccccca gcagcaagag caccagcggc     420
ggcacagccg ccctgggctg cctggtgaag gactacttcc ccgagcccgt gaccgtgagc   480
tggaacagcg gcgccttgac cagcggcgtg cacaccttcc ccgccgtgct gcagagcagc   540
ggcctgtaca gcctgagcag cgtggtgacc gtgcccagca gcctgggc cacccagacc      600
tacatctgca acgtgaacca caagcccagc aacaccaagg tggacaaacg cgtggagccc  660
aagagctgcg acaagaccca cacctgcccc cctgccctg ccccgagct gctgggcgga    720
ccctccgtgt tcctgttccc ccccaagccc aaggacaccc tcatgatcag ccggacccc     780
```

```
gaggtgacct gcgtggtggt ggacgtgagc cacgaggacc ccgaggtgaa gttcaactgg      840
tacgtggacg gcgtggaggt gcacaacgcc aagaccaagc ccgggagga gcagtacaac      900
agcacctacc gggtggtgag cgtgctcacc gtgctgcacc aggactggct gaacggcaag      960
gagtacaagt gcaaggtgag caacaaggcc ctgcctgccc ccatcgagaa gaccatcagc     1020
aaggccaagg gccagccccg ggagcccag gtgtacaccc tgcccccag ccggggagag      1080
atgaccaaga accaggtgtc cctcacctgt ctggtgaagg gcttctaccc cagcgacatc     1140
gccgtggagt gggagagcaa cggccagccc gagaacaact acaagaccac ccccctgtg      1200
ctggacagcg acggcagctt cttcctgtac agcaagctca ccgtggacaa gagccggtgg     1260
cagcagggca acgtgttcag ctgcagcgtg atgcacgagg ccctgcacaa ccactacacc     1320
cagaagagcc tgagcctgag ccccggcaag                                      1350

CR6331 Heavy Chain amino acid sequence
                                                          (SEQ ID NO: 521)
EVQLVESGAEVKKPGSSVKVSCKASGGTFSSYAISWVRQAPGQGLEWMGGIIGMFGTANY
AQKFQGRVTITADEFTSTAYMELSSLRSEDTAVYYCARGNYYYESSLDYWGQGTLVTVSS
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQG
NVFSCSVMHEALHNHYTQKSLSLSPGK CR6331 VH amino acid sequence
                                                          (SEQ ID NO: 519)
EVQLVESGAEVKKPGSSVKVSCKASGGTFSSYAISWVRQAPGQGLEWMGGIIGMFGTANY
AQKFQGRVTITADEFTSTAYMELSSLRSEDTAVYYCARGNYYYESSLDYWGQGTLVTVSS CR6331 Light Chain nucleotide sequence
                                                          (SEQ ID NO: 523)
cagtctgtcg tgacgcagcc gccctcggtg tcagtggccc caggacagac ggccaggatt       60
acctgtgggg gaaacaacat tggaagtaaa agtgtgcact ggtaccagca gaagccaggc      120
caggcccctg tgctggtcgt ctatgatgat agcgaccggc cctcaggat ccctgagcga      180
ttctctggct ccaactctgg gaacacggcc accctgacca tcagcaggt cgaagccggg      240
gatgaggccg actattactg tcaggtgtgg gatagtagta gtgatcatta tgtcttcgga      300
actgggacca aggtcaccgt cctaggtgcg gccgcaggcc agcccaaggc cgctcccagc      360
gtgaccctgt tccccccctc ctccgaggag ctgcaggcca acaaggccac cctggtgtgc      420
ctcatcagcg acttctaccc tggcgccgtg accgtggcct ggaaggccga cagcagcccc      480
gtgaaggccg gcgtggagac caccacccc agcaagcaga gcaacaacaa gtacgccgcc      540
agcagctacc tgagcctcac ccccgagcag tggaagagcc accggagcta cagctgccag      600
gtgacccacg agggcagcac cgtggagaag accgtggccc caccgagtg cagc             654

CR6331 Light Chain amino acid sequence
                                                          (SEQ ID NO: 524)
QSVVTQPPSVSVAPGQTARITCGGNNIGSKSVHWYQQKPGQAPVLVVYDDSDRPSGIPERF
SGSNSGNTATLTISRVEAGDEADYYCQVWDSSSDHYVFGTGTKVTVLGAAAGQPKAAPS
VTLFPPSSEELQANKATLVCLISDFYPGAVTVAWKADSSPVKAGVETTTPSKQSNNKYAAS
SYLSLTPEQWKSHRSYSCQVTHEGSTVEKTVAPTECS CR6331 VL amino acid sequence
                                                          (SEQ ID NO: 522)
QSVVTQPPSVSVAPGQTARITCGGNNIGSKSVHWYQQKPGQAPVLVVYDDSDRPSGIPERF
SGSNSGNTATLTISRVEAGDEADYYCQVWDSSSDHYVFGTGTKVTVLG
```

The CR6332 HA-specific IgG antibody includes a heavy chain variable region (SEQ ID NO: 525) encoded by the heavy chain nucleotide sequence shown in SEQ ID NO: 526 and the heavy chain amino acid sequence shown in SEQ ID NO: 527. The CR6332 HA-specific IgG antibody also includes a light chain variable region (SEQ ID NO: 528) encoded by the light chain nucleotide sequence shown in SEQ ID NO: 529 and the light chain amino acid sequence shown in SEQ ID NO: 530.

```
CR6332 Heavy Chain nucleotide sequence
                                                          (SEQ ID NO: 526)
caggtgcagc tggtgcagtc tggggctgag gtgaagaagc ctgggtcctc ggtaaaggtc       60
tcctgcaagg cttctggagg ccccttccgc aatttgcta tcaactgggt gcgacaggcc      120
cctggacaag gcttgagtg gatgggaggg atcatcgctg tctttgggac gacaaagtac      180
gcacataagt tccagggcag agtcaccatc accgcggacg actccacaaa tacagcttac      240
atggagctgg gcagcctgaa atctgaggac acggccgtgt attactgtgc gagaggtccc      300
cactactact cctcctacat ggacgtctgg ggcgaaggga ccacggtcac cgtctcgagt      360
gctagcacca agggcccag cgtgttcccc ctggccccca gcagcaagag caccagcggc      420
ggcacagccg ccctgggctg cctggtgaag gactacttcc ccgagcccgt gaccgtgagc      480
tggaacagcg gcgccttgac cagcggcgtg cacaccttcc ccgccgtgct gcagagcagc      540
ggcctgtaca gcctgagcag cgtggtgacc gtgcccagca gcctgggc acccagacc       600
tacatctgca acgtgaacca caagcccagc aacaccaagg tggacaaacg cgtggagccc      660
aagagctgcg acaagaccca cacctgcccc cctgccctg ccccgagct gctgggcgga      720
```

-continued

```
ccctccgtgt tcctgttccc ccccaagccc aaggacaccc tcatgatcag ccggaccccc    780
gaggtgacct gcgtggtggt ggacgtgagc cacgaggacc ccgaggtgaa gttcaactgg    840
tacgtggacg gcgtggaggt gcacaacgcc aagaccaagc ccggggagga gcagtacaac    900
agcacctacc gggtggtgag cgtgctcacc gtgctgcacc aggactggct gaacggcaag    960
gagtacaagt gcaaggtgag caacaaggcc ctgcctgccc ccatcgagaa gaccatcagc   1020
aaggccaagg gccagccccg ggagccccag gtgtacaccc tgcccccag ccggagggag    1080
atgaccaaga accaggtgtc cctcacctgt ctggtgaagg gcttctaccc cagcgacatc   1140
gccgtggagt gggagagcaa cggccagccc gagaacaact acaagaccac ccccctgtg    1200
ctggacagcg acggcagctt cctcctgtac agcaagctca ccgtggacaa gagccggtgg   1260
cagcagggca acgtgttcag ctgcagcgtg atgcacgagg ccctgcacaa ccactacacc   1320
cagaagagcc tgagcctgag ccccggcaag                                   1350
```

CR6332 Heavy Chain amino acid sequence (SEQ ID NO: 527)

QVQLVQSGAEVKKPGSSVKVSCKASGGPFRNFAINWVRQAPGQGLEWMGGIIAVFGTTK
YAHKFQGRVTITADDSTNTAYMELGSLKSEDTAVYYCARGPHYYSSYMDVWGEGTTVTV
SSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK

CR6332 VH amino acid sequence (SEQ ID NO: 525)

QVQLVQSGAEVKKPGSSVKVSCKASGGPFRNFAINWVRQAPGQGLEWMGGIIAVFGTTK
YAHKFQGRVTITADDSTNTAYMELGSLKSEDTAVYYCARGPHYYSSYMDVWGEGTTVTV
SS

CR6332 Light Chain nucleotide sequence (SEQ ID NO: 529)

```
gacatccagt tgacccagtc tccatcctcc ctgtctgcat ctgtaggaga cagagtcacc     60
atcacttgcc gggcgagtca gggcattagc acttatttag cctggtatca gcagaaaccc    120
gggaaagttc ctaaactcct gatctatgct gcatccactt tgcaatcagg gtcccatct    180
cggttcagtg gcagtggatc tgggacagat ttcactctca ccatcagcag cctgcagcct    240
gaagatgttg caacttatta ctgtcaaaag tataacagtg ccccttcttt cggccctggg    300
accaaagtgg atatcaaacg tgcggccgca cccagcgtgt tcatcttccc ccctccgac    360
gagcagctga agagcggcac cgccagcgtg gtgtgcctgc tgaacaactt ctaccccgg     420
gaggccaagg tgcagtggaa ggtggacaac gccctgcaga gcggcaacag ccaggagagc    480
gtgaccgagc aggacagcaa ggactccacc tacagcctga gcagcaccct caccctgagc    540
aaggccgact acgagaagca caaggtgtac gcctgcgagg tgacccacca gggcctgagc    600
agccccgtga ccaagagctt caaccggggc gagtgt                              636
```

CR6332 Light Chain amino acid sequence (SEQ ID NO: 530)

DIQLTQSPSSLSASVGDRVTITCRASQGISTYLAWYQQKPGKVPKLLIYAASTLQSGVPSRF
SGSGSGTDFTLTISSLQPEDVATYYCQKYNSAPSFGPGTKVDIKRAAAPSVFIFPPSDEQLKS
GTASVVCLLNNFYPREAKVQWKVDNALQSGNSQESVTEQDSKDSTYSLSSTLTLSKADYE
KHKVYACEVTHQGLSSPVTKSFNRGEC

CR6332 VL amino acid sequence (SEQ ID NO: 528)

DIQLTQSPSSLSASVGDRVTITCRASQGISTYLAWYQQKPGKVPKLLIYAASTLQSGVPSRF
SGSGSGTDFTLTISSLQPEDVATYYCQKYNSAPSFGPGTKVDIKR

The CR6334 HA-specific IgG antibody includes a heavy chain variable region (SEQ ID NO: 531) encoded by the heavy chain nucleotide sequence shown in SEQ ID NO: 532 and the heavy chain amino acid sequence shown in SEQ ID NO: 533. The CR6334 HA-specific IgG antibody also includes a light chain variable region (SEQ ID NO: 534) encoded by the light chain nucleotide sequence shown in SEQ ID NO: 535 and the light chain amino acid sequence shown in SEQ ID NO: 536.

CR6334 Heavy Chain nucleotide sequence (SEQ ID NO: 532)

```
gaggtgcagc tggtggagac tgggctgag gtgaagaagc ctgggtcctc ggtgaaggtc      60
ccctgcaaat cttctggaag ccccttcagg agtaatgctg tcagctgggt gcgacaggcc    120
cccggacaag gcttgagtg gtgggagga atcctcggtg tctttggttc accaagctac      180
gcacagaagt tccagggcag agtcacgatt accgcggacg aatccaccaa cacagcccac    240
acggagctga gggtttgag atctgaggac acggccgtgt attattgtgc gagaggtcct     300
acctactact actcctacat ggacgtctgg ggcaaaggga ccacggtcac cgtctcgagt    360
gctagcacca agggcccag cgtgttcccc ctggccccca gcagcaagag caccagcggc    420
ggcacagccg cctggctg cctggtgaag gactacttcc ccgagccgt gaccgtgagc     480
tggaacagcg gcgccttgac cagcggcgtg cacaccttcc ccgccgtgct gcagagcagc    540
ggcctgtaca gcctgagcag cgtggtgacc gtgcccagca gcagcctggg cacccagacc    600
```

-continued

```
tacatctgca acgtgaacca caagcccagc aacaccaagg tggacaaacg cgtggagccc      660
aagagctgcg acaagaccca cacctgcccc cctgccctg ccccgagct gctgggcgga        720
ccctccgtgt tcctgttccc cccaagccc aaggacaccc tcatgatcag ccggacccc        780
gaggtgacct gcgtggtggt ggacgtgagc cacgaggacc ccgaggtgaa gttcaactgg      840
tacgtggacg gcgtggaggt gcacaacgcc aagaccaagc cccgggagga gcagtacaac      900
agcacctacc gggtggtgag cgtgctcacc gtgctgcacc aggactggct gaacggcaag      960
gagtacaagt gcaaggtgag caacaaggcc ctgcctgccc ccatcgagaa gaccatcagc     1020
aaggccaagg gccagccccg ggagcccag gtgtacaccc tgcccccag ccgggaggag       1080
atgaccaaga accaggtgtc cctcacctgt ctggtgaagg gcttctaccc cagcgacatc     1140
gccgtggagt gggagagcaa cggccagccc gagaacaact acaagaccac ccccctgtg      1200
ctggacagcg acggcagctt cttcctgtac agcaagctca ccgtggacaa gagccggtgg     1260
cagcagggca acgtgttcag ctgcagcgtg atgcacgagg cccgcacaa ccdctacacc     1320
cagaagagcc tgagcctgag ccccggcaag                                      1350
```

CR6334 Heavy Chain amino acid sequence
(SEQ ID NO: 533)

EVQLVETGAEVKKPGSSVKVPCKSSGSPFRSNAVSWVRQAPGQGLEWVGGILGVFGSPSY
AQKFQGRVTITADESTNTVHMELRGLRSEDTAVYYCARGPTYYYSYMDVWGKGTTVTVS
SASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK

CR6334 VH amino acid sequence
(SEQ ID NO: 531)

EVQLVETGAEVKKPGSSVKVPCKSSGSPFRSNAVSWVRQAPGQGLEWVGGILGVFGSPSY
AQKFQGRVTITADESTNTVHMELRGLRSEDTAVYYCARGPTYYYSYMDVWGKGTTVTVS
S

CR6334 Light Chain nucleotide sequence
(SEQ ID NO: 535)

```
tcctatgtgc tgactcagcc accctcggag tcagtggccc caggacagac ggccaggatt       60
acctgtgggg gaaataacat tggaagaaat agtgtgcact ggtatcagca gaagccaggc      120
caggcccctg tgctggtcgt gtatgatgat agcgaccggc cctcaggat ccctgagcga       180
ttttctggct ccaagtctgg gaacacggcc accctgatta tcagcagggt cgaagtcggg      240
gatgaggccg actactactg tcaggtgtgg catagtagta gtgatcatta tgtcttcgga      300
actgggacca aggtcaccgt cctaggtgcg ccgcaggcc agcccaaggc cgctcccagc      360
gtgaccctgt tccccccctc ctccgaggag ctgcaggcca acaaggccac cctggtgtgc      420
ctcatcagcg acttctaccc tggcgccgtg accgtggcct ggaaggccga cagcagcccc      480
gtgaaggccg gcgtggagac caccaccccc agcaagcaga gcaacaacaa gtacgccgcc      540
agcagctacc tgagcctcac ccccgagcag tggaagagcc accggagcta cagctgccag      600
gtgacccacg agggcagcac cgtggagaag accgtggccc caccgagtg cagc             654
```

CR6334 Light Chain amino acid sequence
(SEQ ID NO: 536)

SYVLTQPPSESVAPGQTARITCGGNNIGRNSVHWYQQKPGQAPVLVVYDDSDRPSGIPERF
SGSKSGNTATLIISRVEVGDEADYYCQVWHSSSDHYVFGTGTKVTVLGAAAGQPKAAPSV
TLFPPSSEELQANKATLVCLISDFYPGAVTVAWKADSSPVKAGVETTTPSKQSNNKYAASS
YLSLTPEQWKSHRSYSCQVTHEGSTVEKTVAPTECS

CR6334 VL amino acid sequence
(SEQ ID NO: 534)

SYVLTQPPSESVAPGQTARITCGGNNIGRNSVHWYQQKPGQAPVLVVYDDSDRPSGIPERF
SGSKSGNTATLIISRVEVGDEADYYCQVWHSSSDHYVFGTGTKVTVLG

The CR6336 HA-specific IgG antibody includes a heavy chain variable region (SEQ ID NO: 537) encoded by the heavy chain nucleotide sequence shown in SEQ ID NO: 538 and the heavy chain amino acid sequence shown in SEQ ID NO: 539. The CR6336 HA-specific IgG antibody also includes a light chain variable region (SEQ ID NO: 540) encoded by the light chain nucleotide sequence shown in SEQ ID NO: 541 and the light chain amino acid sequence shown in SEQ ID NO: 542.

CR6336 Heavy Chain nucleotide sequence
(SEQ ID NO: 538)

```
cagatgcagc tggtacaatc tggagctgag gtgaagaagc ctgggtcctc ggtgaaggtc       60
tcctgcaagg cttctggagg caccttcagc agctatgcta tcagctgggt gcgacaggcc      120
cctggacaag ggcttgagtg gatgggaggg atcttcggta tgtttggac agcaaactac      180
gcgcagaagt tccagggcag agtcacgatt accgcggacg aattcacgag cgcggcctac     240
atggagctga gcagcctggg atctgaggac acggccatgt attactgtgc gaggtctagt     300
ggttattacc cccaatactt ccaggactgg ggccagggca cctggtcac cgtctcgagt     360
gctagcacca agggcccag cgtgttccc ctggccccca gcagcaagag caccagcggc       420
ggcacagccg ccctgggctg cctggtgaag gactacttcc ccgagcccgt gaccgtgagc     480
```

```
                                                           -continued
tggaacagcg gcgccttgac cagcggcgtg cacaccttcc ccgccgtgct gcagagcagc        540
ggcctgtaca gcctgagcag cgtggtgacc gtgcccagca gcagcctggg cacccagacc        600
tacatctgca acgtgaacca caagcccagc aacaccaagg tggacaaacg cgtggagccc        660
aagagctgcg acaagaccca cacctgcccc cctgccctg ccccgagct gctgggcgga        720
ccctccgtgt tcctgttccc ccccaagccc aaggacacct catgatcag ccggacccc        780
gaggtgacct gcgtggtggt ggacgtgagc cacgaggacc ccgaggtgaa gttcaactgg        840
tacgtggacg gcgtggaggt gcacaacgcc aagaccaagc ccggagga gcagtacaac        900
agcacctacc gggtggtgag cgtgctcacc gtgctgcacc aggactggct gaacggcaag        960
gagtacaagt gcaaggtgag caacaaggcc ctgcctgccc catcgagaa gaccatcagc       1020
aaggccaagg gccagcccg ggagcccag gtgtacaccc tgccccccag ccgggaggag        1080
atgaccaaga accaggtgtc cctcacctgt ctggtgaagg gcttctaccc cagcgacatc       1140
gccgtggagt gggagagcaa cggccagccc gagaacaact acaagaccac ccccctgtg       1200
ctggacagcg acggcagctt cttcctgtac agcaagctca ccgtggacaa gagccggtgg       1260
cagcagggca acgtgttcag ctgcagcgtg atgcacgagg ccctgcacaa ccactacacc       1320
cagaagagcc tgagcctgag ccccggcaag                                       1350

CR6336 Heavy Chain amino acid sequence
                                                               (SEQ ID NO: 539)
QMQLVQSGAEVKKPGSSVKVSCKASGGTFSSYAISWVRQAPGQGLEWMGGIFGMFGTAN
YAQKFQGRVTITADEFTSAAYMELSSLGSEDTAMYYCARSSGYYPQYFQDWGQGTLVTV
SSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK CR6336 VH amino acid sequence
                                                               (SEQ ID NO: 537)
QMQLVQSGAEVKKPGSSVKVSCKASGGTFSSYAISWVRQAPGQGLEWMGGIFGMFGTAN
YAQKFQGRVTITADEFTSAAYMELSSLGSEDTAMYYCARSSGYYPQYFQDWGQGTLVTV
SS CR6336 Light Chain nucleotide sequence
                                                               (SEQ ID NO: 541)
gaaattgtga tgacacagtc tccaggcacc ctgtctttgt ctccaggca aagagccacc         60
ctctcctgca gggccagtca gagtgttagc agcagctact tagcctggta ccagcagaaa       120
cctggccagg ctcccagact cctcatgtat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtatggta gctcatcgct cactttcggc       300
ggagggacca agctggagat caaacgtgcg gccgcaccca gcgtgttcat cttccccccc       360
tccgacgagc agctgaagag cggcaccgcc agcgtggtgt gcctgctgaa caacttctac       420
ccccgcgagg ccaaggtgca gtggaaggtg gacaacgccc tgcagagcgg caacagccag       480
gagagcgtga ccgagcagga cagcaaggac tccacctaca gcctgagcag caccctcacc       540
ctgagcaagg ccgactacga aagcacaag gtgtacgcct gcgaggtgac ccaccagggc        600
ctgagcagcc ccgtgaccaa gagcttcaac cggggcgagt gt                          642

CR6336 Light Chain amino acid sequence
                                                               (SEQ ID NO: 542)
EIVMTQSPGTLSLSPGQRATLSCRASQSVSSSYLAWYQQKPGQAPRLLMYGASSRATGIPD
RFSGSGSGTDFTLTISRLEPEDFAVYYCQQYGSSSLTFGGGTKLEIKRAAAPSVFIFPPSDEQ
LKSGTASVVCLLNNFYPREAKVQWKVDNALQSGNSQESVTEQDSKDSTYSLSSTLTLSKA
DYEKHKVYACEVTHQGLSSPVTKSFNRGEC CR6336 VL amino acid sequence
                                                               (SEQ ID NO: 540)
EIVMTQSPGTLSLSPGQRATLSCRASQSVSSSYLAWYQQKPGQAPRLLMYGASSRATGIPD
RFSGSGSGTDFTLTISRLEPEDFAVYYCQQYGSSSLTFGGGTKLEIKR
```

The CR6339 HA-specific IgG antibody includes a heavy chain variable region (SEQ ID NO: 543) encoded by the heavy chain nucleotide sequence shown in SEQ ID NO: 544 and the heavy chain amino acid sequence shown in SEQ ID NO: 545. The CR6339 HA-specific IgG antibody also includes a light chain variable region (SEQ ID NO: 546) encoded by the light chain nucleotide sequence shown in SEQ ID NO: 547 and the light chain amino acid sequence shown in SEQ ID NO: 548.

```
CR6339 Heavy Chain nucleotide sequence
                                                               (SEQ ID NO: 545)
gaggtgcagc tggtggagtc cggggctgag gtgaagaagc ctgggtcctc ggtgaaggtc         60
tcctgcaagg cttctggagg catcttcaac agttatgcta tcagctgggt gcgacaggcc       120
cctggacaag gccttgagtg gatgggaggc atcatcgcta tctttcatac accaaagtac       180
gcacagaagt tccagggcag agtcacgatt accgcggacg aatccacgaa cacagcctac       240
atggaactga agcctgaa atctgaggac acggccctgt attactgtgc gagagggtcc        300
acttacgatt tttcgagtgg ccttgactac tggggccagg gaaccctggt caccgtctcg       360
```

-continued

```
agtgctagca ccaagggccc cagcgtgttc cccctggccc ccagcagcaa gagcaccagc    420
ggcggcacag ccgccctggg ctgcctggtg aaggactact tccccgagcc cgtgaccgtg    480
agctggaaca cgggcgcctt gaccagcggc gtgcacacct tccccgccgt gctgcagagc    540
agcggcctgt acagcctgag cagcgtggtg accgtgccca gcagcagcct gggcacccag    600
acctacatct gcaacgtgaa ccacaagccc agcaacacca aggtggacaa acgcgtggag    660
cccaagagct gcgacaagac ccacacctgc ccccccctgcc ctgcccccga gctgctgggc    720
ggaccctccg tgttcctgtt cccccccaag cccaaggaca ccctcatgat cagccggacc    780
cccgaggtga cctgcgtggt ggtggacgtg agccacgagg accccgaggt gaagttcaac    840
tggtacgtgg acggcgtgga ggtgcacaac gccaagacca gccccggga ggagcagtac    900
aacagcacct acccgggtgg tgagcgtgctc accgtgctgc accaggactg gctgaacggc    960
aaggagcaca agtgcaaggt gagcaacaag gccctgcctg cccccatcga gaagaccatc   1020
agcaaggcca agggccagcc ccgggagccc caggtgtaca ccctgccccc cagccgggag   1080
gagatgacca agaaccaggt gtccctcacc tgtctggtga agggcttcta ccccagcgac   1140
atcgccgtgg agtgggagag caacggccag cccgagaaca actacaagac cacccccccct   1200
gtgctggaca gcgacggcag cttcttcctg tacagcaagc tcaccgtgga caagagccgg   1260
tggcagcagg gcaacgtgtt cagctgcagc gtgatgcacg aggccctgca caaccactac   1320
acccagaaga gcctgagcct gagccccggc aag                                1353
```

CR6339 Heavy Chain amino acid sequence (SEQ ID NO: 546)

EVQLVESGAEVKKPGSSVKVSCKASGGIFNSYAISWVRQAPGQGLEWMGGIIAIFHTPKYA
QKFQGRVTITADESTNTAYMELRSLKSEDTALYYCARGSTYDFSSGLDYWGQGTLVTVSS
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSR
WQQGNVFSCSVMHEALHNHYTQKSLSLSPGK

CR6339 VH amino acid sequence (SEQ ID NO: 543)

EVQLVESGAEVKKPGSSVKVSCKASGGIFNSYAISWVRQAPGQGLEWMGGIIAIFHTPKYA
QKFQGRVTITADESTNTAYMELRSLKSEDTALYYCARGSTYDFSSGLDYWGQGTLVTVSS

CR6339 Light Chain nucleotide sequence (SEQ ID NO: 548)

```
caggcagggc tgactcagcc accctcggtg tcagtggccc caggacagac ggccaggatt     60
acctgtgggg gaaacaacat tggaagtaaa agtgtgcact ggtaccagca gaagccaggc    120
caggccctg tcctagtcgt ctatgatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcatgt ggtattcggc    300
ggagggacca agctgaccgt cctaggtgcg gccgcaggcc agcccaaggc cgctcccagc    360
gtgaccctgt tccccccctc ctccgaggag ctgcaggcca caaggccac cctggtgtgc    420
ctcatcagcg acttctaccc tggcgccgtg accgtggcct ggaaggccga cagcagcccc    480
gtgaaggccg gcgtggagac caccaccccc agcaagcaga gcaacaacaa gtacgccgcc    540
agcagctacc tgagcctcac ccccgagcag tggaagagcc accggagcta cagctgccag    600
gtgacccacg agggcagcac cgtggagaag accgtggccc ccaccgagtg cagc          654
```

CR6339 Light Chain amino acid sequence (SEQ ID NO: 549)

QAGLTQPPSVSVAPGQTARITCGGNNIGSKSVHWYQQKPGQAPVLVVYDDSDRPSGIPERF
SGSNSGNTATLTISRVEAGDEADYYCQVWDSSSDHVVFGGGTKLTVLGAAAGQPKAAPS
VTLFPPSSEELQANKATLVCLISDFYPGAVTVAWKADSSPVKAGVETTTPSKQSNNKYAAS
SYLSLTPEQWKSHRSYSCQVTHEGSTVEKTVAPTECS

CR6339 VL amino acid sequence (SEQ ID NO: 547)

QAGLTQPPSVSVAPGQTARITCGGNNIGSKSVHWYQQKPGQAPVLVVYDDSDRPSGIPERF
SGSNSGNTATLTISRVEAGDEADYYCQVWDSSSDHVVFGGGTKLTVLG

The CR6342 HA-specific IgG antibody includes a heavy chain variable region (SEQ ID NO: 550) encoded by the heavy chain nucleotide sequence shown in SEQ ID NO: 551 and the heavy chain amino acid sequence shown in SEQ ID NO: 552. The CR6342 HA-specific IgG antibody also includes a light chain variable region (SEQ ID NO: 553) encoded by the light chain nucleotide sequence shown in SEQ ID NO: 554 and the light chain amino acid sequence shown in SEQ ID NO: 555.

CR6342 Heavy Chain nucleotide sequence (SEQ ID NO: 551)

```
caggtccagc tggtgcagtc tggggctgag gtgaagaagc ctgggtcctc ggtgaaggtc     60
tcctgcaagg cttctggagg cttcttcagc agctatgcta tcagctgggt gcgcaggcc    120
cctggacaag gacttgagtg gatggggggg gtcaccccta tctttcgtac agcaaactac    180
gcacagaact tccagggcag agtcaccatt accgcggaca attccacatc gtatatggag    240
ctgagcagcc tgagatctga cgacacggcc gtgtattact gtgcgaggtt gaattaccat    300
```

-continued

```
gattcgggga cttattataa cgcccccggg ggctggttcg accccctgggg ccagggaacc    360
ctggtcaccg tctcgagtgc tagcaccaag ggccccagcg tgttcccct ggccccagc       420
agcaagagca ccagcggcgg cacagccgcc ctgggctgcc tggtgaagga ctacttcccc    480
gagcccgtga ccgtgagctg gaacagcggc gccttgacca cgcggcgtgca caccttcccc   540
gccgtgctgc agagcagcgg cctgtacagc ctgagcagcg tggtgaccgt gcccagcagc    600
agcctgggca ccagaccta catctgcaac gtgaaccaca agcccagcaa caccaaggtg    660
gacaaacgcg tggagcccaa gagctgcgac aagacccaca cctgccccc ctgcccctgcc    720
cccgagctgc tgggcggacc ctccgtgttc ctgttccccc caagcccaa ggacaccctc    780
atgatcagcc ggacccccga ggtgacctgc gtggtggtgg acgtgagcca cgaggacccc    840
gaggtgaagt tcaactggta cgtggacggc gtggaggtgc acaacgccaa gaccaagccc    900
cgggaggagc agtacaacag cacctaccgg gtggtgagcg tgctcaccgt gctgcaccag    960
gactggctga acggcaagga gtacaagtgc aaggtgagca caaggccct gcctgccccc   1020
atcgagaaga ccatcagcaa ggccaagggc cagccccggg agcccaggt gtacaccctg    1080
ccccccagcc gggaggagat gaccaagaac caggtgtccc tcacctgtct ggtgaagggc    1140
ttctacccca gcgacatcgc cgtggagtgg gagagcaacg gccagcccga gaacaactac    1200
aagaccaccc cccctgtgct ggacagcgac ggcagcttct tcctgtacag caagctcacc    1260
gtggacaaga gccggtggca gcagggcaac gtgttcagct gcagcgtgat gcacgaggcc    1320
ctgcacaacc actacaccca gaagagcctg agcctgagcc ccggcaag               1368
```

CR6342 Heavy Chain amino acid sequence
(SEQ ID NO: 552)

QVQLVQSGAEVKKPGSSVKVSCKASGGFFSSYAISWVRQAPGQGLEWMGGVIPIFRTANY
AQNFQGRVTITADEFTSYMELSSLRSDDTAVYYCARLNYHDSGTYYNAPRGWFDPWGQG
TLVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKS
RWQQGNVFSCSVMHEALHNHYTQKSLSLSPGK

CR6342 VH amino acid sequence
(SEQ ID NO: 550)

QVQLVQSGAEVKKPGSSVKVSCKASGGFFSSYAISWVRQAPGQGLEWMGGVIPIFRTANY
AQNFQGRVTITADEFTSYMELSSLRSDDTAVYYCARLNYHDSGTYYNAPRGWFDPWGQG
TLVTVSS

CR6342 Light Chain nucleotide sequence
(SEQ ID NO: 554)

```
gacatccaga tgacccagtc tccagactcc ctggctgtgt ctctgggcga gaaggccacc     60
atcaactgca gtccagcca gagtatttta aacagctcca acaataagaa ctacttagct    120
tggtaccagc agaaaccagg acagcctcct aagctgctca tttactgggc atctacccgg    180
gaatccgggg tccctgaccg attcagtggc agcgggtctg gacagattt cactctcacc    240
atcagcagcc tgcaggctga agatgtggca gtttattact gtcagcaata ttatagtagt    300
ccgccgacgt tcggccaagg gaccaaggtg gaaatcaaac gtgcggccgc acccagcgtg    360
ttcatcttcc cccctccga cgagcagctg aagagcggca ccgccagcgt ggtgtgcctg    420
ctgaacaact ctaccccg ggaggccaag gtgcagtgga aggtggacaa cgccctgcag     480
agcggcaaca gccaggagag cgtgaccgag caggacagca aggactccac ctacagcctg    540
agcagcaccc tcaccctgag caaggccgac tacgagaagc acaaggtgta cgcctgcgag    600
gtgacccacc agggcctgag cagccccgtg accaagagct tcaaccgggg cgagtgt      657
```

CR6342 Light Chain amino acid sequence
(SEQ ID NO: 555)

DIQMTQSPDSLAVSLGEKATINCKSSQSILNSSNNKNYLAWYQQKPGQPPKWYWASTRE
SGVPDRFSGSGSGTDFTLTISSLQAEDVAVYYCQQYYSSPPTFGQGTKVEIKRAAAPSVFIFP
PSDEQLKSGTASVVCLLNNFYPREAKVQWKVDNALQSGNSQESVTEQDSKDSTYSLSSTL
TLSKADYEKHKVYACEVTHQGLSSPVTKSFNRGEC

CR6342 VL amino acid sequence
(SEQ ID NO: 553)

DIQMTQSPDSLAVSLGEKATINCKSSQSILNSSNNKNYLAWYQQKPGQPPKLLIIWASTRE
SGVPDRFSGSGSGTDFTLTISSLQAEDVAVYYCQQYYSSPPTFGQGTKVEIKR

The CR6343 HA-specific IgG antibody includes a heavy chain variable region (SEQ ID NO: 556) encoded by the heavy chain nucleotide sequence shown in SEQ ID NO: 557 and the heavy chain amino acid sequence shown in SEQ ID NO: 558. The CR6343 HA-specific IgG antibody also includes a light chain variable region (SEQ ID NO: 559) encoded by the light chain nucleotide sequence shown in SEQ ID NO: 560 and the light chain amino acid sequence shown in SEQ ID NO: 561.

CR6343 Heavy Chain nucleotide sequence
(SEQ ID NO: 557)

```
caggtccagc tggtgcagtc tggagctgag gtgaagaagc ctgggtcctc ggtgaaggtc     60
tcctgcaagg cttctggagt caccttcagt tactatgcta tgagctgggt gcgacaggcc    120
cctggacaag ggcttgagtg gatgggagga atcagcccta tgtttgggac aacaacctac    180
```

-continued

```
gcacagaagt tccagggcag agtcacgatt actgcggacg actccacgag tacagcctac    240
atggaggtga ggagcctgag atctgaggac acggccgtgt attactgtgc gagatcttcg    300
aattactatg atagtgtata tgactactgg ggccagggaa ccctggtcac cgtctcgagt    360
gctagcacca agggccccag cgtgttcccc ctggccccca gcagcaagag caccagcggc    420
ggcacagccg ccctgggctg cctggtgaag gactacttcc ccgagccgt gaccgtgagc    480
tggaacagcg gcgccttgac cagcggcgtg cacaccttcc ccgccgtgct gcagagcagc    540
ggcctgtaca gcctgagcag cgtggtgacc gtgcccagca gcagcctggg cacccagacc    600
tacatctgca acgtgaacca caagcccagc aacaccaagg tggacaaacg cgtggagccc    660
aagagctgcg acaagaccca cacctgcccc cctgccctg ccccgagct gctgggcgga    720
ccctccgtgt tcctgttccc cccaagccc aaggacaccc tcatgatcag ccggacccc    780
gaggtgacct gcgtggtggt ggacgtgagc cacgaggacc ccgaggtgaa gttcaactgg    840
tacgtggacg gcgtggaggt gcacaacgcc aagaccaagc ccgggagga gcagtacaac    900
agcacctacc gggtggtgag cgtgctcacc gtgctgcacc aggactggct gaacggcaag    960
gagtacaagt gcaaggtgag caacaaggcc ctgcctgccc ccatcgagaa gaccatcgc   1020
aaggccaagg gccagccccg ggagcccag cgtgtacaccc tgcccccag ccggaggag   1080
atgaccaaga accaggtgtc cctcacctgt ctggtgaagg gcttctaccc cagcgacatc   1140
gccgtggagt gggagagcaa cggccagccc gagaacaact acaagaccac ccccctgtg   1200
ctggacagcg acggcagctt cttcctgtac agcaagctca ccgtggacaa gagccggtgg   1260
cagcagggca acgtgttcag ctgcagcgtg atgcacgagg ccctgcacaa ccactacacc   1320
cagaagagcc tgagcctgag ccccggcaag                                      1350
```

CR6343 Heavy Chain amino acid sequence (SEQ ID NO: 558)

QVQLVQSGAEVKKPGSSVKVSCKASGVTFSYYAMSWVRQAPGQGLEWMGGISPMFGTTT
YAQKFQGRVTITADDSTSTAYMEVRSLRSEDTAVYYCARSSNYYDSVVDYWGQGTLVTV
SSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK

CR6343 VH amino acid sequence (SEQ ID NO: 556)

QVQLVQSGAEVKKPGSSVKVSCKASGVTFSYYAMSWVRQAPGQGLEWMGGISPMFGTTT
YAQKFQGRVTITADDSTSTAYMEVRSLRSEDTAVYYCARSSNYYDSVVDYWGQGTLVTV
SS

CR343 Light Chain nucleotide sequence (SEQ ID NO: 560)

```
cagtctgtcg tgacgcagcc gccctcggag tcagtggccc caggacagac ggccaggatt     60
acctgtgggg gacataacat tggaagtaat agtgtgcact ggtaccagca gaagccaggc    120
caggcccctg tgctggtcgt gtatgataat agcgaccggc ctcaggatt ccctgagcga    180
ttctctggct ccaactctgg gaacacggcc accctgacca tcagcaggg cgaagccggg    240
gatgaggccg actattactg tcaggtgtgg ggtagtagta gtgaccatta tgtcttcgga    300
actgggacca aggtcaccgt cctaggtgcg gccgcaggcc agcccaaggc cgctcccagc    360
gtgaccctgt tcccccctc ctccgaggag ctgcaggcca acaaggccac cctggtgtgc    420
ctcatcagcg acttctaccc tggcgccgtg accgtggcct ggaaggccga cagcagcccc    480
gtgaaggccg gcgtggagac caccaccccc agcaagcaga gcaacaacaa gtacgccgcc    540
agcagctacc tgagcctcac ccccgagcag tggaagagcc accggagcta cagctgccag    600
gtgacccacg agggcagcac cgtggagaag accgtggccc ccaccgagtg cagc          654
```

CR6343 Light Chain amino acid sequence (SEQ ID NO: 561)

QSVVTQPPSESVAPGQTARITCGGHNIGSNSVHWYQQKPGQAPVLVVYDNSDRPSGIPERF
SGSNSGNTATLTISRVEAGDEADYYCQVWGSSSDHYVFGTGTKVTVLGAAAGQPKAAPS
VTLFPPSSEELQANKATLVCLISDFYPGAVTVAWKADSSPVKAGVETTTPSKQSNNKYAAS
SYLSLTPEQWKSHRSYSCQVTHEGSTVEKTVAPTECS

CR6343 VL amino acid sequence (SEQ ID NO: 559)

QSVVTQPPSESVAPGQTARITCGGHNIGSNSVHWYQQKPGQAPVLVVYDNSDRPSGIPERF
SGSNSGNTATLTISRVEAGDEADYYCQVWGSSSDHYVFGTGTKVTVLG

The CR6344 HA-specific IgG antibody includes a heavy chain variable region (SEQ ID NO: 562) encoded by the heavy chain nucleotide sequence shown in SEQ ID NO: 563 and the heavy chain amino acid sequence shown in SEQ ID NO: 564. The CR6344 HA-specific IgG antibody also includes a light chain variable region (SEQ ID NO: 565) encoded by the light chain nucleotide sequence shown in SEQ ID NO: 566 and the light chain amino acid sequence shown in SEQ ID NO: 567.

CR6344 Heavy Chain nucleotide sequence (SEQ ID NO: 563)

```
caggtgcagc tggtgcagtc tggggctgag gtgaagaagc ctgggtcctc ggtgagagtc     60
tcctgcaagg cttctggaag catcttcaga aactatgcta tgagctgggt gcgacaggcc    120
```

-continued

```
cctggacaag ggcttgagtg gatgggaggg atcatcgcta tttttgggac accaaagtac        180
gcacagaagt tccagggcag agtcacgatt accgcggacg aatcgacgag cactgtctac        240
atggaactga gcggactgag atctgaggac acggccatgt attactgtgc gaggattccc        300
cactataatt ttggttcggg gagttatttc gactactggg gccagggaac cctggtcacc        360
gtctcgagtg ctagcaccaa gggccccagc gtgttcccc tggcccccag cagcaagagc        420
accagcggcg gcacagccgc cctgggctgc ctggtgaagg actacttccc cgagcccgtg        480
accgtgagct ggaacagcgg cgccttgacc agcggcgtgc acaccttccc cgccgtgctg        540
cagagcagcg gcctgtacag cctgagcagc gtggtgaccg tgcccagcag cagcctgggc        600
acccagacct acatctgcaa cgtgaaccac aagcccagca acaccaaggt ggacaaacgc        660
gtggagccca agagctgcga caagacccac acctgcccc cctgccctgc ccccgagctg        720
ctgggcggac cctccgtgtt cctgttcccc ccaagcccca aggacaccct catgatcagc        780
cggaccccg aggtgacctg cgtggtggtg gacgtgagcc acgaggaccc cgaggtgaag        840
ttcaactggt acgtggacgg cgtggaggtg cacaacgcca agaccaagcc ccgggaggag        900
cagtacaaca gcacctaccg ggtggtgagc gtgctcacca tgctgccacca ggactggctg        960
aacggcaagg agtacaagtg caaggtgagc aacaaggccc tgcctgcccc catcgagaag       1020
accatcagca aggccaaggg ccagccccgg gagcccagg tgtacaccct gcccccagc        1060
cgggaggaga tgaccaagaa ccaggtgtcc ctcacctgtc tggtgaaggg cttctacccc       1140
agcgacatcg ccgtggagtg ggagagcaac ggccagcccg agaacaacta caagaccacc       1200
cccctgtgc tggacagcga cggcagcttc ttcctgtaca gcaagctcac cgtggacaag       1260
agccggtggc agcagggcaa cgtgttcagc tgcagcgtga tgcacgaggc cctgcacaac       1320
cactacaccc agaagagcct gagcctgagc cccggcaag                              1359
```

CR6344 Heavy Chain amino acid sequence (SEQ ID NO: 564)

QVQLVQSGAEVKKPGSSVRVSCKASGSIFRNYAMSWVRQAPGQGLEWMGGIIAIFGTPKY
AQKFQGRVTITADESTSTVYMELSGLRSEDTAMYYCARIPHYNFGSGSYFDYWGQGTLVT
VSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQ
QGNVFSCSVMHEALHNHYTQKSLSLSPGK

CR6344 VH amino acid sequence (SEQ ID NO: 562)

QVQLVQSGAEVKKPGSSVRVSCKASGSIFRNYAMSWVRQAPGQGLEWMGGIIAIFGTPKY
AQKFQGRVTITADESTSTVYMELSGLRSEDTAMYYCARIPHYNFGSGSYFDYWGQGTLVT
VSS

CR6344 Light Chain nucleotide sequence (SEQ ID NO: 566)

```
actgtgttga cacagccgcc ctcagtgtct ggggcccag gcagagggt caccatctcc         60
tgcactggga gcagctccaa catcggggca ggttatgta tacactggta ccagcagctt        120
ccaggaacag cccccaaact cctcatctat ggtaacagca atcggccctc agggtccct        180
gaccgattct ctggctccaa gtctggcacg tcagccaccc tgggcatcac cggactccag        240
actggggacg aggccgatta ttactgcgga acatgggata gcagcctgag tgcttatgtc        300
ttcggaactg ggaccaaggt caccgtccta ggtgcgccg caaggccgct                   360
cccagcgtga ccctgttccc ccctcctcc gaggagctgc aggccaacaa ggccaccctg        420
gtgtgcctca tcagcgactt ctaccctggc gccgtgaccg tggcctggaa ggccgacagc        480
agccccgtga aggccggcgt ggagaccacc accccagca agcagagcaa caacaagtac        540
gccgccagca gctacctgag cctcaccccc gagcagtgga gagccaccg gagctacagc        600
tgccaggtga cccacgaggg cagcaccgtg gagaagaccg tggcccccac cgagtgcagc        660
```

CR6344 Light Chain amino acid sequence (SEQ ID NO: 567)

TVLTQPPSVSGAPGQRVTISCTGSSSNIGAGYDVHWYQQLPGTAPKLLIYGNSNRPSGVPD
RFSGSKSGTSATLGITGLQTGDEADYYCGTWDSSLSAYVFGTGTKVTVLGAAAGQPKAAP
SVTLFPPSSEELQANKATLVCLISDFYPGAVTVAWKADSSPVKAGVETTTPSKQSNNKYAA
SSYLSLTPEQWKSHRSYSCQVTHEGSTVEKTVAPTECS

CR6344 VL amino acid sequence (SEQ ID NO: 565)

TVLTQPPSVSGAPGQRVTISCTGSSSNIGAGYDVHWYQQLPGTAPKLLIYGNSNRPSGVPD
RFSGSKSGTSATLGITGLQTGDEADYYCGTWDSSLSAYVFGTGTKVTVLG

HA Antibody Epitopes

The invention relates to an isolated human HA antibody that is able to recognize and bind to an epitope in the HA2 subunit of the influenza haemagglutinin protein (HA) (also known as hemagglutinin (HA)), characterized in that the HA antibody has neutralizing activity against an influenza virus including HA of the H5 subtype. Examples of influenza strains that contain such a HA of the H5 subtype and that are important strains in view of pandemic threats are H5N1, H5N2, H5N8, and H5N9. Particularly preferred are HA antibodies that at least neutralize the H5N1 influenza strain.

Preferably, an HA antibody of the invention does not depend on an epitope in the HA1 subunit of the HA protein for binding to said HA protein.

A number of the antibodies of the invention (such as CR6307 and CR6323) do not depend on conformational epitopes and recognize the HA2 epitope even in a reduced form (when used in western-blotting). This is an advantage over the antibodies from the art because when a conformational change is induced in the HA protein due to whatever mutation in another part of the protein, such conformational change will not most likely hamper the binding of the antibodies of the present invention to the HA2 epitope, whereas antibodies that do depend on conformation might very well be unable to bind when such mutations occur.

In another preferred embodiment, an HA antibody of the invention also has neutralizing activity against an influenza virus comprising HA of the H1 subtype, and preferably wherein the HA antibody also has neutralizing activity against influenza virus comprising HA of the H2, H6 and/or H9 subtype. The HA antibodies of the invention interact with an epitope present in the HA2 epitopes present in the H5, H1, H2, H6, and H9 subtypes (see, International Patent Application PCT/EP2007/059356, published as WO 2008/028946, the contents of which are incorporated by reference in their entirety), and it has been shown that the HA antibodies of the invention cross-neutralize between influenza subtypes because of this epitope-sharing.

In another preferred aspect of the invention an HA antibody of the invention binds to an epitope that is selected from the group consisting of the amino acid sequence: GVTNKVNSIIDK (SEQ ID NO: 198), GVTNKVNSIINK (SEQ ID NO: 283), GVTNKENSIIDK (SEQ ID NO: 202), GVTNKVNRIIDK (SEQ ID NO: 201), GITNKVNSVIEK (SEQ ID NO: 281), GITNKENSVIEK (SEQ ID NO: 257), GITNKVNSIIDK (SEQ ID NO: 225), and KITSKVNNIVDK (SEQ ID NO: 216). Certain HA antibodies of the invention, CR6261, CR6325, and CR6329 interact with the GVTNKVNSIIDK (SEQ ID NO: 198) epitope present in H5N1, and are not hampered by a mutation in the TGLRN (SEQ ID NO: 200) epitope in HA1 that do influence the binding of C179. Moreover, some HA antibodies, such as CR6307 and CR6323 are not even hampered by a escape mutant, as disclosed in Okuno et al. (1993) with a valine→glutamic acid mutation at position 6 (exemplified by GVTNKENSIIDK (SEQ ID NO: 202)). This epitope is part of an extended alpha helix in the HA2 region. The residues in this putative epitope that are predicted to be most solvent exposed are underlined in bold: GV-TNKENSIIDK (SEQ ID NO: 202). These amino acids would be most accessible to an HA antibody and thus may form the most important region of the epitope. Consistent with this notion the highlighted amino acids are absolutely conserved in identity and position in all the sequences presented. This knowledge could be used to predict binding epitopes in influenza subtypes that do not carry the same sequence as above (i.e. H3, H7 and B strains).

Antibodies

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following definitions are useful in understanding the present invention:

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ϵ isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239: 1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc$_\epsilon$RI.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, HuM2e antibody specifically binds to M2e if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (*Ann. N.Y. Acad. Sci. USA* 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

An "antibody that inhibits the growth of infected cells" or a "growth inhibitory" antibody is one that binds to and results in measurable growth inhibition of infected cells expressing or capable of expressing an M2e epitope bound by an antibody. Preferred growth inhibitory antibodies inhibit growth of infected cells by greater than 20%, preferably from about 20% to about 50%, and even more preferably, by greater than 50% (e.g., from about 50% to about 100%) as compared to the appropriate control, the control typically being infected cells not treated with the antibody being tested. Growth inhibition can be measured at an antibody concentration of about 0.1 to 30 µg/ml or about 0.5 nM to 200 nM in cell culture, where the growth inhibition is determined 1-10 days after exposure of the infected cells to the antibody. Growth inhibition of infected cells in vivo can be determined in various ways known in the art. The antibody is growth inhibitory in vivo if administration of the antibody at about 1 µg/kg to about 100 mg/kg body weight results in reduction the percent of infected cells or total number of infected cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effectorcells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., PNAS (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), may be performed.

The terms "influenza A" and "Influenzavirus A" refer to a genus of the Orthomyxoviridae family of viruses. Influenzavirus A includes only one species: influenza A virus which cause influenza in birds, humans, pigs, and horses. Strains of all subtypes of influenza A virus have been isolated from wild birds, although disease is uncommon. Some isolates of influenza A virus cause severe disease both in domestic poultry and, rarely, in humans.

A "mammal" for purposes of treating n infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "growth inhibitory agent" when used herein refers to a compound or composition which inhibits growth of a cell, either in vitro or in vivo. Examples of growth inhibitory agents include agents that block cell cycle progression, such as agents that induce G1 arrest and M-phase arrest. Classical M-phase blockers include the vinca alkaloids (vincristine, vinorelbine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The term "epitope tagged" as used herein refers to a chimeric polypeptide comprising a polypeptide fused to a "tag polypeptide." The tag polypeptide has enough residues to provide an epitope against which an antibody can be made, yet is short enough such that it does not interfere with activity of the polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen or Influenza A-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr;. (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad, Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below.

As used in this specification and the appended claims, the singular forms "a," "an" and "the" include plural references unless the content clearly dictates otherwise.

The present invention includes HuM2e antibodies comprising a polypeptide of the present invention, including those polypeptides encoded by a polynucleotide sequence set forth in Example 1 and amino acid sequences set forth in Example 1 and 2, and fragments and variants thereof. In one embodiment, the antibody is an antibody designated herein as TCN-032 (8110), 21B15, TCN-031 (23K12), 3241_G23, 3244_I10, 3243_J07, 3259_J21, 3245_O19, 3244_H04, 3136_G05, 3252_C13, 3255_J06, 3420_I23, 3139_P23, 3248_P18, 3253_P10, 3260_D19, 3362_B11, or 3242_P05. These antibodies preferentially bind to or specifically bind to influenza A infected cells as compared to uninfected control cells of the same cell type.

In particular embodiments, the antibodies of the present invention bind to the M2 protein. In certain embodiments, the present invention provides HuM2e antibodies that bind to epitopes within M2e that are only present in the native conformation, i.e., as expressed in cells. In particular embodiments, these antibodies fail to specifically bind to an isolated M2e polypeptide, e.g., the 23 amino acid residue M2e fragment. It is understood that these antibodies recognize non-linear (i.e. conformational) epitope(s) of the M2 peptide.

These specific conformational epitopes within the M2 protein, and particularly within M2e, may be used as vaccines to prevent the development of influenza infection within a subject.

As will be understood by the skilled artisan, general description of antibodies herein and methods of preparing and using the same also apply to individual antibody polypeptide constituents and antibody fragments.

The antibodies of the present invention may be polyclonal or monoclonal antibodies. However, in preferred embodiments, they are monoclonal. In particular embodiments, antibodies of the present invention are fully human antibodies. Methods of producing polyclonal and monoclonal antibodies are known in the art and described generally, e.g., in U.S. Pat. No. 6,824,780. Typically, the antibodies of the present invention are produced recombinantly, using vectors and methods available in the art, as described further below. Human antibodies may also be generated by in vitro activated B cells (see U.S. Pat. Nos. 5,567,610 and 5,229,275).

Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals may be genetically engineered to produce human antibodies comprising a polypeptide of the present invention.

In certain embodiments, antibodies of the present invention are chimeric antibodies that comprise sequences derived from both human and non-human sources. In particular embodiments, these chimeric antibodies are humanized or primatized™. In practice, humanized antibodies are typically human antibodies in which some hypervariable region residues and possibly some FR residues are substituted by residues from analogous sites in rodent antibodies.

In the context of the present invention, chimeric antibodies also include fully human antibodies wherein the human hypervariable region or one or more CDRs are retained, but one or more other regions of sequence have been replaced by corresponding sequences from a non-human animal.

The choice of non-human sequences, both light and heavy, to be used in making the chimeric antibodies is important to reduce antigenicity and human anti-non-human antibody responses when the antibody is intended for human therapeutic use. It is further important that chimeric antibodies retain high binding affinity for the antigen and other favorable biological properties. To achieve this goal, according to a preferred method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As noted above, antibodies (or immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention may be any class, and may, therefore, have a gamma, mu, alpha, delta, or epsilon heavy chain. A gamma chain may be gamma 1, gamma 2, gamma 3, or gamma 4; and an alpha chain may be alpha 1 or alpha 2.

In a preferred embodiment, an antibody of the present invention, or fragment thereof, is an IgG. IgG is considered the most versatile immunoglobulin, because it is capable of carrying out all of the functions of immunoglobulin molecules. IgG is the major Ig in serum, and the only class of Ig that crosses the placenta. IgG also fixes complement, although the IgG4 subclass does not. Macrophages, monocytes, PMN's and some lymphocytes have Fc receptors for the Fc region of IgG. Not all subclasses bind equally well; IgG2 and IgG4 do not bind to Fc receptors. A consequence of binding to the Fc receptors on PMN's, monocytes and macrophages is that the cell can now internalize the antigen better. IgG is an opsonin that enhances phagocytosis. Binding of IgG to Fc receptors on other types of cells results in the activation of other functions. Antibodies of the present invention may be of any IgG subclass.

In another preferred embodiment, an antibody, or fragment thereof, of the present invention is an IgE. IgE is the least common serum Ig since it binds very tightly to Fc receptors on basophils and mast cells even before interacting with antigen. As a consequence of its binding to basophils an mast cells, IgE is involved in allergic reactions. Binding of the allergen to the IgE on the cells results in the release of various pharmacological mediators that result in allergic symptoms. IgE also plays a role in parasitic helminth diseases. Eosinophils have Fc receptors for IgE and binding of eosinophils to IgE-coated helminths results in killing of the parasite. IgE does not fix complement.

In various embodiments, antibodies of the present invention, and fragments thereof, comprise a variable light chain that is either kappa or lambda. The lamba chain may be any of subtype, including, e.g., lambda 1, lambda 2, lambda 3, and lambda 4.

As noted above, the present invention further provides antibody fragments comprising a polypeptide of the present invention. In certain circumstances there are advantages of using antibody fragments, rather than whole antibodies. For example, the smaller size of the fragments allows for rapid clearance, and may lead to improved access to certain tissues, such as solid tumors. Examples of antibody fragments include: Fab, Fab', F(ab')$_2$ and Fv fragments; diabodies; linear antibodies; single-chain antibodies; and multispecific antibodies formed from antibody fragments.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner.

In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions. Thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

In certain embodiments, antibodies of the present invention are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-M2e arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the infected cell. Bispecific antibodies may also be used to localize cytotoxic agents to infected cells. These antibodies possess an M2e-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147: 60 (1991). A multivalent antibody may be internalized (and/or catabolized) faster than a bivalent antibody by a cell expressing an antigen to which the antibodies bind. The antibodies of the present invention can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a $C_L$ domain.

Antibodies of the present invention further include single chain antibodies.

In particular embodiments, antibodies of the present invention are internalizing antibodies.

Amino acid sequence modification(s) of the antibodies described herein are contemplated. For example, it may be desirable to improve the binding affinity and/or other biological properties of the antibody. Amino acid sequence variants of the antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics. The amino acid changes also may alter posttranslational processes of the antibody, such as changing the number or position of glycosylation sites. Any of the variations and modifications described above for polypeptides of the present invention may be included in antibodies of the present invention.

A useful method for identification of certain residues or regions of an antibody that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with PSCA antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of an antibody include the fusion to the N- or C-terminus of the antibody to an enzyme (e.g., for ADEPT) or a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative and non-conservative substitutions are contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody. Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene I10 product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and an antigen or infected cell. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The antibody of the invention is modified with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148:2918-2922 (1992). Homodimeric antibodies with enhanced anti-infection activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies of the present invention may also be modified to include an epitope tag or label, e.g., for use in purification or diagnostic applications. The invention also pertains to therapy with immunoconjugates comprising an antibody conjugated to an anti-cancer agent such as a cytotoxic agent or a growth inhibitory agent. Chemotherapeutic agents useful in the generation of such immunoconjugates have been described above.

Conjugates of an antibody and one or more small molecule toxins, such as a calicheamicin, maytansinoids, a trichothene, and CC1065, and the derivatives of these toxins that have toxin activity, are also contemplated herein.

In one preferred embodiment, an antibody (full length or fragments) of the invention is conjugated to one or more maytansinoid molecules. Maytansinoids are mitototic inhibitors that act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disufide groups, thioether groups, acid labile groups, photolabile groups, peptidase labile groups, or esterase labile groups, as disclosed in the above-identified patents, disulfide and thioether groups being preferred.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage. For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, Cancer Research 52: 127-131 (1992); U.S. Pat. No. 5,208,020) may be used.

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Another drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Examples of other agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof that can be used include, e.g., diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232.

The present invention further includes an immunoconjugate formed between an antibody and a compound with nucleolytic activity (e.g., a ribonuclease or a DNA endonuclease such as a deoxyribonuclease; DNase).

For selective destruction of infected cells, the antibody includes a highly radioactive atom. A variety of radioactive isotopes are available for the production of radioconjugated anti-PSCA antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other label is incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}$m or $I^{123}$, $Re^{186}$, $Re^{188}$ and $In^{111}$ can be attached via a cysteine residue in the peptide. Yttrium-90 can be attached via a lysine residue. The IODOGEN method (Fraker et al. (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Alternatively, a fusion protein comprising the antibody and cytotoxic agent is made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The antibodies of the present invention are also used in antibody dependent enzyme mediated prodrug therapy (ADET) by conjugating the antibody to a prodrug-activating enzyme which converts a prodrug (e.g., a peptidyl chemotherapeutic agent, see WO81/01145) to an active anti-cancer drug (see, e.g., WO 88/07378 and U.S. Pat. No. 4,975,278).

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a infected cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The antibodies disclosed herein are also formulated as immunoliposomes. A "liposome" is a small vesicle composed of various types of lipids, phospholipids and/or surfactant that is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired a diameter. Fab' fragments of the antibody of the present invention can be conjugated to the liposomes as described in Martin et al., J. Biol. Chem. 257: 286-288 (1982) via a disulfide interchange reaction. A chemotherapeutic agent is optionally contained within the liposome. See Gabizon et al., J. National Cancer Inst. 81(19)1484 (1989).

Antibodies of the present invention, or fragments thereof, may possess any of a variety of biological or functional characteristics. In certain embodiments, these antibodies are Influenza A specific or M2 protein specific antibodies, indicating that they specifically bind to or preferentially bind to Influenza A or the M2 protein thereof, respectively, as compared to a normal control cell. In particular embodiments, the antibodies are HuM2e antibodies, indicating that they specifically bind to a M2e protein, preferably to an epitope of the M2e domain that is only present when the M2 protein is expressed in cells or present on a virus, as compared to a normal control cell.

In particular embodiments, an antibody of the present invention is an antagonist antibody, which partially or fully blocks or inhibits a biological activity of a polypeptide or cell to which it specifically or preferentially binds. In other embodiments, an antibody of the present invention is a growth inhibitory antibody, which partially or fully blocks or inhibits the growth of an infected cell to which it binds. In another embodiment, an antibody of the present invention induces apoptosis. In yet another embodiment, an antibody of the present invention induces or promotes antibody-dependent cell-mediated cytotoxicity or complement dependent cytotoxicity.

Methods of Identifying and Producing Antibodies Specific for Influenza Virus

The present invention provides novel methods for the identification of HuM2e antibodies, as exemplified in Example 4. These methods may be readily adapted to identify antibodies specific for other polypeptides expressed on the cell surface by infectious agents, or even polypeptides expressed on the surface of an infectious agent itself.

In general, the methods include obtaining serum samples from patients that have been infected with or vaccinated against an infectious agent. These serum samples are then screened to identify those that contain antibodies specific for a particular polypeptide associated with the infectious agent, such as, e.g., a polypeptide specifically expressed on the surface of cells infected with the infectious agent, but not uninfected cells. In particular embodiments, the serum samples are screened by contacting the samples with a cell that has been transfected with an expression vector that expresses the polypeptide expressed on the surface of infected cells.

Once a patient is identified as having serum containing an antibody specific for the infectious agent polypeptide of interest is identified, mononuclear and/or B cells obtained from the same patient are used to identify a cell or clone thereof that produces the antibody, using any of the methods described herein or available in the art. Once a B cell that produces the antibody is identified, cDNAs encoding the variable regions or fragments thereof of the antibody may be cloned using standard RT-PCR vectors and primers specific for conserved antibody sequences, and subcloned in to expression vectors used for the recombinant production of monoclonal antibodies specific for the infectious agent polypeptide of interest.

In one embodiment, the present invention provides a method of identifying an antibody that specifically binds influenza A-infected cells, comprising: contacting an Influenza A virus or a cell expressing the M2 protein with a biological sample obtained from a patient having been infected by Influenza A; determining an amount of antibody in the biological sample that binds to the cell; and comparing the amount determined with a control value, wherein if the value determined is at least two-fold greater than the control value, an antibody that specifically binds influenza A-infected cells is indicated. In various embodiments, the cells expressing an M2 protein are cells infected with an Influenza A virus or cells that have been transfected with a polynucleotide that expressed the M2 protein. Alternatively, the cells may express a portion of the M2 protein that includes the M2e domain and enough additional M2 sequence that the protein remains associated with the cell and the M2e domain is presented on the cell surface in the same manner as when present within full length M2 protein. Methods of preparing an M2 expression vector and transfecting an appropriate cell, including those described herein, may be readily accomplished, in view of the M2 sequence being publicly available. See, for example, the Influenza Sequence Database (ISD) (flu.lan1.gov on the World Wide Web, described in Macken et al., 2001, "The value of a database in surveillance and vaccine selection" in Options for the Control of Influenza IV. A.D.M.E., Osterhaus & Hampson (Eds.), Elsevier Science, Amsterdam, pp. 103-106) and the Microbial Sequencing Center (MSC) at The Institute for Genomic Research (TIGR) (tigr.org/msc/infl_a-_virus.shtml on the World Wide Web).

The M2e-expressing cells or virus described above are used to screen the biological sample obtained from a patient infected with influenza A for the presence of antibodies that preferentially bind to the cell expressing the M2 polypeptide using standard biological techniques. For example, in certain embodiments, the antibodies may be labeled, and the presence of label associated with the cell detected, e.g., using FMAT or FACs analysis. In particular embodiments, the biological sample is blood, serum, plasma, bronchial lavage, or saliva. Methods of the present invention may be practiced using high throughput techniques.

Identified human antibodies may then be characterized further. For example the particular conformational epitopes with in the M2e protein that are necessary or sufficient for binding of the antibody may be determined, e.g., using site-directed mutagenesis of, expressed M2e polypeptides. These methods may be readily adapted to identify human antibodies that bind any protein expressed on a cell surface. Furthermore, these methods may be adapted to determine binding of the antibody to the virus itself, as opposed to a cell expressing recombinant M2e or infected with the virus.

Polynucleotide sequences encoding the antibodies, variable regions thereof, or antigen-binding fragments thereof may be subcloned into expression vectors for the recombinant production of HuM2e antibodies. In one embodiment, this is accomplished by obtaining mononuclear cells from the patient from the serum containing the identified HuM2e antibody was obtained; producing B cell clones from the mononuclear cells; inducing the B cells to become antibody-producing plasma cells; and screening the supernatants produced by the plasma cells to determine if it contains the HuM2e antibody. Once a B cell clone that produces an HuM2e antibody is identified, reverse-transcription polymerase chain reaction (RT-PCR) is performed to clone the DNAs encoding the variable regions or portions thereof of the HuM2e antibody. These sequences are then subcloned into expression vectors suitable for the recombinant production of human HuM2e antibodies. The binding specificity may be confirmed by determining the recombinant antibody's ability to bind cells expressing M2e polypeptide.

In particular embodiments of the methods described herein, B cells isolated from peripheral blood or lymph nodes are sorted, e.g., based on their being CD19 positive, and plated, e.g., as low as a single cell specificity per well, e.g., in 96, 384, or 1536 well configurations. The cells are induced to differentiate into antibody-producing cells, e.g., plasma cells, and the culture supernatants are harvested and tested for binding to cells expressing the infectious agent polypeptide on their surface using, e.g., FMAT or FACS analysis. Positive wells are then subjected to whole well RT-PCR to amplify heavy and light chain variable regions of the IgG molecule expressed by the clonal daughter plasma cells. The resulting PCR products encoding the heavy and light chain variable regions, or portions thereof, are subcloned into human antibody expression vectors for recombinant expression. The resulting recombinant antibodies are then tested to confirm their original binding specificity and may be further tested for pan-specificity across various strains of isolates of the infectious agent.

Thus, in one embodiment, a method of identifying HuM2e antibodies is practiced as follows. First, full length or approximately full length M2 cDNAs are transfected into a cell line for expression of M2 protein. Secondly, individual human plasma or sera samples are tested for antibodies that bind the cell-expressed M2. And lastly, MAbs derived from plasma- or serum-positive individuals are characterized for binding to the same cell-expressed M2. Further definition of the fine specificities of the MAbs can be performed at this point.

These methods may be practiced to identify a variety of different HuM2e antibodies, including antibodies specific for (a) epitopes in a linear M2e peptide, (b) common epitopes in multiple variants of M2e, (c) conformational determinants of an M2 homotetramer, and (d) common conformational determinants of multiple variants of the M2 homotetramer. The last category is particularly desirable, as this specificity is perhaps specific for all A strains of influenza.

Polynucleotides that encode the HuM2e antibodies or portions thereof of the present invention may be isolated from cells expressing HuM2e antibodies, according to methods available in the art and described herein, including amplification by polymerase chain reaction using primers specific for conserved regions of human antibody polypeptides. For example, light chain and heavy chain variable regions may be cloned from the B cell according to molecular biology techniques described in WO 92/02551; U.S. Pat. No. 5,627,052; or Babcook et al., *Proc. Natl. Acad. Sci. USA* 93:7843-48 (1996). In certain embodiments, polynucleotides encoding all or a region of both the heavy and light chain variable regions of the IgG molecule expressed by the clonal daughter plasma cells expressing the HuM2e antibody are subcloned and sequenced. The sequence of the encoded polypeptide may be readily determined from the polynucleotide sequence. Isolated polynucleotides encoding a polypeptide of the present invention may be subcloned into an expression vector to recombinantly produce antibodies and polypeptides of the present invention, using procedures known in the art and described herein.

Binding properties of an antibody (or fragment thereof) to M2e or infected cells or tissues may generally be determined and assessed using immunodetection methods including, for example, immunofluorescence-based assays, such as immuno-histochemistry (IHC) and/or fluorescence-activated cell sorting (FACS). Immunoassay methods may include controls and procedures to determine whether antibodies bind specifically to M2e from one or more specific strains of Influenza A, and do not recognize or cross-react with normal control cells.

Following pre-screening of serum to identify patients that produce antibodies to an infectious agent or polypeptide thereof, e.g., M2, the methods of the present invention typically include the isolation or purification of B cells from a biological sample previously obtained from a patient or subject. The patient or subject may be currently or previously diagnosed with or suspect or having a particular disease or infection, or the patient or subject may be considered free or a particular disease or infection. Typically, the patient or subject is a mammal and, in particular embodiments, a human. The biological sample may be any sample that contains B cells, including but not limited to, lymph node or lymph node tissue, pleural effusions, peripheral blood, ascites, tumor tissue, or cerebrospinal fluid (CSF). In various embodiments, B cells are isolated from different types of biological samples, such as a biological sample affected by a particular disease or infection. However, it is understood that any biological sample comprising B cells may be used for any of the embodiments of the present invention.

Once isolated, the B cells are induced to produce antibodies, e.g., by culturing the B cells under conditions that support B cell proliferation or development into a plasmacyte, plasmablast, or plasma cell. The antibodies are then screened, typically using high throughput techniques, to identify an antibody that specifically binds to a target antigen, e.g., a particular tissue, cell, infectious agent, or polypeptide. In certain embodiments, the specific antigen, e.g., cell surface polypeptide bound by the antibody is not known, while in other embodiments, the antigen specifically bound by the antibody is known.

According to the present invention, B cells may be isolated from a biological sample, e.g., a tumor, tissue, peripheral blood or lymph node sample, by any means known and available in the art. B cells are typically sorted by FACS based on the presence on their surface of a B cell-specific marker, e.g., CD19, CD138, and/or surface IgG. However, other methods known in the art may be employed, such as, e.g., column purification using CD19 magnetic beads or IgG-specific magnetic beads, followed by elution from the column. However, magnetic isolation of B cells utilizing any marker may result in loss of certain B cells. Therefore, in certain embodiments, the isolated cells are not sorted but, instead, phicol-purified mononuclear cells isolated from tumor are directly plated to the appropriate or desired number of specificities per well.

In order to identify B cells that produce an infectious agent-specific antibody, the B cells are typically plated at low density (e.g., a single cell specificity per well, 1-10 cells per well, 10-100 cells per well, 1-100 cells per well, less than 10 cells per well, or less than 100 cells per well) in multi-well or microtitre plates, e.g., in 96, 384, or 1536 well configurations. When the B cells are initially plated at a density greater than one cell per well, then the methods of the present invention may include the step of subsequently diluting cells in a well identified as producing an antigen-specific antibody, until a single cell specificity per well is achieved, thereby facilitating the identification of the B cell that produces the antigen-specific antibody. Cell supernatants or a portion thereof and/or cells may be frozen and stored for future testing and later recovery of antibody polynucleotides.

In certain embodiments, the B cells are cultured under conditions that favor the production of antibodies by the B cells. For example, the B cells may be cultured under conditions favorable for B cell proliferation and differentiation to yield antibody-producing plasmablast, plasmacytes, or plasma cells. In particular embodiments, the B cells are cultured in the presence of a B cell mitogen, such as lipopolysaccharide (LPS) or CD40 ligand. In one specific embodiment, B cells are differentiated to antibody-producing cells by culturing them with feed cells and/or other B cell activators, such as CD40 ligand.

Cell culture supernatants or antibodies obtained therefrom may be tested for their ability to bind to a target antigen, using routine methods available in the art, including those described herein. In particular embodiments, culture supernatants are tested for the presence of antibodies that bind to a target antigen using high-throughput methods. For example, B cells may be cultured in multi-well microtitre dishes, such that robotic plate handlers may be used to simultaneously sample multiple cell supernatants and test for the presence of antibodies that bind to a target antigen. In particular embodiments, antigens are bound to beads, e.g., paramagnetic or latex beads) to facilitate the capture of antibody/antigen complexes. In other embodiments, antigens and antibodies are fluorescently labeled (with different labels) and FACS analysis is performed to identify the presence of antibodies that bind to target antigen. In one embodiment, antibody binding is determined using FMAT™ analysis and instrumentation (Applied Biosystems, Foster City, Calif.). FMAT™ is a fluorescence macro-confocal platform for high-throughput screening, which mix-and-read, non-radioactive assays using live cells or beads.

In the context of comparing the binding of an antibody to a particular target antigen (e.g., a biological sample such as infected tissue or cells, or infectious agents) as compared to a control sample (e.g., a biological sample such as uninfected cells, or a different infectious agent), in various embodiments, the antibody is considered to preferentially bind a particular target antigen if at least two-fold, at least three-fold, at least five-fold, or at least ten-fold more antibody binds to the particular target antigen as compared to the amount that binds a control sample.

Polynucleotides encoding antibody chains, variable regions thereof, or fragments thereof, may be isolated from cells utilizing any means available in the art. In one embodiment, polynucleotides are isolated using polymerase chain reaction (PCR), e.g., reverse transcription-PCR (RT-PCR) using oligonucleotide primers that specifically bind to heavy or light chain encoding polynucleotide sequences or complements thereof using routine procedures available in the art. In one embodiment, positive wells are subjected to whole well RT-PCR to amplify the heavy and light chain variable regions of the IgG molecule expressed by the clonal daughter plasma cells. These PCR products may be sequenced.

The resulting PCR products encoding the heavy and light chain variable regions or portions thereof are then subcloned into human antibody expression vectors and recombinantly expressed according to routine procedures in the art (see, e.g., U.S. Pat. No. 7,112,439). The nucleic acid molecules encoding a tumor-specific antibody or fragment thereof, as described herein, may be propagated and expressed according to any of a variety of well-known procedures for nucleic acid excision, ligation, transformation, and transfection. Thus, in certain embodiments expression of an antibody fragment may be preferred in a prokaryotic host cell, such as *Escherichia coli* (see, e.g., Pluckthun et al., *Methods Enzymol.* 178:497-515 (1989)). In certain other embodiments, expression of the antibody or an antigen-binding fragment thereof may be preferred in a eukaryotic host cell, including yeast (e.g., *Saccharomyces cerevisiae, Schizosaccharomyces pombe*, and *Pichia pastoris*); animal cells (including mammalian cells); or plant cells. Examples of suitable animal cells include, but are not limited to, myeloma, COS, CHO, or hybridoma cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the tumor-specific antibody (or fragment thereof) may be inserted. The regulatory elements will vary according to the particular host.

One or more replicable expression vectors containing a polynucleotide encoding a variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the polynucleotide sequence in each vector should include appropriate regulatory sequences, particularly a promoter and leader sequence operatively linked to the variable domain sequence. Particular methods for producing antibodies in this way are generally well known and routinely used. For example, molecular biology procedures are described by Sambrook et al. (*Molecular Cloning, A Laboratory Manual,* 2nd ed., Cold Spring Harbor Laboratory, New York, 1989; see also Sambrook et al., 3rd ed., Cold Spring Harbor Laboratory, New York, (2001)). While not required, in certain embodiments, regions of polynucleotides encoding the recombinant antibodies may be sequenced. DNA sequencing can be performed as described in Sanger et al. (*Proc. Natl. Acad. Sci. USA* 74:5463 (1977)) and the Amersham International plc sequencing handbook and including improvements thereto.

In particular embodiments, the resulting recombinant antibodies or fragments thereof are then tested to confirm their original specificity and may be further tested for pan-specificity, e.g., with related infectious agents. In particular embodiments, an antibody identified or produced according to methods described herein is tested for cell killing via antibody dependent cellular cytotoxicity (ADCC) or apoptosis, and/or well as its ability to internalize.

Polynucleotides

The present invention, in other aspects, provides polynucleotide compositions. In preferred embodiments, these polynucleotides encode a polypeptide of the invention, e.g., a region of a variable chain of an antibody that binds to Influenza A, M2, or M2e. Polynucleotides of the invention are single-stranded (coding or antisense) or double-stranded DNA (genomic, cDNA or synthetic) or RNA molecules. RNA molecules include, but are not limited to, HnRNA molecules, which contain introns and correspond to a DNA molecule in a one-to-one manner, and mRNA molecules, which do not contain introns. Alternatively, or in addition, coding or non-coding sequences are present within a polynucleotide of the present invention. Also alternatively, or in addition, a polynucleotide is linked to other molecules and/or support materials of the invention. Polynucleotides of the invention are used, e.g., in hybridization assays to detect the presence of an Influenza A antibody in a biological sample, and in the recombinant production of polypeptides of the invention.

Therefore, according to another aspect of the present invention, polynucleotide compositions are provided that include some or all of a polynucleotide sequence set forth in Example 1, complements of a polynucleotide sequence set forth in Example 1, and degenerate variants of a polynucleotide sequence set forth in Example 1. In certain preferred embodiments, the polynucleotide sequences set forth herein encode polypeptides capable of preferentially binding a Influenza A-infected cell as compared to a normal control uninfected cell, including a polypeptide having a sequence set forth in Examples 1 or 2. Furthermore, the invention includes all polynucleotides that encode any polypeptide of the present invention.

In other related embodiments, the invention provides polynucleotide variants having substantial identity to the sequences set forth in FIG. 1, for example those comprising at least 70% sequence identity, preferably at least 75%, 80%, 85%, 90%, 95%, 96%, 97%, 98%, or 99% or higher, sequence identity compared to a polynucleotide sequence of this invention, as determined using the methods described herein, (e.g., BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

Typically, polynucleotide variants contain one or more substitutions, additions, deletions and/or insertions, preferably such that the immunogenic binding properties of the polypeptide encoded by the variant polynucleotide is not substantially diminished relative to a polypeptide encoded by a polynucleotide sequence specifically set forth herein. In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. As used herein, the term "intermediate lengths" is meant to describe any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In preferred embodiments, the polypeptide encoded by the polynucleotide variant or fragment has the same binding specificity (i.e., specifically or preferentially binds to the same epitope or Influenza A strain) as the polypeptide encoded by the native polynucleotide. In certain preferred embodiments, the polynucleotides described above, e.g., polynucleotide variants, fragments and hybridizing sequences, encode polypeptides that have a level of binding activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. A nucleic acid fragment of almost any length is employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are included in many implementations of this invention.

It will be appreciated by those of ordinary skill in the art that, as a result of the degeneracy of the genetic code, there are multiple nucleotide sequences that encode a polypeptide as described herein. Some of these polynucleotides bear minimal homology to the nucleotide sequence of any native gene. Nonetheless, polynucleotides that encode a polypeptide of the present invention but which vary due to differences in codon usage are specifically contemplated by the invention. Further, alleles of the genes including the polynucleotide sequences provided herein are within the scope of the invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In certain embodiments of the present invention, mutagenesis of the disclosed polynucleotide sequences is performed in order to alter one or more properties of the encoded polypeptide, such as its binding specificity or binding strength. Techniques for mutagenesis are well-known in the art, and are widely used to create variants of both polypeptides and polynucleotides. A mutagenesis approach, such as site-specific mutagenesis, is employed for the preparation of variants and/or derivatives of the polypeptides described herein. By this approach, specific modifications in a polypeptide sequence are made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide. Site-specific mutagenesis allows the production of mutants through the use of specific oligonucleotide sequences include the nucleotide sequence of the desired mutation, as well as a sufficient number of adjacent nucleotides, to provide a primer sequence of sufficient size and sequence complexity to form a stable duplex on both sides of the deletion junction being traversed. Mutations are employed in a selected polynucleotide sequence to improve, alter, decrease, modify, or otherwise change the properties of the polynucleotide itself, and/or alter the properties, activity, composition, stability, or primary sequence of the encoded polypeptide.

In other embodiments of the present invention, the polynucleotide sequences provided herein are used as probes or primers for nucleic acid hybridization, e.g., as PCR primers. The ability of such nucleic acid probes to specifically hybridize to a sequence of interest enable them to detect the presence of complementary sequences in a given sample. However, other uses are also encompassed by the invention, such as the use of the sequence information for the preparation of mutant species primers, or primers for use in preparing other genetic constructions. As such, nucleic acid segments of the invention that include a sequence region of at least about 15 nucleotide long contiguous sequence that has the same sequence as, or is complementary to, a 15 nucleotide long contiguous sequence disclosed herein is particularly useful. Longer contiguous identical or complementary sequences, e.g., those of about 20, 30, 40, 50, 100, 200, 500, 1000 (including all intermediate lengths) including full length sequences, and all lengths in between, are also used in certain embodiments.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting, and/or primers for use in, e.g., polymerase chain reaction (PCR). The total size of fragment, as well as the size of the complementary stretch(es), ultimately depends on the intended use or application of the particular nucleic acid segment. Smaller fragments are generally used in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 12 bases in length are generally preferred, though, in order to increase stability and selectivity of the hybrid, and thereby improve the quality and degree of specific hybrid molecules obtained. Nucleic acid molecules having gene-complementary stretches of 15 to 25 contiguous nucleotides, or even longer where desired, are generally preferred.

Hybridization probes are selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences is governed by various factors. For example, one may wish to employ primers from towards the termini of the total sequence.

Polynucleotide of the present invention, or fragments or variants thereof, are readily prepared by, for example, directly synthesizing the fragment by chemical means, as is commonly practiced using an automated oligonucleotide synthesizer. Also, fragments are obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology.

Vectors, Host Cells and Recombinant Methods

The invention provides vectors and host cells comprising a nucleic acid of the present invention, as well as recombinant techniques for the production of a polypeptide of the present invention. Vectors of the invention include those capable of replication in any type of cell or organism, including, e.g., plasmids, phage, cosmids, and mini chromosomes. In various embodiments, vectors comprising a polynucleotide of the present invention are vectors suitable for propagation or replication of the polynucleotide, or vectors suitable for expressing a polypeptide of the present invention. Such vectors are known in the art and commercially available.

Polynucleotides of the present invention are synthesized, whole or in parts that are then combined, and inserted into a vector using routine molecular and cell biology techniques, including, e.g., subcloning the polynucleotide into a linearized vector using appropriate restriction sites and restriction enzymes. Polynucleotides of the present invention are amplified by polymerase chain reaction using oligonucleotide primers complementary to each strand of the polynucleotide. These primers also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the present invention, the nucleotide sequences encoding the polypeptide, or functional equivalents, are inserted into an appropriate expression vector, i.e., a vector that contains the necessary elements for the transcription and translation of the inserted coding sequence. Methods well known to those skilled in the art are used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems are utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. Within one embodiment, the variable regions of a gene expressing a monoclonal antibody of interest are amplified from a hybridoma cell using nucleotide primers. These primers are synthesized by one of ordinary skill in the art, or may be purchased from commercially available sources (see, e.g., Stratagene (La Jolla, Calif.), which sells primers for amplifying mouse and human variable regions. The primers are used to amplify heavy or light chain variable regions, which are then inserted into vectors such as ImmunoZAP™H or ImmunoZAP™L (Stratagene), respectively. These vectors are then introduced into *E. coli*, yeast, or mammalian-based systems for expression. Large amounts of a single-chain protein containing a fusion of the $V_H$ and $V_L$ domains are produced using these methods (see Bird et al., *Science* 242:423-426 (1988)).

The "control elements" or "regulatory sequences" present in an expression vector are those non-translated regions of the vector, e.g., enhancers, promoters, 5' and 3' untranslated regions, that interact with host cellular proteins to carry out transcription and translation. Such elements may vary in their strength and specificity. Depending on the vector system and host utilized, any number of suitable transcription and translation elements, including constitutive and inducible promoters, are used.

Examples of promoters suitable for use with prokaryotic hosts include the phoa promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also usually contain a Shine-Dalgarno sequence operably linked to the DNA encoding the polypeptide. Inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like are used.

A variety of promoter sequences are known for eukaryotes and any are used according to the present invention. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

In mammalian cell systems, promoters from mammalian genes or from mammalian viruses are generally preferred. Polypeptide expression from vectors in mammalian host cells are controlled, for example, by promoters obtained from the genomes of viruses such as polyoma virus, fowlpox virus, adenovirus (e.g., Adenovirus 2), bovine papilloma virus, avian sarcoma virus, cytomegalovirus (CMV), a retrovirus, hepatitis-B virus and most preferably Simian Virus 40

(SV40), from heterologous mammalian promoters, e.g., the actin promoter or an immunoglobulin promoter, and from heat-shock promoters, provided such promoters are compatible with the host cell systems. If it is necessary to generate a cell line that contains multiple copies of the sequence encoding a polypeptide, vectors based on SV40 or EBV may be advantageously used with an appropriate selectable marker. One example of a suitable expression vector is pcDNA-3.1 (Invitrogen, Carlsbad, Calif.), which includes a CMV promoter.

A number of viral-based expression systems are available for mammalian expression of polypeptides. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

In bacterial systems, any of a number of expression vectors are selected depending upon the use intended for the expressed polypeptide. For example, when large quantities are desired, vectors that direct high level expression of fusion proteins that are readily purified are used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase, so that a hybrid protein is produced; pIN vectors (Van Heeke, G. and S. M. Schuster (1989) J. Biol. Chem. 264:5503-5509); and the like. pGEX Vectors (Promega, Madison, Wis.) are also used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH are used. Examples of other suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. For reviews, see Ausubel et al. (supra) and Grant et al. (1987) Methods Enzymol. 153:516-544. Other yeast promoters that are inducible promoters having the additional advantage of transcription controlled by growth conditions include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

In cases where plant expression vectors are used, the expression of sequences encoding polypeptides are driven by any of a number of promoters. For example, viral promoters such as the 35S and 19S promoters of CaMV are used alone or in combination with the omega leader sequence from TMV (Takamatsu, N. (1987) *EMBO J.* 6:307-311. Alternatively, plant promoters such as the small subunit of RUBISCO or heat shock promoters are used (Coruzzi, G. et al. (1984) EMBO J. 3:1671-1680; Broglie, R. et al. (1984) Science 224:838-843; and Winter, J., et al. (1991) Results Probl. Cell Differ. 17:85-105). These constructs can be introduced into plant cells by direct DNA transformation or pathogen-mediated transfection. Such techniques are described in a number of generally available reviews (see, e.g., Hobbs, S. or Murry, L. E. in McGraw Hill Yearbook of Science and Technology (1992) McGraw Hill, New York, N.Y.; pp. 191-196).

An insect system is also used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide are cloned into a non-essential region of the virus, such as the polyhedrin gene, and placed under control of the polyhedrin promoter. Successful insertion of the polypeptide-encoding sequence renders the polyhedrin gene inactive and produce recombinant virus lacking coat protein. The recombinant viruses are then used to infect, for example, *S. frugiperda* cells or *Trichoplusia* larvae, in which the polypeptide of interest is expressed (Engelhard, E. K. et al. (1994) Proc. Natl. Acad. Sci. 91:3224-3227).

Specific initiation signals are also used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon are provided. Furthermore, the initiation codon is in the correct reading frame to ensure correct translation of the inserted polynucleotide. Exogenous translational elements and initiation codons are of various origins, both natural and synthetic.

Transcription of a DNA encoding a polypeptide of the invention is often increased by inserting an enhancer sequence into the vector. Many enhancer sequences are known, including, e.g., those identified in genes encoding globin, elastase, albumin, α-fetoprotein, and insulin. Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer is spliced into the vector at a position 5' or 3' to the polypeptide-encoding sequence, but is preferably located at a site 5' from the promoter.

Expression vectors used in eukaryotic host cells (yeast, fungi, insect, plant, animal, human, or nucleated cells from other multicellular organisms) typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-PSCA antibody. One useful transcription termination component is the bovine growth hormone polyadenylation region. See WO94/11026 and the expression vector disclosed therein.

Suitable host cells for cloning or expressing the DNA in the vectors herein are the prokaryote, yeast, plant or higher eukaryote cells described above. Examples of suitable prokaryotes for this purpose include eubacteria, such as Gram-negative or Gram-positive organisms, for example, *Enterobacteriaceae* such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

*Saccharomyces cerevisiae*, or common baker's yeast, is the most commonly used among lower eukaryotic host microorganisms. However, a number of other genera, species, and strains are commonly available and used herein, such as *Schizosaccharomyces pombe*; *Kluyveromyces* hosts such as, e.g., *K lactis, K. fragilis* (ATCC 12,424), *K. bulgaricus* (ATCC 16,045), *K wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris.* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

In certain embodiments, a host cell strain is chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing that cleaves a "prepro" form of the protein is also used to facilitate correct insertion, folding and/or function. Different host cells such as CHO, COS, HeLa, MDCK, HEK293, and WI38, which have specific cellular machinery and characteristic mechanisms for such post-translational activities, are chosen to ensure the correct modification and processing of the foreign protein.

Methods and reagents specifically adapted for the expression of antibodies or fragments thereof are also known and available in the art, including those described, e.g., in U.S. Pat. Nos. 4,816,567 and 6,331,415. In various embodiments, antibody heavy and light chains, or fragments thereof, are expressed from the same or separate expression vectors. In one embodiment, both chains are expressed in the same cell, thereby facilitating the formation of a functional antibody or fragment thereof.

Full length antibody, antibody fragments, and antibody fusion proteins are produced in bacteria, in particular when glycosylation and Fc effector function are not needed, such as when the therapeutic antibody is conjugated to a cytotoxic agent (e.g., a toxin) and the immunoconjugate by itself shows effectiveness in infected cell destruction. For expression of antibody fragments and polypeptides in bacteria, see, e.g., U.S. Pat. Nos. 5,648,237, 5,789,199, and 5,840,523, which describes translation initiation region (TIR) and signal sequences for optimizing expression and secretion. After expression, the antibody is isolated from the *E. coli* cell paste in a soluble fraction and can be purified through, e.g., a protein A or G column depending on the isotype. Final purification can be carried out using a process similar to that used for purifying antibody expressed e.g., in CHO cells.

Suitable host cells for the expression of glycosylated polypeptides and antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopicius* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses are used as the virus herein according to the present invention, particularly for transfection of *Spodoptera frugiperda* cells. Plant cell cultures of cotton, corn, potato, soybean, petunia, tomato, and tobacco are also utilized as hosts.

Methods of propagation of antibody polypeptides and fragments thereof in vertebrate cells in culture (tissue culture) are encompassed by the invention. Examples of mammalian host cell lines used in the methods of the invention are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

For long-term, high-yield production of recombinant proteins, stable expression is generally preferred. For example, cell lines that stably express a polynucleotide of interest are transformed using expression vectors that contain viral origins of replication and/or endogenous expression elements and a selectable marker gene on the same or on a separate vector. Following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells are proliferated using tissue culture techniques appropriate to the cell type.

A plurality of selection systems are used to recover transformed cell lines. These include, but are not limited to, the herpes simplex virus thymidine kinase (Wigler, M. et al. (1977) *Cell* 1:223-32) and adenine phosphoribosyltransferase (Lowy, I. et al. (1990) *Cell* 22:817-23) genes that are employed in tk⁻ or aprt⁻ cells, respectively. Also, antimetabolite, antibiotic or herbicide resistance is used as the basis for selection; for example, dhfr, which confers resistance to methotrexate (Wigler, M. et al. (1980) Proc. Natl. Acad. Sci. 77:3567-70); npt, which confers resistance to the aminoglycosides, neomycin and G-418 (Colbere-Garapin, F. et al. (1981) J. Mol. Biol. 150:1-14); and als or pat, which confer resistance to chlorsulfuron and phosphinotricin acetyltransferase, respectively (Murry, supra). Additional selectable genes have been described. For example, trpB allows cells to utilize indole in place of tryptophan, and hisD allows cells to utilize histinol in place of histidine (Hartman, S. C. and R. C. Mulligan (1988) Proc. Natl. Acad. Sci. 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Although the presence/absence of marker gene expression suggests that the gene of interest is also present, its presence and expression is confirmed. For example, if the sequence encoding a polypeptide is inserted within a marker gene sequence, recombinant cells containing sequences are identified by the absence of marker gene function. Alternatively, a marker gene is placed in tandem with a polypeptide-encoding sequence under the control of a single promoter. Expression of the marker gene in response to induction or selection usually indicates expression of the tandem gene as well. Alternatively, host cells that contain and express a desired polynucleotide sequence are identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Nonlimiting examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide is preferred for some applications, but a competitive binding assay may also be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211-1216).

Various labels and conjugation techniques are known by those skilled in the art and are used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof are cloned into a vector for the production of an mRNA probe. Such vectors are known in the art, are commercially available, and are used to synthesize RNA probes in vitro by addition of an appropriate RNA polymerase such as T7, T3, or SP6 and labeled nucleotides. These procedures are conducted using a variety of commercially available kits. Suitable reporter molecules or labels, which are used include, but are not limited to, radionuclides, enzymes, fluorescent, chemiluminescent, or chromogenic agents as well as substrates, cofactors, inhibitors, magnetic particles, and the like.

The polypeptide produced by a recombinant cell is secreted or contained intracellularly depending on the sequence and/or the vector used. Expression vectors containing polynucleotides of the invention are designed to contain signal sequences that direct secretion of the encoded polypeptide through a prokaryotic or eukaryotic cell membrane.

In certain embodiments, a polypeptide of the invention is produced as a fusion polypeptide further including a polypeptide domain that facilitates purification of soluble proteins. Such purification-facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Amgen, Seattle, Wash.). The inclusion of cleavable linker sequences such as those specific for Factor XA or enterokinase (Invitrogen. San Diego, Calif.) between the purification domain and the encoded polypeptide are used to facilitate purification. An exemplary expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263-281) while the enterokinase cleavage site provides a means for purifying the desired polypeptide from the fusion protein. A discussion of vectors used for producing fusion proteins is provided in Kroll, D. J. et al. (1993; DNA Cell Biol. 12:441-453).

In certain embodiments, a polypeptide of the present invention is fused with a heterologous polypeptide, which may be a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells, the signal sequence is selected, for example, from the group of the alkaline phosphatase, penicillinase, 1pp, or heat-stable enterotoxin II leaders. For yeast secretion, the signal sequence is selected from, e.g., the yeast invertase leader, α factor leader (including Saccharomyces and Kluyveromyces a factor leaders), or acid phosphatase leader, the C. albicans glucoamylase leader, or the signal described in WO 90/13646. In mammalian cell expression, mammalian signal sequences as well as viral secretory leaders, for example, the herpes simplex gD signal, are available.

When using recombinant techniques, the polypeptide or antibody is produced intracellularly, in the periplasmic space, or directly secreted into the medium. If the polypeptide or antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 min. Cell debris is removed by centrifugation. Where the polypeptide or antibody is secreted into the medium, supernatants from such expression systems are generally first concentrated using a commercially available protein concentration filter, for example, an Amicon or Millipore Pellicon ultrafiltration unit. Optionally, a protease inhibitor such as PMSF is included in any of the foregoing steps to inhibit proteolysis and antibiotics is included to prevent the growth of adventitious contaminants.

The polypeptide or antibody composition prepared from the cells are purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the polypeptide or antibody. Protein A is used to purify antibodies or fragments thereof that are based on human $\gamma_1$, $\gamma_2$, or $\gamma_4$ heavy chains (Lindmark et al., J. Immunol. Meth. 62:1-13 (1983)). Protein G is recommended for all mouse isotypes and for human $\gamma_3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the polypeptide or antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the polypeptide or antibody to be recovered. Following any preliminary purification step(s), the mixture comprising the polypeptide or antibody of interest and contaminants are subjected to low pH hydrophobic interaction chromatography using an elution buffer at a pH between about 2.5-4.5, preferably performed at low salt concentrations (e.g., from about 0-0.25M salt).

Pharmaceutical Compositions

The invention further includes pharmaceutical formulations including a polypeptide, antibody, or modulator of the present invention, at a desired degree of purity, and a pharmaceutically acceptable carrier, excipient, or stabilizer (Remington's Pharmaceutical Sciences 16th edition, Osol, A. Ed. (1980)). In certain embodiments, pharmaceutical formulations are prepared to enhance the stability of the polypeptide or antibody during storage, e.g., in the form of lyophilized formulations or aqueous solutions. Acceptable carriers, excipients, or stabilizers are nontoxic to recipients at the dosages and concentrations employed, and include, e.g., buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). In certain embodiments, the therapeutic formulation preferably comprises the polypeptide or antibody at a concentration of between 5-200 mg/ml, preferably between 10-100 mg/ml.

The formulations herein also contain one or more additional therapeutic agents suitable for the treatment of the particular indication, e.g., infection being treated, or to prevent undesired side-effects. Preferably, the additional therapeutic agent has an activity complementary to the polypeptide or antibody of the resent invention, and the two do not adversely affect each other. For example, in addition to the polypeptide or antibody of the invention, an additional or second antibody, anti-viral agent, anti-infective agent and/or cardioprotectant is added to the formulation. Such molecules are suitably present in the pharmaceutical formulation in amounts that are effective for the purpose intended.

The active ingredients, e.g., polypeptides and antibodies of the invention and other therapeutic agents, are also entrapped in microcapsules prepared, for example, by coacervation techniques or by interfacial polymerization, for example, hydroxymethylcellulose or gelatin-microcapsules and polymethylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations are prepared. Suitable examples of sustained-release preparations include, but are not limited to, semi-permeable matrices of solid hydrophobic polymers containing the antibody, which matrices are in the form of shaped articles, e.g., films, or microcapsules. Non-limiting examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and $\gamma$ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxyburyric acid.

Formulations to be used for in vivo administration are preferably sterile. This is readily accomplished by filtration through sterile filtration membranes.

Diagnostic Uses

Antibodies and fragments thereof, and therapeutic compositions, of the invention specifically bind or preferentially bind to infected cells or tissue, as compared to normal control cells and tissue. Thus, these influenza A antibodies are used to detect infected cells or tissues in a patient, biological sample, or cell population, using any of a variety of diagnostic and prognostic methods, including those described herein. The ability of an anti-M2e specific antibody to detect infected cells depends upon its binding specificity, which is readily determined by testing its ability to bind to infected cells or tissues obtained from different patients, and/or from patients infected with different strains of Influenza A. Diagnostic methods generally involve contacting a biological sample obtained from a patient, such as, e.g., blood, serum, saliva, urine, sputum, a cell swab sample, or a tissue biopsy, with an Influenza A, e.g., HuM2e antibody and determining whether the antibody preferentially binds to the sample as compared to a control sample or predetermined cut-off value, thereby indicating the presence of infected cells. In particular embodiments, at least two-fold, three-fold, or five-fold more HuM2e antibody binds to an infected cell as compared to an appropriate control normal cell or tissue sample. A pre-determined cut-off value is determined, e.g., by averaging the amount of HuM2e antibody that binds to several different appropriate control samples under the same conditions used to perform the diagnostic assay of the biological sample being tested.

Bound antibody is detected using procedures described herein and known in the art. In certain embodiments, diagnostic methods of the invention are practiced using HuM2e antibodies that are conjugated to a detectable label, e.g., a fluorophore, to facilitate detection of bound antibody. However, they are also practiced using methods of secondary detection of the HuM2e antibody. These include, for example, RIA, ELISA, precipitation, agglutination, complement fixation and immuno-fluorescence.

In certain procedures, the HuM2e antibodies are labeled. The label is detected directly. Exemplary labels that are detected directly include, but are not limited to, radiolabels and fluorochromes. Alternatively, or in addition, labels are moieties, such as enzymes, that must be reacted or derivatized to be detected. Nonlimiting examples of isotope labels are $^{99}$Tc, $^{14}$C, $^{131}$I, $^{125}$I, $^{3}$H, $^{32}$P and $^{35}$S. Fluorescent materials that are used include, but are not limited to, for example, fluorescein and its derivatives, rhodamine and its derivatives, auramine, dansyl, umbelliferone, luciferia, 2,3-dihydrophthalazinediones, horseradish peroxidase, alkaline phosphatase, lysozyme, and glucose-6-phosphate dehydrogenase.

An enzyme label is detected by any of the currently utilized colorimetric, spectrophotometric, fluorospectro-photometric or gasometric techniques. Many enzymes which are used in these procedures are known and utilized by the methods of the invention. Nonlimiting examples are peroxidase, alkaline phosphatase, β-glucuronidase, β-D-glucosidase, β-D-galactosidase, urease, glucose oxidase plus peroxidase, galactose oxidase plus peroxidase and acid phosphatase.

The antibodies are tagged with such labels by known methods. For instance, coupling agents such as aldehydes, carbodiimides, dimaleimide, imidates, succinimides, bid-diazotized benzadine and the like are used to tag the antibodies with the above-described fluorescent, chemiluminescent, and enzyme labels. An enzyme is typically combined with an antibody using bridging molecules such as carbodiimides, periodate, diisocyanates, glutaraldehyde and the like. Various labeling techniques are described in Morrison, Methods in Enzymology 32b, 103 (1974), Syvanen et al., J. Biol. Chem. 284, 3762 (1973) and Bolton and Hunter, Biochem J. 133, 529(1973).

HuM2e antibodies of the present invention are capable of differentiating between patients with and patients without an Influenza A infection, and determining whether or not a patient has an infection, using the representative assays provided herein. According to one method, a biological sample is obtained from a patient suspected of having or known to have an Influenza A infection. In preferred embodiments, the biological sample includes cells from the patient. The sample is contacted with an HuM2e antibody, e.g., for a time and under conditions sufficient to allow the HuM2e antibody to bind to infected cells present in the sample. For instance, the sample is contacted with an HuM2e antibody for 10 seconds, 30 seconds, 1 minute, 5 minutes, 10 minutes, 30 minutes, 1 hour, 6 hours, 12 hours, 24 hours, 3 days or any point in between. The amount of bound HuM2e antibody is determined and compared to a control value, which may be, e.g., a pre-determined value or a value determined from normal tissue sample. An increased amount of antibody bound to the patient sample as compared to the control sample is indicative of the presence of infected cells in the patient sample.

In a related method, a biological sample obtained from a patient is contacted with an HuM2e antibody for a time and under conditions sufficient to allow the antibody to bind to infected cells. Bound antibody is then detected, and the presence of bound antibody indicates that the sample contains infected cells. This embodiment is particularly useful when the HuM2e antibody does not bind normal cells at a detectable level. Different HuM2e antibodies possess different binding and specificity characteristics. Depending upon these characteristics, particular HuM2e antibodies are used to detect the presence of one or more strains of Influenza A. For example, certain antibodies bind specifically to only one or several strains of Influenza virus, whereas others bind to all or a majority of different strains of Influenza virus. Antibodies specific for only one strain of Influenza A are used to identify the strain of an infection.

In certain embodiments, antibodies that bind to an infected cell preferably generate a signal indicating the presence of an infection in at least about 20% of patients with the infection being detected, more preferably at least about 30% of patients. Alternatively, or in addition, the antibody generates a negative signal indicating the absence of the infection in at least about 90% of individuals without the infection being detected. Each antibody satisfies the above criteria; however, antibodies of the present invention are used in combination to improve sensitivity.

The present invention also includes kits useful in performing diagnostic and prognostic assays using the antibodies of the present invention. Kits of the invention include a suitable container comprising a HuM2e antibody of the invention in either labeled or unlabeled form. In addition, when the antibody is supplied in a labeled form suitable for an indirect binding assay, the kit further includes reagents for performing the appropriate indirect assay. For example, the kit includes one or more suitable containers including enzyme substrates or derivatizing agents, depending on the nature of the label. Control samples and/or instructions are also included.

Therapeutic/Prophylactic Uses

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using human monoclonal antibodies provide an immediate treatment strategy for emergency prophylaxis and treatment of influenza HuM2e antibodies and fragments thereof, and therapeutic compositions, of the invention specifically bind or preferentially bind to infected cells, as compared to normal control uninfected cells and tissue. Thus, these HuM2e antibodies are used to selectively target infected cells or tissues in a patient, biological sample, or cell population. In light of the infection-specific binding properties of these antibodies, the present invention provides methods of regulating (e.g., inhibiting) the growth of infected cells, methods of killing infected cells, and methods of inducing apoptosis of infected cells. These methods include contacting an infected cell with an HuM2e antibody of the invention. These methods are practiced in vitro, ex vivo, and in vivo.

In various embodiments, antibodies of the invention are intrinsically therapeutically active. Alternatively, or in addition, antibodies of the invention are conjugated to a cytotoxic agent or growth inhibitory agent, e.g., a radioisotope or toxin, that is used in treating infected cells bound or contacted by the antibody.

In one embodiment, the invention provides methods of treating or preventing infection in a patient, including the steps of providing an HuM2e antibody of the invention to a patient diagnosed with, at risk of developing, or suspected of having an Influenza A infection. The methods of the invention are used in the first-line treatment of the infection, follow-on treatment, or in the treatment of a relapsed or refractory infection. Treatment with an antibody of the invention is a stand alone treatment. Alternatively, treatment with an antibody of the invention is one component or phase of a combination therapy regime, in which one or more additional therapeutic agents are also used to treat the patient.

Subjects at risk for an influenza virus-related diseases or disorders include patients who have come into contact with an infected person or who have been exposed to the influenza virus in some other way. Administration of a prophylactic agent can occur prior to the manifestation of symptoms characteristic of the influenza virus-related disease or disorder, such that a disease or disorder is prevented or, alternatively, delayed in its progression.

In various aspects, the huM2e is administered substantially contemporaneously with or following infection of the subject, i.e., therapeutic treatment. In another aspect, the antibody provides a therapeutic benefit. In various aspects, a therapeutic benefit includes reducing or decreasing progression, severity, frequency, duration or probability of one or more symptoms or complications of influenza infection, virus titer, virus replication or an amount of a viral protein of one or more influenza strains. still another aspect, a therapeutic benefit includes hastening or accelerating a subject's recovery from influenza infection.

Methods for preventing an increase in influenza virus titer, virus replication, virus proliferation or an amount of an influenza viral protein in a subject are further provided. In one embodiment, a method includes administering to the subject an amount of a huM2e antibody effective to prevent an increase in influenza virus titer, virus replication or an amount of an influenza viral protein of one or more influenza strains or isolates in the subject.

Methods for protecting a subject from infection or decreasing susceptibility of a subject to infection by one or more influenza strains/isolates or subtypes, i.e., prophylactic methods, are additionally provided. In one embodiment, a method includes administering to the subject an amount of huM2e antibody that specifically binds influenza M2 effective to protect the subject from infection, or effective to decrease susceptibility of the subject to infection, by one or more influenza strains/isolates or subtypes.

Optionally, the subject is further administered with a second agent such as, but not limited to, an influenza virus antibody, an anti-viral drug such as a neuraminidase inhibitor, a HA inhibitor, a sialic acid inhibitor or an M2 ion channel inhibitor, a viral entry inhibitor or a viral attachment inhibitor. The M2 ion channel inhibitor is for example amantadine or rimantadine. The neuraminidase inhibitor for example zanamivir, or oseltamivir phosphate.

Symptoms or complications of influenza infection that can be reduced or decreased include, for example, chills, fever, cough, sore throat, nasal congestion, sinus congestion, nasal infection, sinus infection, body ache, head ache, fatigue, pneumonia, bronchitis, ear infection, ear ache or death.

For in vivo treatment of human and non-human patients, the patient is usually administered or provided a pharmaceutical formulation including a HuM2e antibody of the invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies may be administered parenterally, when possible, at the target cell site, or intravenously. Intravenous or subcutaneous administration of the antibody is preferred in certain embodiments. Therapeutic compositions of the invention are administered to a patient or subject systemically, parenterally, or locally.

For parenteral administration, the antibodies are formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate are also used. Liposomes are used as carriers. The vehicle contains minor amounts of additives such as substances that enhance isotonicity and chemical stability, e.g., buffers and preservatives. The antibodies are typically formulated in such vehicles at concentrations of about 1 mg/ml to 10 mg/ml.

The dose and dosage regimen depends upon a variety of factors readily determined by a physician, such as the nature of the infection and the characteristics of the particular cytotoxic agent or growth inhibitory agent conjugated to the antibody (when used), e.g., its therapeutic index, the patient, and the patient's history. Generally, a therapeutically effective amount of an antibody is administered to a patient. In particular embodiments, the amount of antibody administered is in the range of about 0.1 mg/kg to about 50 mg/kg of patient body weight. Depending on the type and severity of the infection, about 0.1 mg/kg to about 50 mg/kg body weight (e.g., about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art.

In one particular embodiment, an immunoconjugate including the antibody conjugated with a cytotoxic agent is administered to the patient. Preferably, the immunoconjugate is internalized by the cell, resulting in increased therapeutic efficacy of the immunoconjugate in killing the cell to which it binds. In one embodiment, the cytotoxic agent targets or interferes with the nucleic acid in the infected cell. Examples of such cytotoxic agents are described above and include, but are not limited to, maytansinoids, calicheamicins, ribonucleases and DNA endonucleases.

Other therapeutic regimens are combined with the administration of the HuM2e antibody of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

In certain embodiments, it is desirable to combine administration of an antibody of the invention with another antibody directed against another antigen associated with the infectious agent.

Aside from administration of the antibody protein to the patient, the invention provides methods of administration of the antibody by gene therapy. Such administration of nucleic acid encoding the antibody is encompassed by the expression "administering a therapeutically effective amount of an antibody". See, for example, PCT Patent Application Publication WO96/07321 concerning the use of gene therapy to generate intracellular antibodies.

In another embodiment, anti-M2e antibodies of the invention are used to determine the structure of bound antigen, e.g., conformational epitopes, the structure of which is then used to develop a vaccine having or mimicking this structure, e.g., through chemical modeling and SAR methods. Such a vaccine could then be used to prevent Influenza A infection.

All of the above U.S. patents, U.S. patent, application publications, U.S. patent applications, foreign patents, foreign patent applications and non-patent publications referred to in this specification and/or listed in the Application Data Sheet are incorporated herein by reference, in their entirety.

EXAMPLES

Example 1

Screening and Characterization of M2e-Specific Antibodies Present in Human Plasma Using Cells Expressing Recombinant M2e Protein Fully human monoclonal antibodies specific for M2 and capable of binding to influenza A infected cells and the influenza virus itself were identified in patient serum, as described below.

Expression of M2 in Cell Lines

An expression construct containing the M2 full length cDNA, corresponding to the derived M2 sequence found in Influenza subtype H3N2, was transfected into 293 cells.

The M2 cDNA is encoded by the following polynucleotide sequence and SEQ ID NO: 53:

```
ATGAGTCTTCTAACCGAGGTCGAAACGCCTATCAGAAACGAATGGGGGTG

CAGATGCAACGATTCAAGTGATCCTCTTGTTGTTGCCGCAAGTATCATTG

GGATCCTGCACTTGATATTGTGGATTCTTGATCGTCTTTTTTTCAAATGC

ATTTATCGTCTCTTTAAACACGGTCTGAAAAGAGGGCCTTCTACGGAAGG

AGTACCAGAGTCTATGAGGGAAGAATATCGAAAGGAACAGCAGAGTGCTG

TGGATGCTGACGATAGTCATTTTGTCAACATAGAGCTGGAG
```

The cell surface expression of M2 was confirmed using the anti-M2e peptide specific MAb 14C2. Two other variants of M2, from A/Hong Kong/483/1997 (HK483) and A/Vietnam/1203/2004 (VN1203), were used for subsequent analyses, and their expression was determined using M2e-specific monoclonal antibodies of the present invention, since 14C2 binding may be abrogated by the various amino acid substitutions in M2e.

Screening of Antibodies in Peripheral Blood

Over 120 individual plasma samples were tested for antibodies that bound M2. None of them exhibited specific binding to the M2e peptide. However, 10% of the plasma samples contained antibodies that bound specifically to the 293-M2 H3N2 cell line. This indicates that the antibodies could be categorized as binding to conformational determinants of an M2 homotetramer, and binding to conformational determinants of multiple variants of the M2 homotetramer; they could not be specific for the linear M2e peptide.

Characterization of Anti-M2 MAbs

The human MAbs identified through this process proved to bind to conformational epitopes on the M2 homotetramer. They bound to the original 293-M2 transfectant, as well as to the two other cell-expressed M2 variants. The 14C2 MAb, in addition to binding the M2e peptide, proved to be more sensitive to the M2 variant sequences. Moreover, 14C2 does not readily bind influenza virions, while the conformation specific anti-M2 MAbs did.

These results demonstrate that the methods of the invention provide for the identification of M2 MAbs from normal human immune responses to influenza without a need for specific immunization of M2. If used for immunotherapy, these fully human MAbs have the potential to be better tolerated by patients that humanized mouse antibodies. Additionally, and in contrast to 14C2 and the Gemini Biosciences MAbs, which bind to linear M2e peptide, the MAbs of the invention bind to conformational epitopes of M2, and are specific not only for cells infected with A strain influenza, but also for the virus itself. Another advantage of the MAbs of the invention is that they each bind all of the M2 variants yet tested, indicating that they are not restricted to a specific linear amino acid sequence.

Example 2

Identification of M2-Specific Antibodies

Mononuclear or B cells expressing three of the MAbs identified in human serum as described in Example 1 were diluted into clonal populations and induced to produce antibodies. Antibody containing supernatants were screened for binding to 293 FT cells stably transfected with the full length M2E protein from influenza strain Influenza subtype H3N2. Supernatants which showed positive staining/binding were re-screened again on 293 FT cells stably transfected with the full length M2E protein from influenza strain Influenza subtype H3N2 and on vector alone transfected cells as a control.

The variable regions of the antibodies were then rescue cloned from the B cell wells whose supernatants showed positive binding. Transient transfections were performed in 293 FT cells to reconstitute and produce these antibodies. Reconstituted antibody supernatants were screened for binding to 293 FT cells stably transfected with the full length M2E protein as detailed above to identify the rescued anti-M2E antibodies. Three different antibodies were identified: 8i10, 21B15 and 23K12. A fourth additional antibody clone was isolated by the rescue screens, 4C2. However, it was not unique and had the exact same sequence as clone 8i10 even though it came from a different donor than clone 8i10.

The sequences of the kappa and gamma variable regions of these antibodies are provided below.

Clone 8i10 (Corresponds to TCN-032):

The Kappa LC variable region of the anti M2 clone 8i10 was cloned as Hind III to BsiW1 fragment (see below), and is encoded by the following polynucleotide sequences, and SEQ ID NO: 54 (top) and SEQ ID NO: 55 (bottom):

```
HindIII
AAGCTTCCACCATGGACATGAGGGTCCTCGCTCAGCTCCTGGGGCTCCTGCTACTCTGGCTCCGAGGT G

TTCGAAGGTGGTACCCTGTACTCCCAGGAGCGAGTCGAGGACCCCGAGGACGATGAGACCGAGGCTCCA C

CCAGATGTGACATCCAGATGACCCAGTCTCCATCCTCCCTGTCTGCATCTGTAGGAGACAGAGTCACC A
```

-continued

```
GGTCTACACTGTAGGTCTACTGGGTCAGAGGTAGGAGGGACAGACGTAGACATCCTCTGTCTCAGTGG T

TCACTTGCCGGGCGAGTCAGAACATTTACAAGTATTTAAATTGGTATCAGCAGAGACCAGGGAAAGCC C

AGTGAACGGCCCGCTCAGTCTTGTAAATGTTCATAAATTTAACCATAGTCGTCTCTGGTCCCTTTCGG G

CTAAGGGCCTGATCTCTGCTGCATCCGGGTTGCAAAGTGGGGTCCCATCAAGGTTCAGTGGCAGTGGA T

GATTCCCGGACTAGAGACGACGTAGGCCCAACGTTTCACCCCAGGGTAGTTCCAAGTCACCGTCACCT A

CTGGGACAGATTTCACTCTCACCATCACCAGTCTGCAACCTGAAGATTTTGCAACTTACTACTGTCAA C

GACCCTGTCTAAAGTGAGAGTGGTAGTGGTCAGACGTTGGACTTCTAAAACGTTGAATGATGACAGTT G

BsiWI
AGAGTTACAGTCCCCCTCTCACTTTCGGCGGAGGGACCAGGGTGGAGATCAAACGTACG

TCTCAATGTCAGGGGAGAGTGAAAGCCGCCTCCCTGGTCCCACCTCTAGTTTGCATGC
```

The translation of the 8i10 Kappa LC variable region is as follows, polynucleotide sequence (above, SEQ ID NO: 54, top) and amino acid sequence (below, corresponding to residues 1-131 of SEQ ID NO: 56):

```
HindIII
AAGCTTCCACCATGGACATGAGGGTCCTCGCTCAGCTCCTGGGGCTCCTGCTACTCTGGCTCCGAGGT G
           M   D   M   R   V   L   A   Q   L   L   G   L   L   L   L   W   L   R   G CCAGATGTGACATCCAGATGACCCAGTCTCCATCCTCCCTGTCTGCATCTGTAGGAGACAGAGTCACC A
A   R   C   D   I   Q   M   T   Q   S   P   S   S   L   S   A   S   V   G   D   R   V   T TCACTTGCCGGGCGAGTCAGAACATTTACAAGTATTTAAATTGGTATCAGCAGAGACCAGGGAAAGCC C
I   T   C   R   A   S   Q   N   I   Y   K   Y   L   N   W   Y   Q   Q   R   P   G   K   A CTAAGGGCCTGATCTCTGCTGCATCCGGGTTGCAAAGTGGGGTCCCATCAAGGTTCAGTGGCAGTGGA T
P   K   G   L   I   S   A   A   S   G   L   Q   S   G   V   P   S   R   F   S   G   S   G CTGGGACAGATTTCACTCTCACCATCACCAGTCTGCAACCTGAAGATTTTGCAACTTACTACTGTCAA C
S   G   T   D   F   T   L   T   I   T   S   L   Q   P   E   D   F   A   T   Y   Y   C   Q BsiWI
AGAGTTACAGTCCCCCTCTCACTTTCGGCGGAGGGACCAGGGTGGAGATCAAACGTACG
Q   S   Y   S   P   P   L   T   F   G   G   G   T   R   V   E   I   K   R   T
```

The amino acid sequence of the 8i10 Kappa LC variable region is as follows, with specific domains identified below (CDR sequences defined according to Kabat methods):

| Sequence | Domain | |
|---|---|---|
| M D M R V L A Q L L G L L L L W L R G A R C | VK leader | (SEQ ID NO: 57) |
| D I Q M T Q S P S S L S A S V G D R V T I T C | FR1 | (SEQ ID NO: 58) |
| R A S Q N I Y K Y L N | CDR1 | (SEQ ID NO: 59) |
| W Y Q Q R P G K A P K G L I S | FR2 | (SEQ ID NO: 60) |
| A A S G L Q S | CDR2 | (SEQ ID NO: 61) |
| G V P S R F S G S G S G T D F T L T I T S L Q P E D F A T Y Y C | FR3 | (SEQ ID NO: 62) |
| Q Q S Y S P P L T | CDR3 | (SEQ ID NO: 63) |
| F G G G T R V E I K | FR4 | (SEQ ID NO: 64) |
| R T | Start of Kappa constant region | |

The following is an example of the Kappa LC variable region of 8i10 cloned into the expression vector pcDNA3.1 which already contained the Kappa LC constant region (upper polynucleotide sequence corresponds to SEQ ID NO: 65, lower polynucleotide sequence corresponds to SEQ ID NO: 66, amino acid sequence corresponds to SEQ ID NO: 56). Bases in black represents pcDNA3.1 vector sequences, blue bases represent the cloned antibody sequences. The antibodies described herein have also been cloned into the expression vector pCEP4.

```
                         NheI(894)  PmeI(900)  HindIII(910)
TCGAAATTAATACGACTCACTATAGGGAGACCCAAGCTGGCTAGCGTTTAAACTTAAGCTTCCACCATGGACATGAGGGTCCTC
AGCTTTAATTATGCTGAGTGATATCCCTCTGGGTTCGACCGATCGCAAATTTGAATTCGAAGGTGGTACCTGTACTCCCAGGAG
                                                          ■   M   D   M   R   V   L GCTCAGCTCCTGGGGCTCCTGCTACTCTGGCTCCGAGGTGCCAGATGTGACATCCAGATGACCCAGTCT
CGAGTCGAGGACCCCGAGGACGATGAGACCGAGGCTCCACGGTCTACACTGTAGGTCTACTGGGTCAGA
■ A  Q  L  L  G  L  L  L  L  W  L  R  G  A  R  C  D  I  Q  M  T  Q  S CCATCCTCCCTGTCTGCATCTGTAGGAGACAGAGTCACCATCACTTGCCGGGCGAGTCAGAACATTTAC
GGTAGGAGGGACAGACGTAGACATCCTCTGTCTCAGTGGTAGTGAACGGCCCGCTCAGTCTTGTAAATG
■ P  S  S  L  S  A  S  V  G  D  R  V  T  I  T  C  R  A  S  Q  N  I  Y AAGTATTTAAATTGGTATCAGCAGAGACCAGGGAAAGCCCCTAAGGGCCTGATCTCTGCTGCATCCGGG
TTCATAAATTTAACCATAGTCGTCTCTGGTCCCTTTCGGGGATTCCCGGACTAGAGACGACGTAGGCCC
■ K  Y  L  N  W  Y  Q  Q  R  P  G  K  A  P  K  G  L  I  S  A  A  S  G TTGCAAAGTGGGGTCCCATCAAGGTTCAGTGGCAGTGGATCTGGGACAGATTTCACTCTCACCATCACC
AACGTTTCACCCCAGGGTAGTTCCAAGTCACCGTCACCTAGACCCTGTCTAAAGTGAGAGTGGTAGTGG
■ L  Q  S  G  V  P  S  R  F  S  G  S  G  S  G  T  D  F  T  L  T  I  T AGTCTGCAACCTGAAGATTTTGCAACTTACTACTGTCAACAGAGTTACAGTCCCCCTCTCACTTTCGGC
TCAGACGTTGGACTTCTAAAACGTTGAATGATGACAGTTGTCTCAATGTCAGGGGGAGAGTGAAAGCCG
■ S  L  Q  P  E  D  F  A  T  Y  Y  C  Q  Q  S  Y  S  P  P  L  T  F  G BsiWI
GGAGGGACCAGGGTGGAGATCAAACGTACGGTGGCTGCACCATCTGTCTTCATCTTCCCGCCATCTGATGAGCAGTTGAAATCTGG
CCTCCCTGGTCCCACCTCTAGTTTGCATGCCACCGACGTGGTAGACAGAAGTAGAAGGGCGGTAGACTACTCGTCAACTTTAGACC
■ G  G  T  R  V  E  I  K  R  T  V  A  A  P  S  V  F  I  F  P  P  S  D  E  Q  L  K  S  G hu Kappa constant
AACTGCCTCTGTTGTGTGCCTGCTGAATAACTTCTATCCCAGAGAGGCCAAAGTACAGTGGAAGGTGGATAACGCCCTCCAATCGGGTAACTCCC
TTGACGGAGACAACACACGGACGACTTATTGAAGATAGGGTCTCTCCGGTTTCATGTCACCTTCCACCTATTGCGGGAGGTTAGCCCATTGAGGG
   T  A  S  V  V  C  L  L  N  N  F  Y  P  R  E  A  K  V  Q  W  K  V  D  N  A  L  Q  S  G  N  S AGGAGAGTGTCACAGAGCAGGACAGCAAGGACAGCACCTACAGCCTCAGCAGCACCCTGACGCTGAGCAAAGCAGACTACGAGAAACACAAAGTC
TCCTCTCACAGTGTCTCGTCCTGTCGTTCCTGTCGTGGATGTCGGAGTCGTCGTGGGACTGCGACTCGTTTCGTCTGATGCTCTTTGTGTTTCAG
Q  E  S  V  T  E  Q  D  S  K  D  S  T  Y  S  L  S  S  T  L  T  L  S  K  A  D  Y  E  K  H  K  V DraII (1641)
                                                                           XbaI(1636)ApaI(1642)
TACGCCTGCGAAGTCACCCATCAGGGCCTGAGCTCGCCCGTCACAAAGAGCTTCAACAGGGGAGAGTGTTAGAGGGTCTAGAGGGCCCGTTTAAA
ATGCGGACGCTTCAGTGGGTAGTCCCGGACTCGAGCGGGCAGTGTTTCTCGAAGTTGTCCCCTCTCACAATCTCCCAGATCTCCCGGGCAAATTT
  Y  A  C  E  V  T  H  Q  G  L  S  S  P  V  T  K  S  F  N  R  G  E  C
```

The 8i10 Gamma HC variable region was cloned as a Hind III to Xho 1 fragment, and is encoded the following polynucleotide sequences, and SEQ ID NO: 67 (top) and SEQ ID NO: 68 (bottom).

```
HindIII
AAGCTTCCACCATGAAACACCTGTGGTTCTTCCTTCTCCTGGTGGCAGCTCCCAGCTGGG T

TTCGAAGGTGGTACTTTGTGGACACCAAGAAGGAAGAGGACCACCGTCGAGGGTCGACCC A

CCTGTCCCAGGTGCAATTGCAGGAGTCGGGCCCAGGACTGGTGAAGCCTTCGGAGACCCT G

GGACAGGGTCCACGTTAACGTCCTCAGCCCGGGTCCTGACCACTTCGGAAGCCTCTGGGA C

TCCCTCACCTGCACTGTCTCTGGTTCGTCCATCAGTAATTACTACTGGAGCTGGATCCGG C

AGGGAGTGGACGTGACAGAGACCAAGCAGGTAGTCATTAATGATGACCTCGACCTAGGCC G

AGTCCCCAGGGAAGGGACTGGAGTGGATTGGGTTTATCTATTACGGTGGAAACACCAAGT A

TCAGGGGTCCCTTCCCTGACCTCACCTAACCCAAATAGATAATGCCACCTTTGTGGTTCA T

CAATCCCTCCCTCAAGAGCCGCGTCACCATATCACAAGCACTTCCAAGAGTCAGGTCTC C

GTTAGGGAGGGAGTTCTCGGCGCAGTGGTATAGTGTTCTGTGAAGGTTCTCAGTCCAGAG G
```

```
                                                   -continued
CTGACGATGAGCTCTGTGACCGCTGCGGAATCGGCCGTCTATTTCTGTGCGAGAGCGTCT T

GACTGCTACTCGAGACACTGGCGACGCCTTAGCCGGCAGATAAAGACACGCTCTCGCAGA A

XhoI
GTAGTGGTGGTTACTGTATCCTTGACTACTGGGGCCAGGGAACCCTGGTCACCGTCTCGA G

CATCACCACCAATGACATAGGAACTGATGACCCCGGTCCCTTGGGACCAGTGGCAGAGCTC
```

The translation of the 8i10 Gamma HC is as follows, polynucleotide sequence (above, SEQ ID NO: 67, top) and amino acid sequence (below, corresponding to residues 1-138 of SEQ ID NO: 69):

```
HindIII
AAGCTTCCACCATGAAACACCTGTGGTTCTTCCTTCTCCTGGTGGCAGCTCCCAGCTGGGT C
            M  K  H  L  W  F  F  L  L  L  V  A  A  P  S  W  V CTGTCCCAGGTGCAATTGCAGGAGTCGGGCCCAGGACTGGTGAAGCCTTCGGAGACCCTG
 L  S  Q  V  Q  L  Q  E  S  G  P  G  L  V  K  P  S  E  T  L TCCCTCACCTGCACTGTCTCTGGTTCGTCCATCAGTAATTACTACTGGAGCTGGATCCGG
 S  L  T  C  T  V  S  G  S  S  I  S  N  Y  Y  W  S  W  I  R CAGTCCCCAGGGAAGGGACTGGAGTGGATTGGGTTTATCTATTACGGTGGAAACACCAAG
 Q  S  P  G  K  G  L  E  W  I  G  F  I  Y  Y  G  G  N  T  K TACAATCCCTCCCTCAAGAGCCGCGTCACCATATCACAAGACACTTCCAAGAGTCAGGTC
 Y  N  P  S  L  K  S  R  V  T  I  S  Q  D  T  S  K  S  Q  V TCCCTGACGATGAGCTCTGTGACCGCTGCGGAATCGGCCGTCTATTTCTGTGCGAGAGCG
 S  L  T  M  S  S  V  T  A  A  E  S  A  V  Y  F  C  A  R  A XhoI
TCTTGTAGTGGTGGTTACTGTATCCTTGACTACTGGGGCCAGGGAACCCTGGTCACCGTC
 S  C  S  G  G  Y  C  I  L  D  Y  W  G  Q  G  T  L  V  T  V

TCGAG
 S
```

The amino acid sequence of the 8i10 Gamma HC is as follows with specific domains identified below (CDR sequences defined according to Kabat methods):

| | | |
|---|---|---|
| M K H L W F F L L L V A A P S W V L S | VH leader | (SEQ ID NO: 70) |
| Q V Q L Q E S G P G L V K P S E T L S L T C T V S G S S I S | FR1 | (SEQ ID NO: 71) |
| N Y Y W S | CDR1 | (SEQ ID NO: 72) |
| W I R Q S P G K G L E W I G | FR2 | (SEQ ID NO: 73) |
| F I Y Y G G N T K Y N P S L K S | CDR2 | (SEQ ID NO: 74) |
| R V T I S Q D T S K S Q V S L T M S S V T A A E S A V Y F C A R | FR3 | (SEQ ID NO: 75) |
| A S C S G G Y C I L D | CDR3 | (SEQ ID NO: 76) |
| Y W G Q G T L V T V S | FR4 | (SEQ ID NO: 77) |
| YWGQGTLVTVSS | Long FR4 | (SEQ ID NO: 266) |

The following is an example of the Gamma HC variable region of 8i10 cloned into the expression vector pcDNA3.1 which already contained the Gamma HC constant region (upper polynucleotide sequence corresponds to SEQ ID NO: 78, lower polynucleotide sequence corresponds to SEQ ID NO: 79, amino acid sequence corresponds to SEQ ID NO: 69). Bases in black represents pcDNA3.1 vector sequences, blue bases represent the cloned antibody sequences.

```
                                                    PmeI(900)
                                    NheI(894)         HindIII(910)
        TGGCTTATCGAAATTAATACGACTCACTATAGGGAGACCCAAGCTGGCTAGCGTTTAAACTTAAGCTTCCACCATGAAACACCTGTGGTT
        ACCGAATAGCTTTAATTATGCTGAGTGATATCCCTCTGGGTTCGACCGATCGCAAATTTGAATTCGAAGGTGGTACTTTGTGGACACCAA
                                                                                      ■ M  K  H  L  W  F
```

```
                                                            -continued
CTTCCTTCTCCTGGTGGCAGCTCCCAGCTGGGTCCTGTCCCAGGTGCAATTGCAGGAGTCGGGCCCA
GAAGGAAGAGGACCACCGTCGAGGGTCGACCCAGGACAGGGTCCACGTTAACGTCCTCAGCCCGGGT
 ■ F  L  L  L  V  A  A  P  S  W  V  L  S  Q  V  Q  L  Q  E  S  G  P GGACTGGTGAAGCCTTCGGAGACCCTGTCCCTCACCTGCACTGTCTCTGGTTCGTCCATCAGTAATT
CCTGACCACTTCGGAAGCCTCTGGGACAGGGAGTGGACGTGACAGAGACCAAGCAGGTAGTCATTAA
 ■ G  L  V  K  P  S  E  T  L  S  L  T  C  T  V  S  G  S  S  I  S  N ACTACTGGAGCTGGATCCGGCAGTCCCCAGGGAAGGGACTGGAGTGGATTGGGTTTATCTATTACGG
TGATGACCTCGACCTAGGCCGTCAGGGGTCCCTTCCCTGACCTCACCTAACCCAAATAGATAATGCC
 ■ Y  Y  W  S  W  I  R  Q  S  P  G  K  G  L  E  W  I  G  F  I  Y  Y  G TGGAAACACCAAGTACAATCCCTCCCTCAAGAGCCGCGTCACCATATCACAAGACACTTCCAAGAGT
ACCTTTGTGGTTCATGTTAGGGAGGGAGTTCTCGGCGCAGTGGTATAGTGTTCTGTGAAGGTTCTCA
 ■ G  N  T  K  Y  N  P  S  L  K  S  R  V  T  I  S  Q  D  T  S  K  S CAGGTCTCCCTGACGATGAGCTCTGTGACCGCTGCGGAATCGGCCGTCTATTTCTGTGCGAGAGCGT
GTCCAGAGGGACTGCTACTCGAGACACTGGCGACGCCTTAGCCGGCAGATAAAGACACGCTCTCGCA
 ■ Q  V  S  L  T  M  S  S  V  T  A  A  E  S  A  V  Y  F  C  A  R  A XhoI(1331)
CTTGTAGTGGTGGTTACTGTATCCTTGACTACTGGGGCCAGGGAACCCTGGTCACCGTCTCGAGAGCCTCCA
GAACATCACCACCAATGACATAGGAACTGATGACCCCGGTCCCTTGGGACCAGTGGCAGAGCTCTCGGAGGT
 ■ S  C  S  G  G  Y  C  I  L  D  Y  W  G  Q  G  T  L  V  T  V  S  R  A  S CCAAGGGCCCATCGGTCTTCCCCCTGGCACCCTCCTCCAAGAGCACCTCTGGGGGCACAGCGGCCCTGGGCTGCCTGGTCAAGGACTAC
GGTTCCCGGGTAGCCAGAAGGGGGACCGTGGGAGGAGGTTCTCGTGGAGACCCCCGTGTCGCCGGGACCCGACGGACCAGTTCCTGATG
 ■ T  K  G  P  S  V  F  P  L  A  P  S  S  K  S  T  S  G  G  T  A  A  L  G  C  L  V  K  D  Y TTCCCCGAACCGGTGACGGTGTCGTGGAACTCAGGCGCCCTGACCAGCGGCGTGCACACCTTCCCGGCTGTCCTACAGTCCTCAGGACT
AAGGGGCTTGGCCACTGCCACAGCACCTTGAGTCCGCGGGACTGGTCGCCGCACGTGTGGAAGGGCCGACAGGATGTCAGGAGTCCTGA
 ■ F  P  E  P  V  T  V  S  W  N  S  G  A  L  T  S  G  V  M  T  F  P  A  V  L  Q  S  S  G  L CTACTCCCTCAGCAGCGTGGTGACCGTGCCCTCCAGCAGCTTGGGCACCCAGACCTACATCTGCAACGTGAATCACAAGCCCAGCAACA
GATGAGGGAGTCGTCGCACCACTGGCACGGGAGGTCGTCGAACCCGTGGGTCTGGATGTAGACGTTGCACTTAGTGTTCGGGTCGTTGT
 ■ Y  S  L  S  S  V  V  T  V  P  S  S  S  L  G  T  Q  T  Y  I  C  N  V  N  G  K  P  S  N  T CCAAGGTGGACAAGAGAGTTGAGCCCAAATCTTGTGACAAAACTCACACATGCCCACCGTGCGCAGCACCTGAACTCCTGGGGGGACCG
GGTTCCACCTGTTCTCTCAACTCGGGTTTAGAACACTGTTTTGAGTGTGTACGGGTGGCACGCGTCGTGGACTTGAGGACCCCCCTGGC
   K  V  D  K  R  V  E  P  K  S  C  D  K  T  H  T  C  P  P  C  P  A  P  E  L  L  G  G  P  S TCAGTCTTCCTCTTCCCCCCAAAACCCAAGGACACCCTCATGATCTCCCGGACCCCTGAGGTCACATGCGTGGTGGTGGACGTGAGCCA
AGTCAGAAGGAGAAGGGGGGTTTTGGGTTCCTGTGGGAGTACTAGAGGGCCTGGGGACTCCAGTGTACGCACCACCACCTGCACTCGGT
   V  F  L  F  P  P  K  P  K  D  T  L  M  I  S  R  T  P  E  V  T  C  V  V  V  D  V  S  H  E CGAAGACCCTGAGGTCAAGTTCAACTGGTACGTGGACGGCGTGGAGGTGCATAATGCCAAGACAAAGCCGCGGGAGGAGCAGTACAACA
GCTTCTGGGACTCCAGTTCAAGTTGACCATGCACCTGCCGCACCTCCACGTATTACGGTTCTGTTTCGGCGCCCTCCTCGTCATGTTGT
   D  P  E  V  K  F  N  W  Y  V  D  G  V  E  V  H  N  A  K  T  K  P  R  E  E  Q  Y  N  S  T GCACGTACCGTGTGGTCAGCGTCCTCACCGTCCTGCACCAGGACTGGCTGAATGGCAAGGAGTACAAGTGCAAGGTCTCCAACAAAGCC
CGTGCATGGCACACCAGTCGCAGGAGTGGCAGGACGTGGTCCTGACCGACTTACCGTTCCTCATGTTCACGTTCCAGAGGTTGTTTCGG
     Y  R  V  V  S  V  L  T  V  L  H  Q  D  W  L  N  G  K  E  V  K  C  K  V  S  N  K  A  L CTCCCAGCCCCCATCGAGAAAACCATCTCCAAAGCCAAAGGGCAGCCCCGAGAACCACAGGTGTACACCCTGCCCCCATCCCGGGAGGA
GAGGGTCGGGGGTAGCTCTTTTGGTAGAGGTTTCGGTTTCCCGTCGGGGCTCTTGGTGTCCACATGTGGGACGGGGTAGGGCCCTCCT
   P  A  P  I  E  K  T  I  S  K  A  K  G  Q  P  R  E  P  Q  V  Y  T  L  P  P  S  R  E  E  M GATGACCAAGAACCAGGTCAGCCTGACCTGCCTGGTCAAAGGCTTCTATCCCAGCGACATCGCCGTGGAGTGGGAGAGCAATGGGCAGC
CTACTGGTTCTTGGTCCAGTCGGACTGGACGGACCAGTTTCCGAAGATAGGGTCGCTGTAGCGGCACCTCACCCTCTCGTTACCCGTCG
   T  K  N  Q  V  S  L  T  C  L  V  K  G  F  Y  P  S  D  I  A  V  E  W  E  S  N  G  Q  P  E CGGAGAACAACTACAAGACCACGCCTCCCGTGCTGGACTCCGACGGCTCCTTCTTCCTCTATAGCAAGCTCACCGTGGACAAGAGCAGG
GCCTCTTGTTGATGTTCTGGTGCGGAGGGCACGACCTGAGGCTGCCGAGGAAGAAGGAGATATCGTTCGAGTGGCACCTGTTCTCGTCC
   N  N  Y  K  T  T  P  P  V  L  D  S  D  G  S  F  F  L  Y  S  K  L  T  V  D  K  S  R  W  Q TGGCAGCAGGGGAACGTCTTCTCATGCTCCGTGATGCATGAGGCTCTGCACAACCACTACACGCAGAAGAGCCTCTCCCTGTCTCCGGG
ACCGTCGTCCCCTTGCAGAAGAGTACGAGGCACTACGTACTCCGAGACGTGTTGGTGATGTGCGTCTTCTCGGAGAGGGACAGAGGCCC
   Q  G  N  V  F  S  C  S  V  M  H  E  A  L  H  N  H  Y  T  Q  K  S  L  S  L  S  P  G  K ApaI(2339)
                DraII(2338)
        XbaI(2333) PmeI(2345)
TAAATGAGTTCTAGAGGGCCCGTTTAAACCCGCTGATCAGCCTCGACTGTGCCTTCTAGTTGCCAGCCATCTGTTGTTTGC
ATTTACTCAAGATCTCCCGGGCAAATTTGGGCGACTAGTCGGAGCTGACACGGAAGATCAACGGTCGGTAGACAACAAACG
```

The framework 4 (FR4) region of the Gamma HC normally ends with two serines (SS), so that the full framework 4 region should be W G Q G T L V T V S S (SEQ ID NO: 80). The accepting Xho 1 site and one additional base downstream of the Xho1 site in the vector, in which the Gamma HC constant region that the Gamma HC variable regions are cloned, supplies the last bases, which encode this final amino acid of framework 4. However, the original vector did not adjust for the silent mutation made when the Xho1 site (CTCGAG, SEQ ID NO: 81) was created and contained an "A" nucleotide downstream of the Xho1 site, which caused an amino acid change at the end of framework 4: a serine to arginine (S to R) substitution present in all the working Gamma HC clones. Thus, the full framework 4 region reads W G Q G T L V TV S R (SEQ ID NO: 82). Future constructs are being created wherein the base downstream of the Xho 1 site is a "C" nucleotide. Thus, the creation of the Xho 1 site used for cloning of the Gamma HC variable region sequences in alternative embodiments is a silent mutation and restores the framework 4 amino acid sequence to its proper W G Q G T L V TV S S (SEQ ID NO: 80). This is true for all M2 Gamma HC clones described herein.

Clone 21 B15:

The Kappa LC variable region of the anti M2 clone 21B15 was cloned as Hind III to BsiW1 fragment, and is encoded by the following polynucleotide sequences and SEQ ID NO: 83 and SEQ ID NO: 84:

```
HindIII
AAGCTTCCACCATGGACATGAGGGTCCTCGCTCAGCTCCTGGGGCTCCTGCTACTCTGGCTCCGAGGTG C
TTCGAAGGTGGTACCTGTACTCCCAGGAGCGAGTCGAGGACCCCGAGGACGATGAGACCGAGGCTCCAC G
CAGATGTGACATCCAGGTGACCCAGTCTCCATCCTCCCTGTCTGCATCTGTAGGAGACAGAGTCACCAT C
GTCTACACTGTAGGTCCACTGGGTCAGAGGTAGGAGGGACAGACGTAGACATCCTCTGTCTCAGTGGTA G
ACTTGCCGCGCGAGTCAGAACATTTACAAGTATTTAAATTGGTATCAGCAGAGACCAGGGAAAGCCCCT A
TGAACGGCGCGCTCAGTCTTGTAAATGTTCATAAATTTAACCATAGTCGTCTCTGGTCCCTTTCGGGGA T
AGGGCCTGATCTCTGCTGCATCCGGGTTGCAAAGTGGGGTCCCATCAAGGTTCAGTGGCAGTGGATCTG G
TCCCGGACTAGAGACGACGTAGGCCCAACGTTTCACCCCAGGGTAGTTCCAAGTCACCGTCACCTAGAC C
GACAGATTTCACTCTCACCATCACCAGTCTGCAACCTGAAGATTTTGCAACTTACTACTGTCAACAGAG T
CTGTCTAAAGTGAGAGTGGTAGTGGTCAGACGTTGGACTTCTAAAACGTTGAATGATGACAGTTGTCTC A
                                                                BsiWI
TACAGTCCCCCTCTCACTTTCGGCGGAGGGACCAGGGTGGATATCAAACGTACG
ATGTCAGGGGAGAGTGAAAGCCGCCTCCCTGGTCCCACCTATAGTTTGCATGC
```

The translation of the 21B15 Kappa LC variable region is as follows; polynucleotide sequence (above, SEQ ID NO: 83, top) and amino acid sequence (below, corresponding to SEQ ID NO: 298):

```
HindIII
AAGCTTCCACCATGGACATGAGGGTCCTCGCTCAGCTCCTGGGGCTCCTGCTACTCTGGCTCCGAGGT
          M   D   M   R   V   L   A   Q   L   L   G   L   L   L   L   W   L   R   G GCCAGATGTGACATCCAGGTGACCCAGTCTCCATCCTCCCTGTCTGCATCTGTAGGAGACAGAGTCAC C
  A   R   C   D   I   Q   V   T   Q   S   P   S   S   L   S   A   S   V   G   D   R   V   T ATCACTTGCCGCGCGAGTCAGAACATTTACAAGTATTTAAATTGGTATCAGCAGAGACCAGGGAAAGC C
  I   T   C   R   A   S   Q   N   I   Y   K   Y   L   N   W   Y   Q   Q   R   P   G   K   A CCTAAGGGCCTGATCTCTGCTGCATCCGGGTTGCAAAGTGGGGTCCCATCAAGGTTCAGTGGCAGTGG A
  P   K   G   L   I   S   A   A   S   G   L   Q   S   G   V   P   S   R   F   S   G   S   G TCTGGGACAGATTTCACTCTCACCATCACCAGTCTGCAACCTGAAGATTTTGCAACTTACTACTGTCA A
  S   G   T   D   F   T   L   T   I   T   S   L   Q   P   E   D   F   A   T   Y   Y   C   Q
                                                                              BsiWI
CAGAGTTACAGTCCCCCTCTCACTTTCGGCGGAGGGACCAGGGTGGATATCAAACGTACG
  Q   S   Y   S   P   P   L   T   F   G   G   G   T   R   V   D   I   K   R   T
```

The amino acid sequence of the 21B15 Kappa LC variable region is as follows, with specific domains identified below (CDR sequences defined according to Kabat methods):

| | | |
|---|---|---|
| M D M R V L A Q L L G L L L L W L R G A R C | VK leader | (SEQ ID NO: 57) |
| D I Q V T Q S P S S L S A S V G D R V T I T C | FR1 | (SEQ ID NO: 58) |
| R A S Q N I Y K Y L N | CDR1 | (SEQ ID NO: 59) |
| W Y Q Q R P G K A P K G L I S | FR2 | (SEQ ID NO: 60) |
| A A S G L Q S | CDR2 | (SEQ ID NO: 61) |

```
G V P S R F S G S G S G T D F T L T I T S L Q P E D F A T Y Y C   FR3                        (SEQ ID NO: 62)

Q Q S Y S P P L T                                                CDR3                       (SEQ ID NO: 63)

F G G G T R V D I K                                              FR4                        (SEQ ID NO: 64)

R T                                                              Start of Kappa constant region
```

The primer used to clone the Kappa LC variable region extended across a region of diversity and had wobble base position in its design. Thus, in the framework 4 region a D or E amino acid could occur. In some cases, the amino acid in this position in the rescued antibody may not be the original parental amino acid that was produced in the B cell. In most kappa LCs the position is an E. Looking at the clone above (21 B 15) a D in framework 4 (DIK RT) (SEQ ID NO: 544) was observed. However, looking at the surrounding amino acids, this may have occurred as the result of the primer and may be an artifact. The native antibody from the B cell may have had an E in this position.

The 21B15 Gamma HC variable region was cloned as a Hind III to Xho 1 fragment, and is encoded by the following polynucleotide sequences and SEQ ID NO: 85 (top), and SEQ ID NO: 86 (bottom):

```
HindIII
AAGCTTCCACCATGAAACACCTGTGGTTCTTCCTTCTCCTGGTGGCAGCTCCCAGCTGGGTC C

TTCGAAGGTGGTACTTTGTGGACACCAAGAAGGAAGAGGACCACCGTCGAGGGTCGACCCAG G

TGTCCCAGGTGCAATTGCAGGAGTCGGGCCCAGGACTGGTGAAGCCTTCGGAGACCCTGTCC C

ACAGGGTCCACGTTAACGTCCTCAGCCCGGGTCCTGACCACTTCGGAAGCCTCTGGGACAGG G

TCACCTGCACTGTCTCTGGTTCGTCCATCAGTAATTACTACTGGAGCTGGATCCGGCAGTCC C

AGTGGACGTGACAGAGACCAAGCAGGTAGTCATTAATGATGACCTCGACCTAGGCCGTCAGG G

CAGGGAAGGGACTGGAGTGGATTGGGTTTATCTATTACGGTGGAAACACCAAGTACAATCCC T

GTCCCTTCCCTGACCTCACCTAACCCAAATAGATAATGCCACCTTTGTGGTTCATGTTAGGG A

CCCTCAAGAGCCGCGTCACCATATCACAAGACACTTCCAAGAGTCAGGTCTCCCTGACGATG A

GGGAGTTCTCGGCGCAGTGGTATAGTGTTCTGTGAAGGTTCTCAGTCCAGAGGGACTGCTAC T

GCTCTGTGACCGCTGCGGAATCGGCCGTCTATTTCTGTGCGAGAGCGTCTTGTAGTGGTGGT T

CGAGACACTGGCGACGCCTTAGCCGGCAGATAAAGACACGCTCTCGCAGAACATCACCACCA A

XhoI
ACTGTATCCTTGACTACTGGGGCCAGGGAACCCTGGTCACCGTCTCGAG

TGACATAGGAACTGATGACCCCGGTCCCTTGGGACCAGTGGCAGAGCTC
```

The translation of the 21B15 Gamma HC is as follows, polynucleotide sequence (above, SEQ ID NO: 87, top) and amino acid sequence (below, corresponding to residues 1-138 of SEQ ID NO: 69):

```
HindIII
AAGCTTCCACCATGAAACACCTGTGGTTCTTCCTTCTCCTGGTGGCAGCTCCCAGCTGGGTC
            M   K   H   L   W   F   F   L   L   L   V   A   A   P   S   W   V CTGTCCCAGGTGCAATTGCAGGAGTCGGGCCCAGGACTGGTGAAGCCTTCGGAGACCCTGTC C
 L   S   Q   V   Q   L   Q   E   S   G   P   G   L   V   K   P   S   E   T   L   S CTCACCTGCACTGTCTCTGGTTCGTCCATCAGTAATTACTACTGGAGCTGGATCCGGCAGTC C
 L   T   C   T   V   S   G   S   S   I   S   N   Y   Y   W   S   W   I   R   Q   S CCAGGGAAGGGACTGGAGTGGATTGGGTTTATCTATTACGGTGGAAACACCAAGTACAATCC C
 P   G   K   G   L   E   W   I   G   F   I   Y   Y   G   G   N   T   K   Y   N   P TCCCTCAAGAGCCGCGTCACCATATCACAAGACACTTCCAAGAGTCAGGTCTCCCTGACGAT G
 S   L   K   S   R   V   T   I   S   Q   D   T   S   K   S   Q   V   S   L   T   M AGCTCTGTGACCGCTGCGGAATCGGCCGTCTATTTCTGTGCGAGAGCGTCTTGTAGTGGTGG T
 S   S   V   T   A   A   E   S   A   V   Y   F   C   A   R   A   S   C   S   G   G
```

```
                                                        XhoI
TACTGTATCCTTGACTACTGGGGCCAGGGAACCCTGGTCACCGTCTCGAG
  Y  C  I  L  D  Y  W  G  Q  G  T  L  V  T  V  S
```

The amino acid sequence of the 21B15 Gamma HC is as follows, with specific domains identified below (CDR sequences defined according to Kabat methods):

| | | |
|---|---|---|
| M K H L W F F L L L V A A P S W V L S | VH leader | (SEQ ID NO: 70) |
| Q V Q L Q E S G P G L V K P S E T L S L T C T V S G S S I S | FR1 | (SEQ ID NO: 71) |
| N Y Y W S | CDR1 | (SEQ ID NO: 72) |
| W I R Q S P G K G L E W I G | FR2 | (SEQ ID NO: 73) |
| F I Y Y G G N T K Y N P S L K S | CDR2 | (SEQ ID NO: 74) |
| R V T I S Q D T S K S Q V S L T M S S V T A A E S A V Y F C A R | FR3 | (SEQ ID NO: 75) |
| A S C S G G Y C I L D | CDR3 | (SEQ ID NO: 76) |
| Y W G Q G T L V T V S | FR4 | (SEQ ID NO: 77) |
| YWGQGTLVTVSS | Long FR4 | (SEQ ID NO: 266) |

Clone 23K12 (Corresponds to TCN-031):

The Kappa LC variable region of the anti M2 clone 23K12 was cloned as Hind III to BsiW1 fragment (see below), and is encoded by the following polynucleotide sequences SEQ ID NO: 88 (top) and SEQ ID NO: 89 (below).

```
HindIII
AAGCTTCCACCATGGACATGAGGGTCCTCGCTCAGCTCCTGGGGCTCCTGCTACTCTGGCTCCGAG G

TTCGAAGGTGGTACCTGTACTCCCAGGAGCGAGTCGAGGACCCCGAGGACGATGAGACCGAGGCTC C

TGCCAGATGTGACATCCAGATGACCCAGTCTCCATCCTCCCTGTCTGCATCTGTAGGAGACAGAGT C

ACGGTCTACACTGTAGGTCTACTGGGTCAGAGGTAGGAGGGACAGACGTAGACATCCTCTGTCTCA G

ACCATCACTTGCCGGACAAGTCAGAGCATTAGCAGCTATTTAAATTGGTATCAGCAGAAACCAGGG A

TGGTAGTGAACGGCCTGTTCAGTCTCGTAATCGTCGATAAATTTAACCATAGTCGTCTTTGGTCCC T

AAGCCCCTAAACTCCTGATCTATGCTGCATCCAGTTTGCAAAGTGGGGTCCCATCAAGGTTCAGTG G

TTCGGGGATTTGAGGACTAGATACGACGTAGGTCAAACGTTTCACCCCAGGGTAGTTCCAAGTCAC C

CAGTGGATCTGGGACAGATTTCACTCTCACCATCAGCGGTCTGCAACCTGAAGATTTTGCAACCTA C

GTCACCTAGACCCTGTCTAAAGTGAGAGTGGTAGTCGCCAGACGTTGGACTTCTAAAACGTTGGAT G
                                                                BsiWI
TACTGTCAACAGAGTTACAGTATGCCTGCCTTTGGCCAGGGGACCAAGCTGGAGATCAAACGTACG

ATGACAGTTGTCTCAATGTCATACGGACGGAAACCGGTCCCCTGGTTCGACCTCTAGTTTGCATGC
```

The translation of the 23K12 Kappa LC variable region is as follows, polynucleotide sequence (above, SEQ ID NO: 90, top) and amino acid sequence (below, corresponding to SEQ ID NO: 91).

```
    HindIII
    AAGCTTCCACCATGGACATGAGGGTCCTCGCTCAGCTCCTGGGGCTCCTGCTACTCTGGCTCCGAG G
              M  D  M  R  V  L  A  Q  L  L  G  L  L  L  L  W  L  R  G TGCCAGATGTGACATCCAGATGACCCAGTCTCCATCCTCCCTGTCTGCATCTGTAGGAGACAGAGT C
      A  R  C  D  I  Q  M  T  Q  S  P  S  S  L  S  A  S  V  G  D  R  V ACCATCACTTGCCGGACAAGTCAGAGCATTAGCAGCTATTTAAATTGGTATCAGCAGAAACCAGGG A
      T  I  T  C  R  T  S  Q  S  I  S  S  Y  L  N  W  Y  Q  Q  K  P  G
```

-continued

```
    AAGCCCCTAAACTCCTGATCTATGCTGCATCCAGTTTGCAAAGTGGGGTCCCATCAAGGTTCAGTG G
    K   A   P   K   L   L   I   Y   A   A   S   S   L   Q   S   G   V   P   S   R   F   S   G

CAGTGGATCTGGGACAGATTTCACTCTCACCATCAGCGGTCTGCAACCTGAAGATTTTGCAACCTA C
      S   G   S   G   T   D   F   T   L   T   I   S   G   L   Q   P   E   D   F   A   T   Y

BsiWI
    TACTGTCAACAGAGTTACAGTATGCCTGCCTTTGGCCAGGGGACCAAGCTGGAGATCAAACGTACG
      Y   C   Q   Q   S   Y   S   M   P   A   F   G   Q   G   T   K   L   E   I   K   R   T
```

The amino acid sequence of the 23K12 Kappa LC variable region is as follows, with specific domains identified below (CDR sequences defined according to Kabat methods):

| | | |
|---|---|---|
| M D M R V L A Q L L G L L L L W L R G A R C | VK leader | (SEQ ID NO: 57) |
| D I Q M T Q S P S S L S A S V G D R V T I T C | FR1 | (SEQ ID NO: 58) |
| R T S Q S I S S Y L N | CDR1 | (SEQ ID NO: 92) |
| W Y Q Q K P G K A P K L L I Y | FR2 | (SEQ ID NO: 93) |
| A A S S L Q S G V P S R F | CDR2 | (SEQ ID NO: 94) |
| S G S G S G T D F T L T I S G L Q P E D F A T Y Y C | FR3 | (SEQ ID NO: 95) |
| Q Q S Y S M P A | CDR3 | (SEQ ID NO: 96) |
| F G Q G T K L E I K | FR4 | (SEQ ID NO: 114) |
| R T | Start of Kappa LC constant region | |

The 23K12 Gamma HC variable region was cloned as a Hind III to Xho 1 fragment, and is encoded by the following polynucleotide sequences and SEQ ID NO: 97 (top) and SEQ ID NO: 98 (bottom):

```
HindIII
AAGCTTCCACCATGGAGTTGGGGCTGTGCTGGGTTTTCCTTGTTGCTATTTTAAAAGGTGTCCAG T

TTCGAAGGTGGTACCTCAACCCCGACACGACCCAAAAGGAACAACGATAAAATTTTCCACAGGTC A

GTGAGGTGCAGCTGGTGGAGTCTGGGGGAGGCTTGGTCCAGCCTGGGGGGTCCCTGAGAATCTCC T

CACTCCACGTCGACCACCTCAGACCCCCTCCGAACCAGGTCGGACCCCCCAGGGACTCTTAGAGG A

GTGCAGCCTCTGGATTCACCGTCAGTAGCAACTACATGAGTTGGGTCCGCCAGGCTCCAGGGAAG G

CACGTCGGAGACCTAAGTGGCAGTCATCGTTGATGTACTCAACCCAGGCGGTCCGAGGTCCCTTC C

GGCTGGAGTGGGTCTCAGTTATTTATAGTGGTGGTAGCACATACTACGCAGACTCCGTGAAGGGC A

CCGACCTCACCCAGAGTCAATAAATATCACCACCATCGTGTATGATGCGTCTGAGGCACTTCCCG T

GATTCTCCTTCTCCAGAGACAACTCCAAGAACACAGTGTTTCTTCAAATGAACAGCCTGAGAGCC G

CTAAGAGGAAGAGGTCTCTGTTGAGGTTCTTGTGTCACAAAGAAGTTTACTTGTCGGACTCTCGG C

AGGACACGGCTGTGTATTACTGTGCGAGATGTCTGAGCAGGATGCGGGGTTACGGTTTAGACGTC T

TCCTGTGCCGACACATAATGACACGCTCTACAGACTCGTCCTACGCCCCAATGCCAAATCTGCAG A

XhoI
GGGGCCAAGGGACCACGGTCACCGTCTCGAG

CCCCGGTTCCCTGGTGCCAGTGGCAGAGCTC
```

The translation of the 23K12 Gamma HC variable region is as follows, polynucleotide sequence (above, SEQ ID NO: 99, top), and amino acid sequence (below, corresponding to SEQ ID NO: 100):

```
HindIII
AAGCTTCCACCATGGAGTTGGGGCTGTGCTGGGTTTTCCTTGTTGCTATTTTAAAAGGTGTCCAG
               M  E  L  G  L  C  W  V  F  L  V  A  I  L  K  G  V  Q TGTGAGGTGCAGCTGGTGGAGTCTGGGGGAGGCTTGGTCCAGCCTGGGGGGTCCCTGAGAATCTC C
 C  E  V  Q  L  V  E  S  G  G  G  L  V  Q  P  G  G  S  L  R  I  S TGTGCAGCCTCTGGATTCACCGTCAGTAGCAACTACATGAGTTGGGTCCGCCAGGCTCCAGGGAA G
 C  A  A  S  G  F  T  V  S  S  N  Y  M  S  W  V  R  Q  A  P  G  K GGGCTGGAGTGGGTCTCAGTTATTTATAGTGGTGGTAGCACATACTACGCAGACTCCGTGAAGGG C
 G  L  E  W  V  S  V  I  Y  S  G  G  S  T  Y  Y  A  D  S  V  K  G AGATTCTCCTTCTCCAGAGACAACTCCAAGAACACAGTGTTTCTTCAAATGAACAGCCTGAGAGC C
 R  F  S  F  S  R  D  N  S  K  N  T  V  F  L  Q  M  N  S  L  R  A GAGGACACGGCTGTGTATTACTGTGCGAGATGTCTGAGCAGGATGCGGGGTTACGGTTTAGACGT C
 E  D  T  A  V  Y  Y  C  A  R  C  L  S  R  M  R  G  Y  G  L  D  V XhoI
TGGGGCCAAGGGACCACGGTCACCGTCTCGAG
 W  G  Q  G  T  T  V  T  V  S
```

The amino acid sequence of the 23K12 Gamma HC variable region is as follows, with specific domains identified below (CDR sequences defined according to Kabat methods):

| | | |
|---|---|---|
| M E L G L C W V F L V A I L K G V Q C | VH leader | (SEQ ID NO: 101) |
| E V Q L V E S G G G L V Q P G G S L R I S C A A S G F T V S | FR1 | (SEQ ID NO: 102) |
| S N Y M S | CDR1 | (SEQ ID NO: 103) |
| W V R Q A P G K G L E W V S | FR2 | (SEQ ID NO: 104) |
| V I Y S G G S T Y Y A D S V K | CDR2 | (SEQ ID NO: 105) |
| G R F S F S R D N S K N T V F L Q M N S L R A E D T A V Y Y C A R | FR3 | (SEQ ID NO: 106) |
| C L S R M R G Y G L D V | CDR3 | (SEQ ID NO: 107) |
| W G Q G T T V T V S | FR4 | (SEQ ID NO: 108) |
| WGQGTTVTVSS | Long FR4 | (SEQ ID NO: 111) |

Example 3

Identification of Conserved Antibody Variable Regions

The amino acid sequences of the three antibody Kappa LC and Gamma HC variable regions were aligned to identify conserved regions and residues, as shown below.

Amino acid sequence alignment of the Kappa LC variable regions of the three clones (SEQ ID NOS 673-675, respectively, in order of appearance):

```
           10          20          30
1  A S T M D M R V L A Q L L G L L L L W L R G A R C D I Q V T Q S P S S L
2  A S T M D M R V L A Q L L G L L L L W L R G A R C D I Q M T Q S P S S L
3  A S T M D M R V L A Q L L G L L L L W L R G A R C D I Q M T Q S P S S L 40          50          60          70
1  S A S V G D R V T I T C R A S Q N I Y K Y L N W Y Q Q R P G K A P K G L
2  S A S V G D R V T I T C R A S Q N I Y K Y L N W Y Q Q R P G K A P K G L
3  S A S V G D R V T I T C R T S Q S I S S Y L N W Y Q Q R P G K A P K G L 80          90         100
1  I S A A S G L Q S G V P S R F S G S G S G T D F T L T I T S L Q P E D F
2  I S A A S G L Q S G V P S R F S G S G S G T D F T L T I T S L Q P E D F
3  I Y A A S S L Q S G V P S R F S G S G S G T D F T L T I S G L Q P E D F
```

-continued

```
           110                 120                 130
1    A T Y Y C Q Q S Y S P P L T F G G G T R V D I K R T
2    A T Y Y C Q Q S Y S P P L T F G G G T R V E I K R T
3    A T Y Y C Q Q S Y S M P - A F G Q G T R L E I K R T
1 = Translation of mp 73 21B15
2 = Translation of mp 147 8i10
3 = Translation of mp 137 23K12
```

Amino acid sequence alignment of the Gamma HC variable regions of the three clones (SEQ ID NOS 676-678, respectively, in order of appearance):

```
              10                  20
1    A S T M K H L W F F L L L V A A P S W V L S Q V Q L Q E S
2    A S T M E L G L C W V F L V A I L K G V Q C E V Q L V E S
3    A S T M K H L W F F L L L V A A P S W V L S Q V Q L Q E S 30                  40                  50
1    G P G L V K P S E T L S L T C T V S G S S I S N Y Y W S W
2    G G G L V Q P G G S L R I S C A A S G F T V S S N Y M S W
3    G P G L V K P S E T L S L T C T V S G S S I S N Y Y W S W 60                  70                  80
1    I R Q S P G K G L E W I G F I Y Y G G N T K Y N P S L K S
2    V R Q A P G K G L E W V S V I Y S G G S T Y Y A D S V K G
3    I R Q S P G K G L E W I G F I Y Y G G N T K Y N P S L K S 90                 100                 110
1    R V T I S Q D T S K S Q V S L T M S S V T A A E S A V Y F
2    R F S F S R D N S K N T V F L Q M N S L R A E D T A V Y Y
3    R V T I S Q D T S K S Q V S L T M S S V T A A E S A V Y F 120                 130                 140
1    C A R A S C S G G Y C I L D Y W G Q T L V T V S
2    C A R C L S R M R G Y G L D V W G Q T T V T V S
3    C A R A S C S G G Y C I L D Y W G Q T L V T V S
1 = Translation of mp 81 21B15
2 = Translation of mp 153 8i10
3 = Translation of mp 145 23K12
```

Clones 8I10 and 21B15 came from two different donors, yet they have the same exact Gamma HC and differ in the Kappa LC by only one amino acid at position 4 in the framework 1 region (amino acids M versus V, see above), (excluding the D versus E wobble position in framework 4 of the Kappa LC).

Sequence comparisons of the variable regions of the antibodies revealed that the heavy chain of clone 8i10 was derived from germline sequence IgHV4 and that the light chain was derived from the germline sequence IgKV1.

Sequence comparisons of the variable regions of the antibodies revealed that the heavy chain of clone 21B15 was derived from germline sequence IgHV4 and that the light chain was derived from the germline sequence IgKV1.

Sequence comparisons of the variable regions of the antibodies revealed that the heavy chain of clone 23K12 was derived from germline sequence IgHV3 and that the light chain was derived from the germline sequence IgKV1.

Example 4

Production and Characterization of M2 Antibodies

Figure 9:
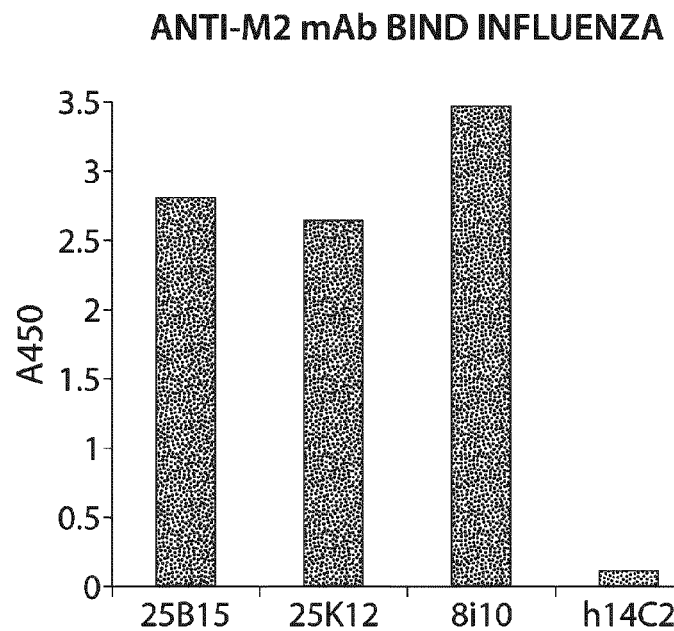
FIG. 9 is a graph showing anti-M2 rHMAb clones from crude supernatant bound to influenza on ELISA, whereas the control anti-M2e mAb 14C2 did not readily bind virus.

The antibodies described above were produced in milligram quantities by larger scale transient transfections in 293 PEAK cells. Crude un-purified antibody supernatants were used to examine antibody binding to influenza A/Puerto Rico/ 8/1932 (PR8) virus on ELISA plates, and were compared to the binding of the control antibody 14C2, which was also produced by larger scale transient transfection. The anti-M2 recombinant human monoclonal antibodies bound to influenza while the control antibody did not (FIG. 9).

Figure 10:
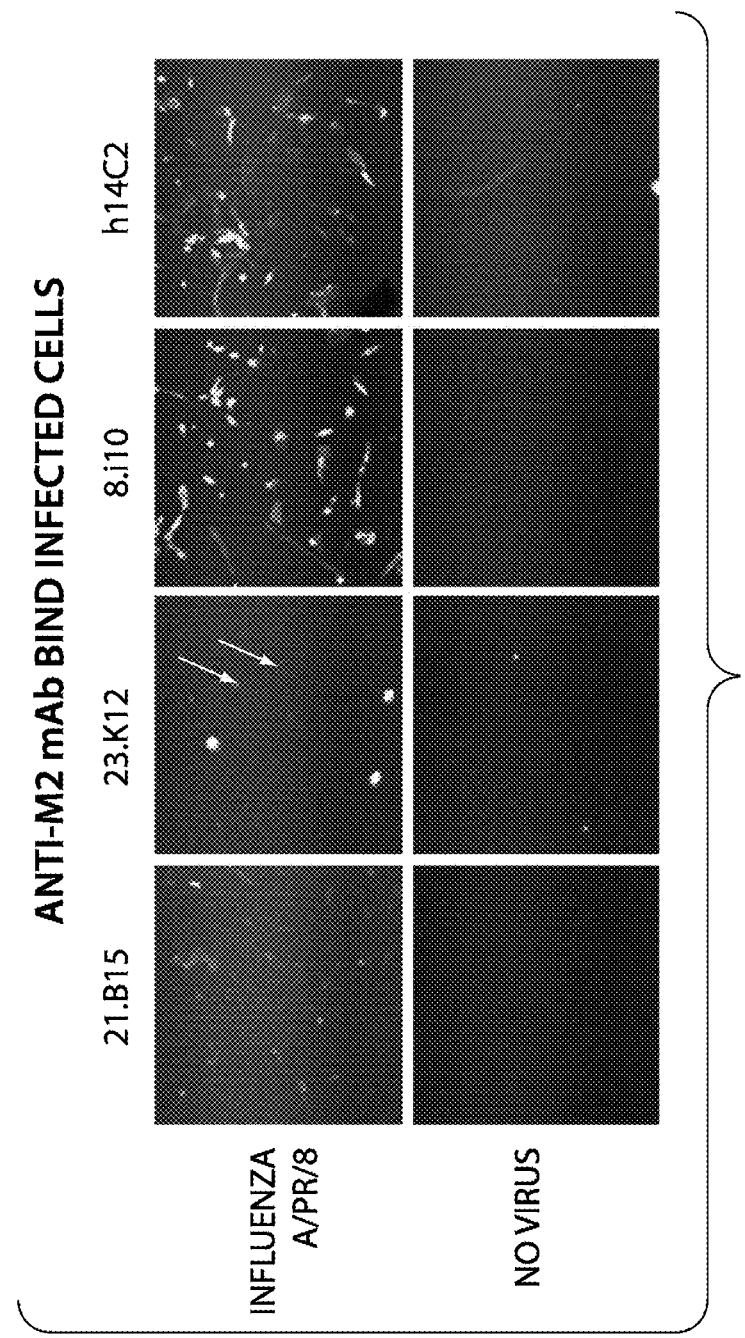
FIG. 10 is a series of photographs showing anti-M2 rHMAbs bound to cells infected with influenza. MDCK cells were or were not infected with influencza A/PR/8/32 and Ab binding from crude supernatant was tested 24 hours later. Data were gathered from the FMAT plate scanner.

Binding was also tested on MDCK cells infected with the PR8 virus (FIG. 10). The control antibody 14C2 and the three anti M2E clones: 8I10, 21B15 and 23K12, all showed specific binding to the M2 protein expressed on the surface of PR8-infected cells. No binding was observed on uninfected cells.

Figure 11:
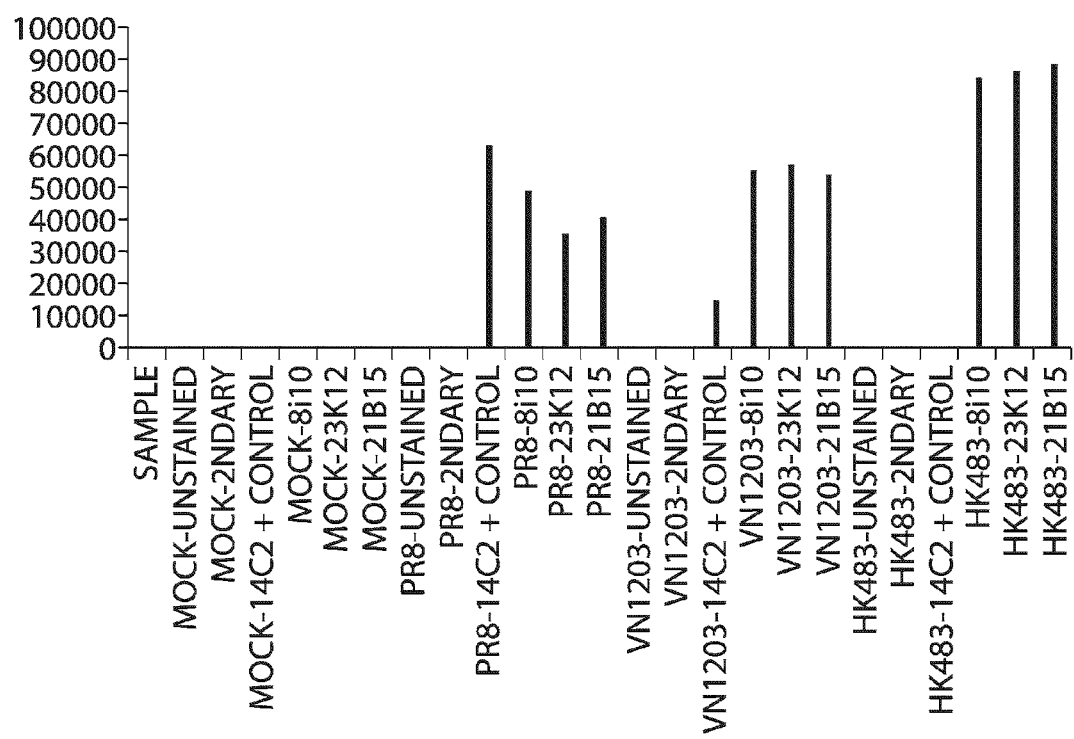
FIG. 11 is a graph showing anti-M2 rHMAb clones from crude supernatant bound to cells transfected with the influenza subtypes H3N2, HK483, and VN1203 M2 proteins. Plasmids encoding full length M2 cDNAs corresponding to influenza strains H3N2, HK483, and VN1203, as well as a mock plasmid control, were transiently transfected into 293 cells. The 14C2, 8i10, 23K12, and 21B15 mABs were tested for binding to the transfectants, and were detected with an AF647-conjugated anti-human IgG secondary antibody. Shown are the mean fluorescence intensities of the specific mAB bound after FACS analysis.

The antibodies were purified over protein A columns from the supernatants. FACs analysis was performed using purified antibodies at a concentration of 1 ug per ml to examine the binding of the antibodies to transiently transfected 293 PEAK cells expressing the M2 proteins on the cell surface. Binding was measured testing binding to mock transfected cells and cells transiently transfected with the Influenza subtype H3N2, A/Vietnam/1203/2004 (VN1203), or A/Hong Kong/ 483/1997 HK483 M2 proteins. As a positive control the antibody 14C2 was used. Unstained and secondary antibody alone controls helped determined background. Specific staining for cells transfected with the M2 protein was observed for all three clones. Furthermore, all three clones bound to the high path strains A/Vietnam/1203/2004 and A/Hong Kong/ 483/1997 M2 proteins very well, whereas the positive control 14C2 which bound well to H3N2 M2 protein, bound much weaker to the A/Vietnam/1203/2004 M2 protein and did not bind the A/Hong Kong/483/1997 M2 protein. See FIG. 11.

Antibodies 21B15, 23K12, and 8I10 bound to the surface of 293-HEK cells stably expressing the M2 protein, but not to vector transfected cells (see FIG. 1). In addition, binding of these antibodies was not competed by the presence of 5 mg/ml 24-mer M2 peptide, whereas the binding of the control chimeric mouse V-region/human IgG1 kappa 14C2 antibody (hu14C2) generated against the linear M2 peptide was completely inhibited by the M2 peptide (see FIG. 1). These data confirm that these antibodies bind to conformational epitopes present in M2e expressed on the cell or virus surface, as opposed to the linear M2e peptide.

Example 5

Viral Binding of Human Anti-Influenza Monoclonal Antibodies

Figure 2A:
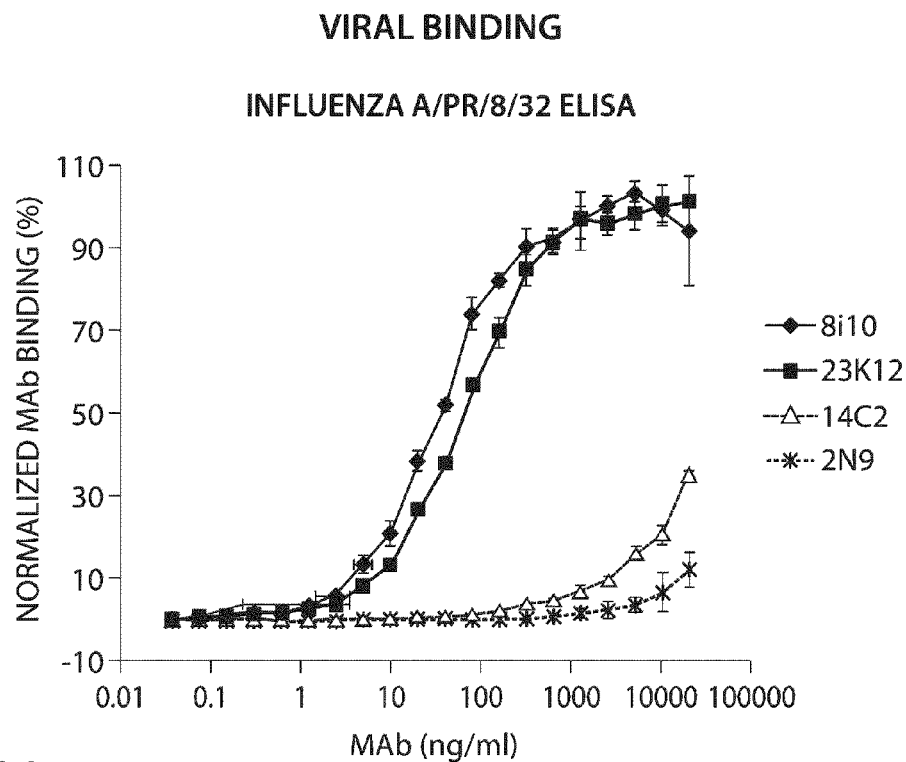
FIGS. 2A and B are graphs showing human monoclonal antibody binding to influenza A/Puerto Rico/8/32.
Figure 2B:
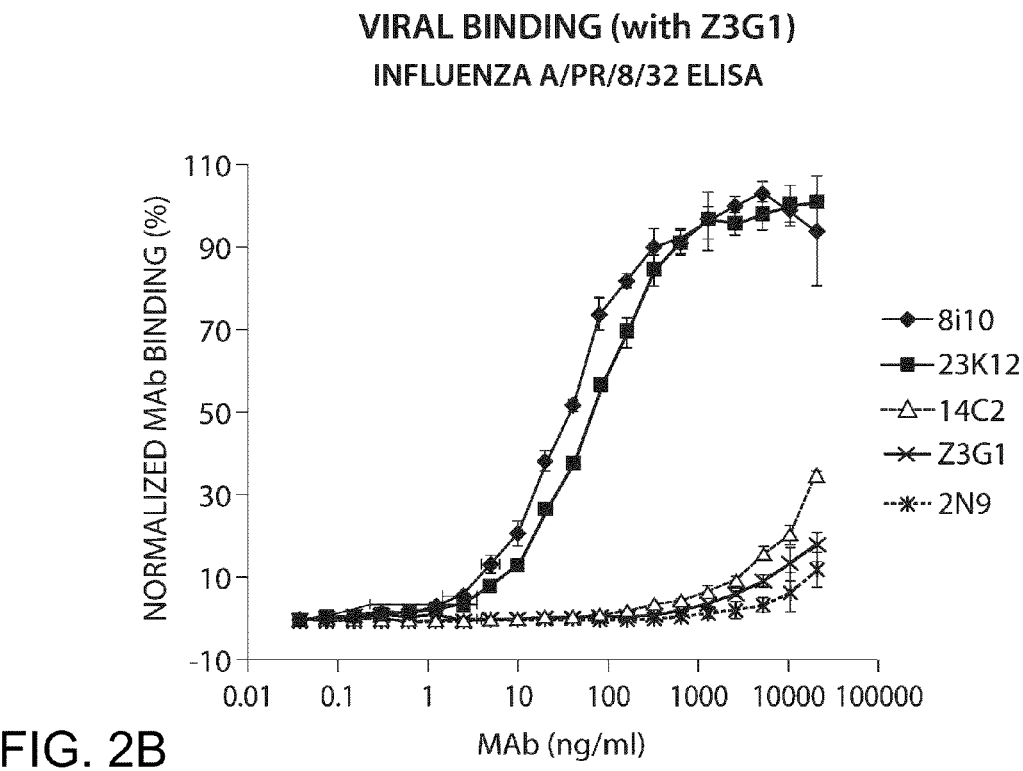

UV-inactivated influenza A virus (A/PR/8/34) (Applied Biotechnologies) was plated in 384-well MaxiSorp plates (Nunc) at 1.2 µg/ml in PBS, with 25 µl/well, and was incubated at 4° C. overnight. The plates were then washed three times with PBS, and blocked with 1% Nonfat dry milk in PBS, 50 µl/well, and then were incubated at room temp for 1 hr. After a second wash with PBS, MAbs were added at the indicated concentrations in triplicate, and the plates were incubated at room temp for 1 hour. After another wash with PBS, to each well was added 25 µl of a 1/5000 dilution of horseradish peroxidase (HRP) conjugated goat anti-human IgG Fc (Pierce) in PBS/1% Milk, and the plates were left at room temp for 1 hr. After the final PBS wash, the HRP substrate 1—Step™ Ultra-TMB-ELISA (Pierce) was added at 25 µl/well, and the reaction proceeded in the dark at room temp. The assay was stopped with 25 µl/well 1N $H_2SO_4$, and light absorbance at 450 nm (A450) was read on a SpectroMax Plus plate reader. Data are normalized to the absorbance of MAb 8I10 binding at 10 µg/ml. Results are shown in FIGS. 2A and 2B.

Example 6

Binding of Human Anti-Influenza Monoclonal Antibodies to Full-Length M2 Variants M2 variants (including those with a high pathology phenotype in vivo) were selected for analysis. See FIG. 3A for sequences.

Figures 1, 3B:
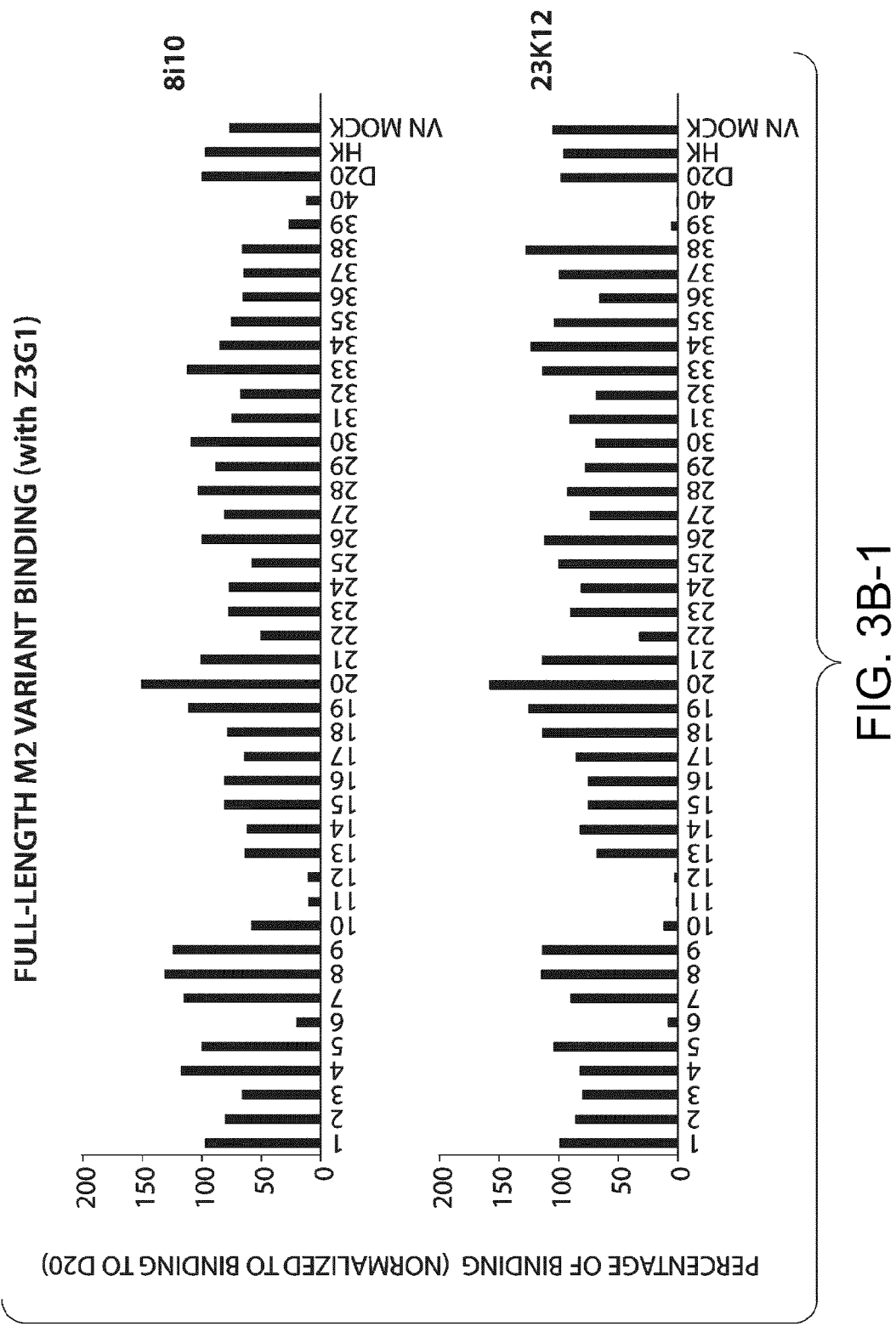
Figures 2, 3B:
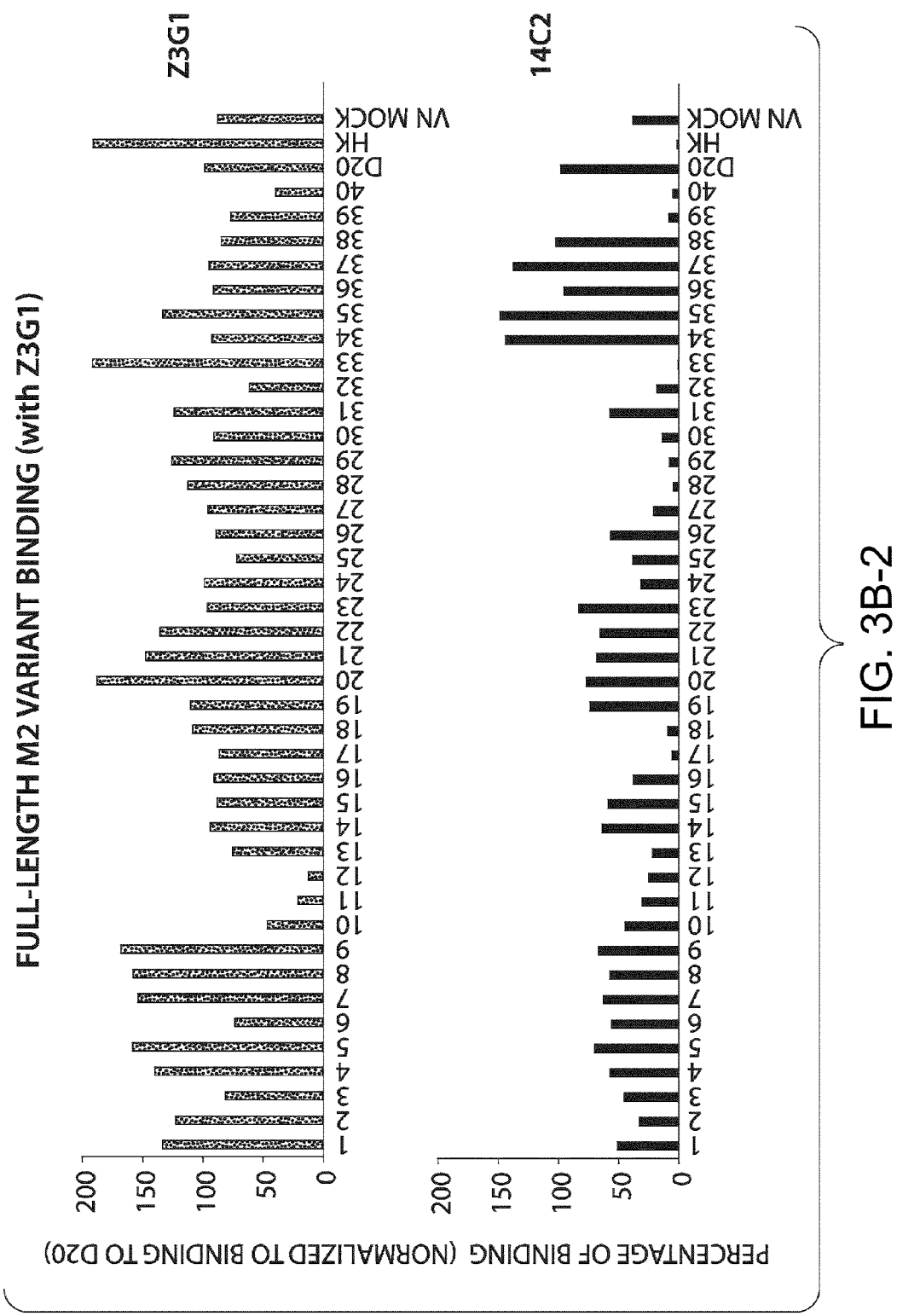
FIG. 3A is a chart showing amino acid sequences of extracellular domains of M2 variants. (SEQ ID NOS 1-3, 679 & 5-40, respectively, in order of appearance), FIGS. 3B and C are bar charts showing binding of human monoclonal anti-influenza antibody binding to M2 variants shown in FIG. 3A.
Figures 1, 3C:
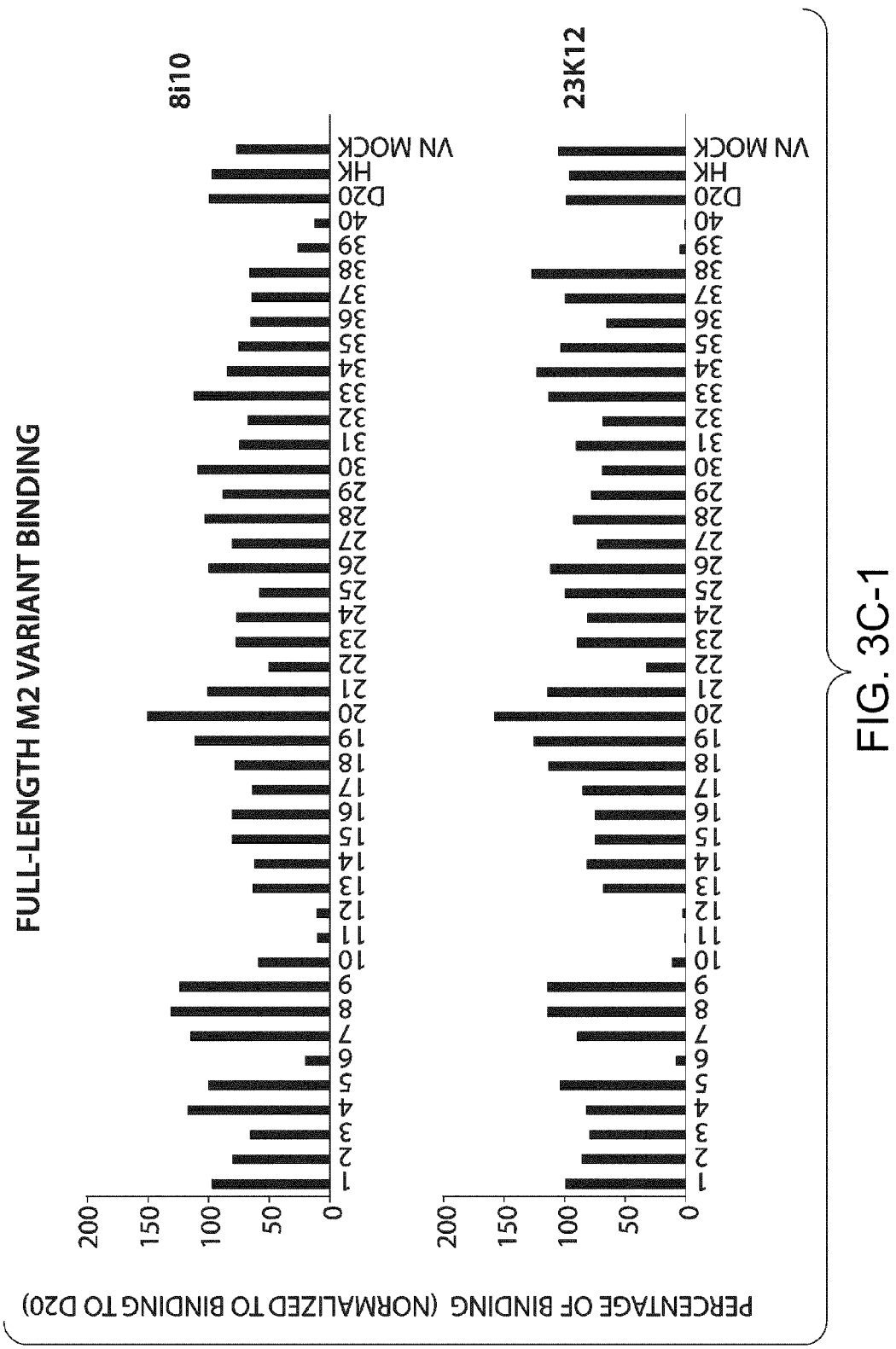
Figures 2, 3C:
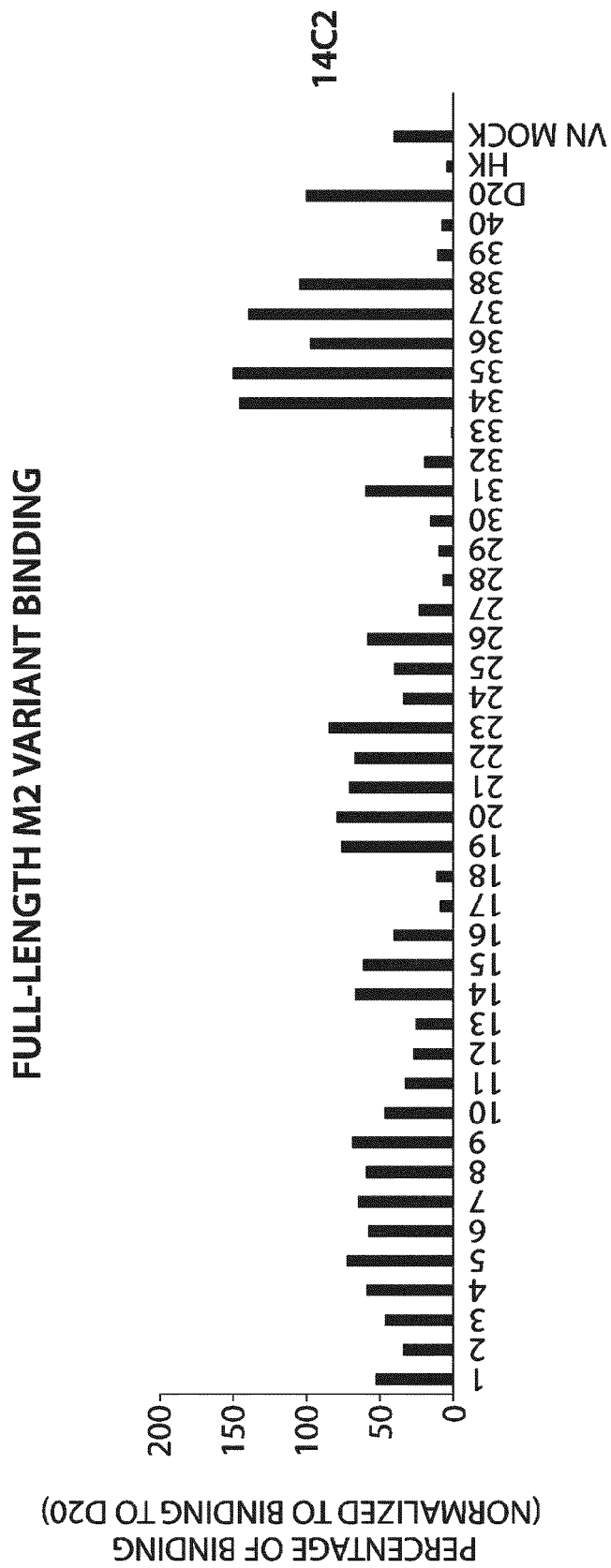

M2 cDNA constructs were transiently transfected in HEK293 cells and analyzed as follows: To analyze the transient transfectants by FACS, cells on 10 cm tissue culture plates were treated with 0.5 ml Cell Dissociation Buffer (Invitrogen), and harvested. Cells were washed in PBS containing 1% FBS, 0.2% $NaN_3$ (FACS buffer), and resuspended with 0.6 ml FACS buffer supplemented with 100 µg/ml rabbit IgG. Each transfectant was mixed with the indicated MAbs at 1 µg/ml in 0.2 ml FACS buffer, with $5 \times 10^5$ to $10^6$ cells per sample. Cells were washed three times with FACS buffer, and each sample was resuspended in 0.1 ml containing 1 µg/ml alexafluor (AF) 647-anti human IgG H&L (Invitrogen). Cells were again washed and flow cytometry was performed on a FACSCanto device (Becton-Dickenson). The data is expressed as a percentage of the mean fluorescence of the M2-D20 transient transfectant. Data for variant binding are representative of 2 experiments. Data for alanine mutants are average readouts from 3 separate experiments with standard error. Results are shown in FIGS. 3B and 3C.

Example 7

Alanine Scanning Mutagenesis to Evaluate M2 Binding

To evaluate the antibody binding sites, alanine was substituted at individual amino acid positions as indicated by site-directed mutagenesis.

Figure 4A:
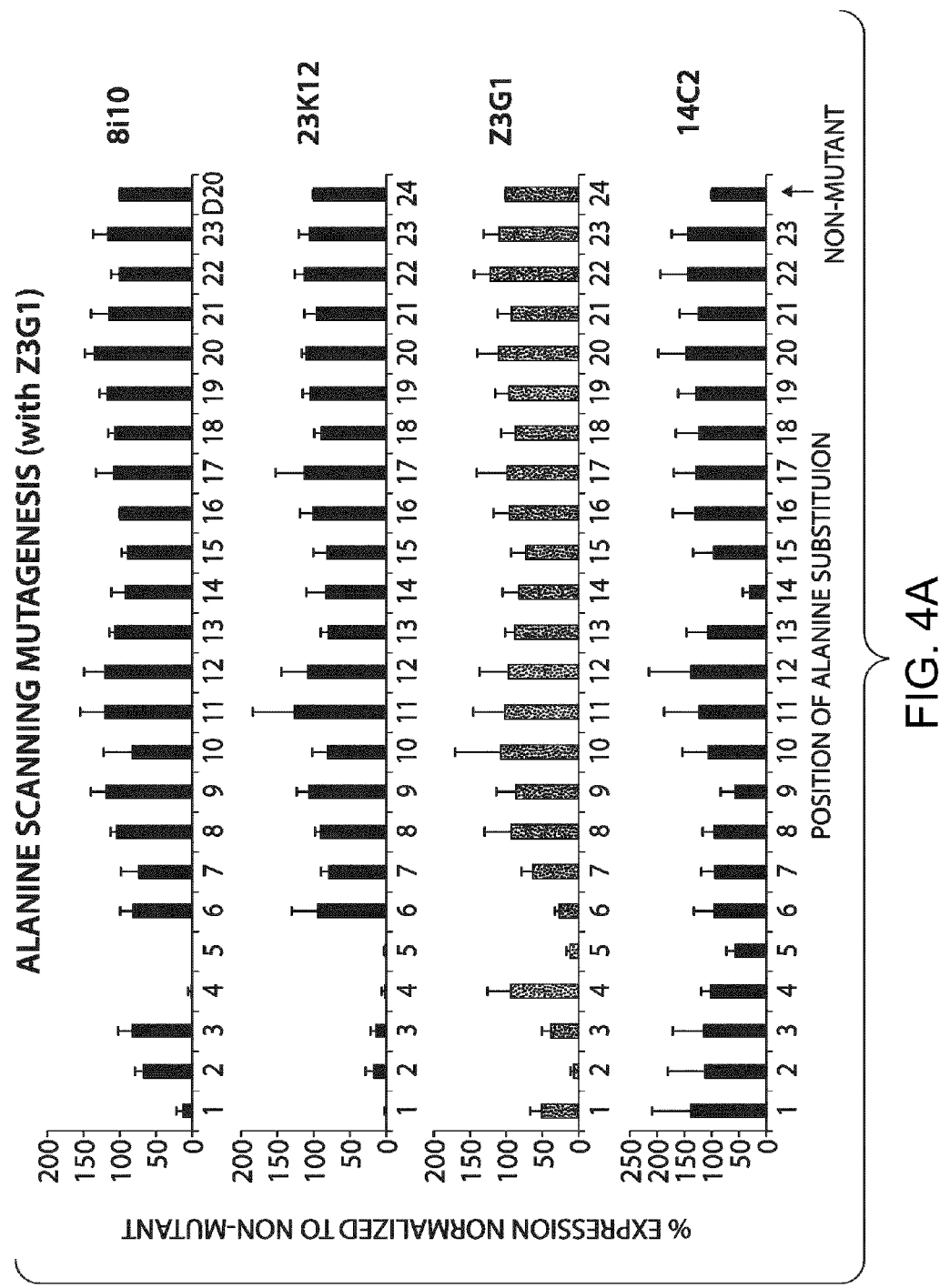
FIGS. 4A and B are bar charts showing binding of human monoclonal anti-influenza antibody binding to M2 peptides subjected to alanine scanning mutagenesis.
Figure 4B:
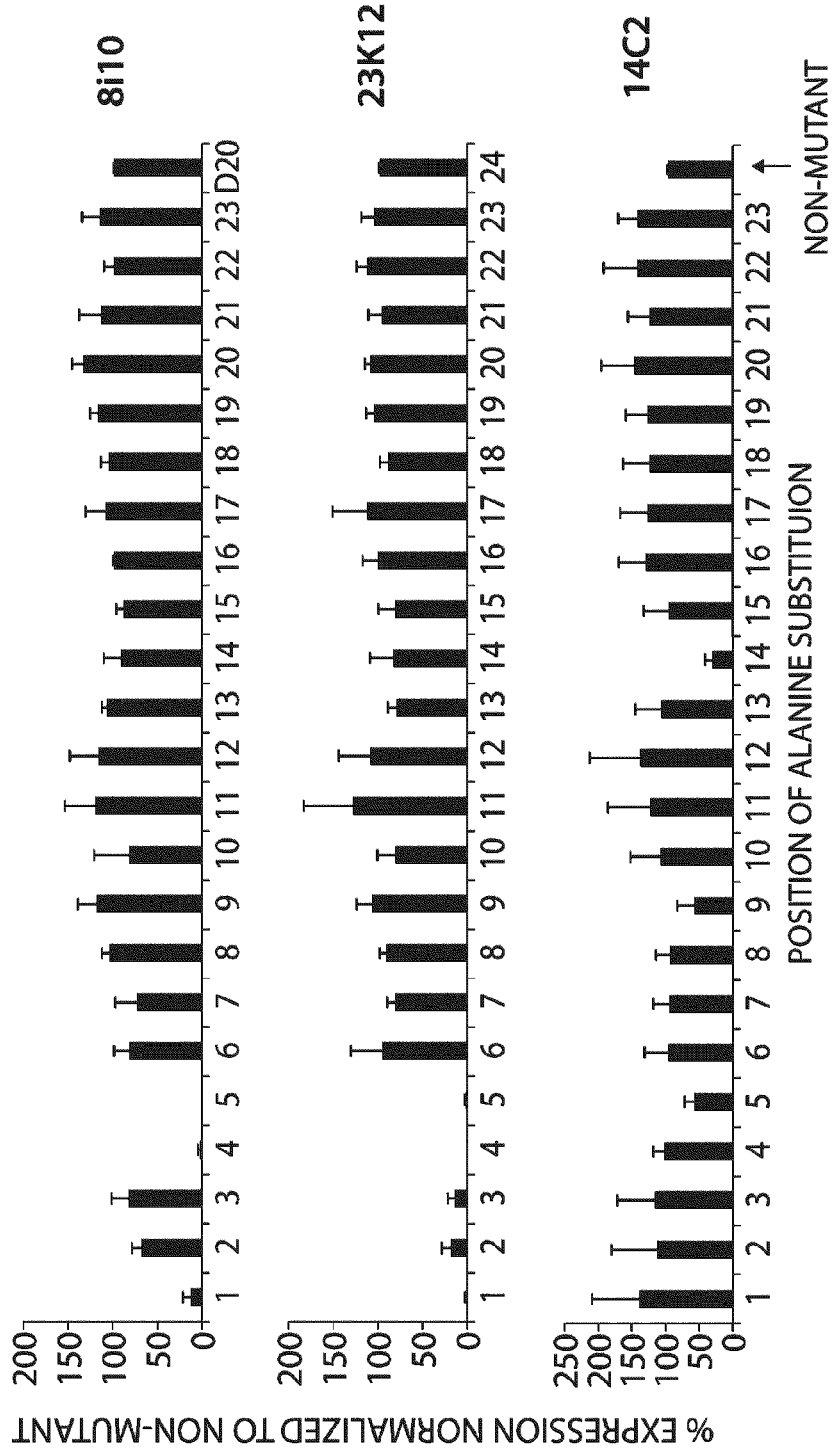
Figure 8:
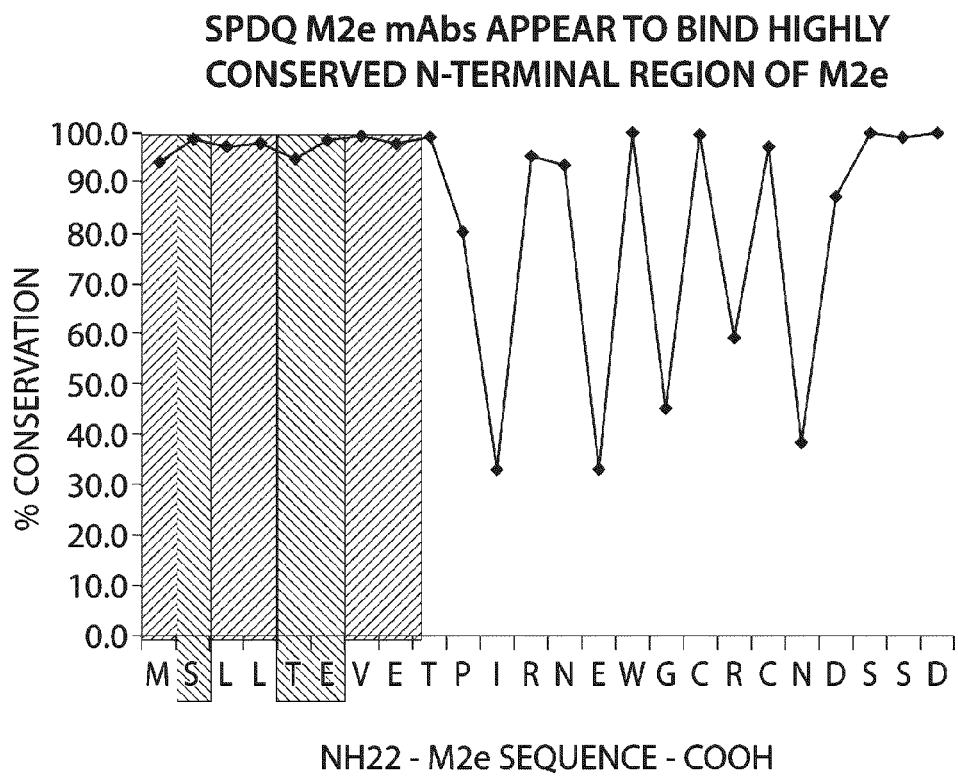
FIG. 8 is an illustration showing the anti-M2 antibodies bind a highly conserved region in the N-Terminus of M2e. (SEQ ID NO: 19)

M2 cDNA constructs were transiently transfected in HEK293 cells and analyzed as described above in Example 6. Results are shown in FIGS. 4A and 4B. FIG. 8 shows that the epitope is in a highly conserved region of the amino terminus of the M2 polypeptide. As shown in FIGS. 4A, 4B and FIG. 8, the epitope includes the serine at position 2, the threonine at position 5 and the glutamic acid at position 6 of the M2 polypeptide.

Example 8

Epitope Blocking

Figure 5:
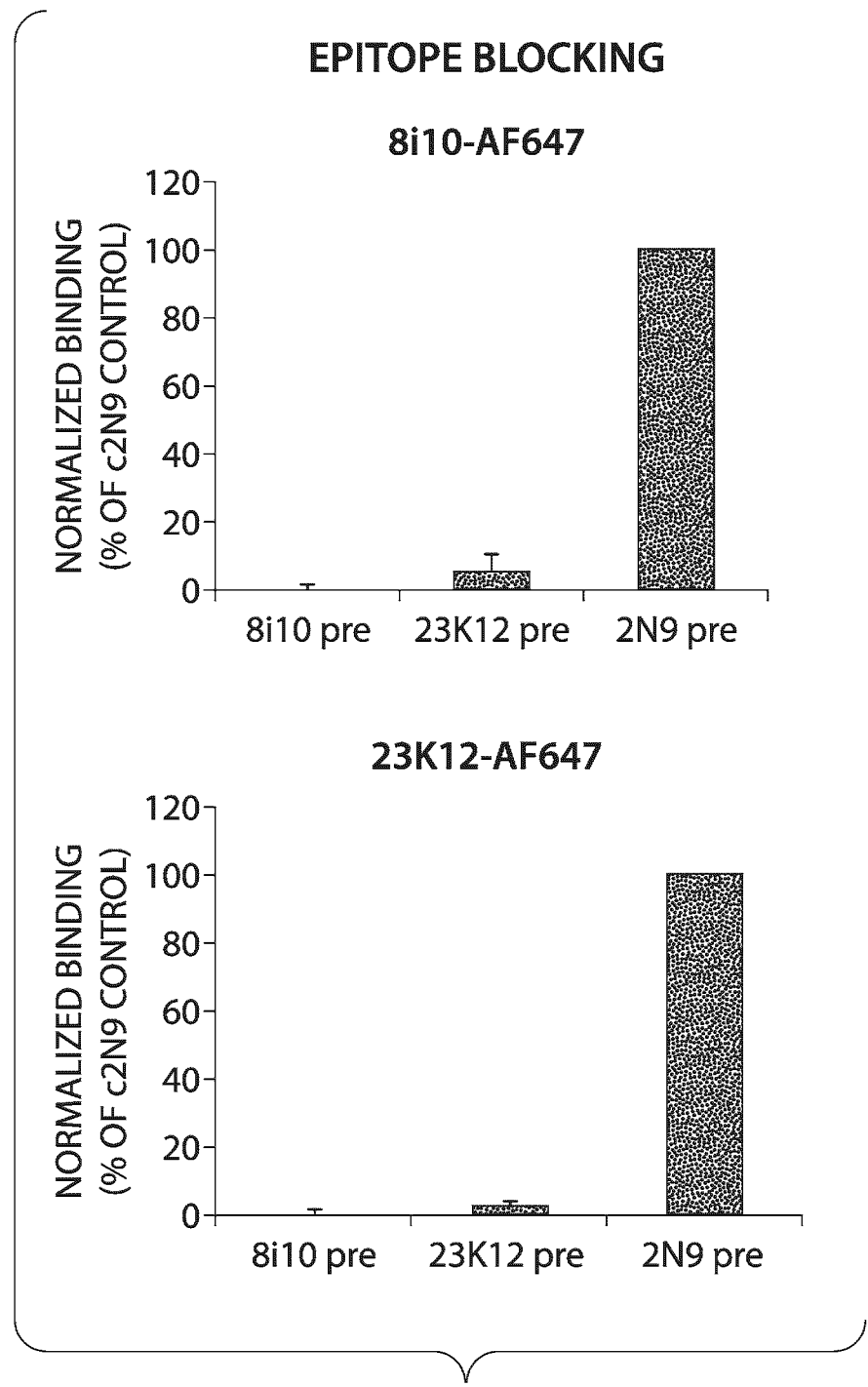
FIG. 5 is a series of bar charts showing binding of MAbs 8i10 and 23K12 to M2 protein representing influenza strain A/HK/483/1997 sequence that was stably expressed in the CHO cell line DG44.

To determine whether the MAbs 8I10 and 23K12 bind to the same site, M2 protein representing influenza strain A/HK/483/1997 sequence was stably expressed in the CHO (Chinese Hamster Ovary) cell line DG44. Cells were treated with Cell Dissociation Buffer (Invitrogen), and harvested. Cells were washed in PBS containing 1% FBS, 0.2% $NaN_3$ (FACS buffer), and resuspended at $10^7$ cells/ml in FACS buffer supplemented with 100 µg/ml rabbit IgG. The cells were pre-bound by either MAb (or the 2N9 control) at 10 µg/ml for 1 hr at 4° C., and were then washed with FACS buffer. Directly conjugated AF647-8I10 or -23K12 (labeled with the AlexaFluor® 647 Protein Labeling kit (Invitrogen) was then used to stain the three pre-blocked cell samples at 1 µg/ml for $10^6$ cells per sample. Flow cytometric analyses proceeded as before with the FACSCanto. Data are average readouts from 3 separate experiments with standard error. Results are shown in FIG. 5.

Example 9

Binding of Human Anti-Influenza Monoclonal Antibodies to M2 Variants and Truncated M2 Peptides The cross reactivity of mAbs 8i10 and 23K12 to other M2 peptide variants was assessed by ELISA. Peptide sequences are shown in FIGS. 6A and 6B. Additionally, a similar ELISA assay was used to determine binding activity to M2 truncated peptides.

In brief, each peptide was coated at 2 µg/mL to a flat bottom 384 well plate (Nunc) in 25 µL/well of PBS buffer overnight at 4° C. Plates were washed three times and blocked with 1% Milk/PBS for one hour at room temperature. After washing three times, MAb titers were added and incubated for one hour at room temperature. Diluted HRP conjugated goat anti-human immunoglobulin FC specific (Pierce) was added to each well after washing three times. Plates were incubated for one hour at room temperature and washed three times. 1-Step™ Ultra-TMB-ELISA (Pierce) was added at 25 µl/well, and the reaction proceeded in the dark at room temp. The assay was stopped with 25 µl/well 1N $H_2SO_4$, and light absorbance at 450 nm (A450) was read on a SpectroMax Plus plate reader. Results are shown in FIGS. 6A and 6B.

Example 10

In Vivo Evaluation of the Ability of Human Anti-Influenza Monoclonal Antibodies to Protect from Lethal Viral Challenge The ability of antibodies, 23K12 and 8I10, to protect mice from lethal viral challenge with a high path avian influenza strain was tested.

Figure 7:
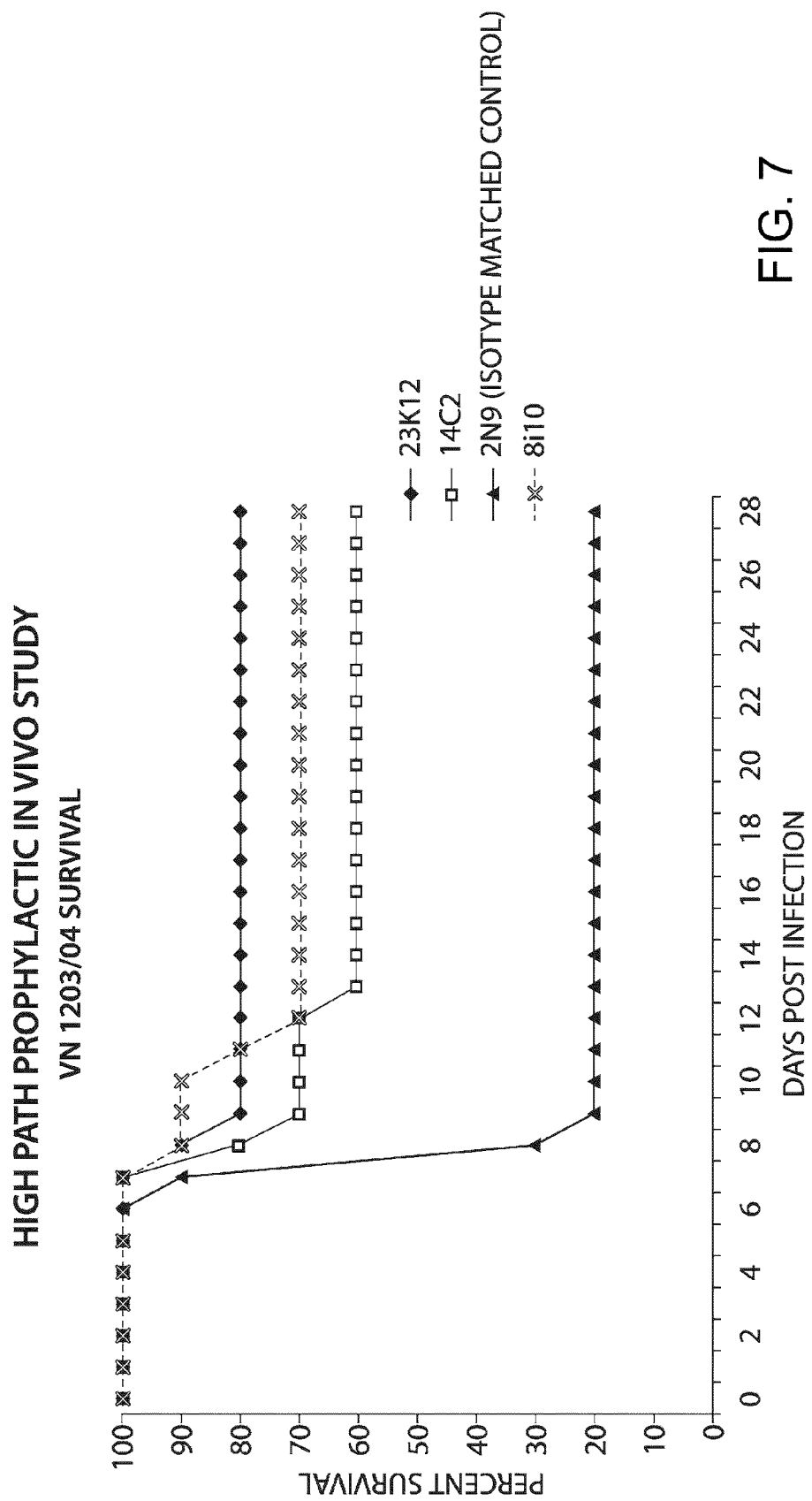
FIG. 7 is a graph showing survival of influenza infected mice treated with human anti-influenza monoclonal antibodies.

Female BALB/c mice were randomized into 5 groups of 10. One day prior (Day −1 (minus one)) and two days post infection (Day +2 (plus two)), 200 ug of antibody was given via 200 ul intra-peritoneal injection. On Day 0 (zero), an approximate LD90 (lethal dose 90) of A/Vietnam/1203/04 influenza virus, in a volume of 30 μl was given intra-nasally. Survival rate was observed from Day 1 through Day 28 post-infection. Results are shown in FIG. 7.

Example 11

Characterization of M2 Antibodies TCN-032 (8I10), 21B15, TCN-031 (23K12), 3241_G23, 3244_I10, 3243_J07, 3259_J21, 3245_O19, 3244_H04, 3136_G05, 3252_C13, 3255_J06, 3420_I23, 3139_P23, 3248_P18, 3253_P10, 3260_D19, 3362_B11, and 3242_P05

FACS

Full length M2 cDNA (A/Hong Kong/483/97) were synthesized (Blue Heron Technology) and cloned into the plasmid vector pcDNA3.1 which was then transfected into CHO cells with Lipofectamine (Invitrogen) to create a stable pool of CHO-HK M2-expressing cells. For the panel of anti-M2 Mabs, 20 μl samples of supernatant from transient transfections from each of the IgG heavy and light chain combinations was used to stain the CHO-1-HK M2 stable cell line. Bound anti-M2 mabs were visualized on viable cells with Alexafluor 647-conjugated goat anti-Human IgG H&L antibody (Invitrogen). Flow cytometry was performed with a FACSCanto, and analysis on the accompanying FACSDiva software (Becton Dickenson).

ELISA

Purified Influenza A (A/Puerto Rico/8/34) inactivated by β-propiolactone (Advanced Biotechnologies, Inc.) was biotinylated (EZ-Link Sulfo-NHS-LC-Biotin, Pierce) and adsorbed for 16 hours at 4° C. to 384-well plates in 25 μl PBS that were pre-coated with neutravidin (Pierce). Plates were blocked with BSA in PBS, samples of supernatant from transient transfections from each of the IgG heavy and light chain combinations were added at a final dilution of 1:5, followed by HRP-conjugated goat anti-human Fc antibody (Pierce), and developed with TMB substrate (ThermoFisher).

The results of this analysis are shown below in Table 2.

TABLE 2

| Transfection no. | BCC well ID | Sequence ID Gamma | Sequence ID Light | FACS M2-HK MFI | Virus ELISA OD $A_{450}$ |
|---|---|---|---|---|---|
| 322 | 3241_G23 | G4_005 | K1_004 | 1697 | 3.02 |
| 352 | 3244_I10 | G4_007 | K2_006 | 434 | 3.01 |
| 339 | 3243_J07 | G4_007 | K1_007 | 131 | 2.94 |
| 336 | 3259_J21 | G4_005 | K2_005 | 1673 | 2.40 |
| 348 | 3245_O19 | G3_004 | K1_001 | 919 | 3.51 |
| 345 | 3244_H04 | G3_003 | K1_006 | 963 | 3.31 |
| 346 | | Pos Cont (HC) | Pos Cont (LC) | 754 | 2.69 |
| 347 | | Neg Cont (HC) | Neg Cont (LC) | 11 | 0.15 |
| 374 | 3136_G05 | G4_007 | K1_007 | 109 | ND |
| 386 | 3252_C13 | G4_013 | K1_002 | 449 | ND |
| 390 | 3255_J06 | G4_013 | K2_007 | 442 | ND |
| 400 | 3420_I23 | G4_004 | K1_003 | 112 | ND |
| 432 | 3139_P23 | G4_016 | K1_007a | 110 | 1.02 |
| 412 | 3248_P18 | G4_009 | K1_006 | 967 | 0.56 |
| 413 | 3253_P10 | G4_007 | K1_004 | 43 | 0.50 |
| 434 | 3260_D19 | G3_004a | K2_001 | 846 | 2.46 |
| 439 | 3362_B11 | G4_010a | K1_007 | 218 | 1.83 |
| 408 | 3242_P05 | G3_005 | K2_004 | 596 | 0.50 |
| 451 | | Pos Cont (HC) | Pos Cont (LC) | 1083 | 1.87 |
| 452 | | Neg Cont (HC) | Neg Cont (LC) | 6 | 0.05 |

Positive control: supernatant from transient transfection with the IgG heavy and light chain combination of mAb 8I10
Negative control: supernatant from transient transfection with the IgG heavy and light chain combination of mAb 2N9
MFI = mean fluorescence intensity Example 12

Human Antibodies Reveal a Protective Epitope that is Highly Conserved Among Human and Non-Human Influenza A Viruses Influenza remains a serious public health threat throughout the world. Vaccines and antivirals are available that can provide protection from infection. However, new viral strains emerge continuously, because of the plasticity of the influenza genome which necessitates annual reformulation of vaccine antigens, and resistance to antivirals can appear rapidly and become entrenched in circulating virus populations. In addition, the spread of new pandemic strains is difficult to contain due to the time required to engineer and manufacture effective vaccines. Monoclonal antibodies that target highly conserved viral epitopes might offer an alternative protection paradigm. Herein we describe the isolation of a panel of monoclonal antibodies derived from the IgG⁺ memory B cells of healthy, human subjects that recognize a previously unknown conformational epitope within the ectodomain of the influenza matrix 2 protein, M2e. This antibody binding region is highly conserved in influenza A viruses, being present in nearly all strains detected to date including highly pathogenic viruses that infect primarily birds and swine, and the current 2009 swine-origin H1N1 pandemic strain (S-OIV). Furthermore, these human anti-M2e monoclonal antibodies protect mice from lethal challenges with either H5N1 or H1N1 influenza viruses. These results suggest that viral M2e can elicit broadly cross-reactive and protective antibodies in humans. Accordingly, recombinant forms of these human antibodies may provide useful therapeutic agents to protect against infection from a broad spectrum of influenza A strains.

Introduction

Seasonal influenza epidemics hospitalize more than 200,000 people each year in the US and kill an estimated 500,000 worldwide (1). The immune system affords only partial protection from seasonal strains in most individuals because of constantly arising point mutations in the viral genome which lead to structural variability known as antigenic drift. Pandemic strains encounter even less immune resistance due to genomic reassortment events among different viruses which result in more radical shifts in viral antigenic determinants. Consequently, pandemic influenza has the potential to cause widespread illness, death, and economic disruption. Vaccines and antiviral agents are available to counter the threat of influenza epidemics and pandemics. However, the strain composition of influenza vaccines must be determined prior to the influenza season on an annual basis, and predicting in advance which strains will become dominant is challenging. Moreover, the emergence of strains that evade vaccine-induced, protective immune responses is relatively rapid which often results in inadequate protection (2). Antiviral drugs include oseltamivir and zanamivir which inhibit the function of the viral protein neuraminidase (NA), and adamantanes which inhibit the ion channel function of the viral M2 protein (3, 4). Antiviral agents are effective for sensitive virus strains but viral resistance can develop quickly and has the potential to render these drugs ineffective. In the 2008-2009 US influenza season nearly 100% of seasonal H1N1 or H3N2 influenza isolates tested were resistant to oseltamivir or adamantane antivirals, respectively (CDC Influenza Survey: www.cdc.gov/flu/weekly/weeklyarchives2008-2009/weekly23.htm).

Passive immunotherapy using anti-influenza antibodies represents an alternative paradigm for preventing or treating viral infection. Evidence for the utility of this approach dates back nearly 100 years when passive serum transfer was used during the 1918 influenza pandemic with some success (5). While protection provided by anti-influenza monoclonal antibodies (mAbs) is typically narrow in breadth because of the antigenic heterogeneity of influenza viruses, several groups have recently reported protective mAbs that bind to conserved epitopes within the stem region of viral hemagglutinin (HA) (6, 7, 8, 44). These epitopes appear to be restricted to a subset of influenza viruses; these anti-HA mAbs would not be expected to provide protection against viruses of the H3 and H7 subtypes. Of these, the former comprises an important component of circulating human strains (9) while the latter includes highly pathogenic avian strains which have caused mortality in humans (10, 34).

Of the three antibody targets present on the surface of the influenza virus, the ectodomain of the viral M2 protein (M2e) is much more highly conserved than either HA or NA which makes it an attractive target for broadly protective mAbs. Monoclonal antibodies to M2e have been shown to be protective in vivo (11-13, 40, 43), and several groups have demonstrated protection against infection with vaccine strategies based on M2e (14-19). In these cases, purified M2 protein or peptides derived from M2e sequence have been used as immunogens to generate anti-M2e antibodies in animals or as vaccine candidates. In the present study, we have isolated mAbs directly from human B cells that bind to the M2 protein displayed on virus particles and on virus-infected cells. Further, we demonstrate that these antibodies protect mice from a lethal influenza A virus challenge and that they can recognize M2 variants derived from a wide range of human and animal influenza A virus isolates. This combination of properties may enhance the utility of these antibodies to prevent and treat influenza A virus infections.

Results and Discussion

Figure 12B:
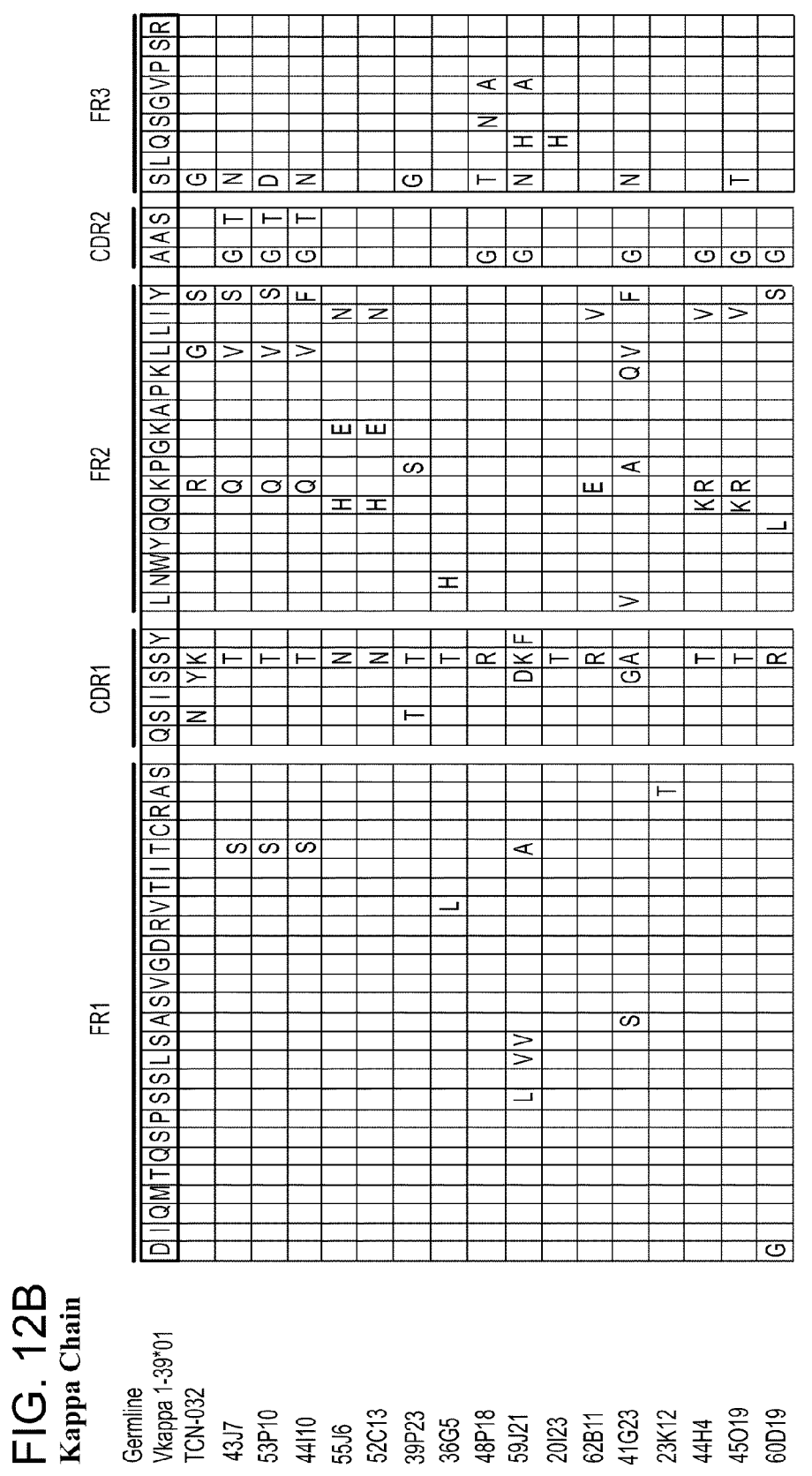
Figure 13:
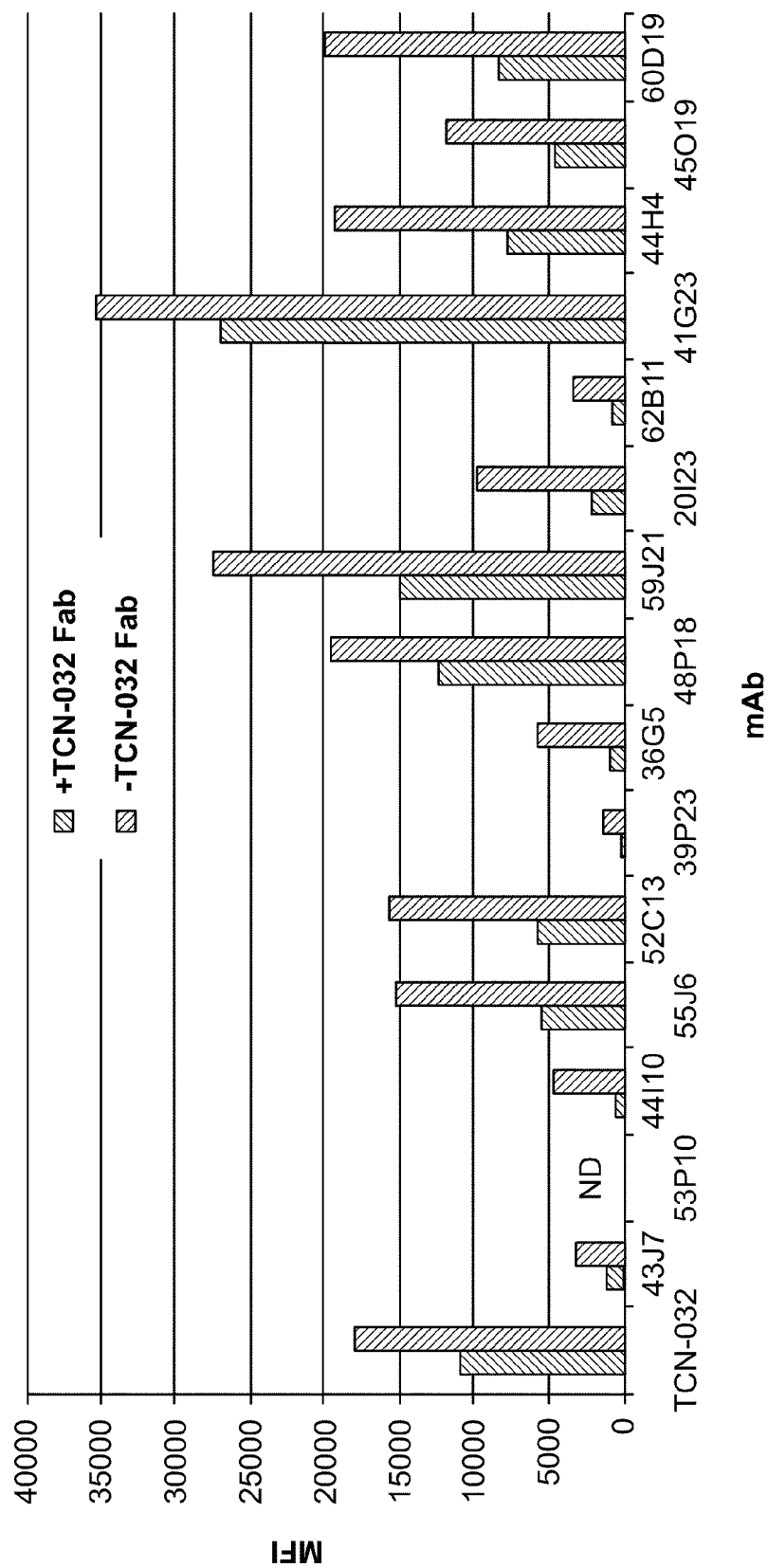
FIG. 13 is a graph depicting the results of a competition binding analysis of a panel of anti-M2e mAbs with TCN-032 Fab. The indicated anti-M2e mAbs were used to bind to the stable CHO transfectant expressing M2 of A/Hong Kong/483/97 that had previously been treated with or without 10 µg/mL TCN-032 Fab fragment. The anti-M2e mAb bound to the cell surface was detected with goat anti-huIgG FcAlex-afluor488 FACS and analyzed by flow cytometry. The results are derived from one experiment.

Isolation of a Family of Anti-M2e mAbs from Human B Cells. To explore the humoral immune response to natural influenza infection in humans, we have isolated antibodies from IgG$^+$ memory B cells of M2e-seropositive subjects. Serum samples from 140 healthy adult, United States-sourced donors were tested for reactivity with M2e expressed on the surface of HEK293 cells that were transfected with a viral M2 gene (derived from A/Fort Worth/50 H1N1). IgG$^+$ memory B cells from 5 of the 23 M2e-seropositive subjects were cultured under conditions where they proliferated and differentiated into IgG-secreting plasma cells. B cell culture wells were screened for IgG reactivity to cell-surface M2e and immunoglobulin heavy and light chain variable region ($V_H$ and $V_L$) genes were rescued by RT-PCR from 17 positive wells and incorporated into a human IgG1 constant region background for recombinant expression and purification. $V_H$ and $V_L$ sequences of 15 of the 17 anti-M2e mAbs cluster into two related groups (Table 3) (IMGT®, the International ImMunoGeneTics Information system®, available at www.imgt.org). In group A, assignment of the germline VH gene segment is IGHV4-59*01 while in the group B, the germline gene segment is IGHV3-66*01. The two more distantly related mAbs 62B11 and 41G23 (group C) utilize the germline V gene segment IGHV4-31*03 which has only 5 amino acid residue differences from the germline V gene segment IGHV4-59*01 of group A. All of these mAbs utilize the same light chain V gene, IGKV1-39*01 or its allele IGKV1D-39*01 and show evidence of somatic hypermutation from the germline heavy or kappa chain sequence (FIG. 12). Competitive binding experiments showed that all of these human mAbs appear to bind similar sites on native M2e expressed on the surface of Chinese hamster ovary (CHO) cells (FIG. 13). We selected for further characterization one mAb from each of groups A and B, designated TCN-031 and TCN-032, respectively.

TABLE 3

Immunoglobulin gene segment usage of human anti-M2e antibodies.

| | mAb | Heavy chain germline gene segments | | | Light chain germline gene segments | |
| | | Variable | Diversity | Joining | Variable | Joining |
|---|---|---|---|---|---|---|
| Group A | TCN-032 | IGHV4-59*01 | IGHD2-15*01 | IGHJ4*02 | IGKV1-39*01, or IGKV1D-39*01 | IGKJ4*01 |
| | 43J7 | IGHV4-59*07 | IGHD1-26*01 | IGHJ4*02 | IGKV1-39*01, or IGKV1D-39*01 | IGKJ2*01 |
| | 53P10 | IGHV4-59*07 | IGHD1-26*01 | IGHJ4*02 | IGKV1-39*01, or IGKV1D-39*01 | IGKJ2*01 |
| | 44I10 | IGHV4-59*07 | IGHD1-26*01 | IGHJ4*02 | IGKV1-39*01, or IGKV1D-39*01 | IGKJ2*01 |
| | 55J6 | IGHV4-59*01 | IGHD5-18*01 | IGHJ4*02 | IGKV1-39*01, or IGKV1D-39*01 | IGKJ5*01 |
| | 52C13 | IGHV4-59*01 | IGHD5-18*01 | IGHJ4*02 | IGKV1-39*01, or IGKV1D-39*01 | IGKJ5*01 |
| | 39P23 | IGHV4-59*01 | IGHD4-23*01 | IGHJ4*01 | IGKV1-39*01, or IGKV1D-39*01 | IGKJ1*01 |
| | 36G5 | IGHV4-59*01 | IGHD2-8*01 | IGHJ6*04 | IGKV1-39*01, or IGKV1D-39*01 | IGKJ3*01 |
| | 48P18 | IGHV4-59*01 | IGHD2-15*01 | IGHJ6*02 | IGKV1-39*01, or IGKV1D-39*01 | IGKJ4*01 |
| | 59J21 | IGHV4-59*01 | IGHD2-15*01 | IGHJ6*02 | IGKV1-39*01, or IGKV1D-39*01 | IGKJ4*01 |
| | 20I23 | IGHV4-59*01 | IGHD6-6*01 | IGHJ6*02 | IGKV1-39*01, or IGKV1D-39*01 | IGKJ5*01 |
| Group C | 62B11 | IGHV4-31*03 | IGHD4-23*01 | IGHJ6*02 (a) | IGKV1-39*01, or IGKV1D-39*01 | IGKJ5*01 |
| | 41G23 | IGHV4-31*03 | IGHD3-16*01 | IGHJ6*02 | IGKV1-39*01, or IGKV1D-39*01 | IGKJ5*01 |
| Group B | TCN-031 | IGHV3-66*01 | IGHD3-10*01 | IGHJ3*01 | IGKV1-39*01, or IGKV1D-39*01 | IGKJ2*01 |
| | 44H4 | IGHV3-66*01 | Cannot assign | IGHJ6*02 | IGKV1-39*01, or IGKV1D-39*01 | IGKJ5*01 |
| | 45O19 | IGHV3-66*01 | Cannot assign | IGHJ6*02 | IGKV1-39*01, or IGKV1D-39*01 | IGKJ5*01 |
| | 60D19 | IGHV3-66*01 | Cannot assign | IGHJ6*02 | IGKV1-39*01, or IGKV1D-39*01 | IGKJ2*01 |

Reference sequences for each mAb heavy and light chain were analysed using IMGT/V-QUEST to determine gene usage.

High Affinity Binding to the Surface of Influenza Virus.

Figure 14A:
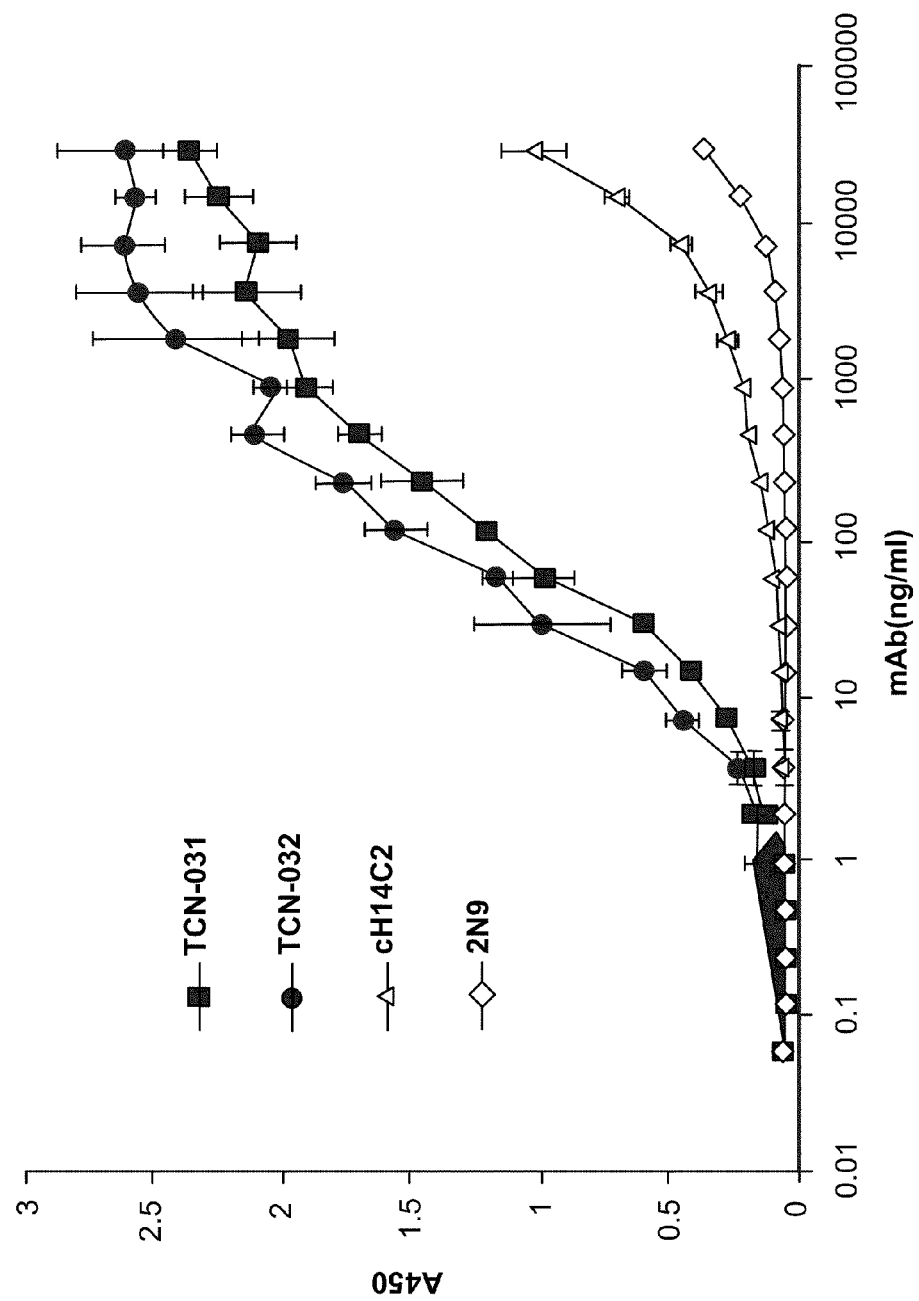
FIG. 14A is a graph depicting the ability of anti-M2e mAbs TCN-032 and TCN-031 to bind virus particles and virus-infected cells but not M2e-derived synthetic peptide. Purified influenza virus (A/Puerto Rico/8/34) was coated at 10 μg/ml on ELISA wells and binding of anti-M2e mAbs TCN-031, TCN-032, ch14C2, and the HCMV mAbs 2N9 was evaluated using HRP-labeled goat anti-human Fc. Results shown are representative of 3 experiments.
Figure 14B:
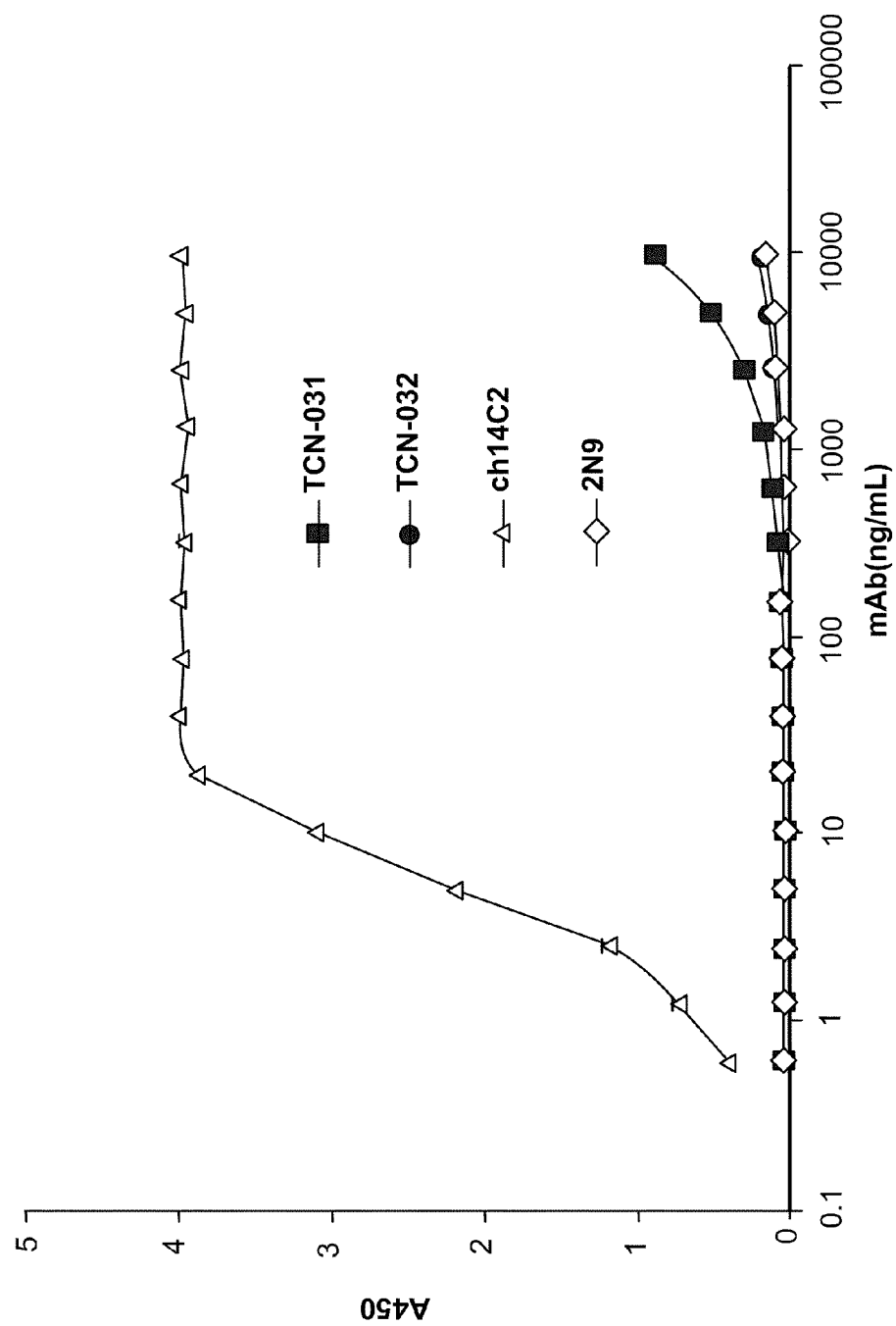
FIG. 14B is a graph depicting the ability of anti-M2e mAbs TCN-032 and TCN-031 to bind virus particles and virus-infected cells but not M2e-derived synthetic peptide. 23mer synthetic peptide of M2 derived from A/Fort Worth/1/50 was coated at 1 μg/ml on ELISA wells and binding of mAbs TCN-031, TCN-032, ch14C2, and 2N9 were evaluated as in panel a. Results shown are representative of 3 experiments.
Figure 14C:
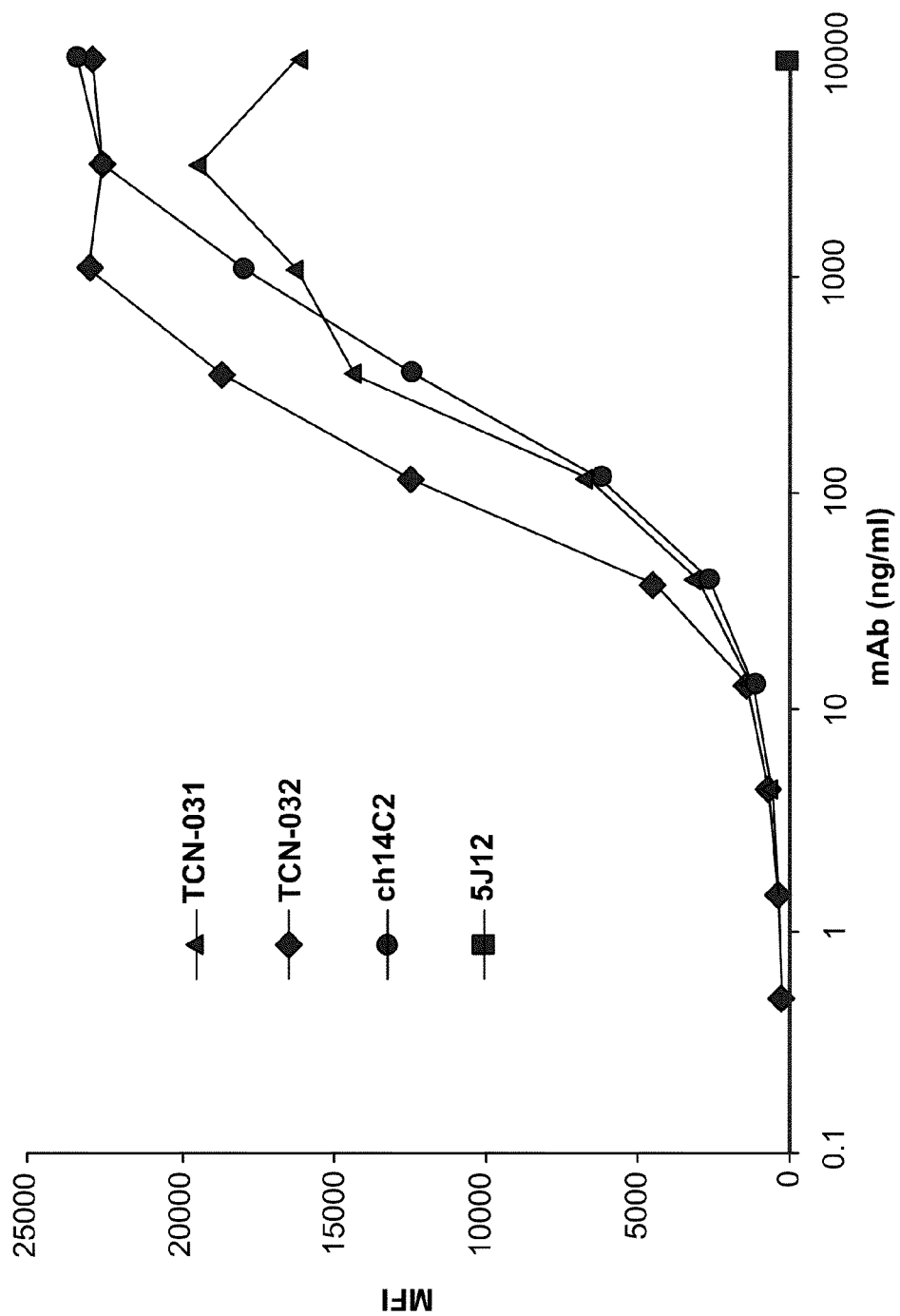
FIG. 14C is a graph depicting the ability of anti-M2e mAbs TCN-032 and TCN-031 to bind virus particles and virus-infected cells but not M2e-derived synthetic peptide. MDCK cells were infected with A/Puerto Rico/8/34 (PR8) and subsequently stained with mAbs TCN-031, TCN-032, ch14C2 and the HCMV mAb 5J12. Binding of antibodies was detected using Alexafluor 647-conjugated goat anti-Human IgG H&L antibody and quantified by flow cytometry. Results shown are representative of 3 experiments.
Figure 14D:
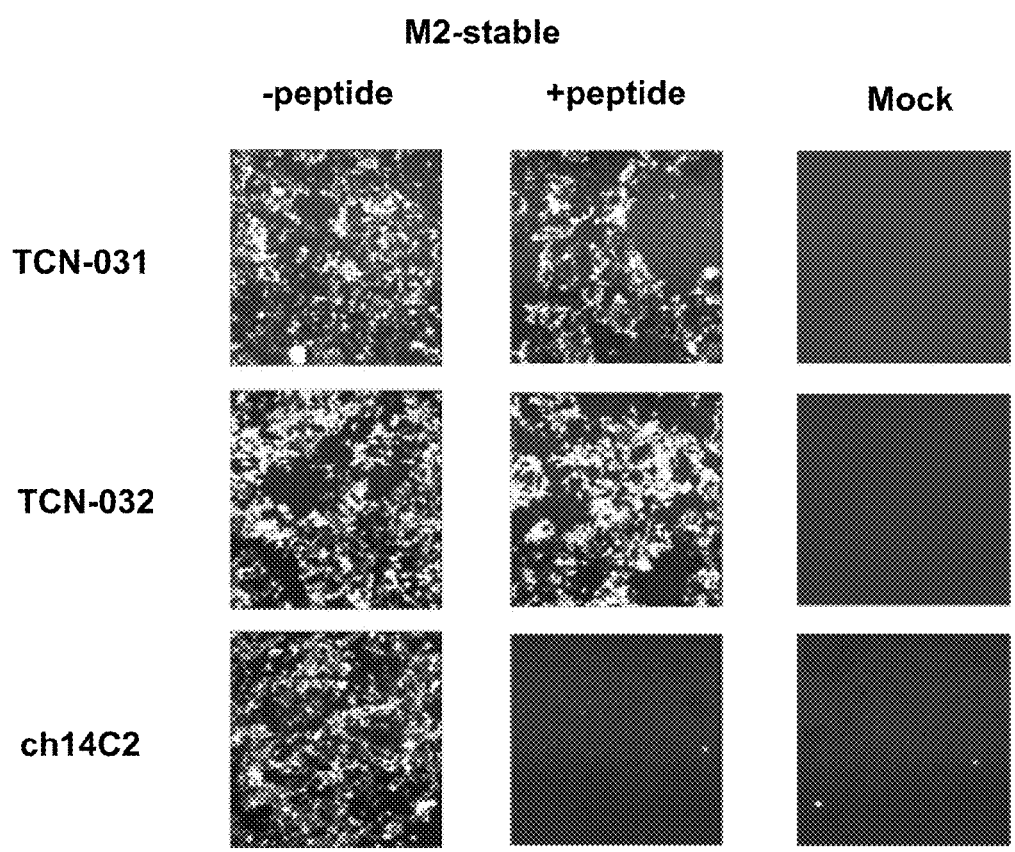
FIG. 14D is a series of photographs depicting HEK 293 cells stably transfected with the M2 ectodomain of A/Fort Worth/1/50 (D20) were stained with transient transfection supernatant containing mAbs TCN-031, TCN-032, or the control ch14C2 and analyzed by FMAT for binding to M2 in the presence or absence of 5 ug/ml M2e peptide. Mock transfected cells are 293 cells stably transfected with vector alone. Results shown are representative of one experiment.

Both TCN-031 and TCN-032 bound directly to an H1N1 virus (A/Puerto Rico/8/34) with high avidity, with half-maximal binding, at about 100 ng/mL (FIG. 14a). Fab fragments prepared from TCN-031 and TCN-032 bound virus with affinities (KD) of 14 and 3 nM, respectively, as determined by surface plasmon resonance (Table 4). The human mAbs did not bind appreciably to a 23 amino acid synthetic peptide corresponding to the M2e domain of an H1N1 virus (A/Fort Worth/1/50) (FIG. 14b). A chimeric derivative of the murine anti-M2e mAb 14C2 (ch14C2), which was originally generated by immunization with purified M2 (20), exhibited the opposite behavior to that observed with the human mAbs, with little binding to virus but robust binding to the isolated 23mer M2e peptide with half-maximal binding to peptide at 10 ng/mL (FIGS. 14a and 14b). Interestingly, both the human mAbs and ch14C2 bound to the surface of Madin-Darby canine kidney (MDCK) cells infected with H1N1 virus (A/Puerto Rico/8/34) with similar avidities (FIG. 14c). It thus appears that viral epitopes recognized by the human anti-M2e mAbs are present and accessible on the surface of both virus and infected cells, while the epitope bound by ch14C2 is accessible only on the surface of infected cells. Our observation that the human anti-M2e mAbs do not bind appreciably to immobilized synthetic peptides derived from M2e, and further that such peptides do not compete for binding of these antibodies to M2e expressed on the surface of mammalian cells (FIG. 14d), supports the idea that secondary structure within the M2e epitope is important for binding by the human antibodies. That ch14C2 binds peptide immobilized on plastic suggests a lesser importance of higher order structure for binding of this mAb.

TABLE 4

Affinity of anti-M2e Fab fragments for influenza virus.

| Fab | ka ($M^{-1} * s^{-1}$) | kd ($s^{-1}$) | KD |
|---|---|---|---|
| TCN-031 | 1.0e6 | 1.4e−2 | 14 nM |
| TCN-032 | 7.4e5 | 2.3e−3 | 3.2 nM |
| cH14C2 | 5.0e2 | 1.8e−3 | 4.0 µM |

Protection from Lethal Challenges with H5N1 and H1N1 Viruses.

Figure 15A:
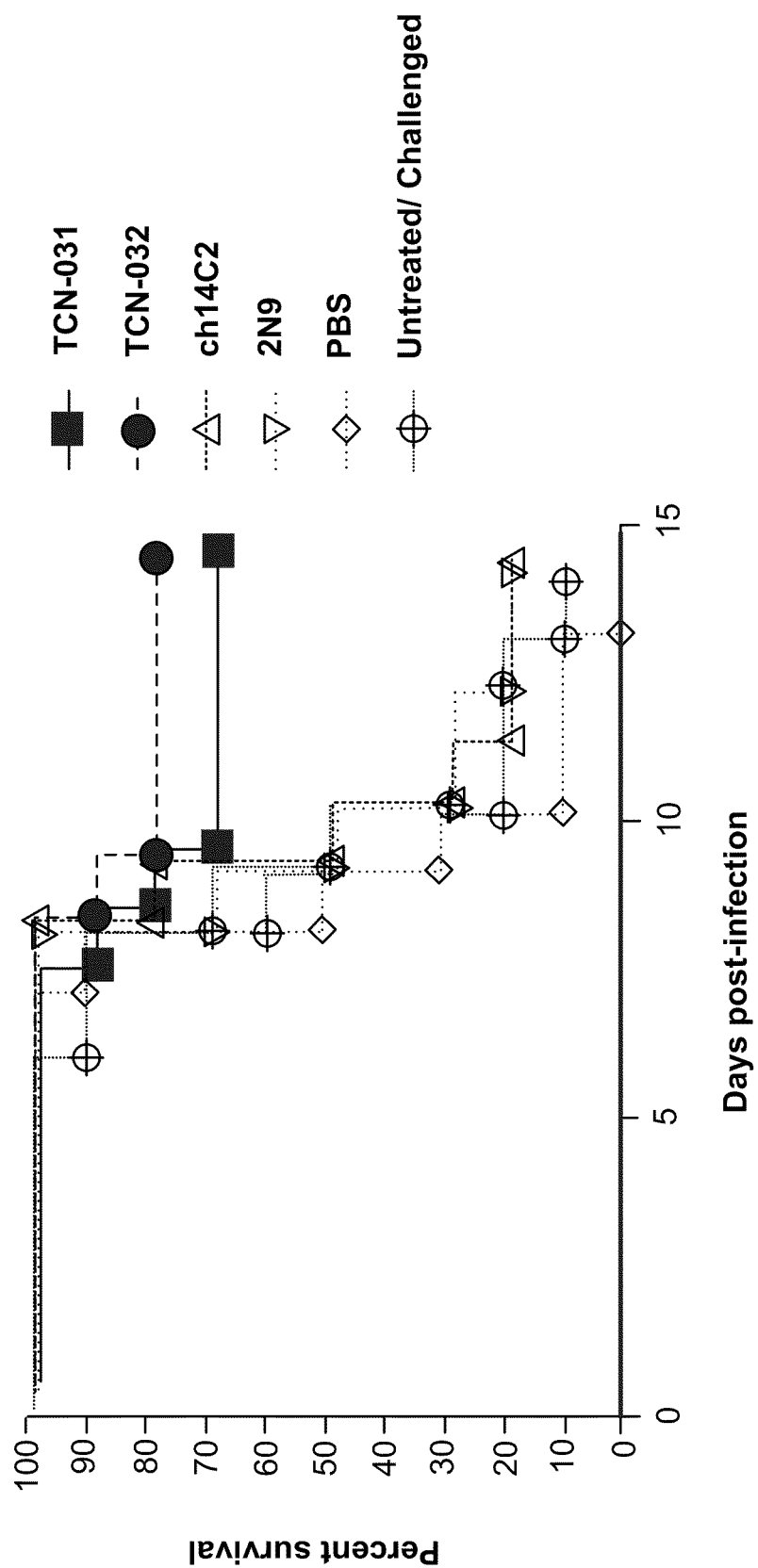
FIGS. 15A-D are graphs depicting the Therapeutic efficacy of anti-M2 mAbs TCN-031 and TCN-032 in mice. Mice (n=10) were infected by intranasal inoculation with $5 \times_{LD50}$ A/Vietnam/1203/04 (H5N1) (panels A-B) or (n=5) with $5 \times_{LD50}$ A/Puerto Rico 8/34 (H1N1) (panels C-D), followed by 3 intraperitoneal (ip) injections with mAbs at 24, 72, and 120 hours post-infection (a total of 3 mAb injections per mouse) and weighed daily for 14 days. Percentage survival is shown in a and c, whereas percent weight change of mice is shown in B and D. The results shown for the treatment study of mice infected with A/Vietnam/1203/04 (H5N1) are representative of 2 experiments.
Figure 15B:
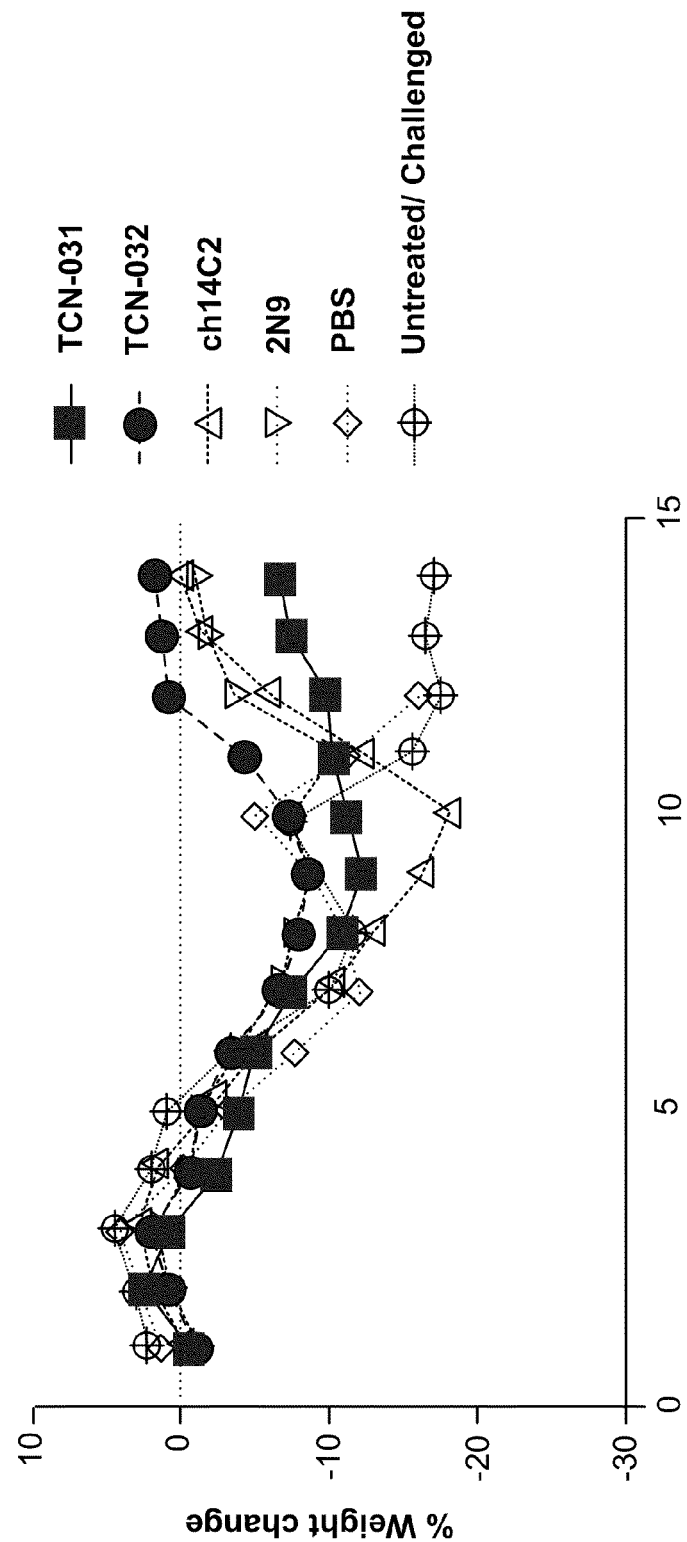
Figure 16:
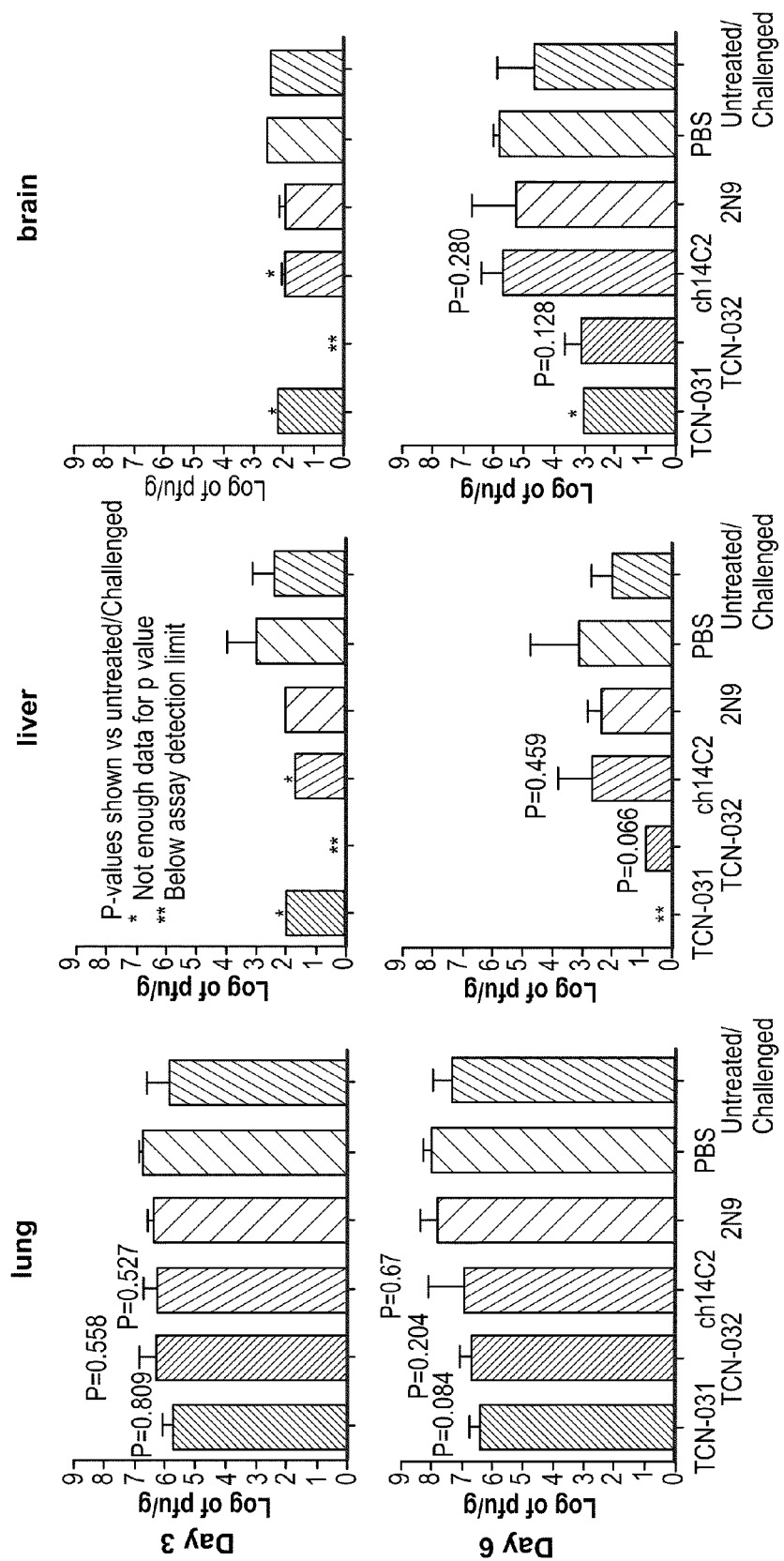
FIG. 16 is a series of graphs depicting the viral titers in lung, liver, and brain of mice treated with anti-M2e mAbs TCN-031 and TCN-032 after challenge with H5N1 A/Vietnam/1203/04. BALB/C mice (n=19) were treated i.p. injection of a 400 μg/200 μL dose of TCN-031, TCN-032, control human mAb 2N9, control chimeric mAb ch14C2, PBS, or left untreated. Tissue viral titers were determined from 3 mice per group at 3 and 6 days post-infection in the lungs (as an indicator of local replication) and in liver and brain (as an indicator of the systemic spread which is characteristic of H5N1 infection).

We next examined the protective efficacy of the human anti-M2e mAbs TCN-031 and TCN-032 in a lethal challenge model of influenza infection in mice. Animals were challenged intranasally with $5 \times LD_{50}$ units of a high-pathogenicity H5N1 virus (A/Vietnam/1203/04) and both human mAbs were protective when treatment was initiated one day after viral challenge. In contrast, mice that were subjected to similar treatment regimens with a subclass-matched, irrelevant control mAb 2N9, which targets the AD2 epitope of the gp116 portion of the human cytomegalovirus gB, or with a vehicle control were protected to a lesser extent, or not at all, resulting in 70-80% survival for mice treated with human mAbs versus 20% survival for control mAb and 0% survival for vehicle (FIG. 15a). The anti-M2e mAb ch14C2 did not confer substantial protection in this model (20% survival; FIG. 15a), though this mAb has been shown to reduce the titer of virus in the lungs of mice infected with other strains of influenza virus (40). All of the animals, including those in the TCN-031 and TCN-032 treatment groups, exhibited weight loss from days 4 to 8 post infection followed by a gradual increase in weight in the surviving animals through the end of the study on day 14 (FIG. 15b), indicating that the human anti-M2e mAbs afforded protection by reducing the severity or extent of infection rather than by completely preventing infection. Indeed, results of immunohistological and viral load analyses of lung, brain and liver tissue from additional animals in each treatment cohort are consistent with a reduction in the spread of virus beyond the lung to the brain and also possibly liver in animals that were treated with the human anti-M2e mAbs, but not with ch14C2 or the subclass-matched control mAb 2N9. The effect of the human anti-M2e mAbs on viral load in the lung versus the control mAbs was, however, more moderate (Table 5 and FIG. 16, respectively).

Figure 15C:
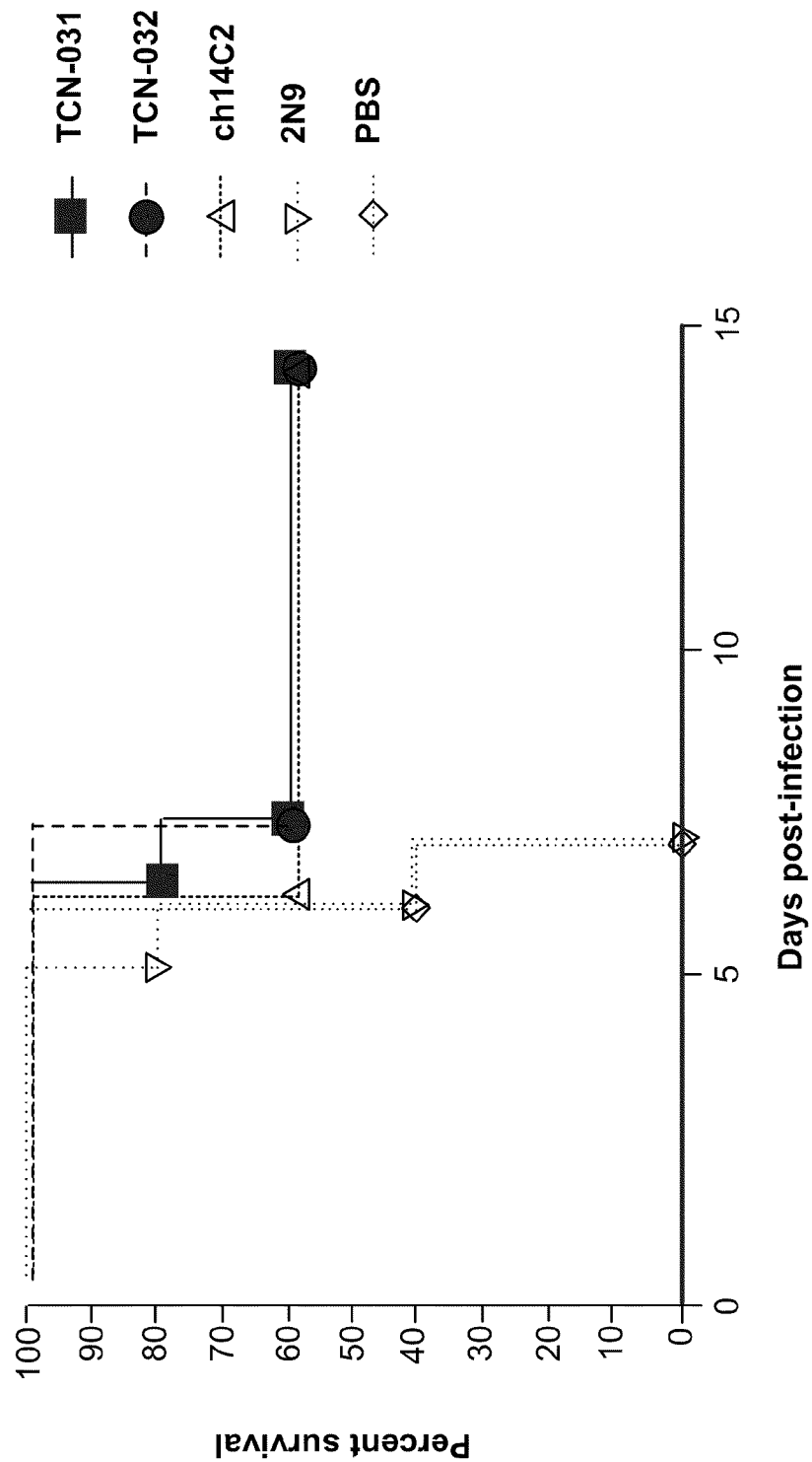
Figure 15D:
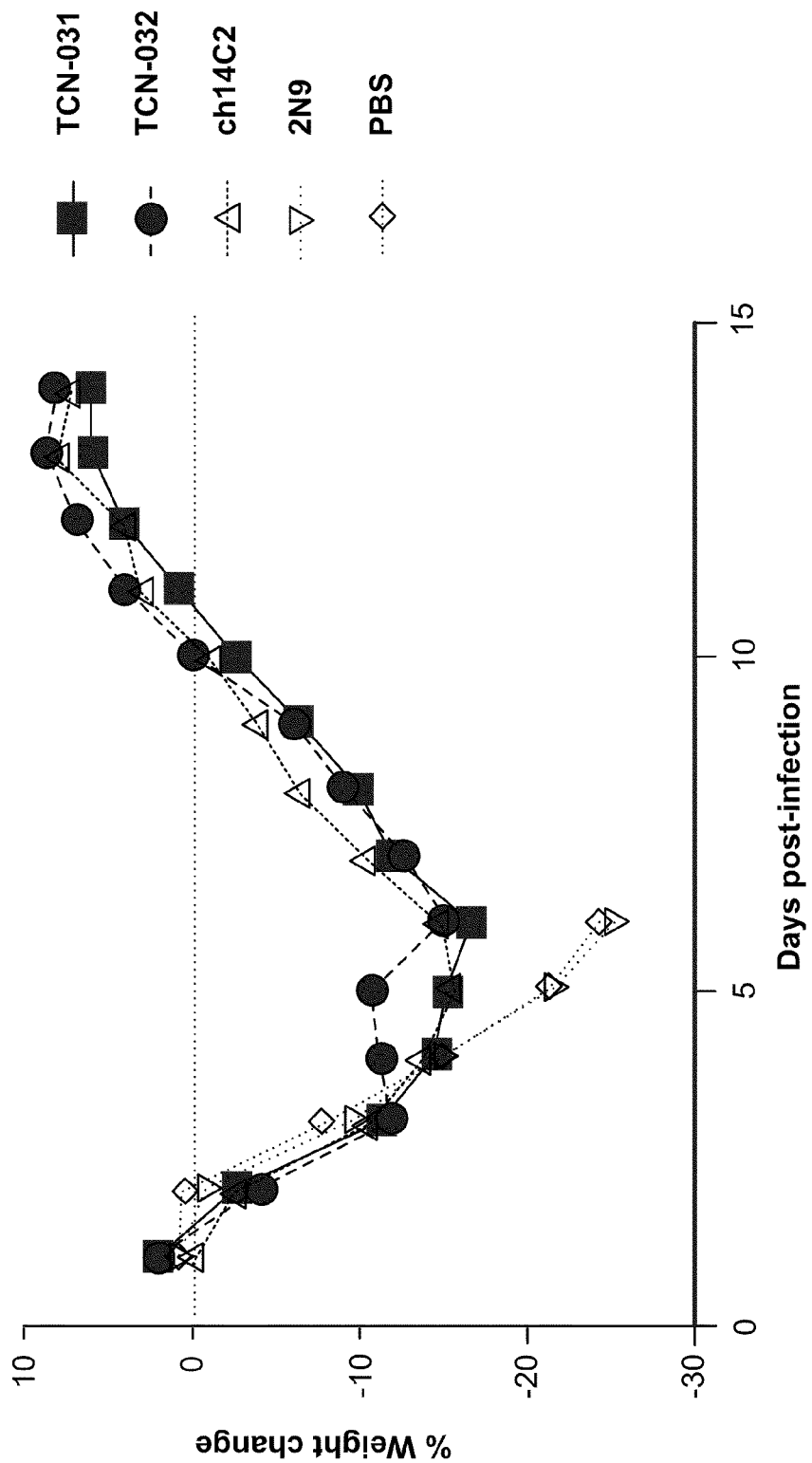
Figure 17:
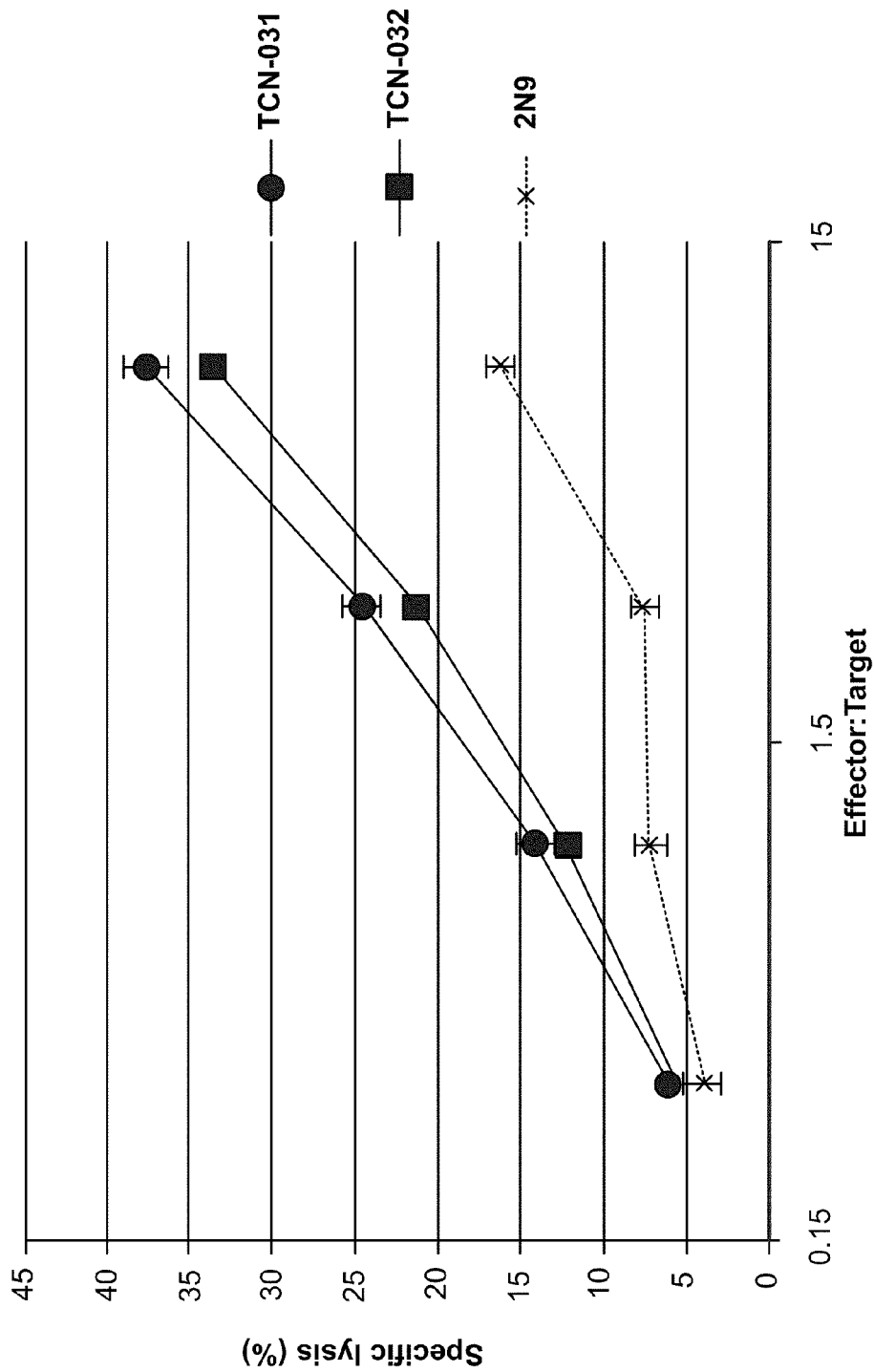
FIG. 17 is a graph depicting the ability of TCN-031 and TCN-032 can potentiate cytolysis by NK cells. MDCK cells were infected with A/Solomon Island/3/2006 (H1N1) virus, and were treated with mAbs TCN-031, TCN-032, or the subclass-matched negative control mAb 2N9. The cells were then challenged with purified human NK cells, and the lactate dehydrogenase released as a result of cell lysis was measured through light absorbance. The results are representative of two separate experiments with two different normal human donors.
Figure 18:
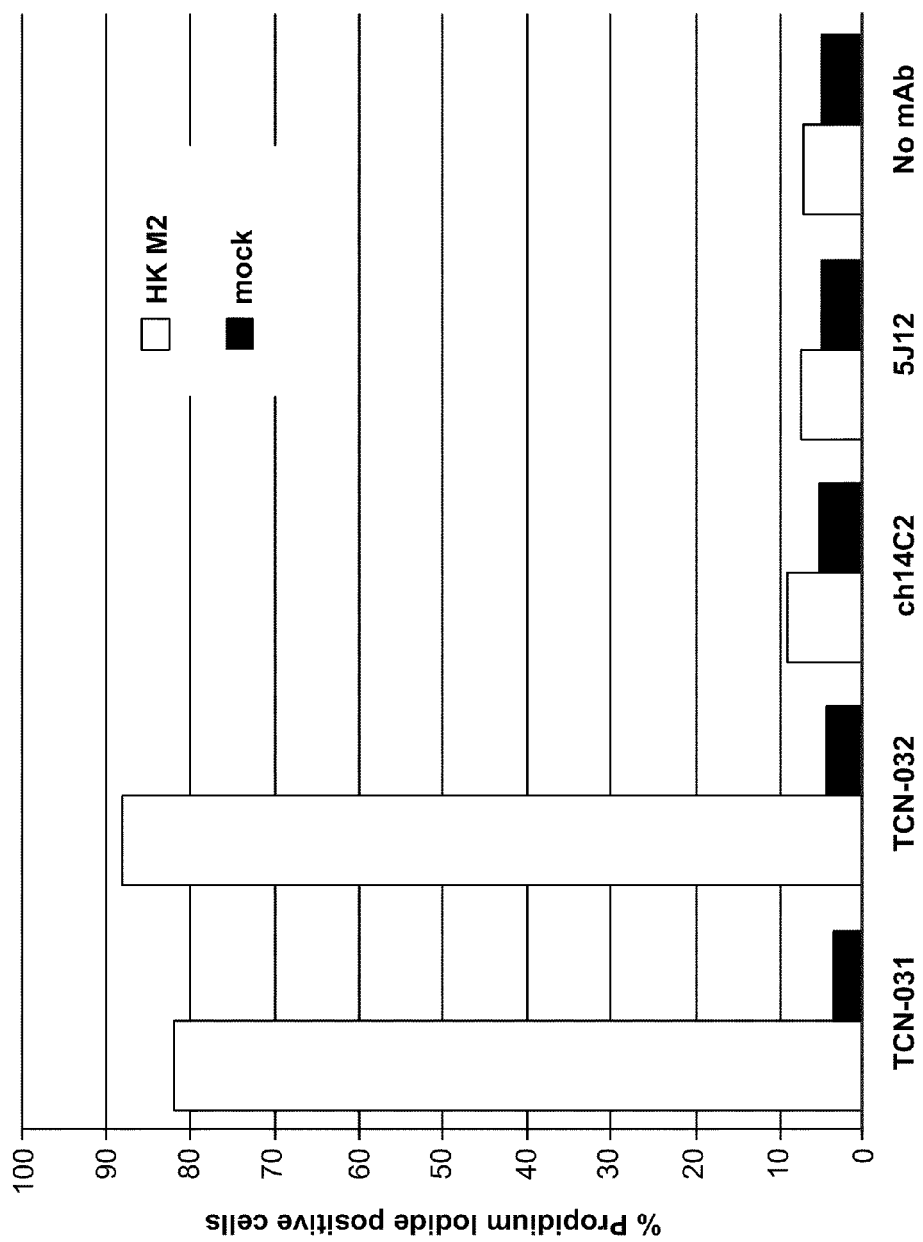
FIG. 18 is a graph depicting complement-dependent cytolysis (CDC) of M2-expressing cells bound with anti-M2 mAb. The stable transfectant expressing M2 of A/Hong Kong/483/97 and a mock control were treated with the indicated mAbs and subsequently challenged with human complement. Lysed cells were visualized by Propidium Iodide staining followed by FACS analysis. The data are representative of two experiments.

To test whether protection conferred by the human anti-M2e mAbs mirrors their broad binding behavior, we performed a similar in vivo challenge study with a mouse-adapted isolate of the relatively divergent H1N1 virus A/Puerto Rico/8/34. One hundred percent of PBS-treated or subclass-matched, control antibody-treated mice were killed by this virus, while a majority of the animals treated with the human anti-M2e mAbs TCN-031 and TCN-032 survived (60%; FIG. 15c). With this virus mice treated with ch1 4C2 provided a similar survival benefit to that of the human anti-M2e mAbs (FIG. 15c). Weight changes in each treatment group throughout the course of infection and its subsequent resolution followed a pattern that was similar to that of mice infected with the H5N1 virus (FIG. 15d):

The human anti-M2e mAbs and ch14C2 bound to cell surface-expressed M2e from A/Vietnam/1203/04 and A/Puerto Rico/8/34 viruses (FIG. 19b, Table 6) and cells infected with A/Puerto Rico/8/34 (FIG. 14c). Mechanisms for antibody-mediated protection could include killing of infected host cells by antibody-dependent cell-mediated cytotoxicity or complement-dependent cytotoxicity (11, 21). We found in vitro evidence for both of these mechanisms with the human anti-M2e mAbs and ch14C2 (FIGS. 17 and 6). An explanation for the enhanced in vivo protection observed with the human anti-M2e mAbs as compared to ch14C2 following challenge by the high-pathogenicity avian virus A/Vietnam/1203/04 as compared with A/Puerto Rico/8/34 could be due to the unique capability of the human mAbs to bind virus directly whereas ch14C2 does not appear to bind influenza virions (FIG. 14a). Protective properties of antibodies that bind to virus might be expected to include mechanisms such as antibody-dependent virolysis (22) and clearance via opsonophagocytosis by host cells (23). Some of these mechanisms require efficient interaction between antibodies and host Fc receptors. In our mouse challenge experiments all of the mAbs tested had human constant regions; however other studies have shown that human antibodies can interact productively with murine Fc receptors (24).

TABLE 5

Pathological assessment of lung, liver, and brain of mice treated with anti-M2e mAbs TCN-031 and TCN-032 after challenge with H5N1 A/Vietnam/1203/04.

| Organs | Mouse | TCN-031 | TCN-032 | 2N9 | CH14C2 | PBS | UT/C |
|---|---|---|---|---|---|---|---|
| Lung | 1 | ++/++ | ++/++ | ++/++ | ++/++ | ++/++ | ++/+++ |
|  | 2 | ++/++ | ++/++ | ++/+++ | ++/++ | ++/++ | ++/++ |
|  | 3 | ++/++ | ++/++ | ++/++ | ++/++ | ++/+++ | ++/++ |
| Brain | 1 | −/− | −/− | +/+ | −/− | +/+++ | ++/+++ |
|  | 2 | −/− | ±/+ | +/+++ | +/+ | −/− | +/+ |
|  | 3 | −/− | −/− | +/+ | +/++ | +/+++ | ++/+++ |
| Liver | 1 | −/− | −/− | +/+ | +/− | +/+ | +/+ |
|  | 2 | −/− | −/− | +/+ | +/− | +/− | +/− |
|  | 3 | −/− | +/− | +/+ | +/+ | +/+ | +/+ |

Pathological changes and viral antigens were detected in the lungs of all virus-challenged mice. The mice had similar lung lesions across all groups, although mice in the TCN-031 and TCN-032 groups had a tendency toward less viral antigen expression in the lung. In the brain and liver, lesions were not detected in mice in the TCN-31 group and only one of three mice in the TCN-032 group showed some evidence of viral antigens in the brain.

Pathological changes/viral antigens:
+++ severe/many,
++ moderate/moderate,
+ mild/few,
± scant/rare,
− not observed/negative.

TABLE 6

| # | Strain | Amino acids 1-23 of the M2 extracellular domain |   |   |   |   |   |   |   |   |   |   |   |   |   |   |   |   |   |   |   |   |   |   |
|---|---|---|---|---|---|---|---|---|---|---|---|---|---|---|---|---|---|---|---|---|---|---|---|---|
|  |  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| 1 | A/Brovig Mission/1/1918 H1N1 | S | L | L | T | E | V | E | T | P | T | R | N | E | W | G | C | R | C | N | D | S | S | D |
| 2 | A/Fort Monmouth/1/1947 H1N1 |   |   |   |   |   |   |   |   |   |   | K |   |   |   | E |   |   |   |   |   |   |   |   |
| 3 | A/Singapore/02/2005 H3N2 |   |   |   |   |   |   |   |   |   | I |   |   |   |   | E |   |   |   |   |   |   |   |   |
| 4 | A/Wisconsin/10/1998 H1N1 |   |   |   |   |   |   |   |   |   | I |   |   |   |   | G |   | E |   |   |   |   |   |   |
| 5 | A/Wisconsin/301/1976.H1N1 |   |   |   |   |   |   |   |   |   | I |   | S |   |   |   |   |   |   |   |   |   |   |   |
| 6 | A/Panama/1/1966 H2N2 |   |   |   | F |   | P |   |   |   | I |   |   |   |   |   |   |   |   |   |   |   |   |   |
| 7 | A/New York/321/1999 H3N2 |   |   |   |   |   |   |   |   |   | I |   |   |   |   |   |   |   |   |   |   |   |   | N |
| 8 | A/Caracas/1/1971 H3N2 |   |   |   |   |   |   |   |   |   | I |   | K |   |   |   |   |   |   |   |   |   |   |   |
| 9 | A/Taiwan/3/1971 H3N2 |   |   |   | F |   |   |   |   |   | I |   | S |   |   |   |   |   |   |   |   |   |   |   |
| 10 | A/Wuhan/359/1995 H3N2 |   |   |   |   |   | P |   |   |   | I |   | S |   |   |   |   |   |   |   |   |   |   |   |
| 11 | A/Hong Kong/1144/1999 H3N2 |   |   |   |   |   | P |   |   |   | I |   |   |   |   |   |   |   |   |   |   |   |   |   |
| 12 | A/Hong Kong/1180/1999 H3N2 |   |   |   |   |   | P |   |   |   | I |   |   |   |   | G |   |   |   |   |   |   |   |   |
| 13 | A/Hong Kong/1774/1999 H3N2 |   |   |   |   |   |   |   |   |   |   |   |   |   |   | G |   | E |   |   |   | S | G |   |
| 14 | A/New York/217/2002 H1N2 |   |   |   |   |   |   |   |   |   | I |   |   |   |   |   |   | E | Y |   |   |   |   |   |
| 15 | A/New York/300/2003 H1N2 |   |   |   |   |   |   |   |   |   | I |   |   |   |   |   |   | E | Y |   |   | S |   |   |
| 16 | A/swine/Spain/54008/2004 H3N2 |   |   |   |   |   |   |   |   |   |   |   |   |   |   | G |   | E |   |   | Y | S |   |   |
| 17 | A/Guangzhou/333/99 H9N2 |   |   |   | F |   |   |   |   |   |   |   | L |   |   | G |   | E |   |   |   | S |   |   |
| 18 | A/Hong Kong/1073/1999 H9N2 |   |   |   |   |   |   |   |   |   |   |   | L |   |   | G |   | E |   | K |   | R |   |   |
| 19 | A/Hong Kong/1/1968 H3N2 |   |   |   |   |   |   |   |   |   | I |   |   |   |   |   |   |   |   |   |   |   |   |   |
| 20 | A/swine/Hong Kong/126/1982 H3N2 |   |   |   |   |   |   |   |   |   | I |   | S |   |   |   |   |   |   |   |   |   |   | G |
| 21 | A/New York/703/1995 H3N2 |   |   |   |   |   |   |   |   |   | I |   |   |   |   | E |   |   |   |   |   | G |   |   |
| 22 | A/swine/Quebec/192/1981 H1N1 |   |   |   |   |   | P |   |   |   | I |   |   |   |   |   |   |   |   |   |   |   |   |   |

TABLE 6-continued

| | | | | | | | | | |
|---|---|---|---|---|---|---|---|---|---|
| 23 | A/Puerto Rico/8/1934 H1N1 | | | | I | | | | G |
| 24 | A/Hong Kong/485/1997 H5N1 | | D | L | | G | | S | |
| 25 | A/Hong Kong.542/1997 H5N1 | | | L | K | G | | S | |
| 26 | A/silky chicken/Shantou/1826/2004 H9N2 | | | | | G | E | K | S |
| 27 | A/chicken/Taiwan/0305/2004 H6N1 | | | H | | G | E | K | S |
| 28 | A/Quall/Arkansas/16309-7/1994 H7N3 | | K | | | G | E | K | S |
| 29 | A/Hong Kong/486/1997 H5N1 | | | L | | G | | S | |
| 30 | A/chicken/Pennsylvania/13552-1/1998 H7N2 | | | | D | G | E | K | S |
| 31 | A/chicken/Hellong jiang/48/2001 H9N2 | | | | | G | | S | |
| 32 | A/swine/Korea/S5/2005 H1N2 | | | | | G | E | K | |
| 33 | A/Hong Kong/1073/1999 H9N2 | | | L | | G | E | K | S |
| 34 | A/Wisconsin/3523/1988 H1N1 | | | | I | | | K | |
| 35 | A/X-31 Vaccine strain H3N2 | F | | | I | | | | G |
| 36 | A/Chicken/Rostock/8/1934 H7N1 | | | | | G | E | | |
| 37 | A/environment/New York/16326-1/2005 H7N2 | | | | I | K | G | E | N | S |
| 38 | A/chicken/Hong Kong/SF1/2003 H9N2 | | G | H | | G | | K | S |
| 39 | A/chicken/Hong Kong/YU427/2003 H9N2 | P | | H | | G | | | S |
| 40 | A/Indonesia/560H/2006 H5N1 | | | | | | E | | |
| HK | A/Hong Kong/483/1997 H5N1 | | | L | | G | | | S |
| VN | A/Vietnam/1203/2004 H5N1 | | | | | | E | | S |
| D20 | A/FW/1/1950 H1N1 | | | | I | | | | |

The M2e sequence at the top is from A/Brevig Mission/1/18 (H1N1) and is used as the reference sequence for alignment of the M2 ectodomain amino acids 1-23 of 43 wild-type variants.
Grey boxes denote amino acid identity with the reference sequence and white boxes are amino acid replacement mutations.
This list of non-identical sequences, except for HK, VN, and D20, was derived from M2 sequences used in references 11 and 27.
Sequence data are from The Influenza Virus Resource at the National Center for Biotechnology Information (http://www.ncbi.nlm.nih.gov/genomes/FLU/FLU.html).

Binding to the Highly Conserved N-Terminal Segment of M2e.

Figure 19A:
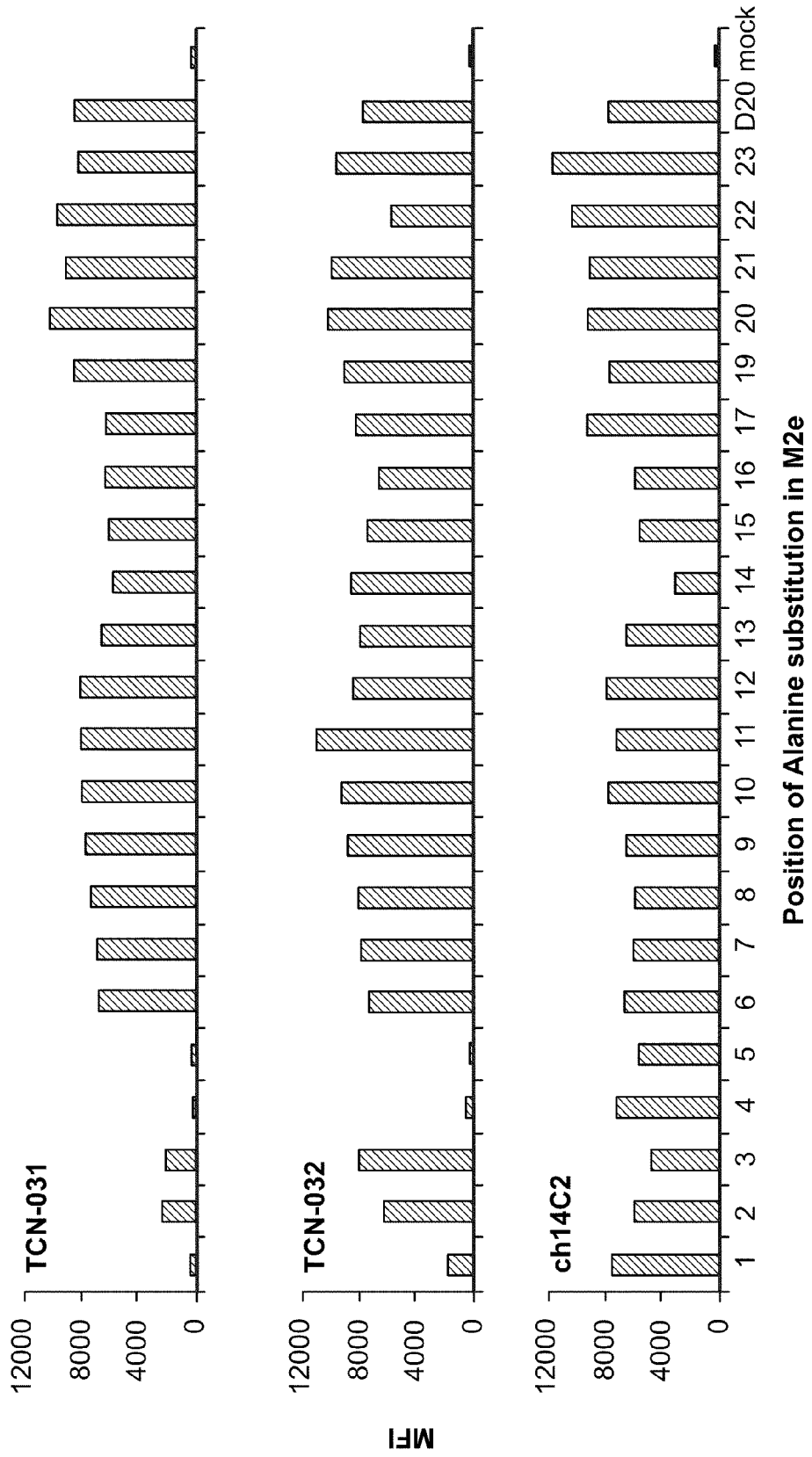
FIGS. 19A-C are graphs depicting binding of anti-M2e mAbs TCN-031 and TCN-032 to M2 mutants indicates the epitope is located in the highly conserved N-terminal of M2e. Mutants with alanine substituted at each position, of the M2 ectodomain of A/Fort Worth/1/50 (D20)(A) or forty wild-type M2 mutants including A/Vietnam/1203/04 (VN) and A/Hong Kong/483/97 (HK) (B) were transiently transfected into 293 cells. The identity of each wild-type M2 mutant is listed in Table 6. Transfected cells were stained with mAbs TCN-031, TCN-032, or the control ch14C2 and analyzed by FACS for binding to M2 at 24 hours post-transfection. mAbs TCN-031 and TCN-032 do not bind variants with amino acid substitutions at positions 1, 4, or 5 of M2e. (C) The deduced epitope for TCN-031 and TCN-032 occurs in a highly conserved region of M2e and is distinct from that found for ch14C2. Results shown for (A) and (B) are representative of 3 experiments.
Figure 19B:
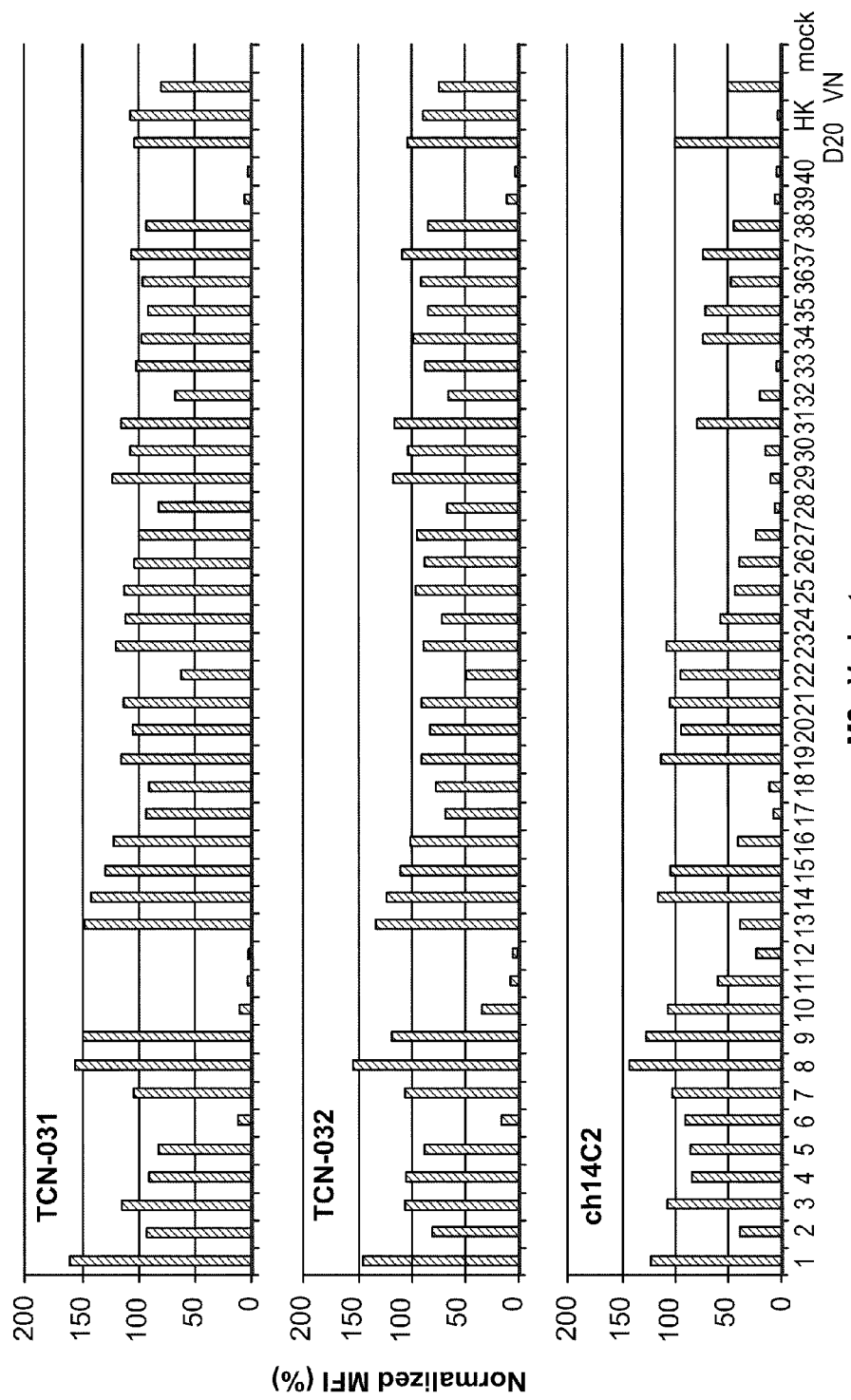
Figure 20:
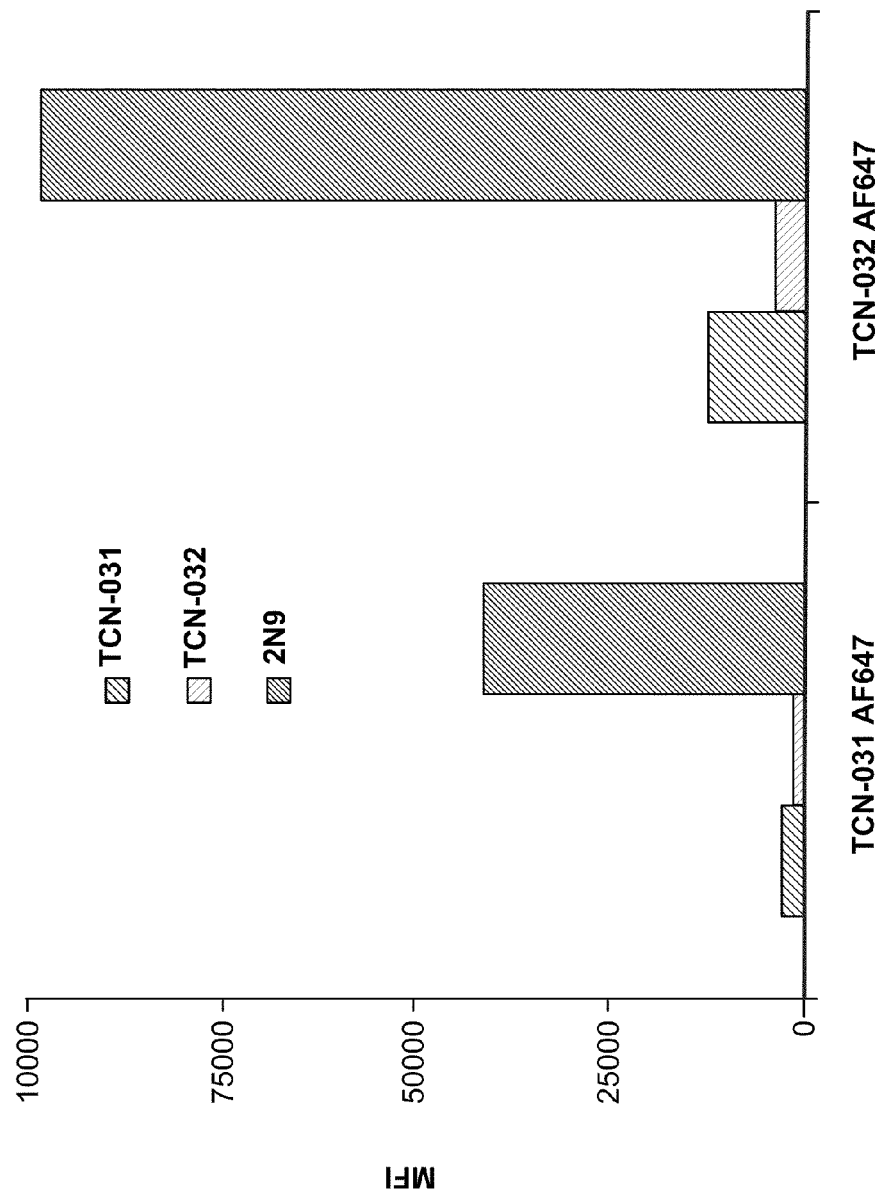
FIG. 20 is a graph depicting mAbs TCN-031 and TCN-032 recognize the same region on M2e. The CHO transfectant stably expressing M2 for A/Hong Kong/483/97 as stained with 10 μg/mL TCN-031, TCN-032, or 2N9, followed by detection with Alexafluor647-labeled TCN-031 (TCN-031AF647) or TCN-032(TCN-032AF647) and analysis by flow cytometry. The results are representative of three experiments.

To better understand the unique viral binding property of the human anti-M2e mAbs we mapped their binding sites within the M2e domain. The lack of appreciable binding of the human mAbs to M2e-derived linear peptides precluded a synthetic peptide approach to fine structure mapping of their epitopes. Instead, binding of the mAbs to M2e alanine substitution mutants and naturally occurring M2 variants that were expressed on the surface of cDNA-transfected mammalian cells was quantified by flow cytometry. Binding experiments with a panel of M2 mutant proteins where each position in the 23 amino acid M2 ectodomain was substituted with alanine revealed that the first (S), fourth (T), and fifth (E) positions of the mature (methionine-clipped) M2 polypeptide were critical for binding of both TCN-031 and TCN-032 (FIG. 19a). In contrast, the binding of ch14C2 was selectively diminished when alanine was substituted at position 14 of mature M2 (FIG. 19a). These observations were confirmed in studies with a panel of divergent, naturally occurring M2 variants; substitution with proline at position 4 (Table 6: A/Panama/1/1966 H2N2, A/Hong Kong/1144/1999 H3N2, A/Hong Kong/1180/1999 H3N2, and A/chicken/Hong Kong/YU427/2003 H9N2) and glycine at position 5 (Table 6: A/chicken/Hong Kong/SF1/2003 H9N2) correlated with diminished binding of the human anti-M2e mAbs but not ch14C2 (FIG. 19b, Table 6). These results suggest that both TCN-031 and TCN-032 recognize a core sequence of SLLTE at positions 1-5 of the N-terminus of mature M2e. This is supported by data which show that these mAbs compete effectively with each other for binding to M2e expressed on the surface of CHO cells (FIG. 20). In contrast, our results indicate that ch14C2 binds to a site that is spatially distinct and downstream of the SLLTE core that is recognized by the human anti-M2e mAbs. Indeed, previous studies have shown that 14C2 binds a relatively broad, linear epitope with the sequence EVERTPIRNEW at positions 5-14 of processed M2e (11).

While the epitopes recognized by TCN-031 and TCN-032 are likely very similar, there were some differences between these human mAbs in their binding to several of the M2e mutants. For instance, TCN-031 appears to have a greater dependence than TCN-032 on residues 2 (L) and 3 (L) of the mature M2e sequence (FIG. 19a). The VH regions of these two human mAbs utilize different variable, diversity, and joining gene segments which may explain the minor differences in binding observed between these mAbs. Interestingly, despite the differences in their VH make-up these human mAbs utilize the same germline kappa chain V gene segments, albeit with distinct kappa chain joining segments.

Figure 19C:
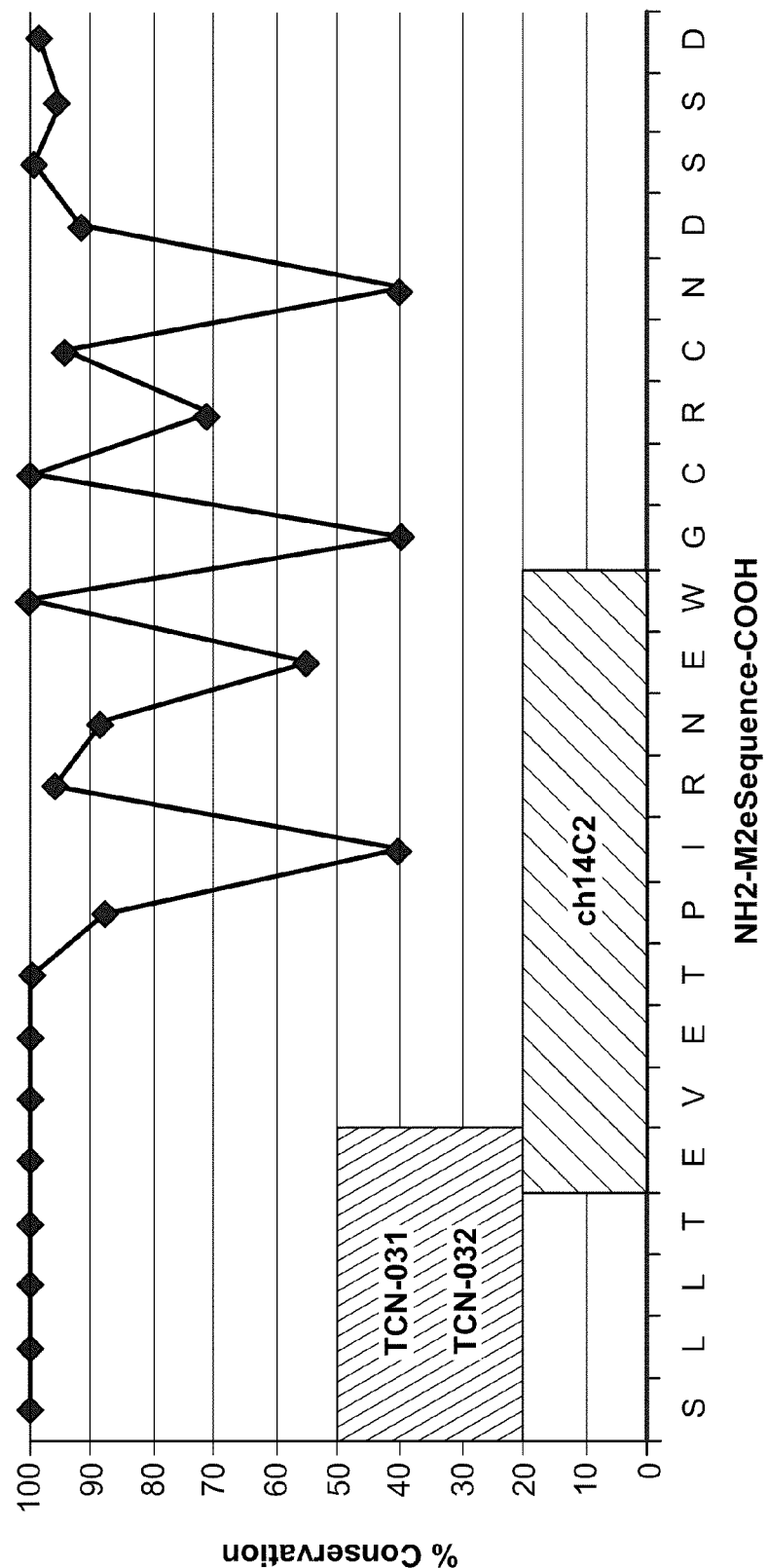

Localization of the binding region of the human anti-M2e mAbs at the N-terminal region of M2e is especially significant in light of the remarkably high sequence conservation in this part of the polypeptide among influenza A viruses. The viral M gene segment that encodes M2 also encodes the internal viral protein M1 via differential splicing. However, the splice site is located downstream of the shared N-terminus of M2 and M1 resulting in two distinct mature polypeptides with an identical 8 amino acid N-terminal sequence (25). Options for viral escape from host anti-M2e antibodies that bind this region might be limited as escape mutations in the N-terminal region would result in changes to not just M2 but also the M1 protein. Indeed, this N-terminal 8 amino acid segment of M2e shows nearly complete identity in the 1364 unique full-length M2 variants catalogued in the NCBI Influenza Database (www.ncbi.nlm.nih.gov/genomes/FLU/Database/multiple.cgi) while much lower levels of conservation are seen in M2e sequences downstream of this region (FIG. 19c). In fact, the core human anti-M2e antibody epitope SLLTE is present in ~98% of the 1364 unique full-length M2e sequences catalogued in the NCBI Influenza Database, including 97%, 98% and 98% of the human, swine and avian viruses, respectively. This contrasts to the much lower conservation within the linear binding sites of anti-M2e mAbs elicited by immunization with M2e peptides or proteins. For instance, 14C2 and Z3G1 (11) bind sequences that are conserved in less than 40% of influenza A viruses, and conservation within this region is even lower in avian and swine viruses (Table 7).

The linear M2e epitopes recognized by peptide-elicited antibodies may be more sensitive to escape mutations and natural substitutions that are present in some viral isolates. For example, P10L and P10H escape mutations to mAb 14C2 have been mapped to the central portion of M2e (27) and those same substitutions also occur in M2e variants from some highly pathogenic H5N1 strains. We have found that the human mAbs TCN-031 and TCN-032 but not ch14C2 bind to the M2 variant from the H5N1 virus A/Hong Kong/483/97 (HK) which contains the P10L substitution (FIG. 19b, Table 6). Thus, monoclonal antibodies with specificities similar to that of 14C2 are likely to have limited utility as broad spectrum therapeutic agents.

In the examination of 5 human subjects we found 17 unique anti-M2e antibodies that bind the conserved N-terminal region of M2e, but did not observe IgG-reactivity with M2e-derived peptides that contain the linear epitopes recognized by 14C2 and other peptide-elicited antibodies. In contrast to the apparently uniform antibody response to M2e in naturally infected or vaccinated humans, mice immunized with M2e-derived peptides produced antibodies with a range of specificities within M2e, including the conserved N-terminus and also downstream regions (13). It is tempting to speculate that the human immune system has evolved a humoral response that exclusively targets the highly conserved N-terminal segment of M2e rather than the more divergent, and thus less sustainably protective, downstream sites. Despite the lack of evidence for human antibodies that recognize this internal region of M2e, analysis of the evolution of the M gene suggests that this region of M2e is under strong positive selection in human influenza viruses (37). One explanation for this finding is that selective pressure is being directed at this internal region by immune mechanisms other than antibodies. For instance, human T cell epitopes have been mapped to these internal M2e sites (38).

TABLE 7

Conservation of the viral binding site for human anti-M2e mAbs compared with those for mAbs derived from immunized mice, in influenza A.

| mAb | Human (n = 506) | Swine (n = 193) | Avian (n = 665) | All (n = 1364) |
|---|---|---|---|---|
| TCN-031, TCN-032 [1-SLLTE-5] | 97 | 98 | 98 | 98 |
| Z3G1 [2-LLTEVETPIR-11] (Ref. 11) | 79 | 39 | 7 | 38 |
| 14C2 [5-EVETPIRNEW-14] (Ref. 11) | 75 | 19 | 2 | 31 |

Recognition of 2009 H1N1 S-OIV.

Figure 21:
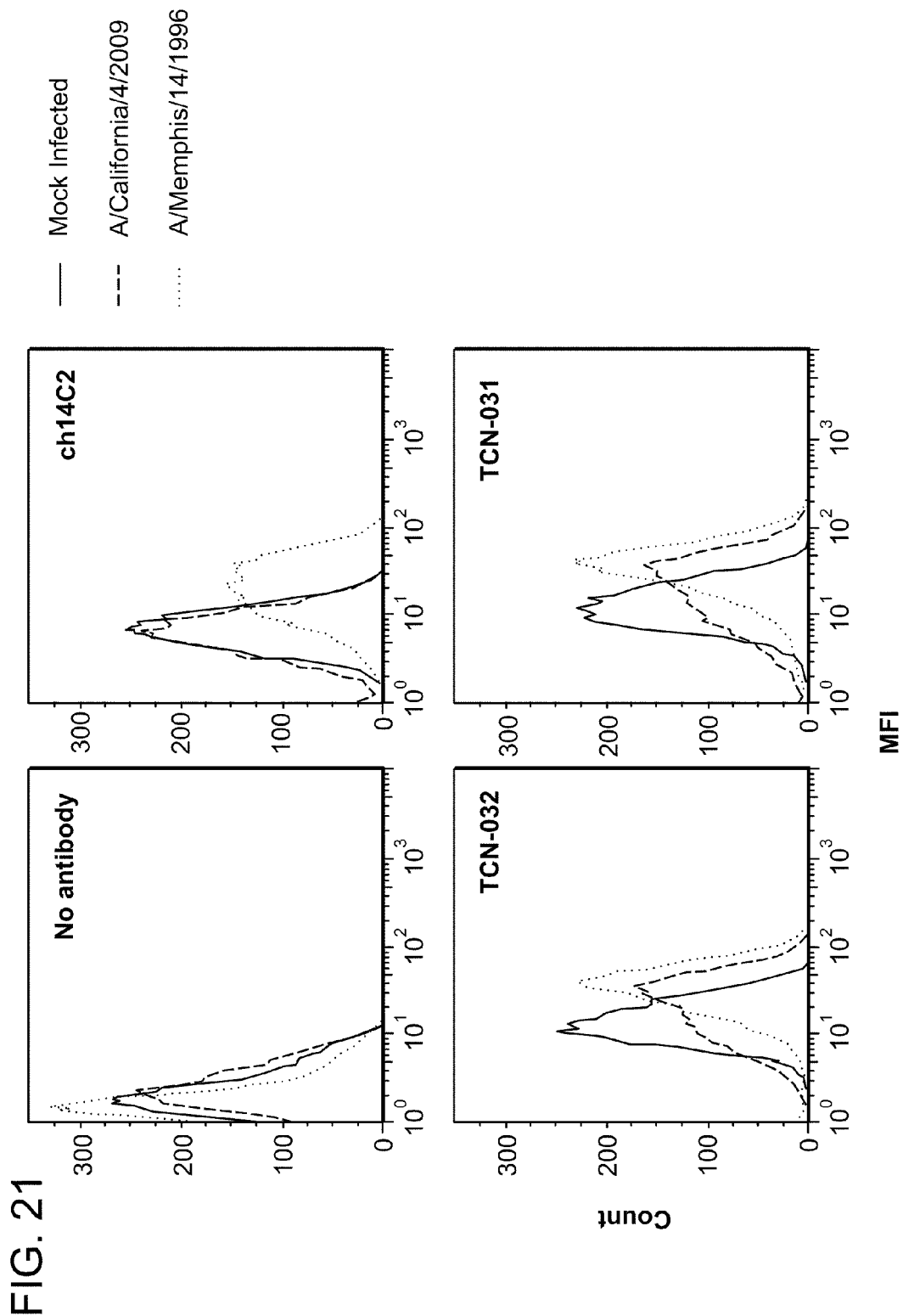
FIG. 21 is a graph depicting anti-M2e mAbs TCN-031 and TCN-032 bind cells that have been infected with H1N1 A/California/4/09. MDCK cells were infected with Influenza A strain H1N1 A/Memphis/14/96, H1N1 A/California/4/09, or mock infected. Twenty four hours post-infection cells were stained with mAbs TCN-031, TCN-032, or the control ch14C2 and analyzed by FACS for binding to M2. Results shown are for one experiment.

Broadly protective anti-influenza mAbs could be used in passive immunotherapy to protect or treat humans in the event of outbreaks from highly pathogenic, pandemic viral strains. A critical test of the potential for such mAbs as immunotherapeutic agents is whether they are capable of recognizing virus strains that may evolve from future viral reassortment events. As a case in point, the human anti-M2e mAbs TCN-031 and TCN-032 were tested for their ability to recognize the current H1N1 swine-origin pandemic strain (S-OIV). These mAbs were derived from human blood samples taken in 2007 or earlier, prior to the time that this strain is thought to have emerged in humans (41). Both human mAbs bound to MDCK cells infected with A/California/4/2009 (S-OIV H1N1, pandemic) and A/Memphis/14/1996 (H1N1, seasonal) whereas ch14C2 bound only to cells infected with the seasonal virus (FIG. 21). If this broad binding behavior proves to correlate with protection, as was the case with A/Vietnam/1203/2004 and A/Puerto Rico/8/34, then these human mAbs might be useful to prevent or treat the S-OIV pandemic strain or possibly other pandemic strains that might emerge in the future.

While it is remarkable that humans have the capability to make antibodies that may confer nearly universal protection against influenza infection, the discovery of this heretofore un-described class of antibodies raises the question of why this virus is able to mount a productive infection in immuno-competent individuals at all. This apparent paradox may be explained by the nature of the protective M2e epitope and its relative immunogenicity. It has been noted by others that M2e appears to exhibit low immunogenicity in humans (29, 39), especially when compared to the immunodominant virus glycoproteins HA and NA. Therefore, protective anti-M2e antibodies may exist in many individuals but at suboptimal titers. In support of this notion is our observation that most individuals did not display a detectable humoral response to M2e. We observed that fewer than 20% (23/140) of the individuals that we sampled in our cohort of healthy subjects had detectable serum levels of anti-M2e antibodies. The reasons for this phenomenon are not clear but a similar situation exists in HCMV where only a minority of HCMV seropositive subjects has measurable antibodies to the broadly conserved, neutralizing AD2 epitope within the gB complex of HCMV (30-32).

An important requirement for an immunotherapeutic solution to the influenza threat will be the identification of protective epitopes that are conserved in pre-existing and emerging viruses. Using large-scale sampling of the human immune response to native influenza M2 we have identified a naturally immunogenic and protective epitope within the highly conserved N-terminal region of M2e. Human antibodies directed to this epitope, including those described in the present study, may be useful for the prevention and treatment of pandemic and seasonal influenza.

Methods

Memory B Cell Culture.

Whole blood samples were collected from normal donors under IRB approved informed consent and peripheral blood mononuclear cells (PBMC) were purified by standard techniques. B cell cultures were set up using PBMC, B cells enriched by selection with M2-expressing cells, or IgG$^+$ memory B cells enriched from PBMC via negative depletion of nonIgG$^+$ cells with antibodies to CD3, CD14, CD16, IgM, IgA, and IgD on magnetic beads (Miltenyi, Auburn, Calif.) as previously described (35). Briefly, to promote B cell activation, proliferation, terminal differentiation and antibody secretion, cells were seeded in 384-well microtiter plates in the presence of feeder cells and conditioned media generated from mitogen-stimulated human T cells from healthy donors. The culture supernatants were collected 8 days later and screened in a high throughput format for binding reactivity to M2 protein expressed on HEK 293 cells stably transfected with influenza virus M2 (A/Fort Worth/50 H1N1) using fluorescent imaging (FMAT system, Applied Biosystems).

Reconstitution of Recombinant mAbs from B Cell Cultures.

mRNA was isolated from lysed B-cell cultures using magnetic beads (Ambion). After reverse transcription (RT) with gene-specific primers, variable domain genes were PCR amplified using VH, V, and Vλ family-specific primers with flanking restriction sites (35). PCR reactions producing an amplicon of the expected size were identified using 96-well E-gels (Invitrogen) and the variable domain amplicons were cloned into the pTT5 expression vector (National Research of Canada, Ottawa, Canada) containing human IgG1, Igκ, or Igλ constant regions. Each VH pool was combined with the corresponding Vκ, or Vλ pools from individual BCC wells and was transiently transfected in 293-6E cells to generate recombinant antibody. Conditioned media was harvested 3-5 days after transfection and assayed for antibody binding to M2 protein expressed on HEK 293 cells. Individual clones were isolated from positive pools and unique VH and VL genes were identified by sequencing. From these, monoclonal antibodies were subsequently expressed and re-assayed for binding activity.

ELISA. To detect viral antigen, either 10.2 µg/mL UV-inactivated H1N1 A/Puerto Rico/8/34 (PR8) virus (Advanced Biotechnologies, Inc.) was passively adsorbed to 384-well plates in 25 µL PBS/well for 16 hr at 4° C., or PR8 inactivated by β-propiolactone (Advanced Biotechnologies, Inc.) was biotinylated (EZ-Link Sulfo-NHS-LC-Biotin, Pierce) and likewise adsorbed to plates coated with neutravidin (Pierce). Virus-coated and biotinylated virus-coated plates were blocked with PBS containing 1% milk or BSA, respectively. Binding of mAbs at the indicated concentrations was detected with HRP-conjugated goat anti-human Fc antibody (Pierce) and visualized with TMB substrate (ThermoFisher). The M2e peptide, SLLTEVETPIRNEWGCRCNDSSD (SEQ ID NO: 680) (Genscript) was passively adsorbed at 1 µg/mL and antibody binding to the peptide was detected by the same method.

FACS Analysis of Virally Infected Cells.

To detect M2e following in vitro infection, MDCK cells were treated with PR8 at multiplicity of infection (MOI) of 60:1 for 1 hr at 37° C. after which the culture media was replaced. The infected MDCK cells were further cultured for 16 hr before harvesting for cell staining with the indicated mAbs. Bound anti-M2 mAbs were visualized on viable cells with Alexafluor 647-conjugated goat anti-Human IgG H&L antibody (Invitrogen). Flow cytometry was performed on FACSCanto equipped with the FACSDiva software (Becton Dickenson). For the panel of anti-M2 mAbs, 20 µL samples of supernatant from transient transfections from each of the IgG heavy and light chain combinations was used to stain the 293 stable cell line expressing M2 of A/Hong Kong/483/97 FACS analysis was performed as above.

M2 Variant Analyses.

Individual full length M2 cDNA mutants were synthesized with single ala mutations at each position of the ectodomain representing A/Fort Worth/1/1950 (D20), as well as were the forty-three naturally occurring variants of M2 (Blue Heron Technology). They were cloned into the plasmid vector pcDNA3.1. After transient transfection with Lipofectamine (Invitrogen), HEK293 cells were treated with 1 µg/mL of the indicated mAbs in PBS supplemented with 1% fetal bovine serum and 0.2% NaN3 (FACS buffer). Bound anti-M2 mAbs were visualized on viable cells with Alexafluor 647-conjugated goat anti-Human IgG H&L antibody (Invitrogen). Flow cytometry was performed with FACSCanto equipped with the FACSDiva software (Becton Dickenson). The relative binding to the naturally occurring variants was expressed as the percentage of the respective mAb staining of the D20 transiently transfected cells, using the formula of Normalized MFI (%) 100×(MFIexperimental−MFImock transfected)/(MFID20−MFImock transfected).

Therapeutic Efficacy Studies in Mice.

Animal studies were conducted under Institutional Animal Care and Use Committee protocols. We inoculated 6 groups of 10 mice (female 6-8 week old BALB/C) intranasally with $5 \times_{LD50}$ of A/Vietnam/1203/04 (FIGS. 15a and b) or 6 groups of 5 mice intranasally with $5 \times_{LD50}$ A/Puerto Rico/8/34 (FIGS. 15c and d). At 24, 72, and 120 hours post-infection the mice received intraperitoneal injections of 400 µg/200 µL dose of the anti-M2e mAbs TCN-031 TCN-032, control human mAb 2N9, control chimeric mAb ch14C2, PBS, or were left untreated. Mice were weighed daily for 2 weeks and were euthanized when weight loss exceeded 20% (H5N1 study shown in FIGS. 15a and 15b and H1N1 study shown in FIGS. 15c and 15d) of the pre-infection body weight.

Antibody Reactivity to A/California/4/2009 Infected Cells.

MDCK cells were infected with media alone or media containing A/California/4/2009 (H1N1) or A/Memphis/14/1996 (H1N1) at an MOI of approximately 1 and were cultured for 24 hours at 37° C. The cells were detached from the tissue culture plates with trypsin, washed extensively, and then fixed in 2% paraformaldehyde for 15 minutes. The cells were incubated with 1 µg/ml of the indicated antibodies and the primary antibody binding was detected with Alexafluor 647-conjugated goat anti-Human IgG H&L antibody (Invitrogen). The cells were analyzed with a Becton Dickinson FACSCalibur and data were processed using FlowJo software.

Competition Analysis of Antibody Binding.

Transient transfection supernatant containing antibody was screened for binding to 293 cells stably transfected with M2 from H1N1 (A/Fort Worth/50 H1N1), or mock transfected cells, in the presence or absence of the M2e peptide SLLTEVETPIRNEWGCRCNDSSD (Genscript) at 5 µg/mL. Bound anti-M2 mAbs were detected with anti-huIgG Fc FMAT Blue at 700 ng/ml in DMEM with 10% FCS and visualized by fluorescent imaging (FMAT system, Applied Biosystems).

REFERENCES

1. Thompson, W. W. et al. (2004) Influenza-Associated Hospitalizations in the United States. *JAMA* 292:1333-1340.
2. Carrat F, Flahault A. (2007) Influenza vaccine: the challenge of antigenic drift. *Vaccine* 25:6852-6862
3. Gubareva L V, Kaiser L, Hayden F G. (2000) Influenza virus neuraminidase inhibitors. *Lancet* 355:827-835.
4. Wang C, Takeuchi K, Pinto L H, Lamb R A. (1993) Ion channel activity of influenza A virus M2 protein: characterization of the amantadine block. *J Virol* 67:5585-5594.
5. Luke T C, Kilbane E M, Jackson J L, Hoffman S L. (2006) Meta-analysis: convalescent blood products for Spanish influenza pneumonia: a future H5N1 treatment? *Ann Intern Med* 145:599-609.
6. Okuno Y, Isegawa Y, Sasao F, Ueda S. (1993) A common neutralizing epitope conserved between the hemagglutinins of influenza A virus H1 and H2 strains. *J Virol* 67:2552-2558.
7. Throsby M, et al. (2008) Heterosubtypic neutralizing monoclonal antibodies cross-protective against H5N1 and H1N1 recovered from human IgM+ memory B cells. *PLoS One.* 3: e3942.
8. Sui J, et al. (2009) Structural and functional bases for broad-spectrum neutralization of avian and human influenza A viruses. *Nat Struct Mol Biol* 16:265-273.

9. Russell C A, et al. (2008) The global circulation of seasonal influenza A (H3N2) viruses. *Science* 320:340-346.
10. Fouchier R A, et al. (2004) Avian influenza A virus (H7N7) associated with human conjunctivitis and a fatal case of acute respiratory distress syndrome. *Proc Natl Acad Sci USA* 101:1356-1361.
11. Wang R, et al. (2008) Therapeutic potential of a fully human monoclonal antibody against influenza A virus M2 protein. *Antiviral Res* 80:168-177.
12. Liu W, Zou P, Chen Y H. (2004) Monoclonal antibodies recognizing EVETPIRN epitope of influenza A virus M2 protein could protect mice from lethal influenza A virus challenge. *Immunol Lett* 93:131-6.
13. Fu T M, et al. (2008) Characterizations of four monoclonal antibodies against M2 protein ectodomain of influenza A virus. *Virology* 385:218-226.
14. Fu T M, et al. (2009) Comparative immunogenicity evaluations of influenza A virus M2 peptide as recombinant virus like particle or conjugate vaccines in mice and monkeys. *Vaccine* 27:1440-1447.
15. Fan J, et al. (2004) Preclinical study of influenza virus A M2 peptide conjugate vaccines in mice, ferrets, and rhesus monkeys. *Vaccine* 22:2993-3003.
16. Slepushkin V A, et al. (1995) Protection of mice against influenza A virus challenge by vaccination with baculovirus-expressed M2 protein. *Vaccine* 13:1399-1402.
17. Neirynck S, et al. (1999) A universal influenza A vaccine based on the extracellular domain of the M2 protein. *Nat Med* 5:1157-1163.
18. Tompkins S M, et al. (2007) Matrix protein 2 vaccination and protection against influenza viruses, including subtype H5N1. *Emerg Infect Dis* 13:426-435.
19. Mozdzanowska K, et al. (2003) Induction of influenza type A virus-specific resistance by immunization of mice with a synthetic multiple antigenic peptide vaccine that contains ectodomains of matrix protein 2. *Vaccine* 21:2616-2626.
20. Zebedee S L, Lamb R A. (1988) Influenza A virus M2 protein: monoclonal antibody restriction of virus growth and detection of M2 in virions. *J Virol* 62:2762-2772.
21. Jegerlehner A, Schmitz N, Storni T, Bachmann M F (2004) Influenza A vaccine based on the extracellular domain of M2: weak protection mediated via antibody-dependent NK cell activity. *J Immunol* 172:5598-5605.
22. Nakamura M, Terada M, Sasaki H, Kamada M, Ohno T. (2000) Virolysis and in vitro neutralization of HIV-1 by humanized monoclonal antibody hNM-01. *Hybridoma* 19:427-434.
23. Huber V C, Lynch J M, Bucher D J, Le J, Metzger D W (2001) Fc receptor-mediated phagocytosis makes a significant contribution to clearance of influenza virus infections. *J Immunol* 166:7381-7388.
24. Clynes R A, Towers T L, Presta L G, Ravetch J V (2000) Inhibitory Fc receptors modulate in vivo cytotoxicity against tumor targets. *Nat Med* 6:443-446.
25. Lamb R A, Choppin P W (1981) Identification of a second protein (M2) encoded by RNA segment 7 of influenza virus. *Virology* 112:729-737.
26. Shinde V, et al. (2009) Triple-reassortant swine influenza A (H1) in humans in the United States, 2005-2009. *N Engl J Med* 360:2616-2625.
27. Zharikova D, Mozdzanowska K, Feng J, Zhang M, Gerhard W (2005). Influenza type A virus escape mutants emerge in vivo in the presence of antibodies to the ectodomain of matrix protein 2. *J Virol* 79:6644-6654.
28. Neumann G, Noda T, Kawaoka Y (2009) Emergence and pandemic potential of swine-origin H1N1 influenza virus. *Nature* 459:931-939.
29. Feng J, et al. (2006) Influenza A virus infection engenders a poor antibody response against the ectodomain of matrix protein 2. *Virol J* 3:102.
30. Meyer H, Sundqvist V A, Pereira L, Mach M (1992) Glycoprotein gp116 of human cytomegalovirus contains epitopes for strain-common and strain-specific antibodies. *J Gen Virol* 73:2375-2383.
31. Ayata M, et al. (1994) Different antibody response to a neutralizing epitope of human cytomegalovirus glycoprotein B among seropositive individuals. *J Med Virol* 43:386-392.
32. Navarro D, Lennette E, Tugizov S, Pereira L (1997) Humoral immune response to functional regions of human cytomegalovirus glycoprotein B. *J Med Virol* 52:451-459.
33. Kashyap A K, et al. (2008) Combinatorial antibody libraries from survivors of the Turkish H5N1 avian influenza outbreak reveal virus neutralization strategies. *Proc Natl Acad Sci USA* 105:5986-5991.
34. Belser J A, Bridges C B, Katz J M, Tumpey T M (2009) Past, present, and possible future human infection with influenza virus A subtype H7. *Emerg Infect Dis* 15:859-865.
35. Walker L, et al. (2009) Broad and Potent Neutralizing Antibodies from an African Donor Reveal a New HIV-1 Vaccine Target. *Science* 326:289-293
36. Zou P, Liu W, Wu F, Chen Y H (2008) Fine-epitope mapping of an antibody that binds the ectodomain of influenza matrix protein 2. *FEMS Immunol Med Microbiol* 5:379-384.
37. Furuse Y, Suzuki A, Kamigaki T, Oshitani H (2009) Evolution of the M gene if the influenza virus in different host species: large-scale sequence analysis. *J Virol* 29:67.
38. Jameson J, Cruz J, Ennis F A (1998) Human cytotoxic T-lymphocyte repertoire to influenza A viruses. *J Virol* 72:8682-8689.
39. Liu W, Li H, Chen Y H (2003) N-terminus of M2 protein could induce antibodies with inhibitory activity against influenza virus replication. *FEMS Immunol Med Microbio* 35:141-146.
40. Treanor J J, Tierney E L, Zebedee S L, Lamb R A, Murphy B R (1990) Passively transferred monoclonal antibody to the M2 protein inhibits influenza A virus replication in mice. *J Virol* 64:1375-1357.
41. Neumann G, Noda T, Kawaoka Y (2009) Emergence and pandemic potential of swine-origin H1N1 influenza virus. *Nature* 459:931-939.
42. Bao Y, et al. (2008) The Influenza Virus Resource at the National Center for Biotechnology Information. *J Virol* 82:596-601.
43. Beerli R, et al. (2009) Prophylactic and therapeutic activity of fully human monoclonal antibodies directed against Influenza A M2 protein. *Virology J* 6:224-234.
44. Corti D, et al. (2010) Heterosubtypic neutralizing antibodies are produced by individuals immunized with a seasonal influenza vaccine. *J Clin Invest* doi:10.1172/JCI41902.

OTHER EMBODIMENTS

Although specific embodiments of the invention have been described herein for purposes of illustration, various modifications may be made without deviating from the spirit and scope of the invention. Accordingly, the invention is not limited except as by the appended claims.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

SEQUENCE LISTING

```
<160> NUMBER OF SEQ ID NOS: 725

<210> SEQ ID NO 1
<211> LENGTH: 24
<212> TYPE: PRT
<213> ORGANISM: Influenza A virus

<400> SEQUENCE: 1

Met Ser Leu Leu Thr Glu Val Glu Thr Pro Thr Arg Asn Glu Trp Gly
1               5                   10                  15

Cys Arg Cys Asn Asp Ser Ser Asp
            20

<210> SEQ ID NO 2
<211> LENGTH: 24
<212> TYPE: PRT
<213> ORGANISM: Influenza A virus

<400> SEQUENCE: 2

Met Ser Leu Leu Thr Glu Val Glu Thr Pro Thr Lys Asn Glu Trp Glu
1               5                   10                  15

Cys Arg Cys Asn Asp Ser Ser Asp
            20

<210> SEQ ID NO 3
<211> LENGTH: 24
<212> TYPE: PRT
<213> ORGANISM: Influenza A virus

<400> SEQUENCE: 3

Met Ser Leu Leu Thr Glu Val Glu Thr Pro Ile Arg Asn Glu Trp Glu
1               5                   10                  15

Cys Arg Cys Asn Asp Ser Ser Asp
            20

<210> SEQ ID NO 4
<211> LENGTH: 24
<212> TYPE: PRT
<213> ORGANISM: Influenza A virus

<400> SEQUENCE: 4

Met Ser Leu Leu Thr Glu Val Glu Thr Pro Ile Arg Asn Gly Trp Glu
1               5                   10                  15

Cys Lys Cys Asn Asp Ser Ser Asp
            20

<210> SEQ ID NO 5
<211> LENGTH: 24
<212> TYPE: PRT
<213> ORGANISM: Influenza A virus
```

<400> SEQUENCE: 5

Met Ser Leu Leu Thr Glu Val Glu Thr Pro Ile Arg Ser Glu Trp Gly
1               5                   10                  15

Cys Arg Cys Asn Asp Ser Ser Asp
            20

<210> SEQ ID NO 6
<211> LENGTH: 24
<212> TYPE: PRT
<213> ORGANISM: Influenza A virus

<400> SEQUENCE: 6

Met Ser Phe Leu Pro Glu Val Glu Thr Pro Ile Arg Asn Glu Trp Gly
1               5                   10                  15

Cys Arg Cys Asn Asp Ser Ser Asp
            20

<210> SEQ ID NO 7
<211> LENGTH: 24
<212> TYPE: PRT
<213> ORGANISM: Influenza A virus

<400> SEQUENCE: 7

Met Ser Leu Leu Thr Glu Val Glu Thr Pro Ile Arg Asn Glu Trp Gly
1               5                   10                  15

Cys Arg Cys Asn Asp Ser Ser Asn
            20

<210> SEQ ID NO 8
<211> LENGTH: 24
<212> TYPE: PRT
<213> ORGANISM: Influenza A virus

<400> SEQUENCE: 8

Met Ser Leu Leu Thr Glu Val Glu Thr Pro Ile Arg Lys Glu Trp Gly
1               5                   10                  15

Cys Arg Cys Asn Asp Ser Ser Asp
            20

<210> SEQ ID NO 9
<211> LENGTH: 24
<212> TYPE: PRT
<213> ORGANISM: Influenza A virus

<400> SEQUENCE: 9

Met Ser Phe Leu Thr Glu Val Glu Thr Pro Ile Arg Asn Glu Trp Gly
1               5                   10                  15

Cys Arg Cys Asn Asp Ser Ser Asp
            20

<210> SEQ ID NO 10
<211> LENGTH: 24
<212> TYPE: PRT
<213> ORGANISM: Influenza A virus

<400> SEQUENCE: 10

Met Ser Leu Pro Thr Glu Val Glu Thr Pro Ile Arg Ser Glu Trp Gly
1               5                   10                  15

Cys Arg Cys Asn Asp Ser Ser Asp
            20

<210> SEQ ID NO 11
<211> LENGTH: 24
<212> TYPE: PRT
<213> ORGANISM: Influenza A virus

<400> SEQUENCE: 11

Met Ser Leu Leu Pro Glu Val Glu Thr Pro Ile Arg Asn Glu Trp Gly
1               5                   10                  15

Cys Arg Cys Asn Asp Ser Ser Asp
            20

<210> SEQ ID NO 12
<211> LENGTH: 24
<212> TYPE: PRT
<213> ORGANISM: Influenza A virus

<400> SEQUENCE: 12

Met Ser Leu Leu Pro Glu Val Glu Thr Pro Ile Arg Asn Gly Trp Gly
1               5                   10                  15

Cys Arg Cys Asn Asp Ser Ser Asp
            20

<210> SEQ ID NO 13
<211> LENGTH: 24
<212> TYPE: PRT
<213> ORGANISM: Influenza A virus

<400> SEQUENCE: 13

Met Ser Leu Leu Thr Glu Val Glu Thr Pro Thr Arg Asn Gly Trp Glu
1               5                   10                  15

Cys Arg Cys Ser Gly Ser Ser Asp
            20

<210> SEQ ID NO 14
<211> LENGTH: 24
<212> TYPE: PRT
<213> ORGANISM: Influenza A virus

<400> SEQUENCE: 14

Met Ser Leu Leu Thr Glu Val Glu Thr Pro Ile Arg Asn Glu Trp Glu
1               5                   10                  15

Tyr Arg Cys Asn Asp Ser Ser Asp
            20

<210> SEQ ID NO 15
<211> LENGTH: 24
<212> TYPE: PRT
<213> ORGANISM: Influenza A virus

<400> SEQUENCE: 15

Met Ser Leu Leu Thr Glu Val Glu Thr Pro Ile Arg Asn Glu Trp Glu
1               5                   10                  15

Tyr Arg Cys Ser Asp Ser Ser Asp
            20

<210> SEQ ID NO 16
<211> LENGTH: 24
<212> TYPE: PRT
<213> ORGANISM: Influenza A virus

<400> SEQUENCE: 16

Met Ser Leu Leu Thr Glu Val Glu Thr Pro Thr Arg Asn Gly Trp Glu

```
1               5                   10                  15

Cys Arg Tyr Ser Asp Ser Ser Asp
            20
```

<210> SEQ ID NO 17
<211> LENGTH: 24
<212> TYPE: PRT
<213> ORGANISM: Influenza A virus

<400> SEQUENCE: 17

```
Met Ser Phe Leu Thr Glu Val Glu Thr Leu Thr Arg Asn Gly Trp Glu
1               5                   10                  15

Cys Arg Cys Ser Asp Ser Ser Asp
            20
```

<210> SEQ ID NO 18
<211> LENGTH: 24
<212> TYPE: PRT
<213> ORGANISM: Influenza A virus

<400> SEQUENCE: 18

```
Met Ser Leu Leu Thr Glu Val Glu Thr Leu Thr Arg Asn Gly Trp Glu
1               5                   10                  15

Cys Lys Cys Arg Asp Ser Ser Asp
            20
```

<210> SEQ ID NO 19
<211> LENGTH: 24
<212> TYPE: PRT
<213> ORGANISM: Influenza A virus

<400> SEQUENCE: 19

```
Met Ser Leu Leu Thr Glu Val Glu Thr Pro Ile Arg Asn Glu Trp Gly
1               5                   10                  15

Cys Arg Cys Asn Asp Ser Ser Asp
            20
```

<210> SEQ ID NO 20
<211> LENGTH: 24
<212> TYPE: PRT
<213> ORGANISM: Influenza A virus

<400> SEQUENCE: 20

```
Met Ser Leu Leu Thr Glu Val Glu Thr Pro Ile Arg Ser Glu Trp Gly
1               5                   10                  15

Cys Arg Cys Asn Asp Ser Gly Asp
            20
```

<210> SEQ ID NO 21
<211> LENGTH: 24
<212> TYPE: PRT
<213> ORGANISM: Influenza A virus

<400> SEQUENCE: 21

```
Met Ser Leu Leu Thr Glu Val Glu Thr Pro Ile Arg Asn Glu Trp Glu
1               5                   10                  15

Cys Arg Cys Asn Gly Ser Ser Asp
            20
```

<210> SEQ ID NO 22
<211> LENGTH: 24
<212> TYPE: PRT

<213> ORGANISM: Influenza A virus

<400> SEQUENCE: 22

Met Ser Leu Pro Thr Glu Val Glu Thr P

<210> SEQ ID NO 28
<211> LENGTH: 24
<212> TYPE: PRT
<213> ORGANISM: Influenza A virus

<400> SEQUENCE: 28

Met Ser Leu Leu Thr Glu Val Lys Thr Pro Thr Arg Asn Gly Trp Glu
1               5                   10                  15

Cys Lys Cys Ser Asp Ser Ser Asp
            20

<210> SEQ ID NO 29
<211> LENGTH: 24
<212> TYPE: PRT
<213> ORGANISM: Influenza A virus

<400> SEQUENCE: 29

Met Ser Leu Leu Thr Glu Val Glu Thr Leu Thr Arg Asn Gly Trp Gly
1               5

```
Met Ser Leu Leu Thr Glu Val Glu Thr Leu Thr Arg Asn Gly Trp Glu
1               5                   10                  15

Cys Lys Cys Ser Asp Ser Ser Asp
            20
```

<210> SEQ ID NO 34
<211> LENGTH: 24
<212> TYPE: PRT
<213> ORGANISM: Influenza A virus

<400> SEQUENCE: 34

```
Met Ser Leu Leu Thr Glu Val Glu Thr Pro Ile Arg Asn Glu Trp Gly
1               5                   10                  15

Cys Lys Cys Asn Asp Ser Ser Asp
            20
```

<210> SEQ ID NO 35
<211> LENGTH: 24
<212> TYPE: PRT
<213> ORGANISM: Influenza A virus

<400> SEQUENCE: 35

```
Met Ser Phe Leu Thr Glu Val Glu Thr Pro Ile Arg Asn Glu Trp Gly
1               5                   10                  15

Cys Arg Cys Asn Gly Ser Ser Asp
            20
```

<210> SEQ ID NO 36
<211> LENGTH: 24
<212> TYPE: PRT
<213> ORGANISM: Influenza A virus

<400> SEQUENCE: 36

Met Ser Leu Leu Thr Glu Val Glu Thr Pro Thr Arg Asn Gly Trp Glu
1 5 10 15

Cys Arg Cys Asn Asp Ser Ser Asp
20

<210> SEQ ID NO 37
<211> LENGTH: 24
<212> TYPE: PRT
<213> ORGANISM: Influenza A virus

<400> SEQUENCE: 37

Met Ser Leu Leu Thr Glu Val Glu Thr Pro Ile Arg Lys Gly Trp Glu
1 5 10 15

Cys Asn Cys Ser Asp Ser Ser Asp
20

<210> SEQ ID NO 38
<211> LENGTH: 24
<212> TYPE: PRT
<213> ORGANISM: Influenza A virus

<400> SEQUENCE: 38

Met Ser Leu Leu Thr Glu Val Glu Thr Pro Thr Arg Asn Glu Trp Glu
1 5 10 15

Cys Arg Cys Ser Asp Ser Ser Asp
20

<210> SEQ ID NO 39
<211> LENGTH: 24

<212> TYPE: PRT
<213> ORGANISM: Influenza A virus

<400> SEQUENCE: 39

Met Ser Leu Leu Thr Gly Val Glu Thr His Thr Arg Asn Gly Trp Gly
1               5                   10                  15

Cys Lys Cys Ser Asp Ser Ser Asp
            20

<210> SEQ ID NO 40
<211> LENGTH: 24
<212> TYPE: PRT
<213> ORGANISM: Influenza A virus

<400> SEQUENCE: 40

Met Ser Leu Leu Pro Glu Val Glu Thr His Thr Arg Asn Gly Trp Gly
1               5                   10                  15

Cys Arg Cys Ser Asp Ser Ser Asp
            20

<210> SEQ ID NO 41
<211> LENGTH: 8
<212> TYPE: PRT
<213> ORGANISM: Influenza A virus

<400> SEQUENCE: 41

Ser Leu Leu Thr Glu Val Glu Thr
1               5

<210> SEQ ID NO 42
<211> LENGTH: 6
<212> TYPE: PRT
<213> ORGANISM: Influenza A virus

<400> SEQUENCE: 42

Ser Leu Leu Thr Glu Val
1               5

<210> SEQ ID NO 43
<211> LENGTH: 357
<212> TYPE: DNA
<213> ORGANISM: Homo sapiens

<400> SEQUENCE: 43
caggtgcaat tgcaggagtc gggcccagga ctggtgaagc cttcggagac cctgtccctc      60
acctgcactg tctctggttc gtccatcagt aattactact ggagctggat ccggcagtcc     120
ccagggaagg gactggagtg gattgggttt atctattacg gtggaaacac caagtacaat     180
ccctccctca gagccgcgt caccatatca caagacactt ccaagagtca ggtctccctg      240
acgatgagct ctgtgaccgc tgcggaatcg ccgtctatt tctgtgcgag agcgtcttgt      300
agtggtggtt actgtatcct tgactactgg ggccaggaa ccctggtcac cgtctcg        357

<210> SEQ ID NO 44
<211> LENGTH: 119
<212> TYPE: PRT
<213> ORGANISM: Homo sapiens

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser Asn Tyr

```
                20                  25                  30
Tyr Trp Ser Trp Ile Arg Gln Ser Pro Gly Lys Gly Leu Glu Trp Ile
            35                  40                  45
Gly Phe Ile Tyr Tyr Gly Gly Asn Thr Lys Tyr Asn Pro Ser Leu Lys
    50                  55                  60
Ser Arg Val Thr Ile Ser Gln Asp Thr Ser Lys Ser Gln Val Ser Leu
65                  70                  75                  80
Thr Met Ser Ser Val Thr Ala Ala Glu Ser Ala Val Tyr Phe Cys Ala
                85                  90                  95
Arg Ala Ser Cys Ser Gly Gly Tyr Cys Ile Leu Asp Tyr Trp Gly Gln
            100                 105                 110
Gly Thr Leu Val Thr Val Ser
            115
```

<210> SEQ ID NO 45
<211> LENGTH: 322
<212> TYPE: DNA
<213> ORGANISM: Homo sapiens

<400> SEQUENCE: 45

```
gacatccaga tgacccagtc tccatcctcc ctgtctgcat ctgtaggaga cagagtcacc    60
atcacttgcc gggcgagtca gaacatttac aagtatttaa attggtatca gcagagacca   120
gggaaagccc ctaagggcct gatctctgct gcatccgggt tgcaaagtgg ggtcccatca   180
aggttcagtg gcagtggatc tgggacagat ttcactctca ccatcaccag tctgcaacct   240
gaagattttg caacttacta ctgtcaacag agttacagtc ccctctcac ttcggcgga   300
gggaccaggg tggagatcaa ac                                            322
```

<210> SEQ ID NO 46
<211> LENGTH: 107
<212> TYPE: PRT
<213> ORGANISM: Homo sapiens

<400> SEQUENCE: 46

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asn Ile Tyr Lys Tyr
            20                  25                  30
Leu Asn Trp Tyr Gln Gln Arg Pro Gly Lys Ala Pro Lys Gly Leu Ile
        35                  40                  45
Ser Ala Ala Ser Gly Leu Gln Ser Gly Val Pro Ser Arg Phe Ser Gly
    50                  55                  60
Ser Gly Ser Gly Thr Asp Phe Thr Leu Thr Ile Thr Ser Leu Gln Pro
65                  70                  75                  80
Glu Asp Phe Ala Thr Tyr Tyr Cys Gln Gln Ser Tyr Ser Pro Pro Leu
                85                  90                  95
Thr Phe Gly Gly Gly Thr Arg Val Glu Ile Lys
            100                 105
```

<210> SEQ ID NO 47
<211> LENGTH: 357
<212> TYPE: DNA
<213> ORGANISM: Homo sapiens

<400> SEQUENCE: 47

```
caggtgcaat tgcaggagtc gggcccagga ctggtgaagc cttcggagac cctgtccctc    60
```

```
acctgcactg tctctggttc gtccatcagt aattactact ggagctggat ccggcagtcc    120
ccagggaagg gactggagtg gattgggttt atctattacg gtggaaacac caagtacaat    180
ccctccctca agagccgcgt caccatatca aagacactt ccaagagtca ggtctccctg     240
acgatgagct ctgtgaccgc tgcggaatcg gccgtctatt tctgtgcgag agcgtcttgt    300
agtggtggtt actgtatcct tgactactgg ggccagggaa ccctggtcac cgtctcg       357
```

<210> SEQ ID NO 48
<211> LENGTH: 322
<212> TYPE: DNA
<213> ORGANISM: Homo sapiens

<400> SEQUENCE: 48

```
gacatccagg tgacccagtc tccatcctcc ctgtctgcat ctgtaggaga cagagtcacc     60
atcacttgcc gcgcgagtca gaacatttac aagtatttaa attggtatca gcagagacca   120
gggaaagccc ctaagggcct gatctctgct catccgggt tgcaaagtgg ggtcccatca    180
aggttcagtg gcagtggatc tgggacagat ttcactctca ccatcaccag tctgcaacct   240
gaagattttg caacttacta ctgtcaacag agttacagtc ccctctcac  tttcggcgga   300 gggaccaggg tggatatcaa ac                                             322
```

<210> SEQ ID NO 49
<211> LENGTH: 357
<212> TYPE: DNA
<213> ORGANISM: Homo sapiens

<400> SEQUENCE: 49

```
gaggtgcagc tggtggagtc tgggggaggc ttggtccagc ctgggggggtc cctgagaatc    60 tcctgtgcag cctctggatt caccgtcagt agcaactaca tgagttgggt ccgccaggct   120
ccagggaagg gctggagtg gtctcagtt atttatagtg gtggtagcac atactacgca    180
gactccgtga aggcagatt ctccttctcc agagacaact ccaagaacac agtgtttctt    240
caaatgaaca gcctgagagc cgaggacacg gctgtgtatt actgtgcgag atgtctgagc   300
aggatgcggg gttacggttt agacgtctgg ggccaaggga ccacggtcac cgtctcg      357
```

<210> SEQ ID NO 50
<211> LENGTH: 119
<212> TYPE: PRT
<213> ORGANISM: Homo sapiens

<400> SEQUENCE: 50

```
Glu Val Gln Leu Val Glu Ser Gly Gly Gly Leu Val Gln Pro Gly Gly
1               5                   10                  15

Ser Leu Arg Ile Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Ser Phe Ser Arg Asp Asn Ser Lys Asn Thr Val Phe Leu
65                  70                  75                  80

Gln Met Asn Ser Leu Arg Ala Glu Asp Thr Ala Val Tyr Tyr Cys Ala
                85                  90                  95

Arg Cys Leu Ser Arg Met Arg Gly Tyr Gly Leu Asp Val Trp Gly Gln
            100                 105                 110
```

```
Gly Thr Thr Val Thr Val Ser
        115

<210> SEQ ID NO 51
<211> LENGTH: 318
<212> TYPE: DNA
<213> ORGANISM: Homo sapiens

<400> SEQUENCE: 51
gacatccaga tgacccagtc tccatcctcc ctgtctgcat ctgtaggaga cagagtcacc      60
atcacttgcc ggacaagtca gagcattagc agctatttaa attggtatca gcagaaacca     120
gggaaagccc ctaaactcct gatctatgct gcatccagtt tgcaaagtgg ggtcccatca     180
aggttcagtg gcagtggatc tgggacagat ttcactctca ccatcagcgg tctgcaacct     240
gaagattttg caacctacta ctgtcaacag agttacagta tgcctgcctt tggccagggg     300
accaagctgg agatcaaa                                                    318

<210> SEQ ID NO 52
<211> LENGTH: 106
<212> TYPE: PRT
<213> ORGANISM: Homo sapiens

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ser Tyr Ser Met Pro Ala
                85                  90                  95

Phe Gly Gln Gly Thr Lys Leu Glu Ile Lys
            100                 105

<210> SEQ ID NO 53
<211> LENGTH: 291
<212> TYPE: DNA
<213> ORGANISM: Influenza A virus

<400> SEQUENCE: 53
atgagtcttc taaccgaggt cgaaacgcct atcagaaacg aatgggggtg cagatgcaac      60
gattcaagtg atcctcttgt tgttgccgca agtatcattg ggatcctgca cttgatattg     120
tggattcttg atcgtctttt tttcaaatgc atttatcgtc tctttaaaca cggtctgaaa     180
agagggccct tctacggaag gtaccagag tctatgaggg aagaatatcg aaaggaacag     240
cagagtgctg tggatgctga cgatagtcat tttgtcaaca tagagctgga g              291

<210> SEQ ID NO 54
<211> LENGTH: 404
<212> TYPE: DNA
<213> ORGANISM: Homo sapiens

<400> SEQUENCE: 54
aagcttccac catggacatg agggtcctcg ctcagctcct ggggctcctg ctactctggc      60
```

| | | | |
|---|---|---|---|
| tccgaggtgc | cagatgtgac | atccagatga | cccagtctcc atcctccctg tctgcatctg | 120 |
| taggagacag | agtcaccatc | acttgccggg | cgagtcagaa catttacaag tatttaaatt | 180 |
| ggtatcagca | gagaccaggg | aaagccccta | agggcctgat ctctgctgca tccgggttgc | 240 |
| aaagtggggt | cccatcaagg | ttcagtggca | gtggatctgg gacagatttc actctcacca | 300 |
| tcaccagtct | gcaacctgaa | gattttgcaa | cttactactg tcaacagagt tacagtcccc | 360 |
| ctctcacttt | cggcggaggg | accagggtgg | agatcaaacg tacg | 404 |

<210> SEQ ID NO 55
<211> LENGTH: 404
<212> TYPE: DNA
<213> ORGANISM: Homo sapiens

<400> SEQUENCE: 55

| | | | |
|---|---|---|---|
| cgtacgtttg | atctccaccc | tggtccctcc | gccgaaagtg agaggggac tgtaactctg | 60 |
| ttgacagtag | taagttgcaa | aatcttcagg | ttgcagactg gtgatggtga gagtgaaatc | 120 |
| tgtcccagat | ccactgccac | tgaaccttga | tgggacccca ctttgcaacc cggatgcagc | 180 |
| agagatcagg | cccttagggg | ctttccctgg | tctctgctga taccaattta aatacttgta | 240 |
| aatgttctga | ctcgcccggc | aagtgatggt | gactctgtct cctacagatg cagacaggga | 300 |
| ggatggagac | tgggtcatct | ggatgtcaca | tctggcacct cggagccaga gtagcaggag | 360 |
| ccccaggagc | tgagcgagga | ccctcatgtc | catggtggaa gctt | 404 |

<210> SEQ ID NO 56
<211> LENGTH: 236
<212> TYPE: PRT
<213> ORGANISM: Homo sapiens

<400> SEQUENCE: 56

Met Asp Met Arg Val Leu Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asn Ile Tyr Lys Tyr Leu Asn Trp Tyr Gln Gln Arg Pro Gly Lys
    50                  55                  60

Ala Pro Lys Gly Leu Ile Ser Ala Ala Ser Gly Leu Gln Ser Gly Val
65                  70                  75                  80

Pro Ser Arg Phe Ser Gly Ser Gly Ser Gly Thr Asp Phe Thr Leu Thr
                85                  90                  95

Ile Thr Ser Leu Gln Pro Glu Asp Phe Ala Thr Tyr Tyr Cys Gln Gln
            100                 105                 110

Ser Tyr Ser Pro Pro Leu Thr Phe Gly Gly Gly Thr Arg Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 57
<211> LENGTH: 22
<212> TYPE: PRT
<213> ORGANISM: Homo sapiens

<400> SEQUENCE: 57

Met Asp Met Arg Val Leu Ala Gln Leu Leu Gly Leu Leu Leu Leu Trp
1               5                   10                  15

Leu Arg Gly Ala Arg Cys
            20

<210> SEQ ID NO 58
<211> LENGTH: 23
<212> TYPE: PRT
<213> ORGANISM: Homo sapiens

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 59
<211> LENGTH: 11
<212> TYPE: PRT
<213> ORGANISM: Homo sapiens

<400> SEQUENCE: 59

Arg Ala Ser Gln Asn Ile Tyr Lys Tyr Leu Asn
1               5                   10

<210> SEQ ID NO 60
<211> LENGTH: 15
<212> TYPE: PRT
<213> ORGANISM: Homo sapiens

<400> SEQUENCE: 60

Trp Tyr Gln Gln Arg Pro Gly Lys Ala Pro Lys Gly Leu Ile Ser
1               5                   10                  15

<210> SEQ ID NO 61
<211> LENGTH: 7
<212> TYPE: PRT
<213> ORGANISM: Homo sapiens

<400> SEQUENCE: 61

Ala Ala Ser Gly Leu Gln Ser
1               5

<210> SEQ ID NO 62
<211> LENGTH: 32
<212> TYPE: PRT
<213> ORGANISM: Homo sapiens

<400> SEQUENCE: 62

Gly Val Pro Ser Arg Phe Ser Gly Ser Gly Ser Gly Thr Asp Phe Thr

```
            1               5                  10                 15
          Leu Thr Ile Thr Ser Leu Gln Pro Glu Asp Phe Ala Thr Tyr Tyr Cys
                            20                 25                 30
```

<210> SEQ ID NO 63
<211> LENGTH: 9
<212> TYPE: PRT
<213> ORGANISM: Homo sapiens

<400> SEQUENCE: 63

```
Gln Gln Ser Tyr Ser Pro Pro Leu Thr
1               5
```

<210> SEQ ID NO 64
<211> LENGTH: 10
<212> TYPE: PRT
<213> ORGANISM: Homo sapiens

<400> SEQUENCE: 64

```
Phe Gly Gly Gly Thr Arg Val Glu Ile Lys
1               5                   10
```

<210> SEQ ID NO 65
<211> LENGTH: 800
<212> TYPE: DNA
<213> ORGANISM: Artificial Sequence
<220> FEATURE:
<223> OTHER INFORMATION: Recombinant human sequence

<400> SEQUENCE: 65

| | | | | | |
|---|---|---|---|---|---|
| tcgaaattaa | tacgactcac | tatagggaga | cccaagctgg | ctagcgttta | aacttaagct | 60 |
| tccaccatgg | acatgagggt | cctcgctcag | ctcctgggc | tcctgctact | ctggctccga | 120 |
| ggtgccagat | gtgacatcca | gatgacccag | tctccatcct | ccctgtctgc | atctgtagga | 180 |
| gacagagtca | ccatcacttg | ccgggcgagt | cagaacattt | acaagtattt | aaattggtat | 240 |
| cagcagagac | cagggaaagc | ccctaagggc | ctgatctctg | ctgcatccgg | gttgcaaagt | 300 |
| ggggtcccat | caaggttcag | tggcagtgga | tctgggacag | atttcactct | caccatcacc | 360 |
| agtctgcaac | ctgaagattt | tgcaacttac | tactgtcaac | agagttacag | tccccctctc | 420 |
| actttcggcg | gagggaccag | ggtggagatc | aaacgtacgg | tggctgcacc | atctgtcttc | 480 |
| atcttcccgc | catctgatga | gcagttgaaa | tctggaactg | cctctgttgt | gtgcctgctg | 540 |
| aataacttct | atcccagaga | ggccaaagta | cagtggaagg | tggataacgc | cctccaatcg | 600 |
| ggtaactccc | aggagagtgt | cacagagcag | gacagcaagg | acagcaccta | cagcctcagc | 660 |
| agcaccctga | cgctgagcaa | agcagactac | gagaaacaca | aagtctacgc | ctgcgaagtc | 720 |
| acccatcagg | gcctgagctc | gcccgtcaca | aagagcttca | acaggggaga | gtgttagagg | 780 |
| gtctagaggg | cccgtttaaa | | | | | 800 |

<210> SEQ ID NO 66
<211> LENGTH: 800
<212> TYPE: DNA
<213> ORGANISM: Artificial Sequence
<220> FEATURE:
<223> OTHER INFORMATION: Recombinant Human sequence

<400> SEQUENCE: 66

| | | | | | |
|---|---|---|---|---|---|
| tttaaacggg | ccctctagac | cctctaacac | tctcccctgt | tgaagctctt | tgtgacgggc | 60 |
| gagctcaggc | cctgatgggt | gacttcgcag | gcgtagactt | tgtgtttctc | gtagtctgct | 120 |

```
ttgctcagcg tcagggtgct gctgaggctg taggtgctgt ccttgctgtc ctgctctgtg      180
acactctcct gggagttacc cgattggagg gcgttatcca ccttccactg tactttggcc      240
tctctgggat agaagttatt cagcaggcac acaacagagg cagttccaga tttcaactgc      300
tcatcagatg gcgggaagat gaagacagat ggtgcagcca ccgtacgttt gatctccacc      360
ctggtccctc cgccgaaagt gagaggggga ctgtaactct gttgacagta gtaagttgca      420
aaatcttcag gttgcagact ggtgatggtg agagtgaaat ctgtcccaga tccactgcca      480
ctgaaccttg atgggacccc actttgcaac ccggatgcag cagagatcag gcccttaggg      540
gctttccctg gtctctgctg ataccaattt aaatacttgt aaatgttctg actcgcccgg      600
caagtgatgg tgactctgtc tcctacagat gcagacagga aggatggaga ctgggtcatc      660
tggatgtcac atctggcacc tcggagccag agtagcagga gccccaggag ctgagcgagg      720
accctcatgt ccatggtgga agcttaagtt taaacgctag ccagcttggg tctccctata      780
gtgagtcgta ttaatttcga                                                 800
```

<210> SEQ ID NO 67
<211> LENGTH: 427
<212> TYPE: DNA
<213> ORGANISM: Homo sapiens

<400> SEQUENCE: 67

```
aagcttccac catgaaacac ctgtggttct tccttctcct ggtggcagct cccagctggg       60
tcctgtccca ggtgcaattg caggagtcgg gcccaggact ggtgaagcct tcggagaccc      120
tgtccctcac ctgcactgtc tctggttcgt ccatcagtaa ttactactgg agctggatcc      180
ggcagtcccc agggaaggga ctggagtgga ttgggtttat ctattacggt ggaaacacca      240
agtacaatcc ctcccctcaag agccgcgtca ccatatcaca agacacttcc aagagtcagg      300
tctccctgac gatgagctct gtgaccgctg cggaatcggc cgtctatttc tgtgcgagag      360
cgtcttgtag tggtggttac tgtatccttg actactgggg ccagggaacc ctggtcaccg      420
tctcgag                                                               427
```

<210> SEQ ID NO 68
<211> LENGTH: 427
<212> TYPE: DNA
<213> ORGANISM: Homo sapiens

<400> SEQUENCE: 68

```
ctcgagacgg tgaccagggt tccctggccc cagtagtcaa ggatacagta accaccacta       60
caagacgctc tcgcacagaa atagacggcc gattccgcag cggtcacaga gctcatcgtc      120
agggagacct gactcttgga agtgtcttgt gatatggtga cgcggctctt gagggaggga      180
ttgtacttgg tgtttccacc gtaatagata aacccaatcc actccagtcc cttccctggg      240
gactgccgga tccagctcca gtagtaatta ctgatggacg aaccagagac agtgcaggtg      300
agggacaggg tctccgaagg cttcaccagt cctgggcccg actcctgcaa ttgcacctgg      360
gacaggaccc agctgggagc tgccaccagg agaaggaaga accacaggtg tttcatggtg      420
gaagctt                                                               427
```

<210> SEQ ID NO 69
<211> LENGTH: 469
<212> TYPE: PRT
<213> ORGANISM: Homo sapiens

<400> SEQUENCE: 69

```
Met Lys His Leu Trp Phe Phe Leu Leu Leu Val Ala Ala Pro Ser Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Ser Ser Ile
            35                  40                  45

Ser Asn Tyr Tyr Trp Ser Trp Ile Arg Gln Ser Pro Gly Lys Gly Leu
        50                  55                  60

Glu Trp Ile Gly Phe Ile Tyr Tyr Gly Gly Asn Thr Lys Tyr Asn Pro
65                  70                  75                  80

Ser Leu Lys Ser Arg Val Thr Ile Ser Gln Asp Thr Ser Lys Ser Gln
                85                  90                  95

Val Ser Leu Thr Met Ser Ser Val Thr Ala Ala Glu Ser Ala Val Tyr
                100                 105                 110

Phe Cys Ala Arg Ala Ser Cys Ser Gly Gly Tyr Cys Ile Leu Asp Tyr
            115                 120                 125

Trp Gly Gln Gly Thr Leu Val Thr Val Ser Arg Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415
```

```
Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Gly Lys
465

<210> SEQ ID NO 70
<211> LENGTH: 19
<212> TYPE: PRT
<213> ORGANISM: Homo sapiens

<400> SEQUENCE: 70

Met Lys His Leu Trp Phe Phe Leu Leu Leu Val Ala Ala Pro Ser Trp
1               5                   10                  15

Val Leu Ser

<210> SEQ ID NO 71
<211> LENGTH: 30
<212> TYPE: PRT
<213> ORGANISM: Homo sapiens

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser
            20                  25                  30

<210> SEQ ID NO 72
<211> LENGTH: 5
<212> TYPE: PRT
<213> ORGANISM: Homo sapiens

<400> SEQUENCE: 72

Asn Tyr Tyr Trp Ser
1               5

<210> SEQ ID NO 73
<211> LENGTH: 14
<212> TYPE: PRT
<213> ORGANISM: Homo sapiens

<400> SEQUENCE: 73

Trp Ile Arg Gln Ser Pro Gly Lys Gly Leu Glu Trp Ile Gly
1               5                   10

<210> SEQ ID NO 74
<211> LENGTH: 16
<212> TYPE: PRT
<213> ORGANISM: Homo sapiens

<400> SEQUENCE: 74

Phe Ile Tyr Tyr Gly Gly Asn Thr Lys Tyr Asn Pro Ser Leu Lys Ser
1               5                   10                  15

<210> SEQ ID NO 75
<211> LENGTH: 32
<212> TYPE: PRT
<213> ORGANISM: Homo sapiens

<400> SEQUENCE: 75
```

```
Arg Val Thr Ile Ser Gln Asp Thr Ser Lys Ser Gln Val Ser Leu Thr
1               5                   10                  15

Met Ser Ser Val Thr Ala Ala Glu Ser Ala Val Tyr Phe Cys Ala Arg
            20                  25                  30
```

<210> SEQ ID NO 76
<211> LENGTH: 11
<212> TYPE: PRT
<213> ORGANISM: Homo sapiens

<400> SEQUENCE: 76

```
Ala Ser Cys Ser Gly Gly Tyr Cys Ile Leu Asp
1               5                   10
```

<210> SEQ ID NO 77
<211> LENGTH: 11
<212> TYPE: PRT
<213> ORGANISM: Homo sapiens

<400> SEQUENCE: 77

```
Tyr Trp Gly Gln Gly Thr Leu Val Thr Val Ser
1               5                   10
```

<210> SEQ ID NO 78
<211> LENGTH: 1557
<212> TYPE: DNA
<213> ORGANISM: Artificial Sequence
<220> FEATURE:
<223> OTHER INFORMATION: Recombinant Human Sequence

<400> SEQUENCE: 78

```
tggcttatcg aaattaatac gactcactat agggagaccc aagctggcta gcgtttaaac      60
ttaagcttcc accatgaaac acctgtggtt cttccttctc ctggtggcag ctcccagctg     120
ggtcctgtcc caggtgcaat tgcaggagtc gggcccagga ctggtgaagc cttcggagac     180
cctgtccctc acctgcactg tctctggttc gtccatcagt aattactact ggagctggat     240
ccggcagtcc ccagggaagg gactggagtg gattgggttt atctattacg gtggaaacac     300
caagtacaat ccctccctca gagccgcgt caccatatca caagacactt ccaagagtca     360
ggtctccctg acgatgagct ctgtgaccgc tgcggaatcg ccgtctatt tctgtgcgag     420
agcgtcttgt agtggtggtt actgtatcct tgactactgg ggccagggaa ccctggtcac     480
cgtctcgaga gcctccacca agggcccatc ggtcttcccc ctggcaccct cctccaagag     540
cacctctggg ggcacagcgg ccctgggctg cctggtcaag gactacttcc ccgaaccggt     600
gacggtgtcg tggaactcag gcgccctgac cagcggcgtg cacaccttcc cggctgtcct     660
acagtcctca ggactctact ccctcagcag cgtggtgacc gtgccctcca gcagcttggg     720
cacccagacc tacatctgca acgtgaatca caagcccagc aacaccaagg tggacaagag     780
agttgagccc aaatcttgtg acaaaactca cacatgccca ccgtgcccag cacctgaact     840
cctgggggga ccgtcagtct tcctcttccc cccaaaaccc aaggacaccc tcatgatctc     900
ccggacccct gaggtcacat gcgtggtggt ggacgtgagc cacgaagacc ctgaggtcaa     960
gttcaactgg tacgtggacg gcgtggaggt gcataatgcc aagacaaagc cgcgggagga    1020
gcagtacaac agcacgtacc gtgtggtcag cgtcctcacc gtcctgcacc aggactggct    1080
gaatggcaag gagtacaagt gcaaggtctc caacaaagcc ctcccagccc ccatcgagaa    1140
aaccatctcc aaagccaaag ggcagccccg agaaccacag gtgtacaccc tgcccccatc    1200
```

| | |
|---|---|
| ccgggaggag atgaccaaga accaggtcag cctgacctgc ctggtcaaag gcttctatcc | 1260 |
| cagcgacatc gccgtggagt gggagagcaa tgggcagccg gagaacaact acaagaccac | 1320 |
| gcctcccgtg ctggactccg acggctcctt cttcctctat agcaagctca ccgtggacaa | 1380 |
| gagcaggtgg cagcaggga acgtcttctc atgctccgtg atgcatgagg ctctgcacaa | 1440 |
| ccactacacg cagaagagcc tctccctgtc tccgggtaaa tgagttctag agggcccgtt | 1500 |
| taaacccgct gatcagcctc gactgtgcct tctagttgcc agccatctgt tgtttgc | 1557 |

<210> SEQ ID NO 79
<211> LENGTH: 1557
<212> TYPE: DNA
<213> ORGANISM: Artificial Sequence
<220> FEATURE:
<223> OTHER INFORMATION: Recombinant Human Sequence

<400> SEQUENCE: 79

| | |
|---|---|
| gcaaacaaca gatggctggc aactagaagg cacagtcgag gctgatcagc gggtttaaac | 60 |
| gggcccttcta gaactcattt acccggagac agggagaggc tcttctgcgt gtagtggttg | 120 |
| tgcagagcct catgcatcac ggagcatgag aagacgttcc cctgctgcca cctgctcttg | 180 |
| tccacggtga gcttgctata gaggaagaag gagccgtcgg agtccagcac gggaggcgtg | 240 |
| gtcttgtagt tgttctccgg ctgcccattg ctctcccact ccacggcgat gtcgctggga | 300 |
| tagaagcctt tgaccaggca ggtcaggctg acctggttct tggtcatctc ctcccgggat | 360 |
| gggggcaggg tgtacacctg tggttctcgg ggctgcccctt tggctttgga gatggttttc | 420 |
| tcgatggggg ctgggagggc tttgttggag accttgcact tgtactcctt gccattcagc | 480 |
| cagtcctggt gcaggacggt gaggacgctg accacacggt acgtgctgtt gtactgctcc | 540 |
| tcccgcggct ttgtcttggc attatgcacc tccacgccgt ccacgtacca gttgaacttg | 600 |
| acctcagggt cttcgtggct cacgtccacc accacgcatg tgacctcagg ggtccgggag | 660 |
| atcatgaggg tgtccttggg ttttgggggg aagaggaaga ctgacggtcc ccccaggagt | 720 |
| tcaggtgctg ggcacggtgg gcatgtgtga gttttgtcac aagatttggg ctcaactctc | 780 |
| ttgtccacct tggtgttgct gggcttgtga ttcacgttgc agatgtaggt ctgggtgccc | 840 |
| aagctgctgg agggcacggt caccacgctg ctgagggagt agagtcctga ggactgtagg | 900 |
| acagccggga aggtgtgcac gccgctggtc agggcgcctg agttccacga caccgtcacc | 960 |
| ggttcgggga agtagtcctt gaccaggcag cccagggccg ctgtgccccc agaggtgctc | 1020 |
| ttggaggagg gtgccagggg gaagaccgat gggcccttgg tggaggctct cgagacggtg | 1080 |
| accagggttc cctggcccca gtagtcaagg atacagtaac caccactaca agacgctctc | 1140 |
| gcacagaaat agacggccga ttccgcagcg gtcacagagc tcatcgtcag ggagacctga | 1200 |
| ctcttggaag tgtcttgtga tatggtgacg cggctcttga ggagggatt gtacttggtg | 1260 |
| tttccaccgt aatagataaa cccaatccac tccagtccct tccctgggga ctgccggatc | 1320 |
| cagctccagt agtaattact gatggacgaa ccagagacag tgcaggtgag ggacagggtc | 1380 |
| tccgaaggct tcaccagtcc tgggcccgac tcctgcaatt gcacctggga caggacccag | 1440 |
| ctgggagctg ccaccaggag aaggaagaac cacaggtgtt tcatggtgga agcttaagtt | 1500 |
| taaacgctag ccagcttggg tctccctata gtgagtcgta ttaatttcga taagcca | 1557 |

<210> SEQ ID NO 80
<211> LENGTH: 11
<212> TYPE: PRT
<213> ORGANISM: Homo sapiens

<400> SEQUENCE: 80

Trp Gly Gln Gly Thr Leu Val Thr Val Ser Ser
1               5                   10

<210> SEQ ID NO 81
<211> LENGTH: 6
<212> TYPE: DNA
<213> ORGANISM: Artificial Sequence
<220> FEATURE:
<223> OTHER INFORMATION: Restriction site

<400> SEQUENCE: 81 ctcgag                                                                      6

<210> SEQ ID NO 82
<211> LENGTH: 11
<212> TYPE: PRT
<213> ORGANISM: Homo sapiens

<400> SEQUENCE: 82

Trp Gly Gln Gly Thr Leu Val Thr Val Ser Arg
1               5                   10

<210> SEQ ID NO 83
<211> LENGTH: 404
<212> TYPE: DNA
<213> ORGANISM: Homo sapiens

<400> SEQUENCE: 83
aagcttccac catggacatg agggtcctcg ctcagctcct ggggctcctg ctactctggc         60
tccgaggtgc cagatgtgac atccaggtga cccagtctcc atcctccctg tctgcatctg        120
taggagacag agtcaccatc acttgccgcg cgagtcagaa catttacaag tatttaaatt        180
ggtatcagca gagaccaggg aaagccccta agggcctgat ctctgctgca tccgggttgc        240
aaagtggggt cccatcaagg ttcagtggca gtggatctgg gacagatttc actctcacca        300
tcaccagtct gcaacctgaa gattttgcaa cttactactg tcaacagagt tacagtcccc        360
ctctcacttt cggcggaggg accagggtgg atatcaaacg tacg                        404

<210> SEQ ID NO 84
<211> LENGTH: 404
<212> TYPE: DNA
<213> ORGANISM: Homo sapiens

<400> SEQUENCE: 84
cgtacgtttg atatccaccc tggtccctcc gccgaaagtg agaggggac tgtaactctg          60 ttgacagtag taagttgcaa aatcttcagg ttgcagactg tgatggtga gagtgaaatc        120 tgtcccagat ccactgccac tgaaccttga tgggacccca ctttgcaacc cggatgcagc        180
agagatcagg cccttagggg ctttcccctgg tctctgctga taccaattta aatacttgta      240
aatgttctga ctcgcgcggc aagtgatggt gactctgtct cctacagatg cagacaggga        300
ggatggagac tgggtcacct ggatgtcaca tctggcacct cggagccaga gtagcaggag        360
ccccaggagc tgagcgagga ccctcatgtc catggtggaa gctt                        404

<210> SEQ ID NO 85
<211> LENGTH: 427
<212> TYPE: DNA
<213> ORGANISM: Homo sapiens

<400> SEQUENCE: 85

| | | | | | | |
|---|---|---|---|---|---|---|
| aagcttccac | catgaaacac | ctgtggttct | tccttctcct | ggtggcagct | cccagctggg | 60 |
| tcctgtccca | ggtgcaattg | caggagtcgg | gcccaggact | ggtgaagcct | tcggagaccc | 120 |
| tgtccctcac | ctgcactgtc | tctggttcgt | ccatcagtaa | ttactactgg | agctggatcc | 180 |
| ggcagtcccc | agggaaggga | ctggagtgga | ttgggtttat | ctattacggt | ggaaacacca | 240 |
| agtacaatcc | ctccctcaag | agccgcgtca | ccatatcaca | agacacttcc | aagagtcagg | 300 |
| tctccctgac | gatgagctct | gtgaccgctg | cggaatcggc | cgtctatttc | tgtgcgagag | 360 |
| cgtcttgtag | tggtggttac | tgtatccttg | actactgggg | ccagggaacc | ctggtcaccg | 420 |
| tctcgag | | | | | | 427 |

<210> SEQ ID NO 86
<211> LENGTH: 427
<212> TYPE: DNA
<213> ORGANISM: Homo sapiens

<400> SEQUENCE: 86

| | | | | | | |
|---|---|---|---|---|---|---|
| ctcgagacgg | tgaccagggt | tccctggccc | cagtagtcaa | ggatacagta | accaccacta | 60 |
| caagacgctc | tcgcacagaa | atagacggcc | gattccgcag | cggtcacaga | gctcatcgtc | 120 |
| agggagacct | gactcttgga | agtgtcttgt | gatatggtga | cgcggctctt | gagggaggga | 180 |
| ttgtacttgg | tgtttccacc | gtaatagata | aacccaatcc | actccagtcc | cttccctggg | 240 |
| gactgccgga | tccagctcca | gtagtaatta | ctgatggacg | aaccagagac | agtgcaggtg | 300 |
| agggacaggg | tctccgaagg | cttcaccagt | cctgggcccg | actcctgcaa | ttgcacctgg | 360 |
| gacaggaccc | agctgggagc | tgccaccagg | agaaggaaga | accacaggtg | tttcatggtg | 420 |
| gaagctt | | | | | | 427 |

<210> SEQ ID NO 87
<211> LENGTH: 427
<212> TYPE: DNA
<213> ORGANISM: Homo sapiens

<400> SEQUENCE: 87

| | | | | | | |
|---|---|---|---|---|---|---|
| aagcttccac | catgaaacac | ctgtggttct | tccttctcct | ggtggcagct | cccagctggg | 60 |
| tcctgtccca | ggtgcaattg | caggagtcgg | gcccaggact | ggtgaagcct | tcggagaccc | 120 |
| tgtccctcac | ctgcactgtc | tctggttcgt | ccatcagtaa | ttactactgg | agctggatcc | 180 |
| ggcagtcccc | agggaaggga | ctggagtgga | ttgggtttat | ctattacggt | ggaaacacca | 240 |
| agtacaatcc | ctccctcaag | agccgcgtca | ccatatcaca | agacacttcc | aagagtcagg | 300 |
| tctccctgac | gatgagctct | gtgaccgctg | cggaatcggc | cgtctatttc | tgtgcgagag | 360 |
| cgtcttgtag | tggtggttac | tgtatccttg | actactgggg | ccagggaacc | ctggtcaccg | 420 |
| tctcgag | | | | | | 427 |

<210> SEQ ID NO 88
<211> LENGTH: 401
<212> TYPE: DNA
<213> ORGANISM: Homo sapiens

<400> SEQUENCE: 88

| | | | | | | |
|---|---|---|---|---|---|---|
| aagcttccac | catggacatg | agggtcctcg | ctcagctcct | ggggctcctg | ctactctggc | 60 |
| tccgaggtgc | cagatgtgac | atccagatga | cccagtctcc | atcctccctg | tctgcatctg | 120 |
| taggagacag | agtcaccatc | acttgccgga | caagtcagag | cattagcagc | tatttaaatt | 180 |

```
ggtatcagca gaaaccaggg aaagcccta   aactcctgat ctatgctgca tccagtttgc        240
aaagtggggt cccatcaagg ttcagtggca gtggatctgg gacagatttc actctcacca        300
tcagcggtct gcaacctgaa gattttgcaa cctactactg tcaacagagt tacagtatgc        360 ctgccttttgg ccaggggacc aagctggaga tcaaacgtac g                            401
```

<210> SEQ ID NO 89
<211> LENGTH: 401
<212> TYPE: DNA
<213> ORGANISM: Homo sapiens

<400> SEQUENCE: 89

```
cgtacgtttg atctccagct tggtccctg  gccaaaggca ggcatactgt aactctgttg         60
acagtagtag gttgcaaaat cttcaggttg cagaccgctg atggtgagag tgaaatctgt       120
cccagatcca ctgccactga accttgatgg accccactt  tgcaaactgg atgcagcata       180
gatcaggagt ttagggggctt tccctggttt ctgctgatac caatttaaat agctgctaat       240
gctctgactt gtccggcaag tgatggtgac tctgtctcct acagatgcag acagggagga       300
tggagactgg gtcatctgga tgtcacatct ggcacctcgg agccagagta gcaggagccc       360
caggagctga gcgaggaccc tcatgtccat ggtggaagct t                             401
```

<210> SEQ ID NO 90
<211> LENGTH: 401
<212> TYPE: DNA
<213> ORGANISM: Homo sapiens

<400> SEQUENCE: 90

```
aagcttccac catggacatg agggtcctcg ctcagctcct ggggctcctg ctactctggc         60
tccgaggtgc cagatgtgac atccagatga cccagtctcc atcctccctg tctgcatctg       120
taggagacag agtcaccatc acttgccgga caagtcagag cattagcagc tatttaaatt       180
ggtatcagca gaaaccaggg aaagcccta  aactcctgat ctatgctgca tccagtttgc       240
aaagtggggt cccatcaagg ttcagtggca gtggatctgg gacagatttc actctcacca       300
tcagcggtct gcaacctgaa gattttgcaa cctactactg tcaacagagt tacagtatgc       360 ctgccttttgg ccaggggacc aagctggaga tcaaacgtac g                            401
```

<210> SEQ ID NO 91
<211> LENGTH: 130
<212> TYPE: PRT
<213> ORGANISM: Homo sapiens

<400> SEQUENCE: 91

```
Met Asp Met Arg Val Leu Ala Gln Leu Gly Leu Leu Leu Leu Trp
1               5                  10                  15

Leu Arg Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Thr Ser
            35                  40                  45

Gln Ser Ile Ser Ser Tyr Leu Asn Trp Tyr Gln Gln Lys Pro Gly Lys
        50                  55                  60

Ala Pro Lys Leu Leu Ile Tyr Ala Ala Ser Leu Gln Ser Gly Val
65                  70                  75                  80

Pro Ser Arg Phe Ser Gly Ser Gly Ser Gly Thr Asp Phe Thr Leu Thr
                85                  90                  95
```

Ile Ser Gly Leu Gln Pro Glu Asp Phe Ala Thr Tyr Tyr Cys Gln Gln
100                 105                 110

Ser Tyr Ser Met Pro Ala Phe Gly Gln Gly Thr Lys Leu Glu Ile Lys
        115                 120                 125

Arg Thr
    130

<210> SEQ ID NO 92
<211> LENGTH: 11
<212> TYPE: PRT
<213> ORGANISM: Homo sapiens

<400> SEQUENCE: 92

Arg Thr Ser Gln Ser Ile Ser Ser Tyr Leu Asn
1               5                   10

<210> SEQ ID NO 93
<211> LENGTH: 15
<212> TYPE: PRT
<213> ORGANISM: Homo sapiens

<400> SEQUENCE: 93

Trp Tyr Gln Gln Lys Pro Gly Lys Ala Pro Lys Leu Leu Ile Tyr
1               5                   10                  15

<210> SEQ ID NO 94
<211> LENGTH: 13
<212> TYPE: PRT
<213> ORGANISM: Homo sapiens

<400> SEQUENCE: 94

Ala Ala Ser Ser Leu Gln Ser Gly Val Pro Ser Arg Phe
1               5                   10

<210> SEQ ID NO 95
<211> LENGTH: 26
<212> TYPE: PRT
<213> ORGANISM: Homo sapiens

<400> SEQUENCE: 95

Ser Gly Ser Gly Ser Gly Thr Asp Phe Thr Leu Thr Ile Ser Gly Leu
1               5                   10                  15

Gln Pro Glu Asp Phe Ala Thr Tyr Tyr Cys
            20                  25

<210> SEQ ID NO 96
<211> LENGTH: 8
<212> TYPE: PRT
<213> ORGANISM: Homo sapiens

<400> SEQUENCE: 96

Gln Gln Ser Tyr Ser Met Pro Ala
1               5

<210> SEQ ID NO 97
<211> LENGTH: 427
<212> TYPE: DNA
<213> ORGANISM: Homo sapiens

<400> SEQUENCE: 97
aagcttccac catggagttg gggctgtgct gggttttcct tgttgctatt ttaaaaggtg    60
tccagtgtga ggtgcagctg gtggagtctg ggggaggctt ggtccagcct ggggggtccc   120

```
tgagaatctc ctgtgcagcc tctggattca ccgtcagtag caactacatg agttgggtcc    180
gccaggctcc agggaagggg ctggagtggg tctcagttat ttatagtggt ggtagcacat    240
actacgcaga ctccgtgaag ggcagattct ccttctccag agacaactcc aagaacacag    300
tgtttcttca aatgaacagc ctgagagccg aggacacggc tgtgtattac tgtgcgagat    360
gtctgagcag gatgcggggt tacggtttag acgtctgggg ccaagggacc acggtcaccg    420
tctcgag                                                              427

<210> SEQ ID NO 98
<211> LENGTH: 427
<212> TYPE: DNA
<213> ORGANISM: Homo sapiens

<400> SEQUENCE: 98
ctcgagacgg tgaccgtggt cccttggccc cagacgtcta aaccgtaacc ccgcatcctg     60
ctcagacatc tcgcacagta atacacagcc gtgtcctcgg ctctcaggct gttcatttga    120
agaaacactg tgttcttgga gttgtctctg gagaaggaga atctgccctt cacggagtct    180
gcgtagtatg tgctaccacc actataaata actgagaccc actccagccc ttccctgga    240 gcctggcgga cccaactcat gtagttgcta ctgacggtga atccagaggc tgcacaggag    300
attctcaggg accccccagg ctggaccaag cctcccccag actccaccag ctgcacctca    360
cactggacac ctttaaaat agcaacaagg aaaacccagc acagcccaa ctccatggtg     420 gaagctt                                                              427

<210> SEQ ID NO 99
<211> LENGTH: 427
<212> TYPE: DNA
<213> ORGANISM: Homo sapiens

<400> SEQUENCE: 99
aagcttccac catggagttg gggctgtgct gggttttcct tgttgctatt ttaaaaggtg     60
tccagtgtga ggtgcagctg gtggagtctg ggggaggctt ggtccagcct ggggggtccc    120
tgagaatctc ctgtgcagcc tctggattca ccgtcagtag caactacatg agttgggtcc    180
gccaggctcc agggaagggg ctggagtggg tctcagttat ttatagtggt ggtagcacat    240
actacgcaga ctccgtgaag ggcagattct ccttctccag agacaactcc aagaacacag    300
tgtttcttca aatgaacagc ctgagagccg aggacacggc tgtgtattac tgtgcgagat    360
gtctgagcag gatgcggggt tacggtttag acgtctgggg ccaagggacc acggtcaccg    420
tctcgag                                                              427

<210> SEQ ID NO 100
<211> LENGTH: 138
<212> TYPE: PRT
<213> ORGANISM: Homo sapiens

<400> SEQUENCE: 100

Met Glu Leu Gly Leu Cys Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Ile Ser Cys Ala Ala Ser Gly Phe Thr Val
        35                  40                  45

Ser Ser Asn Tyr Met Ser Trp Val Arg Gln Ala Pro Gly Lys Gly Leu
    50                  55                  60
```

```
Glu Trp Val Ser Val Ile Tyr Ser Gly Gly Ser Thr Tyr Tyr Ala Asp
 65                  70                  75                  80

Ser Val Lys Gly Arg Phe Ser Phe Ser Arg Asp Asn Ser Lys Asn Thr
                 85                  90                  95

Val Phe Leu Gln Met Asn Ser Leu Arg Ala Glu Asp Thr Ala Val Tyr
            100                 105                 110

Tyr Cys Ala Arg Cys Leu Ser Arg Met Arg Gly Tyr Gly Leu Asp Val
        115                 120                 125

Trp Gly Gln Gly Thr Thr Val Thr Val Ser
130                 135

<210> SEQ ID NO 101
<211> LENGTH: 19
<212> TYPE: PRT
<213> ORGANISM: Homo sapiens

<400> SEQUENCE: 101

Met Glu Leu Gly Leu Cys Trp Val Phe Leu Val Ala Ile Leu Lys Gly
 1               5                  10                  15

Val Gln Cys

<210> SEQ ID NO 102
<211> LENGTH: 30
<212> TYPE: PRT
<213> ORGANISM: Homo sapiens

<400> SEQUENCE: 102

Glu Val Gln Leu Val Glu Ser Gly Gly Gly Leu Val Gln Pro Gly Gly
 1               5                  10                  15

Ser Leu Arg Ile Ser Cys Ala Ala Ser Gly Phe Thr Val Ser
            20                  25                  30

<210> SEQ ID NO 103
<211> LENGTH: 5
<212> TYPE: PRT
<213> ORGANISM: Homo sapiens

<400> SEQUENCE: 103

Ser Asn Tyr Met Ser
 1               5

<210> SEQ ID NO 104
<211> LENGTH: 14
<212> TYPE: PRT
<213> ORGANISM: Homo sapiens

<400> SEQUENCE: 104

Trp Val Arg Gln Ala Pro Gly Lys Gly Leu Glu Trp Val Ser
 1               5                  10

<210> SEQ ID NO 105
<211> LENGTH: 15
<212> TYPE: PRT
<213> ORGANISM: Homo sapiens

<400> SEQUENCE: 105

Val Ile Tyr Ser Gly Gly Ser Thr Tyr Tyr Ala Asp Ser Val Lys
 1               5                  10                  15

<210> SEQ ID NO 106
<211> LENGTH: 33
```

```
<212> TYPE: PRT
<213> ORGANISM: Homo sapiens

<400> SEQUENCE: 106

Gly Arg Phe Ser Phe Ser Arg Asp Asn Ser Lys Asn Thr Val Phe Leu
1               5                   10                  15

Gln Met Asn Ser Leu Arg Ala Glu Asp Thr Ala Val Tyr Tyr Cys Ala
            20                  25                  30

Arg

<210> SEQ ID NO 107
<211> LENGTH: 12
<212> TYPE: PRT
<213> ORGANISM: Homo sapiens

<400> SEQUENCE: 107

Cys Leu Ser Arg Met Arg Gly Tyr Gly Leu Asp Val
1               5                   10

<210> SEQ ID NO 108
<211> LENGTH: 10
<212> TYPE: PRT
<213> ORGANISM: Homo sapiens

<400> SEQUENCE: 108

Trp Gly Gln Gly Thr Thr Val Thr Val Ser
1               5                   10

<210> SEQ ID NO 109
<211> LENGTH: 6
<212> TYPE: PRT
<213> ORGANISM: Homo sapiens

<400> SEQUENCE: 109

Gly Ser Ser Ile Ser Asn
1               5

<210> SEQ ID NO 110
<211> LENGTH: 9
<212> TYPE: PRT
<213> ORGANISM: Homo sapiens

<400> SEQUENCE: 110

Phe Ile Tyr Tyr Gly Gly Asn Thr Lys
1               5

<210> SEQ ID NO 111
<211> LENGTH: 11
<212> TYPE: PRT
<213> ORGANISM: Homo sapiens

<400> SEQUENCE: 111

Trp Gly Gln Gly Thr Thr Val Thr Val Ser Ser
1               5                   10

<210> SEQ ID NO 112
<211> LENGTH: 7
<212> TYPE: PRT
<213> ORGANISM: Homo sapiens

<400> SEQUENCE: 112

Gly Phe Thr Val Ser Ser Asn
1               5
```

<210> SEQ ID NO 113
<211> LENGTH: 9
<212> TYPE: PRT
<213> ORGANISM: Homo sapiens

<400> SEQUENCE: 113

Val Ile Tyr Ser Gly Gly Ser Thr Tyr
1               5

<210> SEQ ID NO 114
<211> LENGTH: 10
<212> TYPE: PRT
<213> ORGANISM: Homo sapiens

<400> SEQUENCE: 114

Phe Gly Gln Gly Thr Lys Leu Glu Ile Lys
1               5                   10

<210> SEQ ID NO 115
<211> LENGTH: 366
<212> TYPE: DNA
<213> ORGANISM: Homo sapiens

<400> SEQUENCE: 115
caggtgcagc tgcagcagtc gggcccagga ctggtgaagc cttcacagac cctgtccctc        60
acttgcactg tctctggtgg ccccgtcagc ggtggtggtt actcctggaa ctggatccgc       120
caacgcccag gacagggcct ggagtgggtt gggttcatgt ttcacagtgg gagtccccgc       180
tacaatccga ccctcaagag tcgaattacc atctcagtcg acacgtctaa gaacctggtc       240
tccctgaagc tgagctctgt gacggccgcg gacacggccg tgtatttttg tgcgcgagtg       300
gggcagatgg acaagtacta tgccatggac gtctggggcc aagggaccac ggtcaccgtc       360
tcgagc                                                                  366

<210> SEQ ID NO 116
<211> LENGTH: 122
<212> TYPE: PRT
<213> ORGANISM: Homo sapiens

<400> SEQUENCE: 116

Gln Val Gln Leu Gln Gln Ser Gly Pro Gly Leu Val Lys Pro Ser Gln
1               5                   10                  15

Thr Leu Ser Leu Thr Cys Thr Val Ser Gly Gly Pro Val Ser Gly Gly
            20                  25                  30

Gly Tyr Ser Trp Asn Trp Ile Arg Gln Arg Pro Gly Gln Gly Leu Glu
        35                  40                  45

Trp Val Gly Phe Met Phe His Ser Gly Ser Pro Arg Tyr Asn Pro Thr
    50                  55                  60

Leu Lys Ser Arg Ile Thr Ile Ser Val Asp Thr Ser Lys Asn Leu Val
65                  70                  75                  80

Ser Leu Lys Leu Ser Ser Val Thr Ala Ala Asp Thr Ala Val Tyr Phe
                85                  90                  95

Cys Ala Arg Val Gly Gln Met Asp Lys Tyr Tyr Ala Met Asp Val Trp
            100                 105                 110

Gly Gln Gly Thr Thr Val Thr Val Ser Ser
        115                 120

<210> SEQ ID NO 117
<211> LENGTH: 323

-continued

<212> TYPE: DNA
<213> ORGANISM: Homo sapiens

<400> SEQUENCE: 117

```
gacatccaga tgacccagtc tccatcctcc ctgtcttcct ctgtcggaga cagagtcacc    60
atcacttgcc gggcaagtca gagcattggc gcctatgtaa attggtatca acagaaagca   120
gggaaagccc cccaggtcct gatctttggt gcttccaatt tacaaagcgg ggtcccatca   180
aggttcagtg gcagtggatc tgggacagat ttcactctca ccatcagcag tctgcaacct   240
gaagactttg caacttactt ctgtcaacag acttacagta ccccgatcac cttcggccaa   300
gggacacgac tggagattaa acg                                           323
```

<210> SEQ ID NO 118
<211> LENGTH: 107
<212> TYPE: PRT
<213> ORGANISM: Homo sapiens

<400> SEQUENCE: 118

Asp Ile Gln Met Thr Gln Ser Pro Ser Ser Leu Ser Ser Val Gly
1               5                   10                  15
Asp Arg Val Thr Ile Thr Cys Arg Ala Ser Gln Ser Ile Gly Ala Tyr
            20                  25                  30
Val Asn Trp Tyr Gln Gln Lys Ala Gly Lys Ala Pro Gln Val Leu Ile
        35                  40                  45
Phe Gly Ala Ser Asn Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Phe Cys Gln Gln Thr Tyr Ser Thr Pro Ile
                85                  90                  95
Thr Phe Gly Gln Gly Thr Arg Leu Glu Ile Lys
            100                 105

<210> SEQ ID NO 119
<211> LENGTH: 363
<212> TYPE: DNA
<213> ORGANISM: Homo sapiens

<400> SEQUENCE: 119

```
caggtccagc tgcaggagtc gggcccagga ctgctgaagc cttcggacac cctggccctc    60
acttgcactg tctctggtgg ctccatcacc agtgactact ggagctggat ccggcaaccc   120
ccagggaggg gactggactg gatcggattc ttctataacg gcggaagcac caagtacaat   180
ccctccctca agagtcgagt caccatttca gcggacacgt ccaagaacca gttgtccctg   240
aaattgacct ctgtgaccgc cgcagacacg gcgtgtatt attgtgcgag acatgatgcc    300
aaatttagtg ggagctacta cgttgcctcc tggggccagg gaacccgagt caccgtctcg   360
agc                                                                  363
```

<210> SEQ ID NO 120
<211> LENGTH: 121
<212> TYPE: PRT
<213> ORGANISM: Homo sapiens

<400> SEQUENCE: 120

Gln Val Gln Leu Gln Glu Ser Gly Pro Gly Leu Leu Lys Pro Ser Asp
1               5                   10                  15

Thr Leu Ala Leu Thr Cys Thr Val Ser Gly Gly Ser Ile Thr Ser Asp
            20                  25                  30

Tyr Trp Ser Trp Ile Arg Gln Pro Pro Gly Arg Gly Leu Asp Trp Ile
        35                  40                  45

Gly Phe Phe Tyr Asn Gly Gly Ser Thr Lys Tyr Asn Pro Ser Leu Lys
    50                  55                  60

Ser Arg Val Thr Ile Ser Ala Asp Thr Ser Lys Asn Gln Leu Ser Leu
65                  70                  75                  80

Lys Leu Thr Ser Val Thr Ala Ala Asp Thr Gly Val Tyr Tyr Cys Ala
                85                  90                  95

Arg His Asp Ala Lys Phe Ser Gly Ser Tyr Tyr Val Ala Ser Trp Gly
            100                 105                 110

Gln Gly Thr Arg Val Thr Val Ser Ser
        115                 120

<210> SEQ ID NO 121
<211> LENGTH: 323
<212> TYPE: DNA
<213> ORGANISM: Homo sapiens

<400> SEQUENCE: 121
gacatccaga tgacccagtc tccatcctcc ctgtctgcat ctgtaggaga cagagtcacc      60
atctcttgcc gggcaagtca gagcattagc acctatttaa attggtatca gcagcaacct    120
gggaaagccc ctaaggtcct catttttggt gcaaccaact tgcaaagtgg ggtcccatct    180
cgcttcagtg gcagtggatc tgggacagat ttcactctca ccatcagcag tctgcaacct    240
gaagattttg caacttacta ctgtcaacag agttacaata ccccccctcat ttttggccag    300 gggaccaagc tggagatcaa acg                                             323

<210> SEQ ID NO 122
<211> LENGTH: 107
<212> TYPE: PRT
<213> ORGANISM: Homo sapiens

<400> SEQUENCE: 122

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Ser Ile Ser Thr Tyr
            20                  25                  30

Leu Asn Trp Tyr Gln Gln Pro Gly Lys Ala Pro Lys Val Leu Ile
        35                  40                  45

Phe Gly Ala Thr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Ile Phe Gly Gln Gly Thr Lys Leu Glu Ile Lys
            100                 105

<210> SEQ ID NO 123
<211> LENGTH: 363
<212> TYPE: DNA
<213> ORGANISM: Homo sapiens

<400> SEQUENCE: 123
caggtccagc tgcaggagtc gggcccagga ctgctgaagc cttcggacac cctggccctc      60

```
acttgcactg tctctggtgg ctccatcacc agtgactact ggagctggat ccggcaaccc    120
ccagggaggg gactggactg gatcggattc ttctataacg gcgggagcac caagtacaat    180
ccctccctca agagtcgagt caccatatca gcggacacgt ccaagaacca gttgtccctg    240
aaattgacct ctgtgaccgc cgcagacacg gccgtgtatt attgtgcgag acatgatgtc    300
aaatttagtg ggagctacta cgttgcctcc tggggccagg gaacccgagt caccgtctcg    360
agc                                                                  363
```

<210> SEQ ID NO 124
<211> LENGTH: 121
<212> TYPE: PRT
<213> ORGANISM: Homo sapiens

<400> SEQUENCE: 124

```
Gln Val Gln Leu Gln Glu Ser Gly Pro Gly Leu Leu Lys Pro Ser Asp
1               5                   10                  15

Thr Leu Ala Leu Thr Cys Thr Val Ser Gly Gly Ser Ile Thr Ser Asp
            20                  25                  30

Tyr Trp Ser Trp Ile Arg Gln Pro Pro Gly Arg Gly Leu Asp Trp Ile
        35                  40                  45

Gly Phe Phe Tyr Asn Gly Gly Ser Thr Lys Tyr Asn Pro Ser Leu Lys
    50                  55                  60

Ser Arg Val Thr Ile Ser Ala Asp Thr Ser Lys Asn Gln Leu Ser Leu
65                  70                  75                  80

Lys Leu Thr Ser Val Thr Ala Ala Asp Thr Gly Val Tyr Tyr Cys Ala
                85                  90                  95

Arg His Asp Val Lys Phe Ser Gly Ser Tyr Tyr Val Ala Ser Trp Gly
            100                 105                 110

Gln Gly Thr Arg Val Thr Val Ser Ser
        115                 120
```

<210> SEQ ID NO 125
<211> LENGTH: 323
<212> TYPE: DNA
<213> ORGANISM: Homo sapiens

<400> SEQUENCE: 125

```
gacatccaga tgacccagtc tccatcctcc ctgtctgcat ctgtaggaga cagagtcacc     60
atctcttgcc gggcaagtca gagcattagc acctatttaa attggtatca gcagcaacct    120
gggaaagccc ctaaggtcct gatctctggt gcaaccaact tgcaaagtgg ggtcccatct    180
cgcttcagtg gcagtggatc tgggacagat ttcactctca ccatcagcag tctgcaacct    240
gaagattttg caacttacta ctgtcaacag agttacaata ccccccctcat ttttggccag    300 gggaccaagc tggagatcaa acg                                            323
```

<210> SEQ ID NO 126
<211> LENGTH: 107
<212> TYPE: PRT
<213> ORGANISM: Homo sapiens

<400> SEQUENCE: 126

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Ser Ile Ser Thr Tyr
            20                  25                  30
```

Leu Asn Trp Tyr Gln Gln Pro Gly Lys Ala Pro Lys Val Leu Ile
            35                  40                  45

Ser Gly Ala Thr Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asn Thr Pro Leu
                85                  90                  95

Ile Phe Gly Gln Gly Thr Lys Leu Glu Ile Lys
            100                 105

<210> SEQ ID NO 127
<211> LENGTH: 360
<212> TYPE: DNA
<213> ORGANISM: Homo sapiens

<400> SEQUENCE: 127
caggtgcagc tgcaggagtc gggcccacga gtggtgaggc cttcggagac cctgtccctc    60
acctgcactg tctcgggggg ctccatcagt tcttacaact ggatttggat ccggcagccc   120
cctgggaagg gactggagtg gattgggcac atatatgact atgggaggac cttctacaac   180
tcctccctcc agagtcgacc taccatatct gtagacgcgt ccaagaatca gctctccctg   240
cgattgacct ctgtgaccgc tcagacacg gccgtctatt actgtgcgag acctctcggt   300
atactccact actacgcgat ggacctctgg ggccaaggga ccacggtcac cgtctcgagc   360

<210> SEQ ID NO 128
<211> LENGTH: 120
<212> TYPE: PRT
<213> ORGANISM: Homo sapiens

<400> SEQUENCE: 128

Gln Val Gln Leu Gln Glu Ser Gly Pro Arg Val Val Arg Pro Ser Glu
 1               5                  10                  15

Thr Leu Ser Leu Thr Cys Thr Val Ser Gly Gly Ser Ile Ser Ser Tyr
            20                  25                  30

Asn Trp Ile Trp Ile Arg Gln Pro Pro Gly Lys Gly Leu Glu Trp Ile
            35                  40                  45

Gly His Ile Tyr Asp Tyr Gly Arg Thr Phe Tyr Asn Ser Ser Leu Gln
 50                  55                  60

Ser Arg Pro Thr Ile Ser Val Asp Ala Ser Lys Asn Gln Leu Ser Leu
 65                  70                  75                  80

Arg Leu Thr Ser Val Thr Ala Ser Asp Thr Ala Val Tyr Tyr Cys Ala
                85                  90                  95

Arg Pro Leu Gly Ile Leu His Tyr Tyr Ala Met Asp Leu Trp Gly Gln
            100                 105                 110

Gly Thr Thr Val Thr Val Ser Ser
        115                 120

<210> SEQ ID NO 129
<211> LENGTH: 320
<212> TYPE: DNA
<213> ORGANISM: Homo sapiens

<400> SEQUENCE: 129
gacatccaga tgacccagtc tccattatcc gtgtctgtat ctgtcgggga cagggtcacc    60
atcgcttgcc gggcaagtca gagtattgac aagttttaa attggtatca gcagaaacca   120

```
gggaaagccc ctaaactcct gatctatggt gcctccaatt tgcacagtgg ggccccatca      180
aggttcagtg ccagtgggtc tgggacagac ttcactctaa caatcaccaa tatacagact      240
gaagatttcg caacttacct ctgtcaacag agtttcagtg tccccgcttt cggcggaggg      300
accaaggttg agatcaaacg                                                  320
```

<210> SEQ ID NO 130
<211> LENGTH: 106
<212> TYPE: PRT
<213> ORGANISM: Homo sapiens

<400> SEQUENCE: 130

Asp Ile Gln Met Thr Gln Ser Pro Leu Ser Val Ser Val Ser Val Gly
1               5                   10                  15

Asp Arg Val Thr Ile Ala Cys Arg Ala Ser Gln Ser Ile Asp Lys Phe
            20                  25                  30

Leu Asn Trp Tyr Gln Gln Lys Pro Gly Lys Ala Pro Lys Leu Leu Ile
        35                  40                  45

Tyr Gly Ala Ser Asn Leu His Ser Gly Ala Pro Ser Arg Phe Ser Ala
    50                  55                  60

Ser Gly Ser Gly Thr Asp Phe Thr Leu Thr Ile Thr Asn Ile Gln Thr
65                  70                  75                  80

Glu Asp Phe Ala Thr Tyr Leu Cys Gln Gln Ser Phe Ser Val Pro Ala
                85                  90                  95

Phe Gly Gly Gly Thr Lys Val Glu Ile Lys
            100                 105

<210> SEQ ID NO 131
<211> LENGTH: 354
<212> TYPE: DNA
<213> ORGANISM: Homo sapiens

<400> SEQUENCE: 131

```
gaggtgcaac tggtggagtc tgagggggc ttggtccagc ctgggggtc cctgagactc         60 tcctgtacgg cctctgggtt aagtgtcagt tccacctaca tgaactgggt ccgccaggct      120
ccagggaagg ggctggaatg ggtctcagtt ttttatagtg agaccaggac gtactacgca      180
gactccgtga agggccgatt caccgtctcc agacacaatt ccaacaacac gctctatctt      240
cagatgaaca gcctgagagt tgaagacacg gccgtgtatt attgtgcgag agtccagaga      300
ttgtcgtacg gtatggacgt ctggggccaa gggaccacgg tcaccgtctc gagc            354
```

<210> SEQ ID NO 132
<211> LENGTH: 118
<212> TYPE: PRT
<213> ORGANISM: Homo sapiens

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Thr Ala Ser Gly Leu Ser Val Ser Ser Thr
            20                  25                  30

Tyr Met Asn Trp Val Arg Gln Ala Pro Gly Lys Gly Leu Glu Trp Val
        35                  40                  45

Ser Val Phe Tyr Ser Glu Thr Arg Thr Tyr Tyr Ala Asp Ser Val Lys
    50                  55                  60

Gly Arg Phe Thr Val Ser Arg His Asn Ser Asn Asn Thr Leu Tyr Leu
65                  70                  75                  80

```
Gln Met Asn Ser Leu Arg Val Glu Asp Thr Ala Val Tyr Tyr Cys Ala
                85                  90                  95

Arg Val Gln Arg Leu Ser Tyr Gly Met Asp Val Trp Gly Gln Gly Thr
            100                 105                 110

Thr Val Thr Val Ser Ser
        115
```

<210> SEQ ID NO 133
<211> LENGTH: 320
<212> TYPE: DNA
<213> ORGANISM: Homo sapiens

<400> SEQUENCE: 133

```
gacatccaga tgacccagtc tccatcctcc ctgtctgcat ctgttggaga cagagtcacc    60
atcacttgcc gggcaagtca gagcattagc acctatttaa attggtatca agagagacca   120
gggaaagccc ctaaactcct ggtctatggt gcatccactt tgcagagtgg ggtcccatca   180
aggttcagtg gcagtggatc tgggacagat ttcactctca ccatcgccag tctgcaacct   240
gaagattctg caacttacta ctgtcaacag acttacagta tccccctctt cggccagggg   300
acacggctgg agattaaacg                                               320
```

<210> SEQ ID NO 134
<211> LENGTH: 106
<212> TYPE: PRT
<213> ORGANISM: Homo sapiens

<400> SEQUENCE: 134

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Lys Arg Pro Gly Lys Ala Pro Lys Leu Leu Val
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Ala Ser Leu Gln Pro
65                  70                  75                  80

Glu Asp Ser Ala Thr Tyr Tyr Cys Gln Gln Thr Tyr Ser Ile Pro Leu
                85                  90                  95

Phe Gly Gln Gly Thr Arg Leu Glu Ile Lys
            100                 105
```

<210> SEQ ID NO 135
<211> LENGTH: 354
<212> TYPE: DNA
<213> ORGANISM: Homo sapiens

<400> SEQUENCE: 135

```
gaggtgcagc tggtggaatc tgagggggc ttggtccagc ctggggggtc cctgagactc     60
tcctgtacag cctctgggtt aagcgtcagt tccacctaca tgaactgggt ccgccaggct   120
ccagggaagg ggctggaatg ggtctcagtt ttttatagtg aaaccaggac gtattacgca   180
gactccgtga agggccgatt caccgtctcc agacacaatt ccaacaacac gctgtatctt   240
caaatgaaca gcctgagagc tgaagacacg gccgtgtatt attgtgcgag agtccagaga   300
ctgtcatacg gtatggacgt ctggggccaa gggaccacgg tcaccgtctc gagc         354
```

<210> SEQ ID NO 136
<211> LENGTH: 118
<212> TYPE: PRT
<213> ORGANISM: Homo sapiens

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Thr Ala Ser Gly Leu Ser Val Ser Ser Thr
            20                  25                  30

Tyr Met Asn Trp Val Arg Gln Ala Pro Gly Lys Gly Leu Glu Trp Val
        35                  40                  45

Ser Val Phe Tyr Ser Glu Thr Arg Thr Tyr Tyr Ala Asp Ser Val Lys
    50                  55                  60

Gly Arg Phe Thr Val Ser Arg His Asn Ser Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Gln Arg Leu Ser Tyr Gly Met Asp Val Trp Gly Gln Gly Thr
            100                 105                 110

Thr Val Thr Val Ser Ser
        115

<210> SEQ ID NO 137
<211> LENGTH: 320
<212> TYPE: DNA
<213> ORGANISM: Homo sapiens

<400> SEQUENCE: 137
gacatccaga tgacccagtc tccatcgtcc ctgtctgcat ctgtaggaga cagagtcacc      60
atcacttgcc gggcaagtca gagcattagc acctatttaa attggtatca agagaccag     120 gggaaagccc ctaaactcct ggtctatggt gcatccagtt tgcagagtgg ggtcccatca    180
aggttcagtg gcagtggatc tgggacagat ttcactctca ccatcgccag tctgcaacct    240
gaagattctg cagtttatta ctgtcaacag acttacagta tcccctctt cggccagggg    300 acacgactgg agattaaacg                                               320

<210> SEQ ID NO 138
<211> LENGTH: 106
<212> TYPE: PRT
<213> ORGANISM: Homo sapiens

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Lys Arg Pro Gly Lys Ala Pro Lys Leu Leu Val
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ala Ser Leu Gln Pro
65                  70                  75                  80

Glu Asp Ser Ala Val Tyr Tyr Cys Gln Gln Thr Tyr Ser Ile Pro Leu
                85                  90                  95

Phe Gly Gln Gly Thr Arg Leu Glu Ile Lys

<210> SEQ ID NO 139
<211> LENGTH: 360
<212> TYPE: DNA
<213> ORGANISM: Homo sapiens

<400> SEQUENCE: 139

```
caggtgcagc tgcaggagtc gggcccagga ctggtgaagc cctcggagac cctgtccctc      60
acctgcagtg tctctggtgg ctccattagt agtgatttct ggagttggat ccgacagccc     120
ccagggaagg gactggagtg gattgggtat gtctataaca gagggagcac taagtacagt     180
ccctccctca agagtcgagt caccatatca gcagacatgt ccaagaacca gttttccctg     240
aatatgagtt ctgtgaccgc tgcggacacg gccgtgtatt actgtgcgaa aaatggtcga     300
agtagcacca gttggggcat cgacgtctgg ggcaaaggga ccacggtcac cgtctcgagc     360
```

<210> SEQ ID NO 140
<211> LENGTH: 120
<212> TYPE: PRT
<213> ORGANISM: Homo sapiens

<400> SEQUENCE: 140

```
Gln Val Gln Leu Gln Glu Ser Gly Pro Gly Leu Val Lys Pro Ser Glu
1               5                   10                  15
Thr Leu Ser Leu Thr Cys Ser Val Ser Gly Gly Ser Ile Ser Ser Asp
            20                  25                  30
Phe Trp Ser Trp Ile Arg Gln Pro Pro Gly Lys Gly Leu Glu Trp Ile
        35                  40                  45
Gly Tyr Val Tyr Asn Arg Gly Ser Thr Lys Tyr Ser Pro Ser Leu Lys
    50                  55                  60
Ser Arg Val Thr Ile Ser Ala Asp Met Ser Lys Asn Gln Phe Ser Leu
65                  70                  75                  80
Asn Met Ser Ser Val Thr Ala Ala Asp Thr Ala Val Tyr Tyr Cys Ala
                85                  90                  95
Lys Asn Gly Arg Ser Ser Thr Ser Trp Gly Ile Asp Val Trp Gly Lys
            100                 105                 110
Gly Thr Thr Val Thr Val Ser Ser
        115                 120
```

<210> SEQ ID NO 141
<211> LENGTH: 323
<212> TYPE: DNA
<213> ORGANISM: Homo sapiens

<400> SEQUENCE: 141

```
gacatccaga tgacccagtc tccatcctcc ctgtctgcat ctgtgggaga cagactcacc      60
atcacttgcc gggcaagtca gagcattagc acctatttac attggtatca gcagaaacca     120
gggaaagccc ctaaactcct gatctatgct gcatccagtt tgcaaagtgg ggtcccatca     180
aggttcagtg gcagtagatc aggaacagat ttcactctca ccatcagcag tctgcaacct     240
gatgactttg caacttacta ctgtcaacag agttacagtc ccccccctca tttcggccct     300
gggaccaaag tggatatgaa acg                                             323
```

<210> SEQ ID NO 142
<211> LENGTH: 107
<212> TYPE: PRT
<213> ORGANISM: Homo sapiens

<400> SEQUENCE: 142

Asp Ile Gln Met Thr Gln Ser Pro Ser Ser Leu Ser Ala Ser Val Gly
1               5                   10                  15

Asp Arg Leu Thr Ile Thr Cys Arg Ala Ser Gln Ser Ile Ser Thr Tyr
            20                  25                  30

Leu His Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Pro Pro Leu
                85                  90                  95

Thr Phe Gly Pro Gly Thr Lys Val Asp Met Lys
            100                 105

<210> SEQ ID NO 143
<211> LENGTH: 357
<212> TYPE: DNA
<213> ORGANISM: Homo sapiens

<400> SEQUENCE: 143
caggtgcagc tgcaggagtc gggcccagga ctggtgaagc cttcggagac cctgtccctc      60
acctgcactg tctctggtgc ctccatcagt agtgactact ggagctggat ccggctgccc     120
ccagggaagg gactggagtg gattgggtat atctataata gagggagtac caagtacacc     180
ccctccctga agagtcgagt caccatatca ctagacacgg ccgagaacca gttctccctg     240
aggctgaggt cggtgaccgc cgcagacacg gccatctatt actgtgcgag acatgtaggt     300
ggccacacct atggaattga ttactggggc cagggaaccc tggtcaccgt ctcgagc       357

<210> SEQ ID NO 144
<211> LENGTH: 119
<212> TYPE: PRT
<213> ORGANISM: Homo sapiens

<400> SEQUENCE: 144

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Asp
            20                  25                  30

Tyr Trp Ser Trp Ile Arg Leu Pro Pro Gly Lys Gly Leu Glu Trp Ile
        35                  40                  45

Gly Tyr Ile Tyr Asn Arg Gly Ser Thr Lys Tyr Thr Pro Ser Leu Lys
    50                  55                  60

Ser Arg Val Thr Ile Ser Leu Asp Thr Ala Glu Asn Gln Phe Ser Leu
65                  70                  75                  80

Arg Leu Arg Ser Val Thr Ala Ala Asp Thr Ala Ile Tyr Tyr Cys Ala
                85                  90                  95

Arg His Val Gly Gly His Thr Tyr Gly Ile Asp Tyr Trp Gly Gln Gly
            100                 105                 110

Thr Leu Val Thr Val Ser Ser
        115

<210> SEQ ID NO 145
<211> LENGTH: 323

<212> TYPE: DNA
<213> ORGANISM: Homo sapiens

<400> SEQUENCE: 145

```
gacatccaga tgacccagtc tccatcgtcc ctgtctgcct ctgtaggaga cagagtcacc    60
atcacttgcc gggcaagtca gagcattagc aactatttaa attggtatca acacaaacct   120
ggggaagccc ccaagctcct gaactatgct gcgtccagtt tgcaaagtgg ggtcccatca   180
aggttcagtg ccagtggatc tgggacagat ttcactctca ccatcagcag tcttcaacct   240
gaagattttg ccacttacta ctgtcaacag agttacaata ctccgatcac cttcggccaa   300
gggacacgac tggaaattaa acg                                           323
```

<210> SEQ ID NO 146
<211> LENGTH: 107
<212> TYPE: PRT
<213> ORGANISM: Homo sapiens

<400> SEQUENCE: 146

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Asn Tyr
            20                  25                  30
Leu Asn Trp Tyr Gln His Lys Pro Gly Glu Ala Pro Lys Leu Leu Asn
        35                  40                  45
Tyr Ala Ala Ser Ser Leu Gln Ser Gly Val Pro Ser Arg Phe Ser Ala
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Asn Thr Pro Ile
                85                  90                  95
Thr Phe Gly Gln Gly Thr Arg Leu Glu Ile Lys
            100                 105
```

<210> SEQ ID NO 147
<211> LENGTH: 357
<212> TYPE: DNA
<213> ORGANISM: Homo sapiens

<400> SEQUENCE: 147

```
caggtgcagc tgcaggagtc gggcccagga ctggtgaagc cttcggagac cctgtccctc    60
acctgcactg tctctggtgc ctccatcagt agtgactact ggagctggat ccggctgccc   120
ccagggaagg gactggagtg gattgggtat atctataata gagggagtac caagtacacc   180
cctcccctga agagtcgagt caccatatca ctagacacgg ccgagaacca gttctccctg   240
aggctgaggt cggtgaccgc cgcagacacg gccgtctatt actgtgcgag acatgtgggt   300
ggccacacct atggaattga ttactggggc cagggaaccc tggtcaccgt ctcgagc      357
```

<210> SEQ ID NO 148
<211> LENGTH: 119
<212> TYPE: PRT
<213> ORGANISM: Homo sapiens

<400> SEQUENCE: 148

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Ala Ser Ile Ser Ser Asp
            20                  25                  30
```

Tyr Trp Ser Trp Ile Arg Leu Pro Pro Gly Lys Gly Leu Glu Trp Ile
            35                  40                  45
Gly Tyr Ile Tyr Asn Arg Gly Ser Thr Lys Tyr Thr Pro Ser Leu Lys
        50                  55                  60
Ser Arg Val Thr Ile Ser Leu Asp Thr Ala Glu Asn Gln Phe Ser Leu
65                  70                  75                  80
Arg Leu Arg Ser Val Thr Ala Ala Asp Thr Ala Val Tyr Tyr Cys Ala
                85                  90                  95
Arg His Val Gly Gly His Thr Tyr Gly Ile Asp Tyr Trp Gly Gln Gly
            100                 105                 110
Thr Leu Val Thr Val Ser Ser
        115

<210> SEQ ID NO 149
<211> LENGTH: 323
<212> TYPE: DNA
<213> ORGANISM: Homo sapiens

<400> SEQUENCE: 149
gacatccaga tgacccagtc tccatcgtcc ctgtctgcct ctgtaggaga cagagtcacc      60
atcacttgcc gggcaagtca gagcattagc aactatttaa attggtatca acacaaacct    120
ggggaagccc ccaagctcct gaactatgct cgtccagtt tgcaaagtgg ggtcccatca     180
aggttcagtg ccagtggatc tgggacagat ttcactctca gcatcagcgg tcttcaacct    240
gaagattttg ccacttacta ctgtcaacag agctacaata ctccgatcac cttcggccca    300
gggacacgac tggaaattaa acg                                            323

<210> SEQ ID NO 150
<211> LENGTH: 107
<212> TYPE: PRT
<213> ORGANISM: Homo sapiens

<400> SEQUENCE: 150

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Asn Tyr
            20                  25                  30
Leu Asn Trp Tyr Gln His Lys Pro Gly Glu Ala Pro Lys Leu Leu Asn
        35                  40                  45
Tyr Ala Ala Ser Ser Leu Gln Ser Gly Val Pro Ser Arg Phe Ser Ala
    50                  55                  60
Ser Gly Ser Gly Thr Asp Phe Thr Leu Ser Ile Ser Gly Leu Gln Pro
65                  70                  75                  80
Glu Asp Phe Ala Thr Tyr Tyr Cys Gln Gln Ser Tyr Asn Thr Pro Ile
                85                  90                  95
Thr Phe Gly Pro Gly Thr Arg Leu Glu Ile Lys
            100                 105

<210> SEQ ID NO 151
<211> LENGTH: 363
<212> TYPE: DNA
<213> ORGANISM: Homo sapiens

<400> SEQUENCE: 151
caggtgcagc tgcaggagtc gggcccagga ctggtgaagc cttcggagac cctgtccgtc      60
acctgcaaag tctctggtga ctccatcagt agttattcct ggagctggat ccggcagccc    120

```
ccagggaagg gactggagtg ggttggctat ttgtattata gtgggagcac caagtacaac    180
ccctccctca agagtcgaac caccatatca gtagacacgt ccacgaacca gttgtccctg    240
aagttgagtt ttgtgaccgc cgcggacacg gccgtgtatt tctgtgcgag aaccggctcg    300
gaatctacta ccggctacgg tatggacgtc tggggccaag gaccacggt caccgtctcg     360 agc                                                                  363
```

<210> SEQ ID NO 152
<211> LENGTH: 121
<212> TYPE: PRT
<213> ORGANISM: Homo sapiens

<400> SEQUENCE: 152

```
Gln Val Gln Leu Gln Glu Ser Gly Pro Gly Leu Val Lys Pro Ser Glu
1               5                   10                  15

Thr Leu Ser Val Thr Cys Lys Val Ser Gly Asp Ser Ile Ser Ser Tyr
            20                  25                  30

Ser Trp Ser Trp Ile Arg Gln Pro Pro Gly Lys Gly Leu Glu Trp Val
        35                  40                  45

Gly Tyr Leu Tyr Tyr Ser Gly Ser Thr Lys Tyr Asn Pro Ser Leu Lys
    50                  55                  60

Ser Arg Thr Thr Ile Ser Val Asp Thr Ser Thr Asn Gln Leu Ser Leu
65                  70                  75                  80

Lys Leu Ser Phe Val Thr Ala Ala Asp Thr Ala Val Tyr Phe Cys Ala
                85                  90                  95

Arg Thr Gly Ser Glu Ser Thr Thr Gly Tyr Gly Met Asp Val Trp Gly
            100                 105                 110

Gln Gly Thr Thr Val Thr Val Ser Ser
        115                 120
```

<210> SEQ ID NO 153
<211> LENGTH: 323
<212> TYPE: DNA
<213> ORGANISM: Homo sapiens

<400> SEQUENCE: 153

```
gacatccaga tgacccagtc tccatcctcc ctgtctgcat ctgtaggaga cagagtcacc    60
atcacttgcc gggcaagtca gagcattagc acctatttaa attggtatca gcagaaacca   120
gggaaagccc ctaagctcct gatctatgct gcatccagtt tgcacagtgg ggtcccatca   180
aggttcagtg gcagtggatc tgggacagat ttcgctctca ccatcagcag tctgcaacct   240
gaagattttg caacttacta ctgtcaacag agttacagtc ccccgatcac cttcggccaa   300
gggacacgac tggagattaa acg                                            323
```

<210> SEQ ID NO 154
<211> LENGTH: 107
<212> TYPE: PRT
<213> ORGANISM: Homo sapiens

<400> SEQUENCE: 154

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu His Ser Gly Val Pro Ser Arg Phe Ser Gly
        50                  55                  60

Ser Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Ser Tyr Ser Pro Pro Ile
                85                  90                  95

Thr Phe Gly Gln Gly Thr Arg Leu Glu Ile Lys
            100                 105

<210> SEQ ID NO 155
<211> LENGTH: 357
<212> TYPE: DNA
<213> ORGANISM: Homo sapiens

<400> SEQUENCE: 155
caggtgcagc tgcaggagtc gggcccaaga ctggtgaagc cttcggagag cctgtccctc      60
acctgcactg tctctggtgg ctccattagt aattccttct ggggctggat ccggcagccc     120
ccaggggagg gactggagtg gattggttat gtctataaca gtggcaacac caagtacaat     180
ccctccctca gagtcgagt caccatttcg cgcgacacgt ccaagagtca actctacatg      240
aagctgaggt ctgtgaccgc cgctgacacg gccgtgtact actgtgcgag catgacgac      300 gcaagtcatg gctacagcat tcctggggc cacggaaccc tggtcaccgt ctcgagc         357

<210> SEQ ID NO 156
<211> LENGTH: 119
<212> TYPE: PRT
<213> ORGANISM: Homo sapiens

<400> SEQUENCE: 156

Gln Val Gln Leu Gln Glu Ser Gly Pro Arg Leu Val Lys Pro Ser Glu
1               5                   10                  15

Ser Leu Ser Leu Thr Cys Thr Val Ser Gly Gly Ser Ile Ser Asn Ser
                20                  25                  30

Phe Trp Gly Trp Ile Arg Gln Pro Pro Gly Glu Gly Leu Glu Trp Ile
            35                  40                  45

Gly Tyr Val Tyr Asn Ser Gly Asn Thr Lys Tyr Asn Pro Ser Leu Lys
        50                  55                  60

Ser Arg Val Thr Ile Ser Arg Asp Thr Ser Lys Ser Gln Leu Tyr Met
65                  70                  75                  80

Lys Leu Arg Ser Val Thr Ala Ala Asp Thr Ala Val Tyr Tyr Cys Ala
                85                  90                  95

Arg His Asp Asp Ala Ser His Gly Tyr Ser Ile Ser Trp Gly His Gly
            100                 105                 110

Thr Leu Val Thr Val Ser Ser
        115

<210> SEQ ID NO 157
<211> LENGTH: 321
<212> TYPE: DNA
<213> ORGANISM: Homo sapiens

<400> SEQUENCE: 157
gacatccaga tgacccagtc tccatcctcc ctgtctgcat ctgtagggga cagagtcacc      60
atcacttgcc gggcaagtca gaccattagt acttatttaa attggtatca acagaaatca     120
gggaaagccc ctaagctcct gatctatgct gcatccggtt tgcaaagtgg agtcccatca     180
```

```
aggttcagtg gcagtggatc tgggacagat ttcactctca ccatcagcag tcttcaaccct    240 gaagattttg caacttactt ctgtcaacag agttacaata ctcccctgac gttcggccaa    300
gggaccaagg tggaaatcaa a                                              321
```

<210> SEQ ID NO 158
<211> LENGTH: 107
<212> TYPE: PRT
<213> ORGANISM: Homo sapiens

<400> SEQUENCE: 158

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Thr Tyr
            20                  25                  30

Leu Asn Trp Tyr Gln Gln Lys Ser Gly Lys Ala Pro Lys Leu Leu Ile
        35                  40                  45

Tyr Ala Ala Ser Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Asn Thr Pro Leu
                85                  90                  95

Thr Phe Gly Gln Gly Thr Lys Val Glu Ile Lys
            100                 105
```

<210> SEQ ID NO 159
<211> LENGTH: 360
<212> TYPE: DNA
<213> ORGANISM: Homo sapiens

<400> SEQUENCE: 159

```
caggtgcaac tgcaggagtc gggcccagga ctggtgaagc cttcggagac cctgtccctc     60
acctgcactg tctcgggtgg ctccatcagt gcttaccact ggagctggat ccgccagccc    120
ccagggaagg gactggagtg gattgggcac atctttgaca gtggagcac ttactacaac     180 ccctccctta agagtcgagt caccatatca ctagacgcgt ccaagaacca gctctccctg    240
agattgacct ctgtgaccgc ctcagacacg gccatatatt actgtgcgag acctctcggg    300
agtcggtact attacggaat ggacgtctgg ggccaaggga ccacggtcac cgtctcgagc    360
```

<210> SEQ ID NO 160
<211> LENGTH: 120
<212> TYPE: PRT
<213> ORGANISM: Homo sapiens

<400> SEQUENCE: 160

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ala Tyr
            20                  25                  30

His Trp Ser Trp Ile Arg Gln Pro Pro Gly Lys Gly Leu Glu Trp Ile
        35                  40                  45

Gly His Ile Phe Asp Ser Gly Ser Thr Tyr Tyr Asn Pro Ser Leu Lys
    50                  55                  60

Ser Arg Val Thr Ile Ser Leu Asp Ala Ser Lys Asn Gln Leu Ser Leu
65                  70                  75                  80

Arg Leu Thr Ser Val Thr Ala Ser Asp Thr Ala Ile Tyr Tyr Cys Ala
```

85                  90                  95
Arg Pro Leu Gly Ser Arg Tyr Tyr Tyr Gly Met Asp Val Trp Gly Gln
            100                 105                 110
Gly Thr Thr Val Thr Val Ser Ser
            115                 120

<210> SEQ ID NO 161
<211> LENGTH: 318
<212> TYPE: DNA
<213> ORGANISM: Homo sapiens

<400> SEQUENCE: 161
gacatccaga tgacccagtc tccgtcctcc ctgtctgcat ctgtcggaga cagagtcacc      60
atcacttgcc gggcaagtca gagtattagc aggtatttaa attggtatca gcagaaacca     120
gggaaagccc ctaagctcct gatctatggt gcctccactt tgcaaaatgg ggccccatca     180
aggttcagcg gcagtggatc tgggacagat ttcactctca ccatcagcag tctacaacct     240
gaagattccg caacttacct ctgtcaacag agttacagtg tccctgcttt cggcggagga     300
accaaggtgg aggtcaaa                                                   318

<210> SEQ ID NO 162
<211> LENGTH: 106
<212> TYPE: PRT
<213> ORGANISM: Homo sapiens

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Gly Ala Ser Thr Leu Gln Asn Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Leu Cys Gln Gln Ser Tyr Ser Val Pro Ala
                85                  90                  95

Phe Gly Gly Gly Thr Lys Val Glu Val Lys
            100                 105

<210> SEQ ID NO 163
<211> LENGTH: 363
<212> TYPE: DNA
<213> ORGANISM: Homo sapiens

<400> SEQUENCE: 163
caggtccagc tgcaggagtc gggcccagga ctgctgaagc cttcggacac cctggccctc      60
acttgcactg tctctggtgg ctccatcacc agtgactact ggagctggat ccggcaaccc     120
ccagggaggg gactgactg gatcggattc ttctataacg cgggagcac caagtacaat      180 ccctccctca gagtcgagt caccatatca gcggacacg ccaagaacca gttgtccctg      240
aaattgacct ctgtgaccgc cgcagacacg gccgtgtatt attgtgcgag acatgatgcc     300
aaatttagtg ggagctacta cgttgcctcc tggggccagg gaacccgagt caccgtctcg     360
agc                                                                   363

<210> SEQ ID NO 164
<211> LENGTH: 121
<212> TYPE: PRT
<213> ORGANISM: Homo sapiens

<400> SEQUENCE: 164

Gln Val Gln Leu Gln Glu Ser Gly Pro Gly Leu Leu Lys Pro Ser Asp
1               5                   10                  15

Thr Leu Ala Leu Thr Cys Thr Val Ser Gly Gly Ser Ile Thr Ser Asp
            20                  25                  30

Tyr Trp Ser Trp Ile Arg Gln Pro Pro Gly Arg Gly Leu Asp Trp Ile
        35                  40                  45

Gly Phe Phe Tyr Asn Gly Gly Ser Thr Lys Tyr Asn Pro Ser Leu Lys
    50                  55                  60

Ser Arg Val Thr Ile Ser Ala Asp Thr Ser Lys Asn Gln Leu Ser Leu
65                  70                  75                  80

Lys Leu Thr Ser Val Thr Ala Ala Asp Thr Gly Val Tyr Tyr Cys Ala
                85                  90                  95

Arg His Asp Ala Lys Phe Ser Gly Ser Tyr Tyr Val Ala Ser Trp Gly
            100                 105                 110

Gln Gly Thr Arg Val Thr Val Ser Ser
        115                 120

<210> SEQ ID NO 165
<211> LENGTH: 321
<212> TYPE: DNA
<213> ORGANISM: Homo sapiens

<400> SEQUENCE: 165
gacatccaga tgacccagtc tccctcctcc ctgtctgcat ctgtaggaga cagagtcacc      60
atctcttgcc gggcaagtca gagcattagc acctatttaa attggtatca gcagcaacct    120
gggaaagccc ctaaggtcct gatctctggt gcaaccgact tgcaaagtgg ggtcccatct    180
cgcttcagtg gcagtggatc tgggacagat ttcactctca ccatcagcag tctgcaacct    240
gaagattttg caacttacta ctgtcaacag agttacaata ccccccctcat ttttggccag    300 gggaccaagc tggagatcaa a                                              321

<210> SEQ ID NO 166
<211> LENGTH: 107
<212> TYPE: PRT
<213> ORGANISM: Homo sapiens

<400> SEQUENCE: 166

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Ser Ile Ser Thr Tyr
            20                  25                  30

Leu Asn Trp Tyr Gln Gln Pro Gly Lys Ala Pro Lys Val Leu Ile
        35                  40                  45

Ser Gly Ala Thr Asp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Ile Phe Gly Gln Gly Thr Lys Leu Glu Ile Lys
            100                 105

<210> SEQ ID NO 167
<211> LENGTH: 354
<212> TYPE: DNA
<213> ORGANISM: Homo sapiens

<400> SEQUENCE: 167

```
gacatgcagc tggtggagtc tggaggaggc ttggtcccgc cggggggtc cctgagactc      60
tcctgcgcag cctctgggtt ttccgtcagt gacaactaca taaactgggt ccgccaggct     120
ccagggaagg ggctggactg ggtctcagtc ttttatagtg ctgatagaac atcctacgca     180
gactccgtga agggccgatt caccgtctcc agccacgatt ccaagaacac agtgtacctt     240
caaatgaaca gtctgagagc tgaggacacg gccgtttatt actgtgcgag agttcagaag     300
tcctattacg gtatggacgt ctggggccaa gggaccacgg tcaccgtctc gagc           354
```

<210> SEQ ID NO 168
<211> LENGTH: 118
<212> TYPE: PRT
<213> ORGANISM: Homo sapiens

<400> SEQUENCE: 168

Asp Met Gln Leu Val Glu Ser Gly Gly Gly Leu Val Pro Pro Gly Gly
1               5                   10                  15
Ser Leu Arg Leu Ser Cys Ala Ala Ser Gly Phe Ser Val Ser Asp Asn
            20                  25                  30
Tyr Ile Asn Trp Val Arg Gln Ala Pro Gly Lys Gly Leu Asp Trp Val
        35                  40                  45
Ser Val Phe Tyr Ser Ala Asp Arg Thr Ser Tyr Ala Asp Ser Val Lys
    50                  55                  60
Gly Arg Phe Thr Val Ser Ser His Asp Ser Lys Asn Thr Val Tyr Leu
65                  70                  75                  80
Gln Met Asn Ser Leu Arg Ala Glu Asp Thr Ala Val Tyr Tyr Cys Ala
                85                  90                  95
Arg Val Gln Lys Ser Tyr Tyr Gly Met Asp Val Trp Gly Gln Gly Thr
            100                 105                 110
Thr Val Thr Val Ser Ser
        115

<210> SEQ ID NO 169
<211> LENGTH: 318
<212> TYPE: DNA
<213> ORGANISM: Homo sapiens

<400> SEQUENCE: 169

```
ggcatccaga tgacccagtc tccatcctcc ctgtctgcat ctgtaggaga cagagtcacc      60
atcacttgcc gggcaagtca gagcattagc agatatttaa attggtatct gcagaaacca     120
gggaaagccc ctaagctcct gatctctggt gcatccagtt tgcaaagtgg ggtcccatca     180
aggttcagtg gcactgggtc tgggacagaa ttcactctca ccatcagcag tttgcaacct     240
gaagattttg caacttacta ctgtcaacag actttcagta tccctctttt tggccagggg     300
accaaggtgg agatcaaa                                                    318
```

<210> SEQ ID NO 170
<211> LENGTH: 106
<212> TYPE: PRT
<213> ORGANISM: Homo sapiens

<400> SEQUENCE: 170

Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Leu Gln Lys Pro Gly Lys Ala Pro Lys Leu Leu Ile
        35                  40                  45

Ser Gly Ala Ser Ser Leu Gln Ser Gly Val Pro Ser Arg Phe Ser Gly
    50                  55                  60

Thr Gly Ser Gly Thr Glu Phe Thr Leu Thr Ile Ser Ser Leu Gln Pro
65              70                  75                  80

Glu Asp Phe Ala Thr Tyr Tyr Cys Gln Gln Thr Phe Ser Ile Pro Leu
                85                  90                  95

Phe Gly Gln Gly Thr Lys Val Glu Ile Lys
            100                 105

<210> SEQ ID NO 171
<211> LENGTH: 369
<212> TYPE: DNA
<213> ORGANISM: Homo sapiens

<400> SEQUENCE: 171
caggtgcagc tgcaggcgtc gggcccagga ctggtgaagc cttcagagac cctgtccctc    60
acctgcactg tctctggtga ctccatcacc agtggtgctt actactggac ctggatccgc   120
cagcacccag ggaagggcct ggagtggatt gggtacatct attacagtgg gaacacctac   180
tacaacccgt ccctcaagag tcgagttacc atatcactag acacgtctaa gaaccagttc   240
tccctgaagg tgaactctgt gactgccgcg gacacggccg tatattactg tgcgcgagct   300
gcttcgactt cagtgctagg atacggtatg gacgtctggg gccaagggac cacggtcacc   360
gtctcgagc                                                          369

<210> SEQ ID NO 172
<211> LENGTH: 123
<212> TYPE: PRT
<213> ORGANISM: Homo sapiens

<400> SEQUENCE: 172

Gln Val Gln Leu Gln Ala Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Ala Tyr Tyr Trp Thr Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Val Thr Ile Ser Leu Asp Thr Ser Lys Asn Gln Phe
65              70                  75                  80

Ser Leu Lys Val Asn Ser Val Thr Ala Ala Asp Thr Ala Val Tyr Tyr
                85                  90                  95

Cys Ala Arg Ala Ala Ser Thr Ser Val Leu Gly Tyr Gly Met Asp Val
                100                 105                 110

Trp Gly Gln Gly Thr Thr Val Thr Val Ser Ser
            115                 120

<210> SEQ ID NO 173
<211> LENGTH: 321
<212> TYPE: DNA
<213> ORGANISM: Homo sapiens

<400> SEQUENCE: 173
gacatccaga tgacccagtc tccatcctcc ctgtctgcat ctgtaggaga cagagtcacc     60
atcacttgcc gggcaagtca gagcattagc agatatttaa attggtatca gcaggaacca    120
gggaaggccc ctaagctcct ggtctatgct gcatccagtt tgcaaagtgg ggtcccatca    180
aggttcagtg gcagtggatc tgggacagat ttcactctca ccataagcag tcttcaacct    240
gaagattttg caacttacta ctgtcaacag agttatagta ccccccctca cttcggccaa    300
gggacacgac tggagattaa a                                              321

<210> SEQ ID NO 174
<211> LENGTH: 107
<212> TYPE: PRT
<213> ORGANISM: Homo sapiens

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Glu Pro Gly Lys Ala Pro Lys Leu Leu Val
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Arg Leu Glu Ile Lys
            100                 105

<210> SEQ ID NO 175
<211> LENGTH: 354
<212> TYPE: DNA
<213> ORGANISM: Homo sapiens

<400> SEQUENCE: 175
gacatgcagc tggtggagtc tggaggaggc ttggtcccgc cggggggtc cctgagactc      60 tcctgcgcag cctctgggtt ttccgtcagt gacaactaca taaactgggt ccgccaggct    120
ccagggaagg ggctggactg gtctcagtc ttttatagtg ctgatagaac atcctacgca     180
gactccgtga agggccgatt caccgtctcc agccacgatt ccaagaacac agtgtacctt    240
caaatgaaca gtctgagagc tgaggacacg gccgtttatt actgtgcgag agttcagaag    300
tcctattacg gtatggacgt ctggggccaa gggaccacgg tcaccgtctc gagc          354

<210> SEQ ID NO 176
<211> LENGTH: 118
<212> TYPE: PRT
<213> ORGANISM: Homo sapiens

<400> SEQUENCE: 176

Asp Met Gln Leu Val Glu Ser Gly Gly Gly Leu Val Pro Pro Gly Gly
1               5                   10                  15

```
Ser Leu Arg Leu Ser Cys Ala Ala Ser Gly Phe Ser Val Ser Asp Asn
            20                  25                  30

Tyr Ile Asn Trp Val Arg Gln Ala Pro Gly Lys Gly Leu Asp Trp Val
        35                  40                  45

Ser Val Phe Tyr Ser Ala Asp Arg Thr Ser Tyr Ala Asp Ser Val Lys
    50                  55                  60

Gly Arg Phe Thr Val Ser Ser His Asp Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Val Gln Lys Ser Tyr Tyr Gly Met Asp Val Trp Gly Gln Gly Thr
            100                 105                 110

Thr Val Thr Val Ser Ser
            115

<210> SEQ ID NO 177
<211> LENGTH: 318
<212> TYPE: DNA
<213> ORGANISM: Homo sapiens

<400> SEQUENCE: 177
ggcatccaga tgacccagtc tccatcctcc ctgtctgcat ctgtaggaga cagagtcacc     60
atcacttgcc gggcaagtca gagcattagc agatatttaa attggtatct gcagaaacca    120
gggaaagccc ctaagctcct gatctctggt gcatccagtt tgcaaagtgg ggtcccatca    180
aggttcagtg gcactgggtc tgggacagaa ttcactctca ccatcagcag tttgcaacct    240
gaagattttg caacttacta ctgtcaacag actttcagta tccctctttt tggccagggg    300
accaaggtgg agatcaaa                                                  318

<210> SEQ ID NO 178
<211> LENGTH: 106
<212> TYPE: PRT
<213> ORGANISM: Homo sapiens

<400> SEQUENCE: 178

Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Leu Gln Lys Pro Gly Lys Ala Pro Lys Leu Leu Ile
        35                  40                  45

Ser Gly Ala Ser Ser Leu Gln Ser Gly Val Pro Ser Arg Phe Ser Gly
    50                  55                  60

Thr Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Thr Phe Ser Ile Pro Leu
                85                  90                  95

Phe Gly Gln Gly Thr Lys Val Glu Ile Lys
            100                 105

<210> SEQ ID NO 179
<211> LENGTH: 7
<212> TYPE: PRT
<213> ORGANISM: Homo sapiens

<400> SEQUENCE: 179

Gly Gly Gly Tyr Ser Trp Asn
```

<210> SEQ ID NO 180
<211> LENGTH: 16
<212> TYPE: PRT
<213> ORGANISM: Homo sapiens

<400> SEQUENCE: 180

Phe Met Phe His Ser Gly Ser Pro Arg Tyr Asn Pro Thr Leu Lys Ser
1               5                   10                  15

<210> SEQ ID NO 181
<211> LENGTH: 12
<212> TYPE: PRT
<213> ORGANISM: Homo sapiens

<400> SEQUENCE: 181

Val Gly Gln Met Asp Lys Tyr Tyr Ala Met Asp Val
1               5                   10

<210> SEQ ID NO 182
<211> LENGTH: 8
<212> TYPE: PRT
<213> ORGANISM: Homo sapiens

<400> SEQUENCE: 182

Gly Gly Pro Val Ser Gly Gly Gly
1               5

<210> SEQ ID NO 183
<211> LENGTH: 9
<212> TYPE: PRT
<213> ORGANISM: Homo sapiens

<400> SEQUENCE: 183

Phe Met Phe His Ser Gly Ser Pro Arg
1               5

<210> SEQ ID NO 184
<211> LENGTH: 11
<212> TYPE: PRT
<213> ORGANISM: Homo sapiens

<400> SEQUENCE: 184

Arg Ala Ser Gln Ser Ile Gly Ala Tyr Val Asn
1               5                   10

<210> SEQ ID NO 185
<211> LENGTH: 7
<212> TYPE: PRT
<213> ORGANISM: Homo sapiens

<400> SEQUENCE: 185

Gly Ala Ser Asn Leu Gln Ser
1               5

<210> SEQ ID NO 186
<211> LENGTH: 9
<212> TYPE: PRT
<213> ORGANISM: Homo sapiens

<400> SEQUENCE: 186

Gln Gln Thr Tyr Ser Thr Pro Ile Thr
1               5

-continued

<210> SEQ ID NO 187
<211> LENGTH: 5
<212> TYPE: PRT
<213> ORGANISM: Homo sapiens
<400> SEQUENCE: 187

Ser Asp Tyr Trp Ser
1               5

<210> SEQ ID NO 188
<211> LENGTH: 16
<212> TYPE: PRT
<213> ORGANISM: Homo sapiens
<400> SEQUENCE: 188

Phe Phe Tyr Asn Gly Gly Ser Thr Lys Tyr Asn Pro Ser Leu Lys Ser
1               5                   10                  15

<210> SEQ ID NO 189
<211> LENGTH: 13
<212> TYPE: PRT
<213> ORGANISM: Homo sapiens
<400> SEQUENCE: 189

His Asp Ala Lys Phe Ser Gly Ser Tyr Tyr Val Ala Ser
1               5                   10

<210> SEQ ID NO 190
<211> LENGTH: 6
<212> TYPE: PRT
<213> ORGANISM: Homo sapiens
<400> SEQUENCE: 190

Gly Gly Ser Ile Thr Ser
1               5

<210> SEQ ID NO 191
<211> LENGTH: 9
<212> TYPE: PRT
<213> ORGANISM: Homo sapiens
<400> SEQUENCE: 191

Phe Phe Tyr Asn Gly Gly Ser Thr Lys
1               5

<210> SEQ ID NO 192
<211> LENGTH: 11
<212> TYPE: PRT
<213> ORGANISM: Homo sapiens
<400> SEQUENCE: 192

Arg Ala Ser Gln Ser Ile Ser Thr Tyr Leu Asn
1               5                   10

<210> SEQ ID NO 193
<211> LENGTH: 7
<212> TYPE: PRT
<213> ORGANISM: Homo sapiens
<400> SEQUENCE: 193

Gly Ala Thr Asn Leu Gln Ser
1               5

<210> SEQ ID NO 194

<210> SEQ ID NO 194
<211> LENGTH: 9
<212> TYPE: PRT
<213> ORGANISM: Homo sapiens

<400> SEQUENCE: 194

Gln Gln Ser Tyr Asn Thr Pro Leu Ile
1               5

<210> SEQ ID NO 195
<211> LENGTH: 360
<212> TYPE: DNA
<213> ORGANISM: Homo sapiens

<400> SEQUENCE: 195

```
gaggtgcagc tggtggagtc tgggggaggc ttggtccagc ctggggggtc cctgagaatc      60
tcctgtgcag cctctggatt caccgtcagt agcaactaca tgagttgggt ccgccaggct     120
ccagggaagg ggctggagtg ggtctcagtt atttatagtg gtggtagcac atactacgca     180
gactccgtga aggcagatt ctccttctcc agagacaact ccaagaacac agtgtttctt     240
caaatgaaca gcctgagagc cgaggacacg gctgtgtatt actgtgcgag atgtctgagc     300
aggatgcggg gttacggttt agacgtctgg ggccaaggga ccacggtcac cgtctcgagc     360
```

<210> SEQ ID NO 196
<211> LENGTH: 360
<212> TYPE: DNA
<213> ORGANISM: Homo sapiens

<400> SEQUENCE: 196

```
caggtgcaat tgcaggagtc gggcccagga ctggtgaagc cttcggagac cctgtccctc      60
acctgcactg tctctggttc gtccatcagt aattactact ggagctggat ccggcagtcc     120
ccagggaagg gactggagtg gattgggttt atctattacg gtggaaacac caagtacaat     180
ccctccctca gagccgcgt caccatatca caagacactt ccaagagtca ggtctccctg     240
acgatgagct ctgtgaccgc tgcggaatcg gccgtctatt tctgtgcgag agcgtcttgt     300
agtggtggtt actgtatcct tgactactgg ggccagggaa ccctggtcac cgtctcgagc     360
```

<210> SEQ ID NO 197
<211> LENGTH: 13
<212> TYPE: PRT
<213> ORGANISM: Homo sapiens

<400> SEQUENCE: 197

His Asp Val Lys Phe Ser Gly Ser Tyr Tyr Val Ala Ser
1               5                   10

<210> SEQ ID NO 198
<211> LENGTH: 12
<212> TYPE: PRT
<213> ORGANISM: Influenza A virus

<400> SEQUENCE: 198

Gly Val Thr Asn Lys Val Asn Ser Ile Ile Asp Lys
1               5                   10

<210> SEQ ID NO 199
<211> LENGTH: 115
<212> TYPE: PRT
<213> ORGANISM: Homo sapiens

<400> SEQUENCE: 199

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Val Tyr Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Ser Leu Asp Val Trp Gly Gln Gly Thr Thr Val Thr
            100                 105                 110

Val Ser Ser
        115

<210> SEQ ID NO 200
<211> LENGTH: 5
<212> TYPE: PRT
<213> ORGANISM: Influenza A virus

<400> SEQUENCE: 200

Thr Gly Leu Arg Asn
1               5

<210> SEQ ID NO 201
<211> LENGTH: 12
<212> TYPE: PRT
<213> ORGANISM: Influenza A virus

<400> SEQUENCE: 201

Gly Val Thr Asn Lys Val Asn Arg Ile Ile Asp Lys
1               5                   10

<210> SEQ ID NO 202
<211> LENGTH: 12
<212> TYPE: PRT
<213> ORGANISM: Influenza A virus

<400> SEQUENCE: 202

Gly Val Thr Asn Lys Glu Asn Ser Ile Ile Asp Lys
1               5                   10

<210> SEQ ID NO 203
<211> LENGTH: 5
<212> TYPE: PRT
<213> ORGANISM: Homo sapiens

<400> SEQUENCE: 203

Ser Tyr Asn Trp Ile
1               5

<210> SEQ ID NO 204
<211> LENGTH: 16
<212> TYPE: PRT
<213> ORGANISM: Homo sapiens

<400> SEQUENCE: 204

His Ile Tyr Asp Tyr Gly Arg Thr Phe Tyr Asn Ser Ser Leu Gln Ser
1               5                   10                  15
```

<210> SEQ ID NO 205
<211> LENGTH: 12
<212> TYPE: PRT
<213> ORGANISM: Homo sapiens

<400> SEQUENCE: 205

Pro Leu Gly Ile Leu His Tyr Tyr Ala Met Asp Leu
1               5                   10

<210> SEQ ID NO 206
<211> LENGTH: 6
<212> TYPE: PRT
<213> ORGANISM: Homo sapiens

<400> SEQUENCE: 206

Gly Gly Ser Ile Ser Ser
1               5

<210> SEQ ID NO 207
<211> LENGTH: 9
<212> TYPE: PRT
<213> ORGANISM: Homo sapiens

<400> SEQUENCE: 207

His Ile Tyr Asp Tyr Gly Arg Thr Phe
1               5

<210> SEQ ID NO 208
<211> LENGTH: 11
<212> TYPE: PRT
<213> ORGANISM: Homo sapiens

<400> SEQUENCE: 208

Arg Ala Ser Gln Ser Ile Asp Lys Phe Leu Asn
1               5                   10

<210> SEQ ID NO 209
<211> LENGTH: 7
<212> TYPE: PRT
<213> ORGANISM: Homo sapiens

<400> SEQUENCE: 209

Gly Ala Ser Asn Leu His Ser
1               5

<210> SEQ ID NO 210
<211> LENGTH: 8
<212> TYPE: PRT
<213> ORGANISM: Homo sapiens

<400> SEQUENCE: 210

Gln Gln Ser Phe Ser Val Pro Ala
1               5

<210> SEQ ID NO 211
<211> LENGTH: 5
<212> TYPE: PRT
<213> ORGANISM: Homo sapiens

<400> SEQUENCE: 211

Ser Thr Tyr Met Asn
1               5

<210> SEQ ID NO 212

-continued

```
<211> LENGTH: 16
<212> TYPE: PRT
<213> ORGANISM: Homo sapiens

<400> SEQUENCE: 212

Val Phe Tyr Ser Glu Thr Arg Thr Tyr Ala Asp Ser Val Lys Gly
1               5                   10                  15

<210> SEQ ID NO 213
<211> LENGTH: 10
<212> TYPE: PRT
<213> ORGANISM: Homo sapiens

<400> SEQUENCE: 213

Val Gln Arg Leu Ser Tyr Gly Met Asp Val
1               5                   10

<210> SEQ ID NO 214
<211> LENGTH: 6
<212> TYPE: PRT
<213> ORGANISM: Homo sapiens

<400> SEQUENCE: 214

Gly Leu Ser Val Ser Ser
1               5

<210> SEQ ID NO 215
<211> LENGTH: 9
<212> TYPE: PRT
<213> ORGANISM: Homo sapiens

<400> SEQUENCE: 215

Val Phe Tyr Ser Glu Thr Arg Thr Tyr
1               5

<210> SEQ ID NO 216
<211> LENGTH: 12
<212> TYPE: PRT
<213> ORGANISM: Influenza A virus

<400> SEQUENCE: 216

Lys Ile Thr Ser Lys Val Asn Asn Ile Val Asp Lys
1               5                   10

<210> SEQ ID NO 217
<211> LENGTH: 7
<212> TYPE: PRT
<213> ORGANISM: Homo sapiens

<400> SEQUENCE: 217

Gly Ala Ser Thr Leu Gln Ser
1               5

<210> SEQ ID NO 218
<211> LENGTH: 8
<212> TYPE: PRT
<213> ORGANISM: Homo sapiens

<400> SEQUENCE: 218

Gln Gln Thr Tyr Ser Ile Pro Leu
1               5

<210> SEQ ID NO 219
<211> LENGTH: 14
<212> TYPE: PRT
```

```
<213> ORGANISM: Homo sapiens

<400> SEQUENCE: 219

Thr Gly Ser Ser Ser Asn Ile Gly Ala Gly Tyr Asp Val His
1               5                   10

<210> SEQ ID NO 220
<211> LENGTH: 14
<212> TYPE: PRT
<213> ORGANISM: Homo sapiens

<400> SEQUENCE: 220

Ile Pro His Tyr Asn Phe Gly Ser Gly Ser Tyr Phe Asp Tyr
1               5                   10

<210> SEQ ID NO 221
<211> LENGTH: 17
<212> TYPE: PRT
<213> ORGANISM: Homo sapiens

<400> SEQUENCE: 221

Gly Ile Ile Ala Ile Phe Gly Thr Pro Lys Tyr Ala Gln Lys Phe Gln
1               5                   10                  15

Gly

<210> SEQ ID NO 222
<211> LENGTH: 5
<212> TYPE: PRT
<213> ORGANISM: Homo sapiens

<400> SEQUENCE: 222

Asn Tyr Ala Met Ser
1               5

<210> SEQ ID NO 223
<211> LENGTH: 7
<212> TYPE: PRT
<213> ORGANISM: Homo sapiens

<400> SEQUENCE: 223

Asp Asn Ser Asp Arg Pro Ser
1               5

<210> SEQ ID NO 224
<211> LENGTH: 11
<212> TYPE: PRT
<213> ORGANISM: Homo sapiens

<400> SEQUENCE: 224

Gly Gly His Asn Ile Gly Ser Asn Ser Val His
1               5                   10

<210> SEQ ID NO 225
<211> LENGTH: 13
<212> TYPE: PRT
<213> ORGANISM: Influenza A virus

<400> SEQUENCE: 225

Gly Ile Thr Asn Lys Val Asn Ser Ile Ile Asp Lys Ile
1               5                   10

<210> SEQ ID NO 226
<211> LENGTH: 7
<212> TYPE: PRT
```

<213> ORGANISM: Homo sapiens

<400> SEQUENCE: 226

Gly Ala Ser Ser Leu Gln Ser
1               5

<210> SEQ ID NO 227
<211> LENGTH: 9
<212> TYPE: PRT
<213> ORGANISM: Homo sapiens

<400> SEQUENCE: 227

Gln Val Trp Gly Ser Ser Ser Asp His
1               5

<210> SEQ ID NO 228
<211> LENGTH: 5
<212> TYPE: PRT
<213> ORGANISM: Homo sapiens

<400> SEQUENCE: 228

Ser Asp Phe Trp Ser
1               5

<210> SEQ ID NO 229
<211> LENGTH: 16
<212> TYPE: PRT
<213> ORGANISM: Homo sapiens

<400> SEQUENCE: 229

Tyr Val Tyr Asn Arg Gly Ser Thr Lys Tyr Ser Pro Ser Leu Lys Ser
1               5                   10                  15

<210> SEQ ID NO 230
<211> LENGTH: 12
<212> TYPE: PRT
<213> ORGANISM: Homo sapiens

<400> SEQUENCE: 230

Asn Gly Arg Ser Ser Thr Ser Trp Gly Ile Asp Val
1               5                   10

<210> SEQ ID NO 231
<211> LENGTH: 7
<212> TYPE: PRT
<213> ORGANISM: Homo sapiens

<400> SEQUENCE: 231

Gly Asn Ser Asn Arg Pro Ser
1               5

<210> SEQ ID NO 232
<211> LENGTH: 9
<212> TYPE: PRT
<213> ORGANISM: Homo sapiens

<400> SEQUENCE: 232

Tyr Val Tyr Asn Arg Gly Ser Thr Lys
1               5

<210> SEQ ID NO 233
<211> LENGTH: 11
<212> TYPE: PRT
<213> ORGANISM: Homo sapiens

```
<400> SEQUENCE: 233

Arg Ala Ser Gln Ser Ile Ser Thr Tyr Leu His
1               5                   10

<210> SEQ ID NO 234
<211> LENGTH: 7
<212> TYPE: PRT
<213> ORGANISM: Homo sapiens

<400> SEQUENCE: 234

Ala Ala Ser Ser Leu Gln Ser
1               5

<210> SEQ ID NO 235
<211> LENGTH: 120
<212> TYPE: PRT
<213> ORGANISM: Homo sapiens

<400> SEQUENCE: 235

Glu Val Gln Leu Val Glu Ser Gly Gly Gly Leu Val Gln Pro Gly Gly
1               5                   10                  15

Ser Leu Arg Ile Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Ser Phe Ser Arg Asp Asn Ser Lys Asn Thr Val Phe Leu
65                  70                  75                  80

Gln Met Asn Ser Leu Arg Ala Glu Asp Thr Ala Val Tyr Tyr Cys Ala
                85                  90                  95

Arg Cys Leu Ser Arg Met Arg Gly Tyr Gly Leu Asp Val Trp Gly Gln
            100                 105                 110

Gly Thr Thr Val Thr Val Ser Ser
        115                 120

<210> SEQ ID NO 236
<211> LENGTH: 119
<212> TYPE: PRT
<213> ORGANISM: Homo sapiens

<400> SEQUENCE: 236

Glu Val Gln Leu Val Glu Ser Gly Gly Gly Leu Val Gln Pro Gly Gly
1               5                   10                  15

Ser Leu Arg Ile Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Ser Phe Ser Arg Asp Asn Ser Lys Asn Thr Val Phe Leu
65                  70                  75                  80

Gln Met Asn Ser Leu Arg Ala Glu Asp Thr Ala Val Tyr Tyr Cys Ala
                85                  90                  95

Arg Cys Leu Ser Arg Met Arg Gly Tyr Gly Leu Asp Val Trp Gly Gln
            100                 105                 110

Gly Thr Thr Val Thr Val Ser
        115
```

<210> SEQ ID NO 237
<211> LENGTH: 16
<212> TYPE: PRT
<213> ORGANISM: Homo sapiens

<400> SEQUENCE: 237

Tyr Ile Tyr Asn Arg Gly Ser Thr Lys Tyr Thr Pro Ser Leu Lys Ser
1               5                   10                  15

<210> SEQ ID NO 238
<211> LENGTH: 11
<212> TYPE: PRT
<213> ORGANISM: Homo sapiens

<400> SEQUENCE: 238

His Val Gly Gly His Thr Tyr Gly Ile Asp Tyr
1               5                   10

<210> SEQ ID NO 239
<211> LENGTH: 6
<212> TYPE: PRT
<213> ORGANISM: Homo sapiens

<400> SEQUENCE: 239

Gly Ala Ser Ile Ser Ser
1               5

<210> SEQ ID NO 240
<211> LENGTH: 9
<212> TYPE: PRT
<213> ORGANISM: Homo sapiens

<400> SEQUENCE: 240

Tyr Ile Tyr Asn Arg Gly Ser Thr Lys
1               5

<210> SEQ ID NO 241
<211> LENGTH: 11
<212> TYPE: PRT
<213> ORGANISM: Homo sapiens

<400> SEQUENCE: 241

Arg Ala Ser Gln Ser Ile Ser Asn Tyr Leu Asn
1               5                   10

<210> SEQ ID NO 242
<211> LENGTH: 5
<212> TYPE: PRT
<213> ORGANISM: Homo sapiens

<400> SEQUENCE: 242

Tyr Tyr Ala Met Ser
1               5

<210> SEQ ID NO 243
<211> LENGTH: 9
<212> TYPE: PRT
<213> ORGANISM: Homo sapiens

<400> SEQUENCE: 243

Gln Gln Ser Tyr Asn Thr Pro Ile Thr
1               5

<210> SEQ ID NO 244
<211> LENGTH: 353
<212> TYPE: DNA
<213> ORGANISM: Homo sapiens

<400> SEQUENCE: 244

```
gaggtgcagc tggtggagtc tgggggaggc ttggtccagc ctggggggtc cctgagaatc    60
tcctgtgcag cctctggatt caccgtcagt agcaactaca tgagttgggt ccgccaggct   120
ccagggaagg ggctggagtg ggtctcagtt atttatagtg gtggtagcac atactacgca   180
gactccgtga agggcagatt ctccttctcc agagacaact ccaagaacac agtgtttctt   240
caaatgaaca gcctgagagc cgaggacacg gctgtgtatt actgtgcgag atgtctgagc   300
aggatgcggg gttacggttt agacgtctgg ggccaaggga ccacggtcac cgt          353
```

<210> SEQ ID NO 245
<211> LENGTH: 17
<212> TYPE: PRT
<213> ORGANISM: Homo sapiens

<400> SEQUENCE: 245

Lys Ser Ser Gln Ser Ile Leu Asn Ser Ser Asn Asn Lys Asn Tyr Leu
1               5                   10                  15

Ala

<210> SEQ ID NO 246
<211> LENGTH: 19
<212> TYPE: PRT
<213> ORGANISM: Homo sapiens

<400> SEQUENCE: 246

Leu Asn Tyr His Asp Ser Gly Thr Tyr Tyr Asn Ala Pro Arg Gly Trp
1               5                   10                  15

Phe Asp Pro

<210> SEQ ID NO 247

<400> SEQUENCE: 247

000

<210> SEQ ID NO 248

<400> SEQUENCE: 248

000

<210> SEQ ID NO 249
<211> LENGTH: 17
<212> TYPE: PRT
<213> ORGANISM: Homo sapiens

<400> SEQUENCE: 249

Gly Val Ile Pro Ile Phe Arg Thr Ala Asn Tyr Ala Gln Asn Phe Gln
1               5                   10                  15

Gly

<210> SEQ ID NO 250
<211> LENGTH: 9
<212> TYPE: PRT
<213> ORGANISM: Homo sapiens

<400> SEQUENCE: 250

```
Gln Gln Tyr Tyr Ser Ser Pro Pro Thr
1               5

<210> SEQ ID NO 251

<400> SEQUENCE: 251

000

<210> SEQ ID NO 252
<211> LENGTH: 5
<212> TYPE: PRT
<213> ORGANISM: Homo sapiens

<400> SEQUENCE: 252

Ser Tyr Ser Trp Ser
1               5

<210> SEQ ID NO 253
<211> LENGTH: 16
<212> TYPE: PRT
<213> ORGANISM: Homo sapiens

<400> SEQUENCE: 253

Tyr Leu Tyr Tyr Ser Gly Ser Thr Lys Tyr Asn Pro Ser Leu Lys Ser
1               5                   10                  15

<210> SEQ ID NO 254
<211> LENGTH: 13
<212> TYPE: PRT
<213> ORGANISM: Homo sapiens

<400> SEQUENCE: 254

Thr Gly Ser Glu Ser Thr Thr Gly Tyr Gly Met Asp Val
1               5                   10

<210> SEQ ID NO 255
<211> LENGTH: 6
<212> TYPE: PRT
<213> ORGANISM: Homo sapiens

<400> SEQUENCE: 255

Gly Asp Ser Ile Ser Ser
1               5

<210> SEQ ID NO 256
<211> LENGTH: 9
<212> TYPE: PRT
<213> ORGANISM: Homo sapiens

<400> SEQUENCE: 256

Tyr Leu Tyr Tyr Ser Gly Ser Thr Lys
1               5

<210> SEQ ID NO 257
<211> LENGTH: 12
<212> TYPE: PRT
<213> ORGANISM: Influenza A virus

<400> SEQUENCE: 257

Gly Ile Thr Asn Lys Glu Asn Ser Val Ile Glu Lys
1               5                   10

<210> SEQ ID NO 258
```

<210> SEQ ID NO 258
<211> LENGTH: 7
<212> TYPE: PRT
<213> ORGANISM: Homo sapiens

<400> SEQUENCE: 258

Ala Ala Ser Ser Leu His Ser
1               5

<210> SEQ ID NO 259
<211> LENGTH: 9
<212> TYPE: PRT
<213> ORGANISM: Homo sapiens

<400> SEQUENCE: 259

Gln Gln Ser Tyr Ser Pro Pro Ile Thr
1               5

<210> SEQ ID NO 260
<211> LENGTH: 5
<212> TYPE: PRT
<213> ORGANISM: Homo sapiens

<400> SEQUENCE: 260

Asn Ser Phe Trp Gly
1               5

<210> SEQ ID NO 261
<211> LENGTH: 16
<212> TYPE: PRT
<213> ORGANISM: Homo sapiens

<400> SEQUENCE: 261

Tyr Val Tyr Asn Ser Gly Asn Thr Lys Tyr Asn Pro Ser Leu Lys Ser
1               5                   10                  15

<210> SEQ ID NO 262
<211> LENGTH: 11
<212> TYPE: PRT
<213> ORGANISM: Homo sapiens

<400> SEQUENCE: 262

His Asp Asp Ala Ser His Gly Tyr Ser Ile Ser
1               5                   10

<210> SEQ ID NO 263
<211> LENGTH: 6
<212> TYPE: PRT
<213> ORGANISM: Homo sapiens

<400> SEQUENCE: 263

Gly Gly Ser Ile Ser Asn
1               5

<210> SEQ ID NO 264
<211> LENGTH: 9
<212> TYPE: PRT
<213> ORGANISM: Homo sapiens

<400> SEQUENCE: 264

Tyr Val Tyr Asn Ser Gly Asn Thr Lys
1               5

<210> SEQ ID NO 265
<211> LENGTH: 11
<212> TYPE: PRT

<213> ORGANISM: Homo sapiens

<400> SEQUENCE: 265

Arg Ala Ser Gln Thr Ile Ser Thr Tyr Leu Asn
1               5                   10

<210> SEQ ID NO 266
<211> LENGTH: 12
<212> TYPE: PRT
<213> ORGANISM: Homo sapiens

<400> SEQUENCE: 266

Tyr Trp Gly Gln Gly Thr Leu Val Thr Val Ser Ser
1               5                   10

<210> SEQ ID NO 267
<211> LENGTH: 9
<212> TYPE: PRT
<213> ORGANISM: Homo sapiens

<400> SEQUENCE: 267

Gln Gln Ser Tyr Asn Thr Pro Leu Thr
1               5

<210> SEQ ID NO 268
<211> LENGTH: 5
<212> TYPE: PRT
<213> ORGANISM: Homo sapiens

<400> SEQUENCE: 268

Ala Tyr His Trp Ser
1               5

<210> SEQ ID NO 269
<211> LENGTH: 16
<212> TYPE: PRT
<213> ORGANISM: Homo sapiens

<400> SEQUENCE: 269

His Ile Phe Asp Ser Gly Ser Thr Tyr Tyr Asn Pro Ser Leu Lys Ser
1               5                   10                  15

<210> SEQ ID NO 270
<211> LENGTH: 12
<212> TYPE: PRT
<213> ORGANISM: Homo sapiens

<400> SEQUENCE: 270

Pro Leu Gly Ser Arg Tyr Tyr Tyr Gly Met Asp Val
1               5                   10

<210> SEQ ID NO 271
<211> LENGTH: 6
<212> TYPE: PRT
<213> ORGANISM: Homo sapiens

<400> SEQUENCE: 271

Gly Gly Ser Ile Ser Ala
1               5

<210> SEQ ID NO 272
<211> LENGTH: 9
<212> TYPE: PRT
<213> ORGANISM: Homo sapiens -continued

<400> SEQUENCE: 272

His Ile Phe Asp Ser Gly Ser Thr Tyr
1               5

<210> SEQ ID NO 273
<211> LENGTH: 11
<212> TYPE: PRT
<213> ORGANISM: Homo sapiens

<400> SEQUENCE: 273

Arg Ala Ser Gln Ser Ile Ser Arg Tyr Leu Asn
1               5                   10

<210> SEQ ID NO 274
<211> LENGTH: 7
<212> TYPE: PRT
<213> ORGANISM: Homo sapiens

<400> SEQUENCE: 274

Gly Ala Ser Thr Leu Gln Asn
1               5

<210> SEQ ID NO 275
<211> LENGTH: 8
<212> TYPE: PRT
<213> ORGANISM: Homo sapiens

<400> SEQUENCE: 275

Gln Gln Ser Tyr Ser Val Pro Ala
1               5

<210> SEQ ID NO 276
<211> LENGTH: 120
<212> TYPE: PRT
<213> ORGANISM: Homo sapiens

<400> SEQUENCE: 276

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser Asn Tyr
            20                  25                  30

Tyr Trp Ser Trp Ile Arg Gln Ser Pro Gly Lys Gly Leu Glu Trp Ile
        35                  40                  45

Gly Phe Ile Tyr Tyr Gly Gly Asn Thr Lys Tyr Asn Pro Ser Leu Lys
    50                  55                  60

Ser Arg Val Thr Ile Ser Gln Asp Thr Ser Lys Ser Gln Val Ser Leu
65                  70                  75                  80

Thr Met Ser Ser Val Thr Ala Ala Glu Ser Ala Val Tyr Phe Cys Ala
                85                  90                  95

Arg Ala Ser Cys Ser Gly Gly Tyr Cys Ile Leu Asp Tyr Trp Gly Gln
            100                 105                 110

Gly Thr Leu Val Thr Val Ser Ser
        115                 120

<210> SEQ ID NO 277
<211> LENGTH: 117
<212> TYPE: PRT
<213> ORGANISM: Homo sapiens

<400> SEQUENCE: 277

Gln Val Gln Leu Gln Glu Ser Gly Pro Gly Leu Val Lys Pro Ser Glu

```
1               5                   10                  15
Thr Leu Ser Leu Thr Cys Thr Val Ser Gly Ser Ser Ile Ser Asn Tyr
            20                  25                  30

Tyr Trp Ser Trp Ile Arg Gln Ser Pro Gly Lys Gly Leu Glu Trp Ile
            35                  40                  45

Gly Phe Ile Tyr Tyr Gly Gly Asn Thr Lys Tyr Asn Pro Ser Leu Lys
            50                  55                  60

Ser Arg Val Thr Ile Ser Gln Asp Thr Ser Lys Ser Gln Val Ser Leu
65                  70                  75                  80

Thr Met Ser Ser Val Thr Ala Ala Glu Ser Ala Val Tyr Phe Cys Ala
                85                  90                  95

Arg Ala Ser Cys Ser Gly Gly Tyr Cys Ile Leu Asp Tyr Trp Gly Gln
            100                 105                 110

Gly Thr Leu Val Thr
            115
```

<210> SEQ ID NO 278
<211> LENGTH: 353
<212> TYPE: DNA
<213> ORGANISM: Homo sapiens

<400> SEQUENCE: 278

```
caggtgcaat tgcaggagtc gggcccagga ctggtgaagc cttcggagac cctgtccctc    60
acctgcactg tctctggttc gtccatcagt aattactact ggagctggat ccggcagtcc   120
ccagggaagg gactggagtg gattgggttt atctattacg gtggaaacac caagtacaat   180
ccctccctca gagccgcgt caccatatca aagacactt ccaagagtca ggtctccctg    240
acgatgagct ctgtgaccgc tgcggaatcg gccgtctatt tctgtgcgag agcgtcttgt   300
agtggtggtt actgtatcct tgactactgg ggccaggaa ccctggtcac cgt          353
```

<210> SEQ ID NO 279
<211> LENGTH: 1335
<212> TYPE: DNA
<213> ORGANISM: Homo sapiens

<400> SEQUENCE: 279

```
gaggtccagc tggtgcagtc tggggctgag gtgaagaagc ctggggcctc agtgaaggtc    60
tcctgcaagg cttctgggta caccttcacc ggctactatg tgtactgggt gcgacaggcc   120
cctggacaag gcttgagtg gatgggatgg atcagcgctt acaatggtaa cacaaactat   180
gcacagaagt tccagggcag agtcacgatt accgcggaca atccacgag cacagcctac   240
atggagctga gcagcctgag atctgaagac acggctgtgt attactgtgc gagaagtaga   300
tccctggacg tctggggcca aggaccacg gtcaccgtct cgagtgctag caccaagggc   360
ccagcgtgt tccccctggc cccagcagc aagagcacca gcggcggcac agccgccctg   420
ggctgcctgg tgaaggacta cttccccgag ccgtgaccg tgagctggaa cagcggcgcc   480
ttgaccagcg gcgtgcacac cttccccgcc gtgctgcaga gcagcggcct gtacagcctg   540
agcagcgtgg tgaccgtgcc agcagcagc ctgggcaccc agacctacat ctgcaacgtg   600
aaccacaagc ccagcaacac caaggtggac aaacgcgtgg agcccaagag ctgcgacaag   660
acccacacct gccccccctg ccctgccccc gagctgctgg gcggaccctc cgtgttcctg   720
ttccccccca gcccaagga cacctcatg atcagccgga ccccgaggt gacctgcgtg   780
gtggtggacg tgagccacga ggaccccgag gtgaagttca ctggtacgt ggacggcgtg   840
```

```
gaggtgcaca acgccaagac caagcccggg gaggagcagt acaacagcac ctaccgggtg    900
gtgagcgtgc tcaccgtgct gcaccaggac tggctgaacg gcaaggagta caagtgcaag    960
gtgagcaaca aggccctgcc tgcccccatc gagaagacca tcagcaaggc caagggccag   1020
ccccgggagc cccaggtgta caccctgccc ccagccggg aggagatgac caagaaccag    1080
gtgtccctca cctgtctggt gaagggcttc taccccagcg acatcgccgt ggagtgggag   1140
agcaacggcc agcccgagaa caactacaag accacccccc ctgtgctgga cagcgacggc   1200
agcttcttcc tgtacagcaa gctcaccgtg gacaagagcc ggtggcagca gggcaacgtg   1260
ttcagctgca gcgtgatgca cgaggccctg cacaaccact acacccagaa gagcctgagc   1320
ctgagccccg gcaag                                                    1335
```

<210> SEQ ID NO 280
<211> LENGTH: 11
<212> TYPE: PRT
<213> ORGANISM: Homo sapiens

<400> SEQUENCE: 280

Gly Thr Trp Asp Ser Ser Leu Ser Ala Tyr Val
1               5                   10

<210> SEQ ID NO 281
<211> LENGTH: 12
<212> TYPE: PRT
<213> ORGANISM: Influenza A virus

<400> SEQUENCE: 281

Gly Ile Thr Asn Lys Val Asn Ser Val Ile Glu Lys
1               5                   10

<210> SEQ ID NO 282
<211> LENGTH: 7
<212> TYPE: PRT
<213> ORGANISM: Homo sapiens

<400> SEQUENCE: 282

Gly Ala Thr Asp Leu Gln Ser
1               5

<210> SEQ ID NO 283
<211> LENGTH: 12
<212> TYPE: PRT
<213> ORGANISM: Influenza A virus

<400> SEQUENCE: 283

Gly Val Thr Asn Lys Val Asn Ser Ile Ile Asn Lys
1               5                   10

<210> SEQ ID NO 284
<211> LENGTH: 5
<212> TYPE: PRT
<213> ORGANISM: Influenza A virus

<400> SEQUENCE: 284

Asp Asn Tyr Ile Asn
1               5

<210> SEQ ID NO 285
<211> LENGTH: 16
<212> TYPE: PRT
<213> ORGANISM: Homo sapiens

<400> SEQUENCE: 285

Val Phe Tyr Ser Ala Asp Arg Thr Ser Tyr Ala Asp Ser Val Lys Gly
1               5                   10                  15

<210> SEQ ID NO 286
<211> LENGTH: 10
<212> TYPE: PRT
<213> ORGANISM: Homo sapiens

<400> SEQUENCE: 286

Val Gln Lys Ser Tyr Tyr Gly Met Asp Val
1               5                   10

<210> SEQ ID NO 287
<211> LENGTH: 6
<212> TYPE: PRT
<213> ORGANISM: Homo sapiens

<400> SEQUENCE: 287

Gly Phe Ser Val Ser Asp
1               5

<210> SEQ ID NO 288
<211> LENGTH: 9
<212> TYPE: PRT
<213> ORGANISM: Homo sapiens

<400> SEQUENCE: 288

Val Phe Tyr Ser Ala Asp Arg Thr Ser
1               5

<210> SEQ ID NO 289

<400> SEQUENCE: 289

000

<210> SEQ ID NO 290
<211> LENGTH: 11
<212> TYPE: PRT
<213> ORGANISM: Homo sapiens

<400> SEQUENCE: 290

Ser Ser Asn Tyr Tyr Asp Ser Val Tyr Asp Tyr
1               5                   10

<210> SEQ ID NO 291
<211> LENGTH: 8
<212> TYPE: PRT
<213> ORGANISM: Homo sapiens

<400> SEQUENCE: 291

Gln Gln Thr Phe Ser Ile Pro Leu
1               5

<210> SEQ ID NO 292
<211> LENGTH: 107
<212> TYPE: PRT
<213> ORGANISM: Homo sapiens

<400> SEQUENCE: 292

Asp Ile Gln Val Thr Gln Ser Pro Ser Ser Leu Ser Ala Ser Val Gly
1               5                   10                  15

Asp Arg Val Thr Ile Thr Cys Arg Ala Ser Gln Asn Ile Tyr Lys Tyr

```
                 20                  25                  30
Leu Asn Trp Tyr Gln Gln Arg Pro Gly Lys Ala Pro Lys Gly Leu Ile
         35                  40                  45

Ser Ala Ala Ser Gly Leu Gln Ser Gly Val Pro Ser Arg Phe Ser Gly
 50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Ser Pro Pro Leu
                 85                  90                  95

Thr Phe Gly Gly Gly Thr Arg Val Asp Ile Lys
                100                 105

<210> SEQ ID NO 293
<211> LENGTH: 7
<212> TYPE: PRT
<213> ORGANISM: Homo sapiens

<400> SEQUENCE: 293

Ser Gly Ala Tyr Tyr Trp Thr
1               5

<210> SEQ ID NO 294
<211> LENGTH: 16
<212> TYPE: PRT
<213> ORGANISM: Homo sapiens

<400> SEQUENCE: 294

Tyr Ile Tyr Tyr Ser Gly Asn Thr Tyr Tyr Asn Pro Ser Leu Lys Ser
1               5                   10                  15

<210> SEQ ID NO 295
<211> LENGTH: 13
<212> TYPE: PRT
<213> ORGANISM: Homo sapiens

<400> SEQUENCE: 295

Ala Ala Ser Thr Ser Val Leu Gly Tyr Gly Met Asp Val
1               5                   10

<210> SEQ ID NO 296
<211> LENGTH: 8
<212> TYPE: PRT
<213> ORGANISM: Homo sapiens

<400> SEQUENCE: 296

Gly Asp Ser Ile Thr Ser Gly Ala
1               5

<210> SEQ ID NO 297
<211> LENGTH: 9
<212> TYPE: PRT
<213> ORGANISM: Homo sapiens

<400> SEQUENCE: 297

Tyr Ile Tyr Tyr Ser Gly Asn Thr Tyr
1               5

<210> SEQ ID NO 298

<400> SEQUENCE: 298

000
```

<210> SEQ ID NO 299
<211> LENGTH: 7
<212> TYPE: PRT
<213> ORGANISM: Homo sapiens

<400> SEQUENCE: 299

Trp Ala Ser Thr Arg Glu Ser
1               5

<210> SEQ ID NO 300
<211> LENGTH: 9
<212> TYPE: PRT
<213> ORGANISM: Homo sapiens

<400> SEQUENCE: 300

Gln Gln Ser Tyr Ser Thr Pro Leu Thr
1               5

<210> SEQ ID NO 301
<211> LENGTH: 7
<212> TYPE: PRT
<213> ORGANISM: Homo sapiens

<400> SEQUENCE: 301

Val Ser Asp Asn Tyr Ile Asn
1               5

<210> SEQ ID NO 302

<400> SEQUENCE: 302

000

<210> SEQ ID NO 303

<400> SEQUENCE: 303

000

<210> SEQ ID NO 304
<211> LENGTH: 5
<212> TYPE: PRT
<213> ORGANISM: Homo sapiens

<400> SEQUENCE: 304

Ser Gly Phe Ser Val
1               5

<210> SEQ ID NO 305

<400> SEQUENCE: 305

000

<210> SEQ ID NO 306
<211> LENGTH: 17
<212> TYPE: PRT
<213> ORGANISM: Homo sapiens

<400> SEQUENCE: 306

Gly Ile Ile Ala Ile Phe His Thr Pro Lys Tyr Ala Gln Lys Phe Gln
1               5                   10                  15

Gly

```
<210> SEQ ID NO 307
<211> LENGTH: 17
<212> TYPE: PRT
<213> ORGANISM: Homo sapiens

<400> SEQUENCE: 307

Gly Ile Ser Pro Met Phe Gly Thr Thr Tyr Ala Gln Lys Phe Gln
1               5                   10                  15

Gly

<210> SEQ ID NO 308
<211> LENGTH: 9
<212> TYPE: PRT
<213> ORGANISM: Homo sapiens

<400> SEQUENCE: 308

Gln Gln Tyr Gly Ser Ser Ser Leu Thr
1               5

<210> SEQ ID NO 309
<211> LENGTH: 115
<212> TYPE: PRT
<213> ORGANISM: Homo sapiens

<400> SEQUENCE: 309

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Val Tyr Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Ser Leu Asp Val Trp Gly Gln Gly Thr Thr Val Thr
            100                 105                 110

Val Ser Ser
        115

<210> SEQ ID NO 310
<211> LENGTH: 114
<212> TYPE: PRT
<213> ORGANISM: Homo sapiens

<400> SEQUENCE: 310

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
```

```
                    85                  90                  95
Tyr Tyr Ser Thr Pro Leu Thr Phe Gly Gly Gly Thr Lys Val Asp Ile
                100                 105                 110

Lys Arg

<210> SEQ ID NO 311
<211> LENGTH: 735
<212> TYPE: DNA
<213> ORGANISM: Homo sapiens

<400> SEQUENCE: 311
gaggtccagc tggtgcagtc tggggctgag gtgaagaagc ctggggcctc agtgaaggtc      60
tcctgcaagg cttctgggta caccttcacc ggctactatg tgtactgggt gcgacaggcc    120
cctggacaag gcttgagtg gatgggatgg atcagcgctt acaatggtaa cacaaactat      180
gcacagaagt tccagggcag agtcacgatt accgcggaca atccacgag cacagcctac      240 atggagctga gcagcctgag atctgaagac acggctgtgt attactgtgc gagaagtaga    300
tccctggacg tctggggcca agggaccacg gtcaccgtct cgagcggtac gggcggttca    360
ggcggaaccg gcagcggcac tggcgggtcg acggatgttg tgatgactca gtctccagac    420
tccctggctg tgtctctggg cgagagggcc accatcaact gcaagtccag ccagagtgtt    480
ttatacagct ccaacaataa gaactactta gcttggtacc agcagaaacc aggacagcct    540
cctaagctgc tcatttactg ggcatctacc cgggaatccg gggtccctga ccgattcagt    600
ggcagcgggt ctgggacaga tttcactctc accatcagca gcctgcaggc tgaagatgtg    660
gcagtttatt actgtcagca atattatagt actcctctca ctttcggcgg agggaccaaa    720
gtggatatca aacgt                                                     735

<210> SEQ ID NO 312
<211> LENGTH: 245
<212> TYPE: PRT
<213> ORGANISM: Homo sapiens

<400> SEQUENCE: 312

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Val Tyr Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Ser Leu Asp Val Trp Gly Gln Gly Thr Thr Val Thr
                100                 105                 110

Val Ser Ser Gly Thr Gly Gly Ser Gly Gly Thr Gly Ser Gly Thr Gly
            115                 120                 125

Gly Ser Thr Asp Val Val Met Thr Gln Ser Pro Asp Ser Leu Ala Val
        130                 135                 140

Ser Leu Gly Glu Arg Ala Thr Ile Asn Cys Lys Ser Ser Gln Ser Val
145                 150                 155                 160
```

```
Leu Tyr Ser Ser Asn Asn Lys Asn Tyr Leu Ala Trp Tyr Gln Gln Lys
                165                 170                 175

Pro Gly Gln Pro Pro Lys Leu Leu Ile Tyr Trp Ala Ser Thr Arg Glu
            180                 185                 190

Ser Gly Val Pro Asp Arg Phe Ser Gly Ser Gly Ser Gly Thr Asp Phe
        195                 200                 205

Thr Leu Thr Ile Ser Ser Leu Gln Ala Glu Asp Val Ala Val Tyr Tyr
    210                 215                 220

Cys Gln Gln Tyr Tyr Ser Thr Pro Leu Thr Phe Gly Gly Gly Thr Lys
225                 230                 235                 240

Val Asp Ile Lys Arg
                245

<210> SEQ ID NO 313
<211> LENGTH: 121
<212> TYPE: PRT
<213> ORGANISM: Homo sapiens

<400> SEQUENCE: 313

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120

<210> SEQ ID NO 314
<211> LENGTH: 111
<212> TYPE: PRT
<213> ORGANISM: Homo sapiens

<400> SEQUENCE: 314

Ser Tyr Val Leu Thr Gln Pro Pro Ser Ala Ser Gly Thr Pro Gly Gln
1               5                   10                  15

Arg Val Thr Ile Ser Cys Ser Gly Ser Thr Phe Asn Ile Gly Ser Asn
            20                  25                  30

Ala Val Asp Trp Tyr Arg Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ile Leu
                85                  90                  95

Asn Val Pro Val Phe Gly Gly Gly Thr Lys Leu Thr Val Leu Gly
            100                 105                 110
```

<210> SEQ ID NO 315
<211> LENGTH: 744
<212> TYPE: DNA
<213> ORGANISM: Homo sapiens

<400> SEQUENCE: 315

```
gaggtgcagc tggtggagtc tgggctgag gtgaagaagc ctgggtcctc ggtgaaagtc      60
tcttgcaagg cttctggagg ccccttccgc agctatgcta tcagctgggt gcgacaggcc    120
cctggacaag ggcctgagtg gatgggaggg atcatccta tttttggtac aacaaaatac    180
gcaccgaagt tccagggcag agtcacgatt accgcggacg atttcgcggg cacagtttac    240
atggagctga gcagcctgcg atctgaggac acggccatgt attactgtgc gaaacatatg    300
gggtaccagg tgcgcgaaac tatgacgtc tggggcaaag ggaccacggt caccgtctcg    360
agcggtacgg gcggttcagg cggaaccggc agcggcactg gcgggtcgac gtcctatgtg    420
ctgactcagc acctcagc gtctgggacc cccgggcaga gggtcaccat ctcttgttct    480
ggaagcacgt tcaacatcgg aagtaatgct gtagactgga ccggcagct cccaggaacg    540
gcccccaaac tcctcatcta tagtaataat cagcggccct caggggtccc tgaccgattc    600
tctggctcca ggtctggcac ctcagcctcc ctggccatca gtgggctcca gtctgaggat    660
gaggctgatt attactgtgc agcatgggat gacatcctga atgttccggt attcggcgga    720
gggaccaagc tgaccgtcct aggt                                          744
```

<210> SEQ ID NO 316
<211> LENGTH: 248
<212> TYPE: PRT
<213> ORGANISM: Homo sapiens

<400> SEQUENCE: 316

```
Glu Val Gln Leu Val Glu Ser Gly Ala Glu Lys Lys Pro Gly Ser
1               5                  10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser Gly Thr Gly Gly Ser Gly Gly
        115                 120                 125

Thr Gly Ser Gly Thr Gly Gly Ser Thr Ser Tyr Val Leu Thr Gln Pro
    130                 135                 140

Pro Ser Ala Ser Gly Thr Pro Gly Gln Arg Val Thr Ile Ser Cys Ser
145                 150                 155                 160

Gly Ser Thr Phe Asn Ile Gly Ser Asn Ala Val Asp Trp Tyr Arg Gln
                165                 170                 175

Leu Pro Gly Thr Ala Pro Lys Leu Leu Ile Tyr Ser Asn Asn Gln Arg
            180                 185                 190

Pro Ser Gly Val Pro Asp Arg Phe Ser Gly Ser Arg Ser Gly Thr Ser
```

```
                195                 200                 205
Ala Ser Leu Ala Ile Ser Gly Leu Gln Ser Glu Asp Glu Ala Asp Tyr
    210                 215                 220

Tyr Cys Ala Ala Trp Asp Asp Ile Leu Asn Val Pro Val Phe Gly Gly
225                 230                 235                 240

Gly Thr Lys Leu Thr Val Leu Gly
                245

<210> SEQ ID NO 317
<211> LENGTH: 121
<212> TYPE: PRT
<213> ORGANISM: Homo sapiens

<400> SEQUENCE: 317

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Arg Ser Tyr
                20                  25                  30

Ala Ile Ser Trp Val Arg Gln Ala Pro Gly Gln Gly Pro Glu Trp Met
            35                  40                  45

Gly Gly Ile Ile Pro Ile Phe Gly Thr Thr Lys Tyr Ala Pro Lys Phe
        50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120

<210> SEQ ID NO 318
<211> LENGTH: 111
<212> TYPE: PRT
<213> ORGANISM: Homo sapiens

<400> SEQUENCE: 318

Gln Ser Ala Leu Thr Gln Pro Ala Ala Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Val Thr Val Leu Gly
            100                 105                 110

<210> SEQ ID NO 319
<211> LENGTH: 744
<212> TYPE: DNA
<213> ORGANISM: Homo sapiens

<400> SEQUENCE: 319
```

```
caggtccagc tggtgcagtc tggggctgag gtgaagaagc ctgggtcctc ggtgaaagtc    60
tcttgcaagg cttctggagg ccccttccgc agctatgcta tcagctgggt gcgacaggcc   120
cctggacaag gcctgagtg atgggaggg atcatccta ttttggtac aacaaaatac   180
gcaccgaagt tccagggcag agtcacgatt accgcgacg atttcgcggg cacagtttac   240
atggagctga gcagcctgcg atctgaggac acggccatgt actactgtgc gaaacatatg   300
gggtaccagt gcgcgaaac tatggacgtc tggggcaaag gaccacggt caccgtctcg   360
agcggtacgg gcggttcagg cggaaccggc agcggcactg gcgggtcgac gcagtctgcc   420
ctgactcagc ctgccgccgt gtctgggtct cctggacagt cgatcaccat tcctgcact   480
ggaaccagca gtgacgttgg tggttataac tatgtctcct ggtaccaaca gcacccaggc   540
aaagcccca aactcatgat ttatgaggtc agtaatcggc cctcaggggt ttctaatcgc   600
ttctctggct ccaagtctgg caacacggcc tccctgacca tctctgggct ccaggctgag   660
gacgaggctg attattactg cagctcatat acaagcagca gcacttatgt cttcggaact   720
gggaccaagg tcaccgtcct aggt                                           744
```

<210> SEQ ID NO 320
<211> LENGTH: 248
<212> TYPE: PRT
<213> ORGANISM: Homo sapiens

<400> SEQUENCE: 320

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Pro Phe Arg Ser Tyr
            20                  25                  30
Ala Ile Ser Trp Val Arg Gln Ala Pro Gly Gln Gly Pro Glu Trp Met
        35                  40                  45
Gly Gly Ile Ile Pro Ile Phe Gly Thr Thr Lys Tyr Ala Pro Lys Phe
    50                  55                  60
Gln Gly Arg Val Thr Ile Thr Ala Asp Asp Phe Ala Gly Thr Val Tyr
65                  70                  75                  80
Met Glu Leu Ser Ser Leu Arg Ser Glu Asp Thr Ala Met Tyr Tyr Cys
                85                  90                  95
Ala Lys His Met Gly Tyr Gln Val Arg Glu Thr Met Asp Val Trp Gly
            100                 105                 110
Lys Gly Thr Thr Val Thr Val Ser Ser Gly Thr Gly Gly Ser Gly Gly
        115                 120                 125
Thr Gly Ser Gly Thr Gly Gly Ser Thr Gln Ser Ala Leu Thr Gln Pro
    130                 135                 140
Ala Ala Val Ser Gly Ser Pro Gly Gln Ser Ile Thr Ile Ser Cys Thr
145                 150                 155                 160
Gly Thr Ser Ser Asp Val Gly Gly Tyr Asn Tyr Val Ser Trp Tyr Gln
                165                 170                 175
Gln His Pro Gly Lys Ala Pro Lys Leu Met Ile Tyr Glu Val Ser Asn
            180                 185                 190
Arg Pro Ser Gly Val Ser Asn Arg Phe Ser Gly Ser Lys Ser Gly Asn
        195                 200                 205
Thr Ala Ser Leu Thr Ile Ser Gly Leu Gln Ala Glu Asp Glu Ala Asp
    210                 215                 220
Tyr Tyr Cys Ser Ser Tyr Thr Ser Ser Ser Thr Tyr Val Phe Gly Thr
225                 230                 235                 240
```

```
Gly Thr Lys Val Thr Val Leu Gly
            245

<210> SEQ ID NO 321
<211> LENGTH: 121
<212> TYPE: PRT
<213> ORGANISM: Homo sapiens

<400> SEQUENCE: 321

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120

<210> SEQ ID NO 322
<211> LENGTH: 111
<212> TYPE: PRT
<213> ORGANISM: Homo sapiens

<400> SEQUENCE: 322

Ser Tyr Val Leu Thr Gln Pro Pro Ser Val Ser Gly Thr Pro Gly Gln
1               5                   10                  15

Arg Val Thr Ile Ser Cys Ser Gly Ser Arg Ser Asn Val Gly Asp Asn
            20                  25                  30

Ser Val Tyr Trp Tyr Gln His Val Pro Glu Met Ala Pro Lys Leu Leu
        35                  40                  45

Val Tyr Lys Asn Thr Gln Arg Pro Ser Gly Val Pro Ala Arg Phe Ser
    50                  55                  60

Gly Ser Lys Ser Gly Thr Ser Ala Ser Leu Ala Ile Ile Gly Leu Gln
65                  70                  75                  80

Ser Gly Asp Glu Ala Asp Tyr Tyr Cys Val Ala Trp Asp Asp Ser Val
                85                  90                  95

Asp Gly Tyr Val Phe Gly Ser Gly Thr Lys Val Thr Val Leu Gly
            100                 105                 110

<210> SEQ ID NO 323
<211> LENGTH: 744
<212> TYPE: DNA
<213> ORGANISM: Homo sapiens

<400> SEQUENCE: 323
gaggtgcagc tggtggagtc tggggctgag gtgaagaagc ctgggtcctc ggtgaaagtc       60
tcttgcaagg cttctggagg ccccttccgc agctatgcta tcagctgggt gcgacaggcc      120
cctggacaag ggcctgagtg gatgggaggg atcatcccta ttttggtac aacaaaatac      180
```

```
gcaccgaagt tccagggcag agtcacgatt accgcggacg atttcgcggg cacagtttac    240
atggagctga gcagcctgcg atctgaggac acggccatgt actactgtgc gaaacatatg    300
gggtaccagg tgcgcgaaac tatggacgtc tggggcaaag ggaccacggt caccgtctcg    360
agcggtacgg gcggttcagg cggaaccggc agcgacactg gcgggtcgac gtcctatgtg    420
ctgactcagc cacccctcagt tctctgggacc cccgggcaga gggtcaccat ctcttgctct    480
ggaagccgct ccaacgtcgg agataattct gtatattggt atcaacacgt cccagaaatg    540
gcccccaaac tcctcgtcta taagaatact caacggccct caggagtccc tgcccggttt    600
tccggctcca gtctggcac ttcagcctcc ctggccatca ttggcctcca gtccggcgat    660
gaggctgatt attattgtgt ggcatgggat gacagcgtag atggctatgt cttcggatct    720
gggaccaagg tcaccgtcct aggt                                           744
```

<210> SEQ ID NO 324
<211> LENGTH: 248
<212> TYPE: PRT
<213> ORGANISM: Homo sapiens

<400> SEQUENCE: 324

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser Gly Thr Gly Gly Ser Gly Gly
        115                 120                 125

Thr Gly Ser Gly Thr Gly Gly Ser Thr Ser Tyr Val Leu Thr Gln Pro
    130                 135                 140

Pro Ser Val Ser Gly Thr Pro Gly Gln Arg Val Thr Ile Ser Cys Ser
145                 150                 155                 160

Gly Ser Arg Ser Asn Val Gly Asp Asn Ser Val Tyr Trp Tyr Gln His
                165                 170                 175

Val Pro Glu Met Ala Pro Lys Leu Leu Val Tyr Lys Asn Thr Gln Arg
            180                 185                 190

Pro Ser Gly Val Pro Ala Arg Phe Ser Gly Ser Lys Ser Gly Thr Ser
        195                 200                 205

Ala Ser Leu Ala Ile Ile Gly Leu Gln Ser Gly Asp Glu Ala Asp Tyr
    210                 215                 220

Tyr Cys Val Ala Trp Asp Asp Ser Val Asp Gly Tyr Val Phe Gly Ser
225                 230                 235                 240

Gly Thr Lys Val Thr Val Leu Gly
                245

<210> SEQ ID NO 325
<211> LENGTH: 121

```
<212> TYPE: PRT
<213> ORGANISM: Homo sapiens

<400> SEQUENCE: 325

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120

<210> SEQ ID NO 326
<211> LENGTH: 111
<212> TYPE: PRT
<213> ORGANISM: Homo sapiens

<400> SEQUENCE: 326

Ser Val Leu Thr Gln Pro Pro Ser Val Ser Ala Ala Pro Gly Gln Lys
1               5                   10                  15

Val Thr Ile Ser Cys Ser Gly Ser Ser Asn Ile Gly Asn Asp Tyr
            20                  25                  30

Val Ser Trp Tyr Gln Gln Leu Pro Gly Thr Ala Pro Lys Leu Leu Ile
        35                  40                  45

Tyr Asp Asn Asn Lys Arg Pro Ser Gly Ile Pro Asp Arg Phe Ser Gly
    50                  55                  60

Ser Lys Ser Gly Thr Ser Ala Thr Leu Gly Ile Thr Gly Leu Gln Thr
65                  70                  75                  80

Gly Asp Glu Ala Asn Tyr Tyr Cys Ala Thr Trp Asp Arg Arg Pro Thr
                85                  90                  95

Ala Tyr Val Val Phe Gly Gly Gly Thr Lys Leu Thr Val Leu Gly
            100                 105                 110

<210> SEQ ID NO 327
<211> LENGTH: 747
<212> TYPE: DNA
<213> ORGANISM: Homo sapiens

<400> SEQUENCE: 327
gaggtgcagc tggtggagtc tggggctgag gtgaagaagc ctgggtcctc ggtgaaagtc       60
tcttgcaagg cttctggagg ccccttccgc agctatgcta tcagctgggt gcgacaggcc      120
cctggacaag ggcctgagtg gatgggaggg atcatcccta tttttggtac aacaaaatac      180
gcaccgaagt tccagggcag agtcacgatt accgcggacg atttcgcggg cacagtttac      240
atggagctga gcagcctgcg atctgaggac acggccatgt actactgtgc gaaacatatg      300
gggtaccagt gcgcgaaac tatggacgtc tggggcaaag ggaccacggt caccgtctcg      360
agcggtacgg gcggttcagg cggaaccggc agcggcactg gcgggtcgac gcagtctgtg      420
```

```
ttgacgcagc cgccctcagt gtctgcggcc ccaggacaga aggtcaccat ctcctgctct    480
ggaagcagct ccaacattgg gaatgattat gtatcctggt accagcagct cccaggaaca    540 gccccaaac  tcctcattta tgacaataat aagcgaccct cagggattcc tgaccgattc    600
tctggctcca gtctggcac  gtcagccacc ctgggcatca ccggactcca gactggggac    660
gaggccaact attactgcgc aacatgggat cgccgcccga ctgcttatgt tgtcttcggc    720
ggagggacca agctgaccgt cctaggt                                        747
```

<210> SEQ ID NO 328
<211> LENGTH: 249
<212> TYPE: PRT
<213> ORGANISM: Homo sapiens

<400> SEQUENCE: 328

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser Gly Thr Gly Gly Ser Gly Gly
        115                 120                 125

Thr Gly Ser Gly Thr Gly Gly Ser Thr Gln Ser Val Leu Thr Gln Pro
    130                 135                 140

Pro Ser Val Ser Ala Ala Pro Gly Gln Lys Val Thr Ile Ser Cys Ser
145                 150                 155                 160

Gly Ser Ser Ser Asn Ile Gly Asn Asp Tyr Val Ser Trp Tyr Gln Gln
                165                 170                 175

Leu Pro Gly Thr Ala Pro Lys Leu Leu Ile Tyr Asp Asn Asn Lys Arg
            180                 185                 190

Pro Ser Gly Ile Pro Asp Arg Phe Ser Gly Ser Lys Ser Gly Thr Ser
        195                 200                 205

Ala Thr Leu Gly Ile Thr Gly Leu Gln Thr Gly Asp Glu Ala Asn Tyr
    210                 215                 220

Tyr Cys Ala Thr Trp Asp Arg Arg Pro Thr Ala Tyr Val Val Phe Gly
225                 230                 235                 240

Gly Gly Thr Lys Leu Thr Val Leu Gly
                245
```

<210> SEQ ID NO 329
<211> LENGTH: 120
<212> TYPE: PRT
<213> ORGANISM: Homo sapiens

<400> SEQUENCE: 329

```
Gln Val Gln Leu Gln Gln Ser Gly Ala Glu Val Lys Lys Pro Gly Ser
1               5                   10                  15
```

Ser Val Lys Val Ser Cys Lys Val Ser Gly Val Ile Phe Ser Gly Ser
            20                  25                  30

Ala Ile Ser Trp Val Arg Gln Ala Pro Gly Gln Gly Leu Glu Trp Met
         35                  40                  45

Gly Gly Ile Ser Pro Leu Phe Gly Thr Thr Asn Tyr Ala Gln Lys Phe
 50                  55                  60

Gln Gly Arg Val Thr Ile Thr Ala Asp Gln Ser Thr Asn Thr Tyr
65                  70                  75                  80

Met Glu Val Asn Ser Leu Arg Tyr Glu Asp Thr Ala Val Tyr Phe Cys
                 85                  90                  95

Ala Arg Gly Pro Lys Tyr Tyr Ser Glu Tyr Met Asp Val Trp Gly Lys
            100                 105                 110

Gly Thr Thr Val Thr Val Ser Ser
            115                 120

<210> SEQ ID NO 330
<211> LENGTH: 109
<212> TYPE: PRT
<213> ORGANISM: Homo sapiens

<400> SEQUENCE: 330

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Val Pro Thr Leu Leu Ile
         35                  40                  45

Tyr Asp Ala Ser Thr Leu Arg Ser Gly Val Pro Ser Arg Phe Ser Gly
 50                  55                  60

Ser Gly Ser Ala Thr Asp Phe Thr Leu Thr Ile Ser Ser Leu Gln Pro
65                  70                  75                  80

Glu Asp Val Ala Thr Tyr Tyr Cys Gln Arg Tyr Asn Ser Ala Pro Pro
                 85                  90                  95

Ile Thr Phe Gly Gln Gly Thr Arg Leu Glu Ile Lys Arg
            100                 105

<210> SEQ ID NO 331
<211> LENGTH: 735
<212> TYPE: DNA
<213> ORGANISM: Homo sapiens

<400> SEQUENCE: 331
caggtacagc tgcagcagtc aggggctgag gtgaagaagc ctgggtcctc ggtgaaggtc      60
tcctgcaagg tttccggagt cattttcagc ggcagtgcga tcagctgggt gcgacaggcc     120
cctggacaag gccttgagtg gatgggaggg atcagccctc tctttggcac aacaaattac     180
gcacaaaagt tccagggcag agtcacgatt accgcggacc aatccacgaa cacaacctac     240
atggaggtga acagcctgag atatgaggac acggccgtgt atttctgtgc gcgaggtcca     300
aaatattaca gtgagtacat ggacgtctgg ggcaaaggga ccacggtcac cgtctcgagc     360
ggtacgggcg gttcaggcgg aaccggcagc ggcactggcg gtcgacgga catccagatg     420
acccagtctc catcctccct gtctgcatct gtaggagaca gagtcaccat cacttgccgg     480
gcgagtcagg gcattagcag ttatttagcc tggtatcagc agaagccagg gaaagttcct     540
acactcctga tctatgatgc atccactttg cgatcagggg tcccatctcg cttcagtggc     600

```
agtggatctg cgacagattt cactctcacc atcagcagcc tgcagcctga agatgttgca    660
acttattact gtcaaaggta taacagtgcc cccccgatca ccttcggcca agggacacga    720
ctggagatta aacgt                                                    735
```

```
<210> SEQ ID NO 332
<211> LENGTH: 245
<212> TYPE: PRT
<213> ORGANISM: Homo sapiens

<400> SEQUENCE: 332
```

Gln Val Gln Leu Gln Gln Ser Gly Ala Glu Val Lys Lys Pro Gly Ser
1               5                   10                  15

Ser Val Lys Val Ser Cys Lys Val Ser Gly Val Ile Phe Ser Gly Ser
            20                  25                  30

Ala Ile Ser Trp Val Arg Gln Ala Pro Gly Gln Gly Leu Glu Trp Met
        35                  40                  45

Gly Gly Ile Ser Pro Leu Phe Gly Thr Thr Asn Tyr Ala Gln Lys Phe
    50                  55                  60

Gln Gly Arg Val Thr Ile Thr Ala Asp Gln Ser Thr Asn Thr Thr Tyr
65                  70                  75                  80

Met Glu Val Asn Ser Leu Arg Tyr Glu Asp Thr Ala Val Tyr Phe Cys
                85                  90                  95

Ala Arg Gly Pro Lys Tyr Tyr Ser Glu Tyr Met Asp Val Trp Gly Lys
            100                 105                 110

Gly Thr Thr Val Thr Val Ser Ser Gly Thr Gly Gly Ser Gly Gly Thr
        115                 120                 125

Gly Ser Gly Thr Gly Gly Ser Thr Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Gly Ile Ser Ser Tyr Leu Ala Trp Tyr Gln Gln Lys Pro
                165                 170                 175

Gly Lys Val Pro Thr Leu Leu Ile Tyr Asp Ala Ser Thr Leu Arg Ser
            180                 185                 190

Gly Val Pro Ser Arg Phe Ser Gly Ser Gly Ser Ala Thr Asp Phe Thr
        195                 200                 205

Leu Thr Ile Ser Ser Leu Gln Pro Glu Asp Val Ala Thr Tyr Tyr Cys
    210                 215                 220

Gln Arg Tyr Asn Ser Ala Pro Pro Ile Thr Phe Gly Gln Gly Thr Arg
225                 230                 235                 240

Leu Glu Ile Lys Arg
                245

```
<210> SEQ ID NO 333
<211> LENGTH: 120
<212> TYPE: PRT
<213> ORGANISM: Homo sapiens

<400> SEQUENCE: 333
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Met Gly Met Phe Gly Thr Thr Asn Tyr Ala Gln Lys Phe
 50                  55                  60

Gln Gly Arg Val Thr Ile Thr Ala Asp Glu Phe Thr Ser Ala Ala Tyr
 65                  70                  75                  80

Met Glu Leu Arg Ser Leu Arg Ser Glu Asp Thr Ala Val Tyr Tyr Cys
                 85                  90                  95

Ala Arg Ser Ser Gly Tyr Tyr Pro Glu Tyr Phe Gln Asp Trp Gly Gln
            100                 105                 110

Gly Thr Leu Val Thr Val Ser Ser
        115                 120

<210> SEQ ID NO 334
<211> LENGTH: 107
<212> TYPE: PRT
<213> ORGANISM: Homo sapiens

<400> SEQUENCE: 334

Gln Ser Val Leu Thr Gln Pro Pro Ser Glu Val Ser Pro Gly Gln
 1               5                  10                  15

Thr Ala Ser Val Thr Cys Ser Gly His Lys Leu Gly Asp Lys Tyr Val
                 20                  25                  30

Ser Trp Tyr Gln Gln Lys Pro Gly Gln Ser Pro Val Leu Leu Ile Tyr
             35                  40                  45

Gln Asp Asn Arg Arg Pro Ser Gly Ile Pro Glu Arg Phe Ile Gly Ser
 50                  55                  60

Asn Ser Gly Asn Thr Ala Thr Leu Thr Ile Ser Gly Thr Gln Ala Leu
 65                  70                  75                  80

Asp Glu Ala Asp Tyr Tyr Cys Gln Ala Trp Asp Ser Ser Thr Ala Val
                 85                  90                  95

Phe Gly Gly Gly Thr Lys Leu Thr Val Leu Gly
            100                 105

<210> SEQ ID NO 335
<211> LENGTH: 729
<212> TYPE: DNA
<213> ORGANISM: Homo sapiens

<400> SEQUENCE: 335
caggtccagc tggtacagtc tggggctgag gtgaagaagc ctgggtcctc ggtgaaggtc    60
tcctgcaagg cttctggagg caccttcagt agttatgcta tcagctgggt gcgacaggcc   120
cctggacaag gccttgagtg gatgggagga atcatgggta tgtttggcac aactaactac   180
gcacagaagt tccagggcag agtcacgatt accgcggacg aattcacgag cgcagcctac   240
atggagctga ggagcctgag atctgaggac acggccgtct actactgtgc gaggtctagt   300
ggttattacc ccgaatactt ccaggactgg ggccagggca ccctggtcac cgtctcgagc   360
ggtacgggcg gttcaggcgg aaccggcagc ggcactggcg gtcgacgca gtctgtgctg   420 actcagccac cctcagagtc cgtgtcccca ggacagacag ccagcgtcac ctgctctgga   480
cataaattgg gggataaata tgtttcgtgg tatcagcaga agccaggcca gtcccctgta   540
ttactcatct atcaagataa caggcggccc tcagggatcc ctgagcgatt cataggctcc   600
aactctggga acacagccac tctgaccatc agcgggaccc aggctctga tgaggctgac   660 tattactgtc aggcgtggga cagcagcact gcggttttcg gcggagggac caagctgacc   720
gtcctaggt                                                           729

<210> SEQ ID NO 336
<211> LENGTH: 243
<212> TYPE: PRT
<213> ORGANISM: Homo sapiens

<400> SEQUENCE: 336

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Met Gly Met Phe Gly Thr Thr Asn Tyr Ala Gln Lys Phe
    50                  55                  60

Gln Gly Arg Val Thr Ile Thr Ala Asp Glu Phe Thr Ser Ala Ala Tyr
65                  70                  75                  80

Met Glu Leu Arg Ser Leu Arg Ser Glu Asp Thr Ala Val Tyr Tyr Cys
                85                  90                  95

Ala Arg Ser Ser Gly Tyr Tyr Pro Glu Tyr Phe Gln Asp Trp Gly Gln
            100                 105                 110

Gly Thr Leu Val Thr Val Ser Gly Thr Gly Ser Gly Gly Thr
        115                 120                 125

Gly Ser Gly Thr Gly Ser Thr Gln Ser Val Leu Thr Gln Pro Pro
    130                 135                 140

Ser Glu Ser Val Ser Pro Gly Gln Thr Ala Ser Val Thr Cys Ser Gly
145                 150                 155                 160

His Lys Leu Gly Asp Lys Tyr Val Ser Trp Tyr Gln Gln Lys Pro Gly
                165                 170                 175

Gln Ser Pro Val Leu Leu Ile Tyr Gln Asp Asn Arg Arg Pro Ser Gly
            180                 185                 190

Ile Pro Glu Arg Phe Ile Gly Ser Asn Ser Gly Asn Thr Ala Thr Leu
        195                 200                 205

Thr Ile Ser Gly Thr Gln Ala Leu Asp Glu Ala Asp Tyr Tyr Cys Gln
    210                 215                 220

Ala Trp Asp Ser Ser Thr Ala Val Phe Gly Gly Gly Thr Lys Leu Thr
225                 230                 235                 240

Val Leu Gly
```

<210> SEQ ID NO 337
<211> LENGTH: 120
<212> TYPE: PRT
<213> ORGANISM: Homo sapiens

<400> SEQUENCE: 337

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Thr Trp Val Arg Gln Ala Pro Gly Gln Gly Leu Glu Trp Met
        35                  40                  45

Gly Gly Ile Ile Gly Met Phe Gly Ser Thr Asn Tyr Ala Gln Asn Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Ser Thr Gly Tyr Tyr Pro Ala Tyr Leu His His Trp Gly Gln
            100                 105                 110

Gly Thr Leu Val Thr Val Ser Ser
        115                 120

<210> SEQ ID NO 338
<211> LENGTH: 111
<212> TYPE: PRT
<213> ORGANISM: Homo sapiens

<400> SEQUENCE: 338

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr His Val Phe Gly Thr Gly Thr Lys Val Thr Val Leu Gly
            100                 105                 110

<210> SEQ ID NO 339
<211> LENGTH: 741
<212> TYPE: DNA
<213> ORGANISM: Homo sapiens

<400> SEQUENCE: 339
cagatgcagc tggtgcagtc tggggctgag gtgaagaagc ctgggtcctc ggtgaaggtc      60
tcctgcaagg cttctggagg caccttctcc agttatgcta tcacctgggt gcgacaggcc    120
cctggacaag gcttgagtg gatgggaggg atcatcggta tgtttggttc aacaaactac     180
gcacagaact tccagggcag agtcacgatt accgcggacg aatccacgag cacagcctac    240
atggagctga gcagcctcag atctgaggac acggccgtgt attactgtgc gagaagtact    300
ggttattacc ctgcataacct ccaccactgg ggccagggca cctggtcac cgtctcgagc    360 ggtacgggcg gttcaggcgg aaccggcagc ggcactggcg gtcgacgca gtctgccctg    420 actcagcctc gctcagtgtc cgggtctcct ggacagtcag tcaccatctc ctgcactgga    480
accagcagtg atgttggtgg ttataactat gtctcctggt accaacagca cccaggcaaa    540
gcccccaaac tcatgattta tgatgtcagt aagcggccct caggggtccc tgatcgcttc    600
tctggctcca agtctggcaa cacggcctcc ctgaccatct ctgggctcca ggctgaggat    660
gaggctgatt attactgcag ctcatatca agcagcagca ctcatgtctt cggaactggg    720
accaaggtca ccgtcctagg t                                              741

<210> SEQ ID NO 340
<211> LENGTH: 246
<212> TYPE: PRT
<213> ORGANISM: Homo sapiens

<400> SEQUENCE: 340

Gln Met Gln Leu Val Gln Ser Gly Ala Glu Val Lys Lys Pro Gly Ser
```

-continued

```
  1               5                  10                 15
Ser Val Lys Val Ser Cys Lys Ala Ser Gly Gly Thr Phe Ser Ser Tyr
                20                  25                 30

Ala Ile Thr Trp Val Arg Gln Ala Pro Gly Gln Gly Leu Glu Trp Met
            35                  40                  45

Gly Gly Ile Ile Gly Met Phe Gly Ser Thr Tyr Ala Gln Asn Phe Gln
        50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ser Thr Gly Tyr Tyr Pro Ala Tyr Leu His His Trp Gly Gln Gly
                100                 105                110

Thr Leu Val Thr Val Ser Ser Gly Thr Gly Gly Ser Gly Gly Thr Gly
            115                 120                 125

Ser Gly Thr Gly Gly Ser Thr Gln Ser Ala Leu Thr Gln Pro Arg Ser
        130                 135                 140

Val Ser Gly Ser Pro Gly Gln Ser Val Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Leu Met Ile Tyr Asp Val Ser Lys Arg Pro
                180                 185                 190

Ser Gly Val Pro Asp Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
        210                 215                 220

Cys Ser Ser Tyr Thr Ser Ser Ser Thr His Val Phe Gly Thr Gly Thr
225                 230                 235                 240

Lys Val Thr Val Leu Gly
                245

<210> SEQ ID NO 341
<211> LENGTH: 121
<212> TYPE: PRT
<213> ORGANISM: Homo sapiens

<400> SEQUENCE: 341

Glu Val Gln Leu Val Glu Thr Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Lys Trp Gly Pro Gln Ala Ala Phe Asp Ile Trp Gly
                100                 105                 110

Gln Gly Thr Met Val Thr Val Ser Ser
            115                 120
```

<210> SEQ ID NO 342
<211> LENGTH: 109
<212> TYPE: PRT
<213> ORGANISM: Homo sapiens

<400> SEQUENCE: 342

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Asp Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Trp Thr Phe Gly Gln Gly Thr Lys Val Glu Ile Lys Arg
            100                 105

<210> SEQ ID NO 343
<211> LENGTH: 738
<212> TYPE: DNA
<213> ORGANISM: Homo sapiens

<400> SEQUENCE: 343
gaggtgcagc tggtggagac cggggctgag gtgaagaagc ctggggcctc agtgaaggtt    60
tcctgcaagg catctggata caccttcacc agctactata tgcactgggt gcgacaggcc   120
cctggacaag gcttgagtg gatgggatgg atcaaccctc acagtggtgg cacaaactat   180
gcacagaagt tcagggcag ggtcaccatg accagggaca cgtccatcag cacagcctac   240
atggagctga gcaggctgag atctgacgac acggccgtgt attactgtgc gagagagggg   300
aaatggggac tcaagcggc ttttgatatc tggggccaag gacaatggt caccgtctcg   360 agcggtacgg gcggttcagg cggaaccggc agtggcagtg gcgggtcgac ggaaattgtg   420
atgacgcagt ctccaggcac cctgtctttg tctccagggg aaagagccac cctctcctgc   480
agggccagtc agagtgttag cagcagctac ttagcctggt accagcagaa acctggccag   540
gctcccaggc tcctcatcta tgatgcatcc agcagggcca ctgacatccc agacaggttc   600
agtggcagtg gtctgggac agacttcact ctcaccatca gcagactgga gcctgaagat   660
tttgcagtgt attactgtca gcagtatggt agctcacttt ggacgttcgg ccaagggacc   720
aaggtggaga tcaaacgt                                                  738

<210> SEQ ID NO 344
<211> LENGTH: 246
<212> TYPE: PRT
<213> ORGANISM: Homo sapiens

<400> SEQUENCE: 344

Glu Val Gln Leu Val Glu Thr Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

```
Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Gly Lys Trp Gly Pro Gln Ala Ala Phe Asp Ile Trp Gly
            100                 105                 110

Gln Gly Thr Met Val Thr Val Ser Ser Gly Thr Gly Gly Ser Gly Gly
        115                 120                 125

Thr Gly Ser Gly Thr Gly Gly Ser Thr Glu Ile Val Met Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Ser Tyr Leu Ala Trp Tyr Gln Gln
                165                 170                 175

Lys Pro Gly Gln Ala Pro Arg Leu Leu Ile Tyr Asp Ala Ser Ser Arg
            180                 185                 190

Ala Thr Asp Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Tyr Gly Ser Ser Leu Trp Thr Phe Gly Gln Gly Thr
225                 230                 235                 240

Lys Val Glu Ile Lys Arg
                245

<210> SEQ ID NO 345
<211> LENGTH: 117
<212> TYPE: PRT
<213> ORGANISM: Homo sapiens

<400> SEQUENCE: 345

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
             20                  25                  30

Ala Met Ser Trp Val Arg Gln Ala Pro Gly Lys Gly Leu Glu Trp Val
         35                  40                  45

Ser Ala Ile Ser Ser Ser Gly Asp Ser Thr Tyr Tyr Ala Asp Ser Val
 50                  55                  60

Lys Gly Arg Phe Thr Ile Ser Arg Asp Asn Ala Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Tyr Gly Tyr Thr Phe Asp Pro Trp Gly Gln Gly Thr Leu
            100                 105                 110

Val Thr Val Ser Ser
        115

<210> SEQ ID NO 346
<211> LENGTH: 113
<212> TYPE: PRT
<213> ORGANISM: Homo sapiens

<400> SEQUENCE: 346
```

```
Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg
```

<210> SEQ ID NO 347
<211> LENGTH: 738
<212> TYPE: DNA
<213> ORGANISM: Homo sapiens

<400> SEQUENCE: 347

```
gaggtgcagc tggtagagtc tgggggaggc ttggtacagc ctgggggtc  cctgagactc      60
tcctgtgcag cctctggatt cacctttagc atctatgcca tgagctgggt ccgccaggca     120
ccagggaagg gctggagtg  gtctcagct  attagtagta gtggtgatag cacatactac     180
gcagactccg tgaagggccg gttcaccatc tccagagaca acgccaggaa cacgctgtat     240
ctgcaaatga acagtctgag agccgaggac acggctgtgt attactgtgc gagagcgtat     300
ggctacacgt tcgacccctg ggccaggga  accctggtca ccgtctcgag cggtacgggc     360
ggttcaggcg gaaccggcag cggcactggc ggtcgacgg  aaattgtgct gactcagtct     420
ccactctccc tgcccgtcac ccctggagag ccggcctcca tctcctgcag gtctagtcag     480
agcctcctgc atagtaatgg atacaactat ttggattggt acctgcagaa gccagggcag     540
tctccacagc tcctgatcta tttgggttct aatcgggcct ccggggtccc tgacaggttc     600
agtggcagtg gatcaggcac agattttaca ctgaaaatca gcagagtgga ggctgaggat     660
gttggggttt attactgcat gcaagctcta caaactcccc tcactttcgg cggagggacc     720
aaggtggaga tcaaacgt                                                   738
```

<210> SEQ ID NO 348
<211> LENGTH: 246
<212> TYPE: PRT
<213> ORGANISM: Homo sapiens

<400> SEQUENCE: 348

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Asp Ser Thr Tyr Tyr Ala Asp Ser Val
    50                  55                  60

Lys Gly Arg Phe Thr Ile Ser Arg Asp Asn Ala Arg Asn Thr Leu Tyr
```

```
            65                  70                  75                  80
Leu Gln Met Asn Ser Leu Arg Ala Glu Asp Thr Ala Val Tyr Tyr Cys
                85                  90                  95

Ala Arg Ala Tyr Gly Tyr Thr Phe Asp Pro Trp Gly Gln Gly Thr Leu
            100                 105                 110

Val Thr Val Ser Ser Gly Thr Gly Gly Ser Gly Gly Thr Gly Ser Gly
        115                 120                 125

Thr Gly Gly Ser Thr Glu Ile Val Leu Thr Gln Ser Pro Leu Ser Leu
    130                 135                 140

Pro Val Thr Pro Gly Glu Pro Ala Ser Ile Ser Cys Arg Ser Ser Gln
145                 150                 155                 160

Ser Leu Leu His Ser Asn Gly Tyr Asn Tyr Leu Asp Trp Tyr Leu Gln
                165                 170                 175

Lys Pro Gly Gln Ser Pro Gln Leu Leu Ile Tyr Leu Gly Ser Asn Arg
            180                 185                 190

Ala Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Met Gln Ala Leu Gln Thr Pro Leu Thr Phe Gly Gly Gly Thr
225                 230                 235                 240

Lys Val Glu Ile Lys Arg
                245

<210> SEQ ID NO 349
<211> LENGTH: 122
<212> TYPE: PRT
<213> ORGANISM: Homo sapiens

<400> SEQUENCE: 349

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ser Tyr Gly Ala Tyr Glu Gly Phe Asp Tyr Trp
            100                 105                 110

Gly Gln Gly Thr Leu Val Thr Val Ser Ser
        115                 120

<210> SEQ ID NO 350
<211> LENGTH: 108
<212> TYPE: PRT
<213> ORGANISM: Homo sapiens

<400> SEQUENCE: 350

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Tyr
```

```
            20                  25                  30
Leu Ala Trp Tyr Gln Gln Lys Pro Gly Gln Ala Pro Arg Leu Leu Ile
         35                  40                  45

Tyr Gly Ala Ser Thr Arg Ala Ala Gly Ile Pro Asp Arg Phe Ser Gly
     50                  55                  60

Ser Gly Ser Gly Thr Asp Phe Thr Leu Thr Ile Ser Arg Leu Glu Pro
65                  70                  75                  80

Glu Asp Ser Ala Val Tyr Tyr Cys Gln Gln Tyr Gly Arg Thr Pro Leu
                 85                  90                  95

Thr Phe Gly Gly Gly Thr Lys Val Glu Ile Lys Arg
            100                 105
```

<210> SEQ ID NO 351
<211> LENGTH: 738
<212> TYPE: DNA
<213> ORGANISM: Homo sapiens

<400> SEQUENCE: 351

```
caggtccagc tggtgcagtc tgggggaggc ctggtcaagc ctgggggtc cctgagactc    60
tcctgtgcag cctctggatt caccttcagt agctatagca tgaactgggt ccgccaggct   120
ccagggaagg gctggagtg gtctcatcc attagtagta gtagtagtta catatactac    180
gtagactcag tgaagggccg attcaccatc tccagagaca acgccaagaa ctcactgtat   240
ctgcaaatga acagcctgag agccgaggac acggctgtgt attactgtgc gagaggtggt   300
gggagctacg gggcctacga aggctttgac tactgggggcc agggcaccct ggtcaccgtc   360
tcgagcggta cgggcggttc aggcggaacc ggcagcggca ctggcgggtc gacggaaatt   420
gtgctgactc agtctccagg caccctgtct ttgtctccag gggaaagagc caccctctcc   480
tgcagggcca gtcagcgtgt tagcagctac ttagcctggt accaacagaa acctggccag   540
gctcccaggc tcctcatcta tggtgcatcc accagggccg ctggcatccc agacaggttc   600
agtggcagtg ggtctgggac agacttcact ctcaccatca gcagactgga gcctgaagat   660
tctgcagtgt attactgtca gcagtatggt aggacaccgc tcactttcgg cggagggacc   720
aaggtggaga tcaaacgt                                                738
```

<210> SEQ ID NO 352
<211> LENGTH: 246
<212> TYPE: PRT
<213> ORGANISM: Homo sapiens

<400> SEQUENCE: 352

```
Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
         35                  40                  45

Ser Ser Ile Ser Ser Ser Ser Ser Tyr Ile Tyr Tyr Val Asp Ser Val
     50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                 85                  90                  95

Ala Arg Gly Gly Gly Ser Tyr Gly Ala Tyr Glu Gly Phe Asp Tyr Trp
            100                 105                 110
```

```
Gly Gln Gly Thr Leu Val Thr Val Ser Ser Gly Thr Gly Gly Ser Gly
            115                 120                 125
Gly Thr Gly Ser Gly Thr Gly Gly Ser Thr Glu Ile Val Leu Thr Gln
        130                 135                 140
Ser Pro Gly Thr Leu Ser Leu Ser Pro Gly Glu Arg Ala Thr Leu Ser
145                 150                 155                 160
Cys Arg Ala Ser Gln Arg Val Ser Ser Tyr Leu Ala Trp Tyr Gln Gln
                165                 170                 175
Lys Pro Gly Gln Ala Pro Arg Leu Leu Ile Tyr Gly Ala Ser Thr Arg
            180                 185                 190
Ala Ala Gly Ile Pro Asp Arg Phe Ser Gly Ser Gly Ser Gly Thr Asp
        195                 200                 205
Phe Thr Leu Thr Ile Ser Arg Leu Glu Pro Glu Asp Ser Ala Val Tyr
210                 215                 220
Tyr Cys Gln Gln Tyr Gly Arg Thr Pro Leu Thr Phe Gly Gly Gly Thr
225                 230                 235                 240
Lys Val Glu Ile Lys Arg
            245
```

<210> SEQ ID NO 353
<211> LENGTH: 121
<212> TYPE: PRT
<213> ORGANISM: Homo sapiens

<400> SEQUENCE: 353

```
Glu Val Gln Leu Val Glu Ser Gly Ala Glu Val Lys Lys Pro Gly Ser
1               5                   10                  15
Ser Val Lys Val Ser Cys Lys Ala Ser Gly Gly Pro Phe Arg Ser Tyr
            20                  25                  30
Ala Ile Ser Trp Val Arg Gln Ala Pro Gly Gln Gly Pro Glu Trp Met
        35                  40                  45
Gly Gly Ile Ile Pro Ile Phe Gly Thr Thr Lys Tyr Ala Pro Lys Phe
    50                  55                  60
Gln Gly Arg Val Thr Ile Thr Ala Asp Asp Phe Ala Gly Thr Val Tyr
65                  70                  75                  80
Met Glu Leu Ser Ser Leu Arg Ser Glu Asp Thr Ala Met Tyr Tyr Cys
                85                  90                  95
Ala Lys His Met Gly Tyr Gln Val Arg Glu Thr Met Asp Val Trp Gly
            100                 105                 110
Lys Gly Thr Thr Val Thr Val Ser Ser
        115                 120
```

<210> SEQ ID NO 354
<211> LENGTH: 109
<212> TYPE: PRT
<213> ORGANISM: Homo sapiens

<400> SEQUENCE: 354

```
Ser Tyr Val Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Val Tyr
        35                  40                  45
Asp Asp Ser Asp Arg Pro Ser Gly Ile Pro Glu Arg Phe Ser Gly Ser
    50                  55                  60
```

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Ala Val Phe Gly Gly Gly Thr Gln Leu Thr Val Leu Gly
            100                 105

<210> SEQ ID NO 355
<211> LENGTH: 738
<212> TYPE: DNA
<213> ORGANISM: Homo sapiens

<400> SEQUENCE: 355
gaggtgcagc tggtggagtc tggggctgag gtgaagaagc ctgggtcctc ggtgaaagtc    60
tcttgcaagg cttctggagg ccccttccgc agctatgcta tcagctgggt gcgacaggcc   120
cctggacaag gcctgagtg gatgggaggg atcatcccta tttttggtac aacaaaatac   180
gcaccgaagt tccagagcag agtcacgatt accacgacg atttcgcggg cacagtttac   240
atggagctga gcagcctgcg atctgaggac acggccatgt actactgtgc gaaacatatg   300
gggtaccagg tgcgcgaaac tatggacgtc tggggcaaag gaccacggt caccgtctcg   360 agcggtacgg gcggttcagg cggaaccggc agcggcactg gcgggtcgac gtcctatgtg   420
ctgactcagc caccctcggt gtcagtggcc caggacaga cggccaggat tacctgtggg   480
ggaaacaaca ttggaagtaa aagtgtgcac tggtaccagc agaagccagg ccaggcccct   540
gtgctggtcg tctatgatga tagcgaccgg ccctcaggga tccctgagcg attctctggc   600
tccaactctg ggaacacggc caccctgacc atcagcaggg tcgaagccgg ggatgaggcc   660
gactattact gtcaggtgtg ggatagtagt agtgatcatg ctgtgttcgg aggaggcacc   720
cagctgaccg tcctcggt                                                 738

<210> SEQ ID NO 356
<211> LENGTH: 246
<212> TYPE: PRT
<213> ORGANISM: Homo sapiens

<400> SEQUENCE: 356

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser Gly Thr Gly Gly Ser Gly Gly
        115                 120                 125

Thr Gly Ser Gly Thr Gly Gly Ser Thr Ser Tyr Val Leu Thr Gln Pro
    130                 135                 140

```
Pro Ser Val Ser Val Ala Pro Gly Gln Thr Ala Arg Ile Thr Cys Gly
145                 150                 155                 160

Gly Asn Asn Ile Gly Ser Lys Ser Val His Trp Tyr Gln Gln Lys Pro
                165                 170                 175

Gly Gln Ala Pro Val Leu Val Val Tyr Asp Asp Ser Asp Arg Pro Ser
            180                 185                 190

Gly Ile Pro Glu Arg Phe Ser Gly Ser Asn Ser Gly Asn Thr Ala Thr
        195                 200                 205

Leu Thr Ile Ser Arg Val Glu Ala Gly Asp Glu Ala Asp Tyr Tyr Cys
    210                 215                 220

Gln Val Trp Asp Ser Ser Ser Asp His Ala Val Phe Gly Gly Gly Thr
225                 230                 235                 240

Gln Leu Thr Val Leu Gly
                245

<210> SEQ ID NO 357
<211> LENGTH: 121
<212> TYPE: PRT
<213> ORGANISM: Homo sapiens

<400> SEQUENCE: 357

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
                20                  25                  30

Ala Ile Ser Trp Val Arg Gln Ala Pro Gly Gln Gly Pro Glu Trp Met
            35                  40                  45

Gly Gly Ile Ile Pro Ile Phe Gly Thr Thr Lys Tyr Ala Pro Lys Phe
        50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
                100                 105                 110

Lys Gly Thr Thr Val Thr Val Ser Ser
            115                 120

<210> SEQ ID NO 358
<211> LENGTH: 111
<212> TYPE: PRT
<213> ORGANISM: Homo sapiens

<400> SEQUENCE: 358

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Asp Gly Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Asp Asp Glu Ala Asp Tyr Tyr Cys Ala Thr Trp Asp Asp Asn Leu
                85                  90                  95
```

Ser Gly Pro Val Phe Gly Gly Gly Thr Lys Leu Thr Val Leu Gly
            100                 105                 110

<210> SEQ ID NO 359
<211> LENGTH: 744
<212> TYPE: DNA
<213> ORGANISM: Homo sapiens

<400> SEQUENCE: 359
gaggtgcagc tggtggagtc tggggctgag gtgaagaagc ctgggtcctc ggtgaaagtc      60
tcttgcaagg cttctggagg ccccttccgc agctatgcta tcagctgggt gcgacaggcc     120
cctggacaag gcctgagtg gatgggaggg atcatcccta ttttggtac aacaaaatac       180 gcaccgaagt tccagggcag agtcacgatt accgcggacg atttcgcggg cacagtttac     240
atggagctga gcagcctgcg atctgaggac acggccatgt actactgtgc gaaacatatg     300
gggtaccagg tgcgcgaaac tatggacgtc tggggcaaag ggaccacggt caccgtctcg     360
agcggtacgg gcggttcagg cggaaccggc agcggcactg gcgggtcgac gtcctatgtg     420
ctgactcagc caccctcagc gtctgggacc cccgggcaga gggtcaccat ctcttgttct     480
ggaagcagct ccaacatcgg aagtaattat gtatactggt accagcagct cccaggcacg     540 gccccaaac tcctcatcta tagggatggt cagcggccct caggggtccc tgaccgattc     600
tctggctcca gtctggcac ctcagcctcc ctggccatca gtggactccg gtccgatgat     660
gaggctgatt attactgtgc aacatgggat gacaacctga gtggtccagt attcggcgga     720
gggaccaagc tgaccgtcct aggt                                             744

<210> SEQ ID NO 360
<211> LENGTH: 248
<212> TYPE: PRT
<213> ORGANISM: Homo sapiens

<400> SEQUENCE: 360

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser Gly Thr Gly Gly Ser Gly Gly
        115                 120                 125

Thr Gly Ser Gly Thr Gly Gly Ser Thr Ser Tyr Val Leu Thr Gln Pro
    130                 135                 140

Pro Ser Ala Ser Gly Thr Pro Gly Gln Arg Val Thr Ile Ser Cys Ser
145                 150                 155                 160

Gly Ser Ser Ser Asn Ile Gly Ser Asn Tyr Val Tyr Trp Tyr Gln Gln
                165                 170                 175

Leu Pro Gly Thr Ala Pro Lys Leu Leu Ile Tyr Arg Asp Gly Gln Arg

```
                180                 185                 190
Pro Ser Gly Val Pro Asp Arg Phe Ser Gly Lys Ser Gly Thr Ser
        195                 200                 205

Ala Ser Leu Ala Ile Ser Gly Leu Arg Ser Asp Asp Glu Ala Asp Tyr
210                 215                 220

Tyr Cys Ala Thr Trp Asp Asp Asn Leu Ser Gly Pro Val Phe Gly Gly
225                 230                 235                 240

Gly Thr Lys Leu Thr Val Leu Gly
            245

<210> SEQ ID NO 361
<211> LENGTH: 120
<212> TYPE: PRT
<213> ORGANISM: Homo sapiens

<400> SEQUENCE: 361

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Asp Ile Ile Gly Met Phe Gly Ser Thr Asn Tyr Ala Gln Asn Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Gly Tyr Tyr Pro Ala Tyr Leu Pro His Trp Gly Gln
            100                 105                 110

Gly Thr Leu Val Thr Val Ser Ser
        115                 120

<210> SEQ ID NO 362
<211> LENGTH: 109
<212> TYPE: PRT
<213> ORGANISM: Homo sapiens

<400> SEQUENCE: 362

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gly Gly Thr Lys Val Glu Ile Lys Arg
            100                 105

<210> SEQ ID NO 363
<211> LENGTH: 735
<212> TYPE: DNA
```

<213> ORGANISM: Homo sapiens

<400> SEQUENCE: 363

```
gaggtgcagc tggtggagtc tgggctgag gtgaagaagc cagggtcctc ggtgaaggtc      60
tcctgtaagg cctctggagg caccttctcc agctatggta tcagctgggt gcgacaggcc    120
cctggacaag ggcttgagtg gatgggagac atcatcggta tgtttggttc aacaaactac    180
gcacagaact tccagggcag actcacgatt accgcggacg aatccacgag cacagcctac    240
atggagctga gcagcctgag atctgaggac acggccgtgt attactgtgc gagaagtagt    300
ggttattacc ctgcatacct cccccactgg ggccagggca ccttggtcac cgtctcgagc    360
ggtacgggcg gttcaggcgg aaccggcagc ggcactggcg ggtcgacgga aattgtgttg    420
acccagtctc caggcaccct gtctttgtct caggggaaa gagccaccct ctcctgcagg    480
gccagtcaga gtgttagcag cagctactta gcctggtacc agcagaaacc tggccaggct    540
cccaggctcc tcatctatgg tgcatccagc agggccactg gcatcccaga caggttcagt    600
ggcagtgggt ctgggacaga cttcactctc accatcagca gactggagcc tgaagatttt    660
gcagtgtatt actgtcagca gtatggtagc tcacccagaa ctttcggcgg agggaccaag    720
gtggagatca aacgt                                                     735
```

<210> SEQ ID NO 364
<211> LENGTH: 245
<212> TYPE: PRT
<213> ORGANISM: Homo sapiens

<400> SEQUENCE: 364

```
Glu Val Gln Leu Val Glu Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Gly Ile Ser Trp Val Arg Gln Ala Pro Gly Gln Gly Leu Glu Trp Met
        35                  40                  45
Gly Asp Ile Ile Gly Met Phe Gly Ser Thr Asn Tyr Ala Gln Asn Phe
    50                  55                  60
Gln Gly Arg Leu Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Ser Gly Tyr Tyr Pro Ala Tyr Leu Pro His Trp Gly Gln
            100                 105                 110
Gly Thr Leu Val Thr Val Ser Ser Gly Thr Gly Gly Ser Gly Gly Thr
        115                 120                 125
Gly Ser Gly Thr Gly Gly Ser Thr Glu Ile Val Leu Thr Gln Ser Pro
    130                 135                 140
Gly Thr Leu Ser Leu Ser Pro Gly Glu Arg Ala Thr Leu Ser Cys Arg
145                 150                 155                 160
Ala Ser Gln Ser Val Ser Ser Ser Tyr Leu Ala Trp Tyr Gln Gln Lys
                165                 170                 175
Pro Gly Gln Ala Pro Arg Leu Leu Ile Tyr Gly Ala Ser Ser Arg Ala
            180                 185                 190
Thr Gly Ile Pro Asp Arg Phe Ser Gly Ser Gly Ser Gly Thr Asp Phe
        195                 200                 205
Thr Leu Thr Ile Ser Arg Leu Glu Pro Glu Asp Phe Ala Val Tyr Tyr
    210                 215                 220
```

Cys Gln Gln Tyr Gly Ser Ser Pro Arg Thr Phe Gly Gly Gly Thr Lys
225                 230                 235                 240

Val Glu Ile Lys Arg
            245

<210> SEQ ID NO 365
<211> LENGTH: 121
<212> TYPE: PRT
<213> ORGANISM: Homo sapiens

<400> SEQUENCE: 365

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ser Met Ser Trp Val Arg Gln Ala Pro Gly Gln Gly Leu Glu Trp Met
        35                  40                  45

Gly Gly Ile Ile Pro Met Phe Gly Thr Thr Asn Tyr Ala Gln Lys Phe
    50                  55                  60

Gln Gly Arg Val Thr Ile Thr Ala Val Glu Ser Thr Ser Thr Ala Tyr
65                  70                  75                  80

Met Glu Val Ser Ser Leu Arg Ser Glu Asp Thr Ala Val Tyr Tyr Cys
                85                  90                  95

Ala Arg Gly Asp Lys Gly Ile Tyr Tyr Tyr Tyr Met Asp Val Trp Gly
            100                 105                 110

Lys Gly Thr Thr Val Thr Val Ser Ser
        115                 120

<210> SEQ ID NO 366
<211> LENGTH: 111
<212> TYPE: PRT
<213> ORGANISM: Homo sapiens

<400> SEQUENCE: 366

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Thr Gly Thr Lys Val Thr Val Leu Gly
            100                 105                 110

<210> SEQ ID NO 367
<211> LENGTH: 744
<212> TYPE: DNA
<213> ORGANISM: Homo sapiens

<400> SEQUENCE: 367
gaggtgcagc tggtggagtc tgggggctgag gtgaagaagc cggggtcctc ggtgaaggtc    60
tcctgcaagg cttctggagg caccttcagc ttctattcta tgagctgggt gcgacaggcc   120

```
cctggacaag gacttgagtg gatgggaggg atcatcccta tgtttggtac aacaaactac    180
gcacagaagt tccagggcag agtcacgatt accgcggtcg aatccacgag cacagcctac    240
atggaggtga gcagcctgag atctgaggac acggccgttt attactgtgc gagaggtgat    300
aagggtatct actactacta catggacgtc tggggcaaag gaccacggt caccgtctcg    360 agcggtacgg gcggttcagg cggaaccggc agcggcactg gcgggtcgac gcagtctgcc    420
ctgactcagc ctgcctccgt gtctgggtct cctggacagt cgatcaccat ctcctgcact    480
ggaaccagca gtgacgttgg tggttataac tatgtctcct ggtaccaaca gcacccaggc    540
aaagccccca aactcatgat ttatgaggtc agtaatcggc cctcagggt ttctaatcgc    600 ttctctggct ccaagtctgg caacacggcc tccctgacca tctctgggct ccaggctgag    660
gacgaggctg attattactg cagctcatat acaagcagca gcactcttgt cttcggaact    720
gggaccaagg tcaccgtcct aggt                                           744
```

<210> SEQ ID NO 368
<211> LENGTH: 248
<212> TYPE: PRT
<213> ORGANISM: Homo sapiens

<400> SEQUENCE: 368

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ser Met Ser Trp Val Arg Gln Ala Pro Gly Gln Gly Leu Glu Trp Met
        35                  40                  45

Gly Gly Ile Ile Pro Met Phe Gly Thr Thr Asn Tyr Ala Gln Lys Phe
    50                  55                  60

Gln Gly Arg Val Thr Ile Thr Ala Val Glu Ser Thr Ser Thr Ala Tyr
65                  70                  75                  80

Met Glu Val Ser Ser Leu Arg Ser Glu Asp Thr Ala Val Tyr Tyr Cys
                85                  90                  95

Ala Arg Gly Asp Lys Gly Ile Tyr Tyr Tyr Met Asp Val Trp Gly
            100                 105                 110

Lys Gly Thr Thr Val Thr Val Ser Ser Gly Thr Gly Gly Ser Gly Gly
        115                 120                 125

Thr Gly Ser Gly Thr Gly Gly Ser Gln Ser Ala Leu Thr Gln Pro
    130                 135                 140

Ala Ser Val Ser Gly Ser Pro Gly Gln Ser Ile Thr Ile Ser Cys Thr
145                 150                 155                 160

Gly Thr Ser Ser Asp Val Gly Gly Tyr Asn Tyr Val Ser Trp Tyr Gln
                165                 170                 175

Gln His Pro Gly Lys Ala Pro Lys Leu Met Ile Tyr Glu Val Ser Asn
            180                 185                 190

Arg Pro Ser Gly Val Ser Asn Arg Phe Ser Gly Ser Lys Ser Gly Asn
        195                 200                 205

Thr Ala Ser Leu Thr Ile Ser Gly Leu Gln Ala Glu Asp Glu Ala Asp
    210                 215                 220

Tyr Tyr Cys Ser Ser Tyr Thr Ser Ser Ser Thr Leu Val Phe Gly Thr
225                 230                 235                 240

Gly Thr Lys Val Thr Val Leu Gly
                245

<210> SEQ ID NO 369
<211> LENGTH: 121
<212> TYPE: PRT
<213> ORGANISM: Homo sapiens

<400> SEQUENCE: 369

Glu Val Gln Leu Val Glu Thr Gly Ala Glu Val Lys Lys Pro Gly Ser
1               5                   10                  15

Ser Val Lys Val Ser Cys Lys Ala Ser Gly Gly Thr Phe Arg Thr His
            20                  25                  30

Ala Ile Ser Trp Val Arg Gln Ala Pro Gly Gln Gly Leu Glu Trp Met
        35                  40                  45

Gly Gly Ile Ile Ala Ile Phe Gly Thr Ala Asn Tyr Ala Gln Lys Phe
    50                  55                  60

Gln Gly Arg Ile Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Ser Gly Tyr His Ile Ser Thr Pro Phe Asp Asn Trp Gly
            100                 105                 110

Gln Gly Thr Leu Val Thr Val Ser Ser
            115                 120

<210> SEQ ID NO 370
<211> LENGTH: 109
<212> TYPE: PRT
<213> ORGANISM: Homo sapiens

<400> SEQUENCE: 370

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Gly Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly
            100                 105

<210> SEQ ID NO 371
<211> LENGTH: 738
<212> TYPE: DNA
<213> ORGANISM: Homo sapiens

<400> SEQUENCE: 371
gaggtgcagc tggtggagac cggggctgag gtgaagaagc ctgggtcctc ggtgaaggtc      60
tcctgcaagg cctctggagg caccttcagg acccatgcta tcagttgggt gcgacaggcc     120
cctggacaag gcttgagtg gatgggaggg atcatcgcta tcttcggaac agcaaactac     180
gcacagaagt tccagggcag aatcacgatt accgcggacg aatccacgag tacagcctac     240
atggagctga gcagcctgag atctgaggac acggccgtgt atttctgtgc gagaggcagt     300

```
ggttatcata tatcgacacc ctttgacaac tggggccagg gaaccctggt caccgtctcg    360
agcggtacgg gcggttcagg cggaaccggc agcggcactg gcgggtcgac gtcctatgtg    420
ctgactcagc caccctcggt gtcagtggcc ccaggacaga cggccaggat tacctgtggg    480
ggaaacaaca ttggaagtaa aggtgtgcac tggtaccagc agaagcctgg ccaggcccct    540
gtgctggtcg tctatgatga tagcgaccgg ccctcaggga tccctgagcg attctctggc    600
tccaactctg ggaacacggc caccctgacc atcagcaggg tcgaagccgg ggatgaggcc    660
gactattact gtcaggtgtg ggatagtagt agtgatcatg tggtattcgg cggagggacc    720
aagctgaccg tcctaggt                                                 738
```

<210> SEQ ID NO 372
<211> LENGTH: 246
<212> TYPE: PRT
<213> ORGANISM: Homo sapiens

<400> SEQUENCE: 372

Glu Val Gln Leu Val Glu Thr Gly Ala Glu Val Lys Lys Pro Gly Ser
1               5                   10                  15

Ser Val Lys Val Ser Cys Lys Ala Ser Gly Gly Thr Phe Arg Thr His
            20                  25                  30

Ala Ile Ser Trp Val Arg Gln Ala Pro Gly Gln Gly Leu Glu Trp Met
        35                  40                  45

Gly Gly Ile Ile Ala Ile Phe Gly Thr Ala Asn Tyr Ala Gln Lys Phe
    50                  55                  60

Gln Gly Arg Ile Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Ser Gly Tyr His Ile Ser Thr Pro Phe Asp Asn Trp Gly
            100                 105                 110

Gln Gly Thr Leu Val Thr Val Ser Ser Gly Thr Gly Ser Gly Gly
        115                 120                 125

Thr Gly Ser Gly Thr Gly Gly Ser Thr Ser Tyr Val Leu Thr Gln Pro
    130                 135                 140

Pro Ser Val Ser Val Ala Pro Gly Gln Thr Ala Arg Ile Thr Cys Gly
145                 150                 155                 160

Gly Asn Asn Ile Gly Ser Lys Gly Val His Trp Tyr Gln Gln Lys Pro
                165                 170                 175

Gly Gln Ala Pro Val Leu Val Val Tyr Asp Asp Ser Asp Arg Pro Ser
            180                 185                 190

Gly Ile Pro Glu Arg Phe Ser Gly Ser Asn Ser Gly Asn Thr Ala Thr
        195                 200                 205

Leu Thr Ile Ser Arg Val Glu Ala Gly Asp Glu Ala Asp Tyr Tyr Cys
    210                 215                 220

Gln Val Trp Asp Ser Ser Ser Asp His Val Val Phe Gly Gly Gly Thr
225                 230                 235                 240

Lys Leu Thr Val Leu Gly
                245

<210> SEQ ID NO 373
<211> LENGTH: 128
<212> TYPE: PRT
<213> ORGANISM: Homo sapiens

<400> SEQUENCE: 373

Glu Val Ala Leu Val Glu Ser Gly Ala Glu Val Lys Pro Gly Ser
1               5                   10                  15

Ser Val Lys Val Ser Cys Lys Ala Ser Gly His Ile Phe Ser Gly Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Lys Phe
    50                  55                  60

Gln Gly Arg Val Thr Ile Thr Ala Asp Gln Ser Thr Ser Thr Ala Tyr
65                  70                  75                  80

Met Asp Leu Ser Asn Leu Arg Ser Glu Asp Thr Ala Val Tyr Tyr Cys
                85                  90                  95

Ala Arg Val Lys Asp Gly Tyr Cys Thr Leu Thr Ser Cys Pro Val Gly
            100                 105                 110

Trp Tyr Phe Asp Leu Trp Gly Arg Gly Thr Leu Val Thr Val Ser Ser
        115                 120                 125

<210> SEQ ID NO 374
<211> LENGTH: 108
<212> TYPE: PRT
<213> ORGANISM: Homo sapiens

<400> SEQUENCE: 374

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Leu Glu Ile Lys Arg
            100                 105

<210> SEQ ID NO 375
<211> LENGTH: 756
<212> TYPE: DNA
<213> ORGANISM: Homo sapiens

<400> SEQUENCE: 375
gaggtgcagc tggtggagtc tggggctgag gtgaagaagc ctgggtcctc ggtgaaggtc    60
tcctgcaagg cttctggaca catcttcagc ggctatgcaa tcagttgggt gcgacaggcc   120
cctggacaag gcttgagtg gatgggaggg atcatcccta tctttggtac aacaaactac   180
gcacagaagt tccagggcag agtcacgatt accgcggacc aatccacgag cacagcctac   240
atggacctga gcaacttgag atctgaggac acggccgtct attactgtgc gagagtgaaa   300
gatggatatt gtactcttac cagcggcact gtcggctggt acttcgatct ctggggccgt   360
ggcaccctgg tcactgtctc gagcggtacg ggcggttcag gcggaaccgg cagcggcact   420
ggcgggtcga cggaaattgt gatgacgcag tctccaggca ccctgtcttt gtctccaggg   480
gaaagagcca ccctctcgtg cagggccagt cagagtgtta gcagcagcta cttagcctgg   540

```
taccagcaga aacctggcca ggctcccagg ctcctcatct ttggtgcctc cagcagggcc    600
actggcatcc agacaggtt cagtggcagt gggtctggga cagacttcac tctcaccatc    660
agcagactgg agcctgaaga ttttgcagtg tattactgtc agcagtatgg tagctcactc    720
actttcggcg agggaccaa gctggagatc aaacgt                              756
```

```
<210> SEQ ID NO 376
<211> LENGTH: 252
<212> TYPE: PRT
<213> ORGANISM: Homo sapiens

<400> SEQUENCE: 376
```

Glu Val Ala Leu Val Glu Ser Gly Ala Glu Val Lys Lys Pro Gly Ser
1               5                   10                  15

Ser Val Lys Val Ser Cys Lys Ala Ser Gly His Ile Phe Ser Gly Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Thr Asn Tyr Ala Gln Lys Phe
        50                  55                  60

Gln Gly Arg Val Thr Ile Thr Ala Asp Gln Ser Thr Ser Thr Ala Tyr
65                  70                  75                  80

Met Asp Leu Ser Asn Leu Arg Ser Glu Asp Thr Ala Val Tyr Tyr Cys
                85                  90                  95

Ala Arg Val Lys Asp Gly Tyr Cys Thr Leu Thr Ser Cys Pro Val Gly
            100                 105                 110

Trp Tyr Phe Asp Leu Trp Gly Arg Gly Thr Leu Val Thr Val Ser Ser
        115                 120                 125

Gly Thr Gly Gly Ser Gly Gly Thr Gly Ser Gly Thr Gly Gly Ser Thr
    130                 135                 140

Glu Ile Val Met Thr Gln Ser Pro Gly Thr Leu Ser Leu Ser Pro Gly
145                 150                 155                 160

Glu Arg Ala Thr Leu Ser Cys Arg Ala Ser Gln Ser Val Ser Ser Ser
                165                 170                 175

Tyr Leu Ala Trp Tyr Gln Gln Lys Pro Gly Gln Ala Pro Arg Leu Leu
            180                 185                 190

Ile Phe Gly Ala Ser Ser Arg Ala Thr Gly Ile Pro Asp Arg Phe Ser
        195                 200                 205

Gly Ser Gly Ser Gly Thr Asp Phe Thr Leu Thr Ile Ser Arg Leu Glu
    210                 215                 220

Pro Glu Asp Phe Ala Val Tyr Tyr Cys Gln Gln Tyr Gly Ser Ser Leu
225                 230                 235                 240

Thr Phe Gly Gly Gly Thr Lys Leu Glu Ile Lys Arg
                245                 250

```
<210> SEQ ID NO 377
<211> LENGTH: 121
<212> TYPE: PRT
<213> ORGANISM: Homo sapiens

<400> SEQUENCE: 377
```

Glu Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Arg Ser Asn
                20                  25                  30

```
Ser Ile Ser Trp Val Arg Gln Ala Pro Gly Gln Gly Leu Glu Trp Met
            35                  40                  45
Gly Gly Ile Phe Ala Leu Phe Gly Thr Thr Asp Tyr Ala Gln Lys Phe
 50                  55                  60
Gln Gly Arg Val Thr Ile Thr Ala Asp Glu Ser Thr Thr Val Tyr
 65                  70                  75                  80
Leu Glu Leu Ser Ser Leu Thr Ser Glu Asp Thr Ala Val Tyr Tyr Cys
                 85                  90                  95
Ala Arg Gly Ser Gly Tyr Thr Thr Arg Asn Tyr Phe Asp Tyr Trp Gly
            100                 105                 110
Gln Gly Thr Leu Val Thr Val Ser Ser
        115                 120
```

<210> SEQ ID NO 378
<211> LENGTH: 109
<212> TYPE: PRT
<213> ORGANISM: Homo sapiens

<400> SEQUENCE: 378

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Tyr Leu Gly Trp Thr Gln Gln Lys Pro Gly Gln Ala Pro Arg Leu Leu
        35                  40                  45
Ile Tyr Gly Ala Ser Ser Arg Ala Ser Gly Ile Pro Asp Arg Phe Ser
 50                  55                  60
Gly Gly Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Leu Thr Phe Gly Gly Gly Thr Lys Val Glu Ile Lys Arg
            100                 105
```

<210> SEQ ID NO 379
<211> LENGTH: 738
<212> TYPE: DNA
<213> ORGANISM: Homo sapiens

<400> SEQUENCE: 379

```
gaggtccagc tggtacagtc tggggctgag gttaagaagc ctgggtcctc ggtgaaggtc      60
tcctgcaagg cttctggagg catcttcaga agcaattcta tcagttgggt gcgacaggcc     120
cctgggcaag gcttgagtg gatgggaggg atcttcgctc ttttcggaac aacagactac     180
gcgcagaagt tccagggcag agtcacgatt accgcggacg aatcttcgac acagtctac     240
ctggagctga gtagcctgac atctgaggac acggccgttt attactgtgc gagaggcagt     300
ggctacacca cacgcaacta cttttgactac tggggccagg gcaccctggt caccgtctcg     360
agcggtacgg gcggttcagg cggaaccggc agcggcactg gcgggtcgac ggaaattgtg     420
ctgactcagt ctccaggcac cctgtctttg tctccagggg aaagagccac actctcctgc     480
agggccagtc agagtgttag cagcaactac ttaggctggt accagcagaa acctggccag     540
gctcccaggc tcctgatcta tggtgcatcc agcagggcca gtggcatccc agacaggttc     600
agtggcggtg ggtctgggac agacttcact ctcaccatca gcagactgga gcctgaagat     660
tttgcagtgt attactgtca gcagtatggt agctcacccc tcactttcgg cggagggacc     720
```

-continued aaggtggaga tcaaacgt                                                    738

<210> SEQ ID NO 380
<211> LENGTH: 246
<212> TYPE: PRT
<213> ORGANISM: Homo sapiens

<400> SEQUENCE: 380

Glu Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Arg Ser Asn
            20                  25                  30

Ser Ile Ser Trp Val Arg Gln Ala Pro Gly Gln Gly Leu Glu Trp Met
        35                  40                  45

Gly Gly Ile Phe Ala Leu Phe Gly Thr Thr Asp Tyr Ala Gln Lys Phe
    50                  55                  60

Gln Gly Arg Val Thr Ile Thr Ala Asp Glu Ser Ser Thr Thr Val Tyr
65                  70                  75                  80

Leu Glu Leu Ser Ser Leu Thr Ser Glu Asp Thr Ala Val Tyr Tyr Cys
                85                  90                  95

Ala Arg Gly Ser Gly Tyr Thr Thr Arg Asn Tyr Phe Asp Tyr Trp Gly
            100                 105                 110

Gln Gly Thr Leu Val Thr Val Ser Ser Gly Thr Gly Gly Ser Gly Gly
        115                 120                 125

Thr Gly Ser Gly Thr Gly Gly Ser Thr Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ser Ser Asn Tyr Leu Gly Trp Thr Gln Gln
                165                 170                 175

Lys Pro Gly Gln Ala Pro Arg Leu Leu Ile Tyr Gly Ala Ser Ser Arg
            180                 185                 190

Ala Ser Gly Ile Pro Asp Arg Phe Ser Gly Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Tyr Gly Ser Ser Pro Leu Thr Phe Gly Gly Gly Thr
225                 230                 235                 240

Lys Val Glu Ile Lys Arg
                245

<210> SEQ ID NO 381
<211> LENGTH: 120
<212> TYPE: PRT
<213> ORGANISM: Homo sapiens

<400> SEQUENCE: 381

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Gly Met Phe Gly Thr Ala Asn Tyr Ala Gln Lys Phe
    50                  55                  60

Gln Gly Arg Val Thr Ile Thr Ala Asp Glu Phe Thr Ser Thr Ala Tyr

Met Glu Leu Ser Ser Leu Arg Ser Glu Asp Thr Ala Val Tyr Tyr Cys
65                  70                  75                  80

Ala Arg Gly Asn Tyr Tyr Tyr Glu Ser Ser Leu Asp Tyr Trp Gly Gln
            85                  90                  95

Gly Thr Leu Val Thr Val Ser Ser
        115                 120

<210> SEQ ID NO 382
<211> LENGTH: 109
<212> TYPE: PRT
<213> ORGANISM: Homo sapiens

<400> SEQUENCE: 382

Gln Ser Val Val Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly
                100                 105

<210> SEQ ID NO 383
<211> LENGTH: 735
<212> TYPE: DNA
<213> ORGANISM: Homo sapiens

<400> SEQUENCE: 383
gaggtgcagc tggtggagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcggta tgttcggtac agcaaactac    180
gcacagaagt tccagggcag agtcacgatt accgcggacg aatttacgag cacagcctac    240
atggagctga gcagcctgag atctgaggac acggccgtgt attactgtgc gagaggaaat    300
tattactatg agagtagtct cgactactgg ggccagggaa ccctggtcac cgtctcgagc    360
ggtacgggcg gttcaggcgg aaccggcagc ggcactggcg gtcgacgca gtctgtcgtg    420 acgcagccgc cctcggtgtc agtggcccca ggacagacgg ccaggattac ctgtggggga    480
aacaacattg gaagtaaaag tgtgcactgg taccagcaga agccaggcca ggcccctgtg    540
ctggtcgtct atgatgatag cgaccggccc tcagggatcc ctgagcgatt ctctggctcc    600
aactctggga acacggccac cctgaccatc agcagggtcg aagccgggga tgaggccgac    660
tattactgtc aggtgtggga tagtagtagt gatcattatg tcttcggaac tgggaccaag    720
gtcaccgtcc taggt                                                    735

<210> SEQ ID NO 384
<211> LENGTH: 245
<212> TYPE: PRT
<213> ORGANISM: Homo sapiens

<400> SEQUENCE: 384

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Gly Met Phe Gly Thr Ala Asn Tyr Ala Gln Lys Phe
50                  55                  60

Gln Gly Arg Val Thr Ile Thr Ala Asp Glu Phe Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Tyr Tyr Glu Ser Ser Leu Asp Tyr Trp Gly Gln Gly
            100                 105                 110

Gly Thr Leu Val Thr Val Ser Gly Thr Gly Gly Ser Gly Gly Thr
        115                 120                 125

Gly Ser Gly Thr Gly Gly Ser Thr Gln Ser Val Thr Gln Pro Pro
130                 135                 140

Ser Val Ser Val Ala Pro Gly Gln Thr Ala Arg Ile Thr Cys Gly Gly
145                 150                 155                 160

Asn Asn Ile Gly Ser Lys Ser Val His Trp Tyr Gln Gln Lys Pro Gly
            165                 170                 175

Gln Ala Pro Val Leu Val Val Tyr Asp Asp Ser Asp Arg Pro Ser Gly
        180                 185                 190

Ile Pro Glu Arg Phe Ser Gly Ser Asn Ser Gly Asn Thr Ala Thr Leu
    195                 200                 205

Thr Ile Ser Arg Val Glu Ala Gly Asp Glu Ala Asp Tyr Tyr Cys Gln
210                 215                 220

Val Trp Asp Ser Ser Ser Asp His Tyr Val Phe Gly Thr Gly Thr Lys
225                 230                 235                 240

Val Thr Val Leu Gly
                245
```

<210> SEQ ID NO 385
<211> LENGTH: 120
<212> TYPE: PRT
<213> ORGANISM: Homo sapiens

<400> SEQUENCE: 385

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Arg Asn Phe
            20                  25                  30

Ala Ile Asn Trp Val Arg Gln Ala Pro Gly Gln Gly Leu Glu Trp Met
        35                  40                  45

Gly Gly Ile Ile Ala Val Phe Gly Thr Thr Lys Tyr Ala His Lys Phe
50                  55                  60

Gln Gly Arg Val Thr Ile Thr Ala Asp Asp Ser Thr Asn Thr Ala Tyr
65                  70                  75                  80

Met Glu Leu Gly Ser Leu Lys Ser Glu Asp Thr Ala Val Tyr Tyr Cys
                85                  90                  95

Ala Arg Gly Pro His Tyr Tyr Ser Ser Tyr Met Asp Val Trp Gly Glu
            100                 105                 110
```

```
Gly Thr Thr Val Thr Val Ser Ser
        115                 120

<210> SEQ ID NO 386
<211> LENGTH: 107
<212> TYPE: PRT
<213> ORGANISM: Homo sapiens

<400> SEQUENCE: 386

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Ser
                85                  90                  95

Phe Gly Pro Gly Thr Lys Val Asp Ile Lys Arg
            100                 105

<210> SEQ ID NO 387
<211> LENGTH: 729
<212> TYPE: DNA
<213> ORGANISM: Homo sapiens

<400> SEQUENCE: 387
caggtgcagc tggtgcagtc tggggctgag gtgaagaagc ctgggtcctc ggtaaaggtc    60
tcctgcaagg cttctggagg ccccttccgc aattttgcta tcaactgggt gcgacaggcc   120
cctggacaag ggcttgagtg gatgggaggg atcatcgctg tctttgggac gacaaagtac   180
gcacataagt tccagggcag agtcaccatc accgcggacg actccacaaa tacagcttac   240
atggagctgg gcagcctgaa atctgaggac acggccgtgt attactgtgc gagaggtccc   300
cactactact cctcctacat ggacgtctgg ggcgaaggga ccacggtcac cgtctcgagc   360
ggtacgggcg gttcaggcgg aaccggcagc ggcactggcg gtcgacgga catccagttg   420 acccagtctc catcctccct gtctgcatct gtaggagaca gagtcaccat cacttgccgg   480
gcgagtcagg gcattagcac ttatttagcc tggtatcagc agaaacccgg gaaagttcct   540
aaactcctga tctatgctgc atccactttg caatcagggg tcccatctcg gttcagtggc   600
agtggatctg ggacagattt cactctcacc atcagcagcc tgcagcctga agatgttgca   660
acttattact gtcaaaagta taacagtgcc ccttctttcg gccctgggac caaagtggat   720
atcaaacgt                                                           729

<210> SEQ ID NO 388
<211> LENGTH: 243
<212> TYPE: PRT
<213> ORGANISM: Homo sapiens

<400> SEQUENCE: 388

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Arg Asn Phe
```

```
            20                  25                  30
Ala Ile Asn Trp Val Arg Gln Ala Pro Gly Gln Gly Leu Glu Trp Met
        35                  40                  45
Gly Gly Ile Ala Val Phe Gly Thr Thr Lys Tyr Ala His Lys Phe
    50                  55                  60
Gln Gly Arg Val Thr Ile Thr Ala Asp Asp Ser Thr Asn Thr Ala Tyr
65                  70                  75                  80
Met Glu Leu Gly Ser Leu Lys Ser Glu Asp Thr Ala Val Tyr Tyr Cys
                85                  90                  95
Ala Arg Gly Pro His Tyr Tyr Ser Ser Tyr Met Asp Val Trp Gly Glu
                100                 105                 110
Gly Thr Thr Val Thr Val Ser Ser Gly Thr Gly Asp Gly Gly Thr
            115                 120                 125
Gly Ser Gly Thr Gly Ser Thr Asp Ile Gln Leu Thr Gln Ser Pro
        130                 135                 140
Ser Ser Leu Ser Ala Ser Val Gly Asp Arg Val Thr Ile Thr Cys Arg
145                 150                 155                 160
Ala Ser Gln Gly Ile Ser Thr Tyr Leu Ala Trp Tyr Gln Gln Lys Pro
                165                 170                 175
Gly Lys Val Pro Lys Leu Leu Ile Tyr Ala Ala Ser Thr Leu Gln Ser
                180                 185                 190
Gly Val Pro Ser Arg Phe Ser Gly Ser Gly Ser Gly Thr Asp Phe Thr
                195                 200                 205
Leu Thr Ile Ser Ser Leu Gln Pro Glu Asp Val Ala Thr Tyr Tyr Cys
            210                 215                 220
Gln Lys Tyr Asn Ser Ala Pro Ser Phe Gly Pro Gly Thr Lys Val Asp
225                 230                 235                 240
Ile Lys Arg

<210> SEQ ID NO 389
<211> LENGTH: 120
<212> TYPE: PRT
<213> ORGANISM: Homo sapiens

<400> SEQUENCE: 389

Glu Val Ala Leu Val Glu Thr Gly Ala Glu Val Lys Lys Pro Gly Ser
1               5                   10                  15
Ser Val Lys Val Pro Cys Lys Ser Ser Gly Ser Pro Phe Arg Ser Asn
            20                  25                  30
Ala Val Ser Trp Val Arg Gln Ala Pro Gly Gln Gly Leu Glu Trp Val
        35                  40                  45
Gly Gly Ile Leu Gly Val Phe Gly Ser Pro Ser Tyr Ala Gln Lys Phe
    50                  55                  60
Gln Gly Arg Val Thr Ile Thr Ala Asp Glu Ser Thr Asn Thr Val His
65                  70                  75                  80
Met Glu Leu Arg Gly Leu Arg Ser Glu Asp Thr Ala Val Tyr Tyr Cys
                85                  90                  95
Ala Arg Gly Pro Thr Tyr Tyr Tyr Ser Tyr Met Asp Val Trp Gly Lys
                100                 105                 110
Gly Thr Thr Val Thr Val Ser Ser
            115                 120

<210> SEQ ID NO 390
<211> LENGTH: 109
<212> TYPE: PRT
```

<213> ORGANISM: Homo sapiens

<400> SEQUENCE: 390

Ser Tyr Val Leu Thr Gln Pro Pro Ser Glu Ser Val Ala Pro Gly Gln
1               5                   10                  15

Thr Ala Arg Ile Thr Cys Gly Gly Asn Asn Ile Gly Arg Asn Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Lys Ser Gly Asn Thr Ala Thr Leu Ile Ile Ser Arg Val Glu Val Gly
65                  70                  75                  80

Asp Glu Ala Asp Tyr Tyr Cys Gln Val Trp His Ser Ser Ser Asp His
                85                  90                  95

Tyr Val Phe Gly Thr Gly Thr Lys Val Thr Val Leu Gly
            100                 105

<210> SEQ ID NO 391
<211> LENGTH: 735
<212> TYPE: DNA
<213> ORGANISM: Homo sapiens

<400> SEQUENCE: 391
gaggtgcagc tggtggagac tggggctgag gtgaagaagc ctgggtcctc ggtgaaggtc      60
ccctgcaaat cttctggaag ccccttcagg agtaatgctg tcagctgggt gcgacaggcc    120
cccggacaag ggcttgagtg ggtgggagga atcctcggtg tctttggttc accaagctac    180
gcacagaagt tccagggcag agtcacgatt accgcggacg aatccaccaa cacagtccac    240
atggagctga gaggtttgag atctgaggac acggccgtgt attattgtgc gagaggtcct    300
acctactact actcctacat ggacgtctgg ggcaaaggga ccacggtcac cgtctcgagc    360
ggtacgggcg gttcaggcgg aaccggcagc ggcactggcg ggtcgacgtc ctatgtgctg    420
actcagccac cctcggagtc agtggcccca ggacagacgg ccaggattac ctgtggggga    480
aataacattg gaagaaatag tgtgcactgg tatcagcaga agccaggcca ggcccctgtg    540
ctggtcgtgt atgatgatag cgaccggccc tcagggatcc ctgagcgatt ttctggctcc    600
aagtctggga cacggccac cctgattatc agcagggtcg aagtcgggga tgaggccgac    660
tactactgtc aggtgtggca tagtagtagt gatcattatg tcttcggaac tgggaccaag    720
gtcaccgtcc taggt                                                     735

<210> SEQ ID NO 392
<211> LENGTH: 245
<212> TYPE: PRT
<213> ORGANISM: Homo sapiens

<400> SEQUENCE: 392

Glu Val Ala Leu Val Glu Thr Gly Ala Glu Val Lys Lys Pro Gly Ser
1               5                   10                  15

Ser Val Lys Val Pro Cys Lys Ser Ser Gly Ser Pro Phe Arg Ser Asn
            20                  25                  30

Ala Val Ser Trp Val Arg Gln Ala Pro Gly Gln Gly Leu Glu Trp Val
        35                  40                  45

Gly Gly Ile Leu Gly Val Phe Gly Ser Pro Ser Tyr Ala Gln Lys Phe
    50                  55                  60

```
Gln Gly Arg Val Thr Ile Thr Ala Asp Glu Ser Thr Asn Thr Val His
 65                  70                  75                  80

Met Glu Leu Arg Gly Leu Arg Ser Glu Asp Thr Ala Val Tyr Tyr Cys
                 85                  90                  95

Ala Arg Gly Pro Thr Tyr Tyr Tyr Ser Tyr Met Asp Val Trp Gly Lys
            100                 105                 110

Gly Thr Thr Val Thr Val Ser Ser Gly Thr Gly Gly Ser Gly Gly Thr
        115                 120                 125

Gly Ser Gly Thr Gly Gly Ser Thr Ser Tyr Val Leu Thr Gln Pro Pro
    130                 135                 140

Ser Glu Ser Val Ala Pro Gly Gln Thr Ala Arg Ile Thr Cys Gly Gly
145                 150                 155                 160

Asn Asn Ile Gly Arg Asn Ser Val His Trp Tyr Gln Gln Lys Pro Gly
                165                 170                 175

Gln Ala Pro Val Leu Val Val Tyr Asp Asp Ser Asp Arg Pro Ser Gly
            180                 185                 190

Ile Pro Glu Arg Phe Ser Gly Ser Lys Ser Gly Asn Thr Ala Thr Leu
        195                 200                 205

Ile Ile Ser Arg Val Glu Val Gly Asp Glu Ala Asp Tyr Tyr Cys Gln
    210                 215                 220

Val Trp His Ser Ser Ser Asp His Tyr Val Phe Gly Thr Gly Thr Lys
225                 230                 235                 240

Val Thr Val Leu Gly
                245

<210> SEQ ID NO 393
<211> LENGTH: 120
<212> TYPE: PRT
<213> ORGANISM: Homo sapiens

<400> SEQUENCE: 393

Gln Met Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
             35                  40                  45

Gly Gly Ile Phe Gly Met Phe Gly Thr Ala Asn Tyr Ala Gln Lys Phe
         50                  55                  60

Gln Gly Arg Val Thr Ile Thr Ala Asp Glu Phe Thr Ser Ala Ala Tyr
 65                  70                  75                  80

Met Glu Leu Ser Ser Leu Gly Ser Glu Asp Thr Ala Met Tyr Tyr Cys
                 85                  90                  95

Ala Arg Ser Ser Gly Tyr Tyr Pro Gln Tyr Phe Gln Asp Trp Gly Gln
            100                 105                 110

Gly Thr Leu Val Thr Val Ser Ser
        115                 120

<210> SEQ ID NO 394
<211> LENGTH: 109
<212> TYPE: PRT
<213> ORGANISM: Homo sapiens

<400> SEQUENCE: 394

Glu Ile Val Met Thr Gln Ser Pro Gly Thr Leu Ser Leu Ser Pro Gly
 1               5                  10                  15
```

Gln Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Met Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ser
                85                  90                  95

Leu Thr Phe Gly Gly Gly Thr Lys Leu Glu Ile Lys Arg
            100                 105

<210> SEQ ID NO 395
<211> LENGTH: 735
<212> TYPE: DNA
<213> ORGANISM: Homo sapiens

<400> SEQUENCE: 395
cagatgcagc tggtacaatc tggagctgag gtgaagaagc ctgggtcctc ggtgaaggtc      60
tcctgcaagg cttctggagg cacccttcagc agctatgcta tcagctgggt gcgacaggcc    120
cctggacaag gcttgagtg gatgggaggg atcttcggta tgtttgggac agcaaactac     180
gcgcagaagt tccagggcag agtcacgatt accgcgacg aattcacgag cgcggcctac      240
atggagctga gcagcctggg atctgaggac acggccatgt attactgtgc gaggtctagt    300
ggttattacc cccaatactt ccaggactgg ggccagggca ccctggtcac cgtctcgagc    360
ggtacgggcg gttcaggcgg aaccggcagc ggcactggcg ggtcgacgga aattgtgatg    420
acacagtctc caggcaccct gtctttgtct ccagggcaaa gagccaccct ctcctgcagg    480
gccagtcaga gtgttagcag cagctactta gcctggtacc agcagaarcc tggccaggct    540
cccagactcc tcatgtatgg tgcatccagc agggccactg gcatcccaga caggttcagt    600
ggcagtgggt ctgggacaga cttcactctc accatcagca gactggagcc tgaagatttt    660
gcagtgtatt actgtcagca gtatggtagc tcatcgctca ctttcggcgg agggaccaag    720
ctggagatca aacgt                                                    735

<210> SEQ ID NO 396
<211> LENGTH: 245
<212> TYPE: PRT
<213> ORGANISM: Homo sapiens

<400> SEQUENCE: 396

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Phe Gly Met Phe Gly Thr Ala Asn Tyr Ala Gln Lys Phe
50                  55                  60

Gln Gly Arg Val Thr Ile Thr Ala Asp Glu Phe Thr Ser Ala Ala Tyr
65                  70                  75                  80

Met Glu Leu Ser Ser Leu Gly Ser Glu Asp Thr Ala Met Tyr Tyr Cys
                85                  90                  95

Ala Arg Ser Ser Gly Tyr Tyr Pro Gln Tyr Phe Gln Asp Trp Gly Gln

```
                100                 105                 110
Gly Thr Leu Val Thr Val Ser Ser Gly Thr Gly Ser Gly Gly Thr
            115                 120                 125
Gly Ser Gly Thr Gly Ser Thr Glu Ile Val Met Thr Gln Ser Pro
130                 135                 140
Gly Thr Leu Ser Leu Ser Pro Gly Gln Arg Ala Thr Leu Ser Cys Arg
145                 150                 155                 160
Ala Ser Gln Ser Val Ser Ser Tyr Leu Ala Trp Tyr Gln Gln Lys
                165                 170                 175
Pro Gly Gln Ala Pro Arg Leu Leu Met Tyr Gly Ala Ser Ser Arg Ala
                180                 185                 190
Thr Gly Ile Pro Asp Arg Phe Ser Gly Ser Gly Ser Gly Thr Asp Phe
            195                 200                 205
Thr Leu Thr Ile Ser Arg Leu Glu Pro Glu Asp Phe Ala Val Tyr Tyr
            210                 215                 220
Cys Gln Gln Tyr Gly Ser Ser Leu Thr Phe Gly Gly Gly Thr Lys
225                 230                 235                 240
Leu Glu Ile Lys Arg
                245
```

<210> SEQ ID NO 397
<211> LENGTH: 121
<212> TYPE: PRT
<213> ORGANISM: Homo sapiens

<400> SEQUENCE: 397

```
Glu Val Gln Leu Val Glu Ser Gly Ala Glu Val Lys Lys Pro Gly Ser
1               5                   10                  15
Ser Val Lys Val Ser Cys Lys Ala Ser Gly Gly Ile Phe Asn Ser Tyr
                20                  25                  30
Ala Ile Ser Trp Val Arg Gln Ala Pro Gly Gln Gly Leu Glu Trp Met
            35                  40                  45
Gly Gly Ile Ile Ala Ile Phe His Thr Pro Lys Tyr Ala Gln Lys Phe
50              55                  60
Gln Gly Arg Val Thr Ile Thr Ala Asp Glu Ser Thr Asn Thr Ala Tyr
65                  70                  75                  80
Met Glu Leu Arg Ser Leu Lys Ser Glu Asp Thr Ala Leu Tyr Tyr Cys
                85                  90                  95
Ala Arg Gly Ser Thr Tyr Asp Phe Ser Ser Gly Leu Asp Tyr Trp Gly
                100                 105                 110
Gln Gly Thr Leu Val Thr Val Ser Ser
            115                 120
```

<210> SEQ ID NO 398
<211> LENGTH: 109
<212> TYPE: PRT
<213> ORGANISM: Homo sapiens

<400> SEQUENCE: 398

```
Gln Ala Gly Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Ser Val
                20                  25                  30
His Trp Tyr Gln Gln Lys Pro Gly Gln Ala Pro Val Leu Val Val Tyr
            35                  40                  45
Asp Asp Ser Asp Arg Pro Ser Gly Ile Pro Glu Arg Phe Ser Gly Ser
```

```
                      50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Lys Leu Thr Val Leu Gly
            100                 105

<210> SEQ ID NO 399
<211> LENGTH: 738
<212> TYPE: DNA
<213> ORGANISM: Homo sapiens

<400> SEQUENCE: 399
gaggtgcagc tggtggagtc cggggctgag gtgaagaagc ctgggtcctc ggtgaaggtc    60
tcctgcaagg cttctggagg catcttcaac agttatgcta tcagctgggt gcgacaggcc   120
cctggacaag gcttgagtg gatgggaggc atcatcgcta tctttcatac accaaagtac    180
gcacagaagt tccagggcag agtcacgatt accgcggacg aatccacgaa cacagcctac   240
atggaactga aagcctgaa atctgaggac acggccctgt attactgtgc gagagggtcc    300
acttacgatt tttcgagtgg ccttgactac tggggccagg aaccctggt caccgtctcg    360 agcggtacgg gcggttcagg cggaaccggc agcggcactg gcgggtcgac gcaggcaggg   420
ctgactcagc cacccctcgt gtcagtggcc ccaggacaga cggccaggat tacctgtggg   480
ggaaacaaca ttggaagtaa aagtgtgcac tggtaccagc agaagccagg ccaggccct   540 gtcctagtcg tctatgatga tagcgaccgg ccctcaggga tccctgagcg attctctggc   600
tccaactctg ggaacacggc caccctgacc atcagcaggg tcgaagccgg ggatgaggcc   660
gactattact gtcaggtgtg ggatagtagt agtgatcatg tggtattcgg cggagggacc   720
aagctgaccg tcctaggt                                                 738

<210> SEQ ID NO 400
<211> LENGTH: 246
<212> TYPE: PRT
<213> ORGANISM: Homo sapiens

<400> SEQUENCE: 400

Glu Val Gln Leu Val Glu Ser Gly Ala Glu Val Lys Lys Pro Gly Ser
  1               5                  10                  15

Ser Val Lys Val Ser Cys Lys Ala Ser Gly Gly Ile Phe Asn Ser Tyr
                 20                  25                  30

Ala Ile Ser Trp Val Arg Gln Ala Pro Gly Gln Gly Leu Glu Trp Met
             35                  40                  45

Gly Gly Ile Ile Ala Ile Phe His Thr Pro Lys Tyr Ala Gln Lys Phe
         50                  55                  60

Gln Gly Arg Val Thr Ile Thr Ala Asp Glu Ser Thr Asn Thr Ala Tyr
 65                  70                  75                  80

Met Glu Leu Arg Ser Leu Lys Ser Glu Asp Thr Ala Leu Tyr Tyr Cys
                 85                  90                  95

Ala Arg Gly Ser Thr Tyr Asp Phe Ser Ser Gly Leu Asp Tyr Trp Gly
            100                 105                 110

Gln Gly Thr Leu Val Thr Val Ser Ser Gly Thr Gly Gly Ser Gly Gly
            115                 120                 125

Thr Gly Ser Gly Thr Gly Gly Ser Thr Gln Ala Gly Leu Thr Gln Pro
        130                 135                 140
```

```
Pro Ser Val Ser Val Ala Pro Gly Gln Thr Ala Arg Ile Thr Cys Gly
145                 150                 155                 160

Gly Asn Asn Ile Gly Ser Lys Ser Val His Trp Tyr Gln Gln Lys Pro
                165                 170                 175

Gly Gln Ala Pro Val Leu Val Val Tyr Asp Asp Ser Asp Arg Pro Ser
            180                 185                 190

Gly Ile Pro Glu Arg Phe Ser Gly Ser Asn Ser Gly Asn Thr Ala Thr
        195                 200                 205

Leu Thr Ile Ser Arg Val Glu Ala Gly Asp Glu Ala Asp Tyr Tyr Cys
    210                 215                 220

Gln Val Trp Asp Ser Ser Asp His Val Val Phe Gly Gly Gly Thr
225                 230                 235                 240

Lys Leu Thr Val Leu Gly
                245
```

<210> SEQ ID NO 401
<211> LENGTH: 126
<212> TYPE: PRT
<213> ORGANISM: Homo sapiens

<400> SEQUENCE: 401

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Phe Ser Ser Tyr
            20                  25                  30

Ala Ile Ser Trp Val Arg Gln Ala Pro Gly Gln Gly Leu Glu Trp Met
        35                  40                  45

Gly Gly Val Ile Pro Ile Phe Arg Thr Ala Asn Tyr Ala Gln Asn Phe
    50                  55                  60

Gln Gly Arg Val Thr Ile Thr Ala Asp Glu Phe Thr Ser Tyr Met Glu
65                  70                  75                  80

Leu Ser Ser Leu Arg Ser Asp Asp Thr Ala Val Tyr Tyr Cys Ala Arg
                85                  90                  95

Leu Asn Tyr His Asp Ser Gly Tyr Tyr Asn Ala Pro Arg Gly Trp
            100                 105                 110

Phe Asp Pro Trp Gly Gln Gly Thr Leu Val Thr Val Ser Ser
        115                 120                 125
```

<210> SEQ ID NO 402
<211> LENGTH: 114
<212> TYPE: PRT
<213> ORGANISM: Homo sapiens

<400> SEQUENCE: 402

```
Asp Ile Gln Met Thr Gln Ser Pro Asp Ser Leu Ala Val Ser Leu Gly
1               5                   10                  15

Glu Lys Ala Thr Ile Asn Cys Lys Ser Ser Gln Ser Ile Leu Asn Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

Tyr Tyr Ser Ser Pro Pro Thr Phe Gly Gln Gly Thr Lys Val Glu Ile
            100                 105                 110

Lys Arg

<210> SEQ ID NO 403
<211> LENGTH: 768
<212> TYPE: DNA
<213> ORGANISM: Homo sapiens

<400> SEQUENCE: 403
caggtccagc tggtgcagtc tggggctgag gtgaagaagc ctgggtcctc ggtgaaggtc      60
tcctgcaagg cttctggagg cttcttcagc agctatgcta tcagctgggt gcgccaggcc     120
cctggacaag gacttgagtg gatggggggg gtcatcccta tctttcgtac agcaaactac     180
gcacagaact tccagggcag agtcaccatt accgcggacg aattcacatc gtatatggag     240
ctgagcagcc tgagatctga cgacacggcc gtgtattact gtgcgaggtt gaattaccat     300
gattcgggga cttattataa cgccccccgg ggctggttcg acccctgggg ccagggaacc     360
ctggtcaccg tctcgagcgg tacgggcggt tcaggcggaa ccggcagcgg cactggcggg     420
tcgacggaca tccagatgac ccagtctcca gactccctgg ctgtgtctct gggcgagaag     480
gccaccatca actgcaagtc cagccagagt attttaaaca gctccaacaa taagaactac     540
ttagcttggt accagcagaa accaggacag cctcctaagc tgctcattta ctgggcatct     600
acccgggaat ccggggtccc tgaccgattc agtggcagcg gtctgggaca gatttcact     660 ctcaccatca gcagcctgca ggctgaagat gtggcagttt attactgtca gcaatattat     720
agtagtccgc cgacgttcgg ccaagggacc aaggtggaaa tcaaacgt                   768

<210> SEQ ID NO 404
<211> LENGTH: 256
<212> TYPE: PRT
<213> ORGANISM: Homo sapiens

<400> SEQUENCE: 404

Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Phe Ser Ser Tyr
            20                  25                  30

Ala Ile Ser Trp Val Arg Gln Ala Pro Gly Gln Gly Leu Glu Trp Met
        35                  40                  45

Gly Gly Val Ile Pro Ile Phe Arg Thr Ala Asn Tyr Ala Gln Asn Phe
    50                  55                  60

Gln Gly Arg Val Thr Ile Thr Ala Asp Glu Phe Thr Ser Tyr Met Glu
65                  70                  75                  80

Leu Ser Ser Leu Arg Ser Asp Asp Thr Ala Val Tyr Tyr Cys Ala Arg
                85                  90                  95

Leu Asn Tyr His Asp Ser Gly Thr Tyr Tyr Asn Ala Pro Arg Gly Trp
            100                 105                 110

Phe Asp Pro Trp Gly Gln Gly Thr Leu Val Thr Val Ser Ser Gly Thr
        115                 120                 125

Gly Gly Ser Gly Gly Thr Gly Ser Gly Thr Gly Gly Ser Thr Asp Ile
    130                 135                 140

Gln Met Thr Gln Ser Pro Asp Ser Leu Ala Val Ser Leu Gly Glu Lys
145                 150                 155                 160

Ala Thr Ile Asn Cys Lys Ser Ser Gln Ser Ile Leu Asn Ser Ser Asn

```
                        165                 170                 175
Asn Lys Asn Tyr Leu Ala Trp Tyr Gln Gln Lys Pro Gly Gln Pro Pro
                180                 185                 190

Lys Leu Leu Ile Tyr Trp Ala Ser Thr Arg Glu Ser Gly Val Pro Asp
            195                 200                 205

Arg Phe Ser Gly Ser Gly Ser Gly Thr Asp Phe Thr Leu Thr Ile Ser
        210                 215                 220

Ser Leu Gln Ala Glu Asp Val Ala Val Tyr Tyr Cys Gln Gln Tyr Tyr
225                 230                 235                 240

Ser Ser Pro Pro Thr Phe Gly Gln Gly Thr Lys Val Glu Ile Lys Arg
                245                 250                 255

<210> SEQ ID NO 405
<211> LENGTH: 120
<212> TYPE: PRT
<213> ORGANISM: Homo sapiens

<400> SEQUENCE: 405

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Tyr Tyr
            20                  25                  30

Ala Met Ser Trp Val Arg Gln Ala Pro Gly Gln Gly Leu Glu Trp Met
        35                  40                  45

Gly Gly Ile Ser Pro Met Phe Gly Thr Thr Thr Tyr Ala Gln Lys Phe
    50                  55                  60

Gln Gly Arg Val Thr Ile Thr Ala Asp Asp Ser Thr Ser Thr Ala Tyr
65                  70                  75                  80

Met Glu Val Arg Ser Leu Arg Ser Glu Asp Thr Ala Val Tyr Tyr Cys
                85                  90                  95

Ala Arg Ser Ser Asn Tyr Tyr Asp Ser Val Tyr Asp Tyr Trp Gly Gln
            100                 105                 110

Gly Thr Leu Val Thr Val Ser Ser
        115                 120

<210> SEQ ID NO 406
<211> LENGTH: 109
<212> TYPE: PRT
<213> ORGANISM: Homo sapiens

<400> SEQUENCE: 406

Gln Ser Val Val Thr Gln Pro Pro Ser Glu Ser Val Ala Pro Gly Gln
1               5                   10                  15

Thr Ala Arg Ile Thr Cys Gly Gly His Asn Ile Gly Ser Asn Ser Val
            20                  25                  30

His Trp Tyr Gln Gln Lys Pro Gly Gln Ala Pro Val Leu Val Val Tyr
        35                  40                  45

Asp Asn Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Gly Ser Ser Ser Asp His
                85                  90                  95

Tyr Val Phe Gly Thr Gly Thr Lys Val Thr Val Leu Gly
            100                 105
```

```
<210> SEQ ID NO 407
<211> LENGTH: 735
<212> TYPE: DNA
<213> ORGANISM: Homo sapiens

<400> SEQUENCE: 407
caggtccagc tggtgcagtc tggagctgag gtgaagaagc ctgggtcctc ggtgaaggtc      60
tcctgcaagg cttctggagt caccttcagt tactatgcta tgagctgggt gcgacaggcc     120
cctggacaag gcttgagtg gatgggagga atcagcccta tgtttgggac aacaacctac     180
gcacagaagt tccagggcag agtcacgatt actgcggacg actccacgag tacagcctac     240
atggaggtga ggagcctgag atctgaggac acggccgtgt attactgtgc gagatcttcg     300
aattactatg atagtgtata tgactactgg ggccagggaa ccctggtcac cgtctcgagc     360
ggtacgggcg gttcaggcgg aaccggcagc ggcactggcg gtcgacgca gtctgtcgtg     420 acgcagccgc cctcggagtc agtggcccca ggacagacgg ccaggattac ctgtggggga     480
cataacattg gaagtaatag tgtgcactgg taccagcaga agccaggcca ggcccctgtg     540
ctggtcgtgt atgataatag cgaccggccc tcagggatcc ctgagcgatt ctctggctcc     600
aactctggga acacgccac cctgaccatc agcagggtcg aagccyyyga tgaggccgac     660
tattactgtc aggtgtgggg tagtagtagt gaccattatg tcttcggaac tgggaccaag     720
gtcaccgtcc taggt                                                      735

<210> SEQ ID NO 408
<211> LENGTH: 245
<212> TYPE: PRT
<213> ORGANISM: Homo sapiens

<400> SEQUENCE: 408

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Tyr Tyr
            20                  25                  30

Ala Met Ser Trp Val Arg Gln Ala Pro Gly Gln Gly Leu Glu Trp Met
        35                  40                  45

Gly Gly Ile Ser Pro Met Phe Gly Thr Thr Thr Tyr Ala Gln Lys Phe
    50                  55                  60

Gln Gly Arg Val Thr Ile Thr Ala Asp Asp Ser Thr Ser Thr Ala Tyr
65                  70                  75                  80

Met Glu Val Arg Ser Leu Arg Ser Glu Asp Thr Ala Val Tyr Tyr Cys
                85                  90                  95

Ala Arg Ser Ser Asn Tyr Tyr Asp Ser Val Tyr Asp Tyr Trp Gly Gln
            100                 105                 110

Gly Thr Leu Val Thr Val Ser Ser Gly Thr Gly Gly Ser Gly Gly Thr
        115                 120                 125

Gly Ser Gly Thr Gly Gly Ser Thr Gln Ser Val Val Thr Gln Pro Pro
    130                 135                 140

Ser Glu Ser Val Ala Pro Gly Gln Thr Ala Arg Ile Thr Cys Gly Gly
145                 150                 155                 160

His Asn Ile Gly Ser Asn Ser Val His Trp Tyr Gln Gln Lys Pro Gly
                165                 170                 175

Gln Ala Pro Val Leu Val Val Tyr Asp Asn Ser Asp Arg Pro Ser Gly
            180                 185                 190

Ile Pro Glu Arg Phe Ser Gly Ser Asn Ser Gly Asn Thr Ala Thr Leu
        195                 200                 205
```

-continued

Thr Ile Ser Arg Val Glu Ala Gly Asp Glu Ala Asp Tyr Tyr Cys Gln
            210                 215                 220

Val Trp Gly Ser Ser Ser Asp His Tyr Val Phe Gly Thr Gly Thr Lys
225                 230                 235                 240

Val Thr Val Leu Gly
                245

<210> SEQ ID NO 409
<211> LENGTH: 123
<212> TYPE: PRT
<213> ORGANISM: Homo sapiens

<400> SEQUENCE: 409

Gln Val Gln Leu Val Gln Ser Gly Ala Glu Val Lys Lys Pro Gly Ser
1               5                   10                  15

Ser Val Arg Val Ser Cys Lys Ala Ser Gly Ser Ile Phe Arg Asn Tyr
                20                  25                  30

Ala Met Ser Trp Val Arg Gln Ala Pro Gly Gln Gly Leu Glu Trp Met
            35                  40                  45

Gly Gly Ile Ile Ala Ile Phe Gly Thr Pro Lys Tyr Ala Gln Lys Phe
        50                  55                  60

Gln Gly Arg Val Thr Ile Thr Ala Asp Glu Ser Thr Ser Thr Val Tyr
65                  70                  75                  80

Met Glu Leu Ser Gly Leu Arg Ser Glu Asp Thr Ala Met Tyr Tyr Cys
                85                  90                  95

Ala Arg Ile Pro His Tyr Asn Phe Gly Ser Gly Ser Tyr Phe Asp Tyr
                100                 105                 110

Trp Gly Gln Gly Thr Leu Val Thr Val Ser Ser
            115                 120

<210> SEQ ID NO 410
<211> LENGTH: 111
<212> TYPE: PRT
<213> ORGANISM: Homo sapiens

<400> SEQUENCE: 410

Thr Val Leu Thr Gln Pro Pro Ser Val Ser Gly Ala Pro Gly Gln Arg
1               5                   10                  15

Val Thr Ile Ser Cys Thr Gly Ser Ser Ser Asn Ile Gly Ala Gly Tyr
                20                  25                  30

Asp Val His Trp Tyr Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu Gly
                100                 105                 110

<210> SEQ ID NO 411
<211> LENGTH: 750
<212> TYPE: DNA
<213> ORGANISM: Homo sapiens

<400> SEQUENCE: 411

```
caggtgcagc tggtgcagtc tggggctgag gtgaagaagc ctgggtcctc ggtgagagtc      60
tcctgcaagg cttctggaag catcttcaga aactatgcta tgagctgggt gcgacaggcc     120
cctggacaag ggcttgagtg gatgggaggg atcatcgcta ttttggggac accaaagtac     180
gcacagaagt tccagggcag agtcacgatt accgcggacg aatcgacgag cactgtctac     240
atggaactga gcggactgag atctgaggac acggccatgt attactgtgc gaggattccc     300
cactataatt ttggttcggg gagttatttc gactactggg gccagggaac cctggtcacc     360
gtctcgagcg gtacgggcgg ttcaggcgga accggcagcg gcactggcgg gtcgacgact     420
gtgttgacac agccgccctc agtgtctggg gccccagggc agagggtcac catctcctgc     480
actgggagca gctccaacat cggggcaggt tatgatgtac actggtacca gcagcttcca     540
ggaacagccc ccaaactcct catctatggt aacagcaatc ggccctcagg ggtccctgac     600
cgattctctg gctccaagtc tggcacgtca gccaccctgg gcatcaccgg actccagact     660
ggggacgagg ccgattatta ctgcggaaca tgggatagca gcctgagtgc ttatgtcttc     720
ggaactggga ccaaggtcac cgtcctaggt                                      750
```

```
<210> SEQ ID NO 412
<211> LENGTH: 250
<212> TYPE: PRT
<213> ORGANISM: Homo sapiens

<400> SEQUENCE: 412
```

Gln Val Gln Leu Val Gln Ser Gly Ala Glu Val Lys Lys Pro Gly Ser
1               5                   10                  15

Ser Val Arg Val Ser Cys Lys Ala Ser Gly Ser Ile Phe Arg Asn Tyr
            20                  25                  30

Ala Met Ser Trp Val Arg Gln Ala Pro Gly Gln Gly Leu Glu Trp Met
        35                  40                  45

Gly Gly Ile Ile Ala Ile Phe Gly Thr Pro Lys Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Gly Leu Arg Ser Glu Asp Thr Ala Met Tyr Tyr Cys
                85                  90                  95

Ala Arg Ile Pro His Tyr Asn Phe Gly Ser Gly Ser Tyr Phe Asp Tyr
            100                 105                 110

Trp Gly Gln Gly Thr Leu Val Thr Val Ser Ser Gly Thr Gly Gly Ser
        115                 120                 125

Gly Gly Thr Gly Ser Gly Thr Gly Gly Ser Thr Thr Val Leu Thr Gln
    130                 135                 140

Pro Pro Ser Val Ser Gly Ala Pro Gly Gln Arg Val Thr Ile Ser Cys
145                 150                 155                 160

Thr Gly Ser Ser Ser Asn Ile Gly Ala Gly Tyr Asp Val His Trp Tyr
                165                 170                 175

Gln Gln Leu Pro Gly Thr Ala Pro Lys Leu Leu Ile Tyr Gly Asn Ser
            180                 185                 190

Asn Arg Pro Ser Gly Val Pro Asp Arg Phe Ser Gly Ser Lys Ser Gly
        195                 200                 205

Thr Ser Ala Thr Leu Gly Ile Thr Gly Leu Gln Thr Gly Asp Glu Ala
    210                 215                 220

Asp Tyr Tyr Cys Gly Thr Trp Asp Ser Ser Leu Ser Ala Tyr Val Phe
225                 230                 235                 240

```
Gly Thr Gly Thr Lys Val Thr Val Leu Gly
                245                 250
```

<210> SEQ ID NO 413
<211> LENGTH: 445
<212> TYPE: PRT
<213> ORGANISM: Homo sapiens

<400> SEQUENCE: 413

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Val Tyr Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Ser Leu Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365
```

```
Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
        435                 440                 445

<210> SEQ ID NO 414
<211> LENGTH: 114
<212> TYPE: PRT
<213> ORGANISM: Homo sapiens

<400> SEQUENCE: 414

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Ser Thr Pro Leu Thr Phe Gly Gly Gly Thr Lys Val Asp Ile
        100                 105                 110

Lys Arg

<210> SEQ ID NO 415
<211> LENGTH: 657
<212> TYPE: DNA
<213> ORGANISM: Homo sapiens

<400> SEQUENCE: 415
gatgttgtga tgactcagtc tccagactcc ctggctgtgt ctctgggcga gagggccacc    60
atcaactgca agtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
cctctcactt tcggcggagg gaccaaagtg gatatcaaac gtgcggccgc acccagcgtg   360
ttcatcttcc ccccctccga cgagcagctg aagagcggca ccgccagcgt ggtgtgcctg   420
ctgaacaact tctaccccg ggaggccaag gtgcagtgga aggtggacaa cgccctgcag   480
agcggcaaca gccaggagag cgtgaccgag caggacagca aggactccac ctacagcctg   540
agcagcaccc tcaccctgag caaggccgac tacgagaagc acaaggtgta cgcctgcgag   600
gtgacccacc agggcctgag cagccccgtg accaagagct caaccggggg cgagtgt     657

<210> SEQ ID NO 416
```

```
<211> LENGTH: 219
<212> TYPE: PRT
<213> ORGANISM: Homo sapiens

<400> SEQUENCE: 416

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Asp Ile
            100                 105                 110

Lys Arg Ala Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 417
<211> LENGTH: 121
<212> TYPE: PRT
<213> ORGANISM: Homo sapiens

<400> SEQUENCE: 417

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120
```

<210> SEQ ID NO 418
<211> LENGTH: 1353
<212> TYPE: DNA
<213> ORGANISM: Homo sapiens

<400> SEQUENCE: 418

```
gaggtgcagc tggtggagtc tggggctgag gtgaagaagc ctgggtcctc ggtgaaagtc      60
tcttgcaagg cttctggagg ccccttccgc agctatgcta tcagctgggt gcgacaggcc     120
cctggacaag ggcctgagtg gatgggaggg atcatcccta tttttggtac aacaaaatac     180
gcaccgaagt tccagggcag agtcacgatt accgcggacg atttcgcggg cacagtttac     240
atggagctga gcagcctgcg atctgaggac acggccatgt actactgtgc gaaacatatg     300
gggtaccagg tgcgcgaaac tatggacgtc tggggcaaag ggaccacggt caccgtctcg     360
agtgctagca ccaagggccc cagcgtgttc cccctggccc ccagcagcaa gagcaccagc     420
ggcggcacag ccgccctggg ctgcctggtg aaggactact cccccgagcc cgtgaccgtg     480
agctggaaca gcggcgcctt gaccagcggc gtgcacacct tccccgccgt gctgcagagc     540
agcggcctgt acagcctgag cagcgtggtg accgtgccca gcagcagcct gggcacccag     600
acctacatct gcaacgtgaa ccacaagccc agcaacacca aggtggacaa gcgcgtggag     660
cccaagagct gcgacaagac ccacacctgc ccccccctgcc ctgccccga gctgctgggc     720
ggaccctccg tgttcctgtt cccccccaag cccaaggaca ccctcatgat cagccggacc     780
cccgaggtga cctgcgtggt ggtggacgtg agccacgagg accccgaggt gaagttcaac     840
tggtacgtgg acggcgtgga ggtgcacaac gccaagacca gccccgggga ggagcagtac     900
aacagcacct accgggtggt gagcgtgctc accgtgctgc accaggactg gctgaacggc     960
aaggagtaca agtgcaaggt gagcaacaag gccctgcctg cccccatcga aagaccatc     1020
agcaaggcca agggccagcc ccgggagccc caggtgtaca ccctgccccc cagccgggag    1080
gagatgacca agaaccaggt gtccctcacc tgtctggtga agggcttcta ccccagcgac    1140
atcgccgtgg agtgggagag caacggccag cccgagaaca actacaagac cacccccccct   1200
gtgctggaca gcgacggcag cttcttcctg tacagcaagc tcaccgtgga caagagccgg    1260
tggcagcagg gcaacgtgtt cagctgcagc gtgatgcacg aggccctgca caaccactac    1320
acccagaaga gcctgagcct gagccccggc aag                                 1353
```

<210> SEQ ID NO 419
<211> LENGTH: 451
<212> TYPE: PRT
<213> ORGANISM: Homo sapiens

<400> SEQUENCE: 419

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
```

85                  90                  95
Ala Lys His Met Gly Tyr Gln Val Arg Glu Thr Met Asp Val Trp Gly
                100                 105                 110
Lys Gly Thr Thr Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Arg Val Glu Pro Lys Ser Cys
            210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
    450

<210> SEQ ID NO 420
<211> LENGTH: 111
<212> TYPE: PRT
<213> ORGANISM: Homo sapiens

<400> SEQUENCE: 420

Ser Tyr Val Leu Thr Gln Pro Pro Ser Ala Ser Gly Thr Pro Gly Gln
1               5                   10                  15

Arg Val Thr Ile Ser Cys Ser Gly Ser Thr Phe Asn Ile Gly Ser Asn
            20                  25                  30

Ala Val Asp Trp Tyr Arg Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ile Leu
                85                  90                  95

Asn Val Pro Val Phe Gly Gly Gly Thr Lys Leu Thr Val Leu Gly
            100                 105                 110

<210> SEQ ID NO 421
<211> LENGTH: 660
<212> TYPE: DNA
<213> ORGANISM: Homo sapiens

<400> SEQUENCE: 421
tcctatgtgc tgactcagcc accctcagcg tctgggaccc ccgggcagag ggtcaccatc     60
tcttgttctg gaagcacgtt caacatcgga agtaatgctg tagactggta ccggcagctc    120
ccaggaacgg cccccaaact cctcatctat agtaataatc agcggccctc aggggtccct    180
gaccgattct ctggctccag gtctggcacc tcagcctccc tggccatcag tgggctccag    240
tctgaggatg aggctgatta ttactgtgca gcatgggatg acatcctgaa tgttccggta    300
ttcggcggag ggaccaagct gaccgtccta ggtgcggccg caggccagcc caaggccgct    360
cccagcgtga ccctgttccc ccctcctcc gaggagctgc aggccaacaa ggccaccctg    420
gtgtgcctca tcagcgactt ctaccctggc gccgtgaccg tggcctggaa ggccgacagc    480
agccccgtga aggccggcgt ggagaccacc acccccagca gcagagcaa caacaagtac    540 gccgccagca gctacctgag cctcacccc gagcagtgga gagccaccg gagctacagc    600 tgccaggtga cccacgaggg cagcaccgtg gagaagaccg tggcccccac cgagtgcagc    660

<210> SEQ ID NO 422
<211> LENGTH: 220
<212> TYPE: PRT
<213> ORGANISM: Homo sapiens

<400> SEQUENCE: 422

Ser Tyr Val Leu Thr Gln Pro Pro Ser Ala Ser Gly Thr Pro Gly Gln
1               5                   10                  15

Arg Val Thr Ile Ser Cys Ser Gly Ser Thr Phe Asn Ile Gly Ser Asn
            20                  25                  30

Ala Val Asp Trp Tyr Arg Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ile Leu
                85                  90                  95

Asn Val Pro Val Phe Gly Gly Gly Thr Lys Leu Thr Val Leu Gly Ala
            100                 105                 110

Ala Ala Gly Gln Pro Lys Ala Ala Pro Ser Val Thr Leu Phe Pro Pro
            115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220

<210> SEQ ID NO 423
<211> LENGTH: 121
<212> TYPE: PRT
<213> ORGANISM: Homo sapiens

<400> SEQUENCE: 423

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120

<210> SEQ ID NO 424
<211> LENGTH: 1352
<212> TYPE: DNA
<213> ORGANISM: Homo sapiens

<400> SEQUENCE: 424
caggtccagc tggtgcagtc tggggctgag gtgaagaagc ctgggtcctc ggtgaaagtc      60
tcttgcaagg cttctggagg ccccttccgc agctatgcta tcagctgggt gcgacaggcc     120
cctggacaag gcctgagtg gatgggaggg atcatcccta tttttggtac aacaaaatac     180
gcaccgaagt tccagggcag agtcacgatt accgcggacg atttcgcggg cacagtttac     240
atggagctga gcagcctgcg atctgaggac acggccatgt actactgtgc aaacatatg     300 gggtaccagg tgcgcgaaac tatggacgtc tggggcaaag ggaccacggt caccgtctcg     360
agtgctagca ccaagggccc cagcgtgttc ccctggcccc cagcagcaa gagcaccagc     420 ggcggcacag ccgccctggg ctgcctggtg aaggactact ccccgagcc cgtgaccgtg     480 agctggaaca cgggcgcctt gaccagcggc gtgcacacct tccccgccgt gctgcagagc     540

```
agcggcctgt acagcctgag cagcgtggtg accgtgcccg cagcagcctg ggcacccaga      600
cctacatctg caacgtgaac cacaagccca gcaacaccaa ggtggacaaa cgcgtggagc      660
ccaagagctg cgacaagacc cacacctgcc cccctgccc tgcccccgag ctgctgggcg       720
gaccctccgt gttcctgttc ccccccaagc ccaaggacac cctcatgatc agccggaccc      780
ccgaggtgac ctgcgtggtg gtggacgtga gccacgagga ccccgaggtg aagttcaact      840
ggtacgtgga cggcgtggag gtgcacaacg ccaagaccaa gccccgggag gagcagtaca      900
acagcaccta ccgggtggtg agcgtgctca ccgtgctgca ccaggactgg ctgaacggca      960
aggagtacaa gtgcaaggtg agcaacaagg ccctgcctgc ccccatcgag aagaccatca      1020
gcaaggccaa gggccagccc cgggagcccc aggtgtacac cctgcccccc agccgggagg      1080
agatgaccaa gaaccaggtg tccctcacct gtctggtgaa gggcttctac cccagcgaca      1140
tcgccgtgga gtgggagagc aacggccagc ccgagaacaa ctacaagacc ccccccctg      1200
tgctggacag cgacggcagc ttcttcctgt acagcaagct caccgtggac aagagccggt      1260
ggcagcaggg caacgtgttc agctgcagcg tgatgcacga ggccctgcac aaccactaca      1320
cccagaagag cctgagcctg agccccggca ag                                   1352
```

<210> SEQ ID NO 425
<211> LENGTH: 451
<212> TYPE: PRT
<213> ORGANISM: Homo sapiens

<400> SEQUENCE: 425

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220
```

Asp Lys Thr His Thr Cys Pro Pro Cys Pro Ala Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
435                 440                 445

Pro Gly Lys
    450

<210> SEQ ID NO 426
<211> LENGTH: 111
<212> TYPE: PRT
<213> ORGANISM: Homo sapiens

<400> SEQUENCE: 426

Gln Ser Ala Leu Thr Gln Pro Ala Ala Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Val Thr Val Leu Gly
            100                 105                 110

<210> SEQ ID NO 427
<211> LENGTH: 660
<212> TYPE: DNA
<213> ORGANISM: Homo sapiens

<400> SEQUENCE: 427

```
cagtctgccc tgactcagcc tgccgccgtg tctgggtctc ctggacagtc gatcaccatc    60
tcctgcactg gaaccagcag tgacgttggt ggttataact atgtctcctg gtaccaacag   120
cacccaggca aagcccccaa actcatgatt tatgaggtca gtaatcggcc ctcagggggtt  180
tctaatcgct tctctggctc caagtctggc aacacggcct ccctgaccat ctctgggctc   240
caggctgagg acgaggctga ttattactgc agctcatata caagcagcag cacttatgtc   300
ttcggaactg ggaccaaggt caccgtccta ggtgcggccg caggccagcc caaggccgct   360
cccagcgtga ccctgttccc ccctcctcc gaggagctgc aggccaacaa ggccaccctg    420
gtgtgcctca tcagcgactt ctaccctggc gccgtgaccg tggcctggaa ggccgacagc   480
agccccgtga aggccggcgt ggagaccacc acccccagca gcagagcaa caacaagtac    540
gccgccagca gctacctgag cctcacccc gagcagtgga gagccaccg agctacagc      600
tgccaggtga cccacgaggg cagcaccgtg agaagaccg tggcccccac cgagtgcagc    660
```

<210> SEQ ID NO 428
<211> LENGTH: 220
<212> TYPE: PRT
<213> ORGANISM: Homo sapiens

<400> SEQUENCE: 428

```
Gln Ser Ala Leu Thr Gln Pro Ala Ala Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Val Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220
```

<210> SEQ ID NO 429
<211> LENGTH: 121
<212> TYPE: PRT

<213> ORGANISM: Homo sapiens

<400> SEQUENCE: 429

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120
```

<210> SEQ ID NO 430
<211> LENGTH: 1353
<212> TYPE: DNA
<213> ORGANISM: Homo sapiens

<400> SEQUENCE: 430

```
gaggtgcagc tggtggagtc tgggggctgag gtgaagaagc tggggtcctc ggtgaaagtc    60
tcttgcaagg cttctggagg ccccttccgc agctatgcta tcagctgggt gcgacaggcc   120
cctggacaag gccctgagtg gatgggaggg atcatcccta ttttttggtac aacaaaatac   180
gcaccgaagt tccagggcag agtcacgatt accgcggacg atttcgcggg cacagtttac   240
atggagctga gcagcctgcg atctgaggac acggccatgt actactgtgc aaaacatatg   300
gggtaccagg tgcgcgaaac tatggacgtc tgggggcaaag ggaccacggt caccgtctcg   360
agtgctagca ccaagggccc cagcgtgttc cccctggccc ccagcagcaa gagcaccagc   420
ggcggcacag ccgccctggg ctgcctggtg aaggactact cccccgagcc cgtgaccgtg   480
agctggaaca gcggcgcctt gaccagcggc gtgcacacct tccccgccgt gctgcagagc   540
agcggcctgt acagcctgag cagcgtggtg accgtgccca gcagcagcct gggcacccag   600
acctacatct gcaacgtgaa ccacaagccc agcaacacca aggtggacaa gcgcgtggag   660
cccaagagct gcgacaagac ccacacctgc cccccctgcc ctgcccccga gctgctgggc   720
ggacccctccg tgttcctgtt cccccccaag cccaaggaca ccctcatgat cagccggacc   780
cccgaggtga cctgcgtggt ggtggacgtg agccacgagg accccgaggt gaagttcaac   840
tggtacgtgg acggcgtgga ggtgcacaac gccaagacca gccccgggga ggagcagtac   900
aacagcacct accgggtggt gagcgtgctc accgtgctgc accaggactg gctgaacggc   960
aaggagtaca agtgcaaggt gagcaacaag gccctgcctg cccccatcga aaagaccatc  1020
agcaaggcca agggccagcc ccgggagccc caggtgtaca ccctgccccc cagccgggag  1080
gagatgacca agaaccaggt gtccctcacc tgtctggtga agggcttcta ccccagcgac  1140
atcgccgtgg agtgggagag caacggccag cccgagaaca actacaagac cacccccct  1200
gtgctggaca gcgacggcag cttcttcctg tacagcaagc tcaccgtgga caagagccgg  1260
tggcagcagg gcaacgtgtt cagctgcagc gtgatgcacg aggccctgca caaccactac  1320
```
acccagaaga gcctgagcct gagccccggc aag                                             1353

<210> SEQ ID NO 431
<211> LENGTH: 451
<212> TYPE: PRT
<213> ORGANISM: Homo sapiens

<400> SEQUENCE: 431

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 432
<211> LENGTH: 111
<212> TYPE: PRT
<213> ORGANISM: Homo sapiens

<400> SEQUENCE: 432

Ser Tyr Val Leu Thr Gln Pro Pro Ser Val Ser Gly Thr Pro Gly Gln
1               5                   10                  15

Arg Val Thr Ile Ser Cys Ser Gly Ser Arg Ser Asn Val Gly Asp Asn
            20                  25                  30

Ser Val Tyr Trp Tyr Gln His Val Pro Glu Met Ala Pro Lys Leu Leu
        35                  40                  45

Val Tyr Lys Asn Thr Gln Arg Pro Ser Gly Val Pro Ala Arg Phe Ser
    50                  55                  60

Gly Ser Lys Ser Gly Thr Ser Ala Ser Leu Ala Ile Ile Gly Leu Gln
65                  70                  75                  80

Ser Gly Asp Glu Ala Asp Tyr Tyr Cys Val Ala Trp Asp Asp Ser Val
                85                  90                  95

Asp Gly Tyr Val Phe Gly Ser Gly Thr Lys Val Thr Val Leu Gly
            100                 105                 110

<210> SEQ ID NO 433
<211> LENGTH: 660
<212> TYPE: DNA
<213> ORGANISM: Homo sapiens

<400> SEQUENCE: 433
tcctatgtgc tgactcagcc accctcagtc tctgggaccc ccgggcagag ggtcaccatc     60
tcttgctctg gaagccgctc caacgtcgga gataattctg tatattggta tcaacacgtc    120
ccagaaatgg cccccaaact cctcgtctat aagaatactc aacggccctc aggagtccct    180
gcccggtttt ccggctccaa gtctggcact tcagcctccc tggccatcat tggcctccag    240
tccggcgatg aggctgatta ttattgtgtg gcatgggatg acagcgtaga tggctatgtc    300
ttcggatctg gcaccaaggt caccgtccta ggtgcggccg caggccagcc caaggccgct    360
cccagcgtga ccctgttccc ccctcctcc gaggagctgc aggccaacaa ggccaccctg    420
gtgtgcctca tcagcgactt ctaccctggc gccgtgaccg tggcctggaa ggccgacagc    480
agccccgtga aggccggcgt ggagaccacc acccccagca gcagagcaa caacaagtac    540 gccgccagca gctacctgag cctcaccccc gagcagtgga gagccaccg agctacagc    600 tgccaggtga cccacgaggg cagcaccgtg gagaagaccg tggcccccac cgagtgcagc    660
```

```
<210> SEQ ID NO 434
<211> LENGTH: 220
<212> TYPE: PRT
<213> ORGANISM: Homo sapiens

<400> SEQUENCE: 434

Ser Tyr Val Leu Thr Gln Pro Pro Ser Val Ser Gly Thr Pro Gly Gln
1               5                   10                  15

Arg Val Thr Ile Ser Cys Ser Gly Ser Arg Ser Asn Val Gly Asp Asn
            20                  25                  30

Ser Val Tyr Trp Tyr Gln His Val Pro Glu Met Ala Pro Lys Leu Leu
        35                  40                  45

Val Tyr Lys Asn Thr Gln Arg Pro Ser Gly Val Pro Ala Arg Phe Ser
    50                  55                  60

Gly Ser Lys Ser Gly Thr Ser Ala Ser Leu Ala Ile Ile Gly Leu Gln
65                  70                  75                  80

Ser Gly Asp Glu Ala Asp Tyr Tyr Cys Val Ala Trp Asp Asp Ser Val
                85                  90                  95

Asp Gly Tyr Val Phe Gly Ser Gly Thr Lys Val Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220

<210> SEQ ID NO 435
<211> LENGTH: 121
<212> TYPE: PRT
<213> ORGANISM: Homo sapiens

<400> SEQUENCE: 435

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
```

<210> SEQ ID NO 436
<211> LENGTH: 1353
<212> TYPE: DNA
<213> ORGANISM: Homo sapiens

<400> SEQUENCE: 436

```
gaggtgcagc tggtggagtc tggggctgag gtgaagaagc ctgggtcctc ggtgaaagtc    60
tcttgcaagg cttctggagg ccccttccgc agctatgcta tcagctgggt gcgacaggcc   120
cctggacaag ggcctgagtg gatgggaggg atcatcccta tttttggtac aacaaaatac   180
gcaccgaagt tccagggcag agtcacgatt accgcggacg atttcgcggg cacagtttac   240
atggagctga gcagcctgcg atctgaggac acggccatgt actactgtgc gaaacatatg   300
gggtaccagg tgcgcgaaac tatggacgtc tggggcaaag ggaccacggt caccgtctcg   360
agtgctagca ccaagggccc cagcgtgttc cccctggccc ccagcagcaa gagcaccagc   420
ggcggcacag ccgccctggg ctgcctggtg aaggactact ccccgagcc cgtgaccgtg   480
agctggaaca gcggcgcctt gaccagcggc gtgcacacct tcccgccgt gctgcagagc   540
agcggcctgt acagcctgag cagcgtggtg accgtgccca gcagcagcct gggcacccag   600
acctacatct gcaacgtgaa ccacaagccc agcaacacca aggtggacaa gcgcgtggag   660
cccaagagct gcgacaagac ccacacctgc cccccctgcc ctgcccccga gctgctgggc   720
ggaccctccg tgttcctgtt ccccccaag cccaaggaca ccctcatgat cagccggacc   780
cccgaggtga cctgcgtggt ggtggacgtg agccacgagg accccgaggt gaagttcaac   840
tggtacgtgg acggcgtgga ggtgcacaac gccaagacca gcccggga ggagcagtac   900
aacagcacct accgggtggt gagcgtgctc accgtgctgc accaggactg gctgaacggc   960
aaggagtaca agtgcaaggt gagcaacaag gccctgcctg cccccatcga aaagaccatc  1020
agcaaggcca agggccagcc ccgggagccc caggtgtaca ccctgccccc cagccggga   1080
gagatgacca gaaccaggt gtccctcacc tgtctggtga aggcttcta ccccagcga   1140
atcgccgtgg agtgggaga caacggccag cccaaggaca actacaagac cacccccct   1200
gtgctggaca gcgacggcag cttcttcctg tacagcaagc tcaccgtgga caagagccgg   1260
tggcagcagg gcaacgtgtt cagctgcagc gtgatgcacg aggccctgca caaccactac  1320
acccagaaga gcctgagcct gagcccgggc aag                                1353
```

<210> SEQ ID NO 437
<211> LENGTH: 451
<212> TYPE: PRT
<213> ORGANISM: Homo sapiens

<400> SEQUENCE: 437

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80
```

Met Glu Leu Ser Ser Leu Arg Ser Glu Asp Thr Ala Met Tyr Tyr Cys
            85                  90                  95

Ala Lys His Met Gly Tyr Gln Val Arg Glu Thr Met Asp Val Trp Gly
            100                 105                 110

Lys Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 438
<211> LENGTH: 112
<212> TYPE: PRT
<213> ORGANISM: Homo sapiens

<400> SEQUENCE: 438

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asp
            20                  25                  30

Tyr Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asn Tyr Tyr Cys Ala Thr Trp Asp Arg Arg Pro
                85                  90                  95

Thr Ala Tyr Val Val Phe Gly Gly Gly Thr Lys Leu Thr Val Leu Gly
            100                 105                 110
```

<210> SEQ ID NO 439
<211> LENGTH: 660
<212> TYPE: DNA
<213> ORGANISM: Homo sapiens

<400> SEQUENCE: 439

```
cagtctgtgt tgacgcagcc gccctcagtg tctgcggccc caggacagaa ggtcaccatc    60
tcctgctctg gaagcagctc caacattggg aatgattatg tatcctggta ccagcagctc   120
ccaggaacag cccccaaact cctcatttat gacaataata agcgaccctc agggattcct   180
gaccgattct ctggctccaa gtctggcacg tcagccaccc tgggcatcac cggactccag   240
actggggacg aggccaacta ttactgcgca acatgggatc gccgcccgac tgcttatgtt   300
gtcttcggcg gagggaccaa gctgaccgtc ctaggtgcgg ccgcaggcca gcccaaggcc   360
gctcccagcg tgaccctgtt cccccccctcc tccgaggagc tgcaggccaa caaggccacc   420
ctggtgtgcc tcatcagcga cttctaccct ggcgccgtga ccgtggcctg aaggccgac   480
agcagccccg tgaaggccgg cgtggagacc accaccccca gcaagcagag caacaacaag   540
tacgccgcca gcagctacct gagcctcacc cccgagcagt ggaagagcca ccggagctac   600
agctgccagg tgacccacga gggcagcacc gtggagaaga ccgtggcccc caccgagtgc   660
```

<210> SEQ ID NO 440
<211> LENGTH: 221
<212> TYPE: PRT
<213> ORGANISM: Homo sapiens

<400> SEQUENCE: 440

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asp
            20                  25                  30

Tyr Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asn Tyr Tyr Cys Ala Thr Trp Asp Arg Arg Pro
                85                  90                  95

Thr Ala Tyr Val Val Phe Gly Gly Gly Thr Lys Leu Thr Val Leu Gly
```

```
            100                 105                 110
Ala Ala Ala Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220

<210> SEQ ID NO 441
<211> LENGTH: 120
<212> TYPE: PRT
<213> ORGANISM: Homo sapiens

<400> SEQUENCE: 441

Gln Val Gln Leu Gln Gln Ser Gly Ala Glu Val Lys Lys Pro Gly Ser
1               5                   10                  15

Ser Val Lys Val Ser Cys Lys Val Ser Gly Val Ile Phe Ser Gly Ser
            20                  25                  30

Ala Ile Ser Trp Val Arg Gln Ala Pro Gly Gln Gly Leu Glu Trp Met
        35                  40                  45

Gly Gly Ile Ser Pro Leu Phe Gly Thr Thr Asn Tyr Ala Gln Lys Phe
    50                  55                  60

Gln Gly Arg Val Thr Ile Thr Ala Asp Gln Ser Thr Asn Thr Thr Tyr
65                  70                  75                  80

Met Glu Val Asn Ser Leu Arg Tyr Glu Asp Thr Ala Val Tyr Phe Cys
                85                  90                  95

Ala Arg Gly Pro Lys Tyr Tyr Ser Glu Tyr Met Asp Val Trp Gly Lys
            100                 105                 110

Gly Thr Thr Val Thr Val Ser Ser
        115                 120

<210> SEQ ID NO 442
<211> LENGTH: 1350
<212> TYPE: DNA
<213> ORGANISM: Homo sapiens

<400> SEQUENCE: 442
caggtacagc tgcagcagtc aggggctgag gtgaagaagc ctgggtcctc ggtgaaggtc      60
tcctgcaagg tttccggagt catttttcagc ggcagtgcga tcagctgggt gcgacaggcc     120
cctggacaag gccttgagtg gatgggaggg atcagccctc tctttggcac aacaaattac     180
gcacaaaagt tccagggcag agtcacgatt accgcggacc aatccacgaa cacaacctac     240
atggaggtga acagcctgag atatgaggac acggccgtgt atttctgtgc gcgaggtcca     300
aaatattaca gtgagtacat ggacgtctgg ggcaaaggga ccacggtcac cgtctcgagt     360
gctagcacca aggccccag cgtgttcccc ctggccccca gcagcaagag caccagcggc      420
ggcacagccg ccctgggctg cctggtgaag gactacttcc ccgagcccgt gaccgtgagc     480
```

-continued

```
tggaacagcg gcgccttgac cagcggcgtg cacaccttcc ccgccgtgct gcagagcagc    540
ggcctgtaca gcctgagcag cgtggtgacc gtgcccagca gcagcctggg cacccagacc    600
tacatctgca acgtgaacca caagcccagc aacaccaagg tggacaaacg cgtggagccc    660
aagagctgcg acaagaccca cacctgcccc ccctgccctg cccccgagct gctgggcgga    720
ccctccgtgt tcctgttccc ccccaagccc aaggacaccc tcatgatcag ccggacccc    780 gaggtgacct gcgtggtggt ggacgtgagc cacgaggacc ccgaggtgaa gttcaactgg    840
tacgtggacg gcgtggaggt gcacaacgcc aagaccaagc ccgggagga gcagtacaac    900 agcacctacc gggtggtgag cgtgctcacc gtgctgcacc aggactggct gaacggcaag    960
gagtacaagt gcaaggtgag caacaaggcc ctgcctgccc ccatcgagaa gaccatcagc   1020
aaggccaagg gccagccccg ggagccccag gtgtacaccc tgcccccag ccggaggag    1080 atgaccaaga accaggtgtc cctcacctgt ctggtgaagg gcttctaccc cagcgacatc   1140
gccgtggagt gggagagcaa cggccagccc gagaacaact acaagaccac ccccctgtg    1200 ctggacagcg acggcagctt cttcctgtac agcaagctca ccgtggacaa gagccggtgg   1260
cagcagggca acgtgttcag ctgcagcgtg atgcacgagg ccctgcacaa ccactacacc   1320
cagaagagcc tgagcctgag ccccggcaag                                    1350
```

<210> SEQ ID NO 443
<211> LENGTH: 450
<212> TYPE: PRT
<213> ORGANISM: Homo sapiens

<400> SEQUENCE: 443

```
Gln Val Gln Leu Gln Gln Ser Gly Ala Glu Val Lys Lys Pro Gly Ser
1               5                   10                  15

Ser Val Lys Val Ser Cys Lys Val Ser Gly Val Ile Phe Ser Gly Ser
            20                  25                  30

Ala Ile Ser Trp Val Arg Gln Ala Pro Gly Gln Gly Leu Glu Trp Met
        35                  40                  45

Gly Gly Ile Ser Pro Leu Phe Gly Thr Thr Asn Tyr Ala Gln Lys Phe
    50                  55                  60

Gln Gly Arg Val Thr Ile Thr Ala Asp Gln Ser Thr Asn Thr Thr Tyr
65                  70                  75                  80

Met Glu Val Asn Ser Leu Arg Tyr Glu Asp Thr Ala Val Tyr Phe Cys
                85                  90                  95

Ala Arg Gly Pro Lys Tyr Tyr Ser Glu Tyr Met Asp Val Trp Gly Lys
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220
```

```
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 444
<211> LENGTH: 109
<212> TYPE: PRT
<213> ORGANISM: Homo sapiens

<400> SEQUENCE: 444

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Val Pro Thr Leu Leu Ile
        35                  40                  45

Tyr Asp Ala Ser Thr Leu Arg Ser Gly Val Pro Ser Arg Phe Ser Gly
    50                  55                  60

Ser Gly Ser Ala Thr Asp Phe Thr Leu Thr Ile Ser Ser Leu Gln Pro
65                  70                  75                  80

Glu Asp Val Ala Thr Tyr Tyr Cys Gln Arg Tyr Asn Ser Ala Pro Pro
            85                  90                  95

Ile Thr Phe Gly Gln Gly Thr Arg Leu Glu Ile Lys Arg
        100                 105

<210> SEQ ID NO 445
<211> LENGTH: 642
<212> TYPE: DNA
```

<213> ORGANISM: Homo sapiens

<400> SEQUENCE: 445

```
gacatccaga tgacccagtc tccatcctcc ctgtctgcat ctgtaggaga cagagtcacc      60
atcacttgcc gggcgagtca gggcattagc agttatttag cctggtatca gcagaagcca     120
gggaaagttc ctacactcct gatctatgat gcatccactt tgcgatcagg ggtcccatct     180
cgcttcagtg gcagtggatc tgcgacagat ttcactctca ccatcagcag cctgcagcct     240
gaagatgttg caacttatta ctgtcaaagg tataacagtg ccccccccgat caccttcggc     300
caagggacac gactggagat taaacgtgcg gccgcaccca gcgtgttcat cttcccccc      360
tccgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gagagcgtga ccgagcagga cagcaaggac tccacctaca gcctgagcag caccctcacc     540
ctgagcaagg ccgactacga aaagcacaag gtgtacgcct gcgaggtgac ccaccagggc     600
ctgagcagcc ccgtgaccaa gagcttcaac cggggcgagt gt                        642
```

<210> SEQ ID NO 446
<211> LENGTH: 214
<212> TYPE: PRT
<213> ORGANISM: Homo sapiens

<400> SEQUENCE: 446

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Val Pro Thr Leu Leu Ile
        35                  40                  45

Tyr Asp Ala Ser Thr Leu Arg Ser Gly Val Pro Ser Arg Phe Ser Gly
    50                  55                  60

Ser Gly Ser Ala Thr Asp Phe Thr Leu Thr Ile Ser Ser Leu Gln Pro
65                  70                  75                  80

Glu Asp Val Ala Thr Tyr Tyr Cys Gln Arg Tyr Asn Ser Ala Pro Pro
                85                  90                  95

Ile Thr Phe Gly Gln Gly Thr Arg Leu Glu Ile Lys Arg Ala Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 447
<211> LENGTH: 120

```
<212> TYPE: PRT
<213> ORGANISM: Homo sapiens

<400> SEQUENCE: 447

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Met Gly Met Phe Gly Thr Thr Asn Tyr Ala Gln Lys Phe
    50                  55                  60

Gln Gly Arg Val Thr Ile Thr Ala Asp Glu Phe Thr Ser Ala Ala Tyr
65                  70                  75                  80

Met Glu Leu Arg Ser Leu Arg Ser Glu Asp Thr Ala Val Tyr Tyr Cys
                85                  90                  95

Ala Arg Ser Ser Gly Tyr Tyr Pro Glu Tyr Phe Gln Asp Trp Gly Gln
            100                 105                 110

Gly Thr Leu Val Thr Val Ser Ser
        115                 120

<210> SEQ ID NO 448
<211> LENGTH: 1350
<212> TYPE: DNA
<213> ORGANISM: Homo sapiens

<400> SEQUENCE: 448
caggtccagc tggtacagtc tggggctgag gtgaagaagc ctgggtcctc ggtgaaggtc      60
tcctgcaagg cttctggagg caccttcagt agttatgcta tcagctgggt gcgacaggcc     120
cctggacaag gccttgagtg gatgggagga atcatgggta tgtttggcac aactaactac     180
gcacagaagt tccagggcag agtcacgatt accgcggacg aattcacgag cgcagcctac     240
atggagctga ggagcctgag atctgaggac acggccgtct actactgtgc gaggtctagt     300
ggttattacc ccgaatactt ccaggactgg ggccagggca ccctggtcac cgtctcgagt     360
gctagcacca agggccccag cgtgttcccc ctggcccca gcagcaagag caccagcggc      420
ggcacagccg ccctgggctg cctggtgaag gactacttcc ccgagccgt gaccgtgagc      480
tggaacagcg gcgccttgac cagcggcgtg cacaccttcc ccgccgtgct gcagagcagc     540
ggcctgtaca gcctgagcag cgtggtgacc gtgcccagca gcctgggcac ccagacc       600
tacatctgca acgtgaacca caagcccagc aacaccaagg tggacaaacg cgtggagccc     660
aagagctgcg acaagaccca cacctgcccc cctgccctg ccccgagct gctgggcgga      720
ccctccgtgt tcctgttccc ccccaagccc aaggacaccc tcatgatcag ccggaccccc     780
gaggtgacct gcgtggtggt ggacgtgagc cacgaggacc ccgaggtgaa gttcaactgg     840
tacgtggacg gcgtggaggt gcacaacgcc aagaccaagc ccggaggga gcagtacaac     900
agcacctacc gggtggtgag cgtgctcacc gtgctgcacc aggactggct gaacggcaag     960
gagtacaagt gcaaggtgag caacaaggcc ctgcctgccc ccatcgagaa gaccatcagc    1020
aaggccaagg gccagccccg ggagccccag gtgtacaccc tgccccccag ccgggaggag    1080
atgaccaaga accaggtgtc cctcacctgt ctggtgaagg gcttctaccc cagcgacatc    1140
gccgtggagt gggagagcaa cggccagccc gagaacaact acaagaccac ccccctgtg    1200
ctggacagcg acggcagctt cttcctgtac agcaagctca ccgtggacaa gagccggtgg    1260
```

```
cagcagggca acgtgttcag ctgcagcgtg atgcacgagg ccctgcacaa ccactacacc    1320
cagaagagcc tgagcctgag ccccggcaag                                    1350
```

<210> SEQ ID NO 449
<211> LENGTH: 450
<212> TYPE: PRT
<213> ORGANISM: Homo sapiens

<400> SEQUENCE: 449

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Gly | Thr | Phe | Ser | Ser | Tyr |
| | | | 20 | | | | | 25 | | | | | 30 | | |

| Ala | Ile | Ser | Trp | Val | Arg | Gln | Ala | Pro | Gly | Gln | Gly | Leu | Glu | Trp | Met |
| | | 35 | | | | | 40 | | | | | 45 | | | |

| Gly | Gly | Ile | Met | Gly | Met | Phe | Gly | Thr | Thr | Asn | Tyr | Ala | Gln | Lys | Phe |
| 50 | | | | | 55 | | | | | 60 | | | | | |

| Gln | Gly | Arg | Val | Thr | Ile | Thr | Ala | Asp | Glu | Phe | Thr | Ser | Ala | Ala | Tyr |
| 65 | | | | 70 | | | | | 75 | | | | | 80 | |

| Met | Glu | Leu | Arg | Ser | Leu | Arg | Ser | Glu | Asp | Thr | Ala | Val | Tyr | Tyr | Cys |
| | | | | 85 | | | | | 90 | | | | | 95 | |

| Ala | Arg | Ser | Ser | Gly | Tyr | Tyr | Pro | Glu | Tyr | Phe | Gln | Asp | Trp | Gly | Gln |
| | | | 100 | | | | | 105 | | | | | 110 | | |

| Gly | Thr | Leu | Val | Thr | Val | Ser | Ser | Ala | Ser | Thr | Lys | Gly | Pro | Ser | Val |
| | | 115 | | | | | 120 | | | | | 125 | | | |

| Phe | Pro | Leu | Ala | Pro | Ser | Ser | Lys | Ser | Thr | Ser | Gly | Gly | Thr | Ala | Ala |
| 130 | | | | | 135 | | | | | 140 | | | | | |

| Leu | Gly | Cys | Leu | Val | Lys | Asp | Tyr | Phe | Pro | Glu | Pro | Val | Thr | Val | Ser |
| 145 | | | | 150 | | | | | 155 | | | | | 160 | |

| Trp | Asn | Ser | Gly | Ala | Leu | Thr | Ser | Gly | Val | His | Thr | Phe | Pro | Ala | Val |
| | | | | 165 | | | | | 170 | | | | | 175 | |

| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |

| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |

| Pro | Ser | Asn | Thr | Lys | Val | Asp | Lys | Arg | Val | Glu | Pro | Lys | Ser | Cys | Asp |
| 210 | | | | | 215 | | | | | 220 | | | | | |

| Lys | Thr | His | Thr | Cys | Pro | Pro | Cys | Pro | Ala | Pro | Glu | Leu | Leu | Gly | Gly |
| 225 | | | | 230 | | | | | 235 | | | | | 240 | |

| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |

| Ser | Arg | Thr | Pro | Glu | Val | Thr | Cys | Val | Val | Val | Asp | Val | Ser | His | Glu |
| | | | 260 | | | | | 265 | | | | | 270 | | |

| Asp | Pro | Glu | Val | Lys | Phe | Asn | Trp | Tyr | Val | Asp | Gly | Val | Glu | Val | His |
| | | 275 | | | | | 280 | | | | | 285 | | | |

| Asn | Ala | Lys | Thr | Lys | Pro | Arg | Glu | Glu | Gln | Tyr | Asn | Ser | Thr | Tyr | Arg |
| | 290 | | | | | 295 | | | | | 300 | | | | |

| Val | Val | Ser | Val | Leu | Thr | Val | Leu | His | Gln | Asp | Trp | Leu | Asn | Gly | Lys |
| 305 | | | | | 310 | | | | | 315 | | | | | 320 |

| Glu | Tyr | Lys | Cys | Lys | Val | Ser | Asn | Lys | Ala | Leu | Pro | Ala | Pro | Ile | Glu |
| | | | 325 | | | | | 330 | | | | | 335 | | |

| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |

| Thr | Leu | Pro | Pro | Ser | Arg | Glu | Glu | Met | Thr | Lys | Asn | Gln | Val | Ser | Leu |

```
                355                 360                 365
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 450
<211> LENGTH: 107
<212> TYPE: PRT
<213> ORGANISM: Homo sapiens

<400> SEQUENCE: 450

Gln Ser Val Leu Thr Gln Pro Pro Ser Glu Ser Val Ser Pro Gly Gln
1               5                   10                  15

Thr Ala Ser Val Thr Cys Ser Gly His Lys Leu Gly Asp Lys Tyr Val
            20                  25                  30

Ser Trp Tyr Gln Gln Lys Pro Gly Gln Ser Pro Val Leu Leu Ile Tyr
        35                  40                  45

Gln Asp Asn Arg Arg Pro Ser Gly Ile Pro Glu Arg Phe Ile Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Gly
            100                 105

<210> SEQ ID NO 451
<211> LENGTH: 648
<212> TYPE: DNA
<213> ORGANISM: Homo sapiens

<400> SEQUENCE: 451
cagtctgtgc tgactcagcc accctcagag tccgtgtccc caggacagac agccagcgtc      60
acctgctctg gacataaatt gggggataaa tatgtttcgt ggtatcagca gaagccaggc     120
cagtcccctg tattactcat ctatcaagat aacaggcggc cctcagggat ccctgagcga     180
ttcataggct ccaactctgg gaacacagcc actctgacca tcagcgggac ccaggctctg     240
gatgaggctg actattactg tcaggcgtgg gacagcagca ctgcggtttt cggcggaggg     300
accaagctga ccgtcctagg tgcggccgca ggccagccca aggccgctcc cagcgtgacc     360
ctgttccccc cctcctccga ggagctgcag gccaacaagg ccaccctggt gtgcctcatc     420
agcgacttct accctggcgc cgtgaccgtg gcctggaagg ccgacagcag ccccgtgaag     480
gccggcgtgg agaccaccac ccccagcaag cagagcaaca caagtacgc cgccagcagc     540 tacctgagcc tcaccccga gcagtggaag agccaccgga gctacagctg ccaggtgacc     600
cacgagggca gcaccgtgga gaagaccgtg gcccccaccg agtgcagc                 648
```

<210> SEQ ID NO 452
<211> LENGTH: 216
<212> TYPE: PRT
<213> ORGANISM: Homo sapiens

<400> SEQUENCE: 452

Gln Ser Val Leu Thr Gln Pro Pro Ser Glu Ser Val Ser Pro Gly Gln
1               5                   10                  15

Thr Ala Ser Val Thr Cys Ser Gly His Lys Leu Gly Asp Lys Tyr Val
            20                  25                  30

Ser Trp Tyr Gln Gln Lys Pro Gly Gln Ser Pro Val Leu Leu Ile Tyr
        35                  40                  45

Gln Asp Asn Arg Arg Pro Ser Gly Ile Pro Glu Arg Phe Ile Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Gly Ala Ala Ala Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 453
<211> LENGTH: 120
<212> TYPE: PRT
<213> ORGANISM: Homo sapiens

<400> SEQUENCE: 453

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Thr Trp Val Arg Gln Ala Pro Gly Gln Gly Leu Glu Trp Met
        35                  40                  45

Gly Gly Ile Ile Gly Met Phe Gly Ser Thr Asn Tyr Ala Gln Asn Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Gly Tyr Tyr Pro Ala Tyr Leu His Trp Gly Gln
            100                 105                 110

Gly Thr Leu Val Thr Val Ser Ser
         115                 120

<210> SEQ ID NO 454
<211> LENGTH: 1350
<212> TYPE: DNA
<213> ORGANISM: Homo sapiens

<400> SEQUENCE: 454

| | | |
|---|---|---|
| cagatgcagc tggtgcagtc tggggctgag gtgaagaagc tggggtcctc ggtgaaggtc | 60 |
| tcctgcaagg cttctggagg caccttctcc agttatgcta tcacctgggt gcgacaggcc | 120 |
| cctggacaag gcttgagtg gatgggaggg atcatcggta tgtttggttc aacaaactac | 180 |
| gcacagaact tccagggcag agtcacgatt accgcggacg aatccacgag cacagcctac | 240 |
| atggagctga gcagcctcag atctgaggac acggccgtgt attactgtgc gagaagtact | 300 |
| ggttattacc ctgcatacct ccaccactgg ggccagggca ccctggtcac cgtctcgagt | 360 |
| gctagcacca agggcccag cgtgttcccc ctggcccca gcagcaagag caccagcggc | 420 |
| ggcacagccg ccctgggctg cctggtgaag gactacttcc ccgagcccgt gaccgtgagc | 480 |
| tggaacagcg gcgccttgac cagcggcgtg cacaccttcc ccgccgtgct gcagagcagc | 540 |
| ggcctgtaca gcctgagcag cgtggtgacc gtgcccagca gcagcctggg cacccagacc | 600 |
| tacatctgca acgtgaacca caagcccagc aacaccaagg tggacaaacg cgtggagccc | 660 |
| aagagctgcg acaagaccca cacctgcccc cctgccctg ccccgagct gctgggcgga | 720 |
| ccctccgtgt tcctgttccc ccccaagccc aaggacaccc tcatgatcag ccggaccccc | 780 |
| gaggtgacct gcgtggtggt ggacgtgagc cacgaggacc ccgaggtgaa gttcaactgg | 840 |
| tacgtggacg gcgtggaggt gcacaacgcc aagaccaagc ccggaggagga gcagtacaac | 900 |
| agcacctacc gggtggtgag cgtgctcacc gtgctgcacc aggactggct gaacggcaag | 960 |
| gagtacaagt gcaaggtgag caacaaggcc ctgcctgcc catcgagaa gaccatcagc | 1020 |
| aaggccaagg gccagccccg ggagccccag gtgtacaccc tgccccccag ccgggaggag | 1080 |
| atgaccaaga accaggtgtc cctcacctgt ctggtgaagg gcttctaccc cagcgacatc | 1140 |
| gccgtggagt gggagagcaa cggccagccc gagaacaact acaagaccac cccccctgtg | 1200 |
| ctggacagcg acggcagctt cttcctgtac agcaagctca ccgtggacaa gagccggtgg | 1260 |
| cagcagggca acgtgttcag ctgcagcgtg atgcacgagg ccctgcacaa ccactacacc | 1320 |
| cagaagagcc tgagcctgag ccccggcaag | 1350 |

<210> SEQ ID NO 455
<211> LENGTH: 450
<212> TYPE: PRT
<213> ORGANISM: Homo sapiens

<400> SEQUENCE: 455

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Thr Trp Val Arg Gln Ala Pro Gly Gln Gly Leu Glu Trp Met
        35                  40                  45

Gly Gly Ile Ile Gly Met Phe Gly Ser Thr Asn Tyr Ala Gln Asn Phe
    50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                 85                  90                  95

Ala Arg Ser Thr Gly Tyr Tyr Pro Ala Tyr Leu His His Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 456
<211> LENGTH: 111
<212> TYPE: PRT
<213> ORGANISM: Homo sapiens
```

<400> SEQUENCE: 456

Gly Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr His Val Phe Gly Thr Gly Thr Lys Val Thr Val Leu Gly
            100                 105                 110

<210> SEQ ID NO 457
<211> LENGTH: 660
<212> TYPE: DNA
<213> ORGANISM: Homo sapiens

<400> SEQUENCE: 457
cagtctgccc tgactcagcc tcgctcagtg tccgggtctc ctggacagtc agtcaccatc     60
tcctgcactg gaaccagcag tgatgttggt ggttataact atgtctcctg gtaccaacag    120
cacccaggca agcccccaa actcatgatt tatgatgtca gtaagcggcc ctcaggggtc    180
cctgatcgct tctctggctc caagtctggc aacacggcct ccctgaccat ctctgggctc    240
caggctgagg atgaggctga ttattactgc agctcatata caagcagcag cactcatgtc    300
ttcggaactg ggaccaaggt caccgtccta ggtgcggccg caggccagcc caaggccgct    360
cccagcgtga ccctgttccc cccctcctcc gaggagctgc aggccaacaa ggccaccctg    420
gtgtgcctca tcagcgactt ctaccctggc gccgtgaccg tggcctggaa ggccgacagc    480
agccccgtga aggccggcgt ggagaccacc acccccagca gcagagcaa caacaagtac    540 gccgccagca gctacctgag cctcacccccc gagcagtgga gagccaccg gagctacagc    600 tgccaggtga cccacgaggg cagcaccgtg agaagaccg tggcccccac cgagtgcagc    660

<210> SEQ ID NO 458
<211> LENGTH: 220
<212> TYPE: PRT
<213> ORGANISM: Homo sapiens

<400> SEQUENCE: 458

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

```
Ser Thr His Val Phe Gly Thr Gly Thr Lys Val Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
            210                 215                 220
```

<210> SEQ ID NO 459
<211> LENGTH: 121
<212> TYPE: PRT
<213> ORGANISM: Homo sapiens

<400> SEQUENCE: 459

```
Glu Val Gln Leu Val Glu Thr Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Lys Trp Gly Pro Gln Ala Ala Phe Asp Ile Trp Gly
            100                 105                 110

Gln Gly Thr Met Val Thr Val Ser Ser
        115                 120
```

<210> SEQ ID NO 460
<211> LENGTH: 1353
<212> TYPE: DNA
<213> ORGANISM: Homo sapiens

<400> SEQUENCE: 460

```
gaggtgcagc tggtggagac cggggctgag gtgaagaagc ctggggcctc agtgaaggtt    60
tcctgcaagg catctggata caccttcacc agctactata tgcactgggt gcgacaggcc   120
cctggacaag gcttgagtg gatgggatgg atcaaccta acagtggtgg cacaaactat    180
gcacagaagt tcagggcag gtcaccatg accaggaca cgtccatcag cacagcctac    240
atggagctga gcaggctgag atctgacgac acggccgtgt attactgtgc gagagagggg    300
aaatggggac tcaagcggc ttttgatatc tggggccaag ggacaatggt caccgtctcg    360
agtgctagca ccaagggccc cagcgtgttc cccctggccc ccagcagcaa gagcaccagc    420
ggcggcacag ccgccctggg ctgcctggtg aaggactact tccccgagcc cgtgaccgtg    480
```

```
agctggaaca gcggcgcctt gaccagcggc gtgcacacct tccccgccgt gctgcagagc    540
agcggcctgt acagcctgag cagcgtggtg accgtgccca gcagcagcct gggcacccag    600
acctacatct gcaacgtgaa ccacaagccc agcaacacca aggtggacaa cgcgtggag    660 cccaagagct gcgacaagac ccacacctgc cccccctgcc ctgccccga gctgctgggc    720 ggaccctccg tgttcctgtt cccccccaag cccaaggaca ccctcatgat cagccggacc    780
cccgaggtga cctgcgtggt ggtggacgtg agccacgagg accccgaggt gaagttcaac    840
tggtacgtgg acggcgtgga ggtgcacaac gccaagacca gccccggga ggagcagtac    900 aacagcacct accgggtggt gagcgtgctc accgtgctgc accaggactg gctgaacggc    960
aaggagtaca agtgcaaggt gagcaacaag gccctgcctg cccccatcga aagaccatc    1020 agcaaggcca agggccagcc ccgggagccc caggtgtaca ccctgccccc cagccgggag    1080
gagatgacca agaaccaggt gtccctcacc tgtctggtga agggcttcta ccccagcgac    1140
atcgccgtgg agtgggagag caacggccag cccgagaaca actacaagac cacccccct    1200 gtgctggaca gcgacggcag cttcttcctg tacagcaagc tcaccgtgga caagagccgg    1260
tggcagcagg gcaacgtgtt cagctgcagc gtgatgcacg aggccctgca caaccactac    1320
acccagaaga gcctgagcct gagccccggc aag    1353
```

<210> SEQ ID NO 461
<211> LENGTH: 451
<212> TYPE: PRT
<213> ORGANISM: Homo sapiens

<400> SEQUENCE: 461

```
Glu Val Gln Leu Val Glu Thr Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Lys Trp Gly Pro Gln Ala Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
```

```
                  210                 215                 220
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 462
<211> LENGTH: 109
<212> TYPE: PRT
<213> ORGANISM: Homo sapiens

<400> SEQUENCE: 462

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Asp Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Trp Thr Phe Gly Gln Gly Thr Lys Val Glu Ile Lys Arg
            100                 105

<210> SEQ ID NO 463
<211> LENGTH: 642
```

<212> TYPE: DNA
<213> ORGANISM: Homo sapiens

<400> SEQUENCE: 463

```
gaaattgtga tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat gatgcatcca gcagggccac tgacatccca   180
gacaggttca gtggcagtgg gtctgggaca gacttcactc tcaccatcag cagactggag   240
cctgaagatt ttgcagtgta ttactgtcag cagtatggta gctcactttg gacgttcggc   300
caagggacca aggtggagat caaacgtgcg gccgcaccca gcgtgttcat cttcccccc    360
tccgacgagc agctgaagag cggcaccgcc agcgtggtgt gcctgctgaa caacttctac   420
ccccgggagg ccaaggtgca gtggaaggtg acaacgccc tgcagagcgg caacagccag   480
gagagcgtga ccgagcagga cagcaaggac tccacctaca gcctgagcag caccctcacc   540
ctgagcaagg ccgactacga gaagcacaag gtgtacgcct gcgaggtgac ccaccagggc   600
ctgagcagcc ccgtgaccaa gagcttcaac cggggcgagt gt                      642
```

<210> SEQ ID NO 464
<211> LENGTH: 214
<212> TYPE: PRT
<213> ORGANISM: Homo sapiens

<400> SEQUENCE: 464

```
Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Asp Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Trp Thr Phe Gly Gln Gly Thr Lys Val Glu Ile Lys Arg Ala Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 465

```
<211> LENGTH: 117
<212> TYPE: PRT
<213> ORGANISM: Homo sapiens

<400> SEQUENCE: 465

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
             20                  25                  30

Ala Met Ser Trp Val Arg Gln Ala Pro Gly Lys Gly Leu Glu Trp Val
         35                  40                  45

Ser Ala Ile Ser Ser Ser Gly Asp Ser Thr Tyr Tyr Ala Asp Ser Val
     50                  55                  60

Lys Gly Arg Phe Thr Ile Ser Arg Asp Asn Ala Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Tyr Gly Tyr Thr Phe Asp Pro Trp Gly Gln Gly Thr Leu
            100                 105                 110

Val Thr Val Ser Ser
        115

<210> SEQ ID NO 466
<211> LENGTH: 1341
<212> TYPE: DNA
<213> ORGANISM: Homo sapiens

<400> SEQUENCE: 466
```

| | |
|---|---|
| gaggtgcagc tggtagagtc tgggggaggc ttggtacagc ctggggggtc cctgagactc | 60 |
| tcctgtgcag cctctggatt cacctttagc atctatgcca tgagctgggt ccgccaggca | 120 |
| ccagggaagg ggctggagtg ggtctcagct attagtagta gtggtgatag cacatactac | 180 |
| gcagactccg tgaagggccg gttcaccatc tccagagaca acgccaggaa cacgctgtat | 240 |
| ctgcaaatga acagtctgag agccgaggac acggctgtgt attactgtgc gagagcgtat | 300 |
| ggctacacgt tcgaccccctg gggccaggga accctggtca ccgtctcgag tgctagcacc | 360 |
| aagggcccca gcgtgttccc cctggccccc agcagcaaga gcaccagcgg cggcacagcc | 420 |
| gccctgggct gcctggtgaa ggactacttc cccgagcccg tgaccgtgag ctggaacagc | 480 |
| ggcgccttga ccagcggcgt gcacaccttc cccgccgtgc tgcagagcag cggcctgtac | 540 |
| agcctgagca gcgtggtgac cgtgccagc agcagcctgg gcacccagac ctacatctgc | 600 |
| aacgtgaacc acaagcccag caacaccaag gtggacaaac gcgtggagcc caagagctgc | 660 |
| gacaagaccc acacctgccc ccctgcccct gcccccgagc tgctgggcgg accctccgtg | 720 |
| ttcctgttcc cccccaagcc caagaacacc ctcatgatca gccggacccc cgaggtgacc | 780 |
| tgcgtggtgg tggacgtgag ccacgaggac cccgaggtga agttcaactg gtacgtggac | 840 |
| ggcgtggagg tgcacaacgc caagaccaag ccccggggag gcagtacaa cagcacctac | 900 |
| cgggtggtga gcgtgctcac cgtgctgcac caggactggc tgaacggcaa ggagtacaag | 960 |
| tgcaaggtga gcaacaaggc cctgcctgcc cccatcgaga agaccatcag caaggccaag | 1020 |
| ggccagcccc gggagcccca ggtgtacacc ctgcccccca gccgggagga gatgaccaag | 1080 |
| aaccaggtgt ccctgacctg tctggtgaag ggcttctacc ccagcgacat cgccgtggag | 1140 |
| tgggagagca acggccagcc cgagaacaac tacaagacca cccccctgt gctggacagc | 1200 |
| gacggcagct tcttcctgta cagcaagctc accgtggaca agagccggtg gcagcagggc | 1260 |

```
aacgtgttca gctgcagcgt gatgcacgag gccctgcaca accactacac ccagaagagc    1320
ctgagcctga gccccggcaa g                                              1341
```

<210> SEQ ID NO 467
<211> LENGTH: 447
<212> TYPE: PRT
<213> ORGANISM: Homo sapiens

<400> SEQUENCE: 467

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Gly | Ser | Leu | Arg | Leu | Ser | Cys | Ala | Ala | Ser | Gly | Phe | Thr | Phe | Ser |
| | | | 20 | | | | | 25 | | | | | 30 | |

Ser Ile Tyr Ala Met Ser Trp Val Arg Gln Ala Pro Gly Lys Gly Leu Glu Trp Val
              35                      40                      45

Ser Ala Ile Ser Ser Ser Gly Asp Ser Thr Tyr Tyr Ala Asp Ser Val
    50                      55                      60

Lys Gly Arg Phe Thr Ile Ser Arg Asp Asn Ala Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Tyr Gly Tyr Thr Phe Asp Pro Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445
```

<210> SEQ ID NO 468
<211> LENGTH: 113
<212> TYPE: PRT
<213> ORGANISM: Homo sapiens

<400> SEQUENCE: 468

```
Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg
```

<210> SEQ ID NO 469
<211> LENGTH: 654
<212> TYPE: DNA
<213> ORGANISM: Homo sapiens

<400> SEQUENCE: 469

```
gaaattgtgc tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactccc     300
ctcactttcg gcggagggac caaggtggag atcaaacgtg cggccgcacc cagcgtgttc     360
atcttccccc cctccgacga gcagctgaag agcggcaccg ccagcgtggt gtgcctgctg     420
aacaacttct accccgggga ggccaaggtg cagtggaagg tggacaacgc cctgcagagc     480
ggcaacagcc aggagagcgt gaccgagcag gacagcaagg actccaccta cagcctgagc     540
agcaccctca ccctgagcaa ggccgactac gagaagcaca aggtgtacgc ctgcgaggtg     600
acccaccagg gcctgagcag ccccgtgacc aagagcttca ccggggcga gtgt            654
```

<210> SEQ ID NO 470
<211> LENGTH: 218
<212> TYPE: PRT
<213> ORGANISM: Homo sapiens

<400> SEQUENCE: 470

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Ala Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 471
<211> LENGTH: 122
<212> TYPE: PRT
<213> ORGANISM: Homo sapiens

<400> SEQUENCE: 471

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ser Tyr Gly Ala Tyr Glu Gly Phe Asp Tyr Trp
            100                 105                 110

Gly Gln Gly Thr Leu Val Thr Val Ser Ser
       115                   120

<210> SEQ ID NO 472
<211> LENGTH: 1356
<212> TYPE: DNA
<213> ORGANISM: Homo sapiens

<400> SEQUENCE: 472

| | |
|---|---|
| caggtccagc tggtgcagtc tggggggaggc ctggtcaagc ctgggggtc cctgagactc | 60 |
| tcctgtgcag cctctggatt caccttcagt agctatagca tgaactgggt ccgccaggct | 120 |
| ccagggaagg gctggagtg gtctcatcc attagtagta gtagtagtta catatactac | 180 |
| gtagactcag tgaagggccg attcaccatc tccagagaca acgccaagaa ctcactgtat | 240 |
| ctgcaaatga acagcctgag agccgaggac acggctgtgt attactgtgc gagaggtggt | 300 |
| gggagctacg gggcctacga aggctttgac tactggggcc agggcaccct ggtcaccgtc | 360 |
| tcgagtgcta gcaccaaggg ccccagcgtg ttccccctgg ccccagcag caagagcacc | 420 |
| agcggcggca cagccgccct gggctgcctg gtgaaggact acttccccga gcccgtgacc | 480 |
| gtgagctgga acagcggcgc cttgaccagc ggcgtgcaca ccttcccgc cgtgctgcag | 540 |
| agcagcggcc tgtacagcct gagcagcgtg gtgaccgtgc cagcagcag cctgggcacc | 600 |
| cagacctaca tctgcaacgt gaaccacaag cccagcaaca ccaaggtgga caaacgcgtg | 660 |
| gagcccaaga gctgcgacaa gacccacacc tgcccccct gccctgcccc cgagctgctg | 720 |
| ggcggaccct ccgtgttcct gttccccccc aagcccaagg acaccctcat gatcagccgg | 780 |
| acccccgagg tgacctgcgt ggtggtggac gtgagccacg aggaccccga ggtgaagttc | 840 |
| aactggtacg tggacggcgt ggaggtgcac aacgccaaga ccaagcccg ggaggagcag | 900 |
| tacaacagca cctaccgggt ggtgagcgtg ctcaccgtgc tgcaccagga ctggctgaac | 960 |
| ggcaaggagt acaagtgcaa ggtgagcaac aaggccctgc ctgccccat cgagaagacc | 1020 |
| atcagcaagg ccaagggcca gccccgggag ccccaggtgt acaccctgcc cccagccgg | 1080 |
| gaggagatga ccaagaacca ggtgtccctc acctgtctgg tgaagggctt ctaccccagc | 1140 |
| gacatcgccg tggagtggga gagcaacggc cagcccgaga caactacaa gaccaccccc | 1200 |
| cctgtgctgg acagcgacgg cagcttcttc ctgtacagca agctcaccgt ggacaagagc | 1260 |
| cggtggcagc agggcaacgt gttcagctgc agcgtgatgc acgaggccct gcacaaccac | 1320 |
| tacacccaga gagcctgag cctgagcccc ggcaag | 1356 |

<210> SEQ ID NO 473
<211> LENGTH: 452
<212> TYPE: PRT
<213> ORGANISM: Homo sapiens

<400> SEQUENCE: 473

Gln Val Gln Leu Val Gln Ser Gly Gly Gly Leu Val Lys Pro Gly Gly
1               5                   10                15

Ser Leu Arg Leu Ser Cys Ala Ala Ser Gly Phe Thr Phe Ser Ser Tyr
            20                   25                  30

Ser Met Asn Trp Val Arg Gln Ala Pro Gly Lys Gly Leu Glu Trp Val
        35                   40                  45

Ser Ser Ile Ser Ser Ser Ser Ser Tyr Ile Tyr Tyr Val Asp Ser Val
    50                   55                  60

Lys Gly Arg Phe Thr Ile Ser Arg Asp Asn Ala Lys Asn Ser Leu Tyr
65                   70                 75                80

```
Leu Gln Met Asn Ser Leu Arg Ala Glu Asp Thr Ala Val Tyr Tyr Cys
                85                  90                  95
Ala Arg Gly Gly Gly Ser Tyr Gly Ala Tyr Glu Gly Phe Asp Tyr Trp
            100                 105                 110
Gly Gln Gly Thr Leu Val Thr Val Ser Ser Ala Ser Thr Lys Gly Pro
            115                 120                 125
Ser Val Phe Pro Leu Ala Pro Ser Ser Lys Ser Thr Ser Gly Gly Thr
        130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Arg Val Glu Pro Lys Ser
        210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
        290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
            405                 410                 415
Val Asp Lys Ser Arg Trp Gln Gln Gly Asn Val Phe Ser Cys Ser Val
        420                 425                 430
Met His Glu Ala Leu His Asn His Tyr Thr Gln Lys Ser Leu Ser Leu
        435                 440                 445
Ser Pro Gly Lys
    450

<210> SEQ ID NO 474
<211> LENGTH: 108
<212> TYPE: PRT
<213> ORGANISM: Homo sapiens
```

<400> SEQUENCE: 474

Glu Ile Val Leu Tyr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ala Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Ser Ala Val Tyr Tyr Cys Gln Gln Tyr Gly Arg Thr Pro Leu
                85                  90                  95

Thr Phe Gly Gly Gly Thr Lys Val Glu Ile Lys Arg
            100                 105

<210> SEQ ID NO 475
<211> LENGTH: 639
<212> TYPE: DNA
<213> ORGANISM: Homo sapiens

<400> SEQUENCE: 475
gaaattgtgc tgactcagtc tccaggcacc ctgtctttgt ctccagggga aagagccacc      60
ctctcctgca gggccagtca gcgtgttagc agctacttag cctggtacca acagaaacct    120
ggccaggctc ccaggctcct catctatggt gcatccacca gggccgctgg catcccagac    180
aggttcagtg gcagtgggtc tgggacagac ttcactctca ccatcagcag actggagcct    240
gaagattctg cagtgtatta ctgtcagcag tatggtagga caccgctcac tttcggcgga    300
gggaccaagg tggagatcaa acgtgcggcc gcacccagcg tgttcatctt cccccctcc    360
gacgagcagc tgaagagcgg caccgccagc gtggtgtgcc tgctgaacaa cttctacccc    420
cgggaggcca aggtgcagtg gaaggtggac aacgccctgc agagcggcaa cagccaggag    480
agcgtgaccg agcaggacag caaggactcc acctacagcc tgagcagcac cctcaccctg    540
agcaaggccg actacgagaa gcacaaggtg tacgcctgcg aggtgaccca ccagggcctg    600
agcagccccg tgaccaagag cttcaaccgg ggcgagtgt                            639

<210> SEQ ID NO 476
<211> LENGTH: 213
<212> TYPE: PRT
<213> ORGANISM: Homo sapiens

<400> SEQUENCE: 476

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ala Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Ser Ala Val Tyr Tyr Cys Gln Gln Tyr Gly Arg Thr Pro Leu
                85                  90                  95

```
Thr Phe Gly Gly Gly Thr Lys Val Glu Ile Lys Arg Ala Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 477
<211> LENGTH: 121
<212> TYPE: PRT
<213> ORGANISM: Homo sapiens

<400> SEQUENCE: 477

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120

<210> SEQ ID NO 478
<211> LENGTH: 1353
<212> TYPE: DNA
<213> ORGANISM: Homo sapiens

<400> SEQUENCE: 478
gaggtgcagc tggtggagtc tggggctgag gtgaagaagc ctgggtcctc ggtgaaagtc      60
tcttgcaagg cttctggagg ccccttccgc agctatgcta tcagctgggt gcgacaggcc     120
cctggacaag ggcctgagtg gatgggaggg atcatcccta ttttggtac aacaaaatac     180 gcaccgaagt tccagggcag agtcacgatt accgcggacg atttcgcggg cacagtttac     240
atggagctga gcagcctgcg atctgaggac acggccatgt actactgtgc gaaacatatg     300
gggtaccagg tgcgcgaaac tatggacgtc tggggcaaag ggaccacggt caccgtctcg     360
agtgctagca ccaagggccc cagcgtgttc cccctggccc ccagcagcaa gagcaccagc     420
ggcggcacag ccgccctggg ctgcctggtg aaggactact tccccgagcc cgtgaccgtg     480
```

```
agctggaaca cggcgccttt gaccagcggc gtgcacacct tccccgccgt gctgcagagc    540
agcggcctgt acagcctgag cagcgtggtg accgtgccca gcagcagcct gggcacccag    600
acctacatct gcaacgtgaa ccacaagccc agcaacacca aggtggacaa acgcgtggag    660
cccaagagct gcgacaagac ccacacctgc ccccctgcc ctgccccga gctgctgggc    720 ggaccctccg tgttcctgtt ccccccaag cccaaggaca ccctcatgat cagccggacc    780
cccgaggtga cctgcgtggt ggtggacgtg agccacgagg accccgaggt gaagttcaac    840
tggtacgtgg acggcgtgga ggtgcacaac gccaagacca gccccgggga ggagcagtac    900
aacagcacct accgggtggt gagcgtgctc accgtgctgc accaggactg gctgaacggc    960
aaggagtaca agtgcaaggt gagcaacaag gccctgcctg cccccatcga aagaccatc   1020 agcaaggcca aggccagcc ccgggagccc caggtgtaca ccctgccccc cagccgggag   1080
gagatgacca gaaccaggt gtccctcacc tgtctggtga agggcttcta ccccagcgac   1140
atcgccgtgg agtgggagag caacggccag cccgagaaca actacaagac cccccccct   1200 gtgctggaca gcgacggcag cttcttcctg tacagcaagc tcaccgtgga caagagccgg   1260
tggcagcagg gcaacgtgtt cagctgcagc gtgatgcacg aggccctgca caaccactac   1320
acccagaaga gcctgagcct gagccccggc aag                                1353
```

<210> SEQ ID NO 479
<211> LENGTH: 451
<212> TYPE: PRT
<213> ORGANISM: Homo sapiens

<400> SEQUENCE: 479

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
```

```
            210                 215                 220
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 480
<211> LENGTH: 109
<212> TYPE: PRT
<213> ORGANISM: Homo sapiens

<400> SEQUENCE: 480

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Ala Val Phe Gly Gly Gly Thr Gln Leu Thr Val Leu Gly
            100                 105

<210> SEQ ID NO 481
<211> LENGTH: 654
```

<212> TYPE: DNA
<213> ORGANISM: Homo sapiens

<400> SEQUENCE: 481

```
tcctatgtgc tgactcagcc accctcggtg tcagtggccc caggacagac ggccaggatt      60
acctgtgggg gaaacaacat tggaagtaaa agtgtgcact ggtaccagca gaagccaggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgatcatgc tgtgttcgga     300
ggaggcaccc agctgaccgt cctcggtgcg gccgcaggcc agcccaaggc cgctcccagc     360
gtgaccctgt tcccccctc ctccgaggag ctgcaggcca acaaggccac cctggtgtgc     420
ctcatcagcg acttctaccc tggcgccgtg accgtggcct ggaaggccga cagcagcccc     480
gtgaaggccg gcgtggagac caccccccc agcaagcaga gcaacaacaa gtacgccgcc     540
agcagctacc tgagcctcac ccccgagcag tggaagagcc accggagcta cagctgccag     600
gtgacccacg agggcagcac cgtggagaag accgtggccc ccaccgagtg cagc            654
```

<210> SEQ ID NO 482
<211> LENGTH: 218
<212> TYPE: PRT
<213> ORGANISM: Homo sapiens

<400> SEQUENCE: 482

```
Ser Tyr Val Leu Thr Gln Pro Pro Ser Val Ser Val Ala Pro Gly Gln
  1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Ala Val Phe Gly Gly Gly Thr Gln Leu Thr Val Leu Gly Ala Ala Ala
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 483

<211> LENGTH: 121
<212> TYPE: PRT
<213> ORGANISM: Homo sapiens

<400> SEQUENCE: 483

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120

<210> SEQ ID NO 484
<211> LENGTH: 1353
<212> TYPE: DNA
<213> ORGANISM: Homo sapiens

<400> SEQUENCE: 484
gaggtgcagc tggtggagtc tggggctgag gtgaagaagc ctgggtcctc ggtgaaagtc      60
tcttgcaagg cttctggagg ccccttccgc agctatgcta tcagctgggt gcgacaggcc     120
cctggacaag ggcctgagtg gatgggaggg atcatcccta tttttggtac aacaaaatac     180
gcaccgaagt tccagggcag agtcacgatt accgcggacg atttcgcggg cacagtttac     240
atggagctga gcagcctgcg atctgaggac acggccatgt actactgtgc gaaacatatg     300
gggtaccagg tgcgcgaaac tatggacgtc tggggcaaag ggaccacggt caccgtctcg     360
agtgctagca ccaagggccc cagcgtgttc cccctggccc ccagcagcaa gagcaccagc     420
ggcggcacag ccgccctggg ctgcctggtg aaggactact ccccgagccc cgtgaccgtg     480
agctggaaca gcggcgcctt gaccagcggc gtgcacacct tccccgccgt gctgcagagc     540
agcggcctgt acagcctgag cagcgtggtg accgtgccca gcagcagcct gggcacccag     600
acctacatct gcaacgtgaa ccacaagccc agcaacacca aggtggacaa gcgcgtggag     660
cccaagagct gcgacaagac ccacacctgc ccccctgcc ctgccccga gctgctgggc      720 ggaccctccg tgttcctgtt ccccccaag cccaaggaca ccctcatgat cagccggacc     780
cccgaggtga cctgcgtggt ggtggacgtg agccacgagg accccgaggt gaagttcaac     840
tggtacgtgg acggcgtgga ggtgcacaac gccaagacca gccccggga ggagcagtac      900 aacagcacct accgggtggt gagcgtgctc accgtgctgc accaggactg gctgaacggc     960
aaggagtaca gtgcaaggt gagcaacaag gccctgcctg cccccatcga aagaccatc      1020 agcaaggcca agggccagcc ccgggagccc caggtgtaca ccctgccccc cagccgggag     1080
gagatgacca agaaccaggt gtccctcacc tgtctggtga agggcttcta cccagcgac      1140 atcgccgtgg agtgggagag caacggccag cccgagaaca actacaagac caccccccct     1200
gtgctggaca gcgacggcag cttcttcctg tacagcaagc tcaccgtgga caagagccgg     1260

```
tggcagcagg gcaacgtgtt cagctgcagc gtgatgcacg aggccctgca caaccactac    1320
acccagaaga gcctgagcct gagccccggc aag                                 1353
```

<210> SEQ ID NO 485
<211> LENGTH: 451
<212> TYPE: PRT
<213> ORGANISM: Homo sapiens

<400> SEQUENCE: 485

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
        450

<210> SEQ ID NO 486
<211> LENGTH: 111
<212> TYPE: PRT
<213> ORGANISM: Homo sapiens

<400> SEQUENCE: 486

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asp Gly Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Asp Asp Glu Ala Asp Tyr Tyr Cys Ala Thr Trp Asp Asp Asn Leu
                85                  90                  95

Ser Gly Pro Val Phe Gly Gly Gly Thr Lys Leu Thr Val Leu Gly
            100                 105                 110

<210> SEQ ID NO 487
<211> LENGTH: 660
<212> TYPE: DNA
<213> ORGANISM: Homo sapiens

<400> SEQUENCE: 487

| | |
|---|---|
| tcctatgtgc tgactcagcc accctcagcg tctgggaccc ccgggcagag ggtcaccatc | 60 |
| tcttgttctg gaagcagctc caacatcgga agtaattatg tatactggta ccagcagctc | 120 |
| ccaggcacgg cccccaaact cctcatctat agggatggtc agcggccctc agggctccct | 180 |
| gaccgattct ctggctccaa gtctggcacc tcagcctccc tggccatcag tggactccgg | 240 |
| tccgatgatg aggctgatta ttactgtgca acatgggatg acaacctgag tggtccagta | 300 |
| ttcggcggag ggaccaagct gaccgtccta ggtgcggccg caggccagcc caaggccgct | 360 |
| cccagcgtga ccctgttccc cccctcctcc gaggagctgc aggccaacaa ggccaccctg | 420 |
| gtgtgcctca tcagcgactt ctaccctggc gccgtgaccg tggcctggaa ggccgacagc | 480 |
| agccccgtga aggccggcgt ggagaccacc accccccagca agcagagcaa caacaagtac | 540 |
| gccgccagca gctacctgag cctcaccccc gagcagtgga gagccaccg gagctacagc | 600 |
| tgccaggtga cccacgaggg cagcaccgtg gagaagaccg tggcccccac cgagtgcagc | 660 |

<210> SEQ ID NO 488
<211> LENGTH: 220
<212> TYPE: PRT
<213> ORGANISM: Homo sapiens

<400> SEQUENCE: 488

```
Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asp Gly Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Asp Asp Glu Ala Asp Tyr Tyr Cys Ala Thr Trp Asp Asp Asn Leu
                85                  90                  95

Ser Gly Pro Val Phe Gly Gly Gly Thr Lys Leu Thr Val Leu Gly Ala
            100                 105                 110

Ala Ala Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Gly Gln Trp
            180                 185                 190

Lys Ser His Arg Ser Tyr Ser Cys Gln Val Thr His Glu Gly Ser Thr
        195                 200                 205

Val Glu Lys Thr Val Ala Pro Thr Glu Cys Ser Gly
    210                 215                 220
```

<210> SEQ ID NO 489
<211> LENGTH: 120
<212> TYPE: PRT
<213> ORGANISM: Homo sapiens

<400> SEQUENCE: 489

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Asp Ile Ile Gly Met Phe Gly Ser Thr Asn Tyr Ala Gln Asn Phe
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Gly Tyr Tyr Pro Ala Tyr Leu Pro His Trp Gly Gln
            100                 105                 110
```

Gly Thr Leu Val Thr Val Ser Ser
        115                 120

<210> SEQ ID NO 490
<211> LENGTH: 1350
<212> TYPE: DNA
<213> ORGANISM: Homo sapiens

<400> SEQUENCE: 490

| | | | | |
|---|---|---|---|---|
| gaggtgcagc tggtggagtc tgggggctgag gtgaagaagc cagggtcctc ggtgaaggtc | | | | 60 |
| tcctgtaagg cctctggagg caccttctcc agctatggta tcagctgggt gcgacaggcc | | | | 120 |
| cctggacaag ggcttgagtg gatgggagac atcatcggta tgtttggttc aacaaactac | | | | 180 |
| gcacagaact tccagggcag actcacgatt accgcggacg aatccacgag cacagcctac | | | | 240 |
| atggagctga gcagcctgag atctgaggac acggccgtgt attactgtgc gagaagtagt | | | | 300 |
| ggttattacc ctgcatacct cccccactgg ggccagggca ccttggtcac cgtctcgagt | | | | 360 |
| gctagcacca agggccccag cgtgttcccc ctggcccca gcagcaagag caccagcggc | | | | 420 |
| ggcacagccg ccctgggctg cctggtgaag gactacttcc ccgagcccgt ggacgtgagc | | | | 480 |
| tggaacagcg gcgccttgac cagcggcgtg cacaccttcc ccgccgtgct gcagagcagc | | | | 540 |
| ggcctgtaca gcctgagcag cgtggtgacc gtgcccagca gcagcctggg cacccagacc | | | | 600 |
| tacatctgca acgtgaacca caagcccagc aacaccaagg tggacaaacg cgtggagccc | | | | 660 |
| aagagctgcg acaagaccca cacctgcccc cctgccctg ccccgagct gctgggcgga | | | | 720 |
| ccctccgtgt tcctgttccc ccccaagccc aaggacaccc tcatgatcag ccggaccccc | | | | 780 |
| gaggtgacct gcgtggtggt ggacgtgagc cacgaggacc ccgaggtgaa gttcaactgg | | | | 840 |
| tacgtggacg gcgtggaggt gcacaacgcc aagaccaagc ccggggagga gcagtacaac | | | | 900 |
| agcacctacc gggtggtgag cgtgctcacc gtgctgcacc aggactggct gaacggcaag | | | | 960 |
| gagtacaagt gcaaggtgag caacaaggcc ctgcctgccc ccatcgagaa gaccatcagc | | | | 1020 |
| aaggccaagg gccagccccg ggagccccag gtgtacaccc tgccccccag ccgggaggag | | | | 1080 |
| atgaccaaga accaggtgtc cctcacctgt ctggtgaagg gcttctaccc cagcgacatc | | | | 1140 |
| gccgtggagt gggagagcaa cggccagccc gagaacaact acaagaccac cccccctgtg | | | | 1200 |
| ctggacagcg acggcagctt cttcctgtac agcaagctca ccgtggacaa gagccggtgg | | | | 1260 |
| cagcagggca acgtgttcag ctgcagcgtg atgcacgagg ccctgcacaa ccactacacc | | | | 1320 |
| cagaagagcc tgagcctgag ccccggcaag | | | | 1350 |

<210> SEQ ID NO 491
<211> LENGTH: 450
<212> TYPE: PRT
<213> ORGANISM: Homo sapiens

<400> SEQUENCE: 491

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Asp Ile Ile Gly Met Phe Gly Ser Thr Asn Tyr Ala Gln Asn Phe
    50                  55                  60

Gln Gly Arg Leu Thr Ile Thr Ala Asp Glu Ser Thr Ser Thr Ala Tyr

```
            65                  70                  75                  80
        Met Glu Leu Ser Ser Leu Arg Ser Glu Asp Thr Ala Val Tyr Tyr Cys
                        85                  90                  95

Ala Arg Ser Ser Gly Tyr Tyr Pro Ala Tyr Leu Pro His Trp Gly Gln
                    100                 105                 110

Gly Thr Leu Val Thr Val Ser Ala Ser Thr Lys Gly Pro Ser Val
                    115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                    180                 185                 190

Ser Ser Ser Leu Gly Thr Gln Thr Tyr Ile Cys Asn Val Asn His Lys
                    195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
        225                 230                 235                 240

Pro Ser Val Phe Leu Phe Pro Pro Lys Pro Lys Asp Thr Leu Met Ile
                        245                 250                 255

Ser Arg Thr Pro Glu Val Thr Cys Val Val Val Asp Val Ser His Glu
                    260                 265                 270

Asp Pro Glu Val Lys Phe Asn Trp Tyr Val Asp Gly Val Glu Val His
                    275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                    340                 345                 350

Thr Leu Pro Pro Ser Arg Glu Glu Met Thr Lys Asn Gln Val Ser Leu
                    355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                    420                 425                 430

Glu Ala Leu His Asn His Tyr Thr Gln Lys Ser Leu Ser Leu Ser Pro
                    435                 440                 445

Gly Lys
            450

<210> SEQ ID NO 492
<211> LENGTH: 109
<212> TYPE: PRT
<213> ORGANISM: Homo sapiens
```

<400> SEQUENCE: 492

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gly Gly Thr Lys Val Glu Ile Lys Arg
            100                 105

<210> SEQ ID NO 493
<211> LENGTH: 642
<212> TYPE: DNA
<213> ORGANISM: Homo sapiens

<400> SEQUENCE: 493

```
gaaattgtgt tgacccagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacccag aactttcggc   300
ggagggacca aggtggagat caaacgtgcg gccgcaccca gcgtgttcat cttcccccc    360
tccgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtga ccgagcagga cagcaaggac tccacctaca gcctgagcag cacctcacc    540
ctgagcaagg ccgactacga aagcacaag gtgtacgcct gcgaggtgac ccaccagggc    600
ctgagcagcc ccgtgaccaa gagcttcaac cggggcgagt gt                      642
```

<210> SEQ ID NO 494
<211> LENGTH: 214
<212> TYPE: PRT
<213> ORGANISM: Homo sapiens

<400> SEQUENCE: 494

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gly Gly Thr Lys Val Glu Ile Lys Arg Ala Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 495
<211> LENGTH: 121
<212> TYPE: PRT
<213> ORGANISM: Homo sapiens

<400> SEQUENCE: 495

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ser Met Ser Trp Val Arg Gln Ala Pro Gly Gln Gly Leu Glu Trp Met
        35                  40                  45

Gly Gly Ile Ile Pro Met Phe Gly Thr Thr Asn Tyr Ala Gln Lys Phe
    50                  55                  60

Gln Gly Arg Val Thr Ile Thr Ala Val Glu Ser Thr Ser Thr Ala Tyr
65                  70                  75                  80

Met Glu Val Ser Ser Leu Arg Ser Glu Asp Thr Ala Val Tyr Tyr Cys
                85                  90                  95

Ala Arg Gly Asp Lys Gly Ile Tyr Tyr Tyr Tyr Met Asp Val Trp Gly
            100                 105                 110

Lys Gly Thr Thr Val Thr Val Ser Ser
        115                 120

<210> SEQ ID NO 496
<211> LENGTH: 1353
<212> TYPE: DNA
<213> ORGANISM: Homo sapiens

<400> SEQUENCE: 496
gaggtgcagc tggtggagtc tggggctgag gtgaagaagc cggggtcctc ggtgaaggtc     60
tcctgcaagg cttctggagg caccttcagc ttctattcta tgagctgggt gcgacaggcc    120
cctggacaag gacttgagtg gatgggaggg atcatcccta tgtttggtac aacaaactac    180
gcacagaagt tccagggcag agtcacgatt accgcggtcg aatccacgag cacagcctac    240
atggaggtga gcagcctgag atctgaggac acggccgttt attactgtgc gagaggtgat    300
aagggtatct actactacta catggacgtc tggggcaaag ggaccacggt caccgtctcg    360
agtgctagca ccaagggccc cagcgtgttc cccctggccc ccagcagcaa gagcaccagc    420

```
ggcggcacag ccgccctggg ctgcctggtg aaggactact tccccgagcc cgtgaccgtg    480
agctggaaca cggcgcctt gaccagcggc gtgcacacct ccccgccgt gctgcagagc      540 agcggcctgt acagcctgag cagcgtggtg accgtgccca gcagcagcct gggcacccag    600
acctacatct gcaacgtgaa ccacaagccc agcaacacca aggtggacaa acgcgtggag    660
cccaagagct gcgacaagac ccacacctgc cccccctgcc ctgcccccga gctgctgggc    720
ggacccctcg tgttcctgtt cccccccaag cccaaggaca ccctcatgat cagccggacc    780
cccgaggtga cctgcgtggt ggtggacgtg agccacgagg accccgaggt gaagttcaac    840
tggtacgtgg acggcgtgga ggtgcacaac gccaagacca gccccgggga ggagcagtac    900
aacagcacct accgggtggt gagcgtgctc accgtgctgc accaggactg gctgaacggc    960
aaggagtaca agtgcaaggt gagcaacaag gccctgcctg cccccatcga aagaccatc    1020 agcaaggcca agggccagcc ccgggagccc caggtgtaca ccctgccccc cagccgggag   1080
gagatgacca gaaccaggt gtccctcacc tgtctggtga agggcttcta ccccagcgac   1140
atcgccgtgg agtgggagag caacggccag cccgagaaca actacaagac cacccccct    1200 gtgctggaca gcgacggcag cttcttcctg tacagcaagc tcaccgtgga caagagccgg   1260
tggcagcagg gcaacgtgtt cagctgcagc gtgatgcacg aggccctgca caaccactac   1320
acccagaaga gcctgagcct gagccccggc aag                                1353
```

<210> SEQ ID NO 497
<211> LENGTH: 451
<212> TYPE: PRT
<213> ORGANISM: Homo sapiens

<400> SEQUENCE: 497

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ser Met Ser Trp Val Arg Gln Ala Pro Gly Gln Gly Leu Glu Trp Met
        35                  40                  45

Gly Gly Ile Ile Pro Met Phe Gly Thr Thr Asn Tyr Ala Gln Lys Phe
    50                  55                  60

Gln Gly Arg Val Thr Ile Thr Ala Val Glu Ser Thr Thr Ala Tyr
65                  70                  75                  80

Met Glu Val Ser Ser Leu Arg Ser Glu Asp Thr Ala Val Tyr Tyr Cys
                85                  90                  95

Ala Arg Gly Asp Lys Gly Ile Tyr Tyr Tyr Met Asp Val Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 498
<211> LENGTH: 111
<212> TYPE: PRT
<213> ORGANISM: Homo sapiens

<400> SEQUENCE: 498

Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Tyr Val Ser Trp Tyr Gln Gln His Pro Gly Lys Ala Pro Lys Leu
        35                  40                  45
Met Ile Tyr Glu Val Ser Asn Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Ser Ser
                85                  90                  95
Ser Thr Leu Val Phe Gly Thr Gly Thr Lys Val Thr Val Leu Gly
            100                 105                 110

<210> SEQ ID NO 499
```

<211> LENGTH: 660
<212> TYPE: DNA
<213> ORGANISM: Homo sapiens

<400> SEQUENCE: 499

```
cagtctgccc tgactcagcc tgcctccgtg tctgggtctc ctggacagtc gatcaccatc      60
tcctgcactg gaaccagcag tgacgttggt ggttataact atgtctcctg gtaccaacag     120
cacccaggca aagcccccaa actcatgatt tatgaggtca gtaatcggcc ctcaggggtt     180
tctaatcgct tctctggctc caagtctggc aacacggcct ccctgaccat ctctgggctc     240
caggctgagg acgaggctga ttattactgc agctcatata caagcagcag cactcttgtc     300
ttcggaactg ggaccaaggt caccgtccta ggtgcggccg caggccagcc caaggccgct     360
cccagcgtga ccctgttccc ccctcctcc gaggagctgc aggccaacaa ggccaccctg     420
gtgtgcctca tcagcgactt ctaccctggc gccgtgaccg tggcctggaa ggccgacagc     480
agccccgtga aggccggcgt ggagaccacc acccccagca gcagagcaa caacaagtac     540
gccgccagca gctacctgag cctcacccccc gagcagtgga gagccaccg gagctacagc     600
tgccaggtga cccacgaggg cagcaccgtg agaagaccg tggcccccac cgagtgcagc     660
```

<210> SEQ ID NO 500
<211> LENGTH: 220
<212> TYPE: PRT
<213> ORGANISM: Homo sapiens

<400> SEQUENCE: 500

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Thr Gly Thr Lys Val Thr Val Leu Gly Ala
            100                 105                 110

Ala Ala Gly Gln Pro Lys Ala Ala Pro Ser Val Thr Leu Phe Pro Pro
        115                 120                 125

Ser Ser Glu Glu Leu Gln Ala Asn Lys Ala Thr Leu Val Cys Leu Ile
    130                 135                 140

Ser Asp Phe Tyr Pro Gly Ala Val Thr Val Ala Trp Lys Ala Asp Ser
145                 150                 155                 160

Ser Pro Val Lys Ala Gly Val Glu Thr Thr Thr Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Gln Val Thr His Glu Gly Ser
        195                 200                 205

Thr Val Glu Lys Thr Val Ala Pro Thr Glu Cys Ser
    210                 215                 220
```

<210> SEQ ID NO 501
<211> LENGTH: 121
<212> TYPE: PRT
<213> ORGANISM: Homo sapiens

<400> SEQUENCE: 501

| Glu | Val | Gln | Leu | Val | Glu | Thr | Gly | Ala | Glu | Val | Lys | Lys | Pro | Gly | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ser Val Lys Val Ser Cys Lys Ala Ser Gly Gly Thr Phe Arg Thr His
        20                  25                  30

Ala Ile Ser Trp Val Arg Gln Ala Pro Gly Gln Gly Leu Glu Trp Met
        35                  40                  45

Gly Gly Ile Ile Ala Ile Phe Gly Thr Ala Asn Tyr Ala Gln Lys Phe
 50                  55                  60

Gln Gly Arg Ile Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Ser Gly Tyr His Ile Ser Thr Pro Phe Asp Asn Trp Gly
            100                 105                 110

Gln Gly Thr Leu Val Thr Val Ser Ser
        115                 120

<210> SEQ ID NO 502
<211> LENGTH: 1353
<212> TYPE: DNA
<213> ORGANISM: Homo sapiens

<400> SEQUENCE: 502

```
gaggtgcagc tggtggagac cggggctgag gtgaagaagc ctgggtcctc ggtgaaggtc      60
tcctgcaagg cctctggagg caccttcagg acccatgcta tcagttgggt gcgacaggcc     120
cctggacaag gcttgagtg gatgggaggg atcatcgcta tcttcggaac agcaaactac     180
gcacagaagt tccagggcag aatcacgatt accgcggacg aatccacgag tacagcctac     240
atggagctga gcagcctgag atctgaggac acggccgtgt atttctgtgc gagaggcagt     300
ggttatcata tatcgacacc ctttgacaac tggggccagg gaaccctggt caccgtctcg     360
agtgctagca ccaagggccc cagcgtgttc cccctggccc ccagcagcaa gagcaccagc     420
ggcggcacag ccgccctggg ctgcctggtg aaggactact ccccgagcc cgtgaccgtg     480
agctggaaca cggcgccctt gaccagcggc gtgcacacct tccccgccgt gctgcagagc     540
agcggcctgt acagcctgag cagcgtggtg accgtgccca gcagcagcct gggcacccag     600
acctacatct gcaacgtgaa ccacaagccc agcaacacca aggtggacaa gcgcgtggag     660
cccaagagct gcgacaagac ccacacctgc ccccccctgcc ctgccccga gctgctgggc     720
ggaccctccg tgttcctgtt ccccccaag cccaaggaca ccctcatgat cagccggacc     780
cccgaggtga cctgcgtggt ggtggacgtg agccacgagg accccgaggt gaagttcaac     840
tggtacgtgg acggcgtgga ggtgcacaac gccaagacca gccccgggga ggagcagtac     900
aacagcacct accgggtggt gagcgtgctc accgtgctgc accaggactg gctgaacggc     960
aaggagtaca agtgcaaggt gagcaacaag gccctgcctg ccccccatcga aagaccatc    1020
agcaaggcca agggccagcc ccgggagccc caggtgtaca ccctgccccc cagccgggag    1080
gagatgacca gaaccaggt gtccctcacc tgtctggtga agggcttcta ccccagcgac    1140
atcgccgtgg agtgggagag caacggccag ccgagaaca actacaagac cacccccct    1200
```

-continued

```
gtgctggaca gcgacggcag cttcttcctg tacagcaagc tcaccgtgga caagagccgg    1260
tggcagcagg gcaacgtgtt cagctgcagc gtgatgcacg aggccctgca caaccactac    1320
acccagaaga gcctgagcct gagccccggc aag                                 1353
```

```
<210> SEQ ID NO 503
<211> LENGTH: 451
<212> TYPE: PRT
<213> ORGANISM: Homo sapiens

<400> SEQUENCE: 503
```

Glu Val Gln Leu Val Glu Thr Gly Ala Glu Val Lys Lys Pro Gly Ser
1               5                   10                  15

Ser Val Lys Val Ser Cys Lys Ala Ser Gly Gly Thr Phe Arg Thr His
            20                  25                  30

Ala Ile Ser Trp Val Arg Gln Ala Pro Gly Gln Gly Leu Glu Trp Met
        35                  40                  45

Gly Gly Ile Ile Ala Ile Phe Gly Thr Ala Asn Tyr Ala Gln Lys Phe
    50                  55                  60

Gln Gly Arg Ile Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Ser Gly Tyr His Ile Ser Thr Pro Phe Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 504
<211> LENGTH: 109
<212> TYPE: PRT
<213> ORGANISM: Homo sapiens

<400> SEQUENCE: 504

Ser Tyr Val Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Gly Val
            20                  25                  30
His Trp Tyr Gln Gln Lys Pro Gly Gln Ala Pro Val Leu Val Val Tyr
        35                  40                  45
Asp Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Ser Asp His
                85                  90                  95
Val Val Phe Gly Gly Gly Thr Lys Leu Thr Val Leu Gly
            100                 105

<210> SEQ ID NO 505
<211> LENGTH: 654
<212> TYPE: DNA
<213> ORGANISM: Homo sapiens

<400> SEQUENCE: 505
tcctatgtgc tgactcagcc accctcggtg tcagtggccc caggacagac ggccaggatt      60
acctgtgggg gaaacaacat tggaagtaaa ggtgtgcact ggtaccagca gaagcctggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg atagtagta gtgatcatgt ggtattcggc     300
ggagggacca agctgaccgt cctaggtgcg gccgcaggcc agcccaaggc cgctcccagc     360
gtgaccctgt tcccccctc ctccgaggag ctgcaggcca caaggccac cctggtgtgc     420
ctcatcagcg acttctaccc tggcgccgtg accgtggcct ggaaggccga cagcagcccc     480
gtgaaggccg cgtggagac caccaccccc agcaagcaga gcaacaacaa gtacgccgcc     540
agcagctacc tgagcctcac ccccgagcag tggaagagcc accggagcta cagctgccag     600
```

```
gtgacccacg agggcagcac cgtggagaag accgtggccc ccaccgagtg cagc        654
```

<210> SEQ ID NO 506
<211> LENGTH: 218
<212> TYPE: PRT
<213> ORGANISM: Homo sapiens

<400> SEQUENCE: 506

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Gly Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Ala Ala Ala
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 507
<211> LENGTH: 128
<212> TYPE: PRT
<213> ORGANISM: Homo sapiens

<400> SEQUENCE: 507

```
Glu Val Gln Leu Val Glu Ser Gly Ala Glu Val Lys Lys Pro Gly Ser
1               5                   10                  15

Ser Val Lys Val Ser Cys Lys Ala Ser Gly His Ile Phe Ser Gly Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Lys Phe
    50                  55                  60

Gln Gly Arg Val Thr Ile Thr Ala Asp Gln Ser Thr Ser Thr Ala Tyr
65                  70                  75                  80

Met Asp Leu Ser Asn Leu Arg Ser Glu Asp Thr Ala Val Tyr Tyr Cys
                85                  90                  95

Ala Arg Val Lys Asp Gly Tyr Cys Thr Leu Thr Ser Cys Pro Val Gly
```

100                 105                 110
Trp Tyr Phe Asp Leu Trp Gly Arg Gly Thr Leu Val Thr Val Ser Ser
            115                 120                 125

<210> SEQ ID NO 508
<211> LENGTH: 1374
<212> TYPE: DNA
<213> ORGANISM: Homo sapiens

<400> SEQUENCE: 508
gaggtgcagc tggtggagtc tggggctgag gtgaagaagc ctgggtcctc ggtgaaggtc    60
tcctgcaagg cttctggaca catcttcagc ggctatgcaa tcagttgggt gcgacaggcc   120
cctggacaag ggcttgagtg gatgggaggg atcatccctaa tctttggtac aacaaactac   180
gcacagaagt tccagggcag agtcacgatt accgcggacc aatccacgag cacagcctac   240
atggacctga gcaacttgag atctgaggac acggccgtct attactgtgc gagagtgaaa   300
gatggatatt gtactcttac cagctgccct gtcggctggt acttcgatct ctggggccgt   360
ggcaccctgg tcactgtctc gagtgctagc accaagggcc cagcgtgttt ccccctggcc   420
cccagcagca gagcaccag cggcggcaca gccgccctgg gctgcctggt gaaggactac   480
ttccccgagc ccgtgaccgt gagctggaac agcggcgcct gaccagcgg cgtgcacacc   540 ttccccgccg tgctgcagag cagcggcctg tacagcctga gcagcgtggt gaccgtgccc   600
agcagcagcc tgggcaccca gacctacatc tgcaacgtga accacaagcc cagcaacacc   660
aaggtggaca acgcgtggag cccaagagc tgcgacaaga cccacacctg ccccccctgc   720 cctgccccg agctgctggg cggaccctcc gtgttcctgt tccccccaa gcccaaggac   780 accctcatga tcagccggac ccccgaggtg acctgcgtgg tggtggacgt gagccacgag   840
gaccccgagg tgaagttcaa ctggtacgtg gacggcgtgg aggtgcacaa cgccaagacc   900
aagccccggg aggagcagta caacagcacc taccgggtgg tgagcgtgct caccgtgctg   960
caccaggact ggctgaacgg caaggagtac aagtgcaagg tgagcaacaa ggccctgcct  1020 gccccatcg agaagaccat cagcaaggcc aagggccagc cccgggagcc ccaggtgtac  1080
accctgcccc ccagccggga ggagatgacc aagaaccagg tgtccctcac ctgtctggtg  1140
aagggcttct accccagcga catcgccgtg gagtgggaga gcaacggcca gcccgagaac  1200
aactacaaga ccacccccc tgtgctggac agcgacggca gcttcttcct gtacagcaag  1260
ctcaccgtgg acaagagccg gtggcagcag ggcaacgtgt tcagctgcag cgtgatgcac  1320
gaggccctgc acaaccacta cacccagaag agcctgagcc tgagccccgg caag         1374

<210> SEQ ID NO 509
<211> LENGTH: 458
<212> TYPE: PRT
<213> ORGANISM: Homo sapiens

<400> SEQUENCE: 509

Glu Val Gln Leu Val Glu Ser Gly Ala Glu Val Lys Lys Pro Gly Ser
1               5                  10                  15

Ser Val Lys Val Ser Cys Lys Ala Ser Gly His Ile Phe Ser Gly Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Lys Phe
    50                  55                  60

```
Gln Gly Arg Val Thr Ile Thr Ala Asp Gln Ser Thr Ser Thr Ala Tyr
 65                  70                  75                  80

Met Asp Leu Ser Asn Leu Arg Ser Glu Asp Thr Ala Val Tyr Tyr Cys
                 85                  90                  95

Ala Arg Val Lys Asp Gly Tyr Cys Thr Leu Thr Ser Cys Pro Val Gly
            100                 105                 110

Trp Tyr Phe Asp Leu Trp Gly Arg Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 510
<211> LENGTH: 108
<212> TYPE: PRT
```

<213> ORGANISM: Homo sapiens

<400> SEQUENCE: 510

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Leu Glu Ile Lys Arg
            100                 105

<210> SEQ ID NO 511
<211> LENGTH: 639
<212> TYPE: DNA
<213> ORGANISM: Homo sapiens

<400> SEQUENCE: 511
gaaattgtga tgacgcagtc tccaggcacc ctgtctttgt ctccagggga aagagccacc      60
ctctcgtgca gggccagtca gagtgttagc agcagctact tagcctggta ccagcagaaa     120
cctggccagg ctcccaggct cctcatcttt ggtgcctcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcactcac tttcggcgga     300
gggaccaagc tggagatcaa acgtgcggcc gcacccagcg tgttcatctt cccccccctcc     360
gacgagcagc tgaagagcgg caccgccagc gtggtgtgcc tgctgaacaa cttctacccc     420
cgggaggcca aggtgcagtg gaaggtggac aacgccctgc agagcggcaa cagccaggag     480
agcgtgaccg agcaggacag caaggactcc acctacagcc tgagcagcac cctcaccctg     540
agcaaggccg actacgagaa gcacaaggtg tacgcctgcg aggtgaccca ccagggcctg     600
agcagccccg tgaccaagag cttcaaccgg ggcgagtgt                           639

<210> SEQ ID NO 512
<211> LENGTH: 213
<212> TYPE: PRT
<213> ORGANISM: Homo sapiens

<400> SEQUENCE: 512

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu

```
            85                  90                  95
Thr Phe Gly Gly Gly Thr Lys Leu Glu Ile Lys Arg Ala Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
            210

<210> SEQ ID NO 513
<211> LENGTH: 121
<212> TYPE: PRT
<213> ORGANISM: Homo sapiens

<400> SEQUENCE: 513

Glu Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Arg Ser Asn
            20                  25                  30

Ser Ile Ser Trp Val Arg Gln Ala Pro Gly Gln Gly Leu Glu Trp Met
        35                  40                  45

Gly Gly Ile Phe Ala Leu Phe Gly Thr Thr Asp Tyr Ala Gln Lys Phe
    50                  55                  60

Gln Gly Arg Val Thr Ile Thr Ala Asp Glu Ser Ser Thr Thr Val Tyr
65                  70                  75                  80

Leu Glu Leu Ser Ser Leu Thr Ser Glu Asp Thr Ala Val Tyr Tyr Cys
                85                  90                  95

Ala Arg Gly Ser Gly Tyr Thr Thr Arg Asn Tyr Phe Asp Tyr Trp Gly
            100                 105                 110

Gln Gly Thr Leu Val Thr Val Ser Ser
        115                 120

<210> SEQ ID NO 514
<211> LENGTH: 1353
<212> TYPE: DNA
<213> ORGANISM: Homo sapiens

<400> SEQUENCE: 514
gaggtccagc tggtacagtc tggggctgag gttaagaagc ctgggtcctc ggtgaaggtc      60
tcctgcaagg cttctggagg catcttcaga agcaattcta tcagttgggt gcgacaggcc     120
cctgggcaag gcttgagtg gatgggaggg atcttcgctc ttttcggaac aacagactac     180
gcgcagaagt tccagggcag agtcacgatt accgcggacg aatcttcgac cacagtctac     240
ctggagctga gtagcctgac atctgaggac acggccgttt attactgtgc gagaggcagt     300
ggctacacca cacgcaacta ctttgactac tggggccagg gcaccctggt caccgtctcg     360
agtgctagca ccaagggccc cagcgtgttc cccctggccc ccagcagcaa gagcaccagc     420
```

-continued

```
ggcggcacag ccgccctggg ctgcctggtg aaggactact tccccgagcc cgtgaccgtg    480
agctggaaca gcggcgcctt gaccagcggc gtgcacacct ccccgccgt gctgcagagc    540 agcggcctgt acagcctgag cagcgtggtg accgtgccca gcagcagcct gggcacccag    600
acctacatct gcaacgtgaa ccacaagccc agcaacacca aggtggacaa acgcgtggag    660
cccaagagct gcgacaggcc ccacacctgc cccccctgcc ctgcccccga gctgctgggc    720
ggaccctccg tgttcctgtt ccccccaag cccaaggaca ccctcatgat cagccggacc    780
cccgaggtga cctgcgtggt ggtggacgtg agccacgagg accccgaggt gaagttcaac    840
tggtacgtgg acggcgtgga ggtgcacaac gccaagacca gccccgggga ggagcagtac    900
aacagcacct accgggtggt gagcgtgctc accgtgctgc accaggactg gctgaacggc    960
aaggagtaca agtgcaaggt gagcaacaag gccctgcctg ccccatcga aagaccatc   1020 agcaaggcca agggccagcc ccgggagccc caggtgtaca ccctgccccc cagactggag   1080
gagatgacca gaaccaggt gtccctcacc tgtctggtga agggcttcta ccccagcgac   1140
atcgccgtgg agtgggagag caacggccag cccgagaaca ctacaagac cacccccct   1200 gtgctggaca cgacggcag cttcttcctg tacagcaagc tcaccgtgga caagagccgg   1260
tggcagcagg gcaacgtgtt cagctgcagc gtgatgcacg aggccctgca caaccactac   1320
acccagaaga gcctgagcct gagccccggc aag                              1353
```

<210> SEQ ID NO 515
<211> LENGTH: 451
<212> TYPE: PRT
<213> ORGANISM: Homo sapiens

<400> SEQUENCE: 515

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Arg Ser Asn
            20                  25                  30

Ser Ile Ser Trp Val Arg Gln Ala Pro Gly Gln Gly Leu Glu Trp Met
        35                  40                  45

Gly Gly Ile Phe Ala Leu Phe Gly Thr Thr Asp Tyr Ala Gln Lys Phe
    50                  55                  60

Gln Gly Arg Val Thr Ile Thr Ala Asp Glu Ser Ser Thr Thr Val Tyr
65                  70                  75                  80

Leu Glu Leu Ser Ser Leu Thr Ser Glu Asp Thr Ala Val Tyr Tyr Cys
                85                  90                  95

Ala Arg Gly Ser Gly Tyr Thr Thr Arg Asn Tyr Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 516
<211> LENGTH: 109
<212> TYPE: PRT
<213> ORGANISM: Homo sapiens

<400> SEQUENCE: 516

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Gly Trp Tyr Gln Gln Lys Pro Gly Gln Ala Pro Arg Leu Leu
        35                  40                  45

Ile Tyr Gly Ala Ser Ser Arg Ala Ser Gly Ile Pro Asp Arg Phe Ser
    50                  55                  60

Gly Gly Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg
            100                 105

```
<210> SEQ ID NO 517
<211> LENGTH: 654
<212> TYPE: DNA
<213> ORGANISM: Homo sapiens

<400> SEQUENCE: 517
gaaattgtgc tgactcagtc tccaggcacc ctgtctttgt ctccagggga aagagccaca      60
ctctcctgca gggccagtca gagtgttagc agcaactact taggctggta ccagcagaaa     120
cctggccagg ctcccaggct cctgatctat ggtgcatcca gcagggccag tggcatccca     180
gacaggttca gtggcggtgg gtctgggaca gacttcactc tcaccatcag cagactggag     240
cctgaagatt ttgcagtgta ttactgtcag cagtatggta gctcacccct cactttcggc     300
ggagggacca aggtggagat caaacgtgcg gccgcaggcc agcccaaggc cgctcccagc     360
gtgaccctgt tcccccccctc ctccgaggag ctgcaggcca caaggccac cctggtgtgc     420 ctcatcagcg acttctaccc tggcgccgtg accgtggcct ggaaggccga caccacccc     480 gtgaaggccg gcgtggagac caccacccc agcaagcaga gcaacaacaa gtacgccgcc     540
agcagctacc tgagcctcac ccccgagcag tggaagagcc accggagcta cagctgccag     600
gtgacccacg agggcagcac cgtggagaag accgtggccc ccaccgagtg cagc          654

<210> SEQ ID NO 518
<211> LENGTH: 218
<212> TYPE: PRT
<213> ORGANISM: Homo sapiens

<400> SEQUENCE: 518

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Gly Trp Tyr Gln Gln Lys Pro Gly Gln Ala Pro Arg Leu Leu
        35                  40                  45

Ile Tyr Gly Ala Ser Ser Arg Ala Ser Gly Ile Pro Asp Arg Phe Ser
    50                  55                  60

Gly Gly Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Ala Ala Ala
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 519
<211> LENGTH: 120
<212> TYPE: PRT
<213> ORGANISM: Homo sapiens

<400> SEQUENCE: 519

| | | | | | | | | | | | | | | | |
|---|---|---|---|---|---|---|---|---|---|---|---|---|---|---|---|
| Glu | Val | Gln | Leu | Val | Glu | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Gly | Thr | Phe | Ser | Ser | Tyr |
| | | | 20 | | | | | 25 | | | | | 30 | | |
| Ala | Ile | Ser | Trp | Val | Arg | Gln | Ala | Pro | Gly | Gln | Gly | Leu | Glu | Trp | Met |
| | | | 35 | | | | | 40 | | | | | 45 | | |
| Gly | Gly | Ile | Ile | Gly | Met | Phe | Gly | Thr | Ala | Asn | Tyr | Ala | Gln | Lys | Phe |
| | 50 | | | | | 55 | | | | | 60 | | | | |
| Gln | Gly | Arg | Val | Thr | Ile | Thr | Ala | Asp | Glu | Phe | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Gly | Asn | Tyr | Tyr | Tyr | Glu | Ser | Ser | Leu | Asp | Tyr | Trp | Gly | Gln |
| | | | 100 | | | | | 105 | | | | | 110 | | |
| Gly | Thr | Leu | Val | Thr | Val | Ser | Ser | | | | | | | | |
| | | | 115 | | | | 120 | | | | | | | | |

<210> SEQ ID NO 520
<211> LENGTH: 1350
<212> TYPE: DNA
<213> ORGANISM: Homo sapiens

<400> SEQUENCE: 520

| | |
|---|---|
| gaggtgcagc tggtggagtc tgggggctgag gtgaagaagc tggggtcctc ggtgaaggtc | 60 |
| tcctgcaagg cttctggagg caccttcagc agctatgcta tcagctgggt gcgacaggcc | 120 |
| cctggacaag gcttgagtg gatgggaggg atcatcggta tgttcggtac agcaaactac | 180 |
| gcacagaagt tccagggcag agtcacgatt accgcggacg aatttacgag cacagcctac | 240 |
| atggagctga gcagcctgag atctgaggac acggccgtgt attactgtgc gagaggaaat | 300 |
| tattactatg agagtagtct cgactactgg ggccagggaa ccctggtcac cgtctcgagt | 360 |
| gctagcacca agggcccag cgtgttcccc ctggccccca gcagcaagag caccagcggc | 420 |
| ggcacagccg ccctgggctg cctggtgaag gactacttcc ccgagcccgt gaccgtgagc | 480 |
| tggaacagcg gcgccttgac cagcggcgtg cacaccttcc ccgccgtgct gcagagcagc | 540 |
| ggcctgtaca gcctgagcag cgtggtgacc gtgcccagca gcagcctggg cacccagacc | 600 |
| tacatctgca acgtgaacca caagcccagc aacaccaagg tggacaaacg cgtggagccc | 660 |
| aagagctgcg acaagaccca cacctgcccc cctgccctg ccccgagct gctgggcgga | 720 |
| ccctccgtgt tcctgttccc ccccaagccc aaggacaccc tcatgatcag ccggaccccc | 780 |
| gaggtgacct gcgtggtggt ggacgtgagc cacgaggacc ccgaggtgaa gttcaactgg | 840 |
| tacgtggacg gcgtggtggt gcacaacgcc aagaccaagc ccgggagga gcagtacaac | 900 |
| agcacctacc gggtggtgag cgtgctcacc gtgctgcacc aggactggct gaacggcaag | 960 |
| gagtacaagt gcaaggtgag caacaaggcc ctgcctgccc ccatcgagaa gaccatcagc | 1020 |
| aaggccaagg gccagccccg ggagccccag gtgtacaccc tgcccccag ccgggaggag | 1080 |
| atgaccaaga accaggtgtc cctcacctgt ctggtgaagg gcttctaccc cagcgacatc | 1140 |
| gccgtggagt gggagagcaa cggccagccc gagaacaact acaagaccac cccccctgtg | 1200 |

-continued

```
ctggacagcg acggcagctt cttcctgtac agcaagctca ccgtggacaa gagccggtgg    1260
cagcagggca acgtgttcag ctgcagcgtg atgcacgagg ccctgcacaa ccactacacc    1320
cagaagagcc tgagcctgag ccccggcaag                                      1350
```

```
<210> SEQ ID NO 521
<211> LENGTH: 450
<212> TYPE: PRT
<213> ORGANISM: Homo sapiens

<400> SEQUENCE: 521
```

| | | | | | | | | | | | | | | |
|---|---|---|---|---|---|---|---|---|---|---|---|---|---|---|
| Glu | Val | Gln | Leu | Val | Glu | Ser | Gly | Ala | Glu | Val | Lys | Lys | Pro | Gly | Ser |
| 1 | | | | 5 | | | | | 10 | | | | | 15 | |

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Gly Met Phe Gly Thr Ala Asn Tyr Ala Gln Lys Phe
        50                  55                  60

Gln Gly Arg Val Thr Ile Thr Ala Asp Glu Phe Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Tyr Tyr Glu Ser Ser Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr

```
            340                 345                 350
Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 522
<211> LENGTH: 109
<212> TYPE: PRT
<213> ORGANISM: Homo sapiens

<400> SEQUENCE: 522

Gln Ser Val Val Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly
            100                 105

<210> SEQ ID NO 523
<211> LENGTH: 654
<212> TYPE: DNA
<213> ORGANISM: Homo sapiens

<400> SEQUENCE: 523
cagtctgtcg tgacgcagcc gccctcggtg tcagtggccc caggacagac ggccaggatt     60
acctgtgggg gaaacaacat tggaagtaaa agtgtgcact ggtaccagca gaagccaggc    120
caggcccctg tgctggtcgt ctatgatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcatta tgtcttcgga    300
actgggacca aggtcaccgt cctaggtgcg gccgcaggcc agcccaaggc cgctcccagc    360
gtgaccctgt tccccccctc ctccgaggag ctgcaggcca caaggccac cctggtgtgc    420 ctcatcagcg acttctaccc tggcgccgtg accgtggcct ggaaggccga cagcagcccc    480
gtgaaggccg gcgtggagac caccaccccc agcaagcaga gcaacaacaa gtacgccgcc    540
agcagctacc tgagcctcac ccccgagcag tggaagagcc accggagcta cagctgccag    600
```

```
gtgacccacg agggcagcac cgtggagaag accgtggccc ccaccgagtg cagc          654
```

<210> SEQ ID NO 524
<211> LENGTH: 218
<212> TYPE: PRT
<213> ORGANISM: Homo sapiens

<400> SEQUENCE: 524

Gln Ser Val Val Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Ala Ala Ala
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 525
<211> LENGTH: 120
<212> TYPE: PRT
<213> ORGANISM: Homo sapiens

<400> SEQUENCE: 525

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Arg Asn Phe
            20                  25                  30

Ala Ile Asn Trp Val Arg Gln Ala Pro Gly Gln Gly Leu Glu Trp Met
        35                  40                  45

Gly Gly Ile Ile Ala Val Phe Gly Thr Thr Lys Tyr Ala His Lys Phe
    50                  55                  60

Gln Gly Arg Val Thr Ile Thr Ala Asp Asp Ser Thr Asn Thr Ala Tyr
65                  70                  75                  80

Met Glu Leu Gly Ser Leu Lys Ser Glu Asp Thr Ala Val Tyr Tyr Cys
                85                  90                  95

Ala Arg Gly Pro His Tyr Tyr Ser Ser Tyr Met Asp Val Trp Gly Glu
            100                 105                 110

Gly Thr Thr Val Thr Val Ser Ser
        115                 120

<210> SEQ ID NO 526
<211> LENGTH: 1350
<212> TYPE: DNA
<213> ORGANISM: Homo sapiens

<400> SEQUENCE: 526
caggtgcagc tggtgcagtc tggggctgag gtgaagaagc ctgggtcctc ggtaaaggtc      60
tcctgcaagg cttctggagg ccccttccgc aattttgcta tcaactgggt gcgacaggcc     120
cctggacaag ggcttgagtg gatgggaggg atcatcgctg tctttgggac gacaaagtac     180
gcacataagt tccagggcag agtcaccatc accgcggacg actccacaaa tacagcttac     240
atggagctgg gcagcctgaa atctgaggac acggccgtgt attactgtgc gagaggtccc     300
cactactact cctcctacat ggacgtctgg ggcgaaggga ccacggtcac cgtctcgagt     360
gctagcacca agggcccag cgtgttcccc ctggccccca gcagcaagag caccagcggc     420
ggcacagccg ccctgggctg cctggtgaag gactacttcc ccgagccgt gaccgtgagc     480 tggaacagcg gcgccttgac cagcggcgtg cacaccttcc cgccgtgct gcagagcagc     540 ggcctgtaca gcctgagcag cgtggtgacc gtgcccagca gcagcctggg cacccagacc     600
tacatctgca acgtgaacca caagcccagc aacaccaagg tggacaaacg cgtggagccc     660
aagagctgcg acaagaccca cacctgcccc cctgccctg cccccgagct gctgggcgga     720
ccctccgtgt tcctgttccc ccccaagccc aaggacaccc tcatgatcag ccggacccc     780 gaggtgacct gcgtggtggt ggacgtgagc cacgaggacc ccgaggtgaa gttcaactgg     840
tacgtggacg gcgtggaggt gcacaacgcc aagaccaagc ccggaggga gcagtacaac     900 agcacctacc gggtggtgag cgtgctcacc gtgctgcacc aggactggct gaacggcaag     960
gagtacaagt gcaaggtgag caacaaggcc ctgcctgccc ccatcgagaa gaccatcagc    1020
aaggccaagg gccagccccg ggagcccag gtgtacaccc tgccccccag ccggaggag    1080 atgaccaaga accaggtgtc cctcacctgt ctggtgaagg gcttctaccc cagcgacatc    1140
gccgtggagt gggagagcaa cggccagccc gagaacaact acaagaccac ccccctgtg    1200 ctggacagcg acggcagctt cttcctgtac agcaagctca ccgtggacaa gagccggtgg    1260
cagcagggca acgtgttcag ctgcagcgtg atgcacgagg ccctgcacaa ccactacacc    1320
cagaagagcc tgagcctgag ccccggcaag                                     1350

<210> SEQ ID NO 527
<211> LENGTH: 450
<212> TYPE: PRT
<213> ORGANISM: Homo sapiens

<400> SEQUENCE: 527

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Arg Asn Phe
            20                  25                  30

Ala Ile Asn Trp Val Arg Gln Ala Pro Gly Gln Gly Leu Glu Trp Met
        35                  40                  45

Gly Gly Ile Ile Ala Val Phe Gly Thr Thr Lys Tyr Ala His Lys Phe
    50                  55                  60

```
Gln Gly Arg Val Thr Ile Thr Ala Asp Asp Ser Thr Asn Thr Ala Tyr
 65                  70                  75                  80

Met Glu Leu Gly Ser Leu Lys Ser Glu Asp Thr Ala Val Tyr Tyr Cys
                 85                  90                  95

Ala Arg Gly Pro His Tyr Tyr Ser Ser Tyr Met Asp Val Trp Gly Glu
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 528
<211> LENGTH: 107
```

```
<212> TYPE: PRT
<213> ORGANISM: Homo sapiens

<400> SEQUENCE: 528

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Ser
                85                  90                  95

Phe Gly Pro Gly Thr Lys Val Asp Ile Lys Arg
            100                 105

<210> SEQ ID NO 529
<211> LENGTH: 636
<212> TYPE: DNA
<213> ORGANISM: Homo sapiens

<400> SEQUENCE: 529
gacatccagt tgacccagtc tccatcctcc ctgtctgcat ctgtaggaga cagagtcacc      60
atcacttgcc gggcgagtca gggcattagc acttatttag cctggtatca gcagaaaccc     120
gggaaagttc ctaaactcct gatctatgct gcatccactt tgcaatcagg ggtcccatct     180
cggttcagtg gcagtggatc tgggacagat ttcactctca ccatcagcag cctgcagcct     240
gaagatgttg caacttatta ctgtcaaaag tataacagtg ccccttcttt cggccctggg     300
accaaagtgg atatcaaacg tgcggccgca cccagcgtgt tcatcttccc ccctccgac      360 gagcagctga agagcggcac cgccagcgtg gtgtgcctgc tgaacaactt ctaccccgg      420 gaggccaagg tgcagtggaa ggtggacaac gccctgcaga gcggcaacag ccaggagagc     480
gtgaccgagc aggacagcaa ggactccacc tacagcctga gcagcaccct caccctgagc     540
aaggccgact acgagaagca caaggtgtac gcctgcgagg tgacccacca gggcctgagc     600
agccccgtga ccaagagctt caaccggggc gagtgt                               636

<210> SEQ ID NO 530
<211> LENGTH: 212
<212> TYPE: PRT
<213> ORGANISM: Homo sapiens

<400> SEQUENCE: 530

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80
```

Glu Asp Val Ala Thr Tyr Tyr Cys Gln Lys Tyr Asn Ser Ala Pro Ser
            85                  90                  95

Phe Gly Pro Gly Thr Lys Val Asp Ile Lys Arg Ala Ala Ala Pro Ser
            100                 105                 110

Val Phe Ile Phe Pro Pro Ser Asp Glu Gln Leu Lys Ser Gly Thr Ala
            115                 120                 125

Ser Val Val Cys Leu Leu Asn Asn Phe Tyr Pro Arg Glu Ala Lys Val
            130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
            195                 200                 205

Arg Gly Glu Cys
        210

<210> SEQ ID NO 531
<211> LENGTH: 120
<212> TYPE: PRT
<213> ORGANISM: Homo sapiens

<400> SEQUENCE: 531

Glu Val Gln Leu Val Glu Thr Gly Ala Glu Val Lys Lys Pro Gly Ser
1               5                   10                  15

Ser Val Lys Val Pro Cys Lys Ser Ser Gly Ser Pro Phe Arg Ser Asn
            20                  25                  30

Ala Val Ser Trp Val Arg Gln Ala Pro Gly Gln Gly Leu Glu Trp Val
        35                  40                  45

Gly Gly Ile Leu Gly Val Phe Gly Ser Pro Ser Tyr Ala Gln Lys Phe
    50                  55                  60

Gln Gly Arg Val Thr Ile Thr Ala Asp Glu Ser Thr Asn Thr Val His
65                  70                  75                  80

Met Glu Leu Arg Gly Leu Arg Ser Glu Asp Thr Ala Val Tyr Tyr Cys
                85                  90                  95

Ala Arg Gly Pro Thr Tyr Tyr Tyr Ser Tyr Met Asp Val Trp Gly Lys
            100                 105                 110

Gly Thr Thr Val Thr Val Ser Ser
        115                 120

<210> SEQ ID NO 532
<211> LENGTH: 1350
<212> TYPE: DNA
<213> ORGANISM: Homo sapiens

<400> SEQUENCE: 532
gaggtgcagc tggtggagac tggggctgag gtgaagaagc ctgggtcctc ggtgaaggtc     60
ccctgcaaat cttctggaag ccccttcagg agtaatgctg tcagctgggt gcgacaggcc    120
cccggacaag gcttgagtg gtgggagga atcctcggtg tctttggttc accaagctac      180
gcacagaagt tccagggcag agtcacgatt accgcggacg aatccaccaa cacagtccac    240
atggagctga gagttttgag atctgaggac acggccgtgt attattgtgc gagaggtcct    300
acctactact actcctacat ggacgtctgg ggcaaaggga ccacggtcac cgtctcgagt    360

```
gctagcacca agggccccag cgtgttcccc ctggccccca gcagcaagag caccagcggc    420
ggcacagccg ccctgggctg cctggtgaag gactacttcc ccgagcccgt gaccgtgagc    480
tggaacagcg gcgccttgac cagcggcgtg cacaccttcc ccgccgtgct gcagagcagc    540
ggcctgtaca gcctgagcag cgtggtgacc gtgcccagca gcagcctggg cacccagacc    600
tacatctgca acgtgaacca caagcccagc aacaccaagg tggacaaacg cgtggtgacc    660
aagagctgcg acaagaccca cacctgcccc cctgccctg ccccgagct gctgggcgga    720 ccctccgtgt tcctgttccc ccccaagccc aaggacaccc tcatgatcag ccggaccccc    780
gaggtgacct gcgtggtggt ggacgtgagc cacgaggacc ccgaggtgaa gttcaactgg    840
tacgtggacg gcgtggaggt gcacaacgcc aagaccaagc ccgggagga gcagtacaac    900 agcacctacc gggtggtgag cgtgctcacc gtgctgcacc aggactggct gaacggcaag    960
gagtacaagt gcaaggtgag caacaaggcc ctgcctgccc ccatcgagaa gaccatcagc    1020
aaggccaagg gccagccccg ggagcccag gtgtacaccc tgcccccag ccgggaggag    1080 atgaccaaga accaggtgtc cctcacctgt ctggtgaagg gcttctaccc cagcgacatc    1140
gccgtggaat gagagagcaa cggccagccc gagaacaact acaagaccac ccccctgtg    1200 ctggacagcg acggcagctt cttcctgtac agcaagctca ccgtggacaa gagccggtgg    1260
cagcagggca acgtgttcag ctgcagcgtg atgcacgagg ccctgcacaa ccactacacc    1320
cagaagagcc tgagcctgag ccccggcaag                                    1350
```

<210> SEQ ID NO 533
<211> LENGTH: 450
<212> TYPE: PRT
<213> ORGANISM: Homo sapiens

<400> SEQUENCE: 533

```
Glu Val Gln Leu Val Glu Thr Gly Ala Glu Val Lys Lys Pro Gly Ser
1               5                   10                  15

Ser Val Lys Val Pro Cys Lys Ser Ser Gly Ser Pro Phe Arg Ser Asn
            20                  25                  30

Ala Val Ser Trp Val Arg Gln Ala Pro Gly Gln Gly Leu Glu Trp Val
        35                  40                  45

Gly Gly Ile Leu Gly Val Phe Gly Ser Pro Ser Tyr Ala Gln Lys Phe
    50                  55                  60

Gln Gly Arg Val Thr Ile Thr Ala Asp Glu Ser Thr Asn Thr Val His
65                  70                  75                  80

Met Glu Leu Arg Gly Leu Arg Ser Glu Asp Thr Ala Val Tyr Tyr Cys
                85                  90                  95

Ala Arg Gly Pro Thr Tyr Tyr Ser Tyr Met Asp Val Trp Gly Lys
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
                195                 200                 205
Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 534
<211> LENGTH: 109
<212> TYPE: PRT
<213> ORGANISM: Homo sapiens

<400> SEQUENCE: 534

Ser Tyr Val Leu Thr Gln Pro Pro Ser Glu Ser Val Ala Pro Gly Gln
1               5                   10                  15

Thr Ala Arg Ile Thr Cys Gly Gly Asn Asn Ile Gly Arg Asn Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Lys Ser Gly Asn Thr Ala Thr Leu Ile Ile Ser Arg Val Glu Val Gly
65                  70                  75                  80

Asp Glu Ala Asp Tyr Tyr Cys Gln Val Trp His Ser Ser Ser Asp His
                85                  90                  95

Tyr Val Phe Gly Thr Gly Thr Lys Val Thr Val Leu Gly
            100                 105
```

<210> SEQ ID NO 535
<211> LENGTH: 654
<212> TYPE: DNA
<213> ORGANISM: Homo sapiens

<400> SEQUENCE: 535

```
tcctatgtgc tgactcagcc accctcggag tcagtggccc caggacagac ggccaggatt      60
acctgtgggg gaaataacat tggaagaaat agtgtgcact ggtatcagca gaagccaggc     120
caggcccctg tgctggtcgt gtatgatgat agcgaccggc cctcagggat ccctgagcga     180
ttttctggct ccaagtctgg gaacacggcc accctgatta tcagcagggt cgaagtcggg     240
gatgaggccg actactactg tcaggtgtgg catagtagta gtgatcatta tgtcttcgga     300
actgggacca aggtcaccgt cctaggtgcg gccgcaggcc agcccaaggc cgctcccagc     360
gtgaccctgt tcccccctc ctccgaggag ctgcaggcca acaaggccac cctggtgtgc     420
ctcatcagcg acttctaccc tggcgccgtg accgtggcct ggaaggccga cagcagcccc     480
gtgaaggccg gcgtggagac caccccccc agcaagcaga gcaacaacaa gtacgccgcc     540
agcagctacc tgagcctcac ccccgagcag tggaagagcc accggagcta cagctgccag     600
gtgacccacg agggcagcac cgtggagaag accgtggccc ccaccgagtg cagc          654
```

<210> SEQ ID NO 536
<211> LENGTH: 218
<212> TYPE: PRT
<213> ORGANISM: Homo sapiens

<400> SEQUENCE: 536

Ser Tyr Val Leu Thr Gln Pro Pro Ser Glu Ser Val Ala Pro Gly Gln
1               5                   10                  15

Thr Ala Arg Ile Thr Cys Gly Gly Asn Asn Ile Gly Arg Asn Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Lys Ser Gly Asn Thr Ala Thr Leu Ile Ile Ser Arg Val Glu Val Gly
65                  70                  75                  80

Asp Glu Ala Asp Tyr Tyr Cys Gln Val Trp His Ser Ser Ser Asp His
                85                  90                  95

Tyr Val Phe Gly Thr Gly Thr Lys Val Thr Val Leu Gly Ala Ala Ala
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 537
<211> LENGTH: 120
<212> TYPE: PRT
<213> ORGANISM: Homo sapiens

<400> SEQUENCE: 537

```
Gln Met Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Phe Gly Met Phe Gly Thr Ala Asn Tyr Ala Gln Lys Phe
    50                  55                  60
Gln Gly Arg Val Thr Ile Thr Ala Asp Glu Phe Thr Ser Ala Ala Tyr
65                  70                  75                  80
Met Glu Leu Ser Ser Leu Gly Ser Glu Asp Thr Ala Met Tyr Tyr Cys
                85                  90                  95
Ala Arg Ser Ser Gly Tyr Tyr Pro Gln Tyr Phe Gln Asp Trp Gly Gln
            100                 105                 110
Gly Thr Leu Val Thr Val Ser Ser
        115                 120
```

<210> SEQ ID NO 538
<211> LENGTH: 1350
<212> TYPE: DNA
<213> ORGANISM: Homo sapiens

<400> SEQUENCE: 538

| | | |
|---|---|---|
| cagatgcagc tggtacaatc tggagctgag gtgaagaagc ctgggtcctc ggtgaaggtc | 60 |
| tcctgcaagg cttctggagg caccttcagc agctatgcta tcagctgggt gcgacaggcc | 120 |
| cctggacaag ggcttgagtg gatgggaggg atcttcggta tgtttgggac agcaaactac | 180 |
| gcgcagaagt tccagggcag agtcacgatt accgcggacg aattcacgag cgcggcctac | 240 |
| atggagctga gcagcctggg atctgaggac acggccatgt attactgtgc gaggtctagt | 300 |
| ggttattacc cccaatactt ccaggactgg ggccagggca ccctggtcac cgtctcgagt | 360 |
| gctagcacca agggcccag cgtgttcccc ctggccccca gcagcaagag caccagcggc | 420 |
| ggcacagccg ccctgggctg cctggtgaag gactacttcc ccgagccgt gaccgtgagc | 480 |
| tggaacagcg gcgccttgac cagcggcgtg cacaccttcc ccgccgtgct gcagagcagc | 540 |
| ggcctgtaca gcctgagcag cgtggtgacc gtgcccagca gcctgggc acccagacc | 600 |
| tacatctgca acgtgaacca caagcccagc aacaccaagg tggacaaacg cgtggagccc | 660 |
| aagagctgcg acaagaccca cacctgcccc cctgccctg ccccgagct gctgggcgga | 720 |
| ccctccgtgt tcctgttccc ccccaagccc aaggacaccc tcatgatcag ccggaccccc | 780 |
| gaggtgacct gcgtggtggt ggacgtgagc cacgaggacc ccgaggtgaa gttcaactgg | 840 |
| tacgtggacg gcgtggaggt gcacaacgcc aagaccaagc ccgggagga gcagtacaac | 900 |
| agcacctacc gggtggtgag cgtgctcacc gtgctgcacc aggactggct gaacggcaag | 960 |
| gagtacaagt gcaaggtgag caacaaggcc ctgcctgccc ccatcgagaa gaccatcagc | 1020 |
| aaggccaagg gccagccccg ggagccccag gtgtacaccc tgcccccag ccggaggag | 1080 |
| atgaccaaga accaggtgtc cctcacctgt ctggtgaagg gcttctaccc cagcgacatc | 1140 |

```
gccgtggagt gggagagcaa cggccagccc gagaacaact acaagaccac ccccctgtg   1200 ctggacagcg acggcagctt cttcctgtac agcaagctca ccgtggacaa gagccggtgg   1260
cagcagggca acgtgttcag ctgcagcgtg atgcacgagg ccctgcacaa ccactacacc   1320
cagaagagcc tgagcctgag ccccggcaag                                    1350
```

<210> SEQ ID NO 539
<211> LENGTH: 450
<212> TYPE: PRT
<213> ORGANISM: Homo sapiens

<400> SEQUENCE: 539

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Phe Gly Met Phe Gly Thr Ala Asn Tyr Ala Gln Lys Phe
    50                  55                  60

Gln Gly Arg Val Thr Ile Thr Ala Asp Glu Phe Thr Ser Ala Ala Tyr
65                  70                  75                  80

Met Glu Leu Ser Ser Leu Gly Ser Glu Asp Thr Ala Met Tyr Tyr Cys
                85                  90                  95

Ala Arg Ser Ser Gly Tyr Tyr Pro Gln Tyr Phe Gln Asp Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 540
<211> LENGTH: 109
<212> TYPE: PRT
<213> ORGANISM: Homo sapiens

<400> SEQUENCE: 540

Glu Ile Val Met Thr Gln Ser Pro Gly Thr Leu Ser Leu Ser Pro Gly
1               5                   10                  15

Gln Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ser
                85                  90                  95

Leu Thr Phe Gly Gly Gly Thr Lys Leu Glu Ile Lys Arg
            100                 105

<210> SEQ ID NO 541
<211> LENGTH: 642
<212> TYPE: DNA
<213> ORGANISM: Homo sapiens

<400> SEQUENCE: 541
gaaattgtga tgacacagtc tccaggcacc ctgtctttgt ctccagggca aagagccacc      60
ctctcctgca gggccagtca gagtgttagc agcagctact tagcctggta ccagcagaaa     120
cctggccagg ctcccagact cctcatgtat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcatcgct cacttttggc     300
ggagggacca agctgagat caaacgtgcg gccgcacccg cgtgttcat cttccccccc      360 tccgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gagagcgtga ccgagcagga cagcaaggac tccacctaca gcctgagcag caccctcacc     540
```

```
ctgagcaagg ccgactacga gaagcacaag gtgtacgcct gcgaggtgac ccaccagggc      600
ctgagcagcc ccgtgaccaa gagcttcaac cggggcgagt gt                         642
```

<210> SEQ ID NO 542
<211> LENGTH: 214
<212> TYPE: PRT
<213> ORGANISM: Homo sapiens

<400> SEQUENCE: 542

```
Glu Ile Val Met Thr Gln Ser Pro Gly Thr Leu Ser Leu Ser Pro Gly
1               5                   10                  15

Gln Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ser
                85                  90                  95

Leu Thr Phe Gly Gly Gly Thr Lys Leu Glu Ile Lys Arg Ala Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 543
<211> LENGTH: 121
<212> TYPE: PRT
<213> ORGANISM: Homo sapiens

<400> SEQUENCE: 543

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Ile Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Ala Ile Phe His Thr Pro Lys Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Arg Ser Leu Lys Ser Glu Asp Thr Ala Leu Tyr Tyr Cys
                85                  90                  95
```

Ala Arg Gly Ser Thr Tyr Asp Phe Ser Ser Gly Leu Asp Tyr Trp Gly
            100                 105                 110

Gln Gly Thr Leu Val Thr Val Ser Ser
        115                 120

<210> SEQ ID NO 544
<211> LENGTH: 5
<212> TYPE: PRT
<213> ORGANISM: Homo sapiens

<400> SEQUENCE: 544

Asp Ile Lys Arg Thr
1               5

<210> SEQ ID NO 545
<211> LENGTH: 1353
<212> TYPE: DNA
<213> ORGANISM: Homo sapiens

<400> SEQUENCE: 545
gaggtgcagc tggtggagtc cggggctgag gtgaagaagc ctgggtcctc ggtgaaggtc      60
tcctgcaagg cttctggagg catcttcaac agttatgcta tcagctgggt gcgacaggcc     120
cctggacaag gcttgagtg gatgggaggc atcatcgcta tctttcatac accaaagtac     180
gcacagaagt tccagggcag agtcacgatt accgcggacg aatccacgaa cacagcctac     240
atggaactga aagcctgaa atctgaggac acggccctgt attactgtgc gagagggtcc     300
acttacgatt tttcgagtgg ccttgactac tggggccagg gaaccctggt caccgtctcg     360
agtgctagca ccaagggccc cagcgtgttc cccctggccc cagcagcaa gagcaccagc     420
ggcggcacag ccgccctggg ctgcctggtg aaggactact cccccagagcc cgtgaccgtg     480
agctggaaca gcggcgcctt gaccagcggc gtgcacacct tccccgccgt gctgcagagc     540
agcggcctgt acagcctgag cagcgtggtg accgtgccca gcagcagcct gggcacccag     600
acctacatct gcaacgtgaa ccacaagccc agcaacacca aggtggacaa gcgtggag     660
cccaagagct gcgacaagac ccacacctgc ccccccctgcc ctgccccccga gctgctgggc     720
ggaccctccg tgttcctgtt ccccccaaag cccaaggaca ccctcatgat cagccggacc     780
cccgaggtga cctgcgtggt ggtggacgtg agccacgagg accccgaggt gaagttcaac     840
tggtacgtgg acggcgtgga ggtgcacaac gccaagacca gccccggga ggagcagtac     900
aacagcaccc taccgggtggt gagcgtgctc accgtgctgc accaggactg gctgaacggc     960
aaggagtaca agtgcaaggt gagcaacaag gccctgcctg cccccatcga aagaccatc    1020
agcaaggcca aggccagcc ccgggagccc caggtgtaca ccctgccccc cagccgggag    1080
gagatgacca gaaccaggt gtccctcacc tgtctggtga agggcttcta ccccagcgac    1140
atcgccgtgg agtgggagag caacggccag cccgagaaca actacaagac caccccccct    1200
gtgctggaca gcgacggcag cttcttcctg tacagcaagc tcaccgtgga caagagccgg    1260
tggcagcagg gcaacgtgtt cagctgcagc gtgatgcacg aggccctgca caaccactac    1320
acccagaaga gcctgagcct gagccccggc aag                                 1353

<210> SEQ ID NO 546
<211> LENGTH: 451
<212> TYPE: PRT
<213> ORGANISM: Homo sapiens

<400> SEQUENCE: 546

-continued

Glu Val Gln Leu Val Glu Ser Gly Ala Glu Lys Lys Pro Gly Ser
1               5                   10                  15

Ser Val Lys Val Ser Cys Lys Ala Ser Gly Gly Ile Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Ala Ile Phe His Thr Pro Lys Tyr Ala Gln Lys Phe
50                  55                  60

Gln Gly Arg Val Thr Ile Thr Ala Asp Glu Ser Thr Asn Thr Ala Tyr
65                  70                  75                  80

Met Glu Leu Arg Ser Leu Lys Ser Glu Asp Thr Ala Leu Tyr Tyr Cys
            85                  90                  95

Ala Arg Gly Ser Thr Tyr Asp Phe Ser Ser Gly Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 547
<211> LENGTH: 109
<212> TYPE: PRT
<213> ORGANISM: Homo sapiens

<400> SEQUENCE: 547

Gln Ala Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Val Val Phe Gly Gly Gly Thr Lys Leu Thr Val Leu Gly
            100                 105

<210> SEQ ID NO 548
<211> LENGTH: 654
<212> TYPE: DNA
<213> ORGANISM: Homo sapiens

<400> SEQUENCE: 548
caggcagggc tgactcagcc accctcggtg tcagtggccc caggacagac ggccaggatt      60
acctgtgggg gaaacaacat tggaagtaaa agtgtgcact ggtaccagca gaagccaggc     120
caggcccctg tcctagtcgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgatcatgt ggtattcggc     300
ggagggacca agctgaccgt cctaggtgcg gccgcaggcc agcccaaggc cgctcccagc     360
gtgaccctgt tccccccctc ctccgaggag ctgcaggcca caaggccac cctggtgtgc     420 ctcatcagcg acttctaccc tggcgccgtg accgtggcct ggaaggccga cagcagcccc     480
gtgaaggccg gcgtggagac caccaccccc agcaagcaga gcaacaacaa gtacgccgcc     540
agcagctacc tgagcctcac ccccgagcag tggaagagcc accggagcta cagctgccag     600
gtgacccacg agggcagcac cgtggagaag accgtggccc ccaccgagtg cagc          654

<210> SEQ ID NO 549
<211> LENGTH: 218
<212> TYPE: PRT
<213> ORGANISM: Homo sapiens

<400> SEQUENCE: 549

Gln Ala Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
           20                  25                  30

His Trp Tyr Gln Gln Lys Pro Gly Gln Ala Pro Val Leu Val Val Tyr
               35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Lys Leu Thr Val Leu Gly Ala Ala Ala
               100                 105                 110

Gly Gln Pro Lys Ala Ala Pro Ser Val Thr Leu Phe Pro Pro Ser Ser
           115                 120                 125

Glu Glu Leu Gln Ala Asn Lys Ala Thr Leu Val Cys Leu Ile Ser Asp
       130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
               165                 170                 175

Lys Tyr Ala Ala Ser Ser Tyr Leu Ser Leu Thr Pro Glu Gln Trp Lys
           180                 185                 190

Ser His Arg Ser Tyr Ser Cys Gln Val Thr His Glu Gly Ser Thr Val
       195                 200                 205

Glu Lys Thr Val Ala Pro Thr Glu Cys Ser
210                 215

<210> SEQ ID NO 550
<211> LENGTH: 126
<212> TYPE: PRT
<213> ORGANISM: Homo sapiens

<400> SEQUENCE: 550

Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Phe Ser Ser Tyr
               20                  25                  30

Ala Ile Ser Trp Val Arg Gln Ala Pro Gly Gln Gly Leu Glu Trp Met
           35                  40                  45

Gly Gly Val Ile Pro Ile Phe Arg Thr Ala Asn Tyr Ala Gln Asn Phe
 50                  55                  60

Gln Gly Arg Val Thr Ile Thr Ala Asp Glu Phe Thr Ser Tyr Met Glu
 65                  70                  75                  80

Leu Ser Ser Leu Arg Ser Asp Asp Thr Ala Val Tyr Tyr Cys Ala Arg
                 85                  90                  95

Leu Asn Tyr His Asp Ser Gly Tyr Tyr Asn Ala Pro Arg Gly Trp
               100                 105                 110

Phe Asp Pro Trp Gly Gln Gly Thr Leu Val Thr Val Ser Ser
           115                 120                 125

<210> SEQ ID NO 551
<211> LENGTH: 1368
<212> TYPE: DNA
<213> ORGANISM: Homo sapiens

<400> SEQUENCE: 551

```
caggtccagc tggtgcagtc tggggctgag gtgaagaagc ctgggtcctc ggtgaaggtc      60
tcctgcaagg cttctggagg cttcttcagc agctatgcta tcagctgggt gcgccaggcc     120
cctggacaag gacttgagtg gatgggggggg gtcatccta tctttcgtac agcaaactac     180
gcacagaact tccagggcag agtcaccatt accgcggacg aattcacatc gtatatggag     240
ctgagcagcc tgagatctga cgacacggcc gtgtattact gtgcgaggtt gaattaccat     300
gattcgggga cttattataa cgccccccgg ggctggttcg acccctgggg ccagggaacc     360
ctggtcaccg tctcgagtgc tagcaccaag ggcccagcg tgttccccct ggcccccagc     420
agcaagagca ccagcggcgg cacagccgcc ctgggctgcc tggtgaagga ctacttcccc     480
gagcccgtga ccgtgagctg gaacagcggc gccttgacca gcggcgtgca caccttcccc     540
gccgtgctgc agagcagcgg cctgtacagc ctgagcagcg tggtgaccgt gcccagcagc     600
agcctgggca cccagaccta catctgcaac gtgaaccaca agcccagcaa caccaaggtg     660
gacaaacgcg tggagcccaa gagctgcgac aagacccaca cctgcccccc ctgccctgcc     720
cccgagctgc tgggcggacc ctccgtgttc ctgttccccc caagcccaa ggacaccctc     780
atgatcagcc ggaccccga ggtgacctgc gtggtggtgg acgtgagcca cgaggacccc     840
gaggtgaagt tcaactggta cgtggacggc gtggaggtgc acaacgccaa gaccaagccc     900
cgggaggagc agtacaacag cacctaccgg gtggtgagcg tgctcaccgt gctgcaccag     960
gactggctga acggcaagga gtacaagtgc aaggtgagca caaggccct gcctgccccc    1020
atcgagaaga ccatcagcaa ggccaagggc cagccccggg agcccaggt gtacaccctg    1080
ccccccagcc gggaggagat gaccaagaac caggtgtccc tcacctgtct ggtgaagggc    1140
ttctacccca gcgacatcgc cgtggagtgg gagagcaacg gccagcccga gaacaactac    1200
aagaccaccc cccctgtgct ggacagcgac ggcagcttct tcctgtacag caagctcacc    1260
gtggacaaga gccggtggca gcagggcaac gtgttcagct gcagcgtgat gcacgaggcc    1320
ctgcacaacc actacaccca gaagagcctg agcctgagcc ccggcaag               1368
```

<210> SEQ ID NO 552
<211> LENGTH: 456
<212> TYPE: PRT
<213> ORGANISM: Homo sapiens

<400> SEQUENCE: 552

Gln Val Gln Leu Val Gln Ser Gly Ala Glu Val Lys Lys Pro Gly Ser
1               5                   10                  15

Ser Val Lys Val Ser Cys Lys Ala Ser Gly Gly Phe Phe Ser Ser Tyr
            20                  25                  30

Ala Ile Ser Trp Val Arg Gln Ala Pro Gly Gln Gly Leu Glu Trp Met
        35                  40                  45

Gly Gly Val Ile Pro Ile Phe Arg Thr Ala Asn Tyr Ala Gln Asn Phe
    50                  55                  60

Gln Gly Arg Val Thr Ile Thr Ala Asp Glu Phe Thr Ser Tyr Met Glu
65                  70                  75                  80

Leu Ser Ser Leu Arg Ser Asp Asp Thr Ala Val Tyr Tyr Cys Ala Arg
                85                  90                  95

Leu Asn Tyr His Asp Ser Gly Thr Tyr Tyr Asn Ala Pro Arg Gly Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr

```
                    130                 135                 140
Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 553
<211> LENGTH: 114
<212> TYPE: PRT
<213> ORGANISM: Homo sapiens

<400> SEQUENCE: 553

Asp Ile Gln Met Thr Gln Ser Pro Asp Ser Leu Ala Val Ser Leu Gly
1               5                   10                  15

Glu Lys Ala Thr Ile Asn Cys Lys Ser Ser Gln Ser Ile Leu Asn Ser
            20                  25                  30

Ser Asn Asn Lys Asn Tyr Leu Ala Trp Tyr Gln Gln Lys Pro Gly Gln
        35                  40                  45
```

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Pro Thr Phe Gly Gln Gly Thr Lys Val Glu Ile
                100                 105                 110

Lys Arg

<210> SEQ ID NO 554
<211> LENGTH: 657
<212> TYPE: DNA
<213> ORGANISM: Homo sapiens

<400> SEQUENCE: 554
gacatccaga tgacccagtc tccagactcc ctggctgtgt ctctgggcga gaaggccacc      60
atcaactgca agtccagcca gagtatttta aacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtagt     300
ccgccgacgt tcggccaagg gaccaaggtg gaaatcaaac gtgcggccgc acccagcgtg     360
ttcatcttcc cccctccga cgagcagctg aagagcggca ccgccagcgt ggtgtgcctg     420
ctgaacaact tctaccccg ggaggccaag gtgcagtgga aggtggacaa cgccctgcag     480
agcggcaaca gccaggagag cgtgaccgag caggacagca aggactccac ctacagcctg     540
agcagcaccc tcaccctgag caaggccgac tacgagaagc acaaggtgta cgcctgcgag     600
gtgacccacc agggcctgag cagccccgtg accaagagct caaccggggg cgagtgt        657

<210> SEQ ID NO 555
<211> LENGTH: 219
<212> TYPE: PRT
<213> ORGANISM: Homo sapiens

<400> SEQUENCE: 555

Asp Ile Gln Met Thr Gln Ser Pro Asp Ser Leu Ala Val Ser Leu Gly
1               5                   10                  15

Glu Lys Ala Thr Ile Asn Cys Lys Ser Ser Gln Ser Ile Leu Asn Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Pro Thr Phe Gly Gln Gly Thr Lys Val Glu Ile
                100                 105                 110

Lys Arg Ala Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 556
<211> LENGTH: 120
<212> TYPE: PRT
<213> ORGANISM: Homo sapiens

<400> SEQUENCE: 556

```
Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Tyr Tyr
                20                  25                  30

Ala Met Ser Trp Val Arg Gln Ala Pro Gly Gln Gly Leu Glu Trp Met
            35                  40                  45

Gly Gly Ile Ser Pro Met Phe Gly Thr Thr Tyr Ala Gln Lys Phe
        50                  55                  60

Gln Gly Arg Val Thr Ile Thr Ala Asp Asp Ser Thr Ser Thr Ala Tyr
65                  70                  75                  80

Met Glu Val Arg Ser Leu Arg Ser Glu Asp Thr Ala Val Tyr Tyr Cys
                85                  90                  95

Ala Arg Ser Ser Asn Tyr Tyr Asp Ser Val Tyr Asp Tyr Trp Gly Gln
            100                 105                 110

Gly Thr Leu Val Thr Val Ser Ser
        115                 120
```

<210> SEQ ID NO 557
<211> LENGTH: 1350
<212> TYPE: DNA
<213> ORGANISM: Homo sapiens

<400> SEQUENCE: 557

```
caggtccagc tggtgcagtc tggagctgag gtgaagaagc ctgggtcctc ggtgaaggtc      60
tcctgcaagg cttctggagt caccttcagt tactatgcta tgagctgggt gcgacaggcc     120
cctggacaag gcttgagtg gatgggagga atcagcccta tgtttggac aacaacctac      180 gcacagaagt tccagggcag agtcacgatt actgcggacg actccacgag tacagcctac     240
atggaggtga ggagcctgag atctgaggac acggccgtgt attactgtgc gagatcttcg     300
aattactatg atagtgtata tgactactgg ggccagggaa ccctggtcac cgtctcgagt     360
gctagcacca agggcccag cgtgttcccc ctggcccca gcagcaagag caccagcggc      420
ggcacagccg ccctgggctg cctggtgaag gactacttcc ccgagcccgt gaccgtgagc     480
tggaacagcg gcgccttgac cagcggcgtg cacaccttcc cgccgtgct gcagagcagc     540 ggcctgtaca gcctgagcag cgtggtgacc gtgcccagca gcagcctggg cacccagacc     600
tacatctgca acgtgaacca caagcccagc aacaccaagg tggacaaacg cgtggagccc     660
aagagctgcg acaagaccca cacctgcccc cctgcccctg ccccgagct gctgggcgga     720
```

```
cctccgtgt tcctgttccc ccccaagccc aaggacaccc tcatgatcag ccggaccccc    780
gaggtgacct gcgtggtggt ggacgtgagc cacgaggacc ccgaggtgaa gttcaactgg    840
tacgtggacg gcgtggtggt gcacaacgcc aagaccaagc ccgggagga gcagtacaac    900
agcacctacc gggtggtgag cgtgctcacc gtgctgcacc aggactggct gaacggcaag    960
gagtacaagt gcaaggtgag caacaaggcc ctgcctgccc ccatcgagaa gaccatcagc   1020
aaggccaagg gccagccccg ggagcccag gtgtacaccc tgccccccag ccggaggag   1080
atgaccaaga accaggtgtc cctcacctgt ctggtgaagg gcttctaccc cagcgacatc   1140
gccgtggagt gggagagcaa cggccagccc gagaacaact acaagaccac ccccctgtg   1200
ctggacagcg acggcagctt cttcctgtac agcaagctca ccgtggacaa gagccggtgg   1260
cagcagggca acgtgttcag ctgcagcgtg atgcacgagg ccctgcacaa ccactacacc   1320
cagaagagcc tgagcctgag ccccggcaag                                    1350
```

<210> SEQ ID NO 558
<211> LENGTH: 450
<212> TYPE: PRT
<213> ORGANISM: Homo sapiens

<400> SEQUENCE: 558

```
Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Ser Tyr Tyr
            20                  25                  30

Ala Met Ser Trp Val Arg Gln Ala Pro Gly Gln Gly Leu Glu Trp Met
        35                  40                  45

Gly Gly Ile Ser Pro Met Phe Gly Thr Thr Thr Tyr Ala Gln Lys Phe
    50                  55                  60

Gln Gly Arg Val Thr Ile Thr Ala Asp Asp Ser Thr Ser Thr Ala Tyr
65                  70                  75                  80

Met Glu Val Arg Ser Leu Arg Ser Glu Asp Thr Ala Val Tyr Tyr Cys
                85                  90                  95

Ala Arg Ser Ser Asn Tyr Tyr Asp Ser Val Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
                    260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
    305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 559
<211> LENGTH: 109
<212> TYPE: PRT
<213> ORGANISM: Homo sapiens

<400> SEQUENCE: 559

Gln Ser Val Val Thr Gln Pro Pro Ser Glu Ser Val Ala Pro Gly Gln
1               5                   10                  15
Thr Ala Arg Ile Thr Cys Gly Gly His Asn Ile Gly Ser Asn Ser Val
            20                  25                  30
His Trp Tyr Gln Gln Lys Pro Gly Gln Ala Pro Val Leu Val Val Tyr
        35                  40                  45
Asp Asn Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Gly Ser Ser Ser Asp His
                85                  90                  95
Tyr Val Phe Gly Thr Gly Thr Lys Val Thr Val Leu Gly
            100                 105

<210> SEQ ID NO 560
<211> LENGTH: 654
<212> TYPE: DNA
<213> ORGANISM: Homo sapiens

<400> SEQUENCE: 560
cagtctgtcg tgacgcagcc gccctcggag tcagtggccc caggacagac ggccaggatt      60
acctgtgggg gacataacat tggaagtaat agtgtgcact ggtaccagca gaagccaggc     120
```

```
caggcccctg tgctggtcgt gtatgataat agcgaccggc cctcagggat ccctgagcga    180
ttctctggct ccaactctgg gaacacggcc accctgacca tcagcagggt cgaagccggg    240
gatgaggccg actattactg tcaggtgtgg ggtagtagta gtgaccatta tgtcttcgga    300
actgggacca aggtcaccgt cctaggtgcg gccgcaggcc agcccaaggc cgctcccagc    360
gtgaccctgt tccccccctc ctccgaggag ctgcaggcca caaggccac cctggtgtgc    420 ctcatcagcg acttctaccc tggcgccgtg accgtggcct ggaaggccga cagcagcccc    480
gtgaaggccg gcgtggagac caccaccccc agcaagcaga gcaacaacaa gtacgccgcc    540
agcagctacc tgagcctcac ccccgagcag tggaagagcc accggagcta cagctgccag    600
gtgacccacg agggcagcac cgtggagaag accgtggccc ccaccgagtg cagc          654
```

<210> SEQ ID NO 561
<211> LENGTH: 218
<212> TYPE: PRT
<213> ORGANISM: Homo sapiens

<400> SEQUENCE: 561

```
Gln Ser Val Val Thr Gln Pro Pro Ser Glu Ser Val Ala Pro Gly Gln
1               5                   10                  15

Thr Ala Arg Ile Thr Cys Gly Gly His Asn Ile Gly Ser Asn Ser Val
            20                  25                  30

His Trp Tyr Gln Gln Lys Pro Gly Gln Ala Pro Val Leu Val Val Tyr
        35                  40                  45

Asp Asn Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Gly Ser Ser Ser Asp His
                85                  90                  95

Tyr Val Phe Gly Thr Gly Thr Lys Val Thr Val Leu Gly Ala Ala Ala
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 562
<211> LENGTH: 123
<212> TYPE: PRT
<213> ORGANISM: Homo sapiens

<400> SEQUENCE: 562

```
Gln Val Gln Leu Val Gln Ser Gly Ala Glu Val Lys Lys Pro Gly Ser
1               5                   10                  15
```

| Ser | Val | Arg | Val | Ser | Cys | Lys | Ala | Ser | Gly | Ser | Ile | Phe | Arg | Asn | Tyr |
|---|---|---|---|---|---|---|---|---|---|---|---|---|---|---|---|
| | | | 20 | | | | | 25 | | | | | 30 | | |

Ala Met Ser Trp Val Arg Gln Ala Pro Gly Gln Gly Leu Glu Trp Met
        35                  40                  45

Gly Gly Ile Ile Ala Ile Phe Gly Thr Pro Lys Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Gly Leu Arg Ser Glu Asp Thr Ala Met Tyr Tyr Cys
            85                  90                  95

Ala Arg Ile Pro His Tyr Asn Phe Gly Ser Gly Ser Tyr Phe Asp Tyr
            100                 105                 110

Trp Gly Gln Gly Thr Leu Val Thr Val Ser Ser
        115                 120

<210> SEQ ID NO 563
<211> LENGTH: 1359
<212> TYPE: DNA
<213> ORGANISM: Homo sapiens

<400> SEQUENCE: 563

```
caggtgcagc tggtgcagtc tggggctgag gtgaagaagc ctgggtcctc ggtgagagtc      60
tcctgcaagg cttctggaag catcttcaga aactatgcta tgagctgggt gcgacaggcc     120
cctggacaag gcttgagtg gatgggaggg atcatcgcta ttttgggac accaaagtac      180
gcacagaagt tccagggcag agtcacgatt accgcggacg aatcgacgag cactgtctac     240
atggaactga gcggactgag atctgaggac acggccatgt attactgtgc gaggattccc     300
cactataatt ttggttcggg gagttatttc gactactggg gccagggaac cctggtcacc     360
ggcttgagtg ctagcaccaa gggcccagc gtgttccccc tggcccccag cagcaagagc      420
accagcggcg gcacagccgc cctgggctgc ctggtgaagg actacttccc cgagcccgtg     480
accgtgagct ggaacagcgg cgccttgacc agcggcgtgc acaccttccc cgccgtgctg     540
cagagcagcg gcctgtacag cctgagcagc gtggtgaccg tgcccagcag cagcctgggc     600
acccagacct acatctgcaa cgtgaaccac aagcccagca caccaaggt ggacaaacgc       660
gtggagccca gagctgcga caagacccac acctgccccc ctgccctgc ccccgagctg        720
ctgggcggac cctccgtgtt cctgttcccc cccaagccca ggacaccct catgatcagc     780
cggacccccg aggtgacctg cgtggtggtg acgtgagcc acgaggaccc cgaggtgaag     840
ttcaactggt acgtggacgg cgtggaggtg cacaacgcca agaccaagcc ccgggaggag     900
cagtacaaca gcacctaccg ggtggtgagc gtgctcaccg tgctgcacca ggactggctg     960
aacggcaagg agtacaagtg caaggtgagc aacaaggccc tgcctgcccc catcgagaag    1020
accatcagca aggccaaggg ccagccccgg gagccccagg tgtacaccct gccccccagc    1080
cgggaggaga tgaccaagaa ccaggtgtcc ctcacctgtc tggtgaaggg cttctacccc    1140
agcgacatcg ccgtggagtg ggagagcaac ggccagcccg agaacaacta caagaccacc    1200
cccctgtgc tggacagcga cggcagcttc ttcctgtaca gcaagctcac cgtggacaag    1260
agccggtggc agcagggcaa cgtgttcagc tgcagcgtga tgcacgaggc cctgcacaac    1320
cactacaccc agaagagcct gagcctgagc cccggcaag                            1359
```

<210> SEQ ID NO 564
<211> LENGTH: 453
<212> TYPE: PRT

<213> ORGANISM: Homo sapiens

<400> SEQUENCE: 564

```
Gln Val Gln Leu Val Gln Ser Gly Ala Glu Val Lys Lys Pro Gly Ser
1               5                   10                  15

Ser Val Arg Val Ser Cys Lys Ala Ser Gly Ile Phe Arg Asn Tyr
            20                  25                  30

Ala Met Ser Trp Val Arg Gln Ala Pro Gly Gln Gly Leu Glu Trp Met
        35                  40                  45

Gly Gly Ile Ile Ala Ile Phe Gly Thr Pro Lys Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Leu Ser Gly Leu Arg Ser Glu Asp Thr Ala Met Tyr Tyr Cys
                85                  90                  95

Ala Arg Ile Pro His Tyr Asn Phe Gly Ser Gly Ser Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 565
<211> LENGTH: 111
<212> TYPE: PRT
<213> ORGANISM: Homo sapiens

<400> SEQUENCE: 565

Thr Val Leu Thr Gln Pro Pro Ser Val Ser Gly Ala Pro Gly Gln Arg
1               5                   10                  15

Val Thr Ile Ser Cys Thr Gly Ser Ser Ser Asn Ile Gly Ala Gly Tyr
            20                  25                  30

Asp Val His Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu Gly
            100                 105                 110

<210> SEQ ID NO 566
<211> LENGTH: 5
<212> TYPE: PRT
<213> ORGANISM: Homo sapiens

<400> SEQUENCE: 566

Gly Tyr Tyr Val Tyr
1               5

<210> SEQ ID NO 567
<211> LENGTH: 17
<212> TYPE: PRT
<213> ORGANISM: Homo sapiens

<400> SEQUENCE: 567

Trp Ile Ser Ala Tyr Asn Gly Asn Thr Asn Tyr Ala Gln Lys Phe Gln
1               5                   10                  15

Gly

<210> SEQ ID NO 568
<211> LENGTH: 6
<212> TYPE: PRT
<213> ORGANISM: Homo sapiens

<400> SEQUENCE: 568

Ser Arg Ser Leu Asp Val
1               5

<210> SEQ ID NO 569
<211> LENGTH: 17
```

```
<212> TYPE: PRT
<213> ORGANISM: Homo sapiens

<400> SEQUENCE: 569

Lys Ser Ser Gln Ser Val Leu Tyr Ser Asn Asn Lys Asn Tyr Leu
1               5                   10                  15

Ala

<210> SEQ ID NO 570
<211> LENGTH: 7
<212> TYPE: PRT
<213> ORGANISM: Homo sapiens

<400> SEQUENCE: 570

Trp Ala Ser Thr Arg Glu Ser
1               5

<210> SEQ ID NO 571
<211> LENGTH: 5
<212> TYPE: PRT
<213> ORGANISM: Homo sapiens

<400> SEQUENCE: 571

Ser Tyr Ala Ile Ser
1               5

<210> SEQ ID NO 572
<211> LENGTH: 17
<212> TYPE: PRT
<213> ORGANISM: Homo sapiens

<400> SEQUENCE: 572

Gly Ile Ile Pro Ile Phe Gly Thr Thr Lys Tyr Ala Pro Lys Phe Gln
1               5                   10                  15

Gly

<210> SEQ ID NO 573
<211> LENGTH: 12
<212> TYPE: PRT
<213> ORGANISM: Homo sapiens

<400> SEQUENCE: 573

His Met Gly Tyr Gln Val Arg Glu Thr Met Asp Val
1               5                   10

<210> SEQ ID NO 574
<211> LENGTH: 13
<212> TYPE: PRT
<213> ORGANISM: Homo sapiens

<400> SEQUENCE: 574

Ser Gly Ser Thr Phe Asn Ile Gly Ser Asn Ala Val Asp
1               5                   10

<210> SEQ ID NO 575
<211> LENGTH: 7
<212> TYPE: PRT
<213> ORGANISM: Homo sapiens

<400> SEQUENCE: 575

Ser Asn Asn Gln Arg Pro Ser
1               5
```

```
<210> SEQ ID NO 576
<211> LENGTH: 11
<212> TYPE: PRT
<213> ORGANISM: Homo sapiens

<400> SEQUENCE: 576

Ala Ala Trp Asp Asp Ile Leu Asn Val Pro Val
1               5                   10

<210> SEQ ID NO 577
<211> LENGTH: 14
<212> TYPE: PRT
<213> ORGANISM: Homo sapiens

<400> SEQUENCE: 577

Thr Gly Thr Ser Ser Asp Val Gly Gly Tyr Asn Tyr Val Ser
1               5                   10

<210> SEQ ID NO 578
<211> LENGTH: 7
<212> TYPE: PRT
<213> ORGANISM: Homo sapiens

<400> SEQUENCE: 578

Glu Val Ser Asn Arg Pro Ser
1               5

<210> SEQ ID NO 579
<211> LENGTH: 9
<212> TYPE: PRT
<213> ORGANISM: Homo sapiens

<400> SEQUENCE: 579

Ser Ser Tyr Thr Ser Ser Ser Thr Tyr
1               5

<210> SEQ ID NO 580
<211> LENGTH: 13
<212> TYPE: PRT
<213> ORGANISM: Homo sapiens

<400> SEQUENCE: 580

Ser Gly Ser Arg Ser Asn Val Gly Asp Asn Ser Val Tyr
1               5                   10

<210> SEQ ID NO 581
<211> LENGTH: 7
<212> TYPE: PRT
<213> ORGANISM: Homo sapiens

<400> SEQUENCE: 581

Lys Asn Thr Gln Arg Pro Ser
1               5

<210> SEQ ID NO 582
<211> LENGTH: 11
<212> TYPE: PRT
<213> ORGANISM: Homo sapiens

<400> SEQUENCE: 582

Val Ala Trp Asp Asp Ser Val Asp Gly Tyr Val
1               5                   10

<210> SEQ ID NO 583
<211> LENGTH: 13
```

```
<212> TYPE: PRT
<213> ORGANISM: Homo sapiens

<400> SEQUENCE: 583

Ser Gly Ser Ser Ser Asn Ile Gly Asn Asp Tyr Val Ser
1               5                   10

<210> SEQ ID NO 584
<211> LENGTH: 7
<212> TYPE: PRT
<213> ORGANISM: Homo sapiens

<400> SEQUENCE: 584

Asp Asn Asn Lys Arg Pro Ser
1               5

<210> SEQ ID NO 585
<211> LENGTH: 12
<212> TYPE: PRT
<213> ORGANISM: Homo sapiens

<400> SEQUENCE: 585

Ala Thr Trp Asp Arg Arg Pro Thr Ala Tyr Val Val
1               5                   10

<210> SEQ ID NO 586
<211> LENGTH: 5
<212> TYPE: PRT
<213> ORGANISM: Homo sapiens

<400> SEQUENCE: 586

Gly Ser Ala Ile Ser
1               5

<210> SEQ ID NO 587
<211> LENGTH: 17
<212> TYPE: PRT
<213> ORGANISM: Homo sapiens

<400> SEQUENCE: 587

Gly Ile Ser Pro Leu Phe Gly Thr Thr Asn Tyr Ala Gln Lys Phe Gln
1               5                   10                  15

Gly

<210> SEQ ID NO 588
<211> LENGTH: 11
<212> TYPE: PRT
<213> ORGANISM: Homo sapiens

<400> SEQUENCE: 588

Gly Pro Lys Tyr Tyr Ser Glu Tyr Met Asp Val
1               5                   10

<210> SEQ ID NO 589
<211> LENGTH: 11
<212> TYPE: PRT
<213> ORGANISM: Homo sapiens

<400> SEQUENCE: 589

Arg Ala Ser Gln Gly Ile Ser Ser Tyr Leu Ala
1               5                   10

<210> SEQ ID NO 590
<211> LENGTH: 7
```

```
<212> TYPE: PRT
<213> ORGANISM: Homo sapiens

<400> SEQUENCE: 590

Asp Ala Ser Thr Leu Arg Ser
1               5

<210> SEQ ID NO 591
<211> LENGTH: 9
<212> TYPE: PRT
<213> ORGANISM: Homo sapiens

<400> SEQUENCE: 591

Gln Arg Tyr Asn Ser Ala Pro Pro Ile
1               5

<210> SEQ ID NO 592
<211> LENGTH: 17
<212> TYPE: PRT
<213> ORGANISM: Homo sapiens

<400> SEQUENCE: 592

Gly Ile Met Gly Met Phe Gly Thr Thr Asn Tyr Ala Gln Lys Phe Gln
1               5                   10                  15

Gly

<210> SEQ ID NO 593
<211> LENGTH: 11
<212> TYPE: PRT
<213> ORGANISM: Homo sapiens

<400> SEQUENCE: 593

Ser Ser Gly Tyr Tyr Pro Glu Tyr Phe Gln Asp
1               5                   10

<210> SEQ ID NO 594
<211> LENGTH: 11
<212> TYPE: PRT
<213> ORGANISM: Homo sapiens

<400> SEQUENCE: 594

Ser Gly His Lys Leu Gly Asp Lys Tyr Val Ser
1               5                   10

<210> SEQ ID NO 595
<211> LENGTH: 7
<212> TYPE: PRT
<213> ORGANISM: Homo sapiens

<400> SEQUENCE: 595

Gln Asp Asn Arg Arg Pro Ser
1               5

<210> SEQ ID NO 596
<211> LENGTH: 8
<212> TYPE: PRT
<213> ORGANISM: Homo sapiens

<400> SEQUENCE: 596

Gln Ala Trp Asp Ser Ser Thr Ala
1               5

<210> SEQ ID NO 597
<211> LENGTH: 5
```

```
<212> TYPE: PRT
<213> ORGANISM: Homo sapiens

<400> SEQUENCE: 597

Ser Tyr Ala Ile Thr
1               5

<210> SEQ ID NO 598
<211> LENGTH: 17
<212> TYPE: PRT
<213> ORGANISM: Homo sapiens

<400> SEQUENCE: 598

Gly Ile Ile Gly Met Phe Gly Ser Thr Asn Tyr Ala Gln Asn Phe Gln
1               5                   10                  15

Gly

<210> SEQ ID NO 599
<211> LENGTH: 11
<212> TYPE: PRT
<213> ORGANISM: Homo sapiens

<400> SEQUENCE: 599

Ser Thr Gly Tyr Tyr Pro Ala Tyr Leu His His
1               5                   10

<210> SEQ ID NO 600

<400> SEQUENCE: 600

000

<210> SEQ ID NO 601
<211> LENGTH: 7
<212> TYPE: PRT
<213> ORGANISM: Homo sapiens

<400> SEQUENCE: 601

Asp Val Ser Lys Arg Pro Ser
1               5

<210> SEQ ID NO 602
<211> LENGTH: 10
<212> TYPE: PRT
<213> ORGANISM: Homo sapiens

<400> SEQUENCE: 602

Ser Ser Tyr Thr Ser Ser Ser Thr His Val
1               5                   10

<210> SEQ ID NO 603
<211> LENGTH: 5
<212> TYPE: PRT
<213> ORGANISM: Homo sapiens

<400> SEQUENCE: 603

Ser Tyr Tyr Met His
1               5

<210> SEQ ID NO 604
<211> LENGTH: 17
<212> TYPE: PRT
<213> ORGANISM: Homo sapiens

<400> SEQUENCE: 604
```

```
Trp Ile Asn Pro Asn Ser Gly Gly Thr Asn Tyr Ala Gln Lys Phe Gln
1               5                   10                  15

Gly

<210> SEQ ID NO 605
<211> LENGTH: 12
<212> TYPE: PRT
<213> ORGANISM: Homo sapiens

<400> SEQUENCE: 605

Glu Gly Lys Trp Gly Pro Gln Ala Ala Phe Asp Ile
1               5                   10

<210> SEQ ID NO 606

<400> SEQUENCE: 606

000

<210> SEQ ID NO 607
<211> LENGTH: 7
<212> TYPE: PRT
<213> ORGANISM: Homo sapiens

<400> SEQUENCE: 607

Asp Ala Ser Ser Arg Ala Thr
1               5

<210> SEQ ID NO 608
<211> LENGTH: 8
<212> TYPE: PRT
<213> ORGANISM: Homo sapiens

<400> SEQUENCE: 608

Gln Gln Tyr Gly Ser Ser Leu Trp
1               5

<210> SEQ ID NO 609
<211> LENGTH: 5
<212> TYPE: PRT
<213> ORGANISM: Homo sapiens

<400> SEQUENCE: 609

Ile Tyr Ala Met Ser
1               5

<210> SEQ ID NO 610
<211> LENGTH: 17
<212> TYPE: PRT
<213> ORGANISM: Homo sapiens

<400> SEQUENCE: 610

Ala Ile Ser Ser Ser Gly Asp Ser Thr Tyr Tyr Ala Asp Ser Val Lys
1               5                   10                  15

Gly

<210> SEQ ID NO 611
<211> LENGTH: 8
<212> TYPE: PRT
<213> ORGANISM: Homo sapiens

<400> SEQUENCE: 611

Ala Tyr Gly Tyr Thr Phe Asp Pro
```

-continued

```
1               5

<210> SEQ ID NO 612
<211> LENGTH: 16
<212> TYPE: PRT
<213> ORGANISM: Homo sapiens

<400> SEQUENCE: 612

Arg Ser Ser Gln Ser Leu Leu His Ser Asn Gly Tyr Asn Tyr Leu Asp
1               5                   10                  15

<210> SEQ ID NO 613
<211> LENGTH: 7
<212> TYPE: PRT
<213> ORGANISM: Homo sapiens

<400> SEQUENCE: 613

Leu Gly Ser Asn Arg Ala Ser
1               5

<210> SEQ ID NO 614
<211> LENGTH: 8
<212> TYPE: PRT
<213> ORGANISM: Homo sapiens

<400> SEQUENCE: 614

Met Gln Ala Leu Gln Thr Pro Leu
1               5

<210> SEQ ID NO 615
<211> LENGTH: 5
<212> TYPE: PRT
<213> ORGANISM: Homo sapiens

<400> SEQUENCE: 615

Ser Tyr Ser Met Asn
1               5

<210> SEQ ID NO 616
<211> LENGTH: 17
<212> TYPE: PRT
<213> ORGANISM: Homo sapiens

<400> SEQUENCE: 616

Ser Ile Ser Ser Ser Ser Ser Tyr Ile Tyr Tyr Val Asp Ser Val Lys
1               5                   10                  15

Gly

<210> SEQ ID NO 617
<211> LENGTH: 13
<212> TYPE: PRT
<213> ORGANISM: Homo sapiens

<400> SEQUENCE: 617

Gly Gly Gly Ser Tyr Gly Ala Tyr Glu Gly Phe Asp Tyr
1               5                   10

<210> SEQ ID NO 618
<211> LENGTH: 11
<212> TYPE: PRT
<213> ORGANISM: Homo sapiens

<400> SEQUENCE: 618

Arg Ala Ser Gln Arg Val Ser Ser Tyr Leu Ala
```

```
1               5               10
```

<210> SEQ ID NO 619
<211> LENGTH: 7
<212> TYPE: PRT
<213> ORGANISM: Homo sapiens

<400> SEQUENCE: 619

```
Gly Ala Ser Thr Arg Ala Ala
1               5
```

<210> SEQ ID NO 620
<211> LENGTH: 9
<212> TYPE: PRT
<213> ORGANISM: Homo sapiens

<400> SEQUENCE: 620

```
Gln Gln Tyr Gly Arg Thr Pro Leu Thr
1               5
```

<210> SEQ ID NO 621
<211> LENGTH: 11
<212> TYPE: PRT
<213> ORGANISM: Homo sapiens

<400> SEQUENCE: 621

```
Gly Gly Asn Asn Ile Gly Ser Lys Ser Val His
1               5                   10
```

<210> SEQ ID NO 622
<211> LENGTH: 7
<212> TYPE: PRT
<213> ORGANISM: Homo sapiens

<400> SEQUENCE: 622

```
Asp Asp Ser Asp Arg Pro Ser
1               5
```

<210> SEQ ID NO 623
<211> LENGTH: 11
<212> TYPE: PRT
<213> ORGANISM: Homo sapiens

<400> SEQUENCE: 623

```
Gln Val Trp Asp Ser Ser Ser Asp His Ala Val
1               5                   10
```

<210> SEQ ID NO 624
<211> LENGTH: 13
<212> TYPE: PRT
<213> ORGANISM: Homo sapiens

<400> SEQUENCE: 624

```
Ser Gly Ser Ser Ser Asn Ile Gly Ser Asn Tyr Val Tyr
1               5                   10
```

<210> SEQ ID NO 625
<211> LENGTH: 7
<212> TYPE: PRT
<213> ORGANISM: Homo sapiens

<400> SEQUENCE: 625

```
Arg Asp Gly Gln Arg Pro Ser
1               5
```

```
<210> SEQ ID NO 626
<211> LENGTH: 11
<212> TYPE: PRT
<213> ORGANISM: Homo sapiens

<400> SEQUENCE: 626

Ala Thr Trp Asp Asp Asn Leu Ser Gly Pro Val
1               5                   10

<210> SEQ ID NO 627
<211> LENGTH: 5
<212> TYPE: PRT
<213> ORGANISM: Homo sapiens

<400> SEQUENCE: 627

Ser Tyr Gly Ile Ser
1               5

<210> SEQ ID NO 628
<211> LENGTH: 17
<212> TYPE: PRT
<213> ORGANISM: Homo sapiens

<400> SEQUENCE: 628

Asp Ile Ile Gly Met Phe Gly Ser Thr Asn Tyr Ala Gln Asn Phe Gln
1               5                   10                  15

Gly

<210> SEQ ID NO 629
<211> LENGTH: 11
<212> TYPE: PRT
<213> ORGANISM: Homo sapiens

<400> SEQUENCE: 629

Ser Ser Gly Tyr Tyr Pro Ala Tyr Leu Pro His
1               5                   10

<210> SEQ ID NO 630

<400> SEQUENCE: 630

000

<210> SEQ ID NO 631
<211> LENGTH: 7
<212> TYPE: PRT
<213> ORGANISM: Homo sapiens

<400> SEQUENCE: 631

Gly Ala Ser Ser Arg Ala Thr
1               5

<210> SEQ ID NO 632
<211> LENGTH: 9
<212> TYPE: PRT
<213> ORGANISM: Homo sapiens

<400> SEQUENCE: 632

Gln Gln Tyr Gly Ser Ser Pro Arg Thr
1               5

<210> SEQ ID NO 633
<211> LENGTH: 5
<212> TYPE: PRT
```

```
<213> ORGANISM: Homo sapiens

<400> SEQUENCE: 633

Phe Tyr Ser Met Ser
1               5

<210> SEQ ID NO 634
<211> LENGTH: 17
<212> TYPE: PRT
<213> ORGANISM: Homo sapiens

<400> SEQUENCE: 634

Gly Ile Ile Pro Met Phe Gly Thr Thr Asn Tyr Ala Gln Lys Phe Gln
1               5                   10                  15

Gly

<210> SEQ ID NO 635
<211> LENGTH: 12
<212> TYPE: PRT
<213> ORGANISM: Homo sapiens

<400> SEQUENCE: 635

Gly Asp Lys Gly Ile Tyr Tyr Tyr Tyr Met Asp Val
1               5                   10

<210> SEQ ID NO 636
<211> LENGTH: 10
<212> TYPE: PRT
<213> ORGANISM: Homo sapiens

<400> SEQUENCE: 636

Ser Ser Tyr Thr Ser Ser Ser Thr Leu Val
1               5                   10

<210> SEQ ID NO 637
<211> LENGTH: 5
<212> TYPE: PRT
<213> ORGANISM: Homo sapiens

<400> SEQUENCE: 637

Thr His Ala Ile Ser
1               5

<210> SEQ ID NO 638
<211> LENGTH: 17
<212> TYPE: PRT
<213> ORGANISM: Homo sapiens

<400> SEQUENCE: 638

Gly Ile Ile Ala Ile Phe Gly Thr Ala Asn Tyr Ala Gln Lys Phe Gln
1               5                   10                  15

Gly

<210> SEQ ID NO 639
<211> LENGTH: 12
<212> TYPE: PRT
<213> ORGANISM: Homo sapiens

<400> SEQUENCE: 639

Gly Ser Gly Tyr His Ile Ser Thr Pro Phe Asp Asn
1               5                   10

<210> SEQ ID NO 640
```

```
<211> LENGTH: 11
<212> TYPE: PRT
<213> ORGANISM: Homo sapiens

<400> SEQUENCE: 640

Gly Gly Asn Asn Ile Gly Ser Lys Gly Val His
1               5                   10

<210> SEQ ID NO 641

<400> SEQUENCE: 641

000

<210> SEQ ID NO 642
<211> LENGTH: 11
<212> TYPE: PRT
<213> ORGANISM: Homo sapiens

<400> SEQUENCE: 642

Gln Val Trp Asp Ser Ser Ser Asp His Val Val
1               5                   10

<210> SEQ ID NO 643
<211> LENGTH: 5
<212> TYPE: PRT
<213> ORGANISM: Homo sapiens

<400> SEQUENCE: 643

Gly Tyr Ala Ile Ser
1               5

<210> SEQ ID NO 644
<211> LENGTH: 17
<212> TYPE: PRT
<213> ORGANISM: Homo sapiens

<400> SEQUENCE: 644

Gly Ile Ile Pro Ile Phe Gly Thr Thr Asn Tyr Ala Gln Lys Phe Gln
1               5                   10                  15

Gly

<210> SEQ ID NO 645
<211> LENGTH: 19
<212> TYPE: PRT
<213> ORGANISM: Homo sapiens

<400> SEQUENCE: 645

Val Lys Asp Gly Tyr Cys Thr Leu Thr Ser Cys Pro Val Gly Trp Tyr
1               5                   10                  15

Phe Asp Leu

<210> SEQ ID NO 646
<211> LENGTH: 12
<212> TYPE: PRT
<213> ORGANISM: Homo sapiens

<400> SEQUENCE: 646

Arg Ala Ser Gln Ser Val Ser Ser Ser Tyr Leu Ala
1               5                   10

<210> SEQ ID NO 647

<400> SEQUENCE: 647
```

000

<210> SEQ ID NO 648
<211> LENGTH: 8
<212> TYPE: PRT
<213> ORGANISM: Homo sapiens

<400> SEQUENCE: 648

Gln Gln Tyr Gly Ser Ser Leu Thr
1               5

<210> SEQ ID NO 649
<211> LENGTH: 5
<212> TYPE: PRT
<213> ORGANISM: Homo sapiens

<400> SEQUENCE: 649

Ser Asn Ser Ile Ser
1               5

<210> SEQ ID NO 650
<211> LENGTH: 17
<212> TYPE: PRT
<213> ORGANISM: Homo sapiens

<400> SEQUENCE: 650

Gly Ile Phe Ala Leu Phe Gly Thr Thr Asp Tyr Ala Gln Lys Phe Gln
1               5                   10                  15

Gly

<210> SEQ ID NO 651
<211> LENGTH: 12
<212> TYPE: PRT
<213> ORGANISM: Homo sapiens

<400> SEQUENCE: 651

Gly Ser Gly Tyr Thr Thr Arg Asn Tyr Phe Asp Tyr
1               5                   10

<210> SEQ ID NO 652
<211> LENGTH: 12
<212> TYPE: PRT
<213> ORGANISM: Homo sapiens

<400> SEQUENCE: 652

Arg Ala Ser Gln Ser Val Ser Ser Asn Tyr Leu Gly
1               5                   10

<210> SEQ ID NO 653
<211> LENGTH: 7
<212> TYPE: PRT
<213> ORGANISM: Homo sapiens

<400> SEQUENCE: 653

Gly Ala Ser Ser Arg Ala Ser
1               5

<210> SEQ ID NO 654
<211> LENGTH: 9
<212> TYPE: PRT
<213> ORGANISM: Homo sapiens

<400> SEQUENCE: 654

Gln Gln Tyr Gly Ser Ser Pro Leu Thr
1               5

<210> SEQ ID NO 655
<211> LENGTH: 17
<212> TYPE: PRT
<213> ORGANISM: Homo sapiens

<400> SEQUENCE: 655

Gly Ile Ile Gly Met Phe Gly Thr Ala Asn Tyr Ala Gln Lys Phe Gln
1               5                   10                  15
Gly

<210> SEQ ID NO 656
<211> LENGTH: 11
<212> TYPE: PRT
<213> ORGANISM: Homo sapiens

<400> SEQUENCE: 656

Gly Asn Tyr Tyr Tyr Glu Ser Ser Leu Asp Tyr
1               5                   10

<210> SEQ ID NO 657
<211> LENGTH: 9
<212> TYPE: PRT
<213> ORGANISM: Homo sapiens

<400> SEQUENCE: 657

Gln Val Trp Asp Ser Ser Ser Asp His
1               5

<210> SEQ ID NO 658
<211> LENGTH: 5
<212> TYPE: PRT
<213> ORGANISM: Homo sapiens

<400> SEQUENCE: 658

Asn Phe Ala Ile Asn
1               5

<210> SEQ ID NO 659
<211> LENGTH: 17
<212> TYPE: PRT
<213> ORGANISM: Homo sapiens

<400> SEQUENCE: 659

Gly Ile Ile Ala Val Phe Gly Thr Thr Lys Tyr Ala His Lys Phe Gln
1               5                   10                  15
Gly

<210> SEQ ID NO 660
<211> LENGTH: 11
<212> TYPE: PRT
<213> ORGANISM: Homo sapiens

<400> SEQUENCE: 660

Gly Pro His Tyr Tyr Ser Ser Tyr Met Asp Val
1               5                   10

<210> SEQ ID NO 661
<211> LENGTH: 11
<212> TYPE: PRT
<213> ORGANISM: Homo sapiens

```
<400> SEQUENCE: 661

Arg Ala Ser Gln Gly Ile Ser Thr Tyr Leu Ala
1               5                   10

<210> SEQ ID NO 662
<211> LENGTH: 7
<212> TYPE: PRT
<213> ORGANISM: Homo sapiens

<400> SEQUENCE: 662

Ala Ala Ser Thr Leu Gln Ser
1               5

<210> SEQ ID NO 663
<211> LENGTH: 8
<212> TYPE: PRT
<213> ORGANISM: Homo sapiens

<400> SEQUENCE: 663

Gln Lys Tyr Asn Ser Ala Pro Ser
1               5

<210> SEQ ID NO 664
<211> LENGTH: 5
<212> TYPE: PRT
<213> ORGANISM: Homo sapiens

<400> SEQUENCE: 664

Ser Asn Ala Val Ser
1               5

<210> SEQ ID NO 665
<211> LENGTH: 17
<212> TYPE: PRT
<213> ORGANISM: Homo sapiens

<400> SEQUENCE: 665

Gly Ile Leu Gly Val Phe Gly Ser Pro Ser Tyr Ala Gln Lys Phe Gln
1               5                   10                  15

Gly

<210> SEQ ID NO 666
<211> LENGTH: 11
<212> TYPE: PRT
<213> ORGANISM: Homo sapiens

<400> SEQUENCE: 666

Gly Pro Thr Tyr Tyr Tyr Ser Tyr Met Asp Val
1               5                   10

<210> SEQ ID NO 667
<211> LENGTH: 11
<212> TYPE: PRT
<213> ORGANISM: Homo sapiens

<400> SEQUENCE: 667

Gly Gly Asn Asn Ile Gly Arg Asn Ser Val His
1               5                   10

<210> SEQ ID NO 668

<400> SEQUENCE: 668

000
```

<210> SEQ ID NO 669
<211> LENGTH: 11
<212> TYPE: PRT
<213> ORGANISM: Homo sapiens

<400> SEQUENCE: 669

Gln Val Trp His Ser Ser Asp His Tyr Val
1               5                   10

<210> SEQ ID NO 670

<400> SEQUENCE: 670

000

<210> SEQ ID NO 671
<211> LENGTH: 17
<212> TYPE: PRT
<213> ORGANISM: Homo sapiens

<400> SEQUENCE: 671

Gly Ile Phe Gly Met Phe Gly Thr Ala Asn Tyr Ala Gln Lys Phe Gln
1               5                   10                  15

Gly

<210> SEQ ID NO 672
<211> LENGTH: 11
<212> TYPE: PRT
<213> ORGANISM: Homo sapiens

<400> SEQUENCE: 672

Ser Ser Gly Tyr Tyr Pro Gln Tyr Phe Gln Asp
1               5                   10

<210> SEQ ID NO 673
<211> LENGTH: 134
<212> TYPE: PRT
<213> ORGANISM: Homo sapiens

<400> SEQUENCE: 673

Ala Ser Thr Met Asp Met Arg Val Leu Ala Gln Leu Gly Leu Leu
1               5                   10                  15

Leu Leu Trp Leu Arg Gly Ala Arg Cys Asp Ile Gln Val Thr Gln Ser
                20                  25                  30

Pro Ser Ser Leu Ser Ala Ser Val Gly Asp Arg Val Thr Ile Thr Cys
            35                  40                  45

Arg Ala Ser Gln Asn Ile Tyr Lys Tyr Leu Asn Trp Tyr Gln Gln Arg
    50                  55                  60

Pro Gly Lys Ala Pro Lys Gly Leu Ile Ser Ala Ala Ser Gly Leu Gln
65                  70                  75                  80

Ser Gly Val Pro Ser Arg Phe Ser Gly Ser Gly Ser Gly Thr Asp Phe
                85                  90                  95

Thr Leu Thr Ile Thr Ser Leu Gln Pro Glu Asp Phe Ala Thr Tyr Tyr
            100                 105                 110

Cys Gln Gln Ser Tyr Ser Pro Pro Leu Thr Phe Gly Gly Gly Thr Arg
    115                 120                 125

Val Asp Ile Lys Arg Thr
    130

```
<210> SEQ ID NO 674
<211> LENGTH: 134
<212> TYPE: PRT
<213> ORGANISM: Homo sapiens

<400> SEQUENCE: 674

Ala Ser Thr Met Asp Met Arg Val Leu Ala Gln Leu Leu Gly Leu Leu
1               5                   10                  15

Leu Leu Trp Leu Arg Gly Ala Arg Cys Asp Ile Gln Met Thr Gln Ser
            20                  25                  30

Pro Ser Ser Leu Ser Ala Ser Val Gly Asp Arg Val Thr Ile Thr Cys
        35                  40                  45

Arg Ala Ser Gln Asn Ile Tyr Lys Tyr Leu Asn Trp Tyr Gln Gln Arg
50                  55                  60

Pro Gly Lys Ala Pro Lys Gly Leu Ile Ser Ala Ala Ser Gly Leu Gln
65                  70                  75                  80

Ser Gly Val Pro Ser Arg Phe Ser Gly Ser Gly Ser Gly Thr Asp Phe
                85                  90                  95

Thr Leu Thr Ile Thr Ser Leu Gln Pro Glu Asp Phe Ala Thr Tyr Tyr
            100                 105                 110

Cys Gln Gln Ser Tyr Ser Pro Pro Leu Thr Phe Gly Gly Thr Arg
        115                 120                 125

Val Glu Ile Lys Arg Thr
    130

<210> SEQ ID NO 675
<211> LENGTH: 133
<212> TYPE: PRT
<213> ORGANISM: Homo sapiens

<400> SEQUENCE: 675

Ala Ser Thr Met Asp Met Arg Val Leu Ala Gln Leu Leu Gly Leu Leu
1               5                   10                  15

Leu Leu Trp Leu Arg Gly Ala Arg Cys Asp Ile Gln Met Thr Gln Ser
            20                  25                  30

Pro Ser Ser Leu Ser Ala Ser Val Gly Asp Arg Val Thr Ile Thr Cys
        35                  40                  45

Arg Thr Ser Gln Ser Ile Ser Ser Tyr Leu Asn Trp Tyr Gln Gln Lys
50                  55                  60

Pro Gly Lys Ala Pro Lys Leu Leu Ile Tyr Ala Ala Ser Ser Leu Gln
65                  70                  75                  80

Ser Gly Val Pro Ser Arg Phe Ser Gly Ser Gly Ser Gly Thr Asp Phe
                85                  90                  95

Thr Leu Thr Ile Ser Gly Leu Gln Pro Glu Asp Phe Ala Thr Tyr Tyr
            100                 105                 110

Cys Gln Gln Ser Tyr Ser Met Pro Ala Phe Gly Gln Gly Thr Lys Leu
        115                 120                 125

Glu Ile Lys Arg Thr
    130

<210> SEQ ID NO 676
<211> LENGTH: 140
<212> TYPE: PRT
<213> ORGANISM: Homo sapiens

<400> SEQUENCE: 676

Ala Ser Thr Met Lys His Leu Trp Phe Phe Leu Leu Leu Val Ala Ala
1               5                   10                  15
```

Pro Ser Trp Val Leu Ser Gln Val Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Ser Ser Ile Ser Asn Tyr Tyr Trp Ser Trp Ile Arg Gln Ser Pro Gly
    50                  55                  60

Lys Gly Leu Glu Trp Ile Gly Phe Ile Tyr Tyr Gly Asn Thr Lys
65                  70                  75                  80

Tyr Asn Pro Ser Leu Lys Ser Arg Val Thr Ile Ser Gln Asp Thr Ser
                85                  90                  95

Lys Ser Gln Val Ser Leu Thr Met Ser Ser Val Thr Ala Ala Glu Ser
            100                 105                 110

Ala Val Tyr Phe Cys Ala Arg Ala Ser Cys Ser Gly Gly Tyr Cys Ile
        115                 120                 125

Leu Asp Tyr Trp Gly Gln Thr Leu Val Thr Val Ser
    130                 135                 140

<210> SEQ ID NO 677
<211> LENGTH: 140
<212> TYPE: PRT
<213> ORGANISM: Homo sapiens

<400> SEQUENCE: 677

Ala Ser Thr Met Glu Leu Gly Leu Cys Trp Val Phe Leu Val Ala Ile
1               5                   10                  15

Leu Lys Gly Val Gln Cys Glu Val Gln Leu Val Glu Ser Gly Gly Gly
            20                  25                  30

Leu Val Gln Pro Gly Gly Ser Leu Arg Ile Ser Cys Ala Ala Ser Gly
        35                  40                  45

Phe Thr Val Ser Ser Asn Tyr Met Ser Trp Val Arg Gln Ala Pro Gly
    50                  55                  60

Lys Gly Leu Glu Trp Val Ser Val Ile Tyr Ser Gly Gly Ser Thr Tyr
65                  70                  75                  80

Tyr Ala Asp Ser Val Lys Gly Arg Phe Ser Phe Ser Arg Asp Asn Ser
                85                  90                  95

Lys Asn Thr Val Phe Leu Gln Met Asn Ser Leu Arg Ala Glu Asp Thr
            100                 105                 110

Ala Val Tyr Tyr Cys Ala Arg Cys Leu Ser Arg Met Arg Gly Tyr Gly
        115                 120                 125

Leu Asp Val Trp Gly Gln Thr Thr Val Thr Val Ser
    130                 135                 140

<210> SEQ ID NO 678
<211> LENGTH: 140
<212> TYPE: PRT
<213> ORGANISM: Homo sapiens

<400> SEQUENCE: 678

Ala Ser Thr Met Lys His Leu Trp Phe Phe Leu Leu Leu Val Ala Ala
1               5                   10                  15

Pro Ser Trp Val Leu Ser Gln Val Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Ser Ser Ile Ser Asn Tyr Tyr Trp Ser Trp Ile Arg Gln Ser Pro Gly
    50                  55                  60

Lys Gly Leu Glu Trp Ile Gly Phe Ile Tyr Tyr Gly Asn Thr Lys
65                  70                  75                  80

Tyr Asn Pro Ser Leu Lys Ser Arg Val Thr Ile Ser Gln Asp Thr Ser
            85                  90                  95

Lys Ser Gln Val Ser Leu Thr Met Ser Ser Val Thr Ala Ala Glu Ser
            100                 105                 110

Ala Val Tyr Phe Cys Ala Arg Ala Ser Cys Ser Gly Gly Tyr Cys Ile
            115                 120                 125

Leu Asp Tyr Trp Gly Gln Thr Leu Val Thr Val Ser
        130                 135                 140

<210> SEQ ID NO 679
<211> LENGTH: 24
<212> TYPE: PRT
<213> ORGANISM: Influenza A virus

<400> SEQUENCE: 679

Met Ser Leu Leu Thr Glu Val Glu Thr Pro Ile Lys Asn Gly Trp Glu
1               5                   10                  15

Cys Lys Cys Asn Asp Ser Ser Asp
            20

<210> SEQ ID NO 680
<211> LENGTH: 23
<212> TYPE: PRT
<213> ORGANISM: Influenza A virus

<400> SEQUENCE: 680

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 681
<211> LENGTH: 23
<212> TYPE: PRT
<213> ORGANISM: Influenza A virus

<400> SEQUENCE: 681

Ser Leu Leu Thr Glu Val Glu Thr Pro Ile Arg Ser Glu Trp Gly Cys
1               5                   10                  15

Arg Cys Asn Asp Ser Gly Asp
            20

<210> SEQ ID NO 682
<211> LENGTH: 23
<212> TYPE: PRT
<213> ORGANISM: Influenza A virus

<400> SEQUENCE: 682

Ser Leu Leu Thr Glu Val Glu Thr Pro Ile Arg Asn Glu Trp Glu Cys
1               5                   10                  15

Arg Cys Asn Gly Ser Ser Asp
            20

<210> SEQ ID NO 683
<211> LENGTH: 23
<212> TYPE: PRT
<213> ORGANISM: Influenza A virus

<400> SEQUENCE: 683

Ser Leu Pro Thr Glu Val Glu Thr Pro Ile Arg Asn Glu Trp Gly Cys
1               5                   10                  15

Arg Cys Asn Asp Ser Ser Asp
            20

<210> SEQ ID NO 684
<211> LENGTH: 23
<212> TYPE: PRT
<213> ORGANISM: Influenza A virus

<400> SEQUENCE: 684

Ser Leu Leu Thr Glu Val Glu Thr Pro Ile Arg Asn Glu Trp Gly Cys
1               5                   10                  15

Arg Cys Asn Gly Ser Ser Asp
            20

<210> SEQ ID NO 685
<211> LENGTH: 23
<212> TYPE: PRT
<213> ORGANISM: Influenza A virus

<400> SEQUENCE: 685

Ser Leu Leu Thr Glu Val Asp Thr Leu Thr Arg Asn Gly Trp Gly Cys
1               5                   10                  15

Arg Cys Ser Asp Ser Ser Asp
            20

<210> SEQ ID NO 686
<211> LENGTH: 23
<212> TYPE: PRT
<213> ORGANISM: Influenza A virus

<400> SEQUENCE: 686

Ser Leu Leu Thr Glu Val Glu Thr Pro Ile Arg Lys Glu Trp Gly Cys
1               5                   10                  15

Asn Cys Ser Asp Ser Ser Asp
            20

<210> SEQ ID NO 687
<211> LENGTH: 23
<212> TYPE: PRT
<213> ORGANISM: Influenza A virus

<400> SEQUENCE: 687

Ser Leu Leu Thr Glu Val Glu Thr Leu Ile Arg Asn Gly Trp Gly Cys
1               5                   10                  15

Arg Cys Ser Asp Ser Ser Asp
            20

<210> SEQ ID NO 688
<211> LENGTH: 23
<212> TYPE: PRT
<213> ORGANISM: Influenza A virus

<400> SEQUENCE: 688

Ser Leu Leu Thr Glu Val Glu Thr Leu Thr Lys Asn Gly Trp Gly Cys
1               5                   10                  15

Arg Cys Ser Asp Ser Ser Asp
            20

<210> SEQ ID NO 689

```
<211> LENGTH: 23
<212> TYPE: PRT
<213> ORGANISM: Influenza A virus

<400> SEQUENCE: 689

Ser Leu Leu Thr Glu Val Glu Thr Pro Ile Arg Ser Glu Trp Gly Cys
1               5                   10                  15

Arg Tyr Asn Asp Ser Ser Asp
            20

<210> SEQ ID NO 690
<211> LENGTH: 23
<212> TYPE: PRT
<213> ORGANISM: Influenza A virus

<400> SEQUENCE: 690

Ser Leu Leu Thr Glu Val Glu Thr Pro Thr Arg Asn Gly Trp Glu Cys
1               5                   10                  15

L

Lys Cys Ser Asp Ser Ser Asp
            20

<210> SEQ ID NO 695
<211> LENGTH: 23
<212> TYPE: PRT
<213> ORGANISM: Influenza A virus

<400> SEQUENCE: 695

Ser Leu Leu Thr Glu Val Glu Thr Pro Thr Arg Asn Gly Trp Gly Cys
1               5                   10                  15

Arg Cys Ser Asp Ser Ser Asp
            20

<210> SEQ ID NO 696
<211> LENGTH: 23
<212> TYPE: PRT
<213> ORGANISM: Influenza A virus

<400> SEQUENCE: 696

Ser Leu Leu Thr Glu Val Glu Thr Pro Thr Arg Asn Gly Trp Glu Cys
1               5                   10                  15

Lys Cys Asn Asp Ser Ser Asp
            20

<210> SEQ ID NO 697
<211> LENGTH: 23
<212> TYPE: PRT
<213> ORGANISM: Influenza A virus

<400> SEQUENCE: 697

Ser Leu Leu Thr Glu Val Glu Thr Pro Thr Arg Asn Gly Trp Glu Cys
1               5                   10                  15

Lys Cys Asn Asp Ser Ser Asp
            20

<210> SEQ ID NO 698
<211> LENGTH: 23
<212> TYPE: PRT
<213> ORGANISM: Influenza A virus

<400> SEQUENCE: 698

Ser Leu Leu Thr Glu Val Glu Thr Pro Ile Arg Asn Glu Trp Gly Cys
1               5                   10                  15

Lys Cys Asn Asp Ser Ser Asp
            20

<210> SEQ ID NO 699
<211> LENGTH: 23
<212> TYPE: PRT
<213> ORGANISM: Influenza A virus

<400> SEQUENCE: 699

Ser Leu Leu Thr Glu Val Glu Thr Pro Thr Arg Asn Gly Trp Glu Cys
1               5                   10                  15

Arg Cys Asn Asp Ser Ser Asp
            20

<210> SEQ ID NO 700
<211> LENGTH: 23
<212> TYPE: PRT
<213> ORGANISM: Influenza A virus

```
<400> SEQUENCE: 700

Ser Leu Leu Thr Glu Val Glu Thr Pro Thr Arg Asn Gly Trp Glu Cys
1               5                   10                  15

Arg Cys Asn Asp Ser Ser Asp
            20

<210> SEQ ID NO 701
<211> LENGTH: 23
<212> TYPE: PRT
<213> ORGANISM: Influenza A virus

<400> SEQUENCE: 701

Ser Leu Leu Thr Glu Val Glu Thr Pro Thr Arg Asn Gly Trp Glu Cys
1               5                   10                  15

Arg Cys Asn Asp Ser Ser Asp
            20

<210> SEQ ID NO 702
<211> LENGTH: 23
<212> TYPE: PRT
<213> ORGANISM: Influenza A virus

<400> SEQUENCE: 702

Ser Leu Leu Thr Glu Val Glu Thr Pro Ile Arg Lys Gly Trp Glu Cys
1               5                   10                  15

Asn Cys Ser Asp Ser Ser Asp
            20

<210> SEQ ID NO 703
<211> LENGTH: 23
<212> TYPE: PRT
<213> ORGANISM: Influenza A virus

<400> SEQUENCE: 703

Ser Leu Leu Thr Gly Val Glu Thr His Thr Arg Asn Gly Trp Gly Cys
1               5                   10                  15

Lys Cys Ser Asp Ser Ser Asp
            20

<210> SEQ ID NO 704
<211> LENGTH: 23
<212> TYPE: PRT
<213> ORGANISM: Influenza A virus

<400> SEQUENCE: 704

Ser Leu Leu Pro Glu Val Glu Thr His Thr Arg Asn Gly Trp Gly Cys
1               5                   10                  15

Arg Cys Ser Asp Ser Ser Asp
            20

<210> SEQ ID NO 705
<211> LENGTH: 16
<212> TYPE: PRT
<213> ORGANISM: Influenza A virus

<400> SEQUENCE: 705

Leu Leu Thr Glu Val Glu Thr Pro Ile Arg Asn Glu Trp Gly Cys Arg
1               5                   10                  15

<210> SEQ ID NO 706
<211> LENGTH: 15
<212> TYPE: PRT
```

<213> ORGANISM: Influenza A virus

<400> SEQUENCE: 706

Leu Thr Glu Val Glu Thr Pro Ile Arg Asn Glu Trp Gly Cys Arg
1               5                   10                  15

<210> SEQ ID NO 707
<211> LENGTH: 12
<212> TYPE: PRT
<213> ORGANISM: Influenza A virus

<400> SEQUENCE: 707

Val Glu Thr Pro Ile Arg Asn Glu Trp Gly Cys Arg
1               5                   10

<210> SEQ ID NO 708
<211> LENGTH: 17
<212> TYPE: PRT
<213> ORGANISM: Influenza A virus

<400> SEQUENCE: 708

Glu Thr Pro Ile Arg Asn Glu Trp Gly Cys Arg Cys Asn Asp Ser Ser
1               5                   10                  15

Asp

<210> SEQ ID NO 709
<211> LENGTH: 16
<212> TYPE: PRT
<213> ORGANISM: Influenza A virus

<400> SEQUENCE: 709

Thr Pro Ile Arg Asn Glu Trp Gly Cys Arg Cys Asn Asp Ser Ser Asp
1               5                   10                  15

<210> SEQ ID NO 710
<211> LENGTH: 15
<212> TYPE: PRT
<213> ORGANISM: Influenza A virus

<400> SEQUENCE: 710

Pro Ile Arg Asn Glu Trp Gly Cys Arg Cys Asn Asp Ser Ser Asp
1               5                   10                  15

<210> SEQ ID NO 711
<211> LENGTH: 14
<212> TYPE: PRT
<213> ORGANISM: Influenza A virus

<400> SEQUENCE: 711

Ile Arg Asn Glu Trp Gly Cys Arg Cys Asn Asp Ser Ser Asp
1               5                   10

<210> SEQ ID NO 712
<211> LENGTH: 13
<212> TYPE: PRT
<213> ORGANISM: Influenza A virus

<400> SEQUENCE: 712

Arg Asn Glu Trp Gly Cys Arg Cys Asn Asp Ser Ser Asp
1               5                   10

<210> SEQ ID NO 713
<211> LENGTH: 12
<212> TYPE: PRT

<213> ORGANISM: Influenza A virus

<400> SEQUENCE: 713

```
Asn Glu Trp Gly Cys Arg Cys Asn Asp Ser Ser Asp
1               5                   10
```

<210> SEQ ID NO 714
<211> LENGTH: 17
<212> TYPE: PRT
<213> ORGANISM: Influenza A virus

<400> SEQUENCE: 714

```
Ser Leu Leu Thr Glu Val Glu Thr Pro Ile Arg Asn Glu Trp Gly Cys
1               5                   10                  15

Arg
```

<210> SEQ ID NO 715
<211> LENGTH: 16
<212> TYPE: PRT
<213> ORGANISM: Influenza A virus

<400> SEQUENCE: 715

```
Ser Leu Leu Thr Glu Val Glu Thr Pro Ile Arg Asn Glu Trp Gly Cys
1               5                   10                  15
```

<210> SEQ ID NO 716
<211> LENGTH: 15
<212> TYPE: PRT
<213> ORGANISM: Influenza A virus

<400> SEQUENCE: 716

```
Ser Leu Leu Thr Glu Val Glu Thr Pro Ile Arg Asn Glu Trp Gly
1               5                   10                  15
```

<210> SEQ ID NO 717
<211> LENGTH: 14
<212> TYPE: PRT
<213> ORGANISM: Influenza A virus

<400> SEQUENCE: 717

```
Ser Leu Leu Thr Glu Val Glu Thr Pro Ile Arg Asn Glu Trp
1               5                   10
```

<210> SEQ ID NO 718
<211> LENGTH: 14
<212> TYPE: PRT
<213> ORGANISM: Influenza A virus

<400> SEQUENCE: 718

```
Ser Leu Leu Thr Glu Val Glu Thr Pro Ile Arg Asn Glu Trp
1               5                   10
```

<210> SEQ ID NO 719
<211> LENGTH: 13
<212> TYPE: PRT
<213> ORGANISM: Influenza A virus

<400> SEQUENCE: 719

```
Ser Leu Leu Thr Glu Val Glu Thr Pro Ile Arg Asn Glu
1               5                   10
```

<210> SEQ ID NO 720
<211> LENGTH: 12
<212> TYPE: PRT

```
<213> ORGANISM: Influenza A virus

<400> SEQUENCE: 720

Ser Leu Leu Thr Glu Val Glu Thr Pro Ile Ar

3. The composition of claim 1, wherein said epitope of the M2e polypeptide includes the amino acid at positions 2, 5, and 6 of MSLLTEVETPTRNEWGCRCNDSSD (SEQ ID NO: 1).

4. A passive immunization composition comprising the composition of claim 1.

5. A pharmaceutical composition comprising the composition of claim 1 and a pharmaceutical carrier.

6. A method for the treatment of an influenza virus infection in a subject in need thereof, comprising administering to the composition of claim 5.

7. The method of claim 6, wherein the subject has been exposed to an influenza virus.

8. The method of claim 6, wherein the method further comprises administering an anti-viral drug, a viral entry inhibitor or a viral attachment inhibitor.

9. The method of claim 8, wherein said anti-viral drug is a neuraminidase inhibitor, a HA inhibitor, a sialic acid inhibitor or an M2 ion channel.

10. The method of claim 9, wherein said M2 ion channel inhibitor is amantadine or rimantadine.

11. The method of claim 9, wherein said neuraminidase inhibitor is zanamivir or oseltamivir phosphate.

12. The method of claim 6, further comprising administering a third anti-Influenza A antibody.

13. A diagnostic kit comprising the composition of claim 1.

14. A prophylactic kit comprising the composition according to claim 4.

* * * * *